US010723723B2

(12) United States Patent
Gunaga et al.

(10) Patent No.: US 10,723,723 B2
(45) Date of Patent: Jul. 28, 2020

(54) SUBSTITUTED BICYCLE HETEROCYCLIC DERIVATIVES USEFUL AS ROMK CHANNEL INHIBITORS

(71) Applicant: BRISTOL-MYERS SQUIBB COMPANY, Princeton, NJ (US)

(72) Inventors: Prashantha Gunaga, Bangalore (IN); Rajeev S. Bhide, Princeton Junction, NJ (US); Rajesh Onkardas Bora, Bangalore (IN); Manoranjan Panda, Bangalore (IN); Navnath Dnyanoba Yadav, Bangalore (IN); Eldon Scott Priestley, Yardley, PA (US); Jeremy Richter, Yardley, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 16/344,823

(22) PCT Filed: Nov. 2, 2017

(86) PCT No.: PCT/US2017/059642
§ 371 (c)(1),
(2) Date: Apr. 25, 2019

(87) PCT Pub. No.: WO2018/093569
PCT Pub. Date: May 24, 2018

(65) Prior Publication Data
US 2019/0248769 A1 Aug. 15, 2019

(30) Foreign Application Priority Data
Nov. 3, 2016 (IN) .............................. 201611037609

(51) Int. Cl.
| C07D 405/14 | (2006.01) |
| C07D 413/14 | (2006.01) |
| C07D 417/14 | (2006.01) |
| A61P 13/02 | (2006.01) |
| A61P 9/00 | (2006.01) |

(Continued)

(52) U.S. Cl.
CPC .............. *C07D 405/14* (2013.01); *A61P 9/00* (2018.01); *A61P 9/04* (2018.01); *A61P 9/12* (2018.01); *A61P 13/02* (2018.01); *C07D 413/14* (2013.01); *C07D 417/14* (2013.01); *C07D 471/04* (2013.01)

(58) Field of Classification Search
CPC .. C07D 405/14; C07D 413/14; C07D 417/14; C07D 417/04; A61P 9/12; A61P 9/04; A61P 13/02

See application file for complete search history.

(56) References Cited

U.S. PATENT DOCUMENTS 10,000,484 B2 * 6/2018 Chobanian ............ A61K 31/519
10,501,449 B2 12/2019 Yadav et al.
(Continued)

FOREIGN PATENT DOCUMENTS

| IN | 03142DE2005 A | 11/2005 |
| JP | 6032074 A | 2/1994 |

(Continued)

OTHER PUBLICATIONS

U.S. Appl. No. 16/679,435, filed Nov. 11, 2019, Yadav et al.
(Continued)

*Primary Examiner* — Timothy R Rozof
(74) *Attorney, Agent, or Firm* — Mary K. VanAtten

(57) ABSTRACT

Disclosed are compounds of Formula (I) or a salt thereof, wherein $R^1$ is (II) or (III); each W is independently $NR_{1b}$ or O; Z is a bond or $CHR^{1d}$; and $R^1$, $R^2$, $R^d$, $R^3$, $L^1$, $L^2$, $R^{1a}$, $R^{1b}$, $R^{1c}$, and n are define herein. Also disclosed are methods of using such compounds as inhibitors of ROMK, and pharmaceutical compositions comprising such compounds. These compounds are useful in treating cardiovascular diseases.

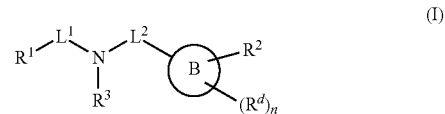

(I)

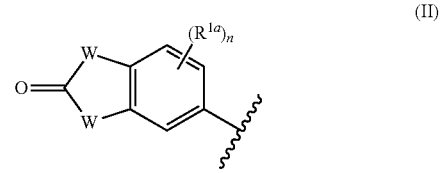

(II)

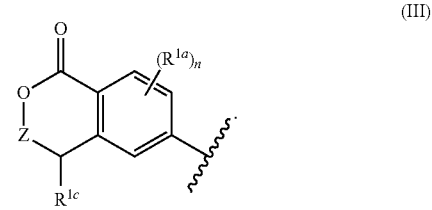

(III)

14 Claims, No Drawings

(51) Int. Cl.
*A61P 9/12* (2006.01)
*A61P 9/04* (2006.01)
*C07D 471/04* (2006.01)

(56) References Cited

U.S. PATENT DOCUMENTS

2008/0280875 A1 11/2008 Bai
2014/0171405 A1 6/2014 Zhuo
2019/0127380 A1 5/2019 Gunaga et al.

FOREIGN PATENT DOCUMENTS

| WO | WO2004098518 A2 | 11/2004 |
| WO | WO2004108133 A2 | 12/2004 |
| WO | WO2007117465 A2 | 10/2007 |
| WO | WO2007122482 A1 | 11/2007 |
| WO | WO2009027392 A1 | 3/2009 |
| WO | WO2010127855 A1 | 11/2010 |
| WO | WO2013039802 A1 | 3/2013 |
| WO | WO2013066714 A1 | 5/2013 |
| WO | WO2013066718 A2 | 5/2013 |
| WO | WO2014028968 A1 | 2/2014 |
| WO | WO2014085210 A1 | 6/2014 |
| WO | WO2015095097 A2 | 6/2015 |
| WO | WO2015103756 A1 | 7/2015 |
| WO | WO2017184662 A1 | 10/2017 |

OTHER PUBLICATIONS

CAS Registry 1111571-77-7 Entered STN: Feb. 25, 2009 1H-2-Benzopyran-6-carboxamide, 3,4-dihydro-N-methyl-1-oxo-3-phenyl-N-[1-[4-(1H-1,2,4-triazol-1-yl)phenyl]ethyl].
CAS Registry 1147387-44-7 Entered STN: May 19, 2009 1H-2-Benzopyran-6-carboxamide, 3,4-dihydro-N-[[2-(1H-imidazol-1-yl)-3-pyridinyl]methyl]-1-oxo-3-phenyl.
CAS Registry 1279382-83-0 Entered STN: Apr. 13, 2011 1H-2-Benzopyran-6-carboxamide, 3,4-dihydro-N-[[1-(4- methoxyphenyl)-1H-pyrazol-3-yl]methyl]-1-oxo-3-phenyl.
CAS Registry 1279667-52-5 Entered STN: Apr. 13, 2011 1H-2-Benzopyran-6-carboxamide, 3,4-dihydro-N-[2-methyl-1-(3-phenyl-1,2,4 oxadiazol-5-yl)propyl]-1-oxo-3-phenyl.
CAS Registry 1287594-07-3 Entered STN: Apr. 29, 2011 1H-2-Benzopyran-6-carboxamide, 3,4-dihydro-1-oxo-3-phenyl-N-[(1,4,5,6-tetrahydro-1-phenyl-3-cyclopentapyrazolyl)methyl].
CAS Registry 1294688-53-1 Entered STN: May 15, 2011 1H-1,2,3-Triazole-4-carboxamide, 1-[4-[1-[[(3,4-dihydro-1-oxo-3-phenyl-1H-2-benzopyran-6-yl)carbonyl]amino]ethyl]phenyl].
CAS Registry 1294797-34-4 Entered STN: May 15, 2011 1H-2-Benzopyran-6-carboxamide, 3,4-dihydro-N-[[4-(1H-imidazol-1-yl)phenyl]methyl]-1-oxo-3-phenyl.
CAS Registry 1294960-28-3 Entered STN: May 15, 2011 1H-2-Benzopyran-6-carboxamide, 3,4-dihydro-N-[2-[5-(2-methyl-4-thiazolyl.
CAS Registry 1298722-97-0 Entered STN: May 22, 2011 1H-2-Benzopyran-6-carboxamide, 3,4-dihydro-1-oxo-3-phenyl-N-[(4-phenyl-2-thiazolyl)methyl].
CAS Registry 1298996-78-7 Entered STN: May 22, 2011 1H-2-Benzopyran-6-carboxamide, 3,4-dihydro-1-oxo-3-phenyl-N-[2-(2-phenyl-4.
CAS Registry 1301229-32-2 Entered STN: May 26, 2011 1H-2-Benzopyran-6-carboxamide, N-[[3-fluoro-4-(1H-imidazol-1-yl)phenyl]methyl]-3,4-dihydro-1-oxo-3-phenyl.
CAS Registry 1302544-86-0 Entered STN: May 29, 2011 1H-2-Benzopyran-6-carboxamide, 3,4-dihydro-1-oxo-3-phenyl-N-[[4-(1H-1,2,4-triazol-1-yl)phenyl]methyl].
CAS Registry 1623375-17-6 Entered STN: Sep. 18, 2014 1H-2-Benzopyran-6-carboxamide, 3,4-dihydro-1-oxo-3-phenyl-N-[[3-(4-pyridinyl)-1,2,4-oxadiazol-5-yl]methyl].
CAS Registry 1623929-47-4 Entered STN: Sep. 21, 2014 1H-2-Benzopyran-6-carboxamide, 3,4-dihydro-1-oxo-3-phenyl-N-[2-[4-(1H-pyrazol-1-yl)phenyl]ethyl.
CAS Registry 872026-46-5 Entered STN: Jan. 17, 2006 1H-2-Benzopyran-6-carboxamide, N-[[5-(2-furanyl)-1,3,4-oxadiazol-2-yl]methyl]-3,4-dihydro-1-oxo-3-phenyl-N-propyl.
CAS Registry 875458-55-2 Entered STN: Feb. 28, 2006 1H-2-Benzopyran-6-carboxamide, 3,4-dihydro-N-(2-methoxyethyl)-1-oxo-3-phenyl-N-[[5-(2-thienyl)-1,3,4-oxadiazol-2-yl]methyl].
CAS Registry 920832-20-8 Entered STN: Feb. 14, 2007 1H-2-Benzopyran-6-carboxamide, 3,4-dihydro-N-[1-[4-(1H-imidazol-1-yl)phenyl]ethyl]-1-oxo-3-phenyl.
CAS Registry 920913-17-3 Entered STN: Feb. 14, 2007 1H-2-Benzopyran-6-carboxamide, 3,4-dihydro-1-oxo-3-phenyl-N-[1-[4-(1H-1,2,4-triazol-1-yl)phenyl]ethyl].
CAS Registry 926731-08-0 Entered STN: Mar. 16, 2007 1H-2-Benzopyran-6-carboxamide, N-[[5-(4-chlorophenyl)-1,3,4-oxadiazol-2-yl]methyl]-N-cyclopropyl-3,4-dihydro-1-oxo-3-phenyl.
CAS Registry 926793-11-5 Entered STN: Mar. 18, 2007 1H-2-Benzopyran-6-carboxamide, N-[[5-(2-chlorophenyl)-1,3,4-oxadiazol-2-yl]methyl]-N-cyclopropyl-3,4-dihydro-1-oxo-3-phenyl.
CAS Registry 956144-71-1 Entered STN: Nov. 28, 2007 1H-2-Benzopyran-6-carboxamide, N-[(3,5-dimethyl-1-phenyl-1H-pyrazol-4-yl)methyl]-3,4-dihydro-N-methyl-1-oxo-3-phenyl.
CAS Registry 956571-62-3 Entered STN: Dec. 3, 2007 1H-2-Benzopyran-6-carboxamide, 3,4-dihydro-1-oxo-3-phenyl-N-[2-(1-phenyl.
CAS Registry 957028-33-0 Entered STN: Dec. 7, 2007 1H-2-Benzopyran-6-carboxamide, 3,4-dihydro-N-methyl-1-oxo-3-phenyl-N-[(1-phenyl-1H-pyrazol-4-yl)methyl].
Hanna, M.A. et al., "Novel Sulphoarylazo-4-pyrazolone-Based Tartrazine Dye Analogues", Phosphorus, Sulfur, and Silicon and TEH Related Elements, vol. 179(6), pp. 1209-1226 (2004).
O'Reilly et al., "Development of Dual PLD1/2 and PLD2 Selective Inhibitors from a Common 1,3,8-Triazaspiro[4.5] decane Core: Discovery of ML298 and ML299 That Decrease Invasive Migration in U87-MG Glioblastoma Cells" J. Med. Chem., vol. 56, 2695-2699 (2013).

* cited by examiner

SUBSTITUTED BICYCLE HETEROCYCLIC DERIVATIVES USEFUL AS ROMK CHANNEL INHIBITORS

CROSS REFERENCE TO RELATED APPLICATIONS

This application is a 371 application of PCT/US2017/059642 filed Nov. 2, 2017 which claims the benefit of Indian Provisional Application Serial No. 201611037609, filed Nov. 3, 2016, which is incorporated herein in its entirety.

DESCRIPTION

The present invention generally relates to substituted benzylamine compounds useful as inhibitors of ROMK channel activity. Provided herein are substituted benzylamine compounds, compositions comprising such compounds, and methods of their use. The invention further pertains to pharmaceutical compositions containing at least one compound according to the invention that are useful for the treatment of conditions related to ROMK channel activity, including cardiovascular diseases.

The renal outer medullary potassium (ROMK. Kirl.1) channel is a weak inward rectifying $K^+$ channel with a key role in renal $K^+$ recycling and secretion (Ho et al., *Nature*, 1993, 362, 31-38; Shuck et al., *The Journal of Biological Chemistry*, 1994, 269(39), 24261-24270; Lee and Hebert, *American Journal of Physiology-Renal Physiology*, 1995, 268(6), F1124-F1131; Lu et al., *The Journal of Biological Chemistry*, 2002, 277, 37881-37887; and Hebert et al., *Physiological Reviews*, 2005, 85:319-371). In the thick ascending limb (TAL) of a nephron, ROMK channel activity provides the $K^+$ gradient necessary for Na and Cl reabsorption by the $Na^+$-$K^+$-$2Cl^-$ (NKCC2) co-transporter. In the distal convoluted tubule (DCT) and cortical collecting duct (CCD), ROMK channels form the major secretory pathway for $K^+$ and as a result, play an important role in $K^+$ homeostasis under physiological conditions (Welling and Ho, *American Journal of Physiology-Renal Physiology*, 2009, 297(4): F849-F863).

Multiple lines of evidence indicate that inhibition of ROMK channel activity results in natriuresis, diuresis and reduced blood pressure. Therefore, ROMK inhibition may offer a novel mechanism of blood pressure regulation and diuresis in patients suffering from hypertension, congestive heart failure or any other edematous disease conditions. The activity of NKCC2 transporter is tightly coupled with ROMK activity in the TAL region and homozygous loss of function mutations in ROMK in humans result in a disease phenotype (renal salt wasting, increased aldosterone levels, metabolic alkalosis, reduction in blood pressure) very similar to that of NKCC2 homozygous mutations but with a milder hypokalemia (Simon et al., *Nature Genetics*, 1996, 14: 152-156). In addition, humans identified with heterozygous ROMK mutations from the Framingham Heart Study presented with reduced blood pressure (Ji et al., *Nature Genetics*, 2008, 40(5): 592-599). Similar to human genetics, mouse genetics also support the role of ROMK in $Na^+$ reabsorption in the kidney and overall blood pressure regulation (Lu et al., *The Journal of Biological Chemistry*, 2002, 277, 37881-37887; and Lorenz et al., *The Journal of Biological Chemistry*, 2002, 277: 37871-37880). Furthermore, pharmacological blockade of the ROMK channel has been shown to induce natriuresis and diuresis in rats upon acute dosing and in dogs upon both acute and prolonged dosing (Tang et al., *Bioorganic and Medicinal Chemistry Letter*, 2013, 23: 5829-5832; Garcia et al., *The Journal of Pharmacology and Experimental Therapeutics*, 2014, 348: 153-164; Walsh et al., *ACS Medicinal Chemistry Letters*, 2015, 6: 747-752; and Dajee et al., *Circulation*, 2014, 130: A12397). Since the ROMK channel is also implicated in regulation of net $K^+$ secretion in the distal part of the nephron, it is believed that ROMK inhibition in this region will mitigate the $K^+$ wasting and hypokalemia associated with loop and thiazide diuretics. Acute or prolonged (up to 122 days) ROMK antagonism does not lead to kaliuresis or hypokalemia in dogs (Garcia et al., *The Journal of Pharmacology and Experimental Therapeutics*, 2014, 348: 153-164; Walsh et al., *ACS Medicinal Chemistry Letters*, 2015, 6: 747-752; Dajee et al., *Circulation*, 2014, 130: A12397). Together, these data suggest that inhibition of ROMK may produce diuretic efficacy that is equivalent to or better than currently available loop diuretics and with potentially lower incidence of hypokalemia.

WO 2015/095097 discloses compounds useful as inhibitors of ROMK. Other publications disclosing compounds useful as inhibitors of ROMK include WO 2010/129379, WO 2010/136144, WO 2012/058116, WO 2012/058134. WO 2013/028474, WO 2013/039802, WO 2013/062892, WO 2013/062900, WO 2013/066714, WO 2013/066717, WO 2013/066718, WO 2013/090271, WO 2014/015495, WO 2014/018764, WO 2014/085210, WO 2014/099633, WO 2014/126944, WO 2014/150132, WO 2015/017305, WO 2015/065866, WO 2015/095097, WO 2015/100147, WO 2015/105736, WO 2016/008064, WO 2016/010801, WO 2016/010802, WO2016/060941, WO2016/065582, WO2016/065602, WO2016/065603, WO2016/069426, WO2016/069427, WO2016/069428, WO2016/069430, WO2016/091042, WO2016/122994, WO2016/127358, WO2016/130444, and CN105693706.

In view of the numerous conditions that are contemplated to benefit by treatment involving inhibition of ROMK, it is immediately apparent that new compounds capable of inhibiting ROMK and methods of using these compounds should provide substantial therapeutic benefits to a wide variety of patients.

The present invention relates to a new class of substituted bicyclic heterocyclic compounds found to be effective inhibitors of ROMK.

SUMMARY OF THE INVENTION

The present invention provides compounds of Formula (I) that are useful as inhibitors of ROMK, and are useful for the treatment of cardiovascular diseases and prophylaxis and/or treatment of diuresis or natriuresis.

The present invention also provides pharmaceutical compositions comprising a pharmaceutically acceptable carrier and at least one of the compounds of Formula (I) or stereoisomers, tautomers, salts, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The present invention also provides a method for inhibiting ROMK comprising administering to a host in need of such treatment a therapeutically effective amount of at least one of the compounds of Formula (I) or stereoisomers, tautomers, salts, pharmaceutically acceptable salts, solvates, or prodrugs thereof.

The present invention also provides a method for treating cardiovascular disease comprising administering to a host in need of such treatment a therapeutically effective amount of at least one of the compounds of Formula (I) or stereoisomers, tautomers, salts, pharmaceutically acceptable salts, solvates, or prodrugs thereof.

The present invention also provides a method for treating cardiovascular disease comprising administering to a host in need of such treatment a therapeutically effective amount of at least one of the compounds of Formula (I) or stereoisomers, tautomers, salts, pharmaceutically acceptable salts, solvates, or prodrugs thereof, either alone or in combination with other compounds of the present invention, or incombination with one or more other agent(s). One embodiment provides a method for treating cardiovascular disease. Particular, cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

One embodiment provides a method for promotion of diuresis or natriuresis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cardiovascular disease or prophylaxis and/or promotion of diuresis or natriuresis. The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I):

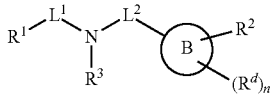

(I)

or a salt, pharmaceutically acceptable salt, stereoisomer, or diasteriomer thereof, wherein:
$R^1$ is:

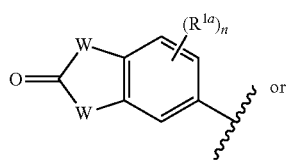

or

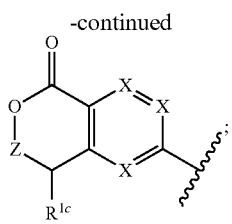

each W is independently $NR^{1b}$ or O:
Z is a bond or $CHR^{1d}$;
X is N or $CR^{1a}$
each $R^{1a}$ is independently H, F, Cl, —OH, $C_{1-3}$ alkyl, $C_{1-3}$ fluoroalkyl, $C_{3-6}$ cycloalkyl, $C_{1-3}$ alkoxy, or $C_{1-3}$ fluoroalkoxy:
each $R^{1b}$ is independently H, $C_{1-3}$ alkyl, $C_{1-3}$ fluoroalkyl, $C_{1-6}$ cycloalkyl
$R^{1c}$ is H, $C_{1-4}$ alkyl, $C_{1-4}$ fluoroalkyl, or $C_{3-6}$ cycloalkyl;
$R^{1d}$ is H, $C_{1-3}$ alkyl, $C_{1-4}$ fluoroalkyl, or $C_{3-6}$ cycloalkyl;
$L^1$ is a bond, —$CHR^b$—, —$CHR^aCHR^b$—, —$CH(R^a)C(O)$—, —$C(R^b)_2$—, —$C(R^a)_2CH(R^b)$—, or —$CH(R^a)C(R^b)_2$—;
$L^2$ is —$CH_2$—, —$C(O)$—, —$CH_2$—$CH_2$—, or —$C(R)_2$—; wherein R is independently selected from hydrogen, F, $C_{1-3}$alkyl, $C_{1-3}$ hyroxyalkyl, $C_{1-3}$ alkoxyalkyl, or $C_{1-3}$ fluoroalkyl;
$R^a$ is H, halo, —OH, $C_{1-4}$ alkyl, $C_{1-3}$ fluoroalkyl, $C_{3-6}$ hydroxyalkyl, $C_{3-6}$ cycloalkyl, $C_{1-3}$ alkoxy, OC(O)—$C_{1-4}$ alkyl substituted with 0-1 OH, halo or $NH_2$, $NR^{1e}R^{1e}$, or $C_{1-3}$ fluoroalkoxy;
each $R^{1e}$ is independently H, $C_{1-6}$ alkyl, $C_{1-6}$ fluoroalkyl, $C_{3-6}$ cycloalkyl, $C_{3-6}$ fluorocycloalkyl, C(O)—$C_{1-6}$ alkyl, C(O)—$C_{1-6}$ fluoroalkyl, C(O)—$C_{3-6}$ cycloalkyl, C(O)heterocyclyl, C(O)O—$C_{1-6}$ alkyl, C(O)O—$C_{1-6}$ cycloalkyl, C(O)O—$C_{1-6}$ fluoroalkyl, C(O)O—$C_{3-6}$ fluorocycloalkyl, $SO_2$—$C_{1-6}$ alkyl, $SO_2$—$C_{3-5}$ cycloalkyl, $SO_2$—$C_{1-6}$ fluoroalkyl, $SO_2$—$C_{3-6}$ fluorocycloalkyl, $C(O)NR^eR^e$, wherein the heterocyclyl is 5 or 6 membered ring having 1, 2, 3, or 4 heteroatoms selected from O, S, and N, and the alkyl, cycloalkyl, or heterocyclyl is substituted with 0-1 of halo, OH, CN, $NH_2$, $C_{1-3}$ alkyl, $C_{1-3}$ alkoxy, $C_{1-3}$ fluoroalkyl, $C_{1-3}$ fluroalkoxy; or two $R^{1e}$ along with the nitrogen atom to which they are attached form a 3-7 membered heterocyclyl having 1, 2, 3, or 4 heteroatoms selected from O, S, and N, and being substituted with 0-1 halo, $C_{1-3}$ alkyl, or =O;
$R^b$ is H, $C_{1-4}$ alkyl, $C_{1-3}$ fluoroalkyl, $C_{1-3}$ hydroxyalkyl, $C_{3-6}$ cycloalkyl, $C_{1-3}$ alkoxyalkyl, or $C_{1-3}$ fluoroalkoxyalkyl;
Ring B is phenyl, pyridinyl, pyrimidinyl, pyrrazolyl, indolyl, indazolyl, thiazolyl, imidizolyl, pyridinonyl, triazolyl, tetrazolyl, oxadiazolyl, thiadiazolyl, isothiazolyl, isoxazolyl, pyrazinyl, oxazolyl, pyridazinyl, furanyl, thiophenyl, pyrrolyl, triazinyl, azaindolyl, benzimidazolyl, bezoxazolyl, bezothiazolyl, benzofuranyl, or benzothiophenyl.
$R^2$ is a $C_{6-10}$ aryl, or a 5 to 10 membered heteroaryl ring containing 1 to 4 heteroatoms selected from N. O, and S, the heteroaryl optionally containing an oxo substitution, and the heteroaryl and aryl being substituted with 0-3 $R^{2a}$;
$R^{2a}$ is OH, =O, CN, halo, $C(O)N(R^e)_2$, $C(O)O$—$C_{1-4}$ alkyl, $C_{1-4}$alkyl, $C_{1-4}$ fluoroalkyl, $C_{1-4}$ alkoxy, $C_{1-4}$ fluoroalkoxy, $C_{3-6}$ cycloalkyl, $C_{3-6}$ cycloalkoxy, $SO_2R^e$, or a 4 to 6 membered heterocyclyl having 1, 2, 3, or 4 heteroatoms selected from O, S, and N, and wherein the heterocyclyl is substituted with 0-3 $R^d$;
each $R^3$ is independently H, $C_{1-4}$ alkyl, $C_{1-4}$ fluoroalkyl, $C_{1-3}$ hydroxyalkyl, $C_{1-3}$ alkoxyalkyl, $C_{3-6}$cycloalkyl, —(CH$_2$)—C$_{3-6}$cycloalkyl, —(CH$_2$)-heterocyclyl, —SO$_2$R$^e$, —C(O)R$^e$, —C(O)OR$^e$, or —C(O)NR$^e$R$^e$, wherein the heterocyclyl is a 5-6 membered ring have 1, 2, or 3 heteroatoms selected from N, O, and S;

each R$^d$ is independently H, C$_{1-3}$ alkyl, C$_{1-3}$ alkoxy, halo, OH, =O, CN OCF$_3$, OCHF$_2$, CHF$_2$ and CF$_3$; and each R$^e$ is independently H, C$_{1-3}$ alkyl, C$_{1-3}$ fluoroalkyl, C$_{3-6}$ cycloalkyl, C$_{3-6}$ fluorocycloalkyl, C$_{1-3}$ hydroxyalkyl, C$_{1-3}$ alkoxyalkyl, C$_{6-10}$ aryl, or a 5 to 10 membered heteroaryl having 1, 2, 3, or 4 heteroatoms selected from O, S, and N; or two R$^e$ along with the nitrogen atom to which the) are attached form a 3-7 membered heterocyclyl having 1, 2, 3, or 4 heteroatoms selected from O, S, and N.

In another first aspect of the present invention provides at least one compound of Formula (I):

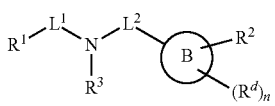

(I)

or a salt, pharmaceutically acceptable salt, stereoisomer, or diasteriomer thereof, wherein:

R$^1$ is:

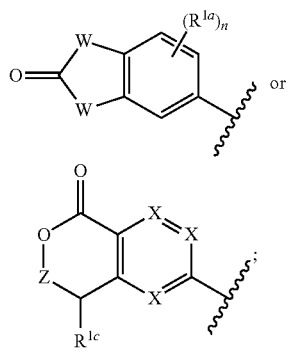

or each W is independently NR$^{1b}$ or O;
Z is a bond or CHR$^{1d}$;
X is N or CR$^{1a}$
each R$^{1a}$ is independently H, F, Cl, —OH, C$_{1-3}$ alkyl, C$_{1-3}$ fluoroalkyl, C$_{3-6}$ cycloalkyl, C$_{1-3}$ alkoxy, or C$_{1-3}$ fluoroalkoxy;
each R$^{1b}$ is independently H, C$_{1-3}$ alkyl, C$_{1-3}$ fluoroalkyl, C$_{1-6}$ cycloalkyl
R$^{1c}$ is H, C$_{1-4}$ alkyl, C$_{1-4}$ fluoroalkyl, or C$_{3-6}$ cycloalkyl;
R$^{1d}$ is H, C$_{1-3}$ alkyl, C$_{1-4}$ fluoroalkyl, or C$_{3-6}$ cycloalkyl;
L$^1$ is a bond, —CHR$^b$—, —CHR$^a$CHR$^b$—, —CH(R$^a$)C(O)—, —C(R$^b$)$_2$—, —C(R$^a$)$_2$CH(R$^b$)—, or —CH(R$^a$)C(R$^b$)$_2$—;
L$^2$ is —CH$_2$—, —C(O)—, —CH$_2$—CH$_2$—, or —C(R)$_2$—;
wherein R is independently selected from hydrogen, F, C$_{1-3}$alkyl, C$_{1-3}$ hyroxyalkyl, C$_{1-3}$ alkoxyalkyl, or C$_{1-3}$ fluoroalkyl;
R$^a$ is H, halo, —OH, C$_{1-4}$ alkyl, C$_{1-3}$ fluoroalkyl, C$_{1-3}$ hydroxyalkyl, C$_{3-6}$ cycloalkyl, C$_{1-3}$ alkoxy, NR$^{1e}$R$^{1e}$, or C$_{1-3}$ fluoroalkoxy;
each R$^{1e}$ is independently H, C$_{1-6}$ alkyl, C$_{1-6}$ fluoroalkyl, C$_{3-6}$ cycloalkyl, C$_{3-6}$ fluorocycloalkyl, C(O)—C$_{1-6}$ alkyl, C(O)—C$_{1-6}$ fluoroalkyl, C(O)—C$_{3-6}$ cycloalkyl, C(O)heterocyclyl, C(O)O—C$_{1-6}$ alkyl, SO$_2$—C$_{1-6}$ alkyl, SO$_2$—C$_{3-5}$ cycloalkyl, SO$_2$—C$_{1-6}$ fluoroalkyl, SO$_2$—C$_{3-6}$ fluorocycloalkyl, C(O)NR$^e$R$^e$; or two R$^{1e}$ along with the nitrogen atom to which they are attached form a 3-7 membered heterocyclyl, wherein each heterocyclyl is a 5 to 10 membered group having 1, 2, 3, or 4 heteroatoms selected from O, S, and N;
R$^b$ is H, C$_{1-4}$ alkyl, C$_{1-3}$ fluoroalkyl, C$_{1-3}$ hydroxyalkyl, C$_{3-6}$ cycloalkyl, C$_{1-3}$ alkoxyalkyl, or C$_{1-3}$ fluoroalkoxyalkyl;
Ring B is phenyl, pyridinyl, pyrimidinyl, pyrrazolyl, indolyl, indazolyl, thiazolyl, imidizolyl, pyridinonyl, triazolyl, tetrazolyl, oxadiazolyl, thiadiazolyl, isothiazolyl, isoxazolyl, pyrazinyl, oxazolyl, pyridazinyl, furanyl, thiophenyl, pyrrolyl, triazinyl, azaindolyl, benzimidazolyl, bezoxazolyl, bezothiazolyl, benzofuranyl, or benzothiophenyl.
R$^2$ is a 5 to 10 membered heteroaryl ring containing 1 to 4 heteroatoms selected from N, O, and S, the heteroaryl optionally containing an oxo substitution, and being substituted with 0-3 R$^{2a}$;
R$^{2a}$ is OH, =O, CN, halo, C$_{1-4}$alkyl, C$_{1-4}$ fluoroalkyl, C$_{1-4}$ alkoxy, C$_{1-4}$ fluoroalkoxy, C$_{3-6}$ cycloalkyl, C$_{3-6}$ cycloalkoxy, SO$_2$R$^e$, or a 4 to 6 membered heterocyclyl having 1, 2, 3, or 4 heteroatoms selected from O, S, and N;
each R$^3$ is independently H, C$_{1-4}$ alkyl, C$_{1-3}$ fluoroalkyl, C$_{1-3}$ hydroxyalkyl, C$_{1-3}$ alkoxyalkyl, C$_{3-6}$cycloalkyl, —(CH$_2$)—C$_{3-6}$cycloalkyl, —(CH$_2$)-heterocyclyl, —SO$_2$R$^e$, —C(O)R$^e$, —C(O)OR$^e$, or —C(O)NR$^e$R$^e$, wherein the heterocyclyl is a 5-6 membered ring have 1, 2, or 3 heteroatoms selected from N, O, and S;
each R$^d$ is independently H, C$_{1-3}$ alkyl, C$_{1-3}$ alkoxy halo, OH, =O, CN OCF$_3$, OCHF$_2$, CHF$_2$ and CF$_3$; and
each R$^e$ is independently H, C$_{1-3}$ alkyl, C$_{1-3}$ fluoroalkyl, C$_{3-6}$ cycloalkyl, C$_{3-6}$ fluorocycloalkyl, C$_{1-3}$ hydroxyalkyl, C$_{1-3}$ alkoxyalkyl, C$_{6-10}$ aryl, or a 5 to 10 membered heteroaryl having 1, 2, 3, or 4 heteroatoms selected from O, S, and N; or two R$^e$ along with the nitrogen atom to which they are attached form a 3-7 membered heterocyclyl.

In a another aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

R$^1$ is

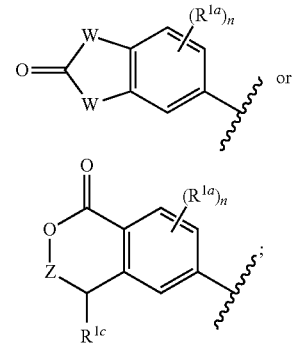

each W is independently NR$^{1b}$ or O;
Z is a bond or CHR$^{1d}$;
each R$^{1a}$ is independently H, F. Cl, —OH, C$_{1-3}$ alkyl, C$_{1-3}$ fluoroalkyl, C$_{3-6}$ cycloalkyl, C$_{1-3}$ alkoxy, or C$_{1-3}$ fluoroalkoxy;
each R$^{1b}$ is independently H, C$_{1-3}$ alkyl, C$_{1-3}$ fluoroalkyl, C$_{6-10}$ aryl, or a 5 to 10 membered heteroaryl, having 1, 2, 3, or 4 heteroatoms selected from O, S, and N;

$R^{1c}$ is H, $C_{1-4}$ alkyl, or $C_{3-6}$ cycloalkyl;
$R^{1d}$ is H, $C_{1-3}$ alkyl, or $C_{3-6}$ cycloalkyl;
n is zero, 1, 2, or 3;
$L^1$ is a bond, —$CHR^b$—, or —$CHR^aCHR^b$—;
$L^2$ is —$CH_2$—, —C(O)—, —$CH_2$—$CH_2$—, or —$C(R)_2$—; wherein R is independently selected from hydrogen, F, $C_{1-3}$alkyl, or $C_{1-3}$fluoroalkyl;
$R^a$ is H, halo, —OH, $C_{1-4}$ alkyl, $C_{1-3}$ fluoroalkyl, $C_{1-3}$ hydroxyalkyl, $C_{3-6}$ cycloalkyl, $C_{1-3}$ alkoxy, or $C_{1-3}$ fluoroalkoxy; $NR^{1e}R^{1e}$
$R^{1e}$ is H, $C_{1-6}$ alkyl, $C_{1-6}$ fluoroalkyl, $C_{3-6}$ cycloalkyl, $C_{3-6}$ fluorocycloalkyl, C(O)—$C_{1-6}$ alkyl, C(O) $C_{1-6}$ fluoroalkyl, C(O)—$C_{3-6}$ cycloalkyl, C(O)heterocyclyl, C(O)O—$C_{1-6}$ alkyl, $SO_2$—$C_{1-6}$ alkyl; or two $R^{1e}$ along with the nitrogen atom to which they are attached form a 3-7 membered heterocyclyl, wherein each heterocyclyl is a 5 to 10 membered group having, 2, 3, or 4 heteroatoms selected from O, S, and N;
$R^b$ is H, $C_{1-4}$ alkyl, $C_{1-3}$ fluoroalkyl, $C_{1-3}$ hydroxyalkyl, $C_{3-6}$ cycloalkyl, $C_{1-3}$ alkoxy, or $C_{1-3}$ fluoroalkoxy;
Ring B is phenyl, pyridinyl, pyrimidinyl, pyrrazolyl, indolyl, indazolyl, thiazolyl, imidizolyl, triazolyl, pyridinonyl, 1,2-dihydro-3H pyrazol-3-onyl, triazolyl, tetrazolyl, oxadiazolyl, thiadiazolyl, isothiazolyl, isoxazolyl, pyrazinyl or pyridazinyl; oxazolyl, pyridazinyl, furanyl, thiophenyl, pyrrolyl
$R^2$ is a 5 to 10 membered heterocycle ring containing 1 to 4 heteroatoms selected from N, O, and S, the heteroaryl optionally containing a —C(O)—, and being substituted with 0-3 $R^{2a}$;
$R^{2a}$ is CN, halo, or $C_{1-4}$alkyl, $C_{1-4}$ fluoroalkyl, $C_{1-4}$ alkoxy, $C_{1-4}$ fluoroalkoxy, $C_{3-6}$ cycloalkyl, $C_{1-6}$ cycloalkoxy, or a 5 to 10 membered heterocyclyl having 1, 2, 3, or 4 heteroatoms selected from O, S, and N;
each $R^d$ is independently H, $C_{1-3}$ alkyl, —($CH_2$)-pyridinyl, —$C(O)R^e$, —$C(O)OR^e$, or —$C(O)NR^eR^e$;
each $R^d$ is independently H, F, Cl, —OH, $C_{1-3}$ alkyl, $C_{1-3}$ fluoroalkyl, $C_{3-6}$ cycloalkyl, $C_{1-3}$ alkoxy, or $C_{1-3}$ fluoroalkoxy; and
each $R^e$ is independently H, $C_{1-3}$ alkyl, $C_{1-3}$ fluoroalkyl, $C_{3-6}$ cycloalkyl, $C_{6-10}$ aryl, or a 5 to 10 membered heteroaryl having 1, 2, 3, or 4 heteroatoms selected from O, S, and N; or two $R^e$ along with the nitrogen atom to which they are attached form a 3-7 membered heterocyclyl.

In a second aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
$R^2$ is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiazolyl, thiophenyl, 1H-1,2,3-triazolyl, 1H-benzo[d][1,2,3]triazolyl, [1,2,4]triazolo[4,3-b]pyridazinyl, 1H-benzo[d]imidazolyl, 1H-imidazolyl, 1H-pyrazolo[3,4-b]pyridinyl, 1H-pyrazolo[3,4-c]pyridinyl, 1H-pyrazolo[4,3-c]pyridinyl, 1H-pyrrolyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, pyrazolo[1,5-a]pyrimidinyl, 1H-tetrazolyl, 4H-1,2,4-triazolyl, isothiazolyl, isoxazolyl, oxazolyl, pyridazinyl, pyrimidinyl, or benzo[d]oxazol-2(3H)-only, each being substituted with with 0-3 $R^{2a}$.

In a third aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
$R^2$ is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, pyrazolo[1,5-a]pyrimidinyl, or benzo[d]oxazol-2(3H)-only, each being substituted with with 0-3 $R^{2a}$.

In a fourth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
$R^2$ is phenyl, pyridinyl, indolyl, indazolyl, benzo[d]oxazol-2(3H)-onyl, 1H-pyrazolo[4,3-b]pyridinyl, or pyridin-2(1H)-onyl.

In a fifth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
Ring B is phenyl, pyridinyl, pyrimidinyl, pyrrazolyl, indolyl, indazolyl, thiazolyl, imidizolyl, pyridinonyl, 1,2-dihydro-3H pyrazol-3-onyl, 1H-1,2,3-triazolyl, pyrazinyl or pyridazinyl, or oxazolyl.

In a sixth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
Ring B is phenyl, pyridinyl, pyrimidinyl, pyrrazolyl, indolyl, or indazolyl.

In a seventh aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
$R^1$ is:

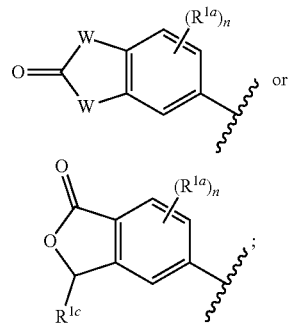

one W is $NR_{1b}$ and the other W is O;
each $R^{1a}$ is independently selected from F, Cl, $C_{1-3}$ alkyl, $C_{1-3}$ fluoroalkyl, and $C_{3-6}$ cycloalkyl;
$R^{1b}$ is H, $C_{1-3}$ alkyl, or $C_{1-3}$ fluoroalkyl;
$R^{1c}$ is H, $C_{1-2}$ alkyl, or $C_{3-6}$ cycloalkyl;
n is zero, 1, or 2:
$R^a$ is H, F, —OH, $C_{1-2}$ alkyl, —$CHF_2$, —$CF_3$, —$CH_2OH$, cyclopropyl, —$OCH_3$, —$OCHF_2$, or —$OCF_3$;
$R^b$ is H, $C_{1-2}$ alkyl, $C_{1-2}$ hydroxyalkyl, or cyclopropyl;
$R^c$ is H or —$CH_3$;

each R³ is independently H, C$_{1-3}$ alkyl, —C(O)R$^e$—C(O)OR$^e$, or —C(O)NR$^e$R$^e$; and each R$^e$ is independently H, —CH$_3$, —CF$_3$, or C$_{3-6}$ cycloalkyl.

In a eighth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

R¹ is

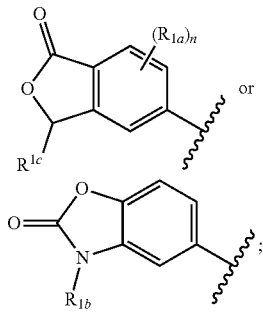

R$^{1b}$ is H or —CH$_3$;

L¹ is a bond, —CH$_2$—, —CH$_2$CH$_2$—, —CH(CH$_2$OH)—, or —CH(OH)CH$_2$—;

R³ is H.

In a ninth aspect of the invention, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

Ring B is phenyl, pyridinyl, pyrimidinyl, indolyl, pyrrazolyl, or indazolyl; and R² is phenyl, indolyl, pyridinyl, benzo[d]oxazol-2(3H)-onyl, pyridin-2(1H)-onyl, or indazolyl.

In another aspect, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein: L² is —CH$_2$—, or —CH$_2$—CH$_2$—; or L² is —CH$_2$—, or —CH(CH$_3$)—.

In another aspect, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein: L¹ is —CH(OH)—CH$_2$—.

In another aspect, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein: R³ is H or CH$_3$.

In another aspect, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein: R$^d$ is H.

In another aspect, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:

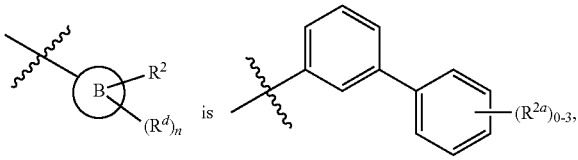

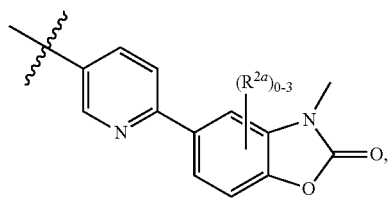

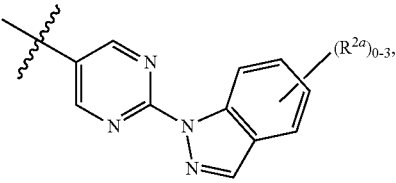

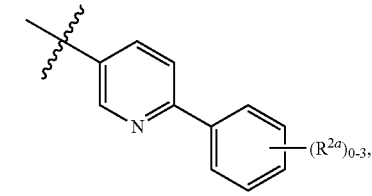

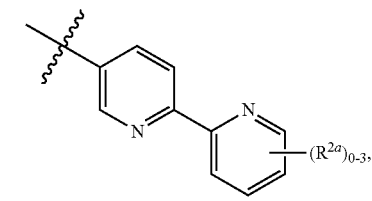

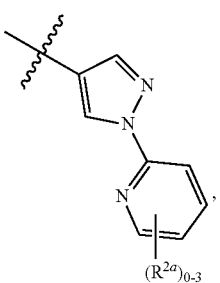

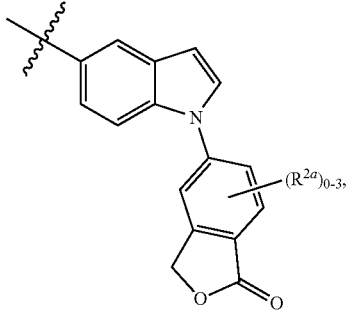

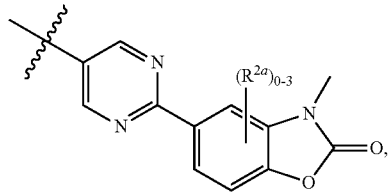

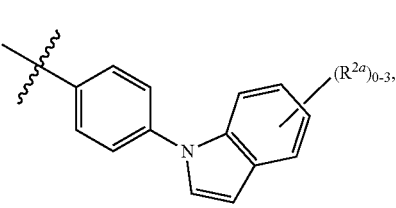

-continued

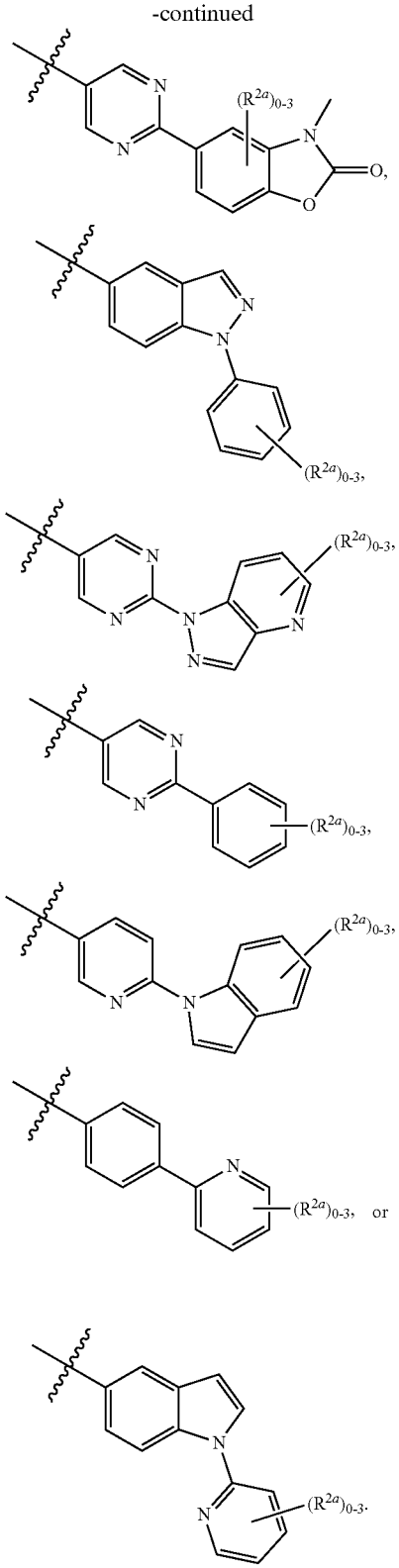

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is

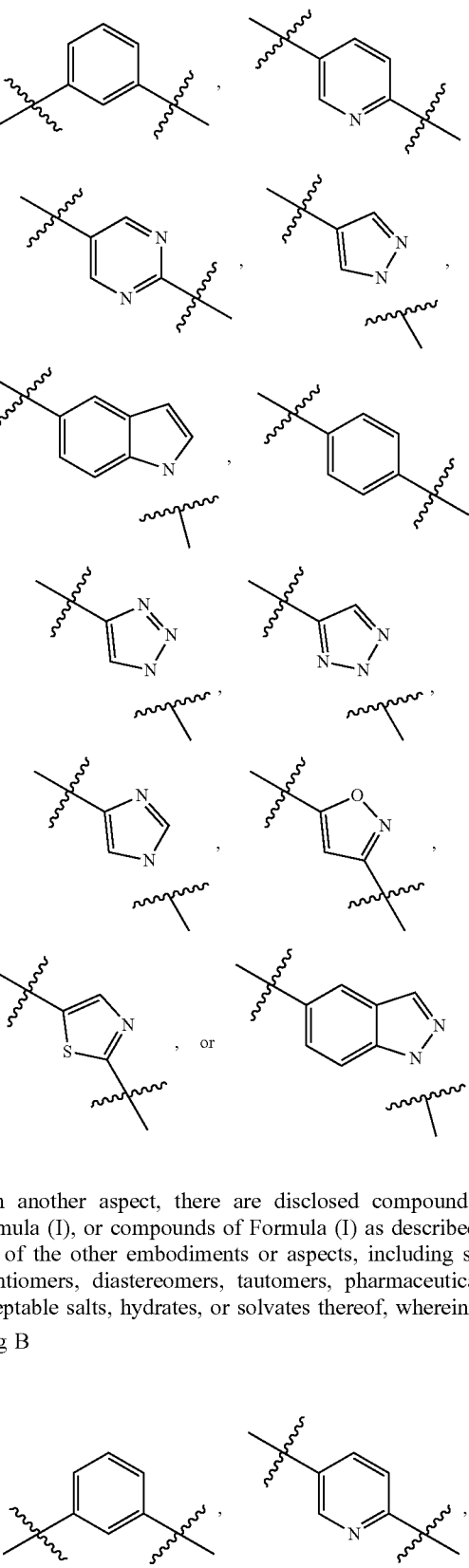

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B

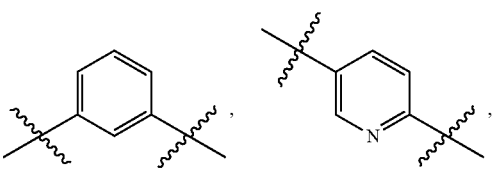

-continued

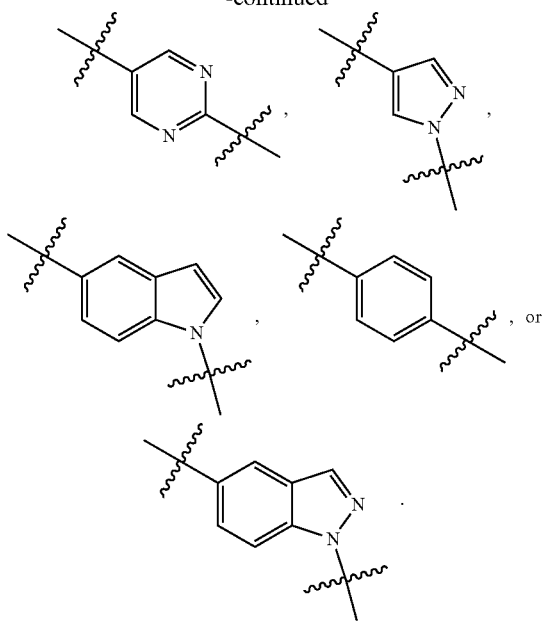

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
Ring B is pyridinyl, pyrimidinyl, thiazolyl, triazolyl, pyrazolyl, or imadazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
$R^2$ is pyridinyl, pyrazolyl, imidazolyl, indazolyl, phenyl, or indolyl.

In another aspect, there are disclosed compounds of Formula (I), or compounds of Formula (I) as described by any of the other embodiments or aspects, salts, enantiomers, diastereomers, tautomers, pharmaceutically-acceptable salts, hydrates, or solvates thereof, wherein:
$L^1$ is $L^1$ is —CH(OH)—CH$_2$—;
$L^2$ is or $L^2$ is —CH$_2$—, or —CH(CH$_3$)—;
$R^3$ is H or CH$_3$;
$R^2$ is pyridinyl, pyrazolyl, imidazolyl, indazolyl, phenyl, or indolyl; and
Ring B is pyridinyl, pyrimidinyl, thiazolyl, triazolyl, pyrazolyl, or imadazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
$R_1$ is

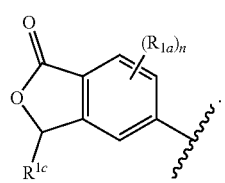

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
$R_1$ is

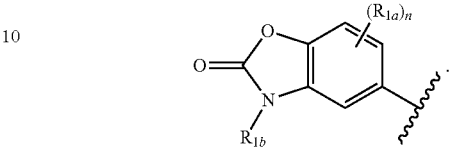

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
wherein $R_1$ is

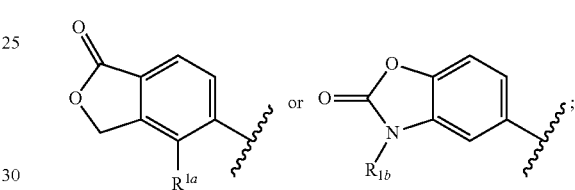

$R^{1a}$ is H or —CH$_3$; $R_{1b}$ is H or —CH$_3$; $L_1$ is a bond, —CH$_2$—, —CH$_2$CH$_2$—, —CH(CH$_2$OH)—, or —CH(OH)CH$_2$—.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{1a}$ is H, F, C$_{1-3}$ alkyl, or CF$_3$; or $R^{1a}$ is H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{1a}$ is CH$_3$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{1c}$ is H$_3$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: each $R^{1b}$ is independently H, or C$_{1-3}$ alkyl; or each $R^{1b}$ is H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^{2a}$ is CN, halo, or C$_{1-4}$alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: each $R^3$ is independently H, $C_{1-3}$ alkyl, —$(CH_2)$-pyridinyl, —$C(O)R^e$, —$C(O)OR^e$, or —$C(O)NR^eR^e$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^3$ is H, $CH_3$, —$(CH_2)$-heterocyclyl, wherein the heterocyclyl is pyridinyl, tetrahydropyranyl or tetrahydrofuranyl, or —$(CH_2)$-cycloprorol.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: each $R^e$ is independently H, $C_{1-3}$ alkyl, $C_{1-3}$ fluoroalkyl, $C_{3-6}$ cycloalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: the compounds are selected from the Examples.

In another aspect, there is disclosed a pharmaceutical composition, comprising a pharmaceutically acceptable carrier and any one or more compounds of Formula (I), or compounds of Formula (I) as described by any of the other embodiments or aspects or examples, or a pharmaceutically acceptable salt thereof.

In another aspect, there is disclosed a method for the treatment of one or more diseases or disorders which can be modulated by inhibition of ROMK, comprising administering to a patient in need of such treatment or prophylaxis a therapeutically effective amount of at least one of the compounds of Formula (I), or compounds of Formula (I) as described by any of the other embodiments or aspects or examples, wherein the disease or disorder is treated by promotion of diuresis or natriuresis.

In another aspect, there is disclosed a method for the treatment or prophylaxis of one or more diseases or disorders which can be modulated by ROMK inhibition, wherein the compound of any of the embodiments is administered in combination with at least one other type of therapeutic agent.

In another aspect, there is disclosed a method for the treatment or prophylaxis of multiple diseases or disorders, comprising administering to a patient in need of such treatment or prophylaxis a therapeutically effective amount of at least one of the compounds of Formula (I), or compounds of Formula (I) as described by any of the other embodiments or aspects, wherein the disease or disorder is treated by the promotion of diuresis or natriuresis, or for ROMK associated disorders.

In another aspect, there is disclosed a method for the treatment or prophylaxis of diseases or disorders, wherein the compound of any of the embodiments is administered in combination with at least one other type of therapeutic agent. In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the examples.

In another aspect, the present invention provides treatment of hypertension or heart failure for patients in need of diuresis or natriuresis.

In another aspect, the present invention provides for the treatment of hypertension.

In another aspect, the present invention provides for the treatment of hypertension, idiopathic hypertension, regractory hypertension, and/or pulmonary hypertension.

In another aspect, the present invention provides for the treatment of heart failure.

In another aspect, the present invention provides for the treatment of edema, cardiac insufficiency, systolic heart failure, diastolic heart failure, diabetic heart failure, and/or acute-decompensated heart failure.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art, ⁃⁃⁃ is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, —CF$_3$, —CCl$_3$, —CFCl$_2$, and —CH$_2$CF$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight-chain saturated alkyl groups substituted with one or more hydroxyl groups. For example, "hydroxyalkyl" includes —CH$_2$OOH, —CH$_2$CH$_2$OH, and $C_{1-4}$ hydroxyalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "aryl" as used herein, refers to a group of atoms derived from a molecule containing aromatic ring(s) by removing one hydrogen that is bonded to the aromatic ring(s), containing 4 to 10, or 6 to 10 carbon atoms. Aryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclyl" or "heterocycle" as used herein, refers to substituted and unsubstituted saturated, partially saturated, and aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring having 1, 2, 3, or 4 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain other heteroatoms or only carbon atoms; and may be saturated, partially saturated, or aromatic. The heterocyclo group may be attached at any available nitrogen or carbon atom in the heterocyclo group. The term "heterocyclyl" includes "heteroaryl" groups. As valence allows, if said further ring is cycloalkyl or heterocyclo it is additionally optionally substituted with =O (oxo).

The term "heteroaryl" refers to substituted and unsubstituted aromatic 5- or 6-membered monocyclic groups, 9- or 10-membered bicyclic groups, and 11- to 14-membered tricyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain other heteroatoms or only carbon atoms. The nitrogen and sulfur atoms may optionally be oxidized and the nitrogen atoms may optionally be quaternized. Bicyclic and tricyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Compounds of the formula I and/or the Examples herein may in some cases form salts which are also within the scope of this invention. Reference to a compound of the formula I and/or Examples herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

"Base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. In one aspect, inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. In another aspect, organic bases are isopropylamine, diethylamine, ethanolamine, trimethylamine, dicyclohexylamine, choline and caffeine.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds. Combinations of substituents and/or variables are permissible only if such combinations result in stable compounds.

"Therapeutically effective amount" is intended to include an amount of a compound of the present invention alone or an amount of the combination of compounds claimed or an amount of a compound of the present invention in combination with other active ingredients effective to act as an inhibitor to ROMK, or effective to treat or prevent cardiovascular disease.

In another aspect, there is disclosed a method for the treatment or prophylaxis of one or more disease or disorder which can be modulated by ROMK inhibition, comprising administering to a patient in need of such treatment or prophylaxis a therapeutically effective amount of at least one of the compounds of Formula (I), or compounds of Formula (I) as described by any of the other embodiments or aspects, wherein the disease or disorder is treated by the promotion of diuresis or natriuresis.

In another aspect, there is disclosed a method for the treatment of one or more disease or disorder which can be treated by promotion of diuresis or natriuresis, wherein the cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, refractory hypertension cardiac insufficiency, nephrotic syndrome and acute kidney insufficiency.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it: (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia, and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplar) water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate: condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture, and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, and flavors) according to techniques such as those well known in the art of pharmaceutical formulation.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Utility

The compounds of the invention inhibit the activity of ROMK. Accordingly, compounds of Formula (I) have utility in treating conditions associated with the inhibition of ROMK.

The compounds described herein are intended for the treatment and/or prophylaxis of any disorders that benefit from increased excretion of water and sodium from the body, or for any patient in need of diuresis or natriuresis. Specific disorders would include any form of hypertension or heart failure (acute-decompensated and chronic, diastolic and systolic). For heart failure treatment, the compounds would be used to treat acute-decompensated heart failure to reduce edema and other symptoms and/or to overcome resistance to other classes of diuretics, or to shorten hospital stay. The compounds could also be used in heart failure after discharge from hospital or during chronic therapy to treat symptoms and reduce recurrences of acute-decompensations and hospital admissions. Other disorders for which a diuretic or natriuretic or both would have therapeutic or prophylactic benefit include post-operative volume overload, any edematous states including idiopathic edema, pulmonary hypertension including pulmonary arterial hypertension, cardiac insufficiency, nephrotic syndrome and acute kidney insufficiency.

The compounds in accordance with the present invention are beneficial in the treatment and/or prevention of various human ailments. The compounds in accordance with the present invention can be beneficial either as a stand alone therapy or in combination with other therapies that therapeutically could provide greater benefit. The ailments for which the compounds in the present invention could be of benefit include cardiovascular disease; and prophylaxis and/or treatment of diuresis or natriuresis.

One embodiment provides a method for treating cardiovascular disease. Particular, cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome and acute kidney insufficiency. For example, a therapeutically effective amount for treating a disorder may be administered in the method of the present embodiment.

One embodiment provides a method for the promotion of diuresis or natriuresis.

One or more additional pharmacologically active agents may be administered in combination with the compounds described herein including any other diuretic from any other diuretic class (thiazides, loops, potassium-sparing, osmotic, carbonic anhydrase inhibitors, mineralocorticoid receptor antagonists), acetylcholinesterase inhibitors, angiotensin receptor blockers, neutral endopeptidase inhibitors, dual angiotensin receptor antagonists and neutral endopeptidase inhibitors, aldosterone antagonists, natriuretic peptides, calcium channel blockers, relaxin or relaxin mimetics, inotropic agents, peripheral vasodilators, or mineralocorticoid receptor antagonists. One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment of cardiovascular disease. In the present embodiment, the use for the manufacture of a medicament may include the administration of a therapeutically-effective amount of a compound of Formula (I) for the treatment of cardiovascular disease.

The present invention also provides the use of the compounds of Formula (I) for the manufacture of a medicament for prophylaxis and/or treatment of diuresis or natriuresis.

In one embodiment, the compounds of Formula (I) inhibit ROMK activity with $IC_{50}$ values of less than 10 µM, for example, from 0.001 to less than 10 µM, as measured by the Thallium Flux assay. Preferably, the compounds of Formula (I) inhibit ROMK activity with $IC_{50}$ values of less than 1 µM, for example, from 0.001 to less than 1 µM. Other compounds inhibit ROMK activity with $IC_{50}$ values of 100 nM and less, for example, from 1 to 100 nM.

Examples of compounds of Formula (I) as specified in the "Examples" section below, have been tested in one or more of the assays described below.

Methods of Preparation

The compounds of the present invention may be synthesized by many methods available to those skilled in the art of organic chemistry. A compendium of synthetic methods which may be applicable to the preparation of compounds of the present invention may be found in Larock, R. C., *Comprehensive Organic Transformations*, VCH, New York (1989). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. In the description of the synthetic methods described below, it is to be understood that all proposed reaction conditions, including choice of solvent, reaction atmosphere, reaction temperature, duration of the experiment and workup procedures, are typically chosen to be the conditions standard for that reaction, which should be readily recognized by one skilled in the art. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds. An authoritative account describing the many alternatives is Greene et al. (*Protective Groups in Organic Synthesis*, Wiley and Sons (1991)). Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

The following are the definitions of symbols used.

Ar Aryl
ACN Acetonitrile
$BF_3 \cdot OEt_2$ Boron trifluoride etherate
$CH_2Cl_2$ Dichloromethane
$CHCl_3$ Chloroform
$CDCl_3$ Deuterated chloroform
$CD_3OD$ Deuterated methanol
DCM Dichloromethane
DMAP 4-Dimethylaminopyridine
DMF N,N-dimethyl formamide
DMSO Dimethyl sulfoxide
DMSO-$d_6$ Deuterated dimethyl sulfoxide
Et Ethyl
EtOAc Ethyl acetate
EtOH Ethanol
HATU (O-(7-azabenzotriazol-1-yl)-N,N, N',N'-tetramethyl uronium hexafluorophosphate)
HCl Hydrochloric acid
HCOOH Formic acid
$HCOONH_4$ Ammonium formate
KI Potassium iodide
$K_2CO_3$ Potassium carbonate
KOAc Potassium acetate
$K_3PO_4$ Potassium phosphate
LiOH Lithium hydroxide
Me Methyl
MeOH Methanol
NaH Sodium hydride
$NaHCO_3$ Sodium bicarbonate
$NaNO_2$ Sodium nitrite
$Na_2SO_4$ Sodium sulfate
$Na_2S_2O_3$ Sodium thiosulfate
$NH_3$ Ammonia
$NH_4OAc$ Ammonium acetate
Pd/C Palladium on carbon
$Pd_2(dba)_3$ Tris(dibenzylideneacetone)dipalladium (0)
$Pd(dppf)_2Cl_2$:$CH_2Cl_2$ [1,1'Bis(diphenylphosphino)ferrocene]dichloropalladium(II), complex with dichloromethane
$POCl_3$ Phosphorus oxychloride
THF Tetrahydrofuran
TFA Trifluoroacetic acid
XANTPHOS 4,5-Bis(diphenylphosphino)-9,9-dimethylxanthene
IPA
DEA Isopropyl alcohol Diethylamine
Synthesis:

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Wiley and Sons (1991)).

Scheme 1:

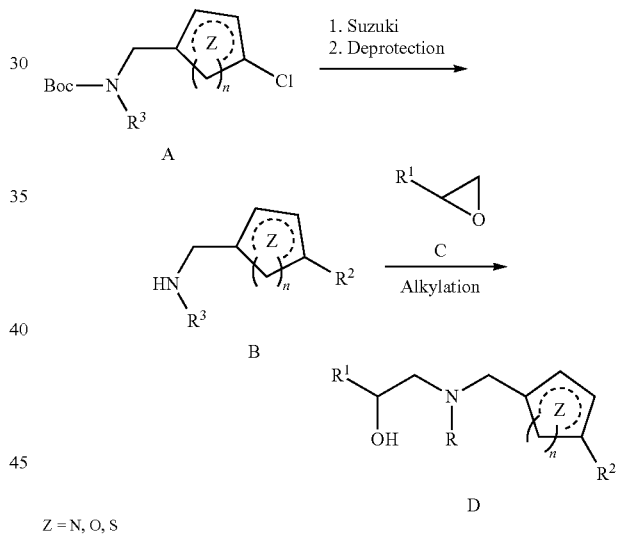

Z = N, O, S

Compounds of general formula D may be synthesized according to Scheme 1.

Appropriately substituted aryl halide (A) was converted to (B) by using Suzuki coupling reaction followed by Boc-deprotection using HCl. Compound B was treated with epoxides or halomethylcarbonyl compounds to generate compounds of the general formula D.

Scheme 2:

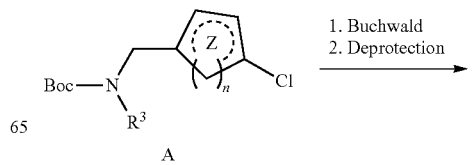

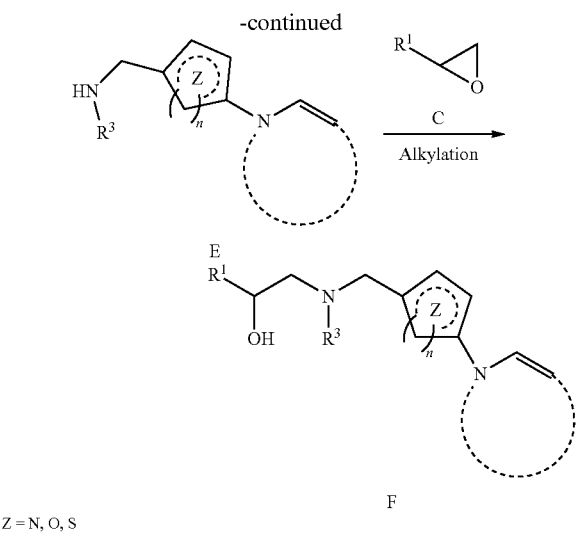

Z = N, O, S

Compounds of general formula F may be synthesized according to Scheme 2.

Appropriately substituted aryl halide (A) was converted to (E) by using Buchwald coupling/copper coupling reactions followed by Boc-deprotection using HCl. Compound F was treated with epoxides or halomethylcarbonyl compounds to generate compounds of the general formula F.

General Methods:

The following methods were used in the working Examples, except where noted otherwise.

Analytical HPLC and HPLC/MS methods employed in characterization of examples:

Reverse phase analytical HPLC/MS was performed on Shimadzu LC10AS systems coupled with Waters ZMD Mass Spectrometers or Waters Aquity system coupled with a Waters Micromass ZQ Mass Spectrometer. Chiral analytical LC was performed on a Berger Analytical SFC instrument.

Method A: Ascentis Express C18 (2.1×50 mm) 2.7 micron; Solvent A: 95% water, 5% acetonitrile, 0.1% TFA; Solvent B: 95% acetonitrile. 5% water, 0.1% TFA; Temperature: 50° C.; Gradient: 0-100% B over 3 minutes, then 1 minute hold at 100% B; Flow: 1.1 mL/min, UV 220 nm.

Method B: Ascentis Express C18 (2.1×50 mm) 2.7 micron; Solvent A: 95%0/water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then 1 minute hold at 100% B; Flow: 1.1 mL/min, UV 220 nm.

Method C: SunFire C18 (4.6×150 mm) 5.0 micron; Solvent A: 95% water, 5% acetonitrile, 0.05% TFA; Solvent B: 5% water, 95% acetonitrile, 0.05% TFA; Gradient: 50-100% B over 15 minutes, then 5 minute hold at 100% B; Flow: 1.1 mL/min, UV 220 nm.

Method D: Kinetex, XB C18 (2.6 μm×75.3 mm); Solvent A: 10 mM NH$_4$CO$_2$H in 98% water, 2% acetonitrile; Solvent B: 10 mM NH—CO$_2$H in 2% water, 98% acetonitrile, Gradient: 20-100% B over 4 minutes, then 0.6 minute hold at 100% B; Flow: 1.1 mL/min, UV 220 nm.

Method E: Sunfire C18 (4.6×150 mm) 3.5 micron; Solvent A: 95% water, 5% acetonitrile, 0.05% TFA; Solvent B: 5% water, 95% acetonitrile. 0.05% TFA; Gradient: 10-100% B over 25 minutes, then 5 minutes hold at 100% B; Flow: 1.1 mL/min, UV 254 nm.

Method F: Sunfire C18 (4.6×150 mm) 3.5 micron; Solvent A: 95% water, 5% acetonitrile, 0.05% TFA; Solvent B: 5% water, 95% acetonitrile, 0.05% TFA; Gradient: 10-100% Solvent B over 18 minutes, then 5 minutes hold at 100% B; Flow: 1.1 mL/min, UV 220 nm.

Method G: XBridge Phenyl (4.6×150 mm) 3.5 micron; Solvent A: 95% water, 5% acetonitrile, 0.05% TFA; Solvent B: 5% water, 95% acetonitrile, 0.05% TFA; Gradient: 10-100% Solvent B over 18 minutes, then 5 minutes hold at 100% B; Flow: 1.1 mL/min, UV 220 nm.

Method H: ZORBAX SB C18 (4.6×50 mm) 5.0 micron; Solvent A: 10 mM NH$_4$CO$_2$H in 98% water, 2% acetonitrile; Solvent B: 10 mM NH$_4$CO$_2$H in 2% water, 98% acetonitrile, Gradient: 30-100% B over 4 minutes, then 0.6 minute hold at 100% B; Flow: 1.0 mL/min, UV 220 nm.

Method I: Acquity BEH C8 (2.1×50 mm) 1.7 micron; Solvent A: 10 mM ammonium acetate in 95% water, 5% acetonitrile; Solvent B: 10 mM ammonium acetate in 5% water, 95% acetonitrile, Gradient: 20-90% B over 1.1 minutes, then 0.7 minute hold at 90% B; Flow: 0.5 mL/min, UV 220 nm.

Method J: Kinetex XB-C18 (3×75 mm) 2.6 micron; Solvent A: 0.1% HCOOH in water; Solvent B: Acetonitrile, Gradient: 20-90% B over 1.1 minutes, then 0.7 minute hold at 90% B; Flow: 0.5 mL/min, UV 220 nm.

Method K: Kinetex C18 (2.1×50 mm) 2.6 micron; Solvent A: 5 mM ammonium acetate in 95% water, 5% acetonitrile; Solvent B: 5 mM ammonium acetate in 5% water, 95% acetonitrile, Gradient: 20-90% B over 1.1 minutes, then 0.6 minute hold at 90% B; Flow: 0.7 mL/min, UV 220 nm.

Method L: Acquity BEH C18 (3×50 mm) 1.7 micron; Solvent A: 0.1% TFA in water, Solvent B: 0.1% TFA in ACN, Gradient: 20-90% B over 1.0 minutes, then 0.6 minute hold at 90% B; Flow: 0.7 mL/min, UV 220 nm.

Method M: Xbridge Phenyl (21.2×250 ID) 5 micron; Solvent A: 0.1% TFA in water, Solvent B: Acetonitrile, Gradient: 5-25% B over 1.0 minutes, then 0.6 minute hold at 90% B Flow: 0.7 mL/min, UV 220 nm.

Method N: ZORBAX SB C18 (4.6×50 mm) 5.0 micron; Solvent A: 0.1% TFA in 95% water, 5% acetonitrile; Solvent B: 0.1% TFA in 5% water, 95% acetonitrile, Gradient: 0-100% B over 3 minutes; Flow: 1.1 mL/min, UV 220 nm.

Method O: Acquity UPLC BEH C18 (3×50 mm) 1.7 micron; Solvent A: 5 mM ammonium acetate in 95% water, 5% acetonitrile; Solvent B: 5 mM ammonium acetate in 5% water, 95% acetonitrile, Gradient: 20-90% B over 1.1 minutes, then 0.6 minute hold at 90% B; Flow: 0.7 mL/min, UV 220 nm.

Method P: Kinetex EVO C18 (4.6×100 mm) 2.6 micron; Solvent A: 95% water, 5% acetonitrile, 0.05% TFA; Solvent B: 5% water, 95% acetonitrile, 0.05% TFA; Gradient: 20-100% B over 11 minutes, then 1.5 minute hold at 100% B; Flow: 1.0 mL/min, UV 300 nm.

Method Q: Kinetex Biphenyl (4.6×11 mm) 2.6 micron; Solvent A: 0.05% TFA in water; Solvent B: Acetonitrile, Gradient: 20-100% B over 11 minutes, then 1.5 minute hold at 100% B; Flow: 1.0 mL/min, UV 300 nm.

Method R: XBidge BEH XP C18 (2.1×50 mm) 2.5 micron; Solvent A: 0.1% TFA in 95% water, 5% acetonitrile; Solvent B: 0.1% TFA in 5% water, 95% acetonitrile, Gradient: 0-100% B over 3 minutes; Flow: 1.1 mL/min. UV 220 nm.

Method S: XBidge BEH XP C18 (2.1×50 mm) 2.5 micron; Solvent A: 10 mM ammonium acetate in 95% water, 5% acetonitrile; Solvent B: 10 mM ammonium acetate in 5% water, 95% acetonitrile, Gradient: 0-100% B over 3 minutes; Flow: 1.1 mL/min, UV 220 nm.

Method T: DAD-1 Kinetix biphenyl (4.6×100 mm) 2.6 micron; Solvent A: 95% water, 5% acetonitrile, 0.05% TFA; Solvent B: 5% water, 95% acetonitrile, 0.05% TFA; Gradient: 0-100% B over 12.5 minutes, then 1.5 minutes hold at 100% B; Flow: 1.0 mL/min. UV 300 nm.

Method U: DAD-1 Kinetex EVO C18 (4.6×100 mm) 2.6 micron; Solvent A: 95% water, 5% acetonitrile, 0.05% TFA; Solvent B: 5% water, 95% acetonitrile, 0.05% TFA; Gradient: 0-100% B over 12.5 minutes, then 1.5 minutes hold at 100% B; Flow: 1.0 mL/min, UV 300 nm.

SFC and Chiral Purity Methods:

Method I: Lux Amylose 2 (250×4.6 mm) 5 micron: 0.2% DEA in n-hexane: EtOH: 5:95, Flow: 2.0 mL/min, Temperature: 25° C., UV: 270 nm.

Method II: Chiralpak AS-H (250×4.6 mm) 5 micron: 0.2% DEA in n-hexane: EtOH: 5:95, Flow: 2.0 mL/min, Temperature: 25° C., UV: 270 nm.

Method III: Chiralpak IE (250×4.6 mm) 5.0 micron; 0.2% DEA in EtOH, Flow: 1.0 mL/min, Temperature: 25° C., UV: 220 nm.

Method IV: Chiralcel IE (250×4.6 mm) 5 micron: 0.2% DEA in n-hexane: EtOH: 50:50, Flow: 1.0 mL/min, Temperature: 25° C. UV: 260 nm.

Method V: Chiralpak IB (250×4.6 mm) 5 micron; 0.1% DEA in EtOH, Flow: 1.0 mL/min, Temperature: 25° C., UV: 270 nm.

Method VI: Chiralpak ID (250×4.6 mm) 5 micron; 0.1% DEA in EtOH, Flow: 1.0 mL/min. Temperature: 25° C., UV: 254 nm.

Method VII: Chiralpak IF (250×4.6 mm) 5 micron; 0.2% DEA in EtOH, Flow: 1.0 mL/min, Temperature: 25° C., UV: 254 nm.

Method VIII: Chiralpak IA (250×4.6 mm) 5 micron: 0.2% DEA in MeOH. Flow: 4.0 mL/min, Temperature: 25° C., UV: 280 nm.

Method IX: Chiralpak ID (250×4.6 mm) 5 micron: 0.2% TEA in n-hexane: EtOH (10:90) Flow: 1.0 mL/min, Temperature: 25° C., UV: 254 nm.

Method X: Chiralcel OJ-H (250×4.6 mm) 5 micron; 0.2% DEA in MeOH, Flow: 4.0 mL/min, Temperature: 30° C., UV: 296 nm.

Method XI: Chiralpak IC (250×4.6 mm) 5 micron; 0.1% DEA in MeOH, Flow: 1.0 mL/min, Temperature: 25° C. UV: 254 nm.

Method XII: Chiralpak ADH (250×4.6 mm) 5 micron; 0.2% DEA in MeOH+IPA (1:1), Flow:1.2 mL/min, Temperature: 25° C., UV: 233 nm.

Method XIII: Chiralpak AS-H (250×4.6 mm) 5 micron; 0.2% DEA in MeOH, Flow: 1.2 mL/min. Temperature: 23.3° C., UV: 271 nm.

Method XIV: Chiralpak IB (250×4.6 mm) 5 micron; 0.2% DEA in MeOH. Flow: 1.0 mL/min, Temperature: 25° C., UV: 254 nm.

Method XV: Chiralpak ID (250×4.6 mm) 5 micron; 0.2% DEA in MeOH. Flow: 1.0 mL/min, Temperature: 25° C., UV: 254 nm.

Method XVI: Lux Amylose 2 (250×4.6 mm) 5 micron: 0.1% DEA in MeOH, Flow: 1.0 mL/min, Temperature: 25° C., UV: 254 nm.

Method XVII: Chiralpak IF (250×4.6 mm) 5 micron; 0.2% DEA in MeOH. Flow: 1.0 mL/min, Temperature: 25° C., UV: 254 nm.

Method XVIII: Chiralpak IE (250×4.6 mm) 5.0 micron; 0.2% DEA in MOH, Flow: 1.0 mL/min, Temperature: 25° C., UV: 220 nm.

Method XIX: Lux Cellulose 4 (250×4.6 mm) 5.0 micron; 0.1% DEA in EtOH, Flow: 1.0 mL/min, Temperature: 25° C., UV: 220 nm.

Method XX: Chiralcel OD-H (250×4.6 mm) 5 micron; 0.2% DEA in MeOH, Flow: 1.0 mL/min. Temperature: 25° C., UV: 220 nm.

Method XXI: Chiralcel OD-H (250×4.6 mm) 5 micron; 0.2% NH$_4$OH in MeOH and ACN (1:1), Flow: 4.0 mL/min, Temperature: 30° C., UV: 290 nm.

Method XXII: Lux Cellulose C2 (250×4.6 mm) 5.0 micron; 0.2% DEA in MeOH, Flow: 1.0 mL/min, Temperature: 25° C., UV: 220 nm.

Method XXIII: Phenomenex IC (250×4.6 mm) 5 micron; 0.2% DEA in EtOH, Flow: 1.0 mL/min, Temperature: 25° C., UV: 254 nm.

NMR Employed in Characterization of Examples:

$^1$H NMR spectra were obtained with Bruker or JEOL fourier transform spectrometers operating at frequencies as follows: $^1$H NMR: 400 MHz or 300 MHz (Bruker). $^{13}$C NMR: 100 MHz or 75 MHz (Bruker). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for CD$_2$HSOCD$_3$, 3.30 ppm for CD$_2$HOD, and 7.24 ppm for CHCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

Intermediate 1-I and 1-II: 4-Methyl-(oxiran-2-yl)isobenzofuran-1(3H)-one

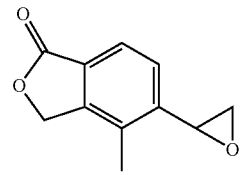

Enantiomer-I (1-I)

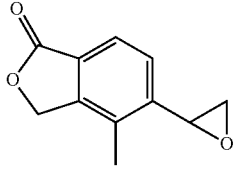

Enantiomer-II (1-II)

Both enantiomers were synthesized according to literature procedures (WO 2010/129379).

Intermediate 2: tert-butyl ((6-chloropyridin-3-yl)methyl)(methyl)carbamate

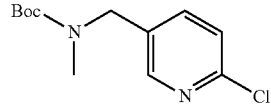 [SMILES: CN(Cc1ccc(Cl)nc1)C(=O)OC(C)(C)C]

Intermediate 2A: tert-butyl ((6-chloropyridin-3-yl)methyl)carbamate

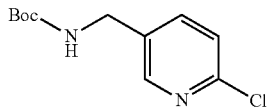 [SMILES: CC(C)(C)OC(=O)NCc1ccc(Cl)nc1]

To a solution of (6-chloropyridin-3-yl)methanamine (3.30 g, 23.1 mmol) in DCM (30 mL) was added TEA (4.84 mL, 34.7 mmol) and BOC₂O (6.72 mL, 28.9 mmol), at 0° C. The resulting mixture was stirred at ambient temperature for 1 h. The reaction was quenched with saturated sodium bicarbonate solution (50 mL) and extracted with DCM (3×100 mL). The combined organic layers were washed with brine (100 mL), dried over anhydrous sodium sulfate and concentrated under reduced pressure to obtain Intermediate 2A (5.50 g, 98.0%) as a yellow oil. $^1$H NMR (300 MHz, DMSO-$d_6$) δ ppm 1.38 (s, 9H), 4.14 (d, J=6.04 Hz, 2H), 7.48 (d, J=7.93 Hz, 2H), 7.71 (dd, J=8.12, 2.46 Hz, 1H), 8.28 (d, J=1.89 Hz, 1H). LCMS (Method D): retention time 2.31 min, [M+H] 243.1.

Intermediate 2

To a solution of Intermediate 2A (2.00 g. 8.24 mmol) in DMF (15 mL) at 0° C. was added NaH (0.494 g, 20.6 mmol). The resulting mixture was stirred for 15 minutes and was allowed to warm to ambient temperature. To the resulting solution was added methyl iodide (0.773 mL, 12.3 mmol) and the reaction mixture was stirred for 30 minutes. The reaction was quenched with saturated ammonium chloride solution, diluted with water (50 mL) and extracted with ethyl acetate (2×30 mL). The combined organic layers were washed with brine (20 mL), dried over sodium sulfate, filtered and concentrated under reduced pressure to obtain Intermediate 2 (2.10 g, 97%) as yellow oil. $^1$H NMR (300 MHz, DMSO-$d_6$) δ ppm 1.39 (d, J=2.64 Hz, 9H), 2.79 (s, 3H), 4.39 (s, 2H), 7.51 (d, J=6.8 Hz, 1H), 7.71 (dd, J=8.12, 2.46 Hz, 1H), 8.29 (d, J=2.27 Hz, 1H). LCMS (Method-D): retention time 2.32 min, [M+H] 257.2.

Intermediate 3: 5-bromo-3-methylbenzo[d]oxazol-2(3H)-one

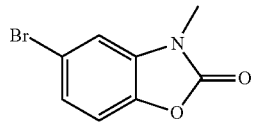

Synthesized according to literature procedures (PCT Int. Appl., 2010130773).

Intermediate 4: 3-methyl-5-(4,4,5,5-tetramethyl-1,3,2-dioxaborolan-2-yl)benzo[d]oxazol-2(3H)-one

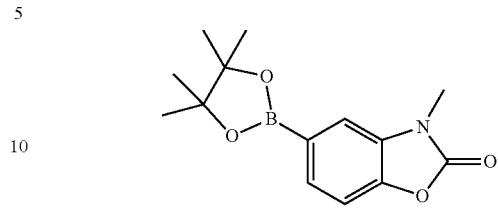

A solution of Intermediate 3 (1.50 g, 6.44 mmol), bispinacolatodiboron (2.45 g, 9.66 mmol) and potassium acetate (1.89 g, 19.3 mmol) in dioxane (20 mL) was degassed with nitrogen for 20 minutes. Then PdCl₂(dppf)₂CH₂Cl₂ (0.520 g, 0.644 mmol) was added and the resulting mixture was degassed again for 10 minutes. The resulting reaction mixture was heated at 100° C. for 5 h then was cooled to ambient temperature, filtered through celite and the filtrate was concentrated under reduced pressure. The residue was purified by column chromatography (Redisep-24 g, 20% EtOAc/n-hexanes), to obtain Intermediate 4 (1.30 g, 59.8%) as a yellow solid. $^1$H NMR (300 MHz, DMSO-$d_6$) δ ppm 1.31 (s, 12H), 3.37 (s, 3H), 7.34 (d, J=7.93 Hz; 1H), 7.41-7.54 (m, 2H). LCMS (Method-D): retention time 2.79 min, [M−H] 292.2 (water adduct).

Intermediate 5: 3'-(2-aminoethyl)-3-fluoro-[1,1'-biphenyl]-4-carbonitrile Intermediate

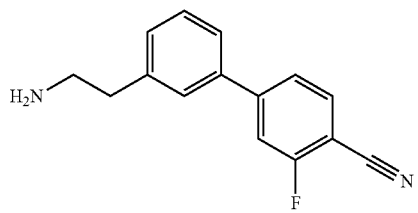 [SMILES: N#Cc1ccc(-c2cccc(CCN)c2)cc1F]

Intermediate 5A: Tert-Butyl (2-(4'-cyano-3'-fluoro-[1,1'-biphenyl]-3-yl)ethyl)carbamate

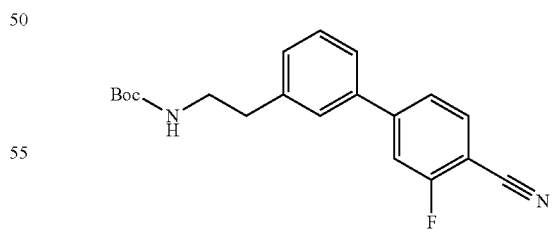

A solution of tert-butyl 3-bromophenethylcarbamate (0.500 g, 1.67 mmol) and (4-cyano-3-fluorophenyl)boronic acid (0.275 g, 1.67 mmol), potassiumphosphate tribasic (0.354 g, 1.67 mmol) in 1,4-dioxane (15 mL) and H₂O (3 mL) was degassed with nitrogen for 10 minutes. Then PdCl₂(dppf)₂CH₂Cl₂ (0.136 g, 0.167 mmol) was added and the resulting mixture was degassed again for 10 minutes. The reaction mixture was heated at 100° C. for 12 h then was cooled to ambient temperature. The reaction mixture was filtered through the celite and the filtrate was concentrated under reduced pressure. The residue was purified by column chromatography (Redisep-24 g. 45% EtOAc/n-hexane) to obtain Intermediate 5A (0.400 g, 70.6%) as a yellow solid. $^1$H NMR (400 MHz. DMSO-$d_6$) δ ppm 1.35 (s, 9H). 2.79 (t, J=7.28 Hz, 2H), 3.20-3.25 (m, 2H), 6.92 (br. s., 1H), 7.31 (d, J=7.53 Hz, 1H), 7.44 (t, J=8.03 Hz, 1H), 7.62-7.66 (m. 2H), 7.76 (dd, J=8.03, 1.51 Hz, 1H), 7.89 (dd, J=11.29, 1.25 Hz, 1H), 8.01 (dd, J=8.03, 7.03 Hz, 1H). LCMS (Method-D): retention time 3.19 min. [M+H] 341.4.

Intermediate 5

To a stirred solution of Intermediate 5A (0.250 g, 0.734 mmol) in DCM (10 mL) at 0° C. was added TFA (0.566 mL, 7.34 mmol). The resulting mixture was stirred at ambient temperature for 3 h. The reaction mixture was concentrated to dryness under reduced pressure and was diluted with water (10 mL). The aqueous layer was washed with ethyl acetate (2×20 mL), basified with saturated NaHCO$_3$ and extracted with DCM (3×20 mL). The combined organic layers were washed with brine (10 mL), dried over anhydrous sodium sulfate, filtered and concentrated under reduced pressure to obtain Intermediate 5 (0.150 g, 85.0%). $^1$H NMR (300 MHz, DMSO-$d_6$) δ ppm 2.74 (d, J=6.42 Hz, 2H), 2.80 (d, J=6.04 Hz, 2H), 7.29-7.34 (m, 1H), 7.43 (t, J=7.93 Hz, 1H), 7.58-7.64 (m, 1H), 7.74 (dd, J=8.12, 1.70 Hz, 1H), 7.85 (d, J=1.51 Hz, 1H), 7.89 (d, J=1.51 Hz, 1H), 7.95-8.01 (m, 1H), (Exchangeable proton not observed). LCMS (Method-D): retention time 1.99 min, [M+H] 241.1.

Intermediate 6: 5-(2-bromoacetyl)-3-methylbenzo[d]oxazol-2(3H)-one

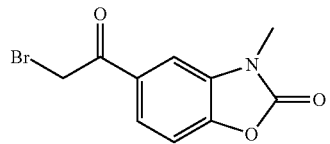

Intermediate 6A: 5-(1-ethoxyvinyl)-3-methylbenzo[d]oxazol-2(3H)-one

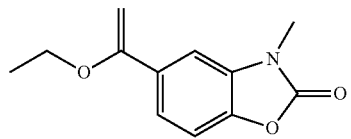 [SMILES: C=C(OCC)c1ccc2oc(=O)n(C)c2c1]

A solution of Intermediate 3 (4.00 g, 17.4 mmol), tributyl (1-ethoxyvinyl)tin (7.05 mL, 20.8 mmol) and LiCl (1.47 g, 34.8 mmol) in toluene (30 mL) was degassed with nitrogen for 15 minutes then tetrakis(triphenylphosphine)palladium (0.603 g, 0.522 mmol) was added. The resulting reaction mixture was degassed with nitrogen for another 5 minutes and was heated to 100° C. for 16 h. The reaction mixture was then cooled, diluted with water (40 mL) and extracted with ethyl acetate (3×100 mL). The combined organic layers were washed with brine (50 mL), dried over anhydrous sodium sulfate, filtered and concentrated under reduced pressure to obtain Intermediate 6A (5.50 g, 70.0%). LCMS (Method E): Retention time 2.50 min, [M+H] 221. The compound was taken directly to the subsequent step without further purification or characterization.

Intermediate 6

To a solution of Intermediate 6A (5.50 g, 12.5 mmol) in dioxane (50 mL) and H$_2$O (15 mL) at 0° C. was added NBS (2.68 g, 15.0 mmol) portion wise. The resulting reaction mixture was stirred for 1 h at ambient temperature, then diluted with water (50 mL) and extracted with ethyl acetate (3×100 mL). The combined organic layers were washed with brine (50 mL), dried over anhydrous sodium sulfate, and evaporated under reduced pressure. The residue obtained, was purified by column chromatography (Redisep-40 g, 50% EtOAc/n-Hexanes), to afford Intermediate 6 (5.00 g, 73.8%) as a brown solid. $^1$H NMR (400 MHz, CDCl$_3$) δ 3.45 (s, 3H), 4.44 (s, 2H), 7.28 (d, J=8.0 Hz, 1H), 7.67 (d, J=1.6 Hz, 1H), 7.82 (dd, J=8.0 Hz, J=1.6 Hz, 1H). LCMS (Method I): retention time 0.99 min, [M−H] 268.

Intermediate 7-I: 5-(2-amino-1-hydroxyethyl)-4-methylisobenzofuran-1(3H)-one

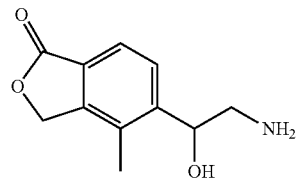

To a solution of Intermediate 1-I (1.00 g, 5.26 mmol) in MeOH (20 mL) was added ammonia in methanol (20 mL, 80 mmol) and the resulting reaction mixture was stirred at 50° C. for 16 h. The reaction mixture was concentrated under reduced pressure and residue was washed with ether (30 mL) to obtain Intermediate 7-1(0.750 g, 68.8%). $^1$H NMR (400 MHz, DMSO-$d_6$) δ ppm 2.26 (s, 3H), 2.52-2.56 (m. 1H), 2.69 (dd, J=13.05, 4.02 Hz, 1H), 4.80 (dd, J=8.03, 3.51 Hz, 1H), 5.38 (d, J=1.51 Hz, 3H), 7.65 (s, 2H), (Exchangeable proton not observed). LCMS (Method-H): retention time 0.54 min, [M+H] 208.2.

Intermediate 9: 6-(4-formyl-1H-pyrazol-1-yl)nicotinonitrile

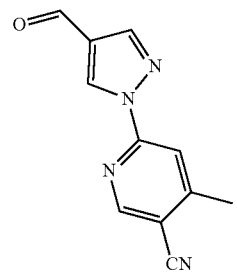 [SMILES: Cc1cc(-n2cc(C=O)cn2)ncc1C#N]

To a stirred solution of 1H-pyrazole-4-carbaldehyde (1.00 g, 10.4 mmol) and 6-bromo-4-methylnicotinonitrile (2.05 g, 10.4 mmol) in dioxane (15 mL) were added K$_2$CO$_3$ (4.31 g, 31.2 mmol) The resulting reaction mixture was degassed with nitrogen for 5 minutes and was added copper(I) iodide (0.595 g, 3.12 mmol), followed by trans-N,N'-dimethylcyclohexane-1,2-diamine (2.59 mL, 16.4 mmol). The resulting reaction mixture was degassed with nitrogen for an additional 5 minutes and heated at 110° C. for 1 h under microwave irradiation. The reaction mixture was cooled to ambient temperature, filtered through celite and the organic layer was concentrated under reduced pressure. The residue was purified by column chromatography (Redisep-24 g, 20-40% EtOAc/n-hexane) to obtain Intermediate 9 (1.15 g, 52.1%6) as a pale yellow solid. $^1$H NMR (300 MHz, DMSO-d$_6$) δ ppm 2.62 (s, 3H), 8.10 (s, 1H). 8.38 (s, 1H), 8.95 (s, 1H), 9.37 (s, 1H), 9.98 (s, 1H). LCMS (method-D), retention time 1.68 min, [M+H] 213.2.

Intermediate 10: 3-methyl-5-(5-((methylamino)methyl)pyridin-2-yl)benzo[d]oxazol-2(3H)-one

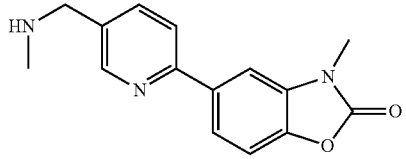 [SMILES: CNCc1ccc(-c2ccc3oc(=O)n(C)c3c2)nc1]

Intermediate 10A: Tert-Butyl methyl((6-(3-methyl-2-oxo-2,3-dihydrobenzo[d]oxazol-5-yl)pyridin-3-yl)methyl)carbamate

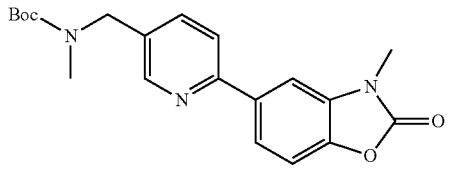 [SMILES: CN(Cc1ccc(-c2ccc3oc(=O)n(C)c3c2)nc1)C(=O)OC(C)(C)C]

A solution of Intermediate 2 (0.467 g, 1.817 mmol), Intermediate 4 (0.500 g, 1.817 mmol) and potassiumphosphate tribasic (1.157 g, 5.45 mmol) in 1,4-dioxane (12 mL) and H$_2$O (3 mL) was degassed with nitrogen for 20 minutes. Then PdCl$_2$(dppf)$_2$CH$_2$Cl$_2$ (0.148 g, 0.182 mmol) was added and the resulting mixture was degassed again for 10 minutes. The reaction mixture was heated at 100° C. for 5 h and then was cooled to ambient temperature. The reaction mixture was filtered through the celite and the filtrate was concentrated under reduced pressure. The residue was purified by silica gel column chromatography (Redisep-40 g. 60% EtOAc/n-hexane) to obtain Intermediate 10A (0.420 g, 62.6%) as a yellow solid. $^1$H NMR (400 MHz, DMSO-d$_6$) δ ppm 1.43 (s, 9H), 2.83 (s, 3H), 3.43 (s, 3H), 4.45 (s, 2H), 7.35-7.49 (m, 1H), 7.71-7.78 (m. 1H), 7.88 (d, J=2.01 Hz, 1H), 7.97 (d, J=1.51 Hz, 1H), 8.03 (d, J=8.03 Hz, 1H), 8.56 (d, J=1.51 Hz, 1H). LCMS (Method-D): retention time 2.50 min, [M+H] 370.2.

Intermediate 10

To a solution of Intermediate 10A (0.420 g. 1.14 mmol) in DCM (10 mL) at 0° C. was added 4N HCl in dioxane (5 mL, 1.14 mmol). The resulting mixture was stirred at ambient temperature for 2 h. The reaction mixture was concentrated to dryness and was diluted with water (10 mL). The aqueous layer was washed with ethyl acetate (2×20 mL), basified with saturated NaHCO$_3$ and extracted with 10% MeOH in DCM (3×50 mL). The combined organic layers were washed with brine (50 mL), dried over anhydrous sodium sulfate, filtered and concentrated under reduced pressure to obtain Intermediate 10 (0.200 g, 65.3%) as a brown solid. $^1$H NMR (300 MHz, DMSO-d6) δ ppm 2.28 (s, 3H), 3.42 (s, 3H), 3.69 (s, 2H), 7.41 (d, J=8.31 Hz, 1H), 7.76-7.91 (m, 2H), 7.93-8.02 (m, 2H), 8.58 (d, J=2.1 Hz, 1H), (Exchangeable proton not observed). LCMS (Method-D): retention time 1.079 min, [M+H] 270.2.

Intermediate 11: 2-fluoro-4-(5-((methylamino)methyl)pyridin-2-yl)benzonitrile

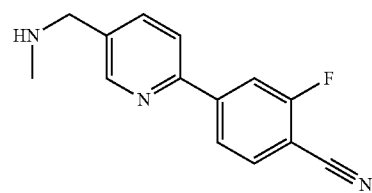 [SMILES: CNCc1ccc(-c2ccc(C#N)c(F)c2)nc1]

Intermediate 11A: Tert-Butyl ((6-(4-cyano-3-fluorophenyl)pyridin-3-yl)methyl)carbamate

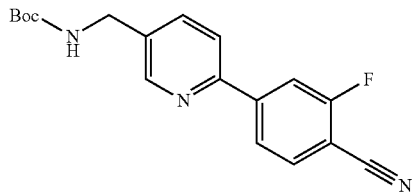 [SMILES: CC(C)(C)OC(=O)NCc1ccc(-c2ccc(C#N)c(F)c2)nc1]

Intermediate 11A was prepared (1.50 g, 76.0%) as a white solid, by using a similar synthetic protocol as that of Intermediate 10A and starting from Intermediate 2A (1.47 g, 6.06 mmol). $^1$H NMR (400 MHz, DMSO-d$_6$) δ ppm 1.41 (s, 9H), 4.23 (d, J=6.02 Hz, 2H), 7.52 (t, J=6.02 Hz, 1H). 7.81 (dd, J=8.28, 2.26 Hz, 1H), 8.00-8.08 (m, 1H), 8.10-8.24 (m, 3H), 8.61 (d, J=2.01 Hz, 1H). LCMS (Method-D): retention time 2.813 min, [M+H] 328.0.

Intermediate 11B: Tert-Butyl ((6-(4-cyano-3-fluorophenyl)pyridin-3-yl)methyl)(methyl)carbamate

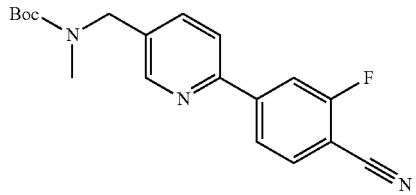 [SMILES: CN(Cc1ccc(-c2ccc(C#N)c(F)c2)nc1)C(=O)OC(C)(C)C]

Intermediate 11B was prepared (0.900 g. 88.0%) as yellow oil, by using a similar synthetic protocol as that of Intermediate 2 and starting from Intermediate 11 A (0.800 g, 2.44 mmol). $^{1}$H NMR (400 MHz, DMSO-$d_{6}$) δ ppm 1.42 (s, 9H), 2.84 (s, 3H), 4.48 (s, 2H), 7.81 (d, J=8.53 Hz, 1H), 8.04-8.09 (m, 1H), 8.14-8.21 (m, 2H), 8.23 (s, 1H), 8.63 (s, 1H). LCMS (Method-D): retention time 3.083 min, [M+H] 342.2.

Intermediate 11

Intermediate 11 was prepared (0.400 g, 67.2%) as a brown solid, by using a similar synthetic protocol as that of Intermediate 10 and starting from Intermediate 11B (0.900 g, 2.32 mmol). $^{1}$H NMR (300 MHz, DMSO-$d_{6}$) δ ppm 2.28 (s, 3H), 3.72 (s, 2H), 7.81-7.94 (m, 1H), 7.98-8.07 (m, 1H), 8.08-8.28 (m, 3H), 8.66 (s, 1H), (Exchangeable proton not observed). LCMS (Method-D): retention time 3.083 min, [M+H] 242.2.

Intermediate 12: 4-(5-(aminomethyl)pyridin-2-yl)-2-fluorobenzonitrile

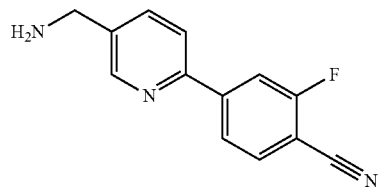 [SMILES: N#Cc1ccc(-c2ccc(CN)cn2)cc1F]

Intermediate 12 was prepared (0.350 g, 63.4%) as a white solid, by using a similar synthetic protocol as that of Intermediate 10 and starting from Intermediate 11A (0.700 g, 2.14 mmol). $^{1}$H NMR (300 MHz, DMSO-$d_{6}$) δ ppm 1.95 (br.s, 2H), 3.80 (s, 2H), 7.91 (dd, J=7.93, 2.27 Hz, 1H), 8.03 (dd, J=8.12, 6.99 Hz, 1H), 8.09 (s, 1H), 8.13 (d, J=1.89 Hz, 1H), 8.15-8.18 (m, 1H), 8.67 (d, J=1.51 Hz, 1H). LCMS (Method-D): retention time 1.470 min. [M+H] 228.2.

Intermediate 13-I: 5-(2-(((6-chloropyridin-3-yl)methyl)amino)-1-hydroxyethyl)-4-methylisobenzofuran-1(3H)-one

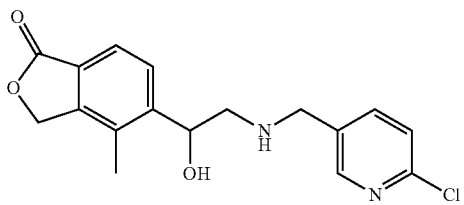 [SMILES: Cc1c(C(O)CNCc2ccc(Cl)nc2)ccc2c1COC2=O]

To a solution of (6-chloropyridin-3-yl)methanamine (0.270 g, 1.89 mmol) in EtOH (10 mL) was added Intermediate 1-I (0.3 g, 1.577 mmol) and the resulting mixture was heated at 85° C. for 48 h. The reaction mixture was evaporated to dryness under reduced pressure. The residue was purified by preparative HPLC [Sunfire OBD (250×30 ID) 5 micron; Solvent A: 10 mM Ammonium Acetate in water, Solvent B: Acetonitrile; Gradient: 0-100% B over 15.5 min, Flow: 25 mL/min, retention time 11.2 min, UV 220 nm] to obtain Intermediate 13-I (0.300 g, 57.2%) as a light yellow solid. $^{1}$H NMR (400 MHz, DMSO-$d_{6}$) δ ppm 2.20 (s, 3H). 2.52-2.65 (m, 2H), 3.77 (s, 2H), 5.00 (dd, J=7.53, 4.52 Hz, 1H), 5.29-5.43 (m, 3H), 7.44 (d, J=7.53 Hz, 1H), 7.66 (d, J=1.00 Hz, 2H), 7.79 (dd, J=8.03, 2.51 Hz, 1H), 8.33 (d, J=2.01 Hz, 1H), (Exchangeable proton not observed). LCMS (Method-H): retention time 1.07 min, [M+H] 333.8.

Intermediate 14: 1-(1-oxo-1,3-dihydroisobenzofuran-5-yl)-1H-indole-5-carbaldehyde

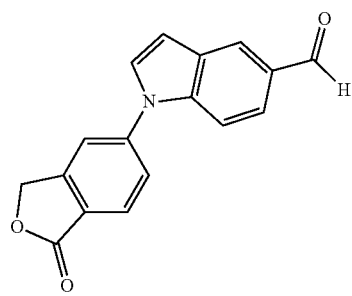 [SMILES: O=Cc1ccc2c(ccn2-c2ccc3c(c2)COC3=O)c1]

Intermediate 14 was prepared (0.500 g, 52.4%), by using a similar synthetic protocol as that of Intermediate 9 and starting from 1H-indole-5-carbaldehyde (0.500 g, 3.44 mmol). LCMS (Method-J): Retention time 2.19 min, [M+H] 278.2. The compound was taken directly to the subsequent step without further purification or characterization.

Intermediate 15-I: 5-(2-(((2-chloropyrimidin-5-yl)methyl)(methyl)amino)-1-hydroxyethyl)-4-methyl-isobenzofuran-1(3H)-one

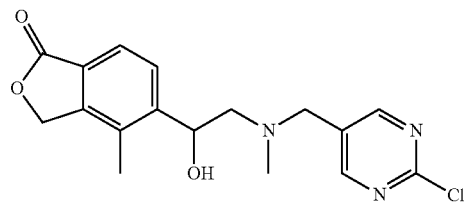 [SMILES: Cc1c(C(O)CN(C)Cc2cnc(Cl)nc2)ccc2c1COC2=O]

Intermediate 15A-I: 5-(1-hydroxy-2-(methylamino)ethyl)-4-methylisobenzofuran-1(3H)-one

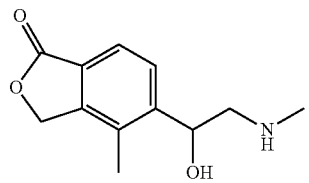

15A-I

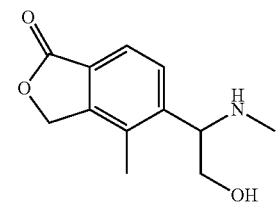

15B-I

Intermediate 15A-I was prepared (0.550 g, 94.5%), by using a similar synthetic protocol as that of Intermediate 7-I and starting from Intermediate 1-I (0.500 g, 2.63 mmol). $^1$H NMR (300 MHz, DMSO-d$_6$) δ ppm 2.26 (s, 3H), 2.30 (s, 3H), 2.57-2.59 (m, 2H), 2.74-2.76 (m, 1H), 4.99 (t J=5.70, 1H), 5.38 (s, 2H), 7.65-7.71 (m, 2H), (Exchangeable proton not observed). LCMS (Method-K): retention time 0.22 min, [M+H] 222.2. Intermediate 15B-I was obtained as a side product. LCMS (Method-K): retention time 1.48 min, [M+H] 222.2. The compound was taken directly to the subsequent step without further purification or characterization.

Intermediate 15-I:

To a solution of 5-(bromomethyl)-2-chloropyrimidine (1.00 g, 4.82 mmol) in acetonitrile was added Intermediate 15A-I (1.07 g, 4.82 mmol) and the reaction mixture was stirred at ambient temperature for 12 h. The reaction mixture was concentrated under reduced pressure, diluted with water and extracted with ethyl acetate (3×100 mL). The combined organic layers were washed with brine (20 mL), dried over anhydrous sodium sulfate, and evaporated under reduced pressure. The residue was purified by silica gel column chromatography (Redisep-40 g, 80% EtOAc/hexane) to obtain Intermediate 15-I (0.800 g, 47.7%). $^1$H NMR (300 MHz, DMSO-d$_6$) δ ppm 2.19 (s, 3H), 2.34 (s, 3H), 2.50-2.54 (m, 2H), 3.61 (d, J=4.53 Hz, 2H), 5.02-5.11 (m, 1H), 5.34-5.43 (m, 3H), 7.59-7.74 (m, 2H), 8.54-8.68 (m, 2H). LCMS (Method-E): retention time 1.78 min, [M+H] 348.1.

Intermediate 16: 4'-aminomethyl)-3-fluoro-[1,1'-biphenyl]-4-carbonitrile

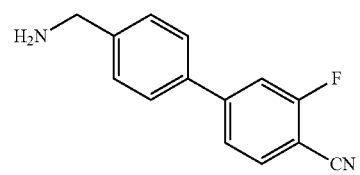 [SMILES: N#Cc1ccc(-c2ccc(CN)cc2)cc1F]

Intermediate 16A: tert-butyl 4-bromobenzylcarbamate

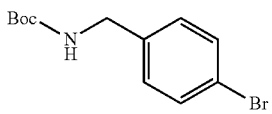

Intermediate 16A was prepared (4.10 g, 89.0%) as a yellow liquid, by using a similar synthetic protocol as that of Intermediate 2A and starting from (4-bromophenyl)methanamine (3.00 g, 16.1 mmol). $^1$H NMR (300 MHz, DMSO-d$_6$) δ ppm 1.47 (s, 9H), 4.08 (d, J=6.04 Hz, 2H), 7.19 (d, J=8.31 Hz, 2H), 7.37-7.45 (m, 1H), 7.50 (d, J=8.31 Hz, 2H). LCMS: Did not ionize.

Intermediate 16B: Tert-Butyl ((4'-cyano-3'-fluoro-[1,1'-biphenyl]-4-yl)methyl)carbamate

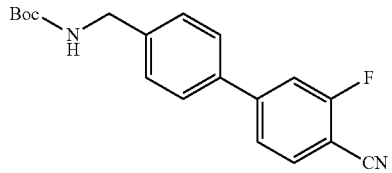 [SMILES: CC(C)(C)OC(=O)NCc1ccc(-c2ccc(C#N)c(F)c2)cc1]

Intermediate 16B was prepared (1.70 g, 74.5%), by using a similar synthetic protocol as that of Intermediate 11A and starting from Intermediate 16A (2.00 g, 6.99 mmol). $^1$H NMR (300 MHz, DMSO-d$_6$) δ ppm 1.40 (s, 9H), 4.18 (d, J=6.42 Hz, 2H), 7.37 (d, J=7.93 Hz, 2H), 7.47 (t, J=6.04 Hz, 1H). 7.70-7.80 (m, 3H). 7.87 (dd, J=11.33, 1.51 Hz, 1H), 7.94-8.02 (m, 1H). LCMS: Did not ionize.

Intermediate 16

Intermediate 16 was prepared (1.10 g. 93.0%), by using similar synthetic protocol as that of Intermediate 10 and starting from Intermediate 16B (1.70 g, 5.21 mmol). $^1$H NMR (300 MHz, DMSO-d$_6$) δ ppm 3.78 (s, 2H), 7.48 (d, J=8.31 Hz, 2H), 7.70-7.80 (m. 3H), 7.89 (dd, J=11.14, 1.70 Hz, 1H), 7.96-8.04 (m. 1H), (Exchangeable proton not observed). LCMS (Method-D): retention time 1.69 min, [M+H] 227.0.

Intermediate 17: 1-(4-((methylamino)methyl)phenyl)-1H-indole-3-carbonitrile

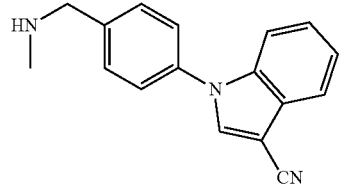 [SMILES: CNCc1ccc(-n2cc(C#N)c3ccccc32)cc1]

Intermediate 17A: 1-(4-bromophenyl)-N-methylmethanamine

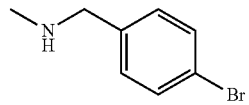

To a solution of 1-bromo-4-(bromomethyl)benzene (5.00 g, 20.0 mmol) in THF (30 mL) was added 2M methylamine in THF (100 mL, 200.0 mmol) and the reaction mixture was stirred at ambient temperature for 18 h. The reaction mixture was diluted with 1.5 N HCl solution (50 mL) extracted with ethyl acetate (3×30 mL). The aqueous extract was basified with NaHCO$_3$ and extracted with ethyl acetate (3×50 mL). The combined organic layers were washed with brine (20 mL), dried over anhydrous sodium sulfate, and evaporated under reduced pressure to obtain Intermediate 17A (3.50 g.

87.0%). ¹H NMR (400 MHz, DMSO-d₆) δ ppm 2.26 (s, 3H), 3.63 (s, 2H), 7.24-7.32 (m, 2H), 7.47-7.54 (m, 2H), (Exchangeable proton not observed). LCMS (Method-T): retention time 0.68 min, (M+H) 201.0.

Intermediate 17B: tert-butyl 4-bromobenzyl(methyl)carbamate

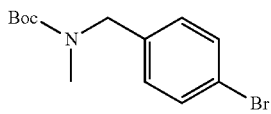

Intermediate 17B was prepared (0.340 g, 45.3%) as an off-white liquid, by using a similar synthetic protocol as that of Intermediate 2A and starting from Intermediate 17A (0.500 g, 2.49 mmol). ¹H NMR (400 MHz, DMSO-d₆) δ ppm 1.41 (d, J=8.53 Hz, 9H), 2.76 (s, 3H), 4.34 (s, 2H), 7.18 (d, J=8.53 Hz, 2H), 7.56 (d, J=8.53 Hz, 2H). LCMS: Did not ionize.

Intermediate 17C: Tert-Butyl 4-(3-cyano-1H-indol-1-yl)benzyl(methyl)carbamate

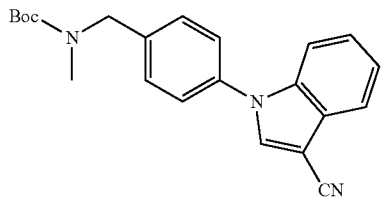 [SMILES: CN(Cc1ccc(-n2cc(C#N)c3ccccc32)cc1)C(=O)OC(C)(C)C]

Intermediate 17C was prepared (0.225 g, 53.4%) as an off-white solid, by using a similar synthetic protocol as that of Intermediate 9 and starting from Intermediate 17B (0.350 g, 1.17 mmol). ¹H NMR (300 MHz, DMSO-d₆) δ ppm 1.44 (br. s. 9H), 2.83 (s, 3H), 4.48 (s, 2H), 7.34-7.41 (m, 2H), 7.43-7.51 (m, 2H), 7.64 (s, 3H), 7.73-7.78 (m, 1H), 8.60 (s, 1H). LCMS (Method-E): retention time 3.33 min. [M+H] 362.0.

Intermediate 17

Intermediate 17 was prepared (0.120 g, 75.0%), by using a similar synthetic protocol as that of Intermediate 10 and starting from Intermediate 17C (0.220 g, 0.609 mmol). ¹H NMR (300 MHz, DMSO-d₆) δ ppm 2.32 (s, 3H), 3.76 (s, 2H), 7.31-7.46 (m, 3H), 7.59 (d, J=3.40 Hz, 5H), 7.72-7.82 (m. 1H), 8.60 (s, 1H), LCMS (Method-E): retention time 1.965 min, [M+H] 262.2.

Example 1-I: 5-(5-(((2-hydroxy-2-(4-methyl-1-oxo-1,3-dihydroisobenzofuran-5-yl)ethyl)(methyl)amino)methyl)pyridin-2-yl)-3-methylbenzo[d]oxazol-2(3H)-one

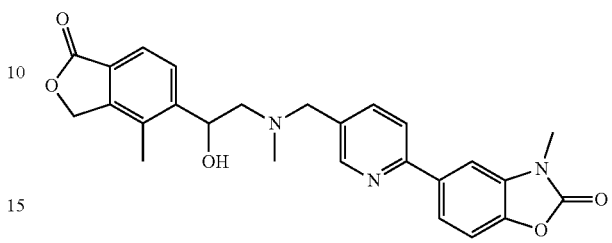

Example 1-I was prepared (0.0350 g, 40.8%), by using a similar synthetic protocol as that of Intermediate 13-I and starting from Intermediate 10 (0.0500 g, 0.186 mmol) and Intermediate 1-I. ¹H NMR (400 MHz, DMSO-d₆) δ ppm 2.20 (s, 3H). 2.35 (s, 3H), 2.66-2.53 (m. 2H), 3.44 (s, 3H), 3.63 (s, 2H), 5.11 (br. s, 1H), 5.36 (s, 3H), 7.43 (d, J=8.5 Hz, 1H), 7.63 (s, 2H), 7.73-7.68 (m, 1H), 7.97-7.82 (m, 3H), 8.46 (s, 1H). LCMS/HPLC (Method-A): retention time 1.157 min, [M+H] 460.2, purity: 99.5%. (Method-B): retention time 1.672 min, [M+H] 460.2, 98.3%. Chiral purity (Method-V): retention time 7.58 min, 97.8% ee.

Example 2-I: 1-(5-((2-hydroxy-1-(4-methyl-1-oxo-1,3-dihydroisobenzofuran-5-yl)ethyl)(methyl)amino)methyl)pyrimidin-2-yl)-1H-indazole-4-carbonitrile

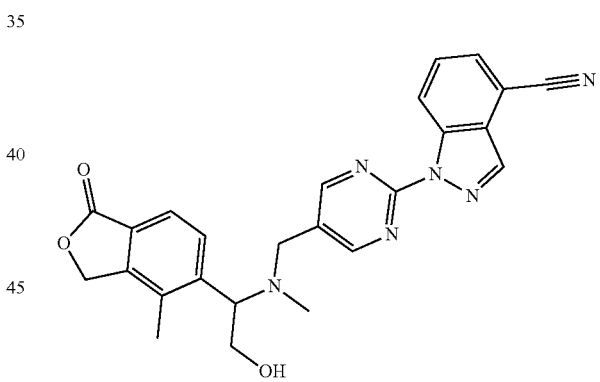

Example 2A-I: 5-(1-(((2-chloropyrimidin-5-yl)methyl)(methyl)amino)-2-hydroxyethyl)-4-methyl-isobenzofuran-1(3H)-one

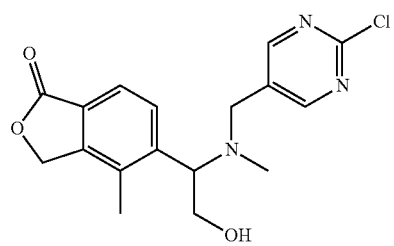 [SMILES: Cc1c(C(CO)N(C)Cc2cnc(Cl)nc2)ccc2c1COC2=O]

Example 2A-I was prepared (0.800 g, 47.7%), by using a similar synthetic protocol as that of Intermediate 15-1 and starting from 5-(bromomethyl)-2-chloropyrimidine (1.00 g, 4.82 mmol) and Intermediate 15B-I. LCMS (Method-D): retention time 1.78 min, [M+H] 348.1. The compound was taken directly to the subsequent step without further purification or characterization.

Example 2-I

To a solution of Intermediate 2A-I (0.025 g, 0.072 mmol) and 1H-indazole-4-carbonitrile (0.010 g, 0.072 mmol) in dioxane (3 mL) was added K₂CO₃ (0.020 g, 0.144 mmol) followed by XANTPHOS (0.002 g, 3.59 μmol). The resulting reaction mixture was degassed with nitrogen for 5 minutes and then Pd₂(dba)₃ (0.006 g, 7.19 μmol) was added and the reaction mixture was degassed with nitrogen for an additional 5 minutes. The reaction mixture was heated in a sealed tube at 100° C. for 12 h. cooled and concentrated under reduced pressure. The residue was diluted with EtOAc (20 mL) and filtered through celite. The filtrate was dried over anhydrous sodium sulfate, filtered and concentrated under reduced pressure. The crude residue was purified by Prep HPLC [Inertsil ODS (250×4.6 mm) 5 micron; Solvent A: 10 mM Ammonium Acetate pH 4.5, Solvent B: Acetonitrile, Gradient: 20-100% B over 25 min, Flow: 2 mL/min retention time 12.5 min, UV 254 nm] to obtain Example 2-I (0.001 g, 3.37%). $^1$H NMR (400 MHz, DMSO-d₆) δ ppm 2.19 (s, 3H), 2.33-2.37 (m, 3H), 3.65-3.83 (m, 3H), 3.95-4.04 (m, 2H), 4.80-4.87 (m, 1H), 5.42 (s, 2H), 7.69 (d, J=7.83 Hz, 1H), 7.74-7.83 (m, 2H), 7.95 (d, J=7.34 Hz, 1H), 8.70 (s, 1H), 8.84 (s, 2H), 8.99 (d, J=8.56 Hz, 1H). LCMS/HPLC (Method-A): retention time 1.16 min, [M+H] 455.1, purity: 100%. (Method-B): retention time 1.72 min, [M+H] 455.1, 100%.

Example 3-I: 2-fluoro-4-(5-(((2-hydroxy-2-(4-methyl-1-oxo-1,3-dihydroisobenzofuran-5-yl)ethyl)amino)methyl)pyridin-2-yl)benzonitrile

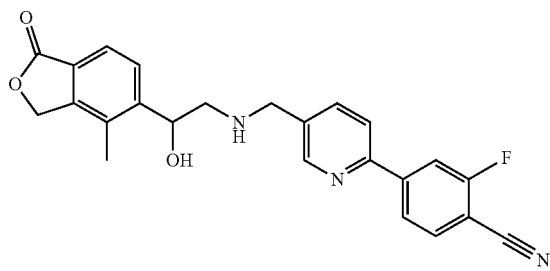 [SMILES: Cc1c(C(O)CNCc2ccc(-c3ccc(C#N)c(F)c3)nc2)ccc2c1COC2=O]

Example 3-I was prepared (0.0260 g. 20.7%), by using a similar synthetic protocol as that of Intermediate 13-1 and starting from Intermediate 12 (0.0700 g, 0.308 mmol) and Intermediate 1-I. $^1$H NMR (400 MHz, DMSO-d₆) δ ppm 2.23 (s, 3H). 2.61-2.76 (m, 2H). 3.92 (br. s, 2H), 5.06 (br. s., 1H), 5.29-5.43 (m, 2H), 5.62 (br. s., 1H), 7.60-7.72 (m, 2H), 7.92 (d, J=8.31 Hz, 1H), 8.00-8.08 (m, 1H), 8.10-8.27 (m, 3H), 8.69 (d, J=1.47 Hz, 1H), (Exchangeable proton not observed). LCMS/HPLC (Method-A): retention time 1.075 min, [M+H] 418.2, purity: 99.7%. (Method-B): retention time 1.447 min, [M+H] 418.2, purity: 100%. Chiral purity (Method-VII): retention time 10.07 min. 93.0% ee.

Example 4-I: 5'-(((2-hydroxy-2-(4-methyl-1-oxo-1,3-dihydroisobenzofuran-5-yl)ethyl)amino)methyl)-4-methyl-[2,2'-bipyridine]-5-carbonitrile (Enantiomer 1)

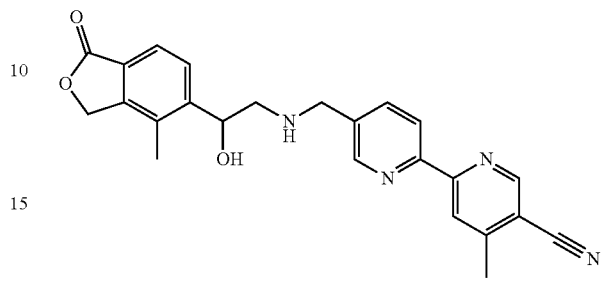

Example 4A-I: 5-(1-hydroxy-2-((6-(trimethylstannyl)pyridin-3-yl)methyl)amino)ethyl)-4-methylisobenzofuran-1(3H)-one

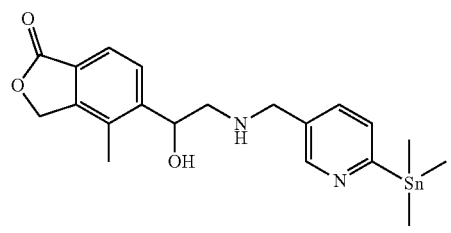 [SMILES: Cc1c(C(O)CNCc2cc[c]([Sn]([CH3])([CH3])[CH3])nc2)ccc2c1COC2=O]

A solution of Intermediate 13-I (0.200 g, 0.601 mmol) in dioxane (10 mL) was degassed with nitrogen for 20 minutes and then hexamethylditin (0.137 mL, 0.661 mmol) and 1,1'-bis(di-tert-butylphosphino)ferrocene palladiumchloride (0.0390 g. 0.0600 mmol) were added. The reaction mixture was heated at 100° C. for 1 h and was cooled to ambient temperature. The reaction mixture was filtered through celite and the filtrate was distilled under reduced pressure to obtain Example 4A-I (0.500 g, 57.7%) as a black syrup. LCMS (Method-I): retention time 1.19 min, [M+H] 463.1. The compound was taken forward directly to the subsequent step without further purification or characterization.

Example 4-I

A solution of Example 4A-I (0.500 g, 0.347 mmol) and 6-bromo-4-methylnicotinonitrile (0.103 g, 0.520 mmol) in dioxane (20 mL) was degassed with nitrogen for 20 minutes. To the resulting reaction mixture was added tetrakistriphenylphospine palladium (0.040 g, 0.035 mmol) followed by copper(I) iodide (0.0060 g, 0.035 mmol) and was degassed again for 10 minutes. The reaction mixture was heated at 100° C. for 16 h then was cooled to ambient temperature. The reaction mixture was filtered through celite and the filtrate was concentrated under reduced pressure. The residue was purified by preparative HPLC [XBridge C18 (19× 150 mm) 5 micron; Solvent A: 10 mM Ammonium Acetate, Solvent B: Acetonitrile, Gradient: 10-45% B over 20 min, Flow: 15 mL/min to obtain Example 4-I (Enantiomer-1) (0.0020 g, 1.60%). $^1$H NMR (400 MHz, DMSO-d₆) δ ppm 2.20 (s, 3H), 2.60 (br. s., 3H), 2.72-2.61 (m, 2H), 3.92 (br.

s., 2H), 5.00-5.11 (m, 1H), 5.36 (d, J=2.4 Hz, 2H), 5.46-5.64 (m, 1H). 7.59-7.76 (m, 2H). 7.96 (d, J=7.34 Hz, 1H), 8.38 (d, J=8 Hz, 1H), 8.46 (s, 1H), 8.68 (br. s., 1H), 9.01 (s, 1H), (Exchangeable proton not observed). LCMS/HPLC (Method-A): retention time 1.187 min. [M+H] 415.1, purity: 100%. (Method-B): retention time 1.589 min, [M+H] 415.1, purity: 100%. Chiral purity (Method-X): retention time 10.2 min, 100% ee.

Example 5-I: 5'-(((2-hydroxy-2-(4-methyl-1-oxo-1, 3-dihydroisobenzofuran-5-yl)ethyl)amino)methyl)-4-methyl-[2,2'-bipyridine]-5-carbonitrile (Enantiomer 1)

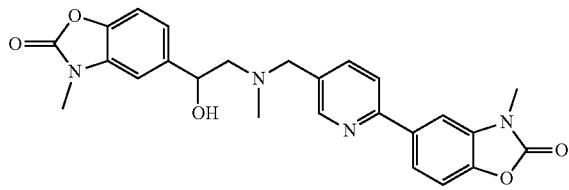 [SMILES: CN(Cc1ccc(-c2ccc3oc(=O)n(C)c3c2)nc1)CC(O)c1ccc2oc(=O)n(C)c2c1]

Example 5A: 3-methyl-5-(2-(methyl((6-(3-methyl-2-oxo-2,3-dihydrobenzo[d]oxazol-5-yl)pyridin-3-yl)methyl)amino)acetyl)benzo[d]oxazol-2(3H)-one

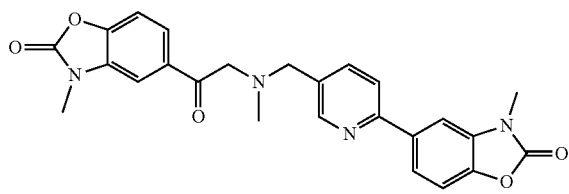 [SMILES: CN(CC(=O)c1ccc2oc(=O)n(C)c2c1)Cc1ccc(-c2ccc3oc(=O)n(C)c3c2)nc1]

To a solution of Intermediate 10 (0.750 g, 0.696 mmol) in THF (20 mL) was added N,N-diisopropylethylamine (0.270 g, 2.08 mmol) followed by Intermediate 6 (0.451 g, 0.836 mmol). The resulting reaction mixture was stirred at ambient temperature for 24 h then concentrated under reduced pressure to obtain Example 5A (1.30 g). LCMS (Method-I): retention time 0.92 min, [M+H] 459.3. The compound was taken forward directly to the subsequent step without further purification or characterization.

Example 5-I

To a solution of Example 5A in THF (20 mL) and MeOH (5 mL) was added sodium borohydride (0.0480 g, 1.27 mmol) portion wise. The reaction mixture was stirred at ambient temperature for 1 h, diluted with water and then extracted with 10% MeOH/DCM (3×50 mL). The combined organic layers were washed with brine (50 mL), dried over anhydrous sodium sulfate, and evaporated under reduced pressure. The crude residue was purified by Prep HPLC [Inertsil ODS (250×20 ID) 5 micron; Solvent A: 10 mM Ammonium Acetate pH 4.5, Solvent B: Acetonitrile, Gradient: 0-100% B over 13.5 min. Flow: 17 mL/min retention time 12.2 min, UV 210 nm] to obtain the racemate. The racemate was chirally separated by SFC [Lux Amylose-2 (250×4.6 mm) 5 micron, Mobile phase: 0.2% DEA in IPA:ACN (1:1), Total flow: 4.0 g/min, Back pressure: 100 bar, temperature: 30° C., UV: 225]. The faster eluting compound (retention time 4.79 min) was designated as Example 5-I (Enantiomer-I), (0.0080 g, 0.40%). $^1$H NMR (400 MHz, DMSO-d$_6$) δ ppm 2.27 (s, 3H), 2.51-2.62 (m, 2H), 3.29 (s, 3H), 3.43 (s, 3H), 3.61 (br. s, 2H). 4.81 (br. s, 1H), 5.25 (br. s, 1H), 7.07-7.19 (m, 2H), 7.26 (br. s, 1H). 7.44 (d, J=8.31 Hz, 1H), 7.73 (br. s, 1H), 7.84-8.03 (m, 3H), 8.47 (br. s, 1H). LCMS/HPLC (Method-A): retention time 1.121 min, [M+H] 461.2, purity: 100%. (Method-B): retention time 1.65 min, [M+H] 461.2, purity: 100%. The slower eluting compound (retention time 5.89 min) was designated as Example 5-II (Enantiomer-II) could not be isolated as a pure material.

Example 7-I: 6-(4-(((2-hydroxy-2-(4-methyl-1-oxo-1,3-dihydroisobenzofuran-5-yl)ethyl)amino)methyl)-1H-pyrazol-1-yl)-4-methylnicotinonitrile

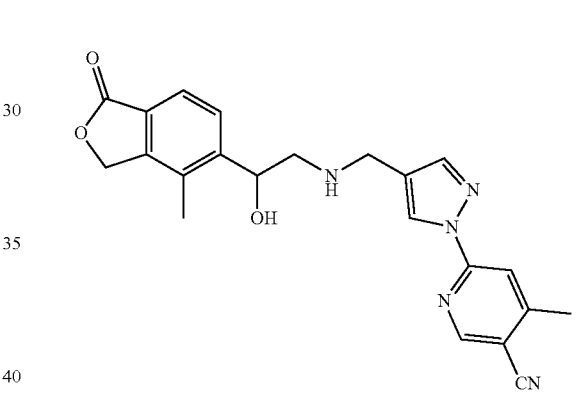

To a solution of Intermediate-9 (0.200 g, 0.942 mmol) in MeOH (5 mL) was added acetic acid (0.081 mL, 1.414 mmol) followed by Intermediate 7-I (0.234 g, 1.131 mmol) and the reaction mixture was stirred at ambient temperature for 10 min. NaCNBH$_3$ (0.178 g, 2.83 mmol) was added and stirring was continued for 12 h. The reaction mixture was diluted with water (20 mL), basified with 10% NaHCO$_3$ solution and extracted with ethyl acetate (2×30 mL). The combined organic layers were washed with brine (20 mL), dried over anhydrous sodium sulfate, and evaporated under reduced pressure. The residue was purified by HPLC [Luna C18 (250×30ID) 5 micron; Solvent A: 0.1% TFA in H$_2$O, Solvent B: Acetonitrile, Gradient: 20-100 over 14 min, Flow: 25 mL/min] to obtain Example 7-I (0.087 g, 22.9%). $^1$H NMR (400 MHz, CDCl$_3$) δ ppm 2.28 (s, 3H), 2.63 (s, 3H), 2.77-2.67 (m, 1H), 3.03-2.93 (m, 1H), 3.620 (m, 2H). 3.86 (d, J=6.0 Hz, 2H), 5.10-5.03 (m, 1H), 5.25 (s, 2H), 7.80-7.74 (m, 3H), 7.95 (d, J=0.8 Hz, 1H), 8.49 (d, J=0.8 Hz, 1H). 8.59 (s, 1H). LCMS/HPLC (Method-H): retention time 1.80 min, [M+H] 404.2, purity: 99.7%. (Method C): retention time 10.54 min, purity: 99.7%. Chiral purity (Method-VI): retention time 9.44 min, 100% ee.

Example 8-I: 5-(1-hydroxy-2-(((1-(1-oxo-1,3-dihydroisobenzofuran-5-yl)-1H-indol-5-yl)methyl)amino)ethyl)-4-methylisobenzofuran-1(3H)-one

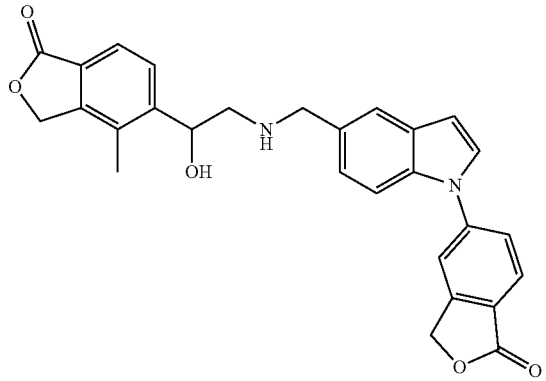 [SMILES: Cc1c(C(O)CNCc2ccc3c(ccn3-c3ccc4c(c3)COC4=O)c2)ccc2c1COC2=O]

Example 8-I was prepared (0.0150 g, 13.3%), by using a similar synthetic protocol as that of Example 7-I and starting from Intermediate 14 (0.0500 g, 0.241 mmol) and Intermediate 7-1. $^1$H NMR (400 MHz, DMSO-$d_6$) δ ppm 2.24 (s, 3H), 2.92 (br. s., 1H), 3.06 (br. s., 1H), 4.35 (br. s., 2H), 5.25 (d, J=10.52 Hz, 1H). 5.39 (d, J=5.38 Hz, 2H), 5.50 (s, 2H), 6.28 (br. s., 1H), 6.85 (d, J=3.42 Hz, 1H), 7.42 (d, J=8.31 Hz, 1H), 7.66-7.74 (m, 3H), 7.78-7.88 (m, 3H), 7.95 (s, 1H), 8.04 (d, J=8.56 Hz, 1H), 9.04 (br. s., 1H). LCMS/HPLC (Method-A): retention time 1.28 min, [M+H] 428.3, purity: 99.8%. (Method-B): retention time 1.47 min, [M+H] 428.3, purity: 98.3%. Chiral purity (Method-II): retention time 11.66 min, 100% ee.

Example 9-I: 5-(5-((((2-hydroxy-2-(4-methyl-1-oxo-1,3-dihydroisobenzofuran-5-yl)ethyl)methyl)amino)methyl)pyrimidin-2-yl)-3-methylbenzo[d]oxazol-2(3H)-one

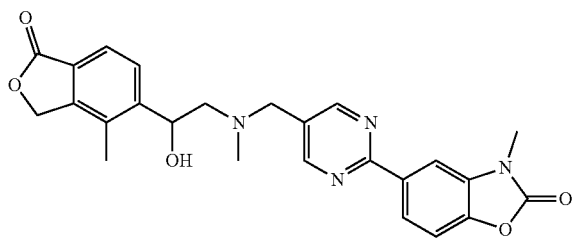 [SMILES: Cc1c(C(O)CN(C)Cc2cnc(-c3ccc4oc(=O)n(C)c4c3)nc2)ccc2c1COC2=O]

Example 9-I was prepared (0.0330 g, 49.8%), by using similar synthetic protocol as that of Intermediate 10A and starting from Intermediate 15-I (0.0500 g, 0.144 mmol). $^1$H NMR (400 MHz, DMSO-$d_6$) δ ppm 2.18 (s, 3H), 2.39 (s, 3H), 2.52-2.63 (m, 2H), 3.44 (s, 3H), 3.61 (s, 2H), 5.04-5.11 (m, 1H), 5.32 (d, J=2.93 Hz, 2H), 5.36-5.43 (m, 1H), 7.42-7.49 (m, 1H). 7.58 (d, J=0.73 Hz, 2H), 8.12 (d, J=1.47 Hz, 1H), 8.21 (dd, J=8.44, 1.83 Hz, 1H), 8.64 (s, 2H). LCMS/HPLC (Method-A): retention time 1.28 min, [M+H] 468.1, purity: 100%. (Method-B): retention time 1.70 min, [M+H] 468.2, purity: 98.5%. Chiral purity (Method-III): retention time 17.74 min, 100% ee.

Example 10-I: 3-fluoro-4'-(((2-hydroxy-2-(4-methyl-1-oxo-1,3-dihydroisobenzofuran-5-yl)ethyl)amino)methyl)-[1,1'-biphenyl]-4-carbonitrile

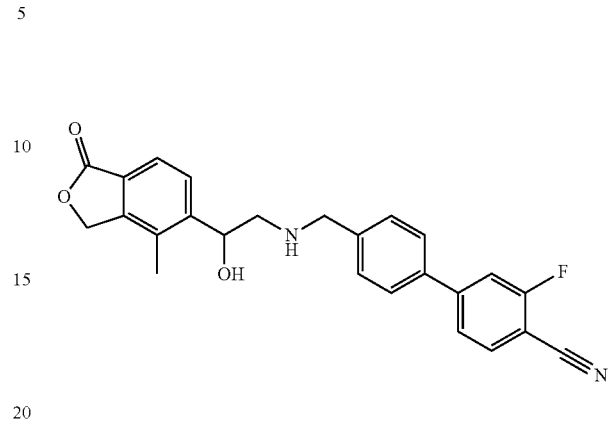

Example 10-I was prepared (0.00700 g, 7.71%), by using a similar synthetic protocol as that of Intermediate 13-I and starting from Intermediate 16 (0.0500 g, 0.221 mmol) and Intermediate 1-I. $^1$H NMR (400 MHz, DMSO-$d_6$) δ 2.21 (s, 3H). 2.67-2.58 (m, 2H), 3.82 (s, 2H), 5.07-4.98 (m, 1H), 5.36 (d, J=2.4 Hz, 2H), 5.50 (br. s., 1H), 7.46 (d, J=8.3 Hz, 2H), 7.69-7.61 (m, 2H), 7.80-7.71 (m, 3H), 7.88 (dd, J=11.2, 1.5 Hz, 1H), 7.98 (dd, J=8.1, 7.1 Hz, 1H), (Exchangeable proton not observed). LCMS/HPLC (Method-A): retention time 1.43 min, [M+H] 417.1, purity: 97.9%. LCMS/HPLC (Method-B): retention time 1.76 min, [M+H] 417.1, purity: 100%.

Example 11-I: 3-fluoro-4'-(((2-hydroxy-2-(4-methyl-1-oxo-1,3-dihydroisobenzofuran-5-yl)ethyl)(pyridin-3-ylmethyl)amino)methyl)-[1,1'-biphenyl]-4-carbonitrile

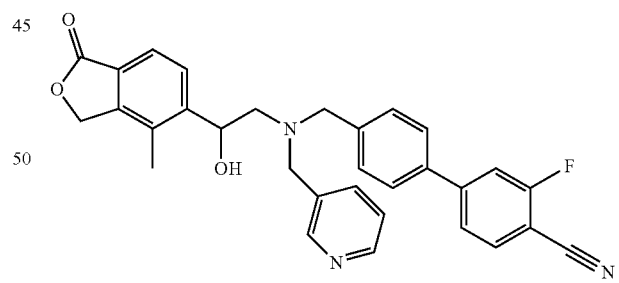

Example 11-I was prepared (0.00200 g, 3.28%), by using a similar synthetic protocol as that of Example 7-I and starting from Example 10-I (0.050 g, 0.120 mmol). $^1$H NMR (400 MHz, CDCl$_3$) δ ppm 2.19 (s, 3H), 3.61-3.74 (m, 2H), 3.95 (d, J=10.03 Hz. 4H), 4.08-4.19 (m 1H), 4.35 (s, 1H), 5.27 (d, J=6.85 Hz, 2H), 7.36-7.47 (m, 5H), 7.52 (d, J=8.07 Hz, 2H), 7.61-7.73 (m, 2H), 7.82 (d, J=16.63 Hz, 2H), 8.55 (s, 2H). LCMS/HPLC (Method-A): retention time 1.656 min, [M+H] 508.2, purity: 100%. (Method-B): retention time 2.086 min, [M+H] 508.2, purity: 100%.

Example 12-I: 1-(4-(((2-hydroxy-2-(4-methyl-1-oxo-1,3-dihydroisobenzofuran-5-yl)ethyl)(methyl)amino)methyl)phenyl)-1H-indole-3-carbonitrile

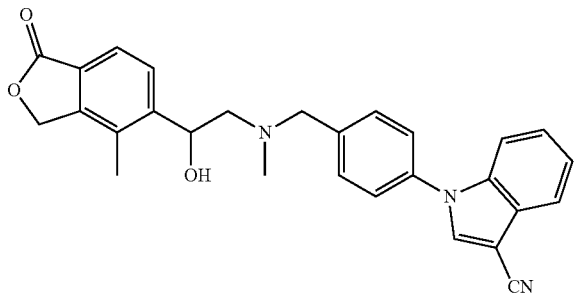 [SMILES: Cc1c(C(O)CN(C)Cc2ccc(-n3cc(C#N)c4ccccc43)cc2)ccc2c1COC2=O]

Example 12-I was prepared (0.0210 g, 24.6%) as an off-white solid, by using a similar synthetic protocol as that of Intermediate 13-I and starting from Intermediate 17 (0.0500 g, 0.191 mmol) and Intermediate 1-I. $^1$H NMR (400 MHz, DMSO-$d_6$) δ ppm 2.22 (s, 3H), 2.34 (s, 3H), 2.53-2.61 (m, 2H), 3.62-3.70 (m, 2H), 5.10-5.17 (m, 1H), 5.33-5.41 (m, 3H), 7.36-7.42 (m, 2H), 7.45-7.50 (m, 2H), 7.53-7.59 (m, 3H), 7.66 (s, 2H), 7.73-7.79 (m, 1H), 8.55-8.59 (m, 1H). LCMS/HPLC (Method-A): retention time 1.54 min, [M+H] 452.2, purity: 99.6%. (Method-B): retention time 2.22 min, [M+H] 452.2, purity: 98.5%. Chiral purity (method-III): retention time 7.81 min, 98.8% ee.

The examples in Table 1 were synthesized using procedures in Example 1 to 12.

| Ex. | Structure | Name | LCMS (M + H)+ | HPLC/LCMS Method: RT (min.), Purity | NMR |
|---|---|---|---|---|---|
| 1-II | 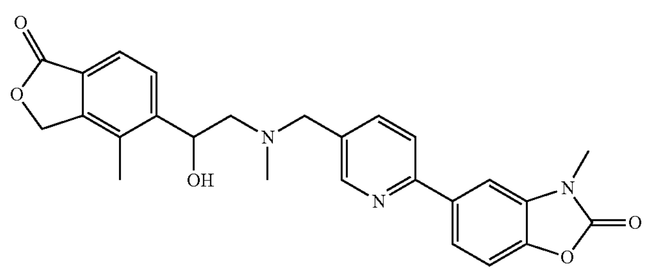 [SMILES: Cc1c(C(O)CN(C)Cc2ccc(-c3ccc4oc(=O)n(C)c4c3)nc2)ccc2c1COC2=O] | 5-(5-(((2-hydroxy-2-(4-methyl-1-oxo-1,3-dihydroisobenzofuran-5-yl)ethyl)(methyl)amino)methyl)pyridin-2-yl)-3-methylbenzo[d]oxazol-2(3H)-one (Enantiomer-II) | 460.2 | A: 1.157, 99.36% B: 1.672, 98.47% V: 6.62, 93.47% ee | $^1$H NMR (400 MHz, DMSO-$d_6$) δ ppm 2.20 (s, 3 H), 2.35 (s, 3 H), 2.53-2.66 (m, 2 H), 3.44 (s, 3 H), 3.63 (s, 2 H), 5.11 (br. s., 1 H), 5.36 (s, 3 H), 7.43 (d, J = 8.5 Hz, 1 H), 7.63 (s, 2 H), 7.68-7.73 (m, 1 H), 7.82-7.97 (m, 3 H), 8.46 (s, 1 H). |
| 3-II | 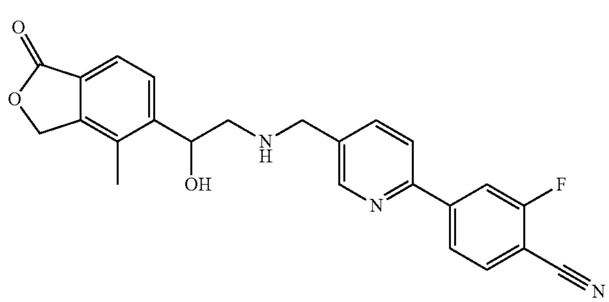 [SMILES: Cc1c(C(O)CNCc2ccc(-c3ccc(C#N)c(F)c3)nc2)ccc2c1COC2=O] | 2-fluoro-4-(5-(((2-hydroxy-2-(4-methyl-1-oxo-1,3-dihydro-isobenzofuran-5-yl)ethyl)amino)methyl)pyridin-2-yl)benzonitrile (Enantiomer-II) | 418.2 | A: 1.078, 100% B: 1.448, 100% VII: 12.99, 95.55 % ee | $^1$H NMR (400 MHz, DMSO-$d_6$) δ ppm 2.23 (s, 3 H), 2.61-2.76 (m, 2 H), 3.92 (br. s, 2 H), 5.06 (br. s, 1 H), 5.29-5.43 (m, 2 H), 5.62 (br. s, 1 H), 7.60-7.72 (m, 2 H), 7.92 (d, J = 8.31 Hz, 1 H), 8.00-8.08 (m, 1 H), 8.10-8.27 (m, 3 H), 8.69 (d, J = 1.47 Hz, 1 H), (Exchangeable proton not observed). $^{19}$F NMR (400 MHz, DMSO-$d_6$) δ ppm- 107.8. |

| Ex. | Structure | Name | LCMS (M + H)⁺ | HPLC/LCMS Method: RT (min.), Purity | NMR |
|---|---|---|---|---|---|
| 4-II | 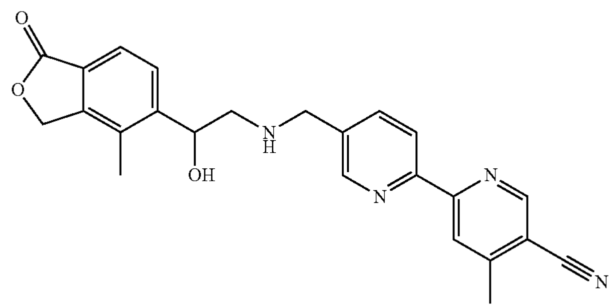 | 5'-(((2-hydroxy-2-(4-methyl-1-oxo-1,3-dihydroisobenzofuran-5-yl)ethyl)amino)methyl)-4-methyl-[2,2'-bipyridine]-5-carbonitrile (Enantiomer-II) | 415.1 | A: 1.20, 96.91% B: 1.545, 96.97% | $^1$H NMR (400 MHz, DMSO-d$_6$) δ ppm 2.20 (s, 3 H), 2.60 (br. s, 3 H), 2.61-2.72 (m, 2 H), 3.92 (br. s, 2 H), 5.00-5.11 (m, 1 H), 5.36 (d, J = 2.4 Hz, 2 H), 5.46-5.64 (m, 1 H), 7.59-7.76 (m, 2 H), 7.96 (d, J = 7.34 Hz, 1 H), 8.38 (d, J = 8 Hz, 1 H), 8.46 (s, 1 H), 8.68 (br. s, 1 H), 9.01 (s, 1 H), (Exchangeable proton not observed). |
| 7-II | 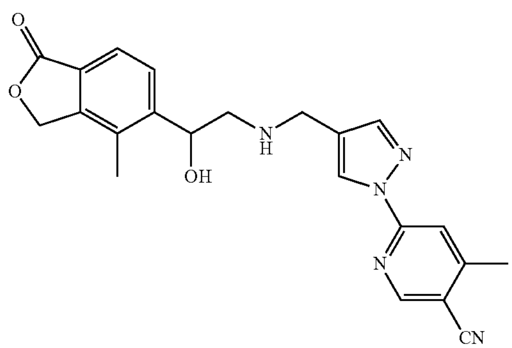 [SMILES: Cc1cc(-n2cc(CNCC(O)c3ccc4c(c3C)COC4=O)cn2)ncc1C#N] | 6-(4-(((2-hydroxy-2-(4-methyl-1-oxo-1,3-dihydroisobenzofuran-5-yl)ethyl)amino)methyl)-1H-pyrazol-1-yl)-4-methylnicotinonitrile (Enantiomer-II) | 404.2 | A: 1.171, 98.978% B: 1.439, 98.625% XI: 14.62 100% ee | $^1$H NMR (400 MHz, DMSO-d$_6$) δ ppm 2.26 (s, 3 H), 2.60 (s, 3 H), 2.90-3.02 (m, 1 H), 3.08-3.18 (m, 1 H), 4.20-4.29 (m, 2 H), 5.18-5.27 (m, 1 H), 5.36-5.43 (m, 2 H), 6.26-6.39 (m, 1 H), 7.73 (s, 2 H), 8.02. (d, J = 4.40 Hz, 1 H), 8.79-8.91 (m, 2 H), 9.03-9.14 (m, 2 H). |
| 10-II | 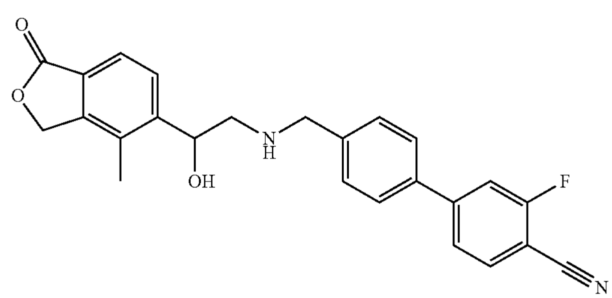 [SMILES: Cc1c(C(O)CNCc2ccc(-c3ccc(C#N)c(F)c3)cc2)ccc2c1COC2=O] | 3-fluoro-4'-(((2-hydroxy-2-(4-methyl-1-oxo-1,3-dihydroisobenzofuran-5-yl)ethyl)amino)methyl)-[1,1'-biphenyl]-4-carbonitrile (Enantiomer-II) | 417 | A: 1.35, 97.14% B: 1.81, 97.7 % IV: 21.16, 98.0% ee | $^1$H NMR (400 MHz, DMSO-d$_6$) δ 2.21 (s, 3 H), 2.58-2.67 (m, 2 H), 3.82 (s, 2 H), 4.98-5.07 (m, 1 H), 5.36 (d, J = 2.4 Hz, 2 H), 5.50 (br. s, 1 H), 7.46 (d, J = 8.3 Hz, 2 H). 7.61-7.69 (m, 2H), 7.71-7.80 (m, 3 H), 7.88 (dd, J = 11.2, 1.5 Hz, 1 H), 7.98 (dd, J = 8.1, 7.1 Hz, 1 H), (Exchangeable proton not observed). $^{19}$F NMR (400 MHz, DMSO-d$_6$) δ ppm- 108.18. |

-continued

| Ex. | Structure | Name | LCMS (M + H)+ | HPLC/LCMS Method: RT (min.), Purity | NMR |
|---|---|---|---|---|---|
| 12-II | 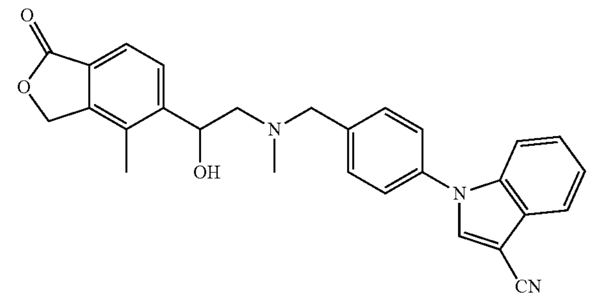 [SMILES: Cc1c(C(O)CN(C)Cc2ccc(-n3cc(C#N)c4ccccc43)cc2)ccc2c1COC2=O] | 1-(4-(((2-hydroxy-2-(4-methyl-1-oxo-1,3-dihydro-isobenzofuran-5-yl)ethyl)(methyl)amino)methyl)phenyl)-1H-indole-3-carbonitrile (Enantiomer-II) | 452.2 | A: 1.545, 100% B: 2.244, 100% XI: 9.93 100% ee | 1H NMR (400 MHz, DMSO-d6) δ ppm 2.22 (s, 3 H), 2.34 (s, 3 H), 2.53-2.61 (m, 2 H), 3.62-3.70 (m, 2 H), 5.10-5.17 (m, 1 H), 5.33-5.41 (m, 3 H), 7.36-7.42 (m, 2 H), 7.45-7.50 (m, 2 H), 7.53-7.59 (m, 3 H), 7.66 (s, 2 H), 7.73-7.79 (m, 1 H), 8.55-8.59 (m, 1 H). |
| 14-I | 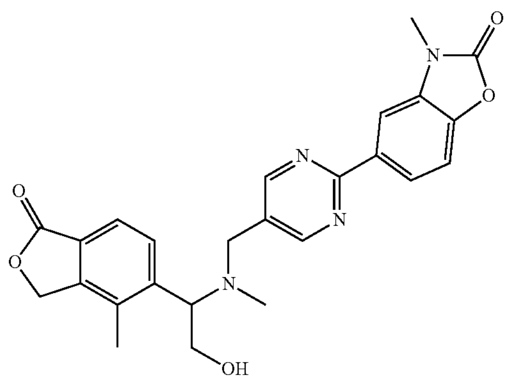 [SMILES: Cc1c(C(CO)N(C)Cc2cnc(-c3ccc4oc(=O)n(C)c4c3)nc2)ccc2c1COC2=O] | 5-(5-(((2-hydroxy-1-(4-methyl-1-oxo-1,3-dihydroiso-benzofuran-5-yl)ethyl)(methyl)amino)methyl)pyrimidin-2-yl)-3-methylbenzo[d]oxazol-2(3H)-one (Enantiomer-I) | 461.1 | A: 1.17, 96.6% B: 1.68, 97.3% III: 19.57, 97.0% ee | 1H NMR (400 MHz, DMSO-d6) δ ppm 2.18 (s, 3 H), 2.34 (s, 3 H), 3.39-3.48 (m, 3 H), 3.67 (d, J = 3.51 Hz, 2 H), 3.74-3.83 (m, 1 H), 3.95-4.05 (m, 2 H), 4.84 (br. s, 1 H), 5.42 (s, 2 H), 7.47 (d, J = 8.53 Hz, 1 H), 7.71 (s, 1 H), 7.74-7.81 (m, 1 H), 8.16 (d, J = 1.51 Hz, 1 H), 8.19-8.26 (m, 1 H), 8.77 (s, 2 H). |
| 15-I | 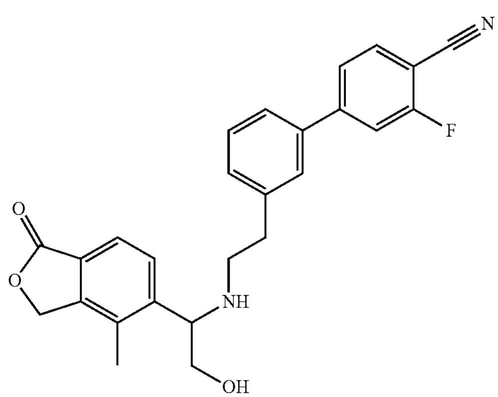 [SMILES: Cc1c(C(CO)NCCc2cccc(-c3ccc(C#N)c(F)c3)c2)ccc2c1COC2=O] | 3-fluoro-3'-(2-((2-hydroxy-1-(4-methyl-1-oxo-1,3-dihydroisobenzo-furan-5-yl)ethyl)amino)ethy)-[1,1'-biphenyl]-4-carbonitrile (Enantiomer-I) | 431.1 | A: 1.52, 97.86% B: 1.90, 95.97% | 1H NMR (400 MHz, DMSO-d6) δ ppm 2.27 (s, 3 H), 2.54-2.62 (m, 1 H), 2.67-2.74 (m, 1 H), 2.78 (d, J = 6.85 Hz, 2 H), 3.24-3.27 (m, 1 H), 3.40-3.49 (m, 1 H), 4.08-4.15 (m, 1 H), 4.96 (s, 1 H), 5.35 (s, 2 H), 7.28 (d, J = 7.58 Hz, 1 H), 7.41 (t, J = 7.58 Hz, 1 H), 7.54-7.67 (m, 4 H), 7.72 (dd, J = 8.07, 1.47 Hz, 1 H), 7.84 (dd, J = 11.13, 1.35 Hz, 1 H), 7.98 (t, J = 7.58 Hz, 1 H). (Exchangeable proton not observed). 19F NMR (400 MHz, DMSO-d6) δ ppm- 108.19. |

-continued

| Ex. | Structure | Name | LCMS (M + H)+ | HPLC/ LCMS Method: RT (min.), Purity | NMR |
|---|---|---|---|---|---|
| 15-II | 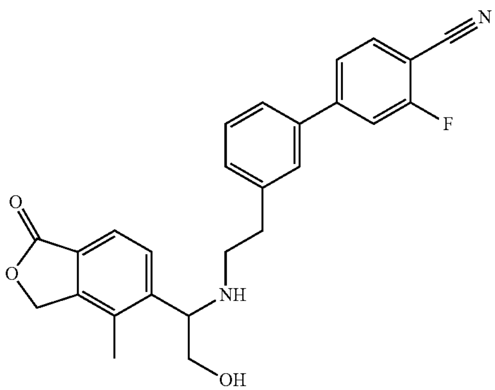 [SMILES: Cc1c(C(CO)NCCc2cccc(-c3ccc(C#N)c(F)c3)c2)ccc2c1COC2=O] | 3-fluoro-3'-(2-((2-hydroxy-1-(4-methyl-1-oxo-1,3-dihydroisobenzofuran-5-yl)ethyl)amino)ethy)-[1,1'-biphenyl]-4-carbonitrile (Enantiomer-II) | 431.1 | A: 1.51, 97.01% B: 1.90, 96.36% | ¹H NMR (400 MHz, DMSO-d₆) δ ppm 2.27 (s, 3 H), 2.54-2.62 (m, 1 H), 2.67-2.74 (m, 1 H), 2.78 (d, J = 6.85 Hz, 2 H), 3.24-3.27 (m, 1 H). 3.40-3.49 (m, 1 H), 4.08-4.15 (m, 1 H), 4.96 (s, 1 H), 5.35 (s, 2 H), 7.28 (d, J = 7.58 Hz, 1 H), 7.41 (t, J = 7.58 Hz, 1 H), 7.54-7.67 (m, 4 H), 7.72 (dd, J = 8.07, 1.47 Hz, 1 H), 7.84 (dd, J = 11.13, 1.35 Hz, 1 H), 7.98 (t, J = 7.58 Hz, 1 H), (Exchangeable proton not observed). ¹⁹F NMR (400 MHz, DMSO-d₆) δ ppm- 108.19. |
| 16-I | 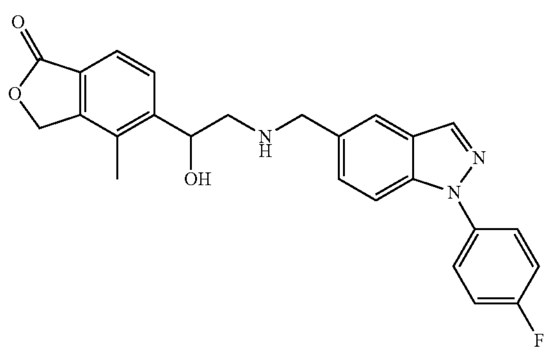 [SMILES: Cc1c(C(O)CNCc2ccc3c(cnn3-c3ccc(F)cc3)c2)ccc2c1COC2=O] | 5-(2-(((1-(4-fluorophenyl)-1H-indazol-5-yl)methyl)amino)-1-hydroxy ethyl)-4-methylisobenzofuran-1(3H)-one (Enantiomer-I) | 432.0 | A: 1.38, 95.7% B: 1.72, 95.1% | ¹H NMR (400 MHz, DMSO-d₆) δ ppm 2.22 (s, 3 H), 2.62-2.70 (m, 2 H), 3.91 (s, 2 H), 5.05 (dd, J = 7.70, 4.28 Hz, 1 H), 5.36 (d, J = 2.93 Hz, 2 H), 5.40 (d, J = 5.38 Hz, 1 H), 7.41-7.46 (m, 2 H), 7.49 (dd, J = 8.56, 1.47 Hz, 1 H), 7.67 (d, J = 19.81 Hz, 2 H), 7.75 (d, J = 8.56 Hz, 1 H), 7.77-7.82 (m, 4 H), 8.31 (d, J = 0.73 Hz, 1 H). |
| 17-I | 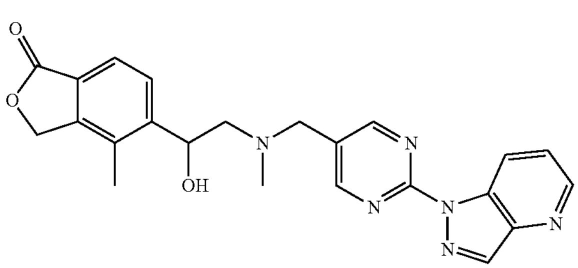 [SMILES: Cc1c(C(O)CN(C)Cc2cnc(-n3ncc4ncccc43)nc2)ccc2c1COC2=O] | 5-(2-(((2-(1H-pyrazolo[4,3-b]pyridin-1-yl)pyrimidin-5-yl)methyl)(mehyl)amino)-1-hydroxyethyl)-4-methylisobenzofuran-1(3H)-one (Enantiomer-I) | 431.0 | A: 0.87. 100% B: 1.39, 100% | ¹H NMR (400 MHz, DMSO-d₆) δ ppm 2.22 (s, 3 H), 2.39 (s, 3 H), 2.55-2.68 (m, 2 H), 3.67 (d, J = 4.16 Hz, 2 H), 5.11 (br. s, 1 H), 5.34 (s, 2 H), 5.40 (d, J = 3.42 Hz, 1 H), 7.55-7.67 (m, 3 H), 8.66-8.74 (m, 4 H), 8.93 (d, J = 8.56 Hz, 1 H). |

-continued

| Ex. | Structure | Name | LCMS (M + H)+ | HPLC/LCMS Method: RT (min.), Purity | NMR |
|---|---|---|---|---|---|
| 18-I | 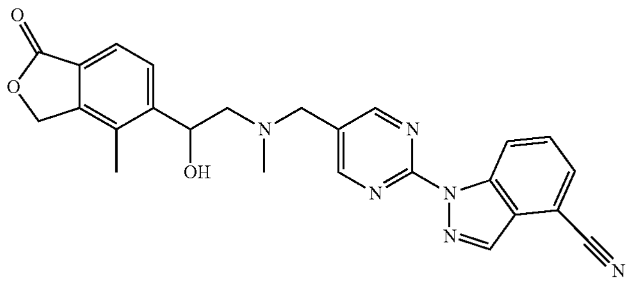 [SMILES: Cc1c(C(O)CN(C)Cc2cnc(-n3ncc4c(C#N)cccc43)nc2)ccc2c1COC2=O] | 1-(5-(((2-hydroxy-2-(4-methyl-1-oxo-1,3-dihydroiso-benzofuran-5-yl)ethyl)(methyl)amino)methyl)pyrimidin-2-yl)-1H-indazole-4-carbonitrile (Enantiomer-I) | 455.1 | A: 1.18, 100% B: 1.76, 100% II: 17.89, 97.0% ee | $^1$H NMR (400 MHz, DMSO-d$_6$) δ ppm 2.22 (s, 3 H), 2.40 (s, 3 H), 2.55 (s, 2 H), 3.69 (d, J = 3.67 Hz, 2 H), 5.12 (d, J = 2.93 Hz, 1 H), 5.35 (s, 2 H), 5.43 (d, J = 3.91 Hz, 1 H), 7.58-7.66 (m, 2 H), 7.80 (dd, J = 8.56, 7.34 Hz, 1 H), 7.97 (d, J = 7.09 Hz, 1 H), 8.72 (d, J = 0.73 Hz, 1 H), 8.75 (s, 2 H), 8.96 (d, J = 8.80 Hz, 1 H). |
| 19-I | 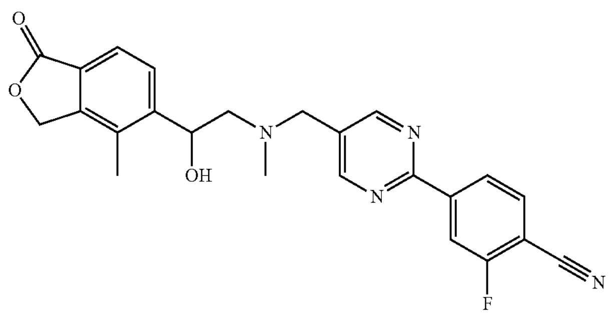 [SMILES: Cc1c(C(O)CN(C)Cc2cnc(-c3ccc(C#N)c(F)c3)nc2)ccc2c1COC2=O] | 2-fluoro-4-(5-(((2-hydroxy-2-(4-methyl-1-oxo-1,3-dihydroiso-benzofuran-5-yl)ethyl)(methyl)amino)methyl)pyrimidin-2-yl)benzonitrile (Enantimoer-I) | 433.2 | A: 1.30, 99.48% B: 1.90, 100% | $^1$H NMR (400 MHz, DMSO-d$_6$) δ ppm 2.20 (s, 3 H), 2.38 (s, 3 H), 2.65-2.69 (m, 2 H), 3.66 (s, 2 H), 5.05-5.10 (m, 1 H), 5.33 (d, J = 3.42 Hz, 2 H), 5.40 (d, J = 3.67 Hz, 1 H), 7.52-7.61 (m, 2 H), 8.06-8.13 (m, 1 H), 8.25-8.38 (m, 2 H), 8.76 (s, 2 H). $^{19}$F NMR (400 MHz, DMSO-d$_6$) δ ppm- 107.82. |
| 20-I | 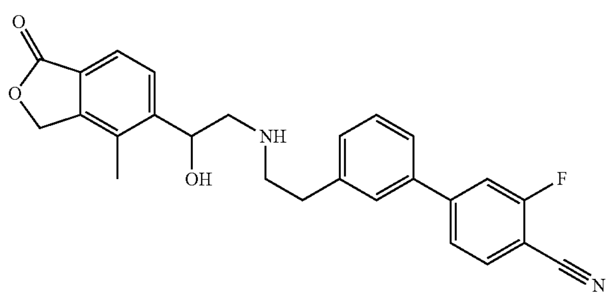 [SMILES: Cc1c(C(O)CNCCc2cccc(-c3ccc(C#N)c(F)c3)c2)ccc2c1COC2=O] | 3-fluoro-4'-(((2-hydroxy-2-(4-methyl-1-oxo-1,3-dihydro-isobenzo-furan-5-yl)ethyl)amino)methyl)-[1,1'-biphenyl]-4-carbonitrile (Enantiomer-I) | 431.1 | A: 1.56, 99.0% B: 1.73, 97.2% IV: 17.71, 99.50% ee | $^1$H NMR (400 MHz, DMSO-d$_6$) δ ppm 2.24 (s, 3 H), 2.64-2.73 (m, 2 H), 2.76-2.85 (m, 4 H), 2.86-2.92 (m, 1 H), 4.98 (dd, J = 7.95, 4.03 Hz, 1 H), 5.31-5.41 (m, 2 H), 5.47 (br. s, 1 H), 7.32 (d, J = 7.83 Hz, 1 H), 7.42 (t, J = 7.70 Hz, 1 H), 7.59-7.68 (m, 4 H), 7.75 (dd, J = 8.07, 1.71 Hz, 1 H), 7.88 (dd, J = 11.25, 1.47 Hz, 1 H), 8.00 (dd, J = 8.19, 7.21 Hz, 1 H). $^{19}$F NMR (400 MHz, DMSO-d$_6$) δ ppm- 108.19. |

| Ex. | Structure | Name | LCMS (M + H)+ | HPLC/LCMS Method: RT (min.), Purity | NMR |
|---|---|---|---|---|---|
| 20-II | 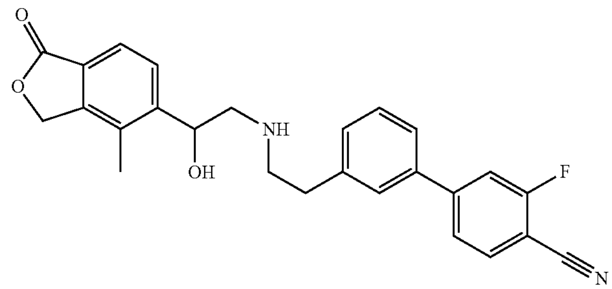 [SMILES: Cc1c(C(O)CNCCc2cccc(-c3ccc(C#N)c(F)c3)c2)ccc2c1COC2=O] | 3-fluoro-3'-(2-((2-hydroxy-2-(4-methyl-1-oxo-1,3-dihydroisobenzofuran-5-yl)ethyl)amino)ethyl)-[1,1'-biphenyl]-4-carbonitrile (Enantiomer-II) | 431.1 | A: 1.55, 99.28% B: 1.73, 98.14% IV: 11.37, 98.42% ee | $^1$H NMR (400 MHz, DMSO-d$_6$) δ ppm 2.24 (s, 3 H), 2.64-2.73 (m, 2 H), 2.76-2.85 (m, 4 H), 2.86-2.92 (m, 1 H), 4.98 (dd, J = 7.95, 4.03 Hz, 1 H), 5.31-5.41 (m, 2 H), 5.47 (br. s, 1 H), 7.32 (d, J = 7.83 Hz, 1 H), 7.42 (t, J = 7.70 Hz, 1 H), 7.59-7.68 (m, 4 H), 7.75 (dd, J = 8.07, 1.71 Hz, 1 H), 7.88 (dd, J = 11.25, 1.47 Hz, 1 H), 8.00 (dd, J = 8.19, 7.21 Hz, 1 H). $^{19}$F NMR (400 MHz, DMSO-d$_6$) δ ppm- 108.19. |
| 21-I | 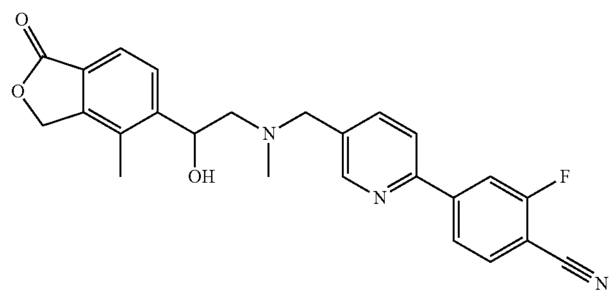 [SMILES: Cc1c(C(O)CN(C)Cc2ccc(-c3ccc(C#N)c(F)c3)nc2)ccc2c1COC2=O] | 2-fluoro-4-(5-(((2-hydroxy-2-(4-methyl-1-oxo-1,3-dihydroisobenzofuran-5-yl)ethyl)(methyl)amino)methyl)pyridin-2-yl)benzonitrile (Enantiomer-I) | 432.1 | A: 1.319, 96.59% B: 1.908, 100% III: 9.92 92.19% ee | $^1$H NMR (400 MHz, DMSO-d$_6$) δ ppm 2.20 (s, 3 H), 2.33 (s, 3 H), 2.54-2.63 (m, 2 H), 3.66 (s, 2 H), 5.09 (br. s, 1 H), 5.31-5.38 (m, 3 H), 7.61 (s, 2 H), 7.79 (d, J = 8.8 Hz, 1 H), 8.00-8.07 (m, 2 H), 8.11-8.21 (m, 2 H), 8.55 (s, 1 H). $^{19}$F NMR (400 MHz, DMSO-d$_6$) δ ppm- 108.107. |
| 21-II | 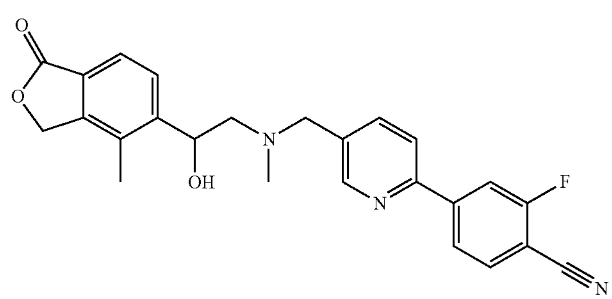 [SMILES: Cc1c(C(O)CN(C)Cc2ccc(-c3ccc(C#N)c(F)c3)nc2)ccc2c1COC2=O] | 2-fluoro-4-(5-(((2-hydroxy-2-(4-methyl-1-oxo-1,3-dihydro-isobenzofuran-5-yl)ethyl)(methyl)amino)methyl)pyridin-2-yl)benzonitrile (Enantiomer-II) | 432.1 | A: 1.313, 96.96% B: 1.908, 100% III: 10.99, 94.88% ee | $^1$H NMR (400 MHz, DMSO-d$_6$) δ ppm 2.20 (s, 3 H), 2.33 (s, 3 H), 2.54-2.63 (m, 2 H), 3.66 (s, 2 H), 5.09 (br. s, 1 H), 5.31-5.38 (m, 3 H), 7.61 (s, 2 H), 7.79 (d, J = 8.8 Hz, 1 H), 8.00-8.07 (m, 2 H), 8.11-8.21 (m, 2 H), 8.55 (s, 1 H). $^{19}$F NMR (400 MHz, DMSO-d$_6$) δ ppm- 108.107. |

| Ex. | Structure | Name | LCMS (M + H)+ | HPLC/LCMS Method: RT (min.), Purity | NMR |
|---|---|---|---|---|---|
| 22-I | 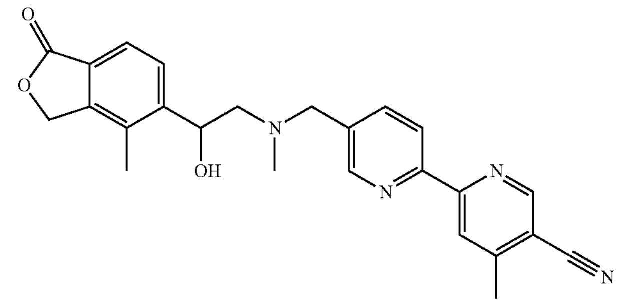 [SMILES: Cc1cc(-c2ccc(CN(C)CC(O)c3ccc4c(c3C)COC4=O)cn2)ncc1C#N] | 5'-(((2-hydroxy-2-(4-methyl-1-oxo-1,3-dihydro-isobenzofuran-5-yl)ethyl)(methyl)amino)methyl)-4-methyl-[2,2'-bipyridine]-5-carbonitrile (Enantiomer-I) | 429.4 | D: 2.40, 99.69% E: 5.69, 99.01% VI: 9.66, 96.71% ee | $^1$H NMR (400 MHz, DMSO-$d_6$) δ ppm 2.10 (s, 3 H), 2.35 (s, 3 H), 2.50-2.60 (m, 2 H), 2.60 (s, 3 H), 3.66 (s, 2 H), 5.07-5.12 (m, 1 H), 5.33 (s, 2 H), 5.38 (s, 1 H), 7.57-7.62 (m, 2 H), 7.79 (dd, 8.0 Hz, 2.4 Hz, 1 H), 8.29 (d, J = 8 Hz, 1 H), 8.42 (s, 1 H), 8.52 (d, J = 1.6 Hz, 1 H), 9.0 (s, 1 H). |
| 22-II | 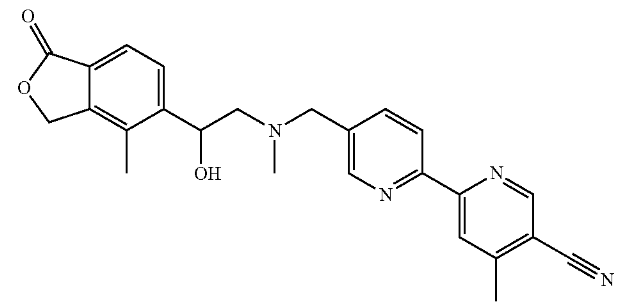 [SMILES: Cc1cc(-c2ccc(CN(C)CC(O)c3ccc4c(c3C)COC4=O)cn2)ncc1C#N] | 5'-(((2-hydroxy-2-(4-methyl-1-oxo-1,3-dihydroisobenzofuran-5-yl)ethyl)(methyl)amino)methyl)-4-methyl-[2,2'-bipyridine]-5-carbonitrile (Enantiomer-II) | 429.3 | A: 0.972, 97.49% B: 1.645, 96.64% VI: 16.08, 96.62% ee | $^1$H NMR (400 MHz, DMSO-$d_6$) δ ppm 2.10 (s, 3 H), 2.35 (s, 3 H), 2.50-2.60 (m, 2 H), 2.60 (s, 3 H), 3.66 (s, 2 H), 5.07-5.12 (m, 1 H), 5.33 (s, 2 H), 5.38 (s, 1 H), 7.57-7.62 (m, 2 H), 7.79 (dd, 8.0 Hz, 2.4 Hz, 1 H), 8.29 (d, J = 8 Hz, 1 H), 8.42 (s, 1 H), 8.52 (d, J = 1.6 Hz, 1 H), 9.0 (s, 1 H). |
| 23-I | 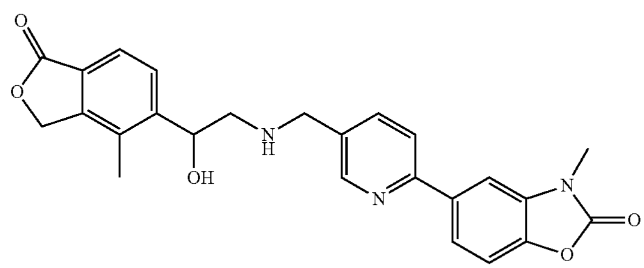 [SMILES: Cc1c(C(O)CNCc2ccc(-c3ccc4oc(=O)n(C)c4c3)nc2)ccc2c1COC2=O] | 5-(5-(((2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one (Enantiomer-I) | 446.3 | A: 0.877, 99.13% B: 1.204, 99.15% VI: 9.028, 93.778% ee | $^1$H NMR (400 MHz, DMSO-$d_6$) δ ppm 2.23 (s, 3 H), 2.61-2.73 (m, 2 H), 3.42 (s, 3 H), 3.88 (br. s, 2 H), 5.05 (br. s, 1 H), 5.32-5.41 (m, 2 H), 5.58 (br. s, 1 H), 7.42 (d, J = 8.53 Hz, 1 H), 7.63-7.70 (m, 2 H), 7.81-7.90 (m, 2H), 7.92-8.03 (m, 2 H), 8.60 (s, 1 H), (Exchangeable proton not observed). |
| 24-I | 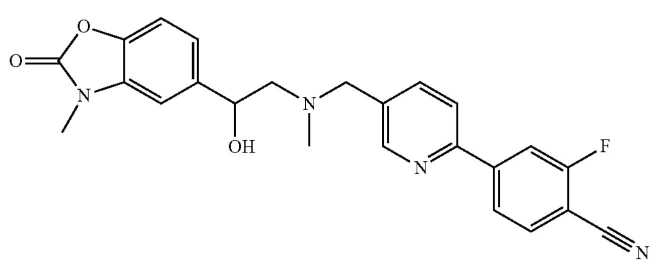 [SMILES: CN(Cc1ccc(-c2ccc(C#N)c(F)c2)nc1)CC(O)c1ccc2oc(=O)n(C)c2c1] | 2-fluoro-4-(5-(((2-hydroxy-2-(3-methyl-2-oxo-2,3-dihydrobenzo[d]oxazol-5-yl)ethyl)(methyl)amino)methyl)pyridin-2-yl)benzonitrile (Enantiomer-I) | 433.2 | D: 2.446, 98.72% C:10.10, 95.46% VIII: 7.93, 100% ee | $^1$H NMR (400 MHz, DMSO-$d_6$) δ ppm 2.28 (s, 3 H), 2.54-2.72 (m, 2 H), 3.28 (s, 3 H), 3.56-3.73 (m, 2 H), 4.79 (br. s, 1 H), 5.25 (d, J = 4.02 Hz, 1 H), 7.03-7.10 (m, 1 H), 7.16 (d, J = 1.51 Hz, 1H), 7.25 (d, J = 8.03 Hz, 1 H), 7.79 (dd, J = 8.28 Hz, 2.26 Hz, 1 H), 8.00-8.10 |

| Ex. | Structure | Name | LCMS (M + H)+ | HPLC/ LCMS Method: RT (min.), Purity | NMR |
|---|---|---|---|---|---|
| | | | | | (m, 2 H), 8.11-8.24 (m, 2 H), 8.55 (d, J = 2.01 Hz, 1 H). |
| 24-II | 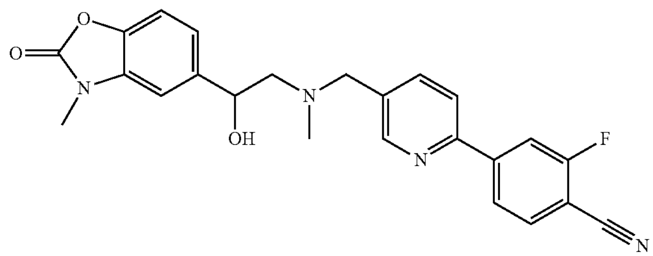 [SMILES: CN(Cc1ccc(-c2ccc(C#N)c(F)c2)nc1)CC(O)c1ccc2oc(=O)n(C)c2c1] | 2-fluoro-4-(5-(((2-hydroxy-2-(3-methyl-2-oxo-2,3-dihydrobenzo[d]oxazol-5-yl)ethyl)(methyl)amino)methyl)pyridin-2-yl)benzonitrile (Enantiomer-II) | 433.2 | G: 13.506, 94.46% F: 11.885, 94.09% VIII: 12.42, 100% ee | $^1$H NMR (400 MHz, DMSO-d$_6$) δ ppm 2.28 (s, 3 H), 2.54-2.72 (m, 2 H), 3.28 (s, 3 H), 3.56-3.73 (m, 2 H), 4.79 (br. s, 1 H), 5.25 (d, J = 4.02 Hz, 1 H), 7.03-7.10 (m, 1 H), 7.16 (d, J = 1.51 Hz, 1H), 7.25 (d, J = 8.03 Hz, 1 H), 7.79 (dd, J = 8.28 Hz, 2.26 Hz, 1 H), 8.00-8.10 (m, 2 H), 8.11-8.24 (m, 2 H), 8.55 (d, J = 2.01 Hz, 1 H). |
| 25-I | 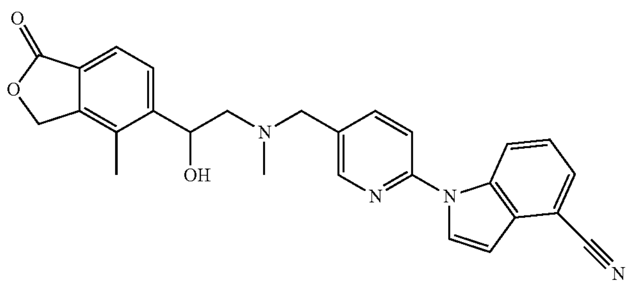 [SMILES: Cc1c(C(O)CN(C)Cc2ccc(-n3ccc4c(C#N)cccc43)nc2)ccc2c1COC2=O] | 1-(5-(((2-hydroxy-2-(4-methyl-1-oxo-1,3-dihydroisobenzofuran-5-yl)ethyl)(methyl)amino)methyl)pyridin-2-yl)-1H-indole-4-carbonitrile (Enantiomer-I) | 453.2 | A: 1.424, 100% B: 2.102, 100% VII: 8.93, 99.65% ee | $^1$H NMR (400 MHz, DMSO-d$_6$) δ ppm 2.22 (s, 3 H), 2.36 (s, 3 H), 2.54-2.65 (m, 2 H), 3.67 (s, 2 H), 5.04-5.18 (m, 1 H), 5.32-5.44 (m, 3 H), 6.92 (d, J = 3.42 Hz, 1 H), 7.43 (t, J = 7.6 Hz, 1 H), 7.64 (s, 2 H), 7.72 (t, J = 8 Hz, 2 H), 7.85 (dd, J = 8.4 Hz, 2 Hz, 1H), 8.31 (d, J = 3.42 Hz, 1 H), 8.41 (d, J = 1.96 Hz, 1 H), 8.69 (d, J = 8.56 Hz, 1 H). |
| 25-II | 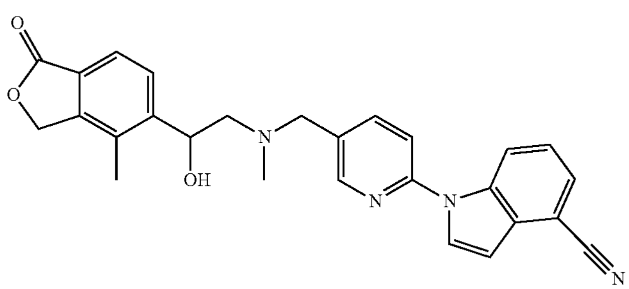 [SMILES: Cc1c(C(O)CN(C)Cc2ccc(-n3ccc4c(C#N)cccc43)nc2)ccc2c1COC2=O] | 1-(5-(((2-hydroxy-2-(4-methyl-1-oxo-1,3-dihydroisobenzofuran-5-yl)ethyl)(methyl)amino)methyl)pyridin-2-yl)-1H-indole-4-carbonitrile (Enantiomer-II) | 453.2 | A: 1.420, 99.55% B: 2.101, 100% VII: 12.70, 95.894% ee | $^1$H NMR (400 MHz, DMSO-d$_6$) δ ppm 2.22 (s, 3 H), 2.36 (s, 3 H), 2.54-2.65 (m, 2 H), 3.67 (s, 2 H), 5.04-5.18 (m, 1 H), 5.32-5.44 (m, 3 H), 6.92 (d, J = 3.42 Hz, 1 H), 7.43 (t, J = 7.6 Hz, 1 H), 7.64 (s, 2 H), 7.72 (t, J = 8 Hz, 2 H), 7.85 (dd, J = 8.4 Hz, 2 Hz, 1H), 8.31 (d, J = 3.42 Hz, 1 H), 8.41 (d, J = 1.96 Hz, 1 H), 8.69 (d, J = 8.56 Hz, 1 H). |

-continued

| Ex. | Structure | Name | LCMS (M + H)+ | HPLC/LCMS Method: RT (min.), Purity | NMR |
|---|---|---|---|---|---|
| 27-I | 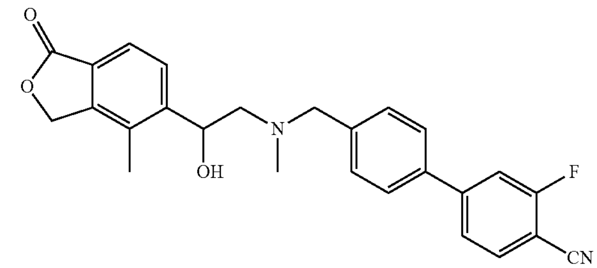 [SMILES: Cc1c(C(O)CN(C)Cc2ccc(-c3ccc(C#N)c(F)c3)cc2)ccc2c1COC2=O] | 3-fluoro-4'-(((2-hydroxy-2-(4-methyl-1-oxo-1,3-dihydroisobenzofuran-5-yl)ethyl)(methyl)amino)methyl)-[1,1'-biphenyl]-4-carbonitrile (Enantiomer-I) | 431.2 | A: 1.456, 98.99 % B: 2.204, 99.68% IX: 17.89 97.04% ee | $^1$H NMR (400 MHz, DMSO-d$_6$) δ 2.20 (s, 3 H), 2.3 (s, 3 H), 2.53-2.62 (m, 2 H), 3.57-3.64 (m, 2 H), 5.07-5.13 (m, 1 H), 5.29-5.40 (m, 3 H), 7.31-7.43 (m, 2 H), 7.63 (s, 2 H), 7.68-7.78 (m, 3 H), 7.85-7.92 (m, 1 H), 7.95 -8.03 (m, 1 H). |
| 27-II | 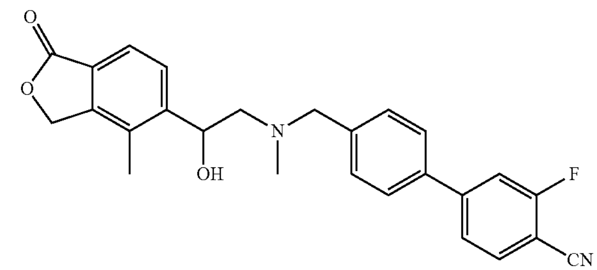 [SMILES: Cc1c(C(O)CN(C)Cc2ccc(-c3ccc(C#N)c(F)c3)cc2)ccc2c1COC2=O] | 3-fluoro-4'-(((2-hydroxy-2-(4-methyl-1-oxo-1,3-dihydroisobenzofuran-5-yl)ethyl)(methyl)amino)methyl)-[1,1'-biphenyl]-4-carbonitrile (Enantiomer-II) | 431.1 | A: 1.44, 100% B; 2.217, 100% XI: 8,80 100% | $^1$H NMR (400 MHz, DMSO-d$_6$) δ 2.20 (s, 3 H), 2.31 (s, 3 H), 2.53-2.62 (m, 2 H), 3.57-3.64 (m, 2 H), 5.07-5.13 (m, 1 H), 5.29-5.40 (m, 3 H), 7.31-7.43 (m, 2 H), 7.63 (s, 2 H), 7.68-7.78 (m, 3 H), 7.85-7.92 (m, 1 H), 7.95-8.03 (m, 1 H). |
| 28-I | 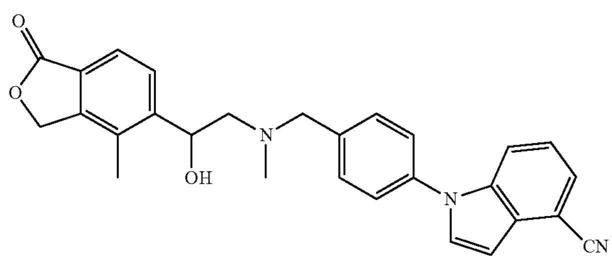 [SMILES: Cc1c(C(O)CN(C)Cc2ccc(-n3ccc4c(C#N)cccc43)cc2)ccc2c1COC2=O] | 1-(4-(((2-hydroxy-2-(4-methyl-1-oxo-1,3-dihydroisobenzofuran-5-yl)ethyl)(methyl)amino)methyl)phenyl)-1H-indole-4-carbonitrile (Enantiomer-I) | 452.2 | A: 1.503, 99.86% B: 2.286, 100% IX: 20.55 99.08% ee | $^1$H NMR (400 MHz, DMSO-d$_6$) δ 2.23 (s, 3 H), 2.35 (s, 3 H), 2.55-2.62 (m, 2 H), 3.66 (d, J = 5.0 Hz, 2 H), 5.09-5.16 (m, 1 H), 5.33-5.41 (m, 3 H), 6.82-6.89 (m, 1 H), 7.37 (dd, J = 8.5, J = 7.5 Hz, 1 H), 7.44-7.48 (m, 2H), 7.50-7.54 (m, 2 H), 7.63-7.71 (m, 3 H), 7.84 (d, J = 8.5 Hz, 1 H), 7.94 (d, J = 3.5 Hz, 1 H). |
| 28-II | 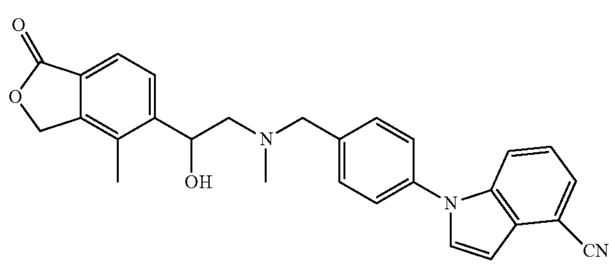 [SMILES: Cc1c(C(O)CN(C)Cc2ccc(-n3ccc4c(C#N)cccc43)cc2)ccc2c1COC2=O] | 1-(4-(((2-hydroxy-2-(4-methyl-1-oxo-1,3-dihydro-isobenzofuran-5-yl)ethyl)(methyl)amino)methyl)phenyl)-1H-indole-4-carbonitrile (Enantiomer-II) | 452.2 | A: 1.529, 99.59% B: 2.356, 99.464% XI: 9.72 100% ee | $^1$H NMR (400 MHz, DMSO-d$_6$) δ 2.23 (s, 3 H), 2.35 (s, 3 H), 2.55-2.62 (m, 2 H), 3.66 (d, J = 5.0 Hz, 2 H), 5.09-5.16 (m, 1 H), 5.33-5.41 (m, 3 H), 6.82-6.89 (m, 1 H), 7.37 (dd, J = 8.5, J = 7.5 Hz, 1 H), 7.44-7.48 (m, 2H), 7.50-7.54 (m, 2 H), 7.63-7.71 (m, 3 H), 7.84 (d, J = 8.5 Hz, 1 H), 7.94 (d, J = 3.5 Hz, 1 H). |

-continued

| Ex. | Structure | Name | LCMS (M + H)+ | HPLC/LCMS Method: RT (min.), Purity | NMR |
|---|---|---|---|---|---|
| 29 | 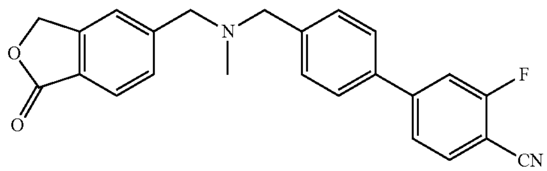 [SMILES: CN(Cc1ccc(-c2ccc(C#N)c(F)c2)cc1)Cc1ccc2c(c1)COC2=O] | 3-fluoro-4'-((methyl((1-oxo-1,3-dihydroisobenzofuran-5-yl)methyl)amino)methyl)-[1,1'-biphenyl]-4-carbonitrile | 387.1 | A: 1.459, 93.581% B: 2.301, 93.77% | $^1$H NMR (400 MHz, DMSO-$d_6$) δ 2.09-2.18 (m, 3 H), 3.60-3.72 (m, 4 H), 5.38-5.45 (m, 2 H), 7.48-7.55 (m, 2 H), 7.58-7.64 (m, 1 H), 7.63-7.71 (m, 1 H), 7.71-7.85 (m, 4 H), 7.87-7.94 (m, 1 H), 7.97-8.07 (m, 1 H). |
| 30-II | 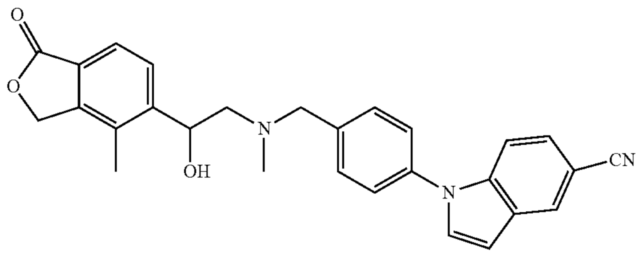 [SMILES: Cc1c(C(O)CN(C)Cc2ccc(-n3ccc4cc(C#N)ccc43)cc2)ccc2c1COC2=O] | 1-(4-(((2-hydroxy-2-(4-methyl-1-oxo-1,3-dihydroisobenzofuran-5-yl)ethyl)(methyl)amino)methyl)phenyl)-1H-indole-5-carbonitrile (Enantiomer-II) | 452.2 | A: 1.485, 99.63% B: 2.140, 99.6% XI: 10.72 100% ee | $^1$H NMR (400 MHz, DMSO-$d_6$) δ ppm 2.22 (s, 3 H), 2.34 (s, 3 H), 2.55-2.61 (m, 2 H), 3.59-3.70 (m, 2 H), 5.09-5.14 (m, 1 H), 5.38 (s, 3 H), 6.84-6.89 (m. 1 H), 7.47 (d, J = 12.23 Hz, 5 H), 7.65 (s, 3 H), 7.82-7.87 (m, 1 H), 8.19-8.24 (m, 1 H). |
| 31-I | 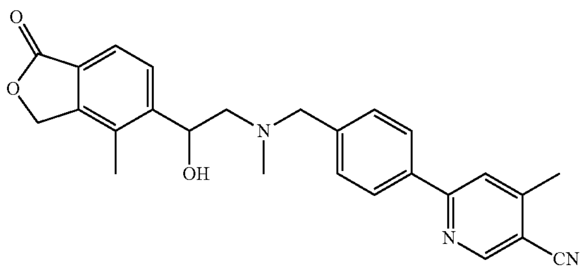 [SMILES: Cc1cc(-c2ccc(CN(C)CC(O)c3ccc4c(c3C)COC4=O)cc2)ncc1C#N] | 6-(4-(((2-hydroxy-2-(4-methyl-1-oxo-1,3-dihydroisobenzofuran-5-yl)ethyl)(methyl)amino)methyl)phenyl)-4-methyl nicotinonitrile (Enantiomer-I) | 428.2 | A: 1.306, 100% B: 1.983, 100% XI: 12.77 100% ee | $^1$H NMR (400 MHz, DMSO-$d_6$) δ ppm 2.18 (s, 3 H), 2.32 (s, 3 H), 2.52-2.55 (m, 2 H), 2.57 (s, 3 H), 3.58-3.68 (m, 2 H), 5.04-5.17 (m, 1 H), 5.30-5.40 (m, 3 H), 7.33-7.43 (m, 2 H), 7.63 (s, 2 H), 7.99-8.12 (m, 3 H), 8.88-9.00 (m, 1 H). |
| 31-II | 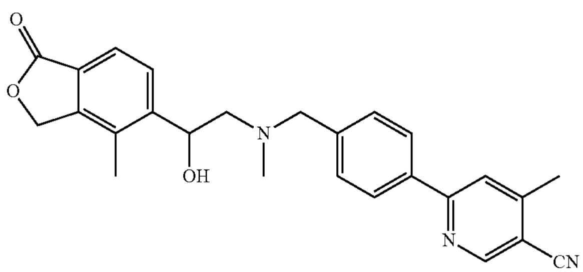 [SMILES: Cc1cc(-c2ccc(CN(C)CC(O)c3ccc4c(c3C)COC4=O)cc2)ncc1C#N] | 6-(4-(((2-hydroxy-2-(4-methyl-1-oxo-1,3-dihydroisobenzofuran-5-yl)ethyl)(methyl)amino)methyl)phenyl)-4-methyl nicotinonitrile (Enantiomer-II) | 428.2 | A: 1.334, 100% B: 1.957, 98.63% XI: 14.67 100% ee | $^1$H NMR (400 MHz, DMSO-$d_6$) δ ppm 2.18 (s, 3 H), 2.32 (s, 3 H), 2.52-2.55 (m, 2 H), 2.57 (s, 3 H), 3.58-3.68 (m, 2 H), 5.04-5.17 (m, 1 H), 5.30-5.40 (m, 3 H), 7.33-7.43 (m, 2 H), 7.63 (s, 2 H), 7.99-8.12 (m, 3 H), 8.88-9.00 (m, 1 H). |
| 32-I | 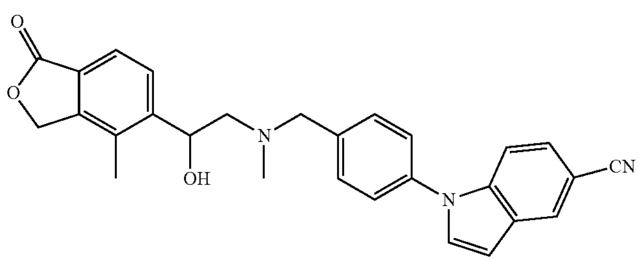 [SMILES: Cc1c(C(O)CN(C)Cc2ccc(-n3ccc4cc(C#N)ccc43)cc2)ccc2c1COC2=O] | 1-(4-(((2-hydroxy-2-(4-methyl-1-oxo-1,3-dihydroisobenzofuran-5-yl)ethyl)(methyl)amino)methyl)phenyl)-1H-indole-5-carbonitrile (Enantiomer-I) | 452.1 | A: 1.486, 99.687% B: 2.141, 98.623% XI: 10.23 100% ee | $^1$H NMR (400 MHz, DMSO-$d_6$) δ ppm 2.22 (s, 3 H), 2.34 (s, 3 H), 2.55-2.61 (m, 2 H), 3.59-3.70 (m, 2 H), 5.09-5.14 (m, 1 H), 5.38 (s, 3 H), 6.84-6.89 (m, 1 H), 7.47 (d, J = 12.23 Hz, 5 H), 7.65 (s, 3 H), |

| Ex. | Structure | Name | LCMS (M + H)+ | HPLC/LCMS Method: RT (min.), Purity | NMR |
|---|---|---|---|---|---|
| | | | | | 7.82-7.87 (m, 1 H), 8.19-8.24 (m, 1 H). |
| 33-I | 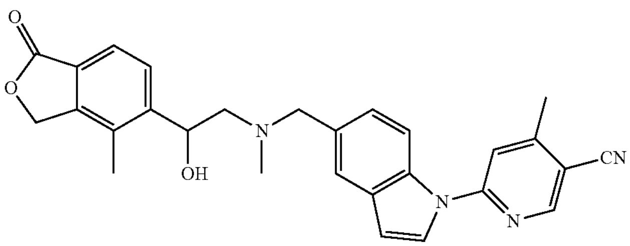 [SMILES: Cc1cc(-n2ccc3cc(CN(C)CC(O)c4ccc5c(c4C)COC5=O)ccc32)ncc1C#N] | 6-(5-(((2-hydroxy-2-(4-methyl-1-oxo-1,3-dihydroisobenzofuran-5-yl)ethyl)(methyl)amino)methyl)-1H-indol-1-yl)-4-methylnicotinonitrile (Enantiomer-I) | 467.3 | A: 1.264, 97.665% B: 1.905, 97.939% | ¹H NMR (400 MHz, CDCl₃) δ ppm 2.02-2.25 (m, 4 H), 2.67 (s, 8 H), 4.05-4.19 (m, 2 H), 5.15-5.33 (m, 3 H), 6.72-6.82 (m, 1 H), 7.42 (s, 2 H), 7.75 (d, J = 4.65 Hz, 4 H), 8.38-8.49 (m, 1 H), 8.75 (s, 1 H). |
| 34-I | 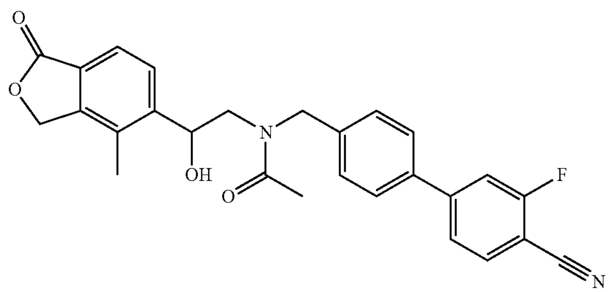 [SMILES: CC(=O)N(Cc1ccc(-c2ccc(C#N)c(F)c2)cc1)CC(O)c1ccc2c(c1C)COC2=O] | N-((4'-cyano-3'-fluoro-[1,1'-biphenyl]-4-yl)methyl)-N-(2-hydroxy-2-(4-methyl-1-oxo-1,3-dihydroisobenzofuran-5-yl)ethyl)acetamide (Enantiomer-I) | 459.0 | A: 1.837, 96.570%, B: 1.829, 97.290% | ¹H NMR (400 MHz, CDCl₃) δ ppm 2.26 (d, J = 12.47 Hz, 3 H), 3.49-3.57 (m, 1 H), 3.60-3.71 (m, 1 H), 4.02-4.12 (m, 2 H), 4.60 (s, 1 H), 4.70 (s, 3 H), 5.23 (s, 2 H), 5.35-5.41 (m, 1 H), 7.30 (s, 2 H), 7.37-7.48 (m, 2 H), 7.59 (d, J = 8.07 Hz, 1 H), 7.70 (s, 2 H), 7.79 (s, 2 H). |

Intermediate 18: 6-(4-formyl-1H-imidazol-1-yl)-4-methoxynicotinonitrile

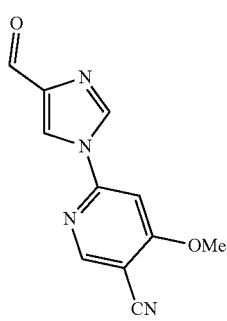 [SMILES: COc1cc(-n2cnc(C=O)c2)ncc1C#N]

To a solution of 1H-imidazole-4-carbaldehyde (0.50 g, 5.20 mmol) and 6-chloro-4-methoxynicotinonitrile (1.05 g, 6.24 mmol) in DMF (10 mL) was added K₂CO₃ (1.08 g, 7.81 mmol) at ambient temperature under a nitrogen atmosphere. The resulting reaction mixture was heated at 90° C. for 1 h. The reaction mixture was cooled to ambient temperature and diluted with ice water (30 mL). The resulting precipitate was filtered and was washed with ethanol (2 mL) to obtain Intermediate 18 (0.30 g, 25.00%). ¹H NMR (400 MHz, DMSO-d₆) δ ppm 4.13 (s, 3H), 7.81 (s, 1H), 8.83 (s, 2H), 8.95 (d, J=1.19 Hz, 1H), 9.87 (s, 1H). LCMS (Method-L): retention time 0.75 min, [M+H] 229.1.

Intermediate 19: 6-(4-methyl-1H-imidazol-1-yl)nicotinaldehyde

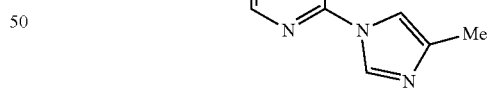

To a stirring solution of 6-bromonicotinaldehyde (1.25 g, 6.72 mmol) in DMF (10 mL) was added K₂CO₃ (2.32 g, 16.80 mmol) and 4-methyl-1H-imidazole (0.55 g, 6.72 mmol). The resulting mixture was heated at 100° C. for 1 h then cooled to ambient temperature. The reaction was poured into ice water (30 mL) and extracted with ethyl acetate (2×75 mL). The combined organic layers were washed with brine (50 mL), dried over sodium sulfate and evaporated under reduced pressure. The residue was purified by flash chromatography (Redisep-40 g, 0-100% EtOAc/n-Hexane)) to obtain Intermediate 19 (0.50 g, 39.70%) as a light brown solid. ¹H NMR (300 MHz, DMSO-d₆) δ ppm 2.50 (s, 3H), 7.76 (s, 1H), 7.95 (dd, J=6.00, 1.20 Hz, 1H), 8.39 (dd, J=6.60, 1.80 Hz, 1H), 8.55 (d, 1.20 Hz, 1H), 8.99 (s, 1H), 10.08 (s, 1H), LCMS (Method-H): retention time 1.03 min, [M+1] 188.0.

Intermediate 20: 1-(5-formylpyridin-2-yl)-1H-imidazole-4-carbonitrile

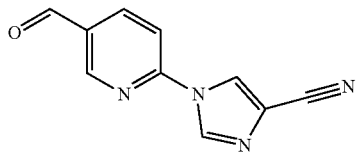 [SMILES: N#Cc1cn(-c2ccc(C=O)cn2)cn1]

Intermediate 20 was prepared (0.40 g, 37.50%) as an off-white solid, by using a similar synthetic protocol as that of Intermediate 19 and starting from 6-bromonicotinaldehyde (1.00 g, 5.38 mmol) and 1H-imidazole-4-carbonitrile. $^1$H NMR (400 MHz, DMSO-d$_6$) δ ppm 8.11 (d, J=8.53 Hz, 1H), 8.53 (dd, J=8.28, 2.26 Hz, 1H), 8.89 (d, J=1.51 Hz, 1H), 9.03 (d, J=1.51 Hz, 1H), 9.05-9.10 (m, 1H), 10.14 (s, 1H). LCMS (Method-H): retention time 0.85 min, [M+1] 199.2.

Intermediate 21: 6-(3-methyl-1H-1,2,4-triazol-1-yl)nicotinaldehyde

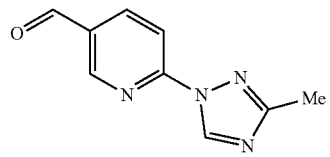 [SMILES: Cc1ncn(-c2ccc(C=O)cn2)n1]

Intermediate 21 was prepared (0.30 g, 59.30%) as an off-white solid, by using a similar synthetic protocol as that of Intermediate 19 and starting from 6-bromonicotinaldehyde (0.50 g, 2.69 mmol) and 3-methyl-1H-1,2,4-triazole (0.33 g, 4.03 mmol). $^1$H NMR (400 MHz, DMSO-d$_6$) δ ppm 2.42 (s, 3H), 7.99 (d, J=8.53 Hz, 1H), 8.47 (dd, J=8.53, 2.01 Hz, 1H), 9.02-9.04 (m, 1H), 9.37 (s, 1H), 10.12 (s, 1H). LCMS (Method-H): retention time 0.88 min, [M+1] 189.0.

Intermediate 22: 2-(3,5-dimethyl-4H-1,2,4-triazol-4-yl)pyrimidine-5-carbaldehyde

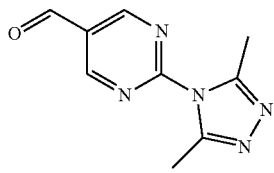

Intermediate 22 was prepared (0.08 g, 5.60%) as an off white solid, by using a similar synthetic protocol as that of Intermediate 19 and starting from 2-chloropyrimidine-5-carbaldehyde (1.00 g, 7.02 mmol) and 3,5-dimethyl-4H-1,2,4-triazole (0.68 g. 7.02 mmol). $^1$H NMR (400 MHz, CDCl$_3$) δ ppm 2.48 (s, 3H), 2.93 (s, 3H), 9.24 (s, 2H), 10.16 (s, 1H). LCMS (Method-D): retention time 0.35 min, [M+H] 204.1.

Intermediate 23: 6-(4-formyl-1H-pyrazol-1-yl)-2-methoxynicotinonitrile

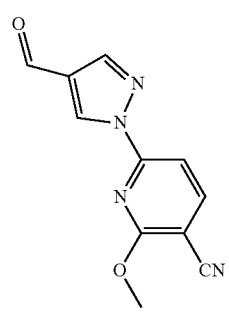 [SMILES: COc1nc(-n2cc(C=O)cn2)ccc1C#N]

Intermediate 23A: 6-Chloro-2-methoxynicotinonitrile

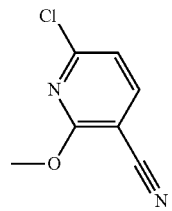

To a stirred solution of 2,6-dichloronicotinonitrile (0.50 g, 2.89 mmol) in MeOH (10 mL) was added sodium methanolate (0.62 g, 2.89 mmol) at ambient temperature. The reaction mixture was stirred at 60° C. for 12 h. The reaction mixture was cooled to ambient temperature and concentrated under reduced pressure, diluted with water (40 mL) and extracted with ethyl acetate (2×75 mL). The combined organic layers were washed with brine (50 mL), dried over sodium sulfate and evaporated under reduced pressure. The residue was purified by preparative HPLC [Xbridge Phenyl (21.2×250 ID) 5 micron; Solvent A: 0.1% TFA, Solvent B: Acetonitrile, Gradient: 5-25% B over 25 min, Flow: 20 mL/min] to obtain Intermediate 23A (0.48 g, 19%) as an off white solid. $^1$H NMR (400 MHz, CDCl$_3$) δ ppm 4.08 (s, 3H), 7.01-7.03 (d, J=7.2 Hz, 1H), 7.80-7.82 (s, J=8.0 Hz, 1H). LCMS (Method-D): retention time 1.94 min, [M+H] 169.2.

Intermediate 23

Intermediate 23 was prepared (0.15 g, 62.20%) as a pale yellow solid, by using a similar synthetic protocol as that of Intermediate 18 and starting from Intermediate 23A (0.17 g, 0.98 mmol) and 1H-pyrazole-4-carbaldehyde (0.09 g, 0.98 mmol). 1H NMR (400 MHz, DMSO-d$_6$) δ ppm 4.15 (s, 3H), 7.65-7.67 (d, 1H), 8.39 (s, J=8.0 Hz, 1H), 8.45-8.47 (d, J=8.0 Hz, 1H), 9.44 (s, 1H), 9.99 (s, 1H). LCMS (Method-I): retention time 1.03 min, [M+H] 229.5.

Intermediate 24: 2-(4-formyl-1H-pyrazol-1-yl)-5-methylisonicotinonitrile

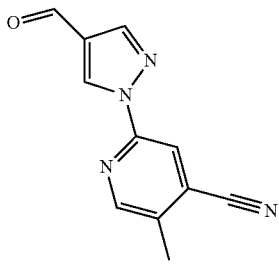 [SMILES: Cc1cnc(-n2cc(C=O)cn2)cc1C#N]

Intermediate 24A: 4-cyano-3-methylpyridine 1-oxide

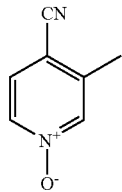

To a stirred solution of 3-methylisonicotinonitrile (5.00 g, 42.30 mmol) in DCM (100 mL) was added 3-chloroperoxybenzoic acid (14.61 g, 85.00 mmol) at 0° C. and stirred at ambient temperature for 16 h. The reaction mixture was diluted with water (50 mL), basified with 10% NaHCO$_3$ and extracted with ethyl acetate (2×75 mL). The combined organic layers were washed with brine (50 mL), dried over sodium sulfate and evaporated under reduced pressure to obtain Intermediate 24A (3.50 g, 61.30%) as a pale yellow solid. $^1$H NMR (400 MHz, DMSO-d$_6$) δ ppm 2.38 (s, 3H), 7.84-7.85 (d, J=6.8 Hz, 1H), 8.21-8.23 (dd, J=1.2 Hz, 6.8 Hz, 1H), 8.41 (s, 1H). LCMS (Method-D): retention time 0.44 min, [M+H] 135.2.

Intermediate 24B: 2-chloro-5-methylisonicotinonitrile

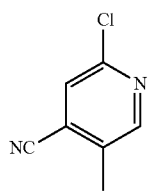

Intermediate 24A was dissolved in POCl$_3$ (48.60 mL, 522.00 mmol) and stirred for 3 h at 100° C. The reaction mixture was cooled to ambient temperature, poured into ice water and basified with 10%° NaHCO$_3$ solution (pH~10) and extracted with ethyl acetate (3×100 mL). The combined organic layers were washed with brine (50 mL), dried over sodium sulfate and evaporated under reduced pressure. The residue was purified by column chromatography (Redisep-80 g, 0-20° % EtOAc/n-Hexane)) to obtain Intermediate 24B (0.70 g, 17.58%) as a pale yellow solid. $^1$H NMR (400 MHz, CDCl$_3$) δ ppm 2.52 (s, 3H), 7.51 (s, 1H), 8.44 (s, 1H). LCMS (Method-D): retention time 1.64 min, [M+H] 153.2.

Intermediate 24

Intermediate 24 was prepared (0.08 g, 88.00%) as an off-white solid, by using a similar synthetic protocol as that of Intermediate 19 and starting from Intermediate 24B (0.20 g, 1.31 mmol). $^1$H NMR (400 MHz, CDCl$_3$) δ ppm 2.50 (s, 3H), 8.29 (s, 1H), 8.35 (s, 1H), 8.72 (s, 1H), 9.32 (s, 1H), 9.97 (s, 1H). LCMS (Method-D): retention time 1.88 min, [M+H] 213.2.

Intermediate 25: 5'-formyl-4-methoxy-[2,2'-bipyridine]-5-carbonitrile

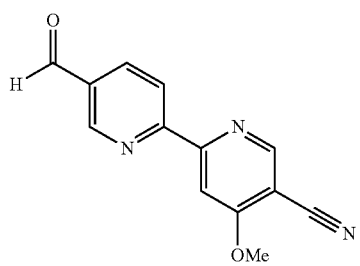 [SMILES: COc1cc(-c2ccc(C=O)cn2)ncc1C#N]

Intermediate 25A: 4-methoxy-6-(trimethylstannyl)nicotinonitrile

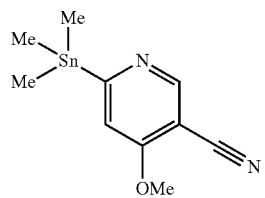

A solution of 6-chloro-4-methoxynicotinonitrile (2.00 g, 11.86 mmol) in dioxane (10 mL) was degassed with nitrogen for 20 minutes. Hexamethylditin (2.71 mL, 13.05 mmol) and 1,1'-bis(di-tert-butylphosphino)ferrocene palladium (II) chloride (0.77 g, 1.19 mmol) were added. The resulting reaction mixture was degassed again for 10 minutes, heated at 100° C. for 12 h and was cooled to ambient temperature. The reaction mixture was filtered through Celite® and the filtrate was concentrated under reduced pressure to obtain Intermediate 25A (5.00 g, 39.50%) as a dark oil. LCMS (Method-I): retention time 1.26 min, [M+H] 299.1. The compound was taken directly to the subsequent step without further purification or characterization.

Intermediate 25

A solution of 6-bromonicotinaldehyde (1.10 g, 5.91 mmol) and Intermediate 25A (4.83 g, 6.51 mmol) in dioxane (20 mL) was degassed with nitrogen for 20 minutes. To the stirring solution was added tetrakistriphenylphospine palladium (0.68 g, 0.59 mmol) followed by copper (I) iodide (0.11 g, 0.59 mmol) and the resulting mixture was degassed again for 10 minutes. The resulting reaction mixture was heated at 100° C. for 16 h then cooled to ambient temperature and filtered through Celite®. The filtrate was concentrated under reduced pressure. The residue was purified by column chromatography (Redisep-40 g, 0-40% EtOAc/n-Hexane) to obtain Intermediate 25 (1.60 g, 79.00%) as an off-white solid. $^1$H NMR (300 MHz, DMSO-$d_6$) δ ppm 4.16 (s, 3H), 8.22 (d, J=14.35 Hz, 1H), 8.46 (d, J=8.31 Hz, 1H), 8.55-8.72 (m, 1H), 8.99 (d, J=1.51 Hz, 1H), 9.24 (s, 1H), 10.20 (s, 1H). LCMS (Method-H): retention time 1.63 min, [M+1] 240.0.

Intermediate 26: 6-(4-formyl-5-methoxy-1H-pyrazol-1-yl)-4-methylnicotinonitrile

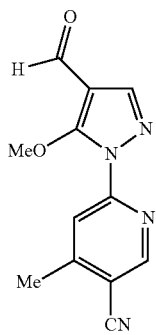 [SMILES: COc1c(C=O)cnn1-c1cc(C)c(C#N)cn1]

Intermediate 26A: dimethyl 2-((dimethylamino)methylene)malonate

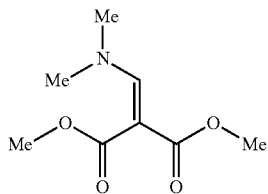 [SMILES: COC(=O)C(=CN(C)C)C(=O)OC]

To a solution of dimethyl malonate (10.00 g, 76.00 mmol) in toluene (100 mL) was added DMF-DMA (20.27 mL, 151.00 mmol) at ambient temperature under a nitrogen atmosphere. The resulting reaction mixture was heated at 100° C. for 5 h. The reaction mixture was cooled to ambient temperature and concentrated under reduced pressure to obtain Intermediate 26A (13.00 g, 84.00%) as a yellow solid. $^1$H NMR (400 MHz, CDCl$_3$) δ ppm 2.92-3.07 (m, 6H), 3.66-3.72 (br.s., 3H), 3.74-3.79 (br.s., 3H), 7.53 (s, 1H). LCMS (Method-D): retention time 0.63 min, [M+H] 188.2.

The compound was taken directly to the subsequent step without further purification or characterization.

Intermediate 26B: methyl 5-methoxy-1H-pyrazole-4-carboxylate

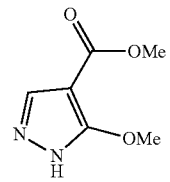 [SMILES: COC(=O)c1cn[nH]c1OC]

To a solution of Intermediate 26A (13.00 g, 69.40 mmol) in EtOH (50 mL) was added hydrazine bishydrochloride (7.29 g, 69.40 mmol) at ambient temperature under a nitrogen atmosphere. The resulting reaction mixture was heated at 70° C. for 5 h. The reaction mixture was cooled to ambient temperature and concentrated under reduced pressure. The residue was dissolved in DCM (250 mL) and basified with saturated NaHCO$_3$ solution (0.5 L). The organic layer was separated, washed with brine (20 mL), dried over anhydrous sodium sulfate and evaporated under reduced pressure. The residue was purified by column chromatography (Redisep-120 g, 45-50% EtOAc/n-hexanes) to obtain Intermediate 26B (2.50 g, 13.14%) as a pale yellow solid. $^1$H NMR (300 MHz, DMSO-$d_6$) δ ppm 3.67 (s, 3H), 3.84 (s, 3H), 8.11 (d, J=2.27 Hz, 1H), 12.56 (br. s., 1H). LCMS (Method-D): retention time 0.48 min, [M+H] 157.0.

Intermediate 26C: methyl 1-(5-cyano-4-methylpyridin-2-yl)-5-methoxy-1H-pyrazole-4-carboxylate

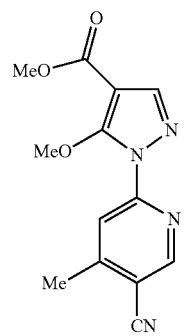 [SMILES: COC(=O)c1cnn(-c2cc(C)c(C#N)cn2)c1OC]

Intermediate 26C was prepared (0.80 g, 15.42%) as a beige solid, using a similar synthetic protocol to that of Intermediate 18 and starting from Intermediate 26B (2.50 g, 16.01 mmol). $^1$H NMR (400 MHz, CDCl$_3$) δ ppm 2.64 (s, 3H), 3.87 (s, 3H), 4.11 (s, 3H), 7.81 (d, J=1.00 Hz, 1H), 8.57 (s, 1H), 8.89 (s, 1H). LCMS (Method-H): retention time 1.81 min, [M+H] 273.0.

Intermediate 26D: 1-(5-cyano-4-methylpyridin-2-yl)-5-methoxy-1H-pyrazole-4-carboxylic Acid

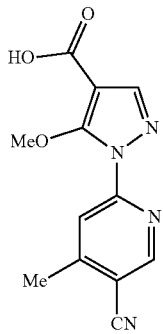 [SMILES: COc1c(C(=O)O)cnn1-c1cc(C)c(C#N)cn1]

To a solution of Intermediate 26C (0.80 g, 2.94 mmol) in THF (25 mL) was added potassium trimethylsilanolate (1.50 g, 11.75 mmol) and stirring was continued at ambient temperature for 16 h. The reaction mixture was diluted with water (80 mL), neutralized with solid citric acid and extracted with ethyl acetate (2×80 mL). The combined organic layers were washed with brine (30 mL), dried over anhydrous sodium sulfate and evaporated under reduced pressure to obtain Intermediate 26D (0.75 g, 61.30%) as a beige solid. $^1$H NMR (300 MHz, DMSO-$d_6$) δ ppm 2.59 (s, 3H), 4.00 (s, 3H), 7.86 (s, 1H), 8.78 (s, 1H), 8.85 (s, 1H), 12.37-12.91 (br. s, 1H). LCMS (Method-H): retention time 0.40 min, [M+H] 259.5.

Intermediate 26E: 6-(4-(hydroxymethyl)-5-methoxy-1H-pyrazol-1-yl)-4-methylnicotinonitrile

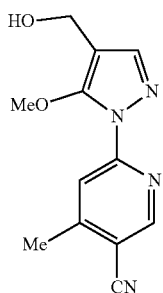 [SMILES: COc1c(CO)cnn1-c1cc(C)c(C#N)cn1]

To a solution of Intermediate 26D (0.75 g. 2.90 mmol) in THF (15 mL) was added TEA (1.21 mL, 8.71 mmol) followed by isobutyl chloroformate (0.76 mL, 5.81 mmol) at 0° C. under a nitrogen atmosphere. The reaction mixture was stirred at ambient temperature for 16 h. The reaction mixture was filtered through a scintered glass funnel and the filtrate was cooled to 0° C. and treated with a solution of sodium borohydride (0.22 g, 5.81 mmol) in water (2 mL) for 10 minutes. The resultant mixture was allowed to reach ambient temperature and stir for 16 h. The reaction mixture was diluted with saturated NH$_4$Cl (40 mL) and extracted with ethyl acetate (2×100 mL). The combined organic layers were washed with 10% NaHCO$_3$ solution (30 mL), dried over anhydrous sodium sulfate and evaporated under reduced pressure to obtain Intermediate 26E (0.43 g, 53.30%) as a beige solid. $^1$H NMR (400 MHz, DMSO-$d_6$) δ ppm 2.54 (s, 3H), 3.96 (s, 3H), 4.30 (d, J=5.02 Hz, 2H), 4.97 (t, J=5.52 Hz, 1H), 7.72 (s, 1H), 8.37 (s, 1H), 8.75 (s, 1H). LCMS (Method-D): retention time 1.681 min, [M+H] 245.0.

Intermediate 26

To a solution of Intermediate 26E (0.40 g, 1.64 mmol) in DCM (30 mL) was added Dess-Martin periodinane (1.39 g, 3.28 mmol) at ambient temperature under a nitrogen atmosphere and stirring was continued for 20 h. The reaction mixture was diluted with DCM (50 mL) and 10% NaHCO$_3$ (50 mL) was added. The organic layer was separated and washed with brine (30 mL), dried over anhydrous sodium sulfate and evaporated under reduced pressure to obtain Intermediate 26 (0.30 g, 68.10%) as a beige solid. $^1$H NMR (400 MHz, DMSO-$d_6$) δ ppm 2.61 (s, 3H), 4.05 (s, 3H), 7.91 (s, 1H), 8.90 (s, 1H), 9.18 (s, 1H), 9.85 (s, 1H). LCMS (Method-H): retention time 2.13 min, [M+H] 243.0.

Intermediate 27: 6-bromo-4-cyclopropylnicotinonitrile

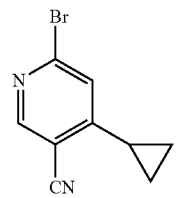

Intermediate 27A: 6-bromo-4-iodonicotinonitrile

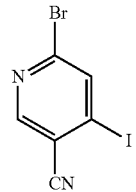

To a solution of diisopropylamine (7.79 mL, 54.60 mmol) in THF (100 mL) was added n-butyllithium (21.86 mL, 54.60 mmol) at −78° C. under a nitrogen atmosphere. After 30 minutes, 6-bromonicotinonitrile (10.00 g, 54.6 mmol) in THF (20 mL) followed by iodine (15.26 g, 60.10 mmol) in THF (10 mL) was added and stirring was continued for 2 h. The resulting reaction mixture was diluted with saturated NH$_4$Cl (40 mL) and extracted with ethyl acetate (2×200 mL). The combined organic layer was washed with brine solution (30 mL), dried over anhydrous sodium sulfate, and evaporated under reduced pressure. The residue was purified by column chromatography (Redisep-80 g, 10-15° % EtOAc/n-Hexanes) to obtain Intermediate 27A (6.50 g, 38.50%) as a brown solid. $^1$H NMR (400 MHz, DMSO-$d_6$) δ ppm 8.51 (s, 1H), 8.76 (s, 1H). LCMS: The compound did not ionize well.

Intermediate 27

To a solution of Intermediate 27A (0.60 g, 1.94 mmol) in a mixture of toluene (10 mL) and water (2 mL) was added cyclopropylboronic acid (0.20 g, 2.33 mmol) followed by K₃PO₄ (0.82 g, 3.88 mmol) and the resulting mixture was degassed for 15 minutes. Palladium(II) acetate (0.05 g, 0.19 mmol) and tricyclohexylphosphine (0.11 g, 0.39 mmol) ware added. The resulting mixture was degassed again for 10 minutes and heated at 140° C. for 1 h in the microwave. The reaction mixture was cooled to ambient temperature and filtered through Celite®. The filtrate was concentrated under reduced pressure. The residue was purified by column chromatography (Redisep-12 g, 15-20% EtOAc/n-Hexanes) to obtain Intermediate 27 (0.10 g, 23.08%) as a yellow solid. $^1$H NMR (400 MHz, DMSO-$d_6$) δ ppm 0.93-1.02 (m, 1H), 1.04-1.13 (m, 1H), 1.19-1.35 (m, 2H), 2.05-2.21 (m, 1H), 8.51 (s, 1H), 8.75 (s, 1H). LCMS (Method-D): retention time 2.25 min, [M+2H] 223.0.

Intermediate 28: 6-(4-formyl-2H-1,2,3-triazol-2-yl)-4-methylnicotinonitrile

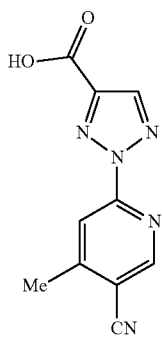 [SMILES: Cc1cc(-n2ncc(C(=O)O)n2)ncc1C#N]

Intermediate 28A: (1H-1,2,3-triazol-4-yl)methanol

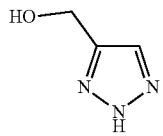

To a solution of prop-2-yn-1-ol (2.00 g, 35.70 mmol) in a mixture of DMF (18 mL) and MeOH (0.50 mL) in a sealed tube was added trimethylsilyl azide (7.10 mL, 53.50 mmol) and copper (I) iodide (0.34 g, 1.78 mmol) at ambient temperature. The resulting reaction mixture was heated at 95° C. for 12 h, cooled to ambient temperature, diluted with DCM (100 mL) and filtered through Celite®. The filtrate was evaporated under reduced pressure to obtain Intermediate 28A (3.30 g 93.00%) as a brown liquid. $^1$H NMR (400 MHz, DMSO-$d_6$) δ ppm 4.55 (d, J=3.51 Hz, 2H), 5.12-5.27 (m, 1H), 7.70 (br. s., 1H), 14.58-15.07 (br. s., 1H). GCMS: retention time 9.36 min, [M] 99.0. The compound was taken directly to the subsequent step without further purification.

Intermediate 28B: 6-(4-(hydroxymethyl)-2H-1,2,3-triazol-2-yl)-4-methylnicotinonitrile Intermediate 28B was prepared (0.50 g, 20.95%) as a light brown solid, by using a similar synthetic protocol as that of Intermediate 9 and starting from Intermediate 28A (1.00 g, 10.09 mmol). $^1$H NMR (400 MHz, DMSO-$d_6$) δ ppm 2.62 (s, 3H), 4.67 (d, J=5.52 Hz, 2H), 5.49-5.54 (m, 1H), 8.12 (d, J=1.00 Hz, 1H), 8.18 (s, 1H), 8.94 (s, 1H). LCMS (Method-D): retention time 0.951 min, [M+H] 216.2.

Intermediate 28

Intermediate 28 was prepared (0.90 g, 64.20%) as a yellow solid, by using a similar synthetic protocol as that of Intermediate 26 and starting from Intermediate 28B (1.40 g, 6.51 mmol). $^1$H NMR (400 MHz, DMSO-$d_6$) δ ppm 2.67 (s, 3H), 8.29 (s, 1H), 8.79 (s, 1H), 9.03 (s, 1H), 10.21 (s, 1H). LCMS (Method-D): retention time 1.32 min, [M+H] 214.2.

Intermediate 29: 2-(3-methyl-2-oxo-2,3-dihydrobenzo[d]oxazol-5-yl)-2H-1,2,3-triazole-4-carbaldehyde

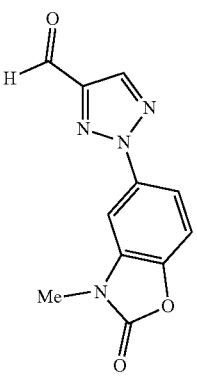 [SMILES: Cn1c(=O)oc2ccc(-n3ncc(C=O)n3)cc21]

Intermediate 29A: 5-(4-(hydroxymethyl)-2H-1,2,3-triazol-2-yl)-3-methylbenzo[d]oxazol-2(3H)-one

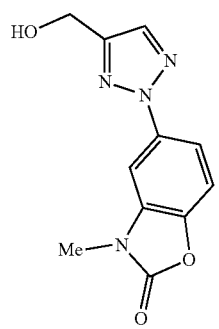 [SMILES: Cn1c(=O)oc2ccc(-n3ncc(CO)n3)cc21]

Intermediate 29A was prepared (0.65 g, 13.78%) as a brown solid, by using a similar synthetic protocol as that of Intermediate 6 and starting from Intermediate 28A (1.50 g, 15.14 mmol). $^1$H NMR (400 MHz, DMSO-d$_6$) δ ppm 3.42 (s, 3H), 4.65 (d, J=5.52 Hz, 2H), 5.43 (t, J=5.77 Hz, 1H), 7.49 (d, J=8.53 Hz, 1H), 7.75 (dd, J=8.78, 2.26 Hz, 1H), 7.85 (d, J=2.26 Hz, 1H), 8.02 (s, 1H). LCMS (Method-D): retention time 1.04 min, [M+H] 247.2.

Intermediate 29

Intermediate 29 was prepared (0.12 g, 79.00%) as an off-white solid, by using a similar synthetic protocol as that of Intermediate 26 and starting from Intermediate 29A (0.15 g, 0.60 mmol). $^1$H NMR (400 MHz, DMSO-d6) δ ppm 3.44 (s, 3H), 7.57 (d, J=8.78 Hz, 1H), 7.88 (dd, J=8.78, 2.26 Hz, 1H), 7.99 (d, J=2.26 Hz, 1H), 8.70 (s, 1H), 10.18 (s, 1H). LCMS (Method-D): retention time 1.687 min, [M+H] 245.2.

Intermediate 30: 6-(4-formyl-1H-1,2,3-triazol-1-yl)-4-methylnicotinonitrile

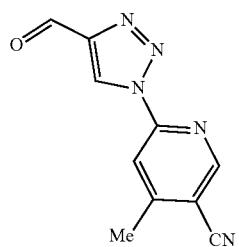 [SMILES: Cc1cc(-n2cc(C=O)nn2)ncc1C#N]

Intermediate 30A: 6-azido-4-methylnicotinonitrile

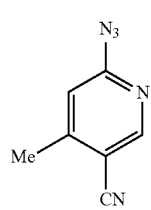

To a stirring solution of 6-bromo-4-methylnicotinonitrile (2.00 g, 10.15 mmol) in DMF (10 mL) was added sodium azide (1.32 g, 20.30 mmol) and stirring was continued for 12 h at ambient temperature. The reaction mixture was diluted with water (300 mL) and extracted with ethyl acetate (3×200 mL). The combined organic layers were dried over anhydrous Na$_2$SO$_4$ and evaporated under reduced pressure. The residue was purified by column chromatography (Redisep-40 g, 20-35% EtOAc/n-Hexane) to obtain Intermediate 30A (0.87 g, 54.00%). $^1$H NMR (400 MHz, DMSO-d$_6$) δ ppm 2.62 (d, J=1.00 Hz, 3H), 8.28 (t, J=1.00 Hz, 1H), 10.21 (s, 1H). LCMS (Method-D): retention time 0.88 min, [M+H] 160.2.

Intermediate 30B: 6-(4-(hydroxymethyl)-1H-1,2,3-triazol-1-yl)-4-methylnicotinonitrile

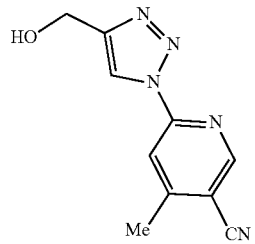 [SMILES: Cc1cc(-n2cc(CO)nn2)ncc1C#N]

Intermediate 30B was prepared (0.21 g. 31.00%), by using a similar synthetic protocol as that of Intermediate 28A and starting from Intermediate 30A (0.50 g, 3.14 mmol). $^1$H NMR (400 MHz, DMSO-d$_6$) δ ppm 2.65 (s, 3H), 4.63 (d, J=6.53 Hz, 2H), 5.33-5.39 (m, 1H), 8.30 (d, J=1.00 Hz, 1H), 8.71 (s, 1H), 9.00 (s, 1H). LCMS (Method-D): retention time 0.87 min, [M+H] 216.2.

Intermediate 30

Intermediate 30 was prepared (0.13 g, 65.60%) from Intermediate 30B, by using a similar synthetic protocol as that of preparation of Intermediate 26 from Intermediate 9E. $^1$H NMR (300 MHz, DMSO-d$_6$) δ ppm 2.64-2.70 (m, 3H), 8.39 (s, 1H), 9.06 (s, 1H), 9.58 (s, 1H), 10.13 (s, 1H). LCMS (Method-D): retention time 1.42 min, [M+H] 214.2.

Intermediate 31: 6-(4-formyl-1H-1,2,3-triazol-1-yl)-4-methoxynicotinonitrile

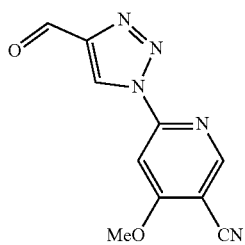 [SMILES: COc1cc(-n2cc(C=O)nn2)ncc1C#N]

Intermediate 31A: 6-azido-4-methoxynicotinonitrile

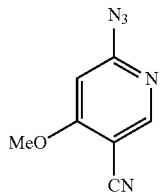 [SMILES: COc1cc(N=[N+]=[N-])ncc1C#N]

Intermediate 31A was prepared (1.40 g, 67.00%), by using a similar synthetic protocol as that of Intermediate 30A and starting from 6-chloro-4-methoxynicotinonitrile (2.00 g, 11.86 mmol). $^1$H NMR (400 MHz, DMSO-$d_6$) δ ppm 4.10 (s, 3H), 7.81 (s, 1H), 7.89 (s, 1H). LCMS (Method-D): retention time 0.79 min, [M+H] 176.0.

Intermediate 31B: 6-(4-(hydroxymethyl)-1H-1,2,3-triazol-1-yl)-4-methoxynicotinonitrile

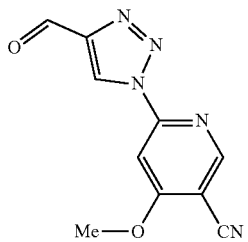 [SMILES: COc1cc(-n2cc(C=O)nn2)ncc1C#N]

Intermediate 31B was prepared (0.23 g, 13.400/%), by using a similar synthetic protocol as that of Intermediate 28A and starting from Intermediate 31A (1.30 g, 7.42 mmol). $^1$H NMR (400 MHz, DMSO-$d_6$) δ ppm 4.15-4.19 (m, 3H), 4.64 (s, 2H), 7.89 (s, 1H), 8.71 (s, 1H), 8.89 (s, 1H), (Exchangeable proton not observed). LCMS (Method-D): retention time 1.01 min, [M+H] 232.2.

Intermediate 31

Intermediate 31 was prepared (0.12 g, 60.50%) from Intermediate 31B (0.20 g, 0.86 mmol) by using a similar synthetic protocol as that of preparation of Intermediate 26 from Intermediate 9E. $^1$H NMR (300 MHz, DMSO-$d_6$) δ ppm 4.19 (s, 3H), 7.99 (s, 1H), 8.96 (s, 1H), 9.59 (s, 1H), 10.14 (s, 1H). LCMS (Method-D): retention time 1.1.42 min, [M+H] 230.2.

Intermediate 32: 1-(3-methyl-2-oxo-2,3-dihydrobenzo[d]oxazol-5-yl)-1H-1,2,3-triazole-4-carbaldehyde

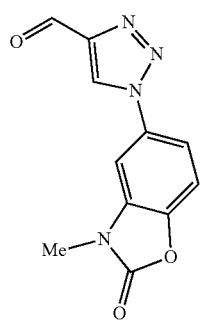 [SMILES: Cn1c(=O)oc2ccc(-n3cc(C=O)nn3)cc21]

Intermediate 32A: 5-nitrobenzo[d]oxazol-2(3H)-one

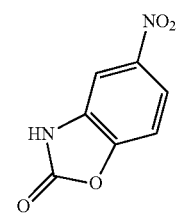 [SMILES: O=c1[nH]c2cc([N+](=O)[O-])ccc2o1]

To a stirred solution of 2-amino-4-nitrophenol (5.00 g, 32.40 mmol) in THF (50 mL) was added CDI (6.84 g, 42.20 mmol) at 70° C. and stirring was continued at ambient temperature for 3 h. The reaction mixture was concentrated under reduced pressure, diluted with water (200 mL) and extracted with ethyl acetate (2×100 mL). The combined organic layers were washed with brine (80 mL), dried over anhydrous sodium sulfate and evaporated under reduced pressure to obtain Intermediate 32A (5.50 g, 94.00%) as a yellow solid. $^1$H NMR (300 MHz, DMSO-$d_6$) δ ppm 7.49 (d, J=8.69 Hz, 1H), 7.82 (d, J=2.27 Hz, 1H), 8.02 (dd, J=8.69, 2.27 Hz, 1H). (Exchangeable proton not observed). LCMS (Method-H): retention time 0.69 min, [M–H] 179.0.

Intermediate 32B: 3-methyl-5-nitrobenzo[d]oxazol-2(3H)-one

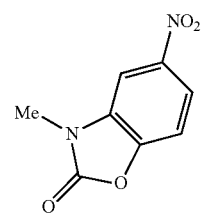 [SMILES: Cn1c(=O)oc2ccc([N+](=O)[O-])cc21]

To a stirring solution of Intermediate 32A (5.00 g, 27.80 mmol) in DMSO (55 mL) was added potassium carbonate (4.22 g, 30.50 mmol), followed by methyl iodide (5.21 mL, 83.00 mmol) and stirring was continued at ambient temperature for 12 h. The reaction mixture was cooled to 0° C. and diluted with ice water (150 mL). The resulting suspension was stirred at ambient temperature for 1 h. The solid that formed was filtered, dried under reduced pressure, to obtain Intermediate 32B (4.50 g, 83.00%) as a yellow solid. $^1$H NMR (300 MHz, DMSO-$d_6$) δ ppm 7.57 (d, J=8.69 Hz, 1H), 8.09 (dd, J=8.69, 2.27 Hz, 1H), 8.21 (d, J=2.64 Hz, 1H), 3.43 (s, 3H). LCMS (Method-H): retention time 1.23 min, [M+H] 195.2.

Intermediate 32C: 5-amino-3-methylbenzo[d]oxazol-2(3H)-one

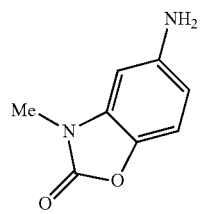 [SMILES: Cn1c(=O)oc2ccc(N)cc21]

To a solution of Intermediate 32B (1.80 g, 9.27 mmol) in acetic acid (50 mL) was added 10% Pd/C (0.10 g, 0.93 mmol) and the reaction mixture was stirred at ambient temperature under an hydrogen atmosphere for 14 h. The reaction mixture was filtered through Celite® then washed with 10% MeOH in DCM (20 mL). The filtrate was evaporated under reduced pressure to obtain Intermediate 32C (1.20 g, 80.00%0). $^1$H NMR (400 MHz, DMSO-$d_6$) δ ppm 3.23 (s, 3H), 5.06 (br. s., 2H), 6.28 (dd, J=8.53, 2.51 Hz, 1H), 6.37 (d, J=2.01 Hz, 1H), 6.95 (d, J=8.53 Hz, 1H). LCMS (Method-D): retention time 0.59 min, [M+H] 165.2.

Intermediate 32D: 5-azido-3-methylbenzo[d]oxazol-2(3H)-one

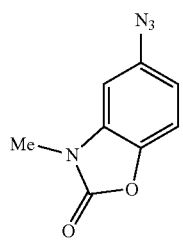 [SMILES: Cn1c(=O)oc2ccc(N=[N+]=[N-])cc21]

To a solution of Intermediate 32C (1.50 g, 9.14 mmol) in acetonitrile (20 mL) at 0° C. was added tert-butyl nitrite (3.26 mL, 27.40 mmol) followed by azidotrimethylsilane (3.61 mL, 27.40 mmol). The resultant reaction mixture was stirred at ambient temperature for 2 h then diluted with water (100 mL) and extracted with ethyl acetate (3×100 mL). The combined organic layers were dried over anhydrous $Na_2SO_4$ and evaporated under reduced pressure to obtain Intermediate 32D (1.00 g, 57.20%). $^1$H NMR (400 MHz, DMSO-$d_6$) δ ppm 3.34 (s, 3H), 6.85 (dd, J=8.53, 2.01 Hz, 1H), 7.14 (d, J=2.51 Hz, 1H), 7.35 (d, J=8.53 Hz, 1H). LCMS (Method-H): retention time 2.30 min, [M+H] 191.2.

Intermediate 32E: 5-(4-(hydroxymethyl)-1H-1,2,3-triazol-1-yl)-3-methylbenzo[d]oxazol-2(3H)-one

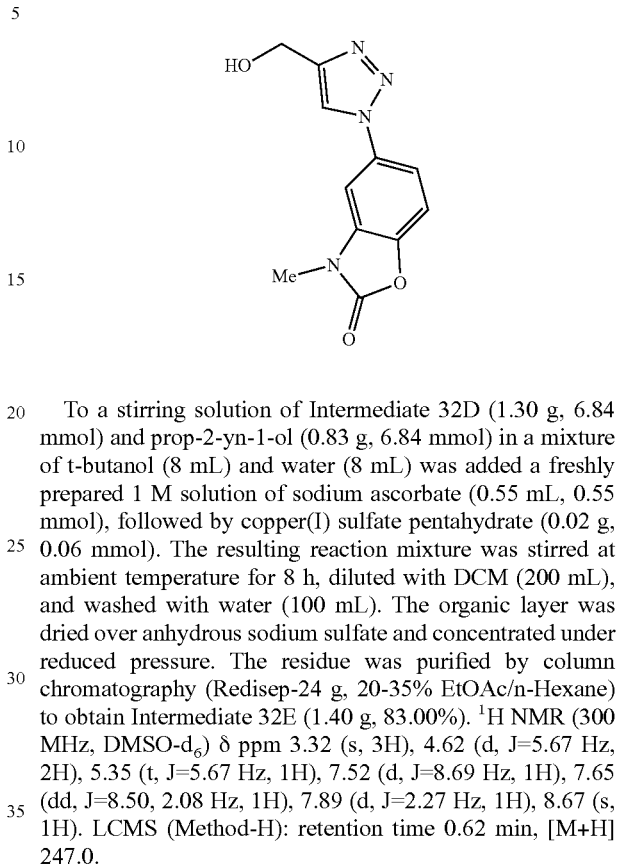

To a stirring solution of Intermediate 32D (1.30 g, 6.84 mmol) and prop-2-yn-1-ol (0.83 g, 6.84 mmol) in a mixture of t-butanol (8 mL) and water (8 mL) was added a freshly prepared 1 M solution of sodium ascorbate (0.55 mL, 0.55 mmol), followed by copper(I) sulfate pentahydrate (0.02 g, 0.06 mmol). The resulting reaction mixture was stirred at ambient temperature for 8 h, diluted with DCM (200 mL), and washed with water (100 mL). The organic layer was dried over anhydrous sodium sulfate and concentrated under reduced pressure. The residue was purified by column chromatography (Redisep-24 g, 20-35% EtOAc/n-Hexane) to obtain Intermediate 32E (1.40 g, 83.00%). $^1$H NMR (300 MHz, DMSO-$d_6$) δ ppm 3.32 (s, 3H), 4.62 (d, J=5.67 Hz, 2H), 5.35 (t, J=5.67 Hz, 1H), 7.52 (d, J=8.69 Hz, 1H), 7.65 (dd, J=8.50, 2.08 Hz, 1H), 7.89 (d, J=2.27 Hz, 1H), 8.67 (s, 1H). LCMS (Method-H): retention time 0.62 min, [M+H] 247.0.

Intermediate 32

Intermediate 32 was prepared (1.00 g, 78.00%), by using a similar synthetic protocol as that of Intermediate 26 and starting from Intermediate 32E (1.30 g, 5.28 mmol). $^1$H NMR (300 MHz, DMSO-$d_6$) δ ppm 3.41 (s, 3H), 7.58 (d, J=8.31 Hz, 1H), 7.69-7.80 (m, 1H), 7.98 (d, J=2.27 Hz, 1H), 9.55 (s, 1H), 10.13 (s, 1H). LCMS (Method-D): retention time 2.55 min, [M+H] 245.0.

Intermediate 33: 1-(7-fluoro-3-methyl-2-oxo-2,3-dihydrobenzo[d]oxazol-5-yl)-1H-pyrazole-4-carbaldehyde

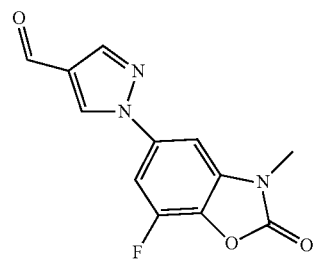 [SMILES: Cn1c(=O)oc2c(F)cc(-n3cc(C=O)cn3)cc21]

Intermediate 33A: 5-bromo-7-fluorobenzo[d]oxazol-2(3H)-one

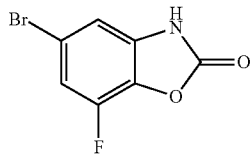 [SMILES: O=c1[nH]c2cc(Br)cc(F)c2o1]

A solution of 2-amino-4-bromo-6-fluorophenol (2.00 g, 9.71 mmol) and carbonyldiimidazole (1.73 g, 10.68 mmol) in THF (20 mL) was heated at 70° C. for 2 h. The reaction mixture was concentrated to dryness and diluted with water (30 mL). The precipitated solid was filtered and dried under reduced pressure to obtain Intermediate 33A (2.00 g, 89.00%) as an off-white solid. $^1$H NMR (400 MHz, DMSO-$d_6$) δ 7.13 (d, J=1.50 Hz, 1H), 7.34 (dd, J=10.00, 2.0 Hz, 1H), 7.82 (br.s, 1H). LCMS (Method-I): retention time 1.17 min, [M+2] 232.0.

Intermediate 33B: 5-bromo-7-fluoro-3-methylbenzo[d]oxazol-2(3H)-one

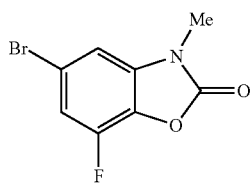 [SMILES: Cn1c(=O)oc2c(F)cc(Br)cc21]

Intermediate 33B was prepared (1.90 g, 90.00%) as a black solid, by using a similar synthetic protocol as that of Intermediate 32B and starting from Intermediate 33A (2.00 g, 8.62 mmol).

$^1$H NMR (400 MHz, CDCl$_3$) δ 3.40 (s, 3H), 6.94 (dd, J=1.60, 0.90 Hz, 1H), 7.10 (dd, J=9.3, 1.8 Hz, 1H). LCMS (Method-I) retention time: 1.17 min, [M+2] 248.0.

Intermediate 33

Intermediate 33 was prepared (0.06 g, 11.30%) as a brown solid, by using a similar synthetic protocol as that of Intermediate 9 and starting from Intermediate 33B (0.50 g, 2.03 mmol) and pyrazole-4-carbaldehyde (0.49 g, 5.08 mmol). $^1$H NMR (400 MHz, DMSO-$d_6$) δ ppm 3.41 (s, 3H), 7.73 (dd, J=11.55, 2.01 Hz, 1H), 7.79 (d, J=2.01 Hz, 1H), 8.32 (s, 1H) 9.26 (s, 1H), 9.93 (s, 1H). LCMS (Method-L) retention time: 0.95 min, [M+1] 262.0.

Intermediate 34: 1-(3,7-dimethyl-2-oxo-2,3-dihydrobenzo[d]oxazol-5-yl)-1H-pyrazole-4-carbaldehyde

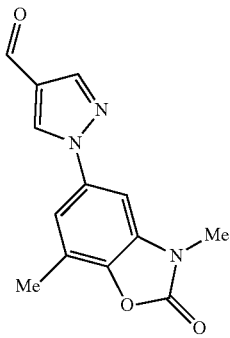 [SMILES: Cc1cc(-n2cc(C=O)cn2)cc2c1oc(=O)n2C]

Intermediate 34A: 4-bromo-2-methyl-6-nitrophenol

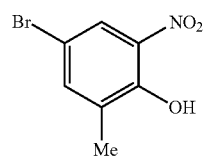 [SMILES: Cc1cc(Br)cc([N+](=O)[O-])c1O]

To a suspension of 4-bromo-2-methylphenol (3.00 g, 16.04 mmol) in water (25 mL) was added AcOH (1.84 mL, 32.10 mmol) followed by nitric acid (3.58 mL, 80.00 mmol) at 0° C. and the resultant reaction mixture was stirred at ambient temperature for 30 minutes. The reaction mixture was diluted with water (50 mL) and extracted with ethyl acetate (2×100 mL). The combined organic layers were washed with brine (50 mL), dried over anhydrous sodium sulfate and evaporated under reduced pressure. The residue was purified by column chromatography (Redisep-40 g, 0-15% EtOAc/n-Hexane) to obtain Intermediate 34A (1.20 g, 30.00%) as a yellow solid. $^1$H NMR (300 MHz, DMSO-$d_6$) δ ppm 2.34 (s, 3H), 8.38 (dd, J=3.05, 0.76 Hz, 1H), 8.59 (d, J=3.02 Hz, 1H), (Exchangeable proton not observed). LCMS (Method-D): retention time 2.93 min, [M+2] 234.0

Intermediate 34B: 2-amino-4-bromo-6-methylphenol

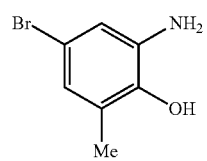

To a solution of tin (II) chloride (5.31 g, 28.00 mmol) and conc. HCl (6.00 mL, 197.00 mmol) in MeOH (25 mL) at 0° C. was added Intermediate 34A (1.30 g, 5.60 mmol). The reaction mixture was stirred at ambient temperature for 14 h, concentrated under reduced pressure and diluted with water (100 mL). The mixture was basified using saturated NaHCO$_3$, filtered through Celite® and the filtrate was extracted with DCM (2×75 ml). The combined organic extracts were dried over anhydrous sodium sulfate and concentrated under reduced pressure to obtain Intermediate 34B (0.90 g, 80.00%) as a brown solid. $^1$H NMR (300 MHz, DMSO-$d_6$) δ ppm 2.15 (s, 3H), 4.83 (br. s., 2H), 6.44 (d, J=2.64 Hz, 1H), 6.61 (d, J=2.27 Hz, 1H), 8.06 (br. s., 1H). LCMS (Method-D): retention time 2.93 min, [M+2] 204.0.

Intermediate 34C:
5-bromo-7-methylbenzo[d]oxazol-2(3H)-one

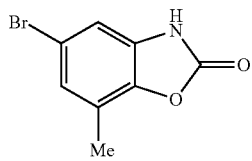 [SMILES: Cc1cc(Br)cc2[nH]c(=O)oc12]

Intermediate 34C was prepared (0.85 g, 84.00%) as a light brown solid, by using a similar synthetic protocol as that of Intermediate 33A and starting from Intermediate 34B (0.90 g, 4.45 mmol). $^1$H NMR (400 MHz, DMSO-$d_6$) δ ppm 2.28 (s, 3H) 7.08 (d, J=1.51 Hz, 1H) 7.14 (s, 1H), 11.80 (br.s., 1H). LCMS (Method-D): retention time 2.93 min, [M+2] 230.0.

Intermediate 34D: 5-bromo-3,7-dimethylbenzo[d]oxazol-2(3H)-one

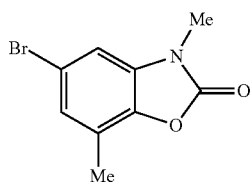

Intermediate 34D was prepared (0.90 g, 89.00%) as a light brown solid, by using a similar synthetic protocol as that of Intermediate 32B and starting from Intermediate 34C (0.95 g, 4.17 mmol). $^1$H NMR (400 MHz, CDCl$_3$) δ ppm 2.35 (s, 3H), 3.37 (s, 3H), 6.94 (d, J=1.51 Hz, 1H), 7.08-7.10 (m, 1H). LCMS (Method-H): retention time 2.09 min, [M+H$_2$O] 260.0.

Intermediate 34

Intermediate 34 was prepared (0.08 g, 15.06%) as an off-white solid, by using a similar synthetic protocol as that of Intermediate 9 and starting from Intermediate 34D (0.50 g, 2.07 mmol). $^1$H NMR (400 MHz, DMSO-$d_6$) δ ppm 2.39 (s, 3H), 3.38 (s, 3H), 7.58 (s, 1H), 7.70 (d, J=2.01 Hz, 1H), 8.28 (s, 1H), 9.19 (s, 1H), 9.92 (s, 1H). LCMS (Method-L): retention time 0.94 min, [M+1] 258.4.

Intermediate 35: 1-(7-methoxy-3-methyl-2-oxo-2,3-dihydrobenzo[d]oxazol-5-yl)-1H-pyrazole-4-carbaldehyde

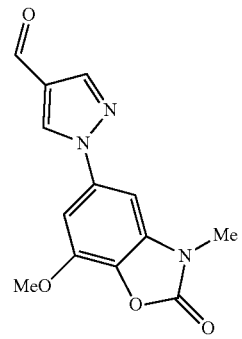 [SMILES: COc1cc(-n2cc(C=O)cn2)cc2c1oc(=O)n2C]

Intermediate 35A:
4-bromo-2-methoxy-6-nitrophenol

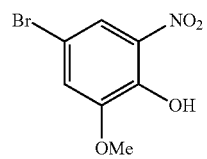 [SMILES: COc1cc(Br)cc([N+](=O)[O-])c1O]

To a stirred solution of 4-bromo-2-methoxyphenol (4.50 g, 22.16 mmol) in a mixture of diethyl ether (30 mL) and water (10 mL), was added nitric acid (1.19 mL, 26.6 mmol) over 5 minutes. The resulting reaction mixture was stirred at ambient temperature for 30 minutes, diluted with water (50 mL) and extracted with ethyl acetate (2×100 mL). The combined organic layer was washed with brine (50 mL), dried over anhydrous sodium sulfate and evaporated under reduced pressure. The residue was purified by column chromatography (Redisep-40 g, 0-20% EtOAc/n-Hexane) to obtain Intermediate 35A (2.50 g, 45.50%) as a yellow solid. $^1$H NMR (400 MHz, DMSO-$d_6$) δ ppm 3.90 (s, 3H), 7.43 (d, J=2.51 Hz, 1H), 7.60-7.64 (m, 1H), 10.70 (br. s., 1H). LCMS (Method-I): retention time 0.94 min, [M+2] 250.2.

Intermediate 35B:
2-amino-4-bromo-6-methoxyphenol

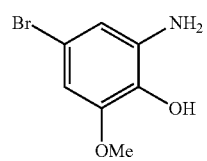 [SMILES: COc1cc(Br)cc(N)c1O]

Intermediate 35B was prepared (1.50 g, 68.30%) as an off-white solid, by using a similar synthetic protocol as that of Intermediate 34B and starting from Intermediate 35A (2.50 g, 10.08 mmol). $^1$H NMR (400 MHz, DMSO-$d_6$) δ ppm 3.73 (s, 3H), 4.79 (br. s., 2H), 6.36 (d, J=2.01 Hz, 1H), 6.43-6.47 (m, 1H), 8.34 (br. s., 1H). LCMS (Method-D): retention time 1.51 min, [M+2] 220.0.

Intermediate 35C: 5-bromo-7-methoxybenzo[d]oxazol-2(3H)-one

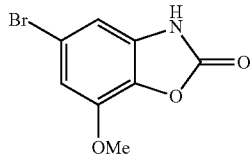

Intermediate 35C was prepared (1.50 g, 82.00%) as an off-white solid, by using a similar synthetic protocol as that of Intermediate 33A and starting from Intermediate 35B (1.63 g, 7.48 mmol). 1H NMR (300 MHz, DMSO-$d_6$) δ ppm 3.90 (s, 3H), 6.89 (d, J=1.13 Hz, 1H), 7.01 (d, J=1.51 Hz, 1H), 11.80 (br. s., 1H). LCMS (Method-D): retention time 1.79 min, [M+2] 246.0.

Intermediate 35D: 5-bromo-7-methoxy-3-methyl-benzo[d]oxazol-2(3H)-one

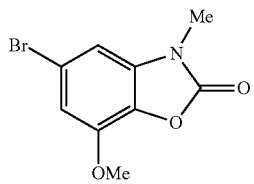 [SMILES: COc1cc(Br)cc2c1oc(=O)n2C]

Intermediate 35D was prepared (1.40 g, 88.00%) as an off-white solid, by using a similar synthetic protocol as that of Intermediate 32B and starting from Intermediate 35C (1.50 g, 6.15 mmol). $^1$H NMR (300 MHz, DMSO-$d_6$) δ ppm 3.31 (s, 3H), 3.91 (s, 3H), 7.06 (d, J=1.51 Hz, 1H), 7.19 (d, J=1.13 Hz, 1H). LCMS (Method-H): retention time 1.84 min, [M+H$_2$O] 275.0.

Intermediate 35

Intermediate 35 was prepared (0.24 g, 45.30%) as an off-white solid, by using a similar synthetic protocol as that of Intermediate 9 and starting from Intermediate 35D (0.50 g, 1.94 mmol). $^1$H NMR (300 MHz, DMSO-$d_6$) δ ppm 3.34 (s, 3H), 4.00 (s, 3H), 7.42 (d, J=1.89 Hz, 1H), 7.51 (d, J=1.89 Hz, 1H), 8.30 (s, 1H), 9.28 (s, 1H), 9.93 (s, 1H). LCMS (Method-L): retention time 0.90 min, [M+1] 274.1.

Intermediate 36: 6-(4-formyl-3-methyl-1H-pyrazol-1-yl)-4-methylnicotinonitrile

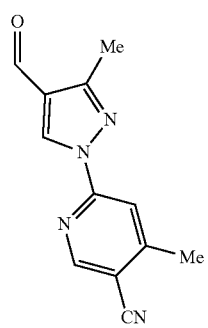 [SMILES: Cc1cc(-n2cc(C=O)c(C)n2)ncc1C#N]

Intermediate 36 was prepared (0.21 g, 25.60%) as a beige solid, by using a similar synthetic protocol as that of Intermediate 9 and starting from 3-methyl-1H-pyrazole-4-carbaldehyde (0.40 g, 3.63 mmol) and 6-bromo-4-methyl-nicotinonitrile. $^1$H NMR (400 MHz, DMSO-$d_6$) δ ppm 2.52 (s, 3H), 2.6 (s, 3H), 8.01 (s, 1H), 8.90 (s, 1H), 9.28 (s, 1H), 10.00 (s, 1H). LCMS (Method-H) retention time 1.85 min, [M+H] 227.0.

Intermediate 37: 6-(3-formyl-1H-pyrazol-1-yl)-4-methylnicotinonitrile

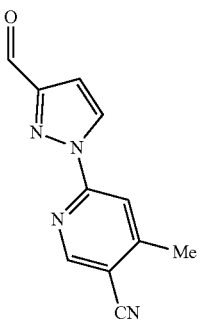 [SMILES: Cc1cc(-n2ccc(C=O)n2)ncc1C#N]

Intermediate 37 was prepared (0.27 g, 30.50%), by using a similar synthetic protocol as that of Intermediate 9 and starting from 1H-pyrazole-3-carbaldehyde (0.40 g, 4.16 mmol) and 6-bromo-4-methylnicotinonitrile. $^1$H NMR (400 MHz, DMSO-$d_6$) δ ppm 2.50-2.68 (s, 3H), 7.20-7.22 (s, 1H), 8.03 (s, 1H), 8.09-8.17 (s, 1H), 8.95-8.99 (s, 1H), 10.48 (s, 1H). LCMS (Method-I) retention time 1.00 min, [M+H] 213.0.

Intermediate 38: 1-(6-(methylsulfonyl)pyridin-3-yl)-1H-pyrazole-4-carbaldehyde

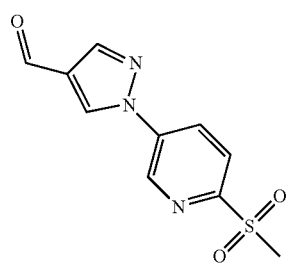 [SMILES: CS(=O)(=O)c1ccc(-n2cc(C=O)cn2)cn1]

To a stirred solution of 5-bromo-2-(methylsulfonyl)pyridine (0.05 g, 0.21 mmol) and 1H-pyrazole-4-carbaldehyde (0.02 g, 0.21 mmol) in 1,4-dioxane (3 mL) was added cesium carbonate (0.17 g, 0.53 mmol) and 9,9-dimethyl-9H-xanthene-4,5-diyl)bis(diphenylphosphane (0.01 g, 0.021 mmol). The reaction mixture was degassed with nitrogen for 10 minutes and Pd$_2$dba$_3$ (0.02 g, 0.021 mmol) was added and the resulting mixture was degassed again for 10 minutes then was heated at 90° C. for 5 h. The reaction mixture was cooled to ambient temperature and diluted with ice cold 1.5 N HCl (2 mL). The solid precipitate was collected by suction filtration and washed with ethanol (1 mL) to obtain Intermediate 38 (0.03 g, 56.00%). $^1$H NMR (400 MHz, DMSO-$d_6$) δ ppm 2.53 (s, 3H), 7.96 (d, J=0.56 Hz, 1H), 8.32 (d, J=2.45 Hz, 1H), 8.33 (s, 1H), 8.71 (d, J=2.45 Hz, 1H), 9.29 (s, 1H), 9.97 (s, 1H). LCMS (Method-L) retention time 1.12 min, [M+H] 252.0.

Intermediate 39: 6-(4-methyl-1H-imidazol-1-yl)pyridazine-3-carbaldehyde

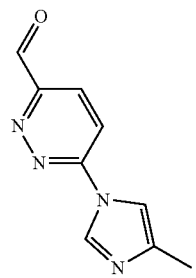

Intermediate 39A: ethyl 6-(4-methyl-1H-imidazol-1-yl)pyridazine-3-carboxylate

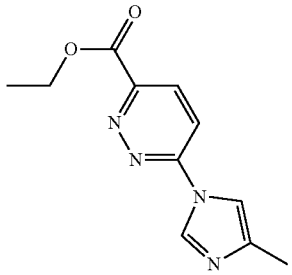 [SMILES: CCOC(=O)c1ccc(-n2cnc(C)c2)nn1]

Intermediate 39A was prepared (0.18 g, 72.00%), by using a similar synthetic protocol as that of Intermediate 19 and starting from 4-methyl-1H-imidazole (0.11 g, 1.34 mmol) and ethyl 6-chloropyridazine-3-carboxylate (0.20 g, 1.07 mmol). 1H NMR (400 MHz, DMSO-$d_6$) δ ppm 1.38 (t, J=7.12 Hz, 3H), 2.22 (d, J=0.94 Hz, 3H), 4.41-4.47 (m, 2H), 7.86 (t, J=1.19 Hz, 1H), 8.28 (d, J=9.2 Hz, 1H), 8.30 (d, J=8.8 Hz, 1H), 8.64 (d, J=1.32 Hz, 1H). LCMS: The compound did not ionize well.

Intermediate 39B: (6-(4-methyl-1H-imidazol-1-yl)pyridazin-3-yl)methanol

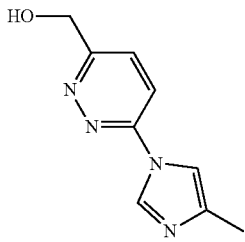

To a solution of Intermediate 39A (0.10 g, 0.43 mmol) in THF (5 mL) was added sodium borohydride (0.17 g, 0.43 mmol) at ambient temperature. MeOH (0.2 mL) was added dropwise and resulting reaction mixture was stirred at ambient temperature for 2 h. The reaction was quenched with saturated ammonium chloride solution, concentrated to dryness, diluted with water (10 mL) and extracted with DCM (2×25 mL). The combined organic layer was washed with brine (10 mL), dried over anhydrous sodium sulfate and evaporated under reduced pressure to obtain Intermediate 39B (0.05 g, 61.00%/). 1H NMR (300 MHz, DMSO-$d_6$) δ ppm 2.20 (s, 3H), 4.77 (d, J=5.52 Hz, 2H), 5.69 (t, J=5.95 Hz, 1H), 7.76 (s, 1H), 7.89 (d, J=9.07 Hz, 1H), 8.13 (d, J=9.11 Hz, 1H), 8.51 (s, 1H). LCMS: The compound did not ionize well.

Intermediate 39

Intermediate 39 was prepared (0.04 g, 85.00%0), by using a similar synthetic protocol as that of Intermediate 26 and starting from Intermediate 3A (0.04 g, 0.21 mmol). LCMS: The compound did not ionize well. The compound was taken directly to the subsequent step without further purification or characterization.

Intermediate 40: 6-(4-formyl-2-methyl-1H-imidazol-1-yl)-4-methoxynicotinonitrile

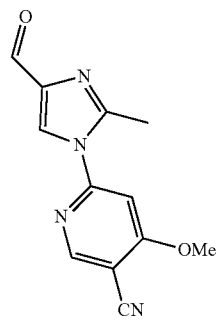 [SMILES: COc1cc(-n2cc(C=O)nc2C)ncc1C#N]

Intermediate 40 was prepared (0.20 g, 36.00%), by using a similar synthetic protocol as that of Intermediate 18 and starting from 2-methyl-1H-imidazole-5-carbaldehyde (0.25 g, 2.27 mmol). ¹H NMR (400 MHz, DMSO-$d_6$) δ ppm 2.59 (s, 3H), 4.12 (s, 3H), 7.63 (s, 1H), 8.61 (s, 1H), 8.87 (s, 1H), 9.78 (s, 1H). LCMS (Method-L): retention time 0.66 min, [M+H] 243.1.

Intermediate 41: 2-(4-formyl-1H-pyrazol-1-yl)-4-methylpyrimidine-5-carbonitrile

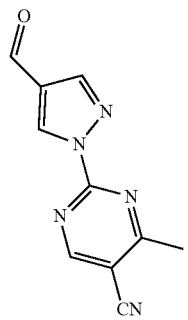 [SMILES: Cc1nc(-n2cc(C=O)cn2)ncc1C#N]

Intermediate 41A: (E)-2-((dimethylamino)methylene)-3-oxobutanenitrile

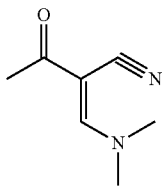

To a stirred solution of 3-oxobutanenitrile (10.00 g, 120.00 mmol) in DMF (30 mL) was added DMF-DMA (19.34 mL, 144.00 mmol) and the reaction mixture was stirred at 80° C. for 16 h. The reaction mixture was cooled to ambient temperature, concentrated to dryness and diluted with n-hexane (200 mL). The precipitate was collected by suction filtration and dried under vacuum to obtain Intermediate 41A (13.00 g, 78.00%). $^1$H NMR (400 MHz, DMSO-$d_6$) δ ppm 2.17 (s, 3H), 3.25 (s, 3H), 3.29 (s, 3H), 7.83 (s, 1H). LCMS (Method-L): retention time 0.54 min, [M+H] 139.2.

Intermediate 41B:
2-amino-4-methylpyrimidine-5-carbonitrile

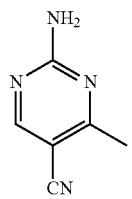

To a stirred solution of Intermediate 41A (12.00 g, 87.00 mmol) in EtOH (25 mL) was added guanidine carbonate (31.30 g, 174.00 mmol) and sodium acetate (21.37 g, 261.00 mmol) and the reaction was stirred at 80° C. for 5 h. The reaction mixture was cooled to ambient temperature, concentrated to dryness and diluted with n-hexane (200 mL). The precipitate was collected by suction filtration, washed with EtOH (30 mL) and dried under vacuum to obtain Intermediate 41B (9.50 g, 82.00%). $^1$H NMR (400 MHz, DMSO-$d_6$) δ ppm 2.38 (s, 3H), 7.62 (s, 2H), 8.53 (s, 1H). LCMS (Method-L): retention time 0.54 min, [M+H] 135.1.

Intermediate 41C:
2-bromo-4-methylpyrimidine-5-carbonitrile

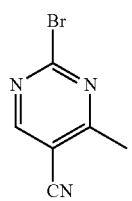

To a stirred solution of Intermediate 41B (5.00 g, 37.30 mmol) in THF (75 mL) and DMF (15 mL) was added copper (II) bromide (16.65 g, 74.50 mmol) and Isoamyl nitrite (7.53 ml, 55.9 mmol) and the reaction was refluxed for 1 h. The reaction mixture was cooled to ambient temperature, concentrated to dryness, diluted with the DCM (200 mL), filtered, and washed with THF (200 mL). The combined organic extracts were washed with 10% NaHCO$_3$ (150 mL). Then brine (50 mL), dried over anhydrous sodium sulfate and evaporated under reduced pressure. The residue was purified by column chromatography (Redisep-120 g, 0-15% EtOAc/n-Hexane) to obtain Intermediate 41C (0.75 g, 10.00%). $^1$H NMR (400 MHz, DMSO-$d_6$) δ ppm 2.65 (s, 3H), 9.08 (s, 1H). LCMS (Method-L): retention time 0.92 min, [M+2H] 199.1.

Intermediate 41

Intermediate 41 was prepared (0.04 g, 14.00%), by using a similar synthetic protocol as that of Intermediate 38 and starting from Intermediate 41C (0.30 g, 1.56 mmol) and 1H-pyrazole-4-carbaldehyde (0.182 g, 1.89 mmol). $^1$H NMR (400 MHz, DMSO-$d_6$) δ ppm 2.66 (s, 3H), 8.37 (s, 1H), 9.31 (s, 1H), 9.44 (s, 1H), 10.00 (s, 1H). LCMS (Method-L): retention time 0.74 min, [M+H] 214.1.

Intermediate 42: 5-(2-amino-1-hydroxyethyl)-4-cyclopropylisobenzofuran-1(3H)-one

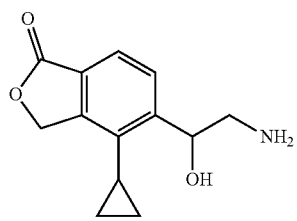 [SMILES: NCC(O)c1ccc2c(c1C1CC1)COC2=O]

Intermediate 42A:
5-bromo-4-iodoisobenzofuran-1(3H)-one

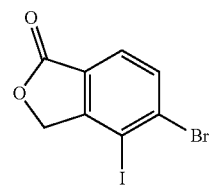 [SMILES: O=C1OCc2c1ccc(Br)c2I]

To a stirred solution of 5-bromoisobenzofuran-1(3H)-one (12.00 g, 56.30 mmol) in trifluoromethanesulfonic acid (49.70 mL, 563.00 mmol) at 0° C. was added n-iodosuccinimide (13.94 g, 62.00 mmol) portion wise. The resulting mixture was stirred for 16 h at ambient temperature. The reaction was poured into ice cold water and stirred for 30 minutes. The precipitated solid was filtered and dried under reduced pressure to obtain Intermediate 42A (6.00 g, 31.40%) as a pale yellow solid, $^1$H NMR (400 MHz, CDCl$_3$) δ ppm 5.07 (s, 2H), 7.74-7.76 (d, J=8 Hz, 1H), 7.79-7.81 (d, J=8 Hz, 1H). LCMS (Method-I): retention time 1.31 min, [M−2H] 337.1.

Intermediate 42B:
5-bromo-4-cyclopropylisobenzofuran-1(3H)-one

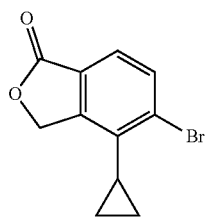 [SMILES: O=C1OCc2c1ccc(Br)c2C1CC1]

To a stirred solution of Intermediate 42A (1.70 g, 5.02 mmol) and cyclopropylboronic acid (0.43 g, 5.02 mmol) in toluene (25 mL) and water (5 mL) was added tripotassium phosphate (1.25 mL, 15.05 mmol) followed by tricyclohexylphosphine (20% molar solution in toluene) (0.70 g, 0.50 mmol). The resulting mixture was degassed with argon for 15 minutes. Then Pd(OAc)$_2$ (0.06 g, 0.25 mmol) was added and reaction mixture was heated at 100° C. for 12 h. The reaction mixture was cooled to ambient temperature, filtered through Celite® and washed with ethyl acetate (150 mL) and the filtrate was evaporated under reduced pressure. The residue was purified by column chromatography (Redisep-80 g, 0-5% EtOAc/n-Hexane) to obtain Intermediate 42B (0.42 g, 33.10%). $^1$H NMR (400 MHz, CDCl$_3$) δ ppm 0.71-0.74 (dd, J=4.8 Hz, 6.0 Hz, 2H), 1.10-1.15 (m, 2H), 1.93 (m, 1H), 5.38 (s, 2H), 7.60-7.62 (d, J=8 Hz, 1H), 7.72-7.74 (d, J=8 Hz, 1H). LCMS (Method-D): retention time 2.47 min, [M+2H] 272.2.

Intermediate 42C:
4-cyclopropyl-5-vinylisobenzofuran-1(3H)-one

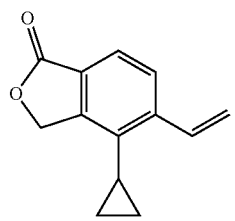

To a stirred solution of Intermediate 42B (0.84 g, 3.32 mmol) and potassium vinyltrifluoroborate (0.53 g, 3.98 mmol) in EtOH (25 mL) was added TEA (1.39 mL, 9.96 mmol) and resulting mixture was degassed with nitrogen for 10 minutes. Then PdCl$_2$(dppf)$_2$CH$_2$Cl$_2$ (0.03 g, 0.03 mmol) was added and the resulting mixture was sealed and heated to 85° C. for 12 h. The reaction mixture was cooled to ambient temperature, filtered through celite and washed with ethyl acetate (100 mL) and the filtrate was evaporated under reduced pressure. The residue was purified by column chromatography (Redisep-24 g, 0-10% EtOAc/n-Hexane) to obtain Intermediate 42C (0.60 g, 90.00%) as an off white solid. $^1$H NMR (400 MHz, DMSO-d$_6$) δ ppm 0.63-0.64 (m, 2H), 0.97-1.01 (m, 2H), 5.50 (s, 2H), 5.52-5.56 (dd, J=1.2 Hz, J=11.2 Hz, 2H), 5.92-5.96 (dd, J=0.8 Hz, J=17.6 Hz, 1H), 7.35-7.42 (dd, J=11.2 Hz, J=17.6 Hz, 1H), 7.67-7.69 (d, J=8 Hz, 1H), 7.77-7.79 (d, J=7.6 Hz, 1H). LCMS (Method-I): retention time 1.25 min, [M+H] 201.4.

Intermediate 42D-I and 42D-II: 4-cyclopropyl-5-(oxiran-2-yl)isobenzofuran-1(3H)-one

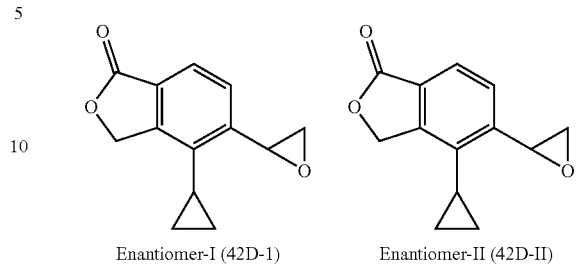

Enantiomer-I (42D-I)    Enantiomer-II (42D-II)

To a stirred solution of Intermediate 42C (0.60 g, 3.00 mmol) in DCM (30 mL) was added m-CPBA (1.38 g, 5.99 mmol) at ambient temperature and reaction was stirred for 16 h. The reaction mixture was diluted with water (30 mL), basified by 10% NaHCO$_3$ (20 mL) and extracted with DCM (2×100 mL). The combined organic layers were washed with brine (50 mL), dried over anhydrous sodium sulfate and evaporated under reduced pressure. The residue was purified by chiral SFC [Column: Chiralpak AD-H (250×4.6 mm) 5.0 micron; 0.2% DEA in MeOH, Flow:3.0 g/min, temperature 30° C., UV: 240 nm] to obtain Intermediate 42D-I (0.19 g, 29.30%) as a pale yellow solid, fast eluting (retention time 4.00 min) $^1$H NMR (400 MHz, CDCl$_3$) δ ppm 0.55-0.85 (m, 2H), 1.02-1.20 (m, 2H), 1.90-2.10 (m, 1H), 2.64-2.82 (m, 1H), 3.17-3.37 (m, 1H), 4.44 (dd, J=4.02, 2.51 Hz, 1H), 5.39 (s, 2H), 7.38 (d, J=8.03 Hz, 1H), 7.77 (d, J=8.03 Hz, 1H). LCMS (Method-D): retention time 1.83 min, [M+H2O] 234.2, and Intermediate 42D-II (0.28 g, 43.20%), slow eluting (retention time 4.65 min). LCMS (Method-D): retention time 1.95 min, [M−H] 215.0.

Intermediate 42

Intermediate 42 was prepared (0.12 g, 77.00%) as a brown solid, by using a similar synthetic protocol as that of Intermediate 7-I and starting from Intermediate 42D-I (0.15 g, 0.66 mmol).

$^1$H NMR (400 MHz, DMSO-d6) δ ppm 0.55-0.85 (m, 2H), 1.02-1.20 (m, 2H), 1.90-2.10 (m, 1H), 2.64-2.82 (m, 1H), 3.17-3.37 (m, 1H), 4.44 (dd, J=4.02, 2.51 Hz, 1H), 5.39 (s, 2H), 7.38 (d, J=8.03 Hz, 1H) 7.77 (d, J=8.03 Hz, 1H) (3 exchangeable protons not observed). LCMS (Method-D): retention time 0.40 min, [M+H] 234.2.

Intermediate 43: 6-(4-formyl-5-methyl-2H-1,2,3-triazol-2-yl)-4-methylnicotinonitrile

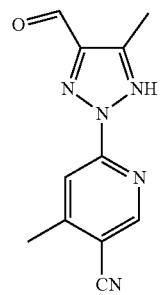 [SMILES: Cc1cc(-n2nc(C)c(C=O)n2)ncc1C#N]

Intermediate 43A: Ethyl 5-methyl-2H-1,2,3-triazole-4-carboxylate

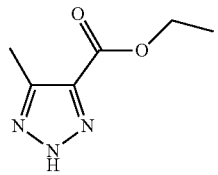

To a stirred solution of ethyl but-2-ynoate (10.00 g, 89.00 mmol) in DMF (70 mL) and MeOH (7 mL) was added azidotrimethylsilane (17.76 mL, 134.00 mmol), Copper (I) Iodide (0.85 g, 4.46 mmol) and the reaction mixture was heated at 95° C. for 12 h. The reaction mixture was cooled to ambient temperature, diluted with DCM (200 mL). Undissolved solids were filtered through celite and filtrate was evaporated under reduced pressure. The residue was stirred with ethylacetate (15 mL) at 5° C. for 1 h and solid was filtered to obtain Intermediate 43A (5.20 g, 35.70%) as a brown solid. $^1$H NMR (400 MHz, DMSO-$d_6$) δ ppm 1.31 (t, J=7.09 Hz, 3H), 2.51 (br. s., 3H), 4.30 (q, J=6.93 Hz, 2H), 15.36 (br. s., 1H). LCMS (Method-D): retention time 0.68 min, [M+H] 156.2.

Intermediate 43B: ethyl 2-(5-cyano-4-methylpyridin-2-yl)-5-methyl-2H-1,2,3-triazole-4-carboxylate

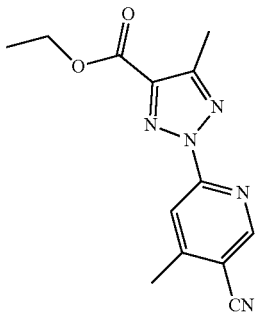 [SMILES: CCOC(=O)c1nn(-c2cc(C)c(C#N)cn2)nc1C]

Intermediate 43B was prepared (0.72 g, 35.40%) as a brown solid, by using a similar synthetic protocol as that of Intermediate 18 and starting from Intermediate 43A (1.00 g, 6.45 mmol) and 6-bromo-4-methylnicotinonitrile (1.52 g, 7.73 mmol). $^1$H NMR (400 MHz, DMSO-$d_6$) δ ppm 1.33-1.38 (m, 3H), 2.56 (s, 3H), 2.64 (s, 3H), 4.39 (q, J=7.03 Hz, 2H), 8.18 (s, 1H), 8.97 (s, 1H). LCMS (Method-D): retention time 2.15 min, [M+H] 272.0.

Intermediate 43C: 6-(4-(hydroxymethyl)-5-methyl-2H-1,2,3-triazol-2-yl)-4-methylnicotinonitrile

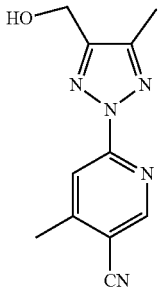

Intermediate 43C was prepared (0.25 g, 48.80%) as a brown solid, by using a similar synthetic protocol as that of Intermediate 39B and starting from Intermediate 43B (0.60 g, 2.21 mmol).
$^1$H NMR (400 MHz, DMSO-$d_6$) δ ppm 2.39 (s, 3H), 2.60 (s, 3H), 4.62 (d, J=5.52 Hz, 2H), 5.39 (t, J=5.77 Hz, 1H), 8.04 (s, 1H), 8.89 (s, 1H). LCMS (Method-D): retention time 1.16 min, [M+H] 230.0.

Intermediate 43

Intermediate 43 was prepared (0.25 g, 48.80%), by using a similar synthetic protocol as that of Intermediate 26 and starting from Intermediate 43C (0.20 g, 0.87 mmol). $^1$H NMR (400 MHz, DMSO-$d_6$) δ ppm 2.58 (s, 3H), 2.66 (s, 3H), 8.24 (s, 1H), 9.01 (s, 1H), 10.23 (s, 1H). LCMS (Method-D): retention time 1.95 min, [M−H] 226.1.

Intermediate 44: 6-(4-acetyl-2H-1,2,3-triazol-2-yl)-4-methylnicotinonitrile

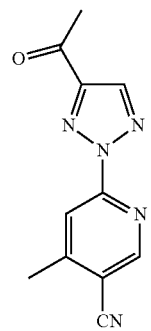 [SMILES: CC(=O)c1cnn(-c2cc(C)c(C#N)cn2)n1]

Intermediate 44A: 6-(4-(1-hydroxyethyl)-2H-1,2,3-triazol-2-yl)-4-methylnicotinonitrile

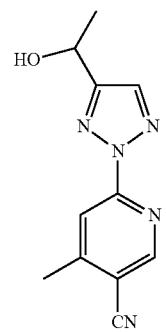 [SMILES: Cc1cc(-n2ncc(C(C)O)n2)ncc1C#N]

To a stirred solution of Intermediate 28 (0.80 g, 3.75 mmol) in THF (15 mL) was added 3.0 M methylmagnesium bromide in diethylether (2.51 mL, 7.50 mmol) at 0° C.-5° C. under a nitrogen atmosphere over a period of 5 min. Stirring was continued for 3 h. The reaction was diluted with saturated NH$_4$Cl (15 mL) and extracted with ethyl acetate (2×30 mL). The combined organic layers were washed with brine (20 mL), dried over anhydrous sodium sulfate and evaporated under reduced pressure. The residue was purified by column chromatography (Redisep-40 g, 60-70% EtOAc/n-Hexane) to obtain Intermediate 44A (0.74 g, 80.0%) as yellow solid. $^1$H NMR (400 MHz, DMSO-d$_6$) δ ppm 1.48 (d, J=6.53 Hz, 3H), 2.62 (s, 3H), 4.93-5.00 (m, 1H), 5.58 (d, J=5.02 Hz, 1H), 8.10-8.11 (m, 1H), 8.17 (s, 1H), 8.93 (s, 1H). LCMS (Method-D): retention time 1.05 min, [M+H] 230.0.

Intermediate 44

Intermediate 44 was prepared (0.32 g, 73.40%) as a yellow solid, by using a similar synthetic protocol as that of Intermediate 26 and starting from Intermediate 44A (0.40 g, 1.75 mmol).
$^1$H NMR (400 MHz, DMSO-d$_6$) δ ppm 2.66-2.67 (m, 6H), 8.27 (s, 1H), 8.70 (s, 1H), 9.03 (s, 1H). LCMS (Method-D): retention time 1.66 min, [M+H] 228.0.

Intermediate 45: (R)-5-(2-((2-(1H-pyrazol-4-yl)propan-2-yl)amino)-1-hydroxyethyl)-4-methylisobenzofuran-1(3H)-one

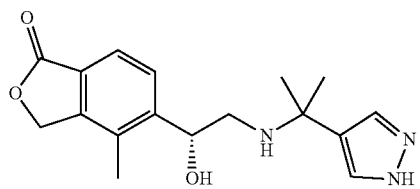 [SMILES: Cc1c([C@@H](O)CNC(C)(C)c2cn[nH]c2)ccc2c1COC2=O]

Intermediate 45A: Ethyl 1-benzyl-1H-pyrazole-4-carboxylate

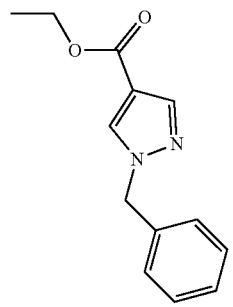 [SMILES: CCOC(=O)c1cnn(Cc2ccccc2)c1]

To a solution of NaH (1.08 g, 25.70 mmol) in THF (30 mL) at ambient temperature under nitrogen atmosphere was added a solution of ethyl 1H-pyrazole-4-carboxylate (3.00 g, 21.41 mmol) in THF (10 mL) and stirring was continued for 1 h. Then benzyl bromide (3.06 mL, 25.7 mmol) was added over the period of 15 min and the reaction was stirred for 22 h. The reaction mixture was cooled to 10° C., diluted with aqueous NH$_4$Cl (100 mL) and extracted with ethyl acetate (2×80 mL). The combined organic layers were washed with brine (30 mL), dried over anhydrous sodium sulfate and evaporated under reduced pressure. The residue was purified by column chromatography (Redisep-120 g, 0-30% EtOAc/n-Hexane) to obtain Intermediate 45A (4.50 g, 88%) as a white solid. $^1$H NMR (400 MHz, DMSO-d$_6$) δ ppm 1.23-1.28 (m, 3H), 4.21 (q, J=7.19 Hz, 2H), 5.37 (s, 2H), 7.25-7.38 (m, 5H), 7.87 (s, 1H), 8.46 (s, 1H). LCMS (Method-H): retention time 1.8 min, [M+H] 231.0.

Intermediate 45B: 2-(1-benzyl-1H-pyrazol-4-yl)propan-2-ol

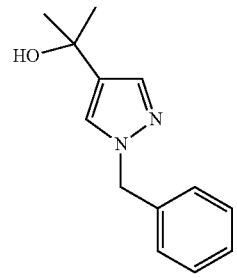 [SMILES: CC(C)(O)c1cnn(Cc2ccccc2)c1]

Intermediate 45B was prepared (4.20 g, 83.00%) as white solid, by using a similar synthetic protocol as that of Intermediate 44A and starting from Intermediate 45A (4.40 g, 19.11 mmol). $^1$H NMR (300 MHz, DMSO-d$_6$) δ ppm 1.38 (s, 6H), 4.76 (s, 1H), 5.24 (s, 2H), 7.21-7.34 (m, 5H), 7.36 (d, J=0.76 Hz, 1H), 7.61 (s, 1H). LCMS (Method-D): retention time 0.89 min, [M+H] 217.0.

Intermediate 45C: N-(2-(1-benzyl-1H-pyrazol-4-yl)propan-2-yl)-2-chloroacetamide

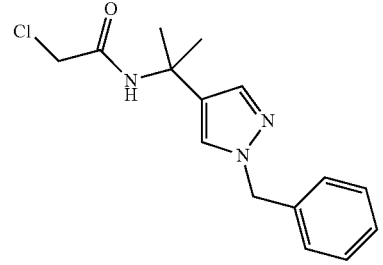 [SMILES: CC(C)(NC(=O)CCl)c1cnn(Cc2ccccc2)c1]

To a solution of Intermediate 45B (4.20 g, 19.42 mmol) in TFA (42 mL) was added chloroacetonitrile (2.47 mL, 38.80 mmol) at ambient temperature and the resulting solution was heated to 50° C. for 12 h. The reaction mixture was cooled to ambient temperature, basified with 10%/NaHCO$_3$ (100 mL) and extracted with ethyl acetate (3×100 mL). The combined organic layers were washed with brine (500 mL), dried over anhydrous sodium sulfate and evaporated under reduced pressure to obtain Intermediate 45C (5.00 g, 89%). $^1$H NMR (400 MHz, DMSO-d$_6$) δ ppm 1.57 (s, 6H), 3.98 (s, 2H), 5.25 (s, 2H), 7.26-7.37 (m, 5H), 7.39 (d, J=1.00 Hz, 1H), 7.71 (s, 1H), 8.07 (s, 1H). LCMS (Method-D): retention time 1.87 min, [M+H] 294.0. The compound was taken directly to the subsequent step without further purification or characterization.

Intermediate 45D: 2-(1-benzyl-1H-pyrazol-4-yl)propan-2-amine

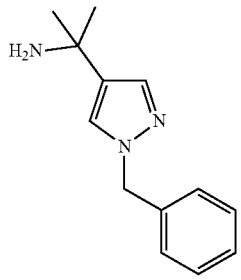 [SMILES: CC(C)(N)c1cnn(Cc2ccccc2)c1]

To a stirred solution of Intermediate 45C (5.00 g, 17.14 mmol) and thiourea (1.57 g, 20.56 mmol) in EtOH (50 mL) was added acetic acid (5 mL) at ambient temperature and the resulting mixture was heated at 75° C. for 10 h. The reaction was cooled to ambient temperature, basified with 10% NaHCO$_3$(100 mL) and extracted with ethyl acetate (3×100 mL). The combined organic layers were evaporated under reduced pressure. The residue was dissolved in 6 N HCl (150 mL) and aqueous layer was washed with ethyl acetate (2×50 mL). The aqueous layer was then basified with solid NaHCO$_3$ and extracted with DCM (2×100 mL). The combined organic layers were washed with brine (50 mL), dried over anhydrous sodium sulfate and evaporated under reduced pressure to obtain Intermediate 45D (2.50 g, 63.00%) as a brown liquid. $^1$H NMR (400 MHz, DMSO-d$_6$) δ ppm 1.30 (s, 6H), 1.67 (br. s., 2H), 5.23 (s, 2H), 7.20-7.24 (m, 2H), 7.25-7.36 (m, 3H), 7.39 (s, 1H), 7.61 (d, J=1.00 Hz, 1H). LCMS (Method-I): retention time 0.99 min, [M+H] 216.0.

Intermediate 45E: (R)-5-(2-((2-(1-benzyl-1H-pyrazol-4-yl)propan-2-yl)amino)-1-hydroxyethyl)-4-methylisobenzofuran-1(3H)-one

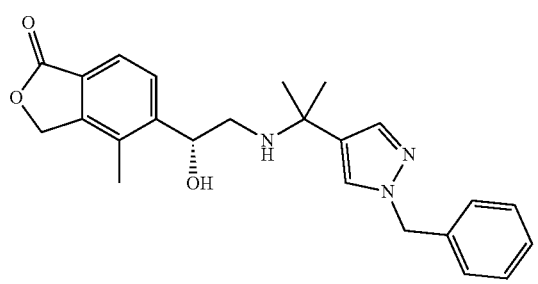 [SMILES: Cc1c([C@@H](O)CNC(C)(C)c2cnn(Cc3ccccc3)c2)ccc2c1COC2=O]

Intermediate 45E was prepared (0.50 g, 46.90%) as a pale yellow solid, by using a similar synthetic protocol as that of Intermediate 13-I and starting from Intermediate 45D (0.60 g, 2.79 mmol) and Intermediate 1-I (0.42 g, 2.23 mmol). $^1$H NMR (300 MHz, DMSO-d$_6$) δ ppm 1.27-1.31 (m, 6H), 2.10 (s, 3H), 2.34-2.41 (m, 2H), 4.79-4.85 (m, 1H), 5.23 (s, 2H), 5.34 (d, J=4.15 Hz, 2H), 5.39 (d, J=3.78 Hz, 1H), 7.14-7.19 (m, 2H), 7.23-7.36 (m, 5H), 7.56-7.62 (m, 2H), (1 Exchangeable proton not observed). LCMS (Method-H): retention time 1.724 min, [M+H] 406.0.

Intermediate 45

To a solution of Intermediate 45E (0.40 g, 0.98 mmol) in MeOH (15 mL) was purged with nitrogen for 1 min and added 20% Pd(OH)$_2$/C (0.40 g, 0.57 mmol) and 1 M HCl (0.99 mL, 0.98 mmol). The reaction was stirred at ambient temperature for 18 h under an hydrogen atmosphere. The reaction was filtered through celite and filtrate was concentrated under reduced pressure. The residue was basified with 10% NaHCO3(40 mL) and extracted with DCM (2×50 mL). The combined organic layers were washed with brine (30 mL), dried over anhydrous sodium sulfate and evaporated under reduced pressure to obtain Intermediate 45 (0.260 g, 51.80%) as an off-white solid. $^1$H NMR (400 MHz, DMSO-d$_6$) δ ppm 1.30 (d, J=6.02 Hz, 6H), 2.15 (s, 3H), 2.32-2.44 (m, 2H), 4.83 (dd, J=8.03, 4.02 Hz, 1H), 5.36 (s, 3H), 7.40 (br. s., 2H), 7.59-7.64 (m, 2H), 12.42-12.52 (m, 1H), (1 Exchangeable proton not observed). LCMS (Method-H): retention time 0.77 min, [M+H] 316.0.

Intermediate 46: 6-(4-formyl-1H-indazol-1-yl)-4-methoxynicotinonitrile

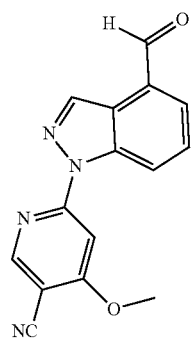 [SMILES: COc1cc(-n2ncc3c(C=O)cccc32)ncc1C#N]

Intermediate 46 was prepared (0.10 g, 15%), by using a similar synthetic protocol as that of Intermediate 9 and starting from 1H-indazole-4-carbaldehyde (0.35 g, 2.39 mmol) and 6-bromo-4-methoxynicotinonitrile (0.76 g. 3.59 mmol). $^1$H NMR (400 MHz, DMSO-d$_6$) δ ppm 4.20 (s, 3H), 7.33 (s, 1H), 7.91-7.93 (t, J=8.0 Hz, 1H), 8.08 (d, J=7.53 Hz, 1H), 8.18 (d, J=9.04 Hz, 1H), 8.50 (s, 1H), 9.60 (s, 1H), 10.17 (s, 1H). LCMS (Method-I): retention time 1.18 min, [M+H] 279.0.

Intermediate 47: 6-(4-(2-aminoethyl)-1H-pyrazol-1-yl)-4-methylnicotinonitrile

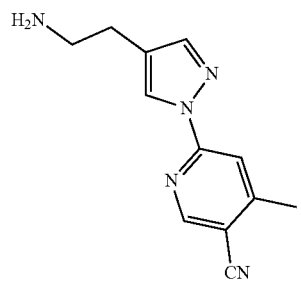 [SMILES: Cc1cc(-n2cc(CCN)cn2)ncc1C#N]

Intermediate 47A:
3-(diethoxymethyl)-2-ethoxytetrahydrofuran

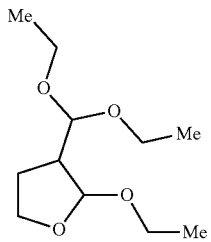 [SMILES: CCOC(OCC)C1CCOC1OCC]

FeCl₃ (0.02 g, 0.14 mmol) was added to a flask containing triethoxymethane (23.26 g, 157.00 mmol) and cooled to 10° C. The resulting reaction mixture was stirred for 30 minutes and 2,3-dihydrofuran (10.00 g. 143.00 mmol) was added dropwise over 30 minutes. The reaction mixture was stirred at 10° C. for 1 h, diluted with DCM (100 mL) and filtered through Celite®. The filtrate was concentrated under reduced pressure to obtain Intermediate 15A (30.00 g, 96.00%) as a brown oil. $^1$H NMR (400 MHz, CDCl₃) δ ppm 1.09-1.29 (m, 9H), 1.76 (dd, J=12.55, 5.52 Hz, 1H), 1.84-2.13 (m, 1H), 2.29-2.57 (m, 1H), 3.38-3.81 (m, 6H), 3.82-4.14 (m, 2H), 4.33 (d, J=8.53 Hz, 1H), 4.88-5.09 (m, 1H).

Intermediate 47B: 2-(1H-pyrazol-4-yl)ethanol

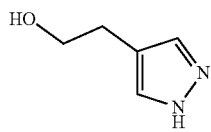

To a solution of hydrazine bishydrochloride (18.75 g, 179.00 mmol) in a mixture of water (50 mL) and ethanol (25 mL) was added Intermediate 47A (30.00 g, 137.00 mmol) at 0° C. The reaction mixture was stirred at 0° C. for 1 h and at ambient temperature for 1 h. Sodium carbonate (30.00 g) was added to the reaction mixture and evaporated to dryness under reduced pressure. The residue was washed with ethanol (100 mL) and evaporated to obtain Intermediate 47B (15.00 g, 92.00%) as a brown oil. $^1$H NMR (400 MHz, CDCl₃) δ ppm 2.78 (t, J=6.38 Hz, 2H), 3.72 (d, J=7.25 Hz, 1H), 3.77-3.88 (m, 2H), 7.49 (s, 2H), 9.52-10.74 (m, 1H). LCMS (Method-I): retention time 0.40 min, [M+H] 113.0.

Intermediate 47C: 6-(4-(2-hydroxyethyl)-1H-pyrazol-1-yl)-4-methoxynicotinonitrile

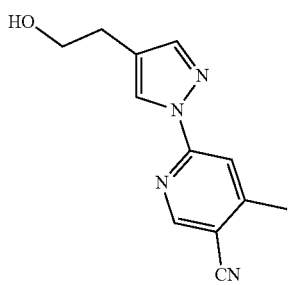 [SMILES: Cc1cc(-n2cc(CCO)cn2)ncc1C#N]

To a solution of Intermediate 47B (1.00 g, 8.92 mmol) and 6-bromo-4-methylnicotinonitrile (1.76 g, 8.92 mmol) in dioxane (20 mL) was added K₂CO₃ (3.08 g, 22.30 mmol) and XANTPHOS (1.03 g 1.78 mmol) and the resulting reaction mixture was degassed with nitrogen for 5 minutes. Pd₂(dba)₃ (0.82 g, 0.89 mmol) was added and the resulting mixture was degassed again for 5 minutes then heated at 100° C. for 16 h. The reaction mixture was cooled to ambient temperature, filtered through Celite® and the filtrate was concentrated under reduced pressure. The residue was purified by column chromatography (Redisep-40 g, 2-2.5%0 MeOH/DCM) to obtain Intermediate 47C (1.20 g, 59.0%0) as a pale yellow solid. $^1$H NMR (300 MHz, DMSO-d₆) δ ppm 2.57 (s, 3H) 2.65 (t, J=6.61 Hz, 2H) 3.55-3.67 (m, 2H) 4.71 (br. s., 1H) 7.80 (s, 1H) 7.96 (d, J=0.76 Hz, 1H) 8.47 (s, 1H) 8.82 (s, 1H). LCMS (Method-D): retention time 0.86 min, [M+1] 229.3.

Intermediate 47

A stirred solution of Intermediate 47 (1.00 g, 4.38 mmol) in thionyl chloride (10.00 mL, 137.00 mmol) was refluxed at 80° C. for 6 h. The reaction mixture was cooled to ambient temperature and evaporated under reduced pressure. The crude residue was dissolved in THF (10 mL), cooled to 0° C. Ammonia was purged for 5 minutes through the solution and the reaction mixture was stirred at 60° C. for 16 h in a sealed tube. The reaction mixture was cooled to ambient temperature and evaporated under reduced pressure. The residue was purified by column chromatography using combiflash (Redisep-40 g, 0-3% MeOH in CHCl₃) to obtain Intermediate 47 (0.70 g, 70.28%) as a yellow solid, $^1$H NMR (400 MHz, DMSO-d₆) δ ppm 1.23 (s, 2H), 2.54-2.60 (m, 5H), 2.76-2.99 (m, 2H), 7.81 (s, 1H), 7.97 (s, 1H), 8.47 (s, 1H), 8.83 (s, 1H). LCMS (Method-D): retention time 0.81 min, [M+1] 228.2.

Intermediate 48: 2-(4-methyl-1-oxo-1,3-dihydroisobenzofuran-5-yl)acetic Acid

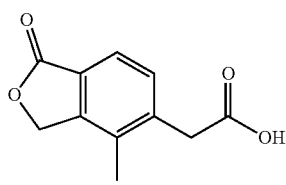

Synthesized according to literature procedures (WO2010/129379 A1, 2010).

Intermediate 49-I: tert-butyl (R)-(2-amino-2-(4-methyl-1-oxo-1,3-dihydroisobenzofuran-5-yl)ethyl) carbamate

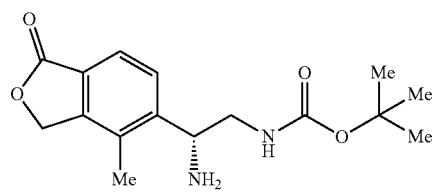 [SMILES: Cc1c([C@@H](N)CNC(=O)OC(C)(C)C)ccc2c1COC2=O]

Intermediate 49A-II: (S)-5-(2-amino-1-hydroxy-ethyl)-4-methylisobenzofuran-1(3H)-one

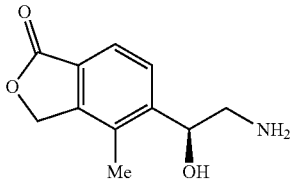 [SMILES: Cc1c([C@H](O)CN)ccc2c1COC2=O]

Intermediate 49A-II was prepared (40.00 g, 68.80%) as a brown solid, by using a similar synthetic protocol as that of Intermediate 7-I and starting from Intermediate 1-II (40.00 g, 210.00 mmol). $^1$H NMR (400 MHz, DMSO-$d_6$) δ ppm 2.26 (s, 3H), 2.52-2.56 (m, 1H), 2.69 (dd, J=13.05, 4.02 Hz, 1H), 4.80 (dd, J=8.03, 3.51 Hz, 1H), 5.38 (d, J=1.51 Hz, 3H), 7.65 (s, 2H). (2 Exchangeable protons not observed). LCMS (Method-H): retention time 0.54 min, [M+H] 208.2.

Intermediate 49B-II: tert-butyl (S)-(2-hydroxy-2-(4-methyl-1-oxo-1,3-dihydroisobenzofuran-5-yl)ethyl)carbamate

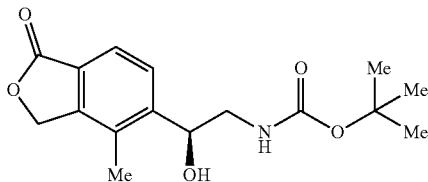 [SMILES: Cc1c([C@H](O)CNC(=O)OC(C)(C)C)ccc2c1COC2=O]

A stirred solution of Intermediate 49A-II (40.00 g, 145.00 mmol) in DCM (400 mL) was cooled to 0° C. TEA (60.50 mL, 434.00 mmol) followed by BOC$_2$O (40.30 mL, 174.00 mmol) were added. The resulting reaction mixture was stirred at ambient temperature overnight, diluted with water (200 mL) and extracted with DCM (3×200 mL). The combined organic layers were washed with brine (150 mL), dried over sodium sulfate and evaporated under reduced pressure. The residue was purified by column chromatography (Redisep-750 g, 2% MeOH in chloroform) to obtain Intermediate 49B-II: (48.00 g, 80.00%) as a colorless oil. $^1$H NMR (400 MHz, DMSO-$d_6$) δ ppm 1.35 (s, 9H), 2.29 (s, 3H), 2.96 (ddd, J=13.70, 7.90, 6.00 Hz, 1H), 3.20-3.06 (m, 1H), 4.89-5.02 (m, 1H), 5.38 (s, 2H), 5.54 (d, J=4.50 Hz, 1H), 6.89 (t, J=5.80 Hz, 1H), 7.66 (s, 2H). LCMS (Method-I): retention time 0.93 min, [M+H] 308.4.

Intermediate 49C-I: tert-butyl (R)-(2-(1,3-dioxoisoindolin-2-yl)-2-(4-methyl-1-oxo-1,3-dihydroisobenzofuran-5-yl)ethyl)carbamate

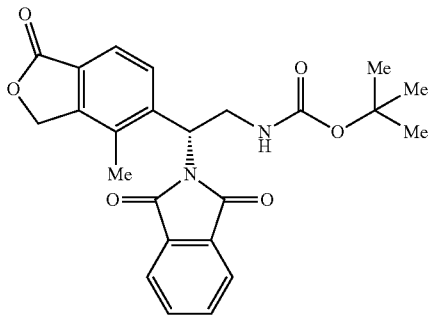 [SMILES: Cc1c([C@H](CNC(=O)OC(C)(C)C)N2C(=O)c3ccccc3C2=O)ccc2c1COC2=O]

To a stirred solution of Intermediate 49B-II (47.00 g, 113.00 mmol) in THF (800 mL) were added triphenylphosphine (65.30 g. 249.00 mmol) followed by DIAD (39.60 mL, 204.00 mmol). The resulting reaction mixture was stirred at ambient temperature for 2 h, diluted with water (1.5 L) and extracted with ethyl acetate (3×500 mL). The combined organic layers were washed with brine (300 mL), dried over anhydrous sodium sulfate and evaporated under reduced pressure. The residue was purified by silica gel column chromatography (Redisep—1.5 kg, 40% EtOAc/n-hexane) to obtain Intermediate 49C-I (50.00 g, 91.00%) as a colorless oil. $^1$H NMR (300 MHz, DMSO-$d_6$) δ ppm 1.19-1.33 (m, 9H), 2.28 (s, 3H), 3.63 (dt, J=13.79, 5.57 Hz, 1H), 3.94-4.15 (m, 1H), 5.26-5.46 (m, 2H), 5.65 (dd, J=9.44, 4.15 Hz, 1H), 7.23 (s, 1H), 7.71 (d, J=8.31 Hz, 1H), 7.78-7.94 (m, 5H). LCMS (Method-I): retention time 1.23 min, [M+H] 437.2.

Intermediate 49-I

To a stirred solution of Intermediate 49C-I (40.00 g, 92.00 mmol) in MeOH (500 mL) was added hydrazine hydrate (44.80 mL, 916.00 mmol). The resulting reaction mixture was heated at 60° C. for 14 h, cooled to ambient temperature and diluted with ethyl acetate (200 mL). The resultant solid was filtered and the filtrate was evaporated under reduced pressure. The residue was purified by silica gel column chromatography (Redisep –330 g, 2% MeOH/chloroform) to obtain Intermediate 49-1(28.50 g, 91.00%) as greenish oil. $^1$H NMR (400 MHz, DMSO-$d_6$) δ ppm 1.35 (s, 9H), 1.87-2.01 (m, 2H), 2.29 (s, 3H), 2.85-2.97 (m, 1H), 3.10 (dd, J=12.30, 6.27 Hz, 1H), 4.24-4.34 (m, 1H), 5.37 (s, 2H), 6.87-6.98 (m, 1H), 7.64 (d, J=8.03 Hz, 1H), 7.75 (d, J=8.03 Hz, 1H). LCMS (Method-I): retention time 0.84 min, [M+H] 307.1.

Intermediate 50-I: (R)—N-(2-amino-1-(4-methyl-1-oxo-1,3-dihydroisobenzofuran-5-yl)ethyl)acetamide

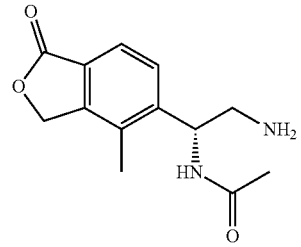 [SMILES: CC(=O)N[C@@H](CN)c1ccc2c(c1C)COC2=O]

Intermediate 50A-I: tert-butyl (R)-(2-acetamido-2-(4-methyl-1-oxo-1,3-dihydroisobenzofuran-5-yl)ethyl)carbamate

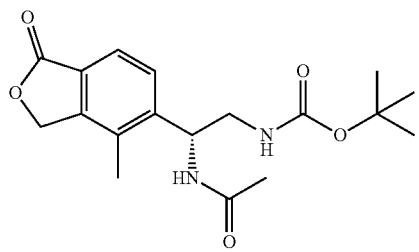 [SMILES: CC(=O)N[C@@H](CNC(=O)OC(C)(C)C)c1ccc2c(c1C)COC2=O]

To a stirred solution of Intermediate 49-I (0.20 g, 0.65 mmol) in DCM (15 mL) was added TEA (0.27 mL, 1.96 mmol), acetyl chloride (0.05 mL, 0.65 mmol) at 0° C. and the reaction mixture was stirred at ambient temperature for 16 h. The reaction mixture was diluted with water (30 mL) and extracted with ethyl acetate (3×30 mL). The combined organic layers were washed with brine (20 mL), dried over anhydrous sodium sulfate and evaporated under reduced pressure. The residue was purified by column chromatography (Redisep-12 g, 0-2% MeOH/CHCl$_3$) to obtain Intermediate 50A-I (0.20 g, 88.00%) as an off white solid. $^1$H NMR (300 MHz, DMSO-d$_6$) δ ppm 1.27-1.41 (m, 9H), 1.80-1.88 (m, 3H), 2.28-2.39 (m, 3H), 3.16 (t, J=5.48 Hz, 2H), 5.23 (q, J=7.18 Hz, 1H), 5.38 (s, 2H), 6.95 (t, J=5.48 Hz, 1H), 7.49-7.60 (m, 1H), 7.61-7.74 (m, 1H), 8.37 (d, J=8.31 Hz, 1H). LCMS (Method-I): retention time 0.89 min, [M+1]349.5.

Intermediate 50-I

To a stirred solution of Intermediate 50A-I (0.02 g, 0.07 mmol) in DCM (5 mL) was added TFA (0.5 mL, 6.49 mmol) and the reaction mixture was stirred at ambient temperature for 30 minutes. The reaction mixture was concentrated under reduced pressure and residue was dissolved in acetonitrile (5 mL), water (0.2 mL). To the resultant mixture, Na$_2$CO$_3$ (38.0 g, 0.36 mmol) was added and the mixture was heated at 80° C. for 1 h. The reaction mixture was cooled to ambient temperature, the solid Na$_2$CO$_3$ was filtered, and the filtrate was dried over sodium sulfate and evaporated under reduced pressure to obtain Intermediate 50-1(0.01 g, 84%) as colorless oil. LCMS (Method-I): retention time: 0.44 min, [M+1] 249.2. The compound was taken directly to the subsequent step without further purification or characterization.

Intermediate 51-I: (R)—N-(2-amino-1-(4-methyl-1-oxo-1,3-dihydroisobenzofuran-5-yl)ethyl)methanesulfonamide

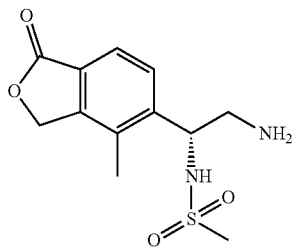 [SMILES: Cc1c([C@H](CN)NS(C)(=O)=O)ccc2c1COC2=O]

Intermediate 51A-I: tert-butyl (R)-(2-(4-methyl-1-oxo-1,3-dihydroisobenzofuran-5-yl)-2-(methylsulfonamido)ethyl)carbamate

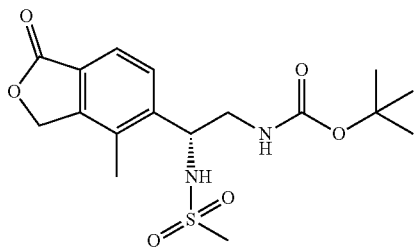 [SMILES: Cc1c([C@H](CNC(=O)OC(C)(C)C)NS(C)(=O)=O)ccc2c1COC2=O]

Intermediate 51A-I was prepared (1.20 g, 47.80%) as an off white solid, by using a similar synthetic protocol as that of Intermediate 50A-I and starting from Intermediate 49-I (2.00 g, 6.53 mmol). $^1$H NMR (400 MHz, DMSO-d6) δ ppm $^1$H NMR (300 MHz, DMSO-d$_6$) δ ppm 1.34 (s, 9H), 2.31 (s, 3H), 2.69 (s, 3H), 3.01-3.24 (m, 2H), 4.88 (d, J=6.80 Hz, 1H), 5.40 (s, 2H), 7.03 (s, 1H), 7.60-7.75 (m, 2H), 7.89 (d, J=8.31 Hz, 1H). LCMS (Method-H): retention time: 0.89 min, [M−1] 383.0.

Intermediate 51-I

Intermediate 51-I was prepared (0.21 g, 95%) as colorless oil, by using a similar synthetic protocol as that of Intermediate 50-1 and starting from Intermediate 51A-I (0.30 g, 0.78 mmol). $^1$H NMR (400 MHz, DMSO-d$_6$) δ ppm 2.30-2.37 (m, 3H), 2.64-2.83 (m, 2H), 3.17 (s, 3H), 4.70 (br. s., 1H), 5.26-5.47 (m, 2H), 7.59-7.66 (m, 1H), 7.72 (d, J=8.03 Hz, 1H), (3 Exchangeable protons not observed). LCMS (Method-I): retention time 0.42 min, [M+1]285.4.

Intermediate 52-I: methyl (R)-(2-amino-1-(4-methyl-1-oxo-1,3-dihydroisobenzofuran-5-yl)ethyl)carbamate

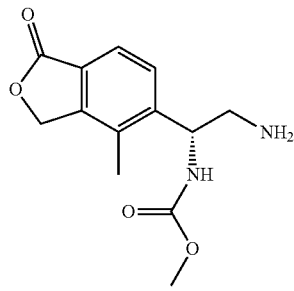 [SMILES: COC(=O)N[C@@H](CN)c1ccc2c(c1C)COC2=O]

Intermediate 52A-I: tert-butyl methyl (1-(4-methyl-1-oxo-1,3-dihydroisobenzofuran-5-yl)ethane-1,2-diyl)(R)-dicarbamate

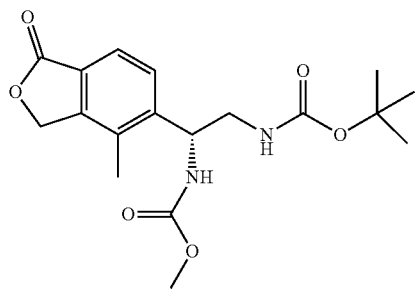 [SMILES: COC(=O)N[C@@H](CNC(=O)OC(C)(C)C)c1ccc2c(c1C)COC2=O]

Intermediate 52A-I was prepared (0.15 g, 63.10%) as an off white solid, by using a similar synthetic protocol as that of Intermediate 50A-I and starting from Intermediate 49-1 (0.20 g, 0.65 mmol). $^1$H NMR (300 MHz, DMSO-d$_6$) δ ppm 1.33 (s, 9H), 2.33 (s, 3H), 3.15 (br. s., 2H), 3.49 (s, 3H), 5.04 (q, J=7.05 Hz, 1H), 5.39 (s, 2H), 6.95 (br. s., 1H), 7.51-7.61 (m, 1H), 7.66 (d, J=8.31 Hz, 1H), 7.77 (d, J=7.93 Hz, 1H). LCMS (Method-I): retention time 1.04 min, [M+1] 365.5.

Intermediate 52-I

Intermediate 52-1 was prepared (0.04 g, 97.00%) as colorless oil, by using a similar synthetic protocol as that of Intermediate 50-I and starting from Intermediate 52A-I (0.05 g, 0.137 mmol). 1H NMR (400 MHz, DMSO-d$_6$) δ ppm 2.33 (s, 3H), 2.65-2.74 (m, 2H), 3.50 (s, 3H), 4.84 (br. s., 1H), 5.39 (d, J=4.02 Hz, 2H), 7.49 (d, J=8.03 Hz, 1H), 7.67 (d, J=8.53 Hz, 1H), 7.84 (br. s., 1H), (2 Exchangeable protons not observed). LCMS (Method-I): retention time 0.50 min, [M+1] 265.2.

Intermediate 53-I: (R)—N-(2-amino-1-(4-methyl-1-oxo-1,3-dihydroisobenzofuran-5-yl)ethyl)cyclopropanesulfonamide

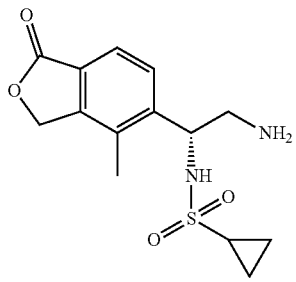 [SMILES: Cc1c([C@H](CN)NS(=O)(=O)C2CC2)ccc2c1COC2=O]

Intermediate 53AI-: tert-butyl (R)-(2-(cyclopropanesulfonamido)-2-(4-methyl-1-oxo-1,3-dihydroisobenzofuran-5-yl)ethyl)carbamate

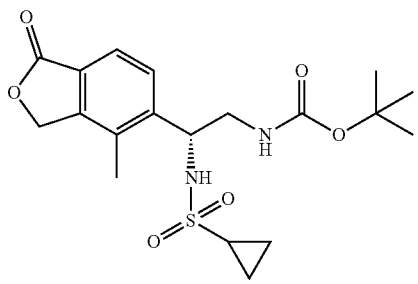 [SMILES: Cc1c([C@H](CNC(=O)OC(C)(C)C)NS(=O)(=O)C2CC2)ccc2c1COC2=O]

Intermediate 53A-I was prepared (0.13 g, 93.00%) as colorless oil, by using a similar synthetic protocol as that of Intermediate 50A- and starting from Intermediate 49-1(0.10 g, 0.32 mmol) and cyclopropanesulfonyl chloride (0.06 g, 0.39 mmol). $^1$H NMR (300 MHz, DMSO-d$_6$) δ ppm 0.92 (s, 4H), 1.11 (t, J=7.18 Hz, 1H), 1.33 (s, 9H), 2.22-2.35 (m, 3H), 3.21-3.34 (m, 2H), 4.90 (s, 1H), 5.40 (s, 2H), 6.98 (s, 1H), 7.70 (s, 2H), 7.89 (d, J=8.31 Hz, 1H). LCMS (Method-I): retention time 1.02 min, [M+1] 411.3.

Intermediate 53-I

Intermediate 53-1 was prepared (0.09 g, 95.00%) as colorless oil, by using a similar synthetic protocol as that of Intermediate 50-I and starting from Intermediate 53A-I (0.13 g, 0.30 mmol). $^1$H NMR (400 MHz, DMSO-d$_6$) δ ppm 0.58-0.98 (m, 5H), 2.29-2.38 (m, 3H), 3.12-3.19 (m, 3H), 4.09 (q, J=5.52 Hz, 2H), 4.61-4.71 (m, 1H), 5.36-5.45 (m, 2H), 7.57-7.78 (m, 2H). LCMS (Method-I): retention time 0.54 min, [M+1] 311.3.

Intermediate 54-I: (R)-5-(2-amino-1-((2-hydroxyethyl)amino)ethyl)-4-methylisobenzofuran-1(3H)-one

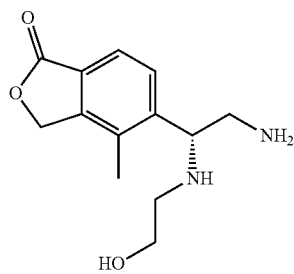 [SMILES: Cc1c([C@H](CN)NCCO)ccc2c1COC2=O]

Intermediate 54A-I: (R)-tert-butyl (2-((2-hydroxyethyl)amino)-2-(4-methyl-1-oxo-1,3-dihydroisobenzofuran-5-yl)ethyl)carbamate

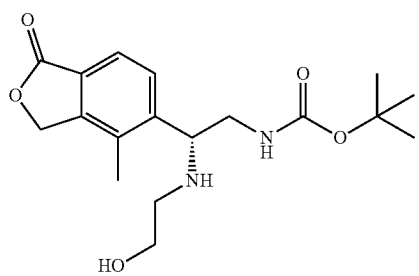 [SMILES: Cc1c([C@H](CNC(=O)OC(C)(C)C)NCCO)ccc2c1COC2=O]

To a stirred solution of Intermediate 49-I (0.50 g, 1.63 mmol) in methanol (10 mL) was added DIPEA (0.86 mL, 4.90 mmol), 2-bromoethanol (0.25 g, 1.96 mmol) at ambient temperature and reaction was heated to 75° C. for 12 h. The reaction mixture was cooled to ambient temperature, concentrated to dryness, diluted with water (30 mL) and extracted with ethyl acetate (2×30 mL). The combined organic layers were washed with brine (20 mL), dried over anhydrous sodium sulfate and evaporated under reduced pressure. The residue was purified by column chromatography (Redisep-40 g, 0-6% MeOH/CHCl$_3$) to obtain Intermediate 54A-I (0.52 g, 41%). $^1$H NMR (400 MHz, DMSO-d$_6$) δ ppm 1.36 (s, 9H), 2.30 (s, 4H), 2.36-2.43 (m, 1H), 2.91-3.00 (m, 1H), 3.01-3.09 (m, 1H), 3.32-3.38 (m, 2H), 4.13 (br. s., 1H), 5.38 (s, 2H), 7.01 (s, 1H), 7.64-7.73 (m, 2H), (2 Exchangeable protons not observed). LCMS (Method-D): retention time 1.25 min, [M+H] 351.2.

Intermediate 54-I

Intermediate 54-I was prepared (0.25 g, 80%) as colorless oil, by using a similar synthetic protocol as that of Intermediate 50-I and starting from Intermediate 54A-I (0.300 g, 0.86 mmol). $^1$H NMR (400 MHz, DMSO-d$_6$) δ ppm 2.41 (s, 3H), 2.64-2.71 (m, 1H), 3.05 (d, J=12.55 Hz, 1H), 3.15 (qd, J=7.36, 4.52 Hz, 2H), 3.45 (d, J=8.03 Hz, 1H), 3.63 (qd, J=6.53, 2.51 Hz, 2H), 4.97-5.03 (m, 1H), 5.46 (d, J=3.51 Hz, 2H), 7.86-7.89 (m, 1H), 7.93-7.97 (m, 1H), 8.42-8.52 (m, 2H), (1 Exchangeable proton not observed). LCMS (Method-D): retention time 0.454 min, [M+H] 251.

Intermediate 55-I: (R)-5-(2-amino-1-((2-methoxy-ethyl)amino)ethyl)-4-methylisobenzofuran-1(3H)-one

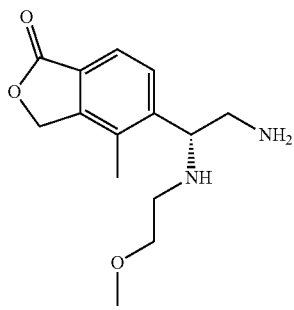 [SMILES: COCCN[C@@H](CN)c1ccc2c(c1C)COC2=O]

Intermediate 55A-I: (R)-tert-butyl (2-((2-methoxy-ethyl)amino)-2-(4-methyl-1-oxo-1,3-dihydroisobenzofuran-5-yl)ethyl)carbamate

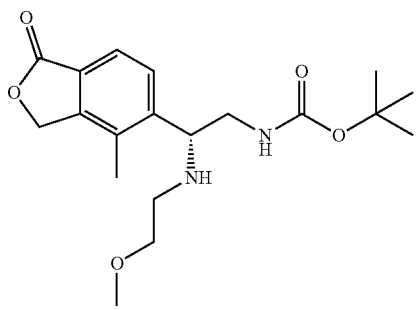 [SMILES: COCCN[C@@H](CNC(=O)OC(C)(C)C)c1ccc2c(c1C)COC2=O]

Intermediate 55A-I was prepared (0.30 g, 33.30) as pale yellow thick liquid, by using a similar synthetic protocol as that of Intermediate 54A-I and starting from Intermediate 49-I (0.50 g, 1.63 mmol) and 1-bromo-2-methoxyethane (0.27 g, 1.96 mmol). ¹H NMR (400 MHz, DMSO-d₆) δ ppm 1.36 (s, 9H), 2.30 (s, 4H), 2.36-2.43 (m, 1H), 2.91-3.00 (m, 1H), 3.01-3.09 (m, 1H), 3.21 (s, 3H), 3.32-3.38 (m, 2H), 4.13 (br. s., 1H), 5.38 (s, 2H), 7.01 (s, 1H), 7.64-7.73 (m, 2H), (1 Exchangeable proton not observed). LCMS (Method-D): retention time 1.823 min, [M+H] 365.0

Intermediate 55-I

Intermediate 55-I was prepared (0.32 g, 95%) as an off-white solid, by using a similar synthetic protocol as that of Intermediate 50-I and starting from Intermediate 55A-I (0.30 g, 0.82 mmol).

¹H NMR (400 MHz, DMSO-d₆) δ ppm 2.36 (s, 3H), 2.76 (d, J=12.05 Hz, 1H), 3.04 (br. s., 1H), 3.17 (s, 2H), 3.28 (s, 3H), 3.33 (br. s., 1H), 3.50 (d, J=4.02 Hz, 2H), 4.83 (br. s., 1H), 5.45 (d, J=4.02 Hz, 2H), 7.81-7.88 (m, 2H), (2 Exchangeable protons not observed). LCMS (Method-D): retention time 0.535 min, [M+H] 265.0.

Intermediate 56-I: (R)—N-(2-amino-1-(4-methyl-1-oxo-1,3-dihydroisobenzofuran-5-yl)ethyl)-2-hydroxyacetamide

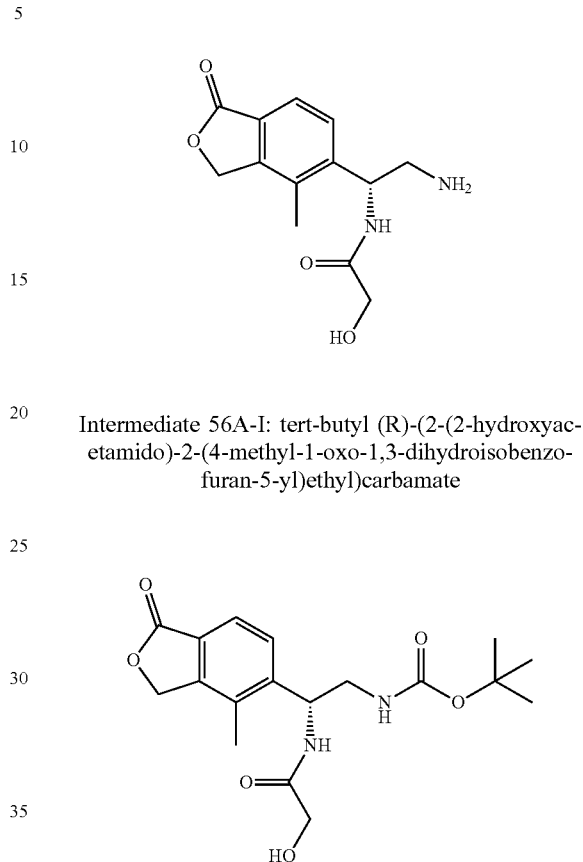

Intermediate 56A-I: tert-butyl (R)-(2-(2-hydroxyacetamido)-2-(4-methyl-1-oxo-1,3-dihydroisobenzofuran-5-yl)ethyl)carbamate To a stirred solution of Intermediate 49-I (0.30 g, 0.98 mmol) and 2-hydroxyacetic acid (0.08 g, 0.98 mmol) in DCM (15 mL) was added HATU (0.08 g, 1.96 mmol), DIPEA (0.51 mL, 2.94 mmol) and the resultant mixture was stirred at ambient temperature for 16 h. The reaction mixture was diluted with water (30 mL) and extracted with DCM (3×30 mL). The combined organic layers were washed with brine (20 mL), dried over anhydrous sodium sulfate and evaporated under reduced pressure. The residue was purified by column chromatography (Redisep-24 g, 0-3% MeOH/CHCl₃) to obtain Intermediate 56A-I (0.18 g, 50.40%) as an off white solid. ¹H NMR (400 MHz, DMSO-d₆) δ ppm 1.34 (s, 9H), 2.31-2.41 (m, 3H), 3.20-3.29 (m, 2H), 3.81 (br. s., 2H), 5.28 (q, J=7.36 Hz, 1H), 5.33-5.44 (m, 2H), 5.50 (br. s., 1H), 6.97 (t, J=5.77 Hz, 1H), 7.54-7.61 (m, 1H), 7.63-7.69 (m, 1H), 8.24-8.38 (m, 1H). LCMS (Method-I): retention time 0.82 min, [M+1] 365.5.

Intermediate 56-I

Intermediate 56-I was prepared (0.04 g, 50.40%) as colourless oil, by using a similar synthetic protocol as that of Intermediate 50-I and starting from Intermediate 56A-I (0.05 g, 0.137 mmol). ¹H NMR (400 MHz, DMSO-d₆) δ ppm 2.31-2.40 (m, 3H), 2.73-2.89 (m, 2H), 3.77-3.88 (m, 2H), 5.08 (s, 1H), 5.39 (d, J=2.51 Hz, 2H), 5.51 (s, 1H), 7.54 (d, J=8.03 Hz, 1H), 7.65 (d, J=8.03 Hz, 1H), 8.30 (d, J=7.03 Hz, 1H), (2 Exchangeable proton not observed). LCMS (Method-I): retention time 0.42 min, [M+1] 265.2.

Intermediate 57-I: (R)-5-(2-amino-1-(methylamino)ethyl)-4-methylisobenzofuran-1(3H)-one

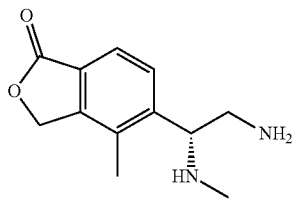 [SMILES: CN[C@@H](CN)c1ccc2c(c1C)COC2=O]

Intermediate 57A-I: tert-butyl (R)-(2-(4-methyl-1-oxo-1,3-dihydroisobenzofuran-5-yl)-2-(methylamino)ethyl)carbamate

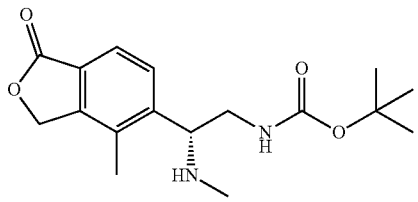 [SMILES: CN[C@@H](CNC(=O)OC(C)(C)C)c1ccc2c(c1C)COC2=O]

To a stirred solution of Intermediate 49-I (0.50 g, 1.63 mmol) and paraformaldehyde (0.05 g, 1.63 mmol) in MeOH (15 mL) was added sodium cyanoborohydride (0.51 g, 8.16 mmol) and the resultant mixture was stirred at ambient temperature for 16 h. The reaction mixture was diluted with water (30 mL) and extracted with DCM (3×30 mL). The combined organic layers were washed with brine (20 mL), dried over anhydrous sodium sulfate and evaporated under reduced pressure. The residue was purified by column chromatography (Redisep-24 g, 0-2% MeOH/CHCl$_3$) to obtain Intermediate 57A-I (0.20 g, 0.37 mmol, 22.95%) as an off white solid. $^1$H NMR (400 MHz, DMSO-d$_6$) δ ppm 1.19-1.39 (m, 9H), 2.10 (d, J=8.53 Hz, 3H), 2.26-2.34 (m, 3H), 2.93-3.12 (m, 2H), 3.90-4.04 (m, 1H), 5.38 (s, 2H), 6.93 (br. s., 1H), 7.62-7.74 (m, 3H). LCMS (Method-I): retention time 0.82 min, [M+1] 321.5.

Intermediate 57-I

Intermediate 57-I was prepared (0.06 g, 87.00%) as colorless oil, by using a similar synthetic protocol as that of Intermediate 50-I and starting from Intermediate 57A-I (0.1.00 g, 0.31 mmol). $^1$H NMR (400 MHz, DMSO-d$_6$) δ ppm 2.12 (s, 2H), 2.28 (s, 3H), 2.22-2.27 (m, 3H), 2.93-3.12 (m, 2H), 3.82-3.89 (m, 1H), 5.38 (s, 2H), 7.63-7.67 (m, 2H), (1 Exchangeable proton not observed). LCMS (Method-I): retention time 0.47 min, [M+1] 221.3.

Intermediate 58-I: (R)—N-(2-amino-1-(4-methyl-1-oxo-1,3-dihydroisobenzofuran-5-yl)ethyl)-N-methyl-methanesulfonamide

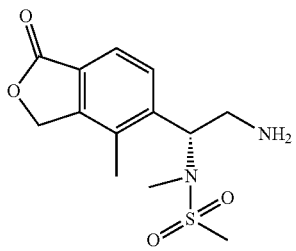 [SMILES: Cc1c([C@H](CN)N(C)S(C)(=O)=O)ccc2c1COC2=O]

Intermediate 58A-I: tert-butyl (R)-(2-(4-methyl-1-oxo-1,3-dihydroisobenzofuran-5-yl)-2-(N-methylmethylsulfonamido)ethyl)carbamate

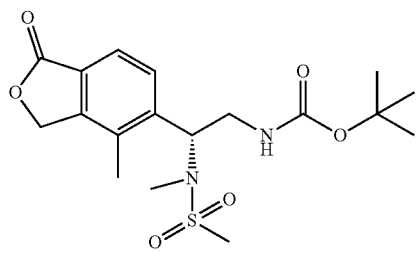

Intermediate 58A-I was prepared (0.12 g, 69.50%) as an off white solid, by using a similar synthetic protocol as that of Intermediate 50A-I and starting from Intermediate 57A-I (0.10 g, 0.31 mmol) and methanesulfonyl chloride (0.03 mL, 0.31 mmol). $^1$H NMR (400 MHz, DMSO-d$_6$) δ ppm 1.33-1.41 (m, 9H), 2.32-2.39 (m, 3H), 2.81 (s, 2H), 2.88 (s, 3H), 3.33-3.42 (m, 1H), 3.50 (ddd, J=14.31, 8.78, 6.02 Hz, 1H), 5.33-5.51 (m, 3H), 5.75 (s, 1H), 7.17 (s, 1H), 7.59-7.65 (m, 1H), 7.66-7.73 (m, 1H). LCMS (Method-I): retention time 1.04 min, [M+1] 399.3.

Intermediate 58-I

Intermediate 58-1 was prepared (0.07 g, 96.00%) as colorless oil, by using a similar synthetic protocol as that of Intermediate 50-I and starting from Intermediate 58B-I (0.09 g, 0.23 mmol). $^1$H NMR (300 MHz, DMSO-d$_6$) δ ppm 2.34 (s, 2H), 2.82 (s, 2H), 2.97 (s, 2H), 3.17 (d, J=4.91 Hz, 4H), 4.12 (q, J=4.91 Hz, 3H), 5.05-5.17 (m, 1H), 5.41 (d, J=2.64 Hz, 2H), 7.57 (d, J=8.31 Hz, 1H), 7.68 (d, J=7.93 Hz, 1H). LCMS (Method-I): retention time 0.54 min, [M+1] 299.3.

Intermediate 59-I: (R)-5-(2-amino-1-(1,1-dioxido-isothiazolidin-2-yl)ethyl)-4-methylisobenzofuran-1(3H)-one

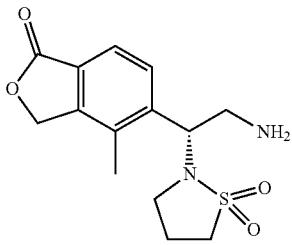 [SMILES: Cc1c([C@H](CN)N2CCCS2(=O)=O)ccc2c1COC2=O]

Intermediate 59A-I: tert-butyl (R)-(2-((3-chloropropyl)sulfonamido)-2-(4-methyl-1-oxo-1,3-dihydroisobenzofuran-5-yl)ethyl)carbamate

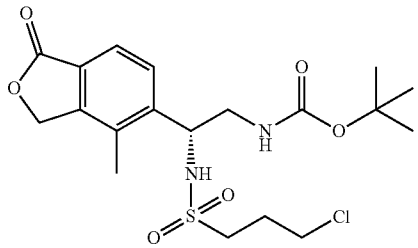 [SMILES: Cc1c([C@H](CNC(=O)OC(C)(C)C)NS(=O)(=O)CCCCl)ccc2c1COC2=O]

Intermediate 59A-I was prepared (0.40 g, 54.80%) as an off white solid, by using a similar synthetic protocol as that of Intermediate 50A-I and starting from Intermediate 49-I (0.50 g, 1.63 mmol) and 3-chloropropane-1-sulfonyl chloride (0.43 g, 2.45 mmol). $^1$H NMR (400 MHz, DMSO-d$_6$) δ ppm 1.35 (s, 9H), 2.19-2.27 (m, 2H), 2.32 (s, 3H), 2.78-3.23 (m, 4H), 3.39-3.41 (m, 2H), 4.89 (q, J=7.05 Hz, 1H), 5.39 (s, 2H), 7.05 (br. s., 1H), 7.69-7.72 (m, 2H), 8.12 (d, J=7.93 Hz, 1H). LCMS (Method-I): retention time 0.82 min, [M−1] 445.3.

Intermediate 59B-I: tert-butyl (R)-(2-(1,1-dioxido-isothiazolidin-2-yl)-2-(4-methyl-1-oxo-1,3-dihydroisobenzofuran-5-yl)ethyl)carbamate

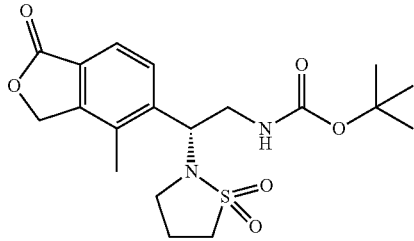 [SMILES: Cc1c([C@H](CNC(=O)OC(C)(C)C)N2CCCS2(=O)=O)ccc2c1COC2=O]

To a stirred solution of Intermediate 59A-I (0.20 g, 0.45 mmol) in DMF (3 mL) was added DBU (0.14 mL, 0.89 mmol) and the resulting reaction mixture was stirred at ambient temperature for 16 h. The reaction mixture was diluted with water (30 mL) and extracted with ethyl acetate (3×25 mL). The combined organic layers were washed with brine (20 mL), dried over anhydrous sodium sulfate and evaporated under reduced pressure. The residue was purified by column chromatography (Redisep-12 g, 0-2% MeOH/CHCl$_3$) to obtain Intermediate 59B-I (0.13 g, 68.10%) as an off white solid. $^1$H NMR (400 MHz, DMSO-d$_6$) δ ppm 1.35 (s, 9H), 2.23-2.32 (m, 2H), 2.32 (s, 3H), 2.94-2.97 (m, 2H), 3.35-3.37 (m, 2H), 3.41-3.43 (m, 2H), 5.04 (q, J=7.05 Hz, 1H), 5.39 (s, 2H), 6.95 (br. s., 1H), 7.65 (d, J=8.31 Hz, 1H), 7.73 (d, J=7.93 Hz, 1H). LCMS (Method-I): retention time 0.82 min, [M−1] 409.3.

Intermediate 59-I

Intermediate 59-I was prepared (0.08 g, 79.00%) as colorless oil, by using a similar synthetic protocol as that of Intermediate 50-I and starting from Intermediate 59B-I (0.13 g, 0.31 mmol). $^1$H NMR (400 MHz, DMSO-d$_6$) δ ppm 2.22-2.32 (m, 2H), 2.32 (s, 3H), 2.91-2.97 (m, 2H), 3.35-3.41 (m, 4H), 4.08 (q, J=7.05 Hz, 1H), 5.41 (s, 2H), 7.59 (d, J=7.6 Hz, 1H), 7.67 (d, J=7.6 Hz, 1H), (2 Exchangeable protons not observed). LCMS (Method-I): retention time 0.46 min, [M−1] 309.3.

Intermediate 60-I: tert-butyl (R)-((5-bromopyrimidin-2-yl)methyl)(2-hydroxy-2-(4-methyl-1-oxo-1,3-dihydroisobenzofuran-5-yl)ethyl)carbamate

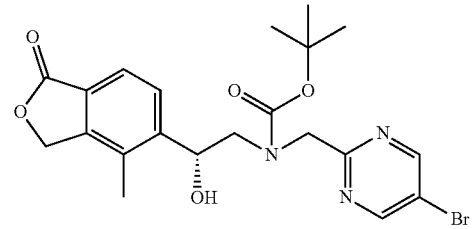 [SMILES: Cc1c([C@@H](O)CN(Cc2ncc(Br)cn2)C(=O)OC(C)(C)C)ccc2c1COC2=O]

Intermediate 60A: 5-bromo-2-(bromomethyl)pyrimidine

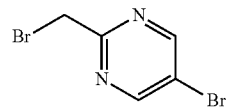

To a stirred solution of 5-bromo-2-methylpyrimidine (5.00 g, 28.90 mmol) in CCl$_4$ (40 mL) was added AIBN (0.48 g, 2.89 mmol) and N-bromosuccinimide (5.14 g, 28.9 mmol) and the reaction mixture was heated at 80° C. for 48 h. The reaction mixture was cooled to ambient temperature. Solid precipitate was filtered off and filtrate was concentrated under reduced pressure. The residue was purified by column chromatography (Redisep-80 g, 0-15% EtOAc/n-hexane) to obtain Intermediate 60A (1.05 g, 12.98%) as a pale yellow solid. $^1$H NMR (400 MHz, DMSO-d$_6$) δ ppm 4.68 (s, 2H), 9.03 (s, 2H). LCMS (Method-I): retention time 1.03 min, [M+1] 252.9.

Intermediate 60B-I: (R)-5-(2-(((5-bromopyrimidin-2-yl)methyl)amino)-1-hydroxyethyl)-4-methyl-isobenzofuran-1(3H)-one

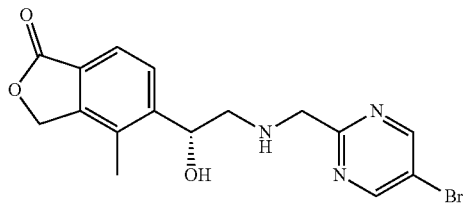 [SMILES: Cc1c([C@@H](O)CNCc2ncc(Br)cn2)ccc2c1COC2=O]

To a stirred solution of Intermediate 60A (0.50 g, 1.99 mmol) and Intermediate 1-I (0.82 g, 3.97 mmol) in THF (20 mL) was added DIPEA (0.69 mL, 3.97 mmol) and the reaction mixture was stirred at room temperature for 16 h. The reaction mixture was diluted with water (40 mL) and extracted with ethyl acetate (3×30 mL). The combined organic layers were washed with brine (30 mL), dried over anhydrous sodium sulfate and evaporated under reduced pressure. The residue was purified by column chromatography (Redisep-24 g, 2-4% MeOH/CHCl$_3$) to obtain Intermediate 60B-I (0.35 g, 24.72%) as a brown solid. $^1$H NMR (400 MHz, DMSO-d$_6$) δ ppm 2.26 (s, 3H), 2.62-2.80 (m, 2H), 3.86-4.03 (m, 2H), 4.96-5.08 (m, 1H), 5.33-5.45 (m, 3H), 5.55 (d, J=4.40 Hz, 1H), 7.59-7.71 (m, 2H), 8.92-8.99 (m, 2H). LCMS (Method-D): retention time 1.01 min, [M+1] 380.0.

Intermediate 60-I

Intermediate 60-I was prepared (0.3 g, 79%) as an off white solid, by using a similar synthetic protocol as that of Intermediate 2A and starting Intermediate 60B-I (0.30 g, 0.79 mmol) and BOC-anhydride (0.22 mL, 0.95 mmol). $^1$H NMR (400 MHz, DMSO-d$_6$) δ ppm 1.16 (br. s., 5H), 1.30 (s, 4H), 2.31 (d, J=11.98 Hz, 3H), 3.21-3.31 (m, 1H), 3.53-3.62 (m, 1H), 4.51-4.71 (m, 2H), 5.14-5.28 (m, 1H), 5.40 (s, 2H), 5.76-5.81 (m, 1H), 7.61-7.79 (m, 2H), 8.88-8.99 (m, 2H). LCMS (Method-D): retention time 1.01 min, [M+1] 480.1.

Intermediate 61A: 6-chloro-2-methoxy-4-methylnicotinonitrile and Intermediate 61A: 2-chloro-6-methoxy-4-methylnicotinonitrile

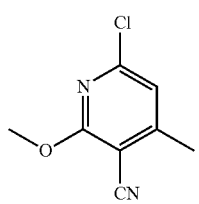

Intermediate-61A

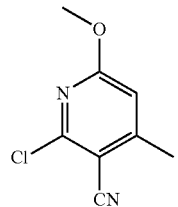

Intermediate-61B

To a stirred solution of 2,6-dichloro-4-methylnicotinonitrile (15.00 g, 80.00 mmol) in MeOH (100 mL) was added sodium methoxide (14.89 mL, 80.00 mmol) and the reaction mixture was stirred at ambient temperature for 16 h. The reaction mixture was diluted with water (300 mL) and extracted with DCM (3×250 mL). The combined organic layers were washed with brine (200 mL), dried over anhydrous sodium sulfate and evaporated under reduced pressure. The residue was purified by SFC [Column: Lux cellulose-2 (50×250 mm) 5 micron; 10% of 0.2% DEA in IPA; total flow: 150 g/min; UV: 220 nm] to obtain Intermediate 61A (5.50 g, 32.30%) as an off-white solid, (retention time: 6.3 min). $^1$H NMR (400 MHz, DMSO-d$_6$) δ ppm 2.46 (s, 3H), 3.99 (s, 3H), 7.27 (s, 1H). LCMS: (Method-I) retention time: 1.22 min, [M+1]: 183.3, and Intermediate 61B (6.50 g, 40.40%) as an off-white solid, (retention time: 5.8 min). $^1$H NMR (400 MHz, DMSO-d$_6$) δ ppm 2.43 (s, 3H), 3.91 (s, 3H), 6.94 (s, 1H). LCMS (Method-I): retention time 1.29 min, [M+1] 183.4.

Intermediate 62A: 6-(4-(hydroxymethyl)-2H-1,2,3-triazol-2-yl)-2-methoxy-4-methylnicotinonitrile and Intermediate 62B: 6-(4-(hydroxymethyl)-1H-1,2,3-triazol-1-yl)-2-methoxy-4-methylnicotinonitrile

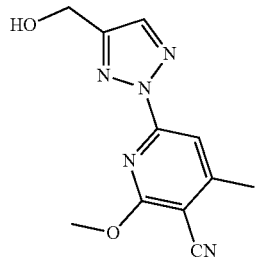

62A

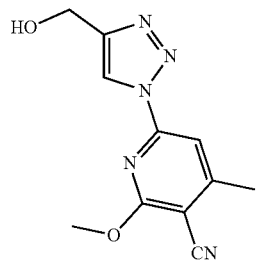

62B

Intermediate 62A and Intermediate 62B was as prepared, by using a similar synthetic protocol as that of Intermediate 19 and starting from Intermediate 61A (2.21 g, 12.11 mmol) and Intermediate 28A (1.00 g, 10.09 mmol).

Intermediate 62A (0.15 g, 5.45%), fast eluting, off-white solid. $^1$H NMR (400 MHz, DMSO-d$_6$) δ ppm 2.56 (s, 3H)

4.07 (s, 3H) 4.67 (d, J=5.52 Hz, 2H) 5.51 (t, J=5.77 Hz, 1H) 7.68 (s, 1H) 8.16 (s, 1H). LCMS (Method-I): retention time 0.82 min, [M+1] 246.4 and Intermediate 62B (0.25 g, 9.60%), slow eluting, off white solid. $^1$H NMR (400 MHz, DMSO-d$_6$) δ ppm 2.55-2.62 (m, 3H), 4.05-4.15 (m, 3H), 4.61-4.72 (m, 2H), 5.38 (t, J=5.77 Hz, 1H), 7.83 (s, 1H), 8.76 (s, 1H). LCMS (Method-I): retention time 0.81 min, [M+1] 246.4.

Intermediate 63: 6-(4-formyl-1H-1,2,3-triazol-1-yl)-2-methoxy-4-methylnicotinonitrile

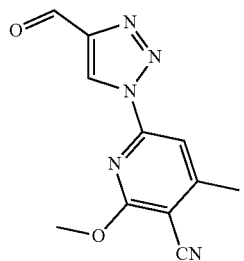 [SMILES: COc1nc(-n2cc(C=O)nn2)cc(C)c1C#N]

Intermediate 63 was prepared (0.08 g, 36.90%) as an off-white solid, by using a similar synthetic protocol as that of Intermediate 26 and starting from Intermediate 62B (0.23 g, 0.89 mmol). $^1$H NMR (400 MHz, DMSO-d$_6$) δ ppm 2.67 (s, 3H), 4.18 (s, 3H), 7.86 (s, 1H), 8.79 (s, 1H), 10.21 (s, 1H). LCMS (Method-I): retention time 1.03 min, [M+1] 244.4.

Intermediate 64: 6-(4-formyl-1H-pyrazol-1-yl)-2-methoxy-4-methylnicotinonitrile

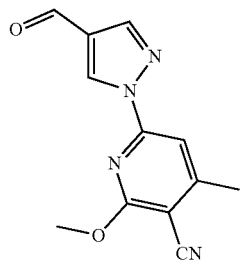 [SMILES: COc1nc(-n2cc(C=O)cn2)cc(C)c1C#N]

Intermediate 64 was prepared (0.10 g, 30.20%) as an off-white solid, by using a similar synthetic protocol as that of Intermediate 9 and starting from Intermediate 61A (0.25 g, 1.37 mmol) and 1H-pyrazole-4-carbaldehyde (0.19 g, 2.05 mmol). $^1$H NMR (400 MHz, DMSO-d$_6$) β ppm 2.51 (s, 3H), 4.02 (s, 3H), 7.01 (d, J=0.98 Hz, 1H), 8.38 (s, 1H), 9.31 (s, 1H), 9.99 (s, 1H). LCMS (Method-I): retention time 1.07 min, [M−1] 241.2.

Intermediate 65: 6-(4-formyl-1H-pyrazol-1-yl)-4-methoxy-2-methylnicotinonitrile

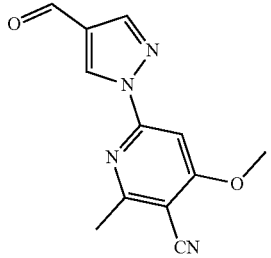 [SMILES: COc1cc(-n2cc(C=O)cn2)nc(C)c1C#N]

Intermediate 65A: bis(2,4,6-trichlorophenyl) Malonate

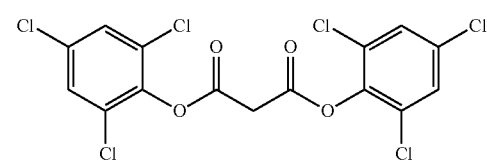 [SMILES: O=C(CC(=O)Oc1c(Cl)cc(Cl)cc1Cl)Oc1c(Cl)cc(Cl)cc1Cl]

A mixture of malonic acid (20.00 g, 192.00 mmol), 2,4,6-trichlorophenol (76.00 g, 384.00 mmol) and POCl$_3$ (50 mL) was refluxed for 12 h. The reaction mixture was cooled to 70° C. and poured into ice water. The solid precipitate was collected by filtration, washed with water and dried under vacuum to obtain Intermediate 65A (70.30 g, 67.20%) as a pale yellow solid. $^1$H NMR (400 MHz, CDCl$_3$) δ ppm 3.91-4.17 (m, 2H) 7.33-7.59 (m, 4H). LCMS: The compound did not ionize well.

Intermediate 65B: 4-hydroxy-2-methyl-6-oxo-1,6-dihydropyridine-3-carbonitrile

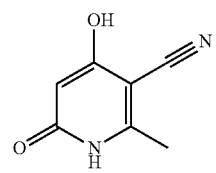

A mixture of 3-aminoacrylonitrile (10.25 g, 151.00 mmol) and Intermediate 65A (70.30 g, 152.00 mmol) in diglyme (75 mL) was heated at 120° C. for 2.5 h. The mixture was cooled to ambient temperature and poured into Et$_2$O (40 mL) and filtered. The precipitate was washed with Et$_2$O (15 mL) to obtain Intermediate 65B (13.50 g, 59.70%) as dark brown solid. $^1$H NMR (400 MHz, DMSO-d$_6$) δ ppm 2.25-2.41 (m, 3H) 5.49 (s, 1H) 11.85 (br. s., 2H). LCMS (Method-I): retention time 0.32 min, [M+1] 151.3.

Intermediate 65C: 4,6-dichloro-2-methylnicotinonitrile

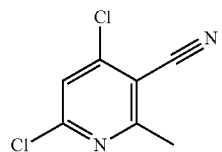

A stirring solution of Intermediate 65B (10.70 g, 71.30 mmol) in POCl$_3$ (6.64 ml, 71.3 mmol) was heated at 100° C. for 16 h. The reaction mixture was concentrated under reduced pressure, diluted water (200 mL), basified with solid Na$_2$CO$_3$ and extracted with ethyl acetate (3×200 mL). The combined organic layers were washed with brine (100 mL), dried over anhydrous sodium sulfate and evaporated under reduced pressure. The residue was purified by column chromatography (Redisep-120 g, 0-5% EtOAc/n-Hexane) to obtain Intermediate 65C (8.50 g, 57.40%) as an off white solid. $^1$H NMR (400 MHz, DMSO-d$_6$) δ ppm 2.69 (s, 3H) 8.02 (s, 1H). LCMS: (Method-I): retention time 1.16 min, [M+1] 188.3.

Intermediate 65D: 6-chloro-4-methoxy-2-methylnicotinonitrile and Intermediate 65E: 4-chloro-6-methoxy-2-methylnicotinonitrile

65D

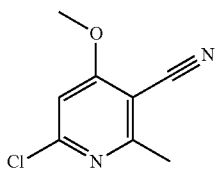

65E

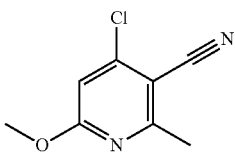

Intermediate 65D and Intermediate 65E was as prepared, by using a similar synthetic protocol as that of Intermediate 61A and starting from Intermediate 65C (8.50 g. 45.40 mmol). Intermediate 65D (5.5 g, 66.30%), fast eluting, off-white solid. $^1$H NMR (400 MHz, DMSO-d$_6$) δ ppm 2.57 (s, 3H) 4.02 (s, 3H) 7.35 (s, 1H). LCMS (Method-I): retention time 0.99 min, [M+1] 183.3 and Intermediate 65E (1.50 g, 18.07%), slow eluting, off white solid. $^1$H NMR (400 MHz, DMSO-d$_6$) δ ppm 2.62 (s, 3H) 3.94 (s, 3H) 7.17 (s, 1H). LCMS (Method-I): retention time 1.24 min, [M+1] 183.3.

Intermediate 65

Intermediate 65 was prepared (0.10 g, 14.12%) as off white solid, by using a similar synthetic protocol as that of Intermediate 9 and starting from Intermediate 65D (0.475 g, 2.60 mmol) and 1H-pyrazole-4-carbaldehyde (0.25 g, 2.60 mmol). $^1$H NMR (400 MHz, DMSO-d$_6$) δ ppm 2.67 (s, 3H), 4.12 (s, 3H), 7.57 (s, 1H), 8.38 (s, 1H), 9.37 (d, J=0.73 Hz, 1H), 9.99 (s, 1H). LCMS (Method-I): retention time 1.04 min, [M+1] 243.4.

Intermediate 66: 6-(4-formyl-1H-pyrazol-1-yl)-2,4-dimethylnicotinonitrile

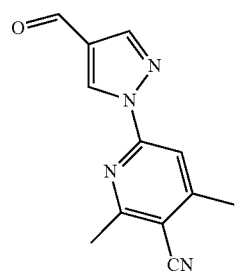 [SMILES: Cc1cc(-n2cc(C=O)cn2)nc(C)c1C#N]

Intermediate 66 was prepared (0.20 g, 21.24%) as an off-white solid, by using a similar synthetic protocol as that of Intermediate 9 and starting from 1H-pyrazole-4-carbaldehyde (0.40 g, 4.16 mmol) and 6-chloro-2,4-dimethylnicotinonitrile (0.55 g, 3.33 mmol). $^1$H NMR (400 MHz, DMSO-d$_6$) δ ppm 2.60 (s, 3H), 2.73 (s, 3H), 7.93 (s, 1H), 8.36 (s, 1H), 9.35 (s, 1H), 9.99 (s, 1H). LCMS (Method-I): retention time 1.14 min, [M+1] 227.5.

Intermediate 67: 6-(4-formyl-1H-imidazol-1-yl)-2,4-dimethylnicotinonitrile

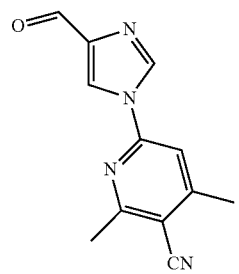 [SMILES: Cc1cc(-n2cnc(C=O)c2)nc(C)c1C#N]

Intermediate 67-I was prepared (0.08 g, 29.50%) as an off-white solid, by using a similar synthetic protocol as that of Intermediate 18 and starting from 6-chloro-2,4-dimethylnicotinonitrile (0.20 g, 1.18 mmol) and 1H-imidazole-4-carbaldehyde (0.12 g, 1.12 mmol). $^1$H NMR (400 MHz, DMSO-d$_6$) δ ppm 2.55-2.61 (m, 3H), 2.73 (s, 3H), 7.98 (s, 1H), 8.76 (d, J=0.98 Hz, 1H), 8.81 (d, J=1.22 Hz, 1H), 9.88 (s, 1H). LCMS (Method-I): retention time 0.92 min, [M+1] 227.5.

Intermediate 68A: 6-(4-(hydroxymethyl)-1H-1,2,3-triazol-1-yl)-2,4-dimethylnicotinonitrile and Intermediate 68B: 6-(4-(hydroxymethyl)-2H-1,2,3-triazol-2-yl)-2,4-dimethylnicotinonitrile

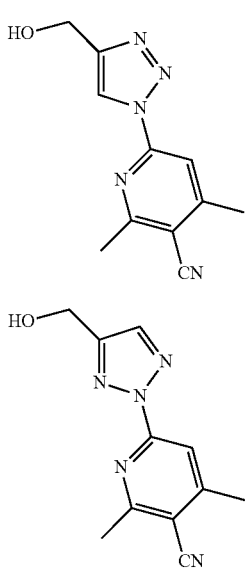

Intermediate 68A and Intermediate 68B was as prepared, by using a similar synthetic protocol as that of Intermediate 19 and starting from Intermediate 28A (1.00 g, 10.09 mmol) and 6-chloro-2,4-dimethylnicotinonitrile (1.85 g, 11.10 mmol).

Intermediate 68A (0.30 g, 12.97% yield), fast eluting, off white solid. $^1$H NMR (400 MHz, DMSO-$d_6$) δ ppm 2.63 (s, 3H), 2.74 (s, 3H), 4.64 (d, J=6.0 Hz, 2H), 5.37 (t, J=6.0 Hz, 1H), 8.12 (s, 1H), 8.69 (s, 1H). LCMS (Method-I): retention time 0.77 min, [M+1] 230.4.

Intermediate 68B (0.32 g, 13.83%), slow eluting, off white solid. $^1$H NMR (400 MHz, DMSO-$d_6$) δ ppm 2.59 (s, 3H), 2.71 (s, 3H), 4.67 (d, J=6.0 Hz, 2H), 5.53 (t, J=6.0 Hz, 1H), 7.95 (s, 1H), 8.16 (s, 1H). LCMS (Method-I): retention time 0.74 min, [M+1] 230.4.

Intermediate 69: 6-(4-formyl-1H-1,2,3-triazol-1-yl)-2,4-dimethylnicotinonitrile

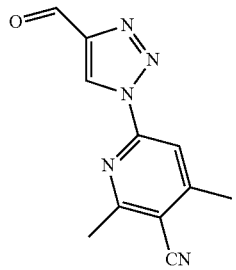 [SMILES: Cc1cc(-n2cc(C=O)nn2)nc(C)c1C#N]

Intermediate 69 was prepared (0.30 g, 66.20%) as an off-white solid, by using a similar synthetic protocol as that of Intermediate 26 and starting from Intermediate 68A (0.32 g, 1.40 mmol). $^1$H NMR (400 MHz, DMSO-$d_6$) δ ppm 2.65 (s, 3H), 2.76 (s, 3H), 8.21 (s, 1H), 9.56 (s, 1H), 10.13 (s, 1H). LCMS (Method-I): retention time 0.98 min, [M−1] 228.4.

Intermediate 70: 1-(3-methyl-2-oxo-2,3-dihydrobenzo[d]oxazol-5-yl)-1H-pyrazole-4-carbaldehyde

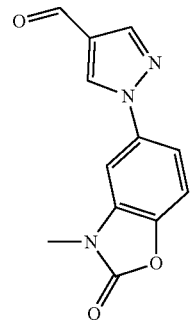 [SMILES: Cn1c(=O)oc2ccc(-n3cc(C=O)cn3)cc21]

Intermediate 70 was prepared (1.10 g, 10.86%) as a pale yellow solid, by using a similar synthetic protocol as that of Intermediate 9 and starting from Intermediate 3 (9.49 g, 41.60 mmol) and 1H-pyrazole-4-carbaldehyde (4.00 g, 41.6 mmol) $^1$H NMR (400 MHz, DMSO-$d_6$) δ ppm 3.39 (s, 3H) 7.48 (d, J=9.04 Hz, 1H) 7.66 (dd, J=8.78, 2.26 Hz, 1H) 7.87 (d, J=2.01 Hz, 1H) 8.29 (s, 1H) 9.21 (s, 1H) 9.92 (s, 1H). LCMS (method-H): retention time 0.97 min, [M+H] 244.2.

Intermediate 71: 5'-formyl-4,6'-dimethoxy-[2,2'-bipyridine]-5-carbonitrile

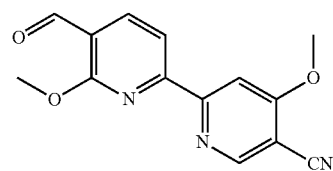 [SMILES: COc1cc(-c2ccc(C=O)c(OC)n2)ncc1C#N]

Intermediate 71A: 6-chloro-2-methoxynicotinaldehyde

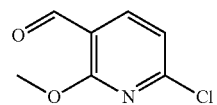

Synthesized according to literature procedures (Kissei Pharmaceutical Co., Ltd. Patent: EP1405859 A1, 2004).

Intermediate 71B: 4-methoxy-6-(trimethylstannyl)nicotinonitrile

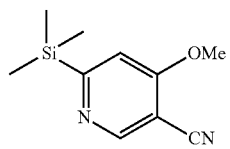

A solution of 6-chloro-4-methoxynicotinonitrile (1.50 g, 8.90 mmol) in 1,4-dioxane (20 mL) was degassed with nitrogen for 20 minutes and hexamethylditin (2.22 mL, 10.68 mmol), Pd(dtbpf)Cl$_2$ (0.58 g, 0.89 mmol) was added. Then reaction mixture was heated at 100° C. for 1 h. The reaction was cooled to ambient temperature, filtered through celite and the filtrate was distilled under reduced pressure to obtain Example 71B (3.00 g, Crude) as a black syrup. LCMS (Method-I): retention time 1.40 min, [M+H] 299.3. The compound was taken forward directly to the subsequent step without further purification or characterization.

Intermediate 71

A solution of Intermediate 71B (0.62 g, 2.09 mmol) and Intermediate 71A (0.30 g, 1.75 mmol) in dioxane (20 mL) was degassed with nitrogen for 20 minutes. Then tetrakis-triphenylphospine palladium (0.202 g, 0.175 mmol), copper (I) iodide (0.033 g, 0.175 mmol) was added and resulting mixture was degassed again for 10 minutes and heated at 100° C. for 16 h. The reaction mixture was cooled to ambient temperature, filtered through Celite® and the filtrate was concentrated under reduced pressure. The residue was purified by combiflash (Redisep-24 g, 50-100% EtOAc/n-hexane) to obtain Intermediate 70 (0.15 g, 39.10%) as a pale yellow solid. $^1$H NMR (400 MHz, DMSO-d$_6$) δ ppm 4.14-4.24 (m, 6H) 8.15-8.22 (m, 2H) 8.28-8.36 (m, 1H) 8.95-9.01 (m, 1H) 10.27-10.35 (m, 1H). LCMS (Method-D): retention time 2.603 min, [M+H] 270.1.

Intermediate 72-I: tert-butyl (R)-((1H-pyrazol-4-yl)methyl)(2-hydroxy-2-(4-methyl-1-oxo-1,3-dihydroisobenzofuran-5-yl)ethyl)carbamate

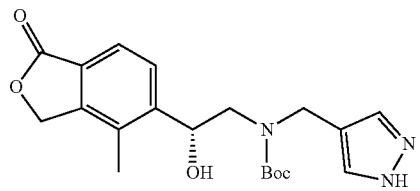 [SMILES: Cc1c([C@@H](O)CN(Cc2cn[nH]c2)C(=O)OC(C)(C)C)ccc2c1COC2=O]

To a stirred solution of 1H-pyrazole-4-carbaldehyde (1.00 g, 10.41 mmol) in MeOH (20 mL) was added acetic acid (0.60 mL, 10.41 mmol), Intermediate 7-I (2.59 g, 12.49 mmol) and the reaction mixture was stirred at ambient temperature for 20 min. Then NaCNBH$_4$ (1.96 g, 31.2 mmol) was added and stirring was continued at ambient temperature for 14 h. The reaction mixture was distilled under reduced pressure and basified with saturated sodium bicarbonate solution (50 mL). To the resulting aqueous mixture was added BOC$_2$O (2.34 ml, 10.09 mmol) and stirred at ambient temperature for 2 h. The reaction mixture was diluted with water (20 mL) and extracted with 5% methanol:DCM (3×30 mL). The combined organic layers were dried over anhydrous sodium sulfate, filtered and concentrated under reduced pressure. The residue was purified by column chromatography (Redisep-24 g, 4% MeOH/CHCl$_3$), to obtain Intermediate 72-I (0.95 g, 24.29%). $^1$H NMR (300 MHz, DMSO-d$_6$) δ ppm 1.23-1.46 (m, 9H) 1.57 (s, 1H) 2.26 (br. s., 3H) 3.08-3.26 (m, 1H) 4.21-4.32 (m, 2H) 5.07-5.19 (m, 1H) 5.37 (s, 2H) 5.59-5.71 (m, 1H) 7.31-7.42 (m, 1H) 7.69 (s, 3H) 12.58-12.73 (m, 1H). LCMS (Method-H): retention time 1.29 min, [M–H] 388.0.

Intermediate 73: 5-(4-formyl-1H-pyrazol-1-yl)-3-methylpicolinonitrile

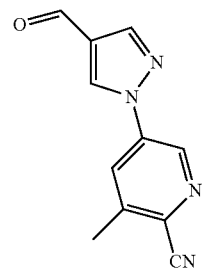 [SMILES: Cc1cc(-n2cc(C=O)cn2)cnc1C#N]

Intermediate 73 was prepared (0.14 g, 21.13%), by using similar synthetic protocol as that of Intermediate 9 and starting from 1H-pyrazole-4-carbaldehyde (0.30 g, 3.12 mmol) and 5-bromo-3-methylpicolinonitrile (0.61 g, 3.12 mmol). $^1$H NMR (300 MHz, DMSO-d$_6$) δ ppm 2.50-2.59 (s, 3H) 8.43 (s, 1H) 8.53 (s, 1H) 9.19 (s, 1H) 9.44 (s, 1H) 9.961 (s, 1H). LCMS (Method-D): retention time 1.475 min, [M+H] 213.0.

Intermediate 74: 5-fluoro-6-(4-methyl-1H-imidazol-1-yl)nicotinaldehyde

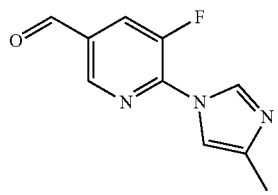

Intermediate 74 was prepared (0.18 g, 59.70%) as pale yellow solid, by using a similar synthetic protocol as that of Intermediate 19 and starting from 6-bromo-5-fluoronicotinaldehyde (0.30 g, 1.47 mmol). $^1$H NMR (400 MHz, DMSO-d$_6$) δ ppm 2.18-2.24 (m, 3H) 7.63-7.72 (m, 1H) 8.31-8.44 (m, 2H) 8.87-8.92 (m, 1H) 10.04-10.13 (m, 1H). LCMS (Method-D), retention time 1.158 min, [M+H] 206.0.

Intermediate 75: 4-methyl-6-(4-methyl-1H-imidazol-1-yl)nicotinaldehyde

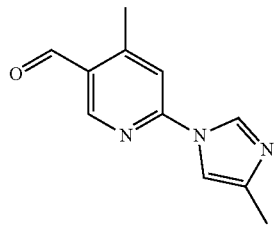

Intermediate 75 was prepared (0.21 g, 54.10%) as a white solid, by using a similar synthetic protocol as that of Intermediate 47C and starting from 6-chloro-4-methylnicotinaldehyde (0.30 g, 1.93 mmol) and 4-methyl-1H-imidazole (0.24 g, 2.89 mmol). $^1$H NMR (400 MHz, DMSO-d$_6$) δ ppm 2.19 (d, J=0.98 Hz, 3H), 2.69 (s, 3H), 7.75 (d, J=1.22 Hz, 1H), 7.80 (s, 1H), 8.53 (d, J=1.22 Hz, 1H), 8.85 (s, 1H), 10.21 (s, 1H). LCMS (Method-D): retention time 1.204 min, [M+H] 202.2.

Intermediate 76: 3-methyl-5-(6-((methylamino)methyl)pyridin-3-yl)benzo[d]oxazol-2(3H)-one

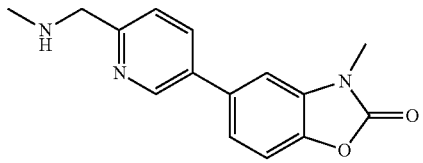 [SMILES: CNCc1ccc(-c2ccc3oc(=O)n(C)c3c2)cn1]

Intermediate 76A: 1-(5-bromopyridin-2-yl)-N-methylmethanamine

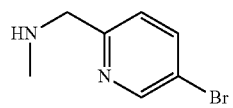

To a solution of 5-bromopicolinaldehyde (1.50 g, 8.06 mmol) in MeOH (10 mL) and acetic acid (0.46 mL, 8.06 mmol), was added 2M methylamine in THF (8.06 mL, 16.13 mmol) and the reaction mixture was stirred at ambient temperature for 15 min. To the resulting reaction mixture was added NaCNBH$_4$ (1.02 g, 16.13 mmol) and stirring was continued for 12 h. The reaction mixture was diluted with saturated sodium bicarbinate solution (50 mL) and extracted with ethyl acetate (2×50 mL). The combined organic layers were washed with brine (20 mL), dried over anhydrous sodium sulfate and evaporated under reduced pressure to obtain Intermediate 76A (1.10 g, 67.80%). $^1$H NMR (300 MHz, DMSO-d$_6$) δ ppm 2.38 (s, 3H), 3.88 (s, 2H), 7.39-7.46 (m, 1H), 8.03-8.09 (m, 1H), 8.64-8.70 (m, 1H), (1 Exchangable proton not observed). LCMS (Method-D): retention time 0.59 min, [M+H] 202.0.

Intermediate 76B: tert-butyl ((5-bromopyridin-2-yl)methyl)(methyl)carbamate

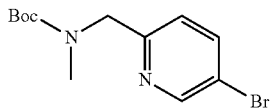

Intermediate 76B was prepared (1.20 g, 72.08%/0) as a white solid, by using a similar synthetic protocol as that of Intermediate 2A and starting from Intermediate 76A (1.10 g, 5.47 mmol) and BOC$_2$O (2.54 mL, 10.94 mmol). $^1$H NMR (400 MHz, DMSO-d$_6$) δ ppm 1.50 (s, 9H), 2.86 (br. s., 3H), 4.43 (s, 2H), 7.15-7.22 (m, 1H), 8.01-8.08 (m, 1H), 8.65 (d, J=2.51 Hz, 1H). LCMS (Method-D): retention time 2.71 min, [M+H] 302.0.

Intermediate 76C: tert-butyl methyl((5-(3-methyl-2-oxo-2,3-dihydrobenzo[d]oxazol-5-yl)pyridin-2-yl)methyl)carbamate

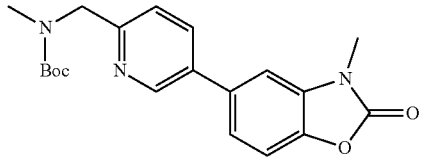 [SMILES: CN(Cc1ccc(-c2ccc3oc(=O)n(C)c3c2)cn1)C(=O)OC(C)(C)C]

Intermediate 76C was prepared (0.18 g, 41.90%), by using a similar synthetic protocol as that of Intermediate 10A and starting from Intermediate 76B (0.35 g, 1.16 mmol) and Intermediate 4 (0.38 g, 1.39 mmol). $^1$H NMR (400 MHz, DMSO-d$_6$) δ ppm 1.28-1.47 (m, 9H), 2.89 (s, 3H), 3.41 (s, 3H), 4.44-4.54 (m, 2H), 7.25-7.32 (m, 1H), 7.41-7.51 (m, 2H), 7.65-7.71 (m, 1H), 8.05-8.15 (m, 1H), 8.84-8.91 (m, 1H). LCMS (Method-I): retention time 1.19 min, [M+H] 370.2.

Intermediate 76

To a solution of Intermediate 76C (0.18 g, 0.48 mmol) in DCM (10 mL) at 0° C. was added trifluoroacetic acid (2 mL, 26.0 mmol). The resulting mixture was stirred at ambient temperature for 10 h. The reaction mixture was concentrated to dryness under reduced pressure and diluted with water (20 mL). The aqueous layer was washed with ethyl acetate (2×20 mL), basified with saturated NaHCO$_3$ and extracted with 10% MeOH in DCM (3×50 mL). The combined organic layers were dried over sodium sulfate, filtered and concentrated under reduced pressure to obtain Intermediate 76 (0.10 g, 80%). $^1$H NMR (300 MHz, DMSO-d$_6$) δ ppm 2.32 (br. s., 3H), 3.41 (s, 3H), 3.79 (br. s., 2H), 7.46 (d, J=4.53 Hz, 3H), 7.67 (s, 1H), 8.02-8.15 (m, 1H), 8.74-8.87 (m, 1H), (1 Exchangable proton not observed). LCMS (Method-D): retention time 2.41 min, [M+H] 270.3

Intermediate 77: 2-methyl-6-(4-methyl-1H-imidazol-1-yl)nicotinaldehyde

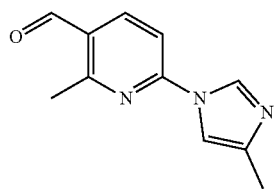

Intermediate 77 was prepared (0.25 g, 64.40%), by using a similar synthetic protocol as that of Intermediate 47C and starting from 6-chloro-2-methylnicotinaldehyde (0.30 g, 1.93 mmol) and 4-methyl-1H-imidazole (0.24 g, 2.89 mmol). $^1$H NMR (400 MHz, DMSO-d$_6$) δ ppm 2.12-2.21 (m, 3H), 2.77-2.84 (m, 3H), 7.69-7.81 (m, 2H), 8.32 (d, J=8.56 Hz, 1H), 8.53 (d, J=0.98 Hz, 1H), 10.23 (s, 1H). LCMS (Method-D), retention time 1.31 min, [M+H] 202.2.

Intermediate 78: 6-(4-formyl-1-methyl-1H-imidazol-2-yl)-4-methylnicotinonitrile

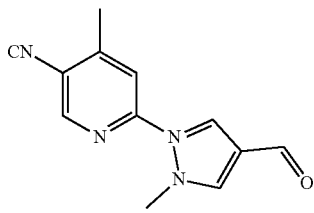

Intermediate 78A: methyl 2-bromo-1-methyl-1H-imidazole-4-carboxylate

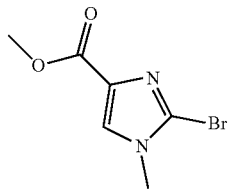

Synthesized according to literature procedures (WO2013/149997 A1, 2013).

Intermediate 78B: 4-methyl-6-(trimethylstannyl)nicotinonitrile

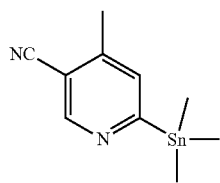

Intermediate 78B was prepared (1.80 g, crude) as black syrup, by using a similar synthetic protocol as that of Intermediate 71B and starting from 6-bromo-4-methylnicotinonitrile (1.00 g, 5.08 mmol). LCMS (Method-I): retention time 1.40 min, [M+H] 299.3. The compound was taken directly to the subsequent step without further purification or characterization.

Intermediate 78C: methyl 2-(5-cyano-4-methylpyridin-2-yl)-1-methyl-1H-imidazole-4-carboxylate

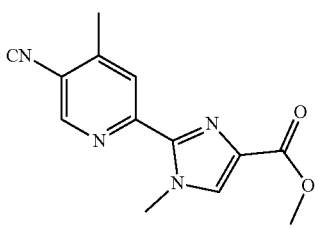

Intermediate 78C was prepared (0.65 g, 39.58%), by using a similar synthetic protocol as that of Intermediate 71 and starting from Intermediate 78A (1.40 g, 6.41 mmol) and Intermediate 78B (1.80 g, 6.41 mmol). $^1$H NMR (300 MHz, DMSO-$d_6$) δ ppm 2.56 (s, 3H), 3.79 (s, 3H), 4.10 (s, 3H), 8.14-8.28 (m, 2H), 8.92-9.04 (m, 1H). LCMS (Method-I): retention time 0.93 min, [M+H] 257.1.

Intermediate 78D: 2-(5-cyano-4-methylpyridin-2-yl)-1-methyl-1H-imidazole-4-carboxylic Acid

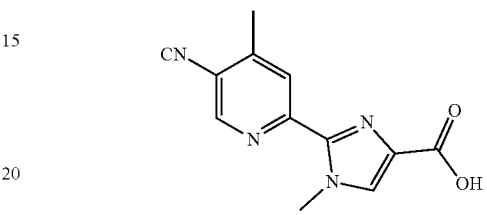

To a stirred solution of Intermediate 78C (0.60 g, 2.34 mmol) in methanol (15 mL) was added a solution of lithium hydroxide (0.11 g, 4.68 mmol) in water (2 mL) and the reaction was stirred at ambient temperature for 15 h. The reaction was evaporated under reduced pressure, cooled to 0° C. and neutralized with 4N HCl. The solid precipitate was collected by suction filtration and dried under vacuum to obtain Intermediate 78D (0.18 g, 31.70%) as a white solid. $^1$H NMR (300 MHz, DMSO-$d_6$) δ ppm 2.58 (s, 3H), 4.09 (s, 3H), 8.05 (s, 1H), 8.21 (s, 1H), 8.98 (s, 1H), (1 Exchangable proton not observed). LCMS (Method D): retention time 0.541 min, [M+H] 243.2.

Intermediate 78E: 6-(4-(hydroxymethyl)-1-methyl-1H-imidazol-2-yl)-4-methylnicotinonitrile

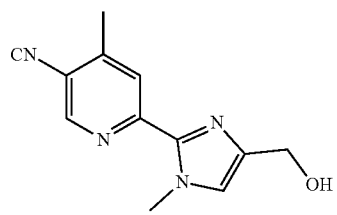

To a stirred solution of Intermediate 78D (0.18 g, 0.74 mmol) in THF (10 mL) at 0° C. was added triethylamine (0.207 mL, 1.486 mmol) followed by isobutyl chloroformate (0.19 mL, 1.49 mmol). The resulting mixture was stirred at ambient temperature for 1 h and diluted with water (10 mL). The aqueous layer was washed with ethyl acetate (2×20 mL) followed by brine (10 mL), dried over anhydrous sodium sulfate, filtered and concentrated under reduced pressure to obtain the crude mixed anhydride. The mixed anhydride was dissolved in THF (10 mL) at 0° C. Sodium borohydride (0.056 g, 1.486 mmol) was added and the reaction was stirred at ambient temperature for 2 h. The reaction mixture was diluted with water (10 mL) and the aqueous layer was extracted with ethyl acetate (2×20 mL). The combined organic layers were washed with brine (10 mL), dried over anhydrous sodium sulfate, filtered and concentrated under reduced pressure. The residue was purified by silica gel column chromatography (Redisep-24 g, 30% EtOAc/t-hexane) to obtain Intermediate 78E (0.09 g, 53.10%). LCMS (Method-I): retention time 0.70 min, [M+H] 228.2. The compound was taken forward directly to the subsequent step without further characterization.

Intermediate 78

Intermediate 78 was prepared (0.06 g, 67.40%), by using a similar synthetic protocol as that of Intermediate 26 and starting from Intermediate 78E (0.09 g, 0.39 mmol). LCMS (Method-I): retention time 0.82 min, [M+H] 227.1. The compound was taken directly to the subsequent step without further purification or characterization.

Intermediate 79: 6-(4-formyl-1H-pyrazol-1-yl)-5-methylnicotinonitrile

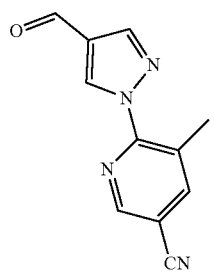 [SMILES: Cc1cc(C#N)cnc1-n1cc(C=O)cn1]

Intermediate 79 was prepared (0.11 g, 16.60%), by using similar synthetic protocol as that of Intermediate 9 and starting from 1H-pyrazole-4-carbaldehyde (0.30 g, 3.12 mmol) and 6-chloro-5-methylnicotinonitrile (0.47 g, 3.12 mmol). $^1$H NMR (400 MHz, DMSO-$d_6$) δ ppm 2.56 (s, 3H), 8.34 (s, 1H), 8.51 (d, J=2.01 Hz, 1H), 8.91 (d, J=1.51 Hz, 1H), 9.19 (s, 1H), 9.99 (s, 1H). LCMS (Method-ID): retention time 1.49 min, [M+H] 213.0.

Intermediate 80: 1-([1,2,4]triazolo[4,3-b]pyridazin-6-yl)-1H-pyrazole-4-carbaldehyde

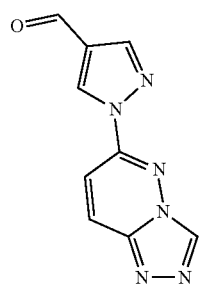 [SMILES: O=Cc1cnn(-c2ccc3nncn3n2)c1]

Intermediate 80 was prepared (0.12 g, 17.20%), by using similar synthetic protocol as that of Intermediate 9 and starting from 1H-pyrazole-4-carbaldehyde (0.30 g, 3.12 mmol) and 6-chloro-[1,2,4]triazolo[4,3-b]pyridazine (0.48 g, 3.12 mmol). $^1$H NMR (300 MHz, DMSO-$d_6$) δ ppm 7.93 (d, J=10.20 Hz, 1H), 8.19 (s, 1H), 8.26 (s, 1H), 8.48-8.53 (m, 1H), 8.82 (s, 1H), 9.61 (s, 1H). LCMS: The compound did not ionize well.

Intermediate 81: 1-(2-methoxypyridin-4-yl)-1H-pyrazole-4-carbaldehyde

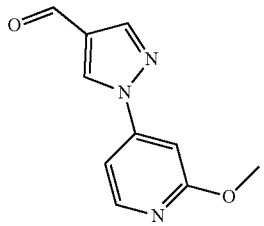

Intermediate 81 was prepared (0.08 g, 12.60%), by using similar synthetic protocol as that of Intermediate 9 and starting from 4-bromo-2-methoxypyridine (0.59 g, 3.12 mmol) and 1H-pyrazole-4-carbaldehyde (0.30 g, 3.12 mmol). $^1$H NMR (400 MHz, DMSO-$d_6$) δ ppm 3.92 (s, 3H), 7.36 (d, J=2.01 Hz, 1H), 7.59 (dd, J=5.52, 2.01 Hz, 1H), 8.28-8.36 (m, 2H), 9.43 (s, 1H), 9.93 (s, 1H). LCMS (Method-I): retention time 0.87 min, [M+H] 204.3.

Intermediate 82: tert-butyl (R)-(2-hydroxy-2-(4-methyl-1-oxo-1,3-dihydroisobenzofuran-5-yl)ethyl)((1-methyl-3-(trimethylstannyl)-1H-1,2,4-triazol-5-yl)methyl)carbamate

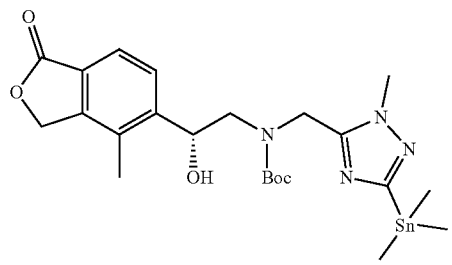 [SMILES: Cc1c([C@@H](O)CN(Cc2n[c]([Sn]([CH3])([CH3])[CH3])nn2C)C(=O)OC(C)(C)C)ccc2c1COC2=O]

Intermediate 82A: 3-bromo-1-methyl-1H-1,2,4-triazole-5-carbaldehyde

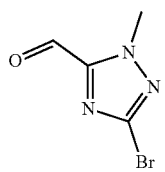

Synthesized according to literature procedures (WO02013/178572 A1, 2013).

Intermediate 82B-I: (R)-5-(2-(((3-bromo-1-methyl-1H-1,2,4-triazol-5-yl)methyl)amino)-1-hydroxy-ethyl)-4-methylisobenzofuran-1(3H)-one

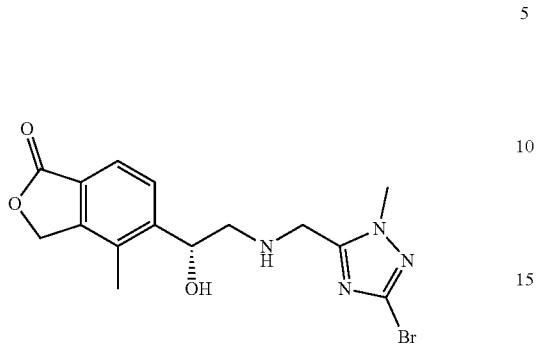

Intermediate 82B-I was prepared (0.54 g, 38.40%), by using similar synthetic protocol as that of Intermediate 76A and starting from Intermediate 82A-I (0.70 g, 3.68 mmol) and Intermediate 7-I (0.92 g, 4.42 mmol). ¹H NMR (300 MHz, DMSO-d₆) δ ppm 2.23 (s, 5H), 3.77 (s, 3H), 3.87-3.95 (m, 2H), 4.93-5.04 (m, 1H), 5.38 (s, 3H), 5.47-5.54 (m, 1H), 7.65 (s, 2H). LCMS (Method-H): retention time 0.802 min, [M+H] 381.0.

Intermediate 82C-I: tert-butyl (R)-((3-bromo-1-methyl-1H-1,2,4-triazol-5-yl)methyl)(2-hydroxy-2-(4-methyl-1-oxo-1,3-dihydroisobenzofuran-5-yl)ethyl)carbamate

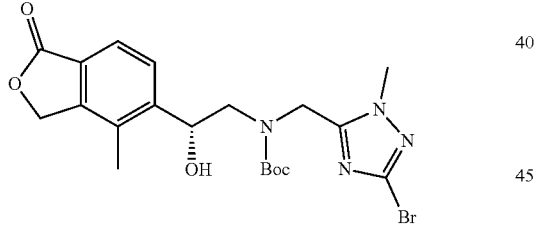

Intermediate 82C-I was prepared (0.14 g, 73.90%), by using a similar synthetic protocol as that of Intermediate 2A and starting from Intermediate 82B-I (0.15 g, 0.39 mmol) and BOC₂O (0.09 mL, 0.39 mmol). ¹H NMR (300 MHz, DMSO-d₆) δ ppm 1.29 (s, 9H), 2.24-2.34 (m, 4H), 3.44-3.54 (m, 1H), 3.75-3.84 (m, 3H), 4.56-4.68 (m, 2H), 5.10-5.23 (m, 1H), 5.34-5.42 (m, 2H), 5.78-5.84 (m, 1H), 7.63-7.73 (m, 2H). LCMS (Method-H): retention time 1.733 min, [M+H] 481.0.

Intermediate 82

Intermediate 82 was prepared (0.29 g, crude), by using a similar synthetic protocol as that of Intermediate 71B and starting from Intermediate 82C-I (0.14 g, 0.29 mmol). LCMS (Method-L): retention time 1.0 min, [M+2H] 568.2. The compound was taken forward directly to the subsequent step without further purification or characterization.

Intermediate 83: 2-(4-formyl-1H-pyrazol-1-yl)-4,6-dimethylpyrimidine-5-carbonitrile

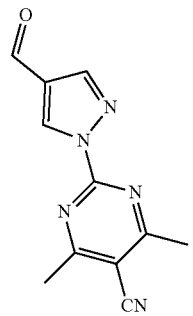 [SMILES: Cc1nc(-n2cc(C=O)cn2)nc(C)c1C#N]

Intermediate 83A: 5-bromo-4,6-dimethylpyrimidin-2-amine

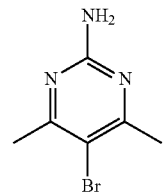

Synthesized according to literature procedures (WO2011/103536 A1, 2011).

Intermediate 83B: 2-amino-4,6-dimethylpyrimidine-5-carbonitrile

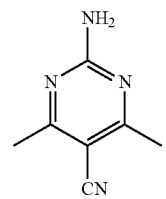

A solution of Intermediate 83A (6.00 g, 29.70 mmol) and copper (I) cyanide (3.99 g, 44.55 mmol) in DMF (50 mL) was heated at 180° C. for 16 h. The reaction mixture was cooled to ambient temperature, diluted with water (50 mL) and EtOAc (100 mL). The resulting mixture was filtered through Celite® and the filtrate was concentrated under reduced pressure to obtain Intermediate 83A (3 g, crude product). ¹H NMR (400 MHz, DMSO-d₆) δ ppm 2.32-2.41 (m, 6H), 7.533 (s, 2H). LCMS (Method-D): retention time 0.725 min, [M+H] 149.1.

Intermediate 83B: 2-bromo-4,6-dimethylpyrimidine-5-carbonitrile

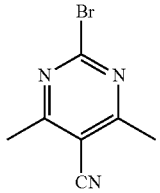

To a stirred solution of isoamyl nitrite (4.91 mL, 36.4 mmol) in acetonitrile (50 mL) at 0° C. was added copper(II) bromide (8.14 g, 36.40 mmol). The resulting mixture was stirred at ambient temperature for 10 minutes and Intermediate 83A (2.70 g, 18.22 mmol) in acetonitrile (10 mL) was added and the stirring was continued for 3 h. The reaction mixture was diluted with water (30 mL) and the aqueous layer was extracted with EtOAc (3×50 mL). The combined organic layers were dried over anhydrous sodium sulfate, filtered and concentrated. The residue was purified by silica gel column chromatography (Redisep-40 g, 10-20% EtOAc/n-hexane) to obtain Intermediate 83B (0.90 g, 23.90%). $^1$H NMR (400 MHz, DMSO-$d_6$) δ ppm 2.50-2.63 (m, 6H). LCMS (Method-D): retention time 1.692 min, [M+H] 211.9.

Intermediate 83

To a stirred solution of 1H-pyrazole-4-carbaldehyde (0.40 g, 4.16 mmol) and Intermediate 83B (0.88 g, 4.16 mmol) in acetonitrile (20 mL) was added $K_2CO_3$ ((1.72 g, 12.49 mmol) The resulting mixture was stirred at ambient temperature for 1.5 h. The reaction mixture was diluted with ethyl acetate (20 mL) and filtered through Celite®. The filtrate was evaporated under reduced pressure. The residue was purified by column chromatography (Redisep-24 g, 40% EtOAc/n-hexane) to obtain Intermediate 17C (0.30 g, 31.70%) as white solid. $^1$H NMR (400 MHz, DMSO-$d_6$) δ ppm 2.74 (s, 6H), 8.36 (s, 1H), 9.44 (s, 1H), 10.01 (s, 1H). LCMS (method-D), retention time 1.282 min, [M+H] 228.1.

Intermediate 84: 2-(4,5-dimethyl-1H-imidazol-1-yl)pyrimidine-5-carbaldehyde

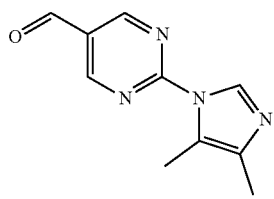

Intermediate 84A: 4,5-dimethyl-1H-imidazole

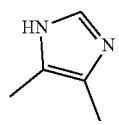

Synthesized according to literature procedures (*Angewandte* Chemie, 49, (2010), 5322-5326).

Intermediate 84

Intermediate 84 was prepared (0.19 g, 86.00%) as pale yellow solid, by using a similar synthetic protocol as that of Intermediate 83 and starting from Intermediate 84A (0.15 g, 1.60 mmol) and 2-bromopyrimidine-5-carbaldehyde (0.20 g, 1.07 mmol). 1H NMR (400 MHz, DMSO-$d_6$) δ ppm 2.13 (d, J=0.49 Hz, 3H), 2.16 (s, 3H), 8.47 (s, 1H), 9.27 (s, 2H), 10.11 (s, 1H). LCMS: The compound did not ionize well.

Intermediate 85: 4-methoxy-6-(4-methyl-1H-imidazol-1-yl)nicotinaldehyde

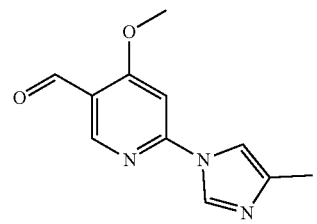 [SMILES: COc1cc(-n2cnc(C)c2)ncc1C=O]

Intermediate 85A: methyl 6-chloro-4-methoxynicotinate

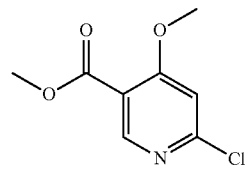

Synthesized according to literature procedures (US2015/166505 A1, 2015).

Intermediate 85B: (6-chloro-4-methoxypyridin-3-yl)methanol

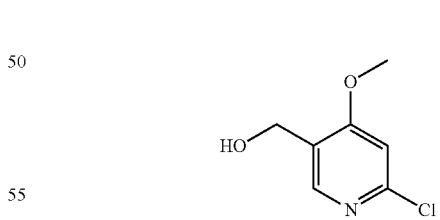

To a solution of Intermediate 85A (2.20 g, 10.91 mmol) in DCM (30 mL) was added DIBAL-H in heptane (16.37 mL, 16.37 mmol) at 0° C. and reaction mixture was stirred at ambient temperature for 1 h. The reaction mixture was quenched with saturated $NH_4Cl$ solution (20 mL), diluted with water (20 mL) and then extracted with ethyl acetate (3×50 mL). The combined organic layers were dried over anhydrous sodium sulfate and evaporated under reduced pressure. The residue was purified by column chromatography (Redisep-24 g, 20% EtOAc/n-hexane) to obtain Intermediate 85B (1.20 g, 63.30%). $^1$H NMR (400 MHz, DMSO-$d_6$) δ ppm 3.88 (s, 3H) 4.46 (dd, J=5.52, 1.00 Hz, 2H), 5.19 (t, J=5.77 Hz, 1H), 7.11 (s, 1H), 8.16 (s, 1H). LCMS (Method-I): retention time 0.69 min, [M+H] 174.4.

Intermediate 85C:
6-chloro-4-methoxynicotinaldehyde

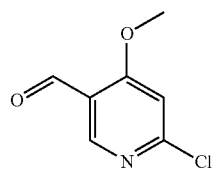

Intermediate 85C was prepared (0.75 g, 63.20%), by using a similar synthetic protocol as that of Intermediate 26 and starting from Intermediate 85B (1.20 g, 6.91 mmol). $^1$H NMR (400 MHz, DMSO-$d_6$) δ ppm 4.02 (s, 3H), 7.45 (s, 1H), 8.55 (s, 1H), 10.24 (s, 1H). LCMS (Method-D): retention time 1.06 min, [M+H] 172.2.

Intermediate 85

Intermediate 85 was prepared (0.12 g, 37.80/o), by using a similar synthetic protocol as that of Intermediate 47C and starting from Intermediate 85C (0.25 g, 1.46 mmol) and 4-methyl-1H-imidazole (0.24 g, 2.91 mmol). $^1$H NMR (400 MHz, DMSO-$d_6$) δ ppm 2.19 (s, 3H), 4.09 (s, 3H), 7.49 (s, 1H), 7.81 (s, 1H), 8.56 (d, J=1.00 Hz, 1H), 8.63 (s, 1H), 10.23 (s, 1H). LCMS (Method-I): retention time 0.89 min, [M+H] 218.3.

Intermediate 86: 2-(5-(difluoromethyl)-4-methyl-1H-imidazol-1-yl)pyrimidine-5-carbaldehyde

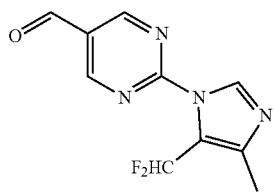 [SMILES: Cc1ncn(-c2ncc(C=O)cn2)c1C(F)F]

Intermediate 86A: tert-butyl 5-formyl-4-methyl-1H-imidazole-1-carboxylate

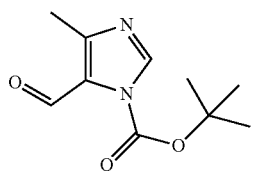

Intermediate 86A was prepared (2.80 g, 73.30%) as a white solid, by using a similar synthetic protocol as that of Intermediate 2A and starting from 4-methyl-1H-imidazole-5-carbaldehyde (2.00 g, 18.16 mmol) and BOC$_2$O (5.06 mL, 21.80 mmol) LCMS (Method-I): retention time 1.07 min, [M+H−56] 155.9. The compound was taken forward directly to the subsequent step without further characterization.

Intermediate 86B: tert-butyl 5-(difluoromethyl)-4-methyl-1H-imidazole-1-carboxylate

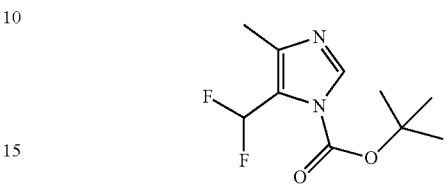

To a stirred solution of Intermediate 86A (1.50 g, 7.14 mmol) in DCM (20 mL) at 0° C. was added DAST (1.89 mL, 14.27 mmol) by drop wise. The resulting mixture was stirred at ambient temperature for 14 h. The reaction was quenched with saturated sodium bicarbonate solution (30 mL) at 0° C. The aqueous layer was extracted with DCM (3×30 mL) and the combined organic layers were washed with brine (10 mL), dried over anhydrous sodium sulfate, filtered and concentrated. The residue was purified by silica gel column chromatography (Redisep-24 g, 20% EtOAc/n-hexane) to obtain Intermediate 86B (0.85 g, 51.30%). $^1$H NMR (400 MHz, DMSO-$d_6$) δ ppm 1.58 (s, 9H), 2.44 (t, J=2.26 Hz, 3H), 6.82-7.18 (m, 1H), 8.19 (s, 1H). The compound did not ionize well.

Intermediate 86C:
5-(difluoromethyl)-4-methyl-1H-imidazole

To a solution of Intermediate 86B (0.85 g, 3.66 mmol) in methanol (5 mL) at 0° C. was added 4M HCl in dioxane (0.91 mL, 3.66 mmol). The resulting mixture was stirred at ambient temperature for 2 h and concentrated to dryness followed by co-distillation with methanol to obtain Intermediate 86C (0.48 g, 99.00%). $^1$H NMR (400 MHz, DMSO-$d_6$) δ ppm 2.38 (t, J=2.08 Hz, 3H), 7.06-7.52 (m, 1H), 9.02 (s, 1H), (1 Exchangeable proton not observed).

LCMS (Method-I): retention time 0.58 min, [M+H] 133.4.

Intermediate 86

Intermediate 86 was prepared (0.10 g, 20.90%), by using a similar synthetic protocol as that of Intermediate 83 and starting from Intermediate 86C (0.28 g, 1.68 mmol) and 2-chloropyrimidine-5-carbaldehyde (0.20 g, 1.40 mmol). $^1$H NMR (400 MHz, DMSO-$d_6$) δ ppm 2.69 (t, J=2.32 Hz, 3H), 6.92-7.26 (m, 1H), 8.62 (s, 1H), 9.34 (s, 2H), 10.15 (s, 1H). LCMS (Method-D): retention time 1.50 min, [M+H] 239.0.

Intermediate 87: 5-(2-amino-1-hydroxypropyl)-4-methylisobenzofuran-1(3H)-one

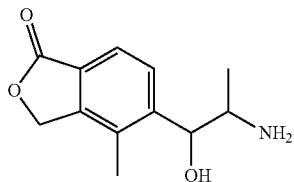 [SMILES: Cc1c(C(O)C(C)N)ccc2c1COC2=O]

Intermediate 87A: 4-methyl-1-oxo-1,3-dihydroisobenzofuran-5-carbaldehyde

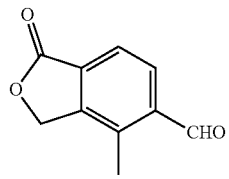

To a stirred solution of 5-bromo-4-methylisobenzofuran-1(3H)-one (2.00 g, 8.81 mmol) in DMF (10 mL) was added tert-butyl isocyanide (1.10 g, 13.21 mmol), 1,4-bis(diphenylphosphino)butane (0.37 g, 0.88 mmol), triethylsilane (3.07 g, 26.40 mmol) and $K_2CO_3$ (3.04 g, 22.02 mmol) at ambient temperature. The resulting reaction mixture was purged with argon gas for 10 minutes and palladium(II) acetate (0.39 g, 1.76 mmol) was added. The reaction mixture was heated at 65° C. in a sealed tube for 8 h and then was cooled to ambient temperature, diluted with water (20 mL), filtered through Celite®, and washed with ethyl acetate (2×50 mL). The filtrate was washed further with water (30 mL), brine solution (20 mL) and dried over sodium sulfate and concentrated under reduced pressure. The crude residue was purified by column chromatography (Redisep-40 g, 0-35% EtOAc/n-Hexane) to obtain Intermediate 87A (0.60 g, 38.70%) as an off-white solid. $^1$H NMR (400 MHz, CDCl$_3$) δ ppm 2.65 (s, 3H), 5.35 (s, 2H), 7.91-7.93 (d, J=8 Hz, 1H), 7.98-8.00 (d, J=8 Hz, 1H), 10.4 (s, 1H). LCMS (Method-D): retention time 1.14 min, [M+H$_2$O] 194.2.

Intermediate 87 B: 5-(1-hydroxy-2-nitropropyl)-4-methylisobenzofuran-1(3H)-one

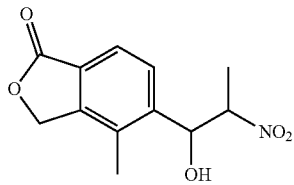

To a stirred solution of Intermediate 87A (0.60 g, 3.41 mmol) in THF (10 mL) was added nitroethane (2.56 g, 34.10 mmol) followed by DIPEA (2.97 mL, 17.03 mmol) at ambient temperature and the reaction mixture was stirred at 80° C. for 14 h. The reaction mixture was cooled to ambient temperature, concentrated to dryness, diluted with water (50 mL) and extracted with ethyl acetate (2×30 mL). The combined organic layers were washed with brine (20 mL), dried over anhydrous sodium sulfate and evaporated under reduced pressure. The residue was purified by column chromatography (Redisep-24 g, 0-5% MeOH/CHCl$_3$) to obtain Intermediate 87B (0.80 g, 93.00%). $^1$H NMR (400 MHz, CDCl$_3$) δ ppm 1.25-1.29 (m, 1H), 1.34-1.36 (d, J=7.2 Hz, 3H), 2.42 (s, 3H), 2.65-2.70 (m, 1H), 5.28 (s, 2H) 7.82-7.84 (d, J=7.6 Hz, 2H), (1 Exchangeable proton not observed). LCMS (Method-D): retention time 1.45 min, [M−H] 250.0.

Intermediate 87

A solution of Intermediate 87B (0.80 g, 3.18 mmol) in EtOH (50 mL) was purged with nitrogen for 1 min. 10% Pd/C (0.34 g, 0.32 mmol) was added and reaction mixture was stirred at ambient temperature for 12 h under an hydrogen atmosphere. The reaction mixture was filtered through Celite®, washed with EtOH (10 mL), and the filtrate was concentrated under reduced pressure to obtain Intermediate 87 (Diastereomeric mixture) (0.35 g, 49.7%) as a pale yellow solid. $^1$H NMR (400 MHz, CD$_3$OD) δ ppm 1.06-1.07 (d, J=6.4 Hz, 3H), 2.37 (s, 3H), 2.38 (s, 3H), 3.13-3.32 (m, 2H), 4.74-4.76 (d, J=7.2 Hz, 1H), 4.97-4.98 (d, J 4.4 Hz, 1H), 7.69-7.76 (m, 2H). LCMS (Method-D): retention time 0.38 min, [M+H] 222.2.

Intermediate 88: 6 6-(3-(difluoromethyl)-4-formyl-1H-pyrazol-1-yl)-4-methylnicotinonitrile

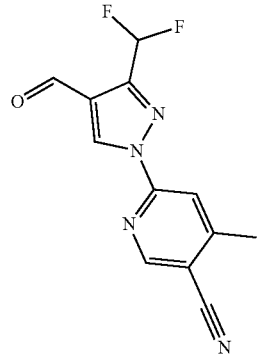 [SMILES: Cc1cc(-n2cc(C=O)c(C(F)F)n2)ncc1C#N]

Intermediate 88A: (3-cyclopropyl-1H-pyrazol-4-yl)methanol

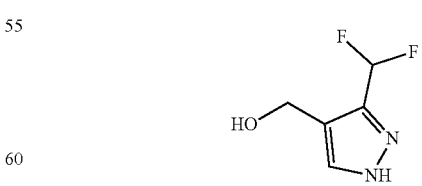

To a stirred solution of ethyl 3-(difluoromethyl)-1H-pyrazole-4-carboxylate (2.50 g, 13.15 mmol) in toluene (75 mL) was added DIBAL-H (39.40 mL, 39.40 mmol) at −78° C. and stirring was continued for 1 h at −78° C. The reaction mixture was quenched with MeOH (5 mL) at −78° C. and the precipitated solid was filtered. The resulting filtrate was concentrated under reduced pressure to obtain Intermediate 88A (1.40 g, 71.90%). $^1$H NMR (400 MHz, DMSO-d$_6$) δ ppm 4.48 (d, J=5.02 Hz, 2H), 4.96 (t, J=5.27 Hz, 1H), 6.77-7.15 (m, 1H), 7.72 (s, 1H), 13.06 (br. s., 1H). LCMS (Method-D): retention time 0.394 min, [M+H] 149.2.

Intermediate 88B:
3-(difluoromethyl)-1H-pyrazole-4-carbaldehyde

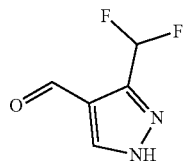

To a solution of Intermediate 88A (1.00 g, 6.75 mmol) in acetone (50 mL) at 0° C. was added manganese dioxide (1.17 g, 13.50 mmol). The resulting solution was stirred at 0° C. for 15 min and then the mixture was stirred at 60° C. for 12 h. The reaction mixture was diluted with water and extracted with DCM (3×100 mL). The organic layer was dried over anhydrous Na$_2$SO$_4$ and concentred under reduced pressure. The resulting residue was washed with ether (5 mL) to obtain Intermediate 88B (1.00 g, 50.70%). $^1$H NMR (400 MHz, DMSO-d$_6$) δ ppm 7.01-7.38 (m, 1H), 8.62 (s, 1H), 9.94 (s, 1H), 13.94 (br. s., 1H). LCMS (Method-H): retention time 0.54 min, [M–H] 145.0.

Intermediate 88

Intermediate 88 was prepared (0.50 g, 43.5%/o), by using a similar synthetic protocol as that of Intermediate 9 and starting from Intermediate 88B (0.25 g, 1.71 mmol) and 6-bromo-4-methylnicotinonitrile (0.34 g, 1.711 mmol). $^1$H NMR (400 MHz, DMSO-d$_6$) δ ppm 2.66 (s, 3H), 7.30-7.41 (m, 1H), 8.12 (s, 1H), 8.99 (s, 1H), 9.50 (s, 1H), 10.04 (s, 1H). LCMS (Method-D): retention time 1.48 min, [M–H] 261.0.

Intermediate 89: 5-(1-hydroxy-2-(((3-(trifluoromethyl)-1H-pyrazol-4-yl)methyl)amino)ethyl)-4-methylisobenzofuran-1(3H)-one

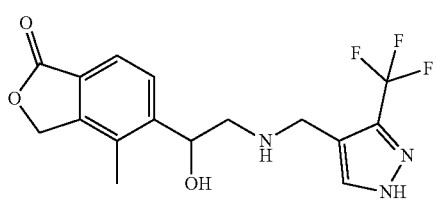 [SMILES: Cc1c(C(O)CNCc2c[nH]nc2C(F)(F)F)ccc2c1COC2=O]

Intermediate 89A:
(3-(trifluoromethyl)-1H-pyrazol-4-yl)methanol

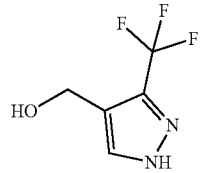

Ethyl 3-(trifluoromethyl)-1H-pyrazole-4-carboxylate (1.50 g, 7.21 mmol) was dissolved in dry THF (50 mL) and the resulting solution cooled to −78° C. To the resulting solution was added, 2 M solution of LAH (6.01 mL, 14.41 mmol) in THF over 30 min by keeping the temperature <10° C. The reaction mixture was allowed to come to ambient temperature, stirred for 4 h and was cooled again with to −10° C. The reaction was quenched with the addition of 1:1 THF:water (50 mL) mixture with cooling (maintaining the temperature <20° C.), followed by 5M HCl to neutralise to pH 6. The reaction mixture was diluted with EtOAc (100 mL), stirred for 30 min and left to settle for 1 h. The resulting solid was removed by filtration through Celite® and washed with EtOAc. The filtered organic layer was washed with brine, dried over MgSO$_4$ and evaporated under reduced pressure. The crude product was triturated with ether (2×25 mL) to obtain Intermediate 89A (0.60 g, 50.10%). $^1$H NMR (400 MHz, DMSO-d$_6$) δ ppm 4.44 (s, 2H), 5.02 (s, 1H), 7.83 (s, 1H), 13.73 (br. s., 1H). LCMS (Method-H): retention time 0.54 min, [M–H] 165.0.

Intermediate 89B:
3-(trifluoromethyl)-1H-pyrazole-4-carbaldehyde

Intermediate 89B was prepared (0.35 g, 64.40%), by using a similar synthetic protocol as that of Intermediate 26 and starting from Intermediate 89A (0.55 g, 3.31 mmol). $^1$H NMR (300 MHz, DMSO-d6) δ ppm 8.74 (s, 1H), 9.91 (s, 1H), 13.73 (br. s., 1H). LCMS (Method-D): retention time 1.01 min, [M–H] 163.0.

Intermediate 89

To a solution of Intermediate 7-I (0.35 g, 1.69 mmol) in MeOH (40 mL) was added Intermediate 89B (0.31 g, 1.86 mmol) and reaction mixture was stirred at ambient temperature for 15 min. To the resulting solution, NaCNBH$_4$ (0.318 g, 5.07 mmol) was added and the mixture was stirred for 12 h. The reaction mixture was diluted with water (30 mL) and extracted with DCM (3×50 mL). The combined organic layers were washed with brine (30 mL), dried over anhydrous sodium sulfate and evaporated under reduced pressure. The residue was washed with diethyl ether (20 mL) to obtain Intermediate 89 (0.25 g, 41.70%). $^1$H NMR (300

MHz, DMSO-d6) δ ppm 2.19 (s, 3H), 2.63 (d, J=6.42 Hz, 2H), 3.57 (s, 2H), 5.00 (d, J=12.46 Hz, 1H), 5.37 (s, 2H), 5.47 (br. s., 1H), 7.63-7.70 (m, 2H), 7.81 (s, 1H). LCMS (Method-H): retention time 0.95 min, [M+H] 356.2.

Intermediate 90: 1-(5-formylpyridin-2-yl)-4-methyl-1H-pyrazole-3-carbonitrile

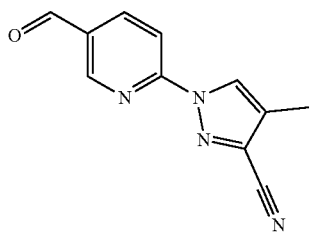 [SMILES: Cc1cn(-c2ccc(C=O)cn2)nc1C#N]

Intermediate 90 was prepared (0.20 g, 58.40/o), by using a similar synthetic protocol as that of Intermediate 19 and starting from 6-bromonicotinaldehyde (0.30 g, 1.61 mmol) and 4-methyl-1H-pyrazole-3-carbonitrile (0.19 g, 1.77 mmol). $^1$H NMR (400 MHz, DMSO-d6) δ ppm 2.25 (d, J=1.00 Hz, 3H), 8.15 (d, J=8.53 Hz, 1H), 8.45-8.50 (m, 1H), 8.83 (s, 1H), 9.03-9.07 (m, 1H), 10.14 (s, 1H). LCMS (Method-D): retention time 2.16 min, [M+H] 213.2.

Intermediate 91: 1-(5-formylpyrimidin-2-yl)-4-methyl-1H-pyrazole-3-carbonitrile

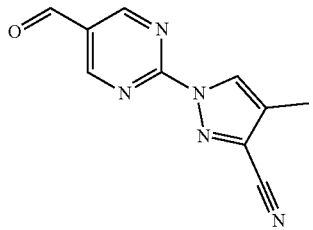 [SMILES: Cc1cn(-c2ncc(C=O)cn2)nc1C#N]

Intermediate 91 was prepared (0.30 g, 40.10%), by using a similar synthetic protocol as that of Intermediate 19 and starting from 2-chloropyrimidine-5-carbaldehyde (0.50 g, 3.51 mmol) and 4-methyl-1H-pyrazole-3-carbonitrile (0.41 g, 3.86 mmol). $^1$H NMR (400 MHz, DMSO-d6) δ ppm 2.23 (d, J=1.00 Hz, 3H), 8.85 (d, J=1.00 Hz, 1H), 8.90 (s, 1H), 9.36 (s, 1H), 10.15 (s, 1H). LCMS (Method-D), retention time 1.54 min, [M+H] 214.0.

Intermediate 92: 1-(5-formylpyrimidin-2-yl)-4-methyl-1H-pyrazole-3-carbonitrile

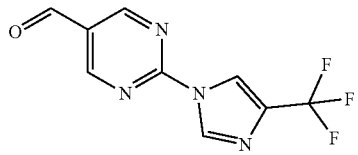 [SMILES: O=Cc1cnc(-n2cnc(C(F)(F)F)c2)nc1]

Intermediate 91 was prepared (0.10 g, 58.90%), by using a similar synthetic protocol as that of Intermediate 19 and starting from 2-chloropyrimidine-5-carbaldehyde (0.10 g, 0.70 mmol) and 4-(trifluoromethyl)-1H-imidazole (0.10 g, 0.77 mmol). $^1$H NMR (400 MHz, DMSO-d6) δ ppm 8.62 (t, J=1.6 Hz, 1H), 8.87 (d, J=1.00 Hz, 1H), 9.36 (s, 2H), 10.16 (s, 1H). LCMS (Method): retention time 1.80 min, [M+H] 243.0.

Intermediate 93: 6-(1H-1,2,4-triazol-1-yl)nicotinaldehyde

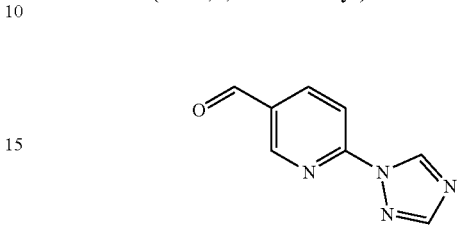

Intermediate 93 was prepared (0.30 g, 49.30%), by using a similar synthetic protocol as that of Intermediate 19 and starting from 6-bromonicotinaldehyde (0.50 g, 2.69 mmol) and 4H-1,2,4-triazole (0.204 g, 2.96 mmol). $^1$H NMR (400 MHz, DMSO-d6) δ ppm 8.07 (d, J=8.31 Hz, 1H), 8.41 (br. s., 1H), 8.51 (d, J=7.83 Hz, 1H), 9.07 (br. s., 1H), 9.52 (br. s., 1H), 10.15 (br. s., 1H). LCMS (Method-O): retention time 0.62 min, [M+H] 175.2.

Intermediate 94: 5-(1-hydroxy-2-(((5-iodo-1-methyl-1H-pyrazol-3-yl)methyl)amino)ethyl)-4-methylisobenzofuran-1(3H)-one

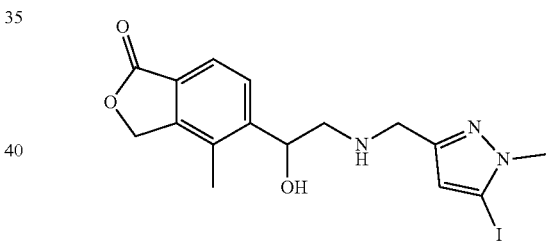

Intermediate 94A: ethyl 5-iodo-1-methyl-1H-pyrazole-3-carboxylate

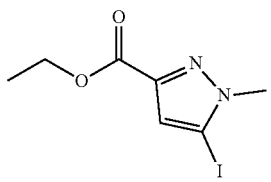

94A

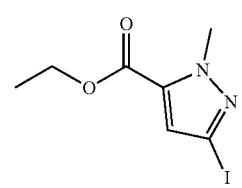

94B

To a stirred solution of ethyl 5-iodo-1H-pyrazole-3-carboxylate (0.15 g, 0.56 mmol) in THF (10 mL) was added K₂CO₃ (0.16 g, 1.13 mmol), MeI (0.042 mL, 0.677 mmol) and the reaction mixture was heated at 75° C. for 12 h. The reaction mixture was cooled to ambient temperature, concentrated to dryness, diluted with water (50 mL) and extracted with ethyl acetate (2×50 mL). The combined organic layers were washed with brine (30 mL), dried over anhydrous sodium sulfate and evaporated under reduced pressure. The residue was purified by column chromatography (Redisep-12 g, 0-35% EtOAc/n-Hexane) to obtain Intermediate 94A (0.10 g, 63.3%). $^1$H NMR (400 MHz, DMSO-d₆) δ ppm 1.25-1.38 (m, 3H), 4.05-4.11 (m, 3H), 4.25-4.38 (m, 2H), 7.03 (s, 1H). LCMS (Method-D): retention time 2.48 min, [M+H] 281.0. and Intermediate 94B (0.05 g, 31.70%). 1H NMR (400 MHz, DMSO-d6) δ ppm 1.23-1.32 (m, 3H), 3.93 (s, 3H), 4.25 (q, J=7.03 Hz, 2H), 6.94 (s, 1H). LCMS (Method-D): retention time 1.80 min, [M+H] 281.0.

Intermediate 94C:
5-iodo-1-methyl-1H-pyrazole-3-carbaldehyde

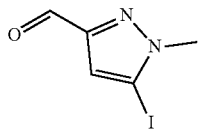

To a stirred solution of Intermediate 94A (1.00 g, 3.57 mmol) in DCM (3 mL) at −78° C. was added DIBAL-H (2.68 mL, 5.36 mmol) and stirring was continued for 1 h. The reaction mixture was quenched with MeOH and diluted with DCM. The resulting mixture was stirred at ambient temperature for 15 min, filtered through Celite® and the filtrate was concentrated under reduced pressure to obtain Intermediate 94C (0.50 g, 59.30%). $^1$H NMR (400 MHz, DMSO-d₆) δ ppm 3.99 (s, 3H), 7.02 (s, 1H), 9.79 (s, 1H). LCMS (Method-H): retention time 0.62 min, [M+H] 238.8.

Intermediate 94

Intermediate 94 was prepared (0.30 g, 33.10%), by using a similar synthetic protocol as that of Intermediate 89 and starting from Intermediate 94C (0.50 g, 2.12 mmol) and Intermediate 7-I (0.44 g, 2.12 mmol). $^1$H NMR (400 MHz, DMSO-d₆) δ ppm 2.22 (s, 3H), 2.31-2.34 (m, 2H), 2.67 (dt, J=3.64, 1.95 Hz, 1H), 3.64 (d, J=4.52 Hz, 1H), 3.78 (s, 1H), 3.79 (s, 3H), 4.34 (d, J=5.52 Hz, 1H), 4.98-5.03 (m, 1H), 5.38 (s, 2H), 6.36 (d, J=18.57 Hz, 1H), 7.65 (d, J=1.51 Hz, 2H). LCMS (Method-H): retention time 1.35 min, [M+H] 427.8.

Intermediate 95: 5-(1-hydroxy-2-(((3-iodo-1-methyl-1H-pyrazol-5-yl)methyl)amino)ethyl)-4-methylisobenzofuran-1(3H)-one

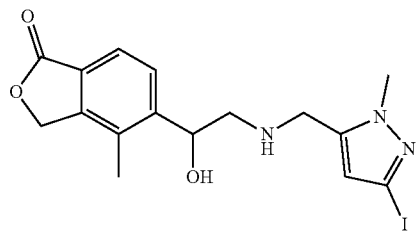 [SMILES: Cc1c(C(O)CNCc2cc(I)nn2C)ccc2c1COC2=O]

Intermediate 95A:
3-iodo-1H-pyrazole-5-carbaldehyde

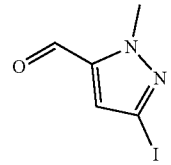

Intermediate 95A was prepared (0.02 g, 59.30%), by using a similar synthetic protocol as that of Intermediate 94C and starting from Intermediate 94B (0.05 g, 0.18 mmol). LCMS (Method-D): retention time 0.88 min, [M+H] 237.4. The compound was taken directly to the subsequent step without further purification or characterization.

Intermediate 95

Intermediate 95 was prepared (0.10 g, 36.80%), by using a similar synthetic protocol as that of Intermediate 89 and starting from Intermediate 95A (0.15 g, 0.64 mmol) and Intermediate 7-I (0.132 g, 0.636 mmol). $^1$H NMR (400 MHz, DMSO-d₆) δ ppm 2.22 (s, 3H), 2.31-2.34 (m, 2H), 2.65-2.68 (m, 1H), 3.64 (d, J=4.02 Hz, 1H), 3.77 (s, 1H), 3.79 (s, 3H), 4.34 (d, J=6.02 Hz, 1H), 4.97-5.03 (m, 1H), 5.38 (s, 2H), 6.36 (d, J=18.57 Hz, 1H), 7.64-7.67 (m, 2H). LCMS (Method-D): retention time 1.05 min, [M+H] 428.0.

Intermediate 96: 6-(3-cyclopropyl-4-formyl-1H-pyrazol-1-yl)-4-methylnicotinonitrile

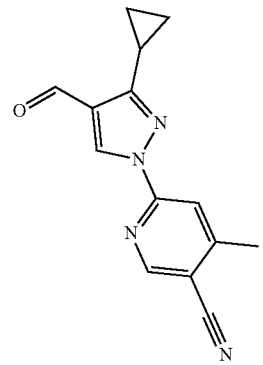 [SMILES: Cc1cc(-n2cc(C=O)c(C3CC3)n2)ncc1C#N]

Intermediate 96A:
(3-cyclopropyl-1H-pyrazol-4-yl)methanol

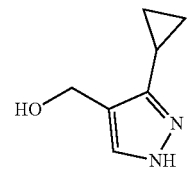

Intermediate 96B was prepared (2.60 g, 67.10%), by using a similar synthetic protocol as that of Intermediate 88A and starting from ethyl 3-cyclopropyl-1H-pyrazole-4-carboxylate (5.00 g, 27.7 mmol). ¹H NMR (400 MHz, DMSO-d6) δ ppm 0.78-0.90 (m, 4H), 1.78-1.94 (m, 1H), 4.37 (d, J=5.14 Hz, 2H), 4.65 (t, J=5.26 Hz, 1H), 7.24-7.43 (m, 1H), 12.16 (br. s., 1H), (1 Exchangeable proton not observed). LCMS (Method-H): retention time 0.54 min, [M+H] 208.2.

Intermediate 96B:
3-cyclopropyl-1H-pyrazole-4-carbaldehyde

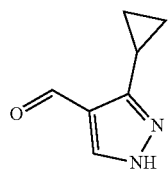

Intermediate 96B was prepared (1.20 g, 39.30%), by using a similar synthetic protocol as that of Intermediate 88B and starting from Intermediate 96A (2.00 g, 14.48 mmol). ¹H NMR (400 MHz, DMSO-d6) δ ppm 0.78-0.90 (m, 4H), 2.08-2.14 (m, 1H), 7.98-8.19 (m, 1H), 9.90 (s, 1H), (Exchangeable proton not observed). LCMS (Method-D): retention time 0.57 min, [M+H] 137.1.

Intermediate 96

Intermediate 96 was prepared (0.03 g, 52.90%), by using a similar synthetic protocol as that of Intermediate 9 and starting from Intermediate 96B (0.03 g, 1.83 mmol) and 6-bromo-4-methylnicotinonitrile (0.04 g, 1.836 mmol). ¹H NMR (400 MHz, DMSO-d6) δ ppm 0.93-1.12 (m, 4H) 2.50-2.52 (m, 1H) 2.60 (s, 3H) 7.94 (s, 1H) 8.91 (s, 1H) 9.27 (s, 1H) 10.05 (s, 1H). L CMS (Method-H): retention time 2.72 min, [M+H] 253.1.

Intermediate 96: 5-(2-(((6-bromopyridin-2-yl) methyl)amino)-1-hydroxyethyl)-4-methylisobenzo-furan-1(3H)-one

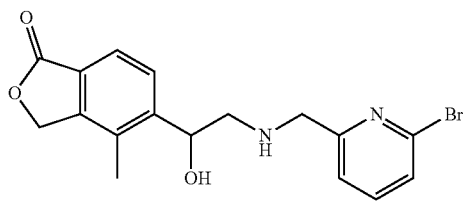 [SMILES: Cc1c(C(O)CNCc2cccc(Br)n2)ccc2c1COC2=O]

To a solution of 6-bromopicolinaldehyde (0.14 g, 0.72 mmol) and Intermediate 7-1(0.15 g, 0.72 mmol) in DCM (10 mL) and MeOH (3 mL) was added AcOH (0.17 mL, 2.90 mmol) and the reaction mixture stirred for 16 h. Then NaBH₄ (0.08 g, 2.17 mmol) was added portionwise and stirred at ambient temperature for 1 h. The reaction mixture was quenched with water (20 mL) and extracted with DCM (3×30 mL). The combined organic layers were washed with brine (20 mL), dried over sodium sulfate and distilled under reduced pressure to obtain Intermediate 96 (0.29 g, 42.5%)

as a light brown solid. LCMS (Method-H): retention time 1.04 min, [M+1]378.0. The compound was taken directly to the subsequent step without further purification or characterization.

Intermediate 97:
6-(5-methyl-2H-tetrazol-2-yl)nicotinaldehyde

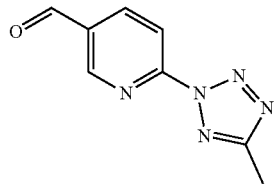

Intermediate 97 was prepared (0.22 g, 43.30%) as a light brown solid, by using a similar synthetic protocol as that of Intermediate 19 and starting from 6-bromonicotinaldehyde (0.50 g, 2.69 mmol) and 5-methyl-2H-tetrazole (0.34 g, 4.03 mmol). ¹H NMR (400 MHz, DMSO-d₆) δ ppm 2.87 (s, 3H), 8.22 (d, J=8.03 Hz, 1H), 8.59 (dd, J=8.53, 2.01 Hz, 1H), 9.12-9.21 (m, 1H), 10.20 (s, 1H). LCMS (Method-H): retention time 0.86 min, [M+1] 190.0.

Intermediate 98: (R)-5-(2-(((2-chloropyrimidin-5-yl) methyl)amino)-1-hydroxyethyl)-4-methylisobenzo-furan-1(3H)-one

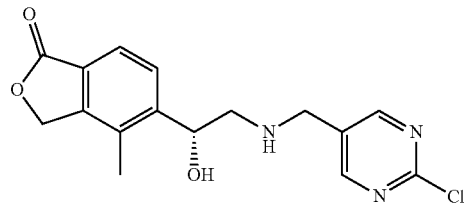 [SMILES: Cc1c([C@@H](O)CNCc2cnc(Cl)nc2)ccc2c1COC2=O]

Intermediate 98A:
5-(bromomethyl)-2-chloropyrimidine

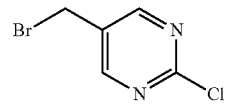

To a solution of 2-chloro-5-methylpyrimidine (5.00 g, 38.90 mmol) in CCl₄ (100 mL) was added NBS (10.38 g, 58.30 mmol) and AIBN (0.13 g, 0.78 mmol). The resulting mixture was heated at 75° C. for 6 h. The reaction was cooled to ambient temperature, filtered and evaporated under reduced pressure. The residue was purified by silica gel column chromatography (Redisep-24 g, 0-20% EtOAc/n-hexane) to obtain Intermediate 98A (2.50 g, 31.00%) as a colorless liquid. ¹H NMR (400 MHz, CDCl₃) δ ppm 4.42 (s, 2H), 8.67 (s, 2H). LCMS: The compound did not ionize well.

Intermediate 98

To a solution of 2-chloropyrimidine-5-carbaldehyde (0.30 g, 2.11 mmol) in THF (10 mL) was added Intermediate 7-I (0.36 g, 1.75 mmol) and the reaction mixture was stirred at ambient temperature for 1 h. To the resulting solution was added sodium cyanoborohydride (0.27 g, 4.38 mmol) and MeOH (1 mL) and stirring was continued for 14 h. The reaction mixture was diluted with water (20 mL) and extracted with 7% MeOH:DCM (3×30 mL). The combined organic layers were dried over anhydrous sodium sulfate and evaporated under reduced pressure. The residue was triturated with DCM/n-hexane to obtain Intermediate 98 (0.45 g, 43.00%). $^1$H NMR (400 MHz, DMSO-$d_6$) δ ppm 2.23 (s, 3H), 2.59-2.67 (m, 2H), 3.17 (d, J=4.16 Hz, 1H), 3.80 (s, 1H), 4.57 (d, J=4.65 Hz, 1H), 5.01 (d, J=3.67 Hz, 1H), 5.38 (d, J=3.42 Hz, 2H), 5.48-5.62 (m, 1H), 7.56-7.74 (m, 2H), 8.64-8.76 (m, 2H). LCMS (Method-O): retention time 0.72 min, [M+H] 334.5

Intermediate 99: 2-(3-methyl-2-oxo-2,3-dihydrobenzo[d]oxazol-5-yl)-1H-imidazole-4-carbaldehyde

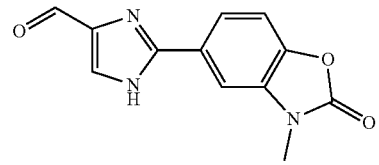 [SMILES: Cn1c(=O)oc2ccc(-c3nc(C=O)c[nH]3)cc21]

Intermediate 99A: ethyl 1-((2-(trimethylsilyl)ethoxy)methyl)-1H-imidazole-4-carboxylate

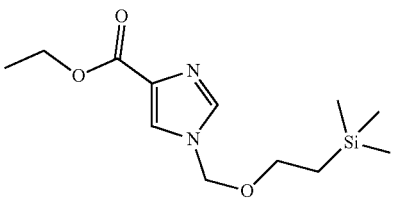 [SMILES: CCOC(=O)c1cn(COCC[Si](C)(C)C)cn1]

To a solution of ethyl 1H-imidazole-4-carboxylate (3.50 g, 24.98 mmol) in DMF (10 mL) was added NaH (1.80 g, 37.5 mmol) at 0° C. and the reaction was stirred for 15 minutes. SEM-Cl (4.87 mL, 27.5 mmol) was added dropwise and the reaction mixture was stirred at ambient temperature for 4 h. The reaction was quenched with saturated ammonium chloride solution and diluted with water (100 ml). The aqueous layers were extracted with ethyl acetate (3×150 mL). The combined organic layers were washed with brine (100 mL), dried over sodium sulfate and concentrated under reduced pressure to obtain Intermediate 99A (3.80 g, crude). $^1$H NMR (400 MHz, DMSO-$d_6$) δ ppm −0.12-0.04 (m, 9H), 0.74-0.91 (m, 2H), 1.20-1.34 (m, 2H), 3.44-3.56 (m, 3H), 4.15-4.31 (m, 2H), 5.62 (s, 2H), 7.67 (d, J=1.00 Hz, 1H), 8.12 (d, J=1.00 Hz, 1H). LCMS (Method-H): retention time 2.20 min, [M+1] 271.2.

Intermediate 99B: ethyl 2-bromo-1-((2-(trimethylsilyl)ethoxy)methyl)-1H-imidazole-4-carboxylate

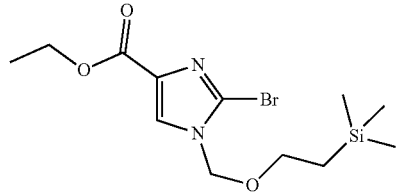 [SMILES: CCOC(=O)c1cn(COCC[Si](C)(C)C)c(Br)n1]

Intermediate 99B was prepared (2.70 g, 38.00%) as brown viscous liquid, by using a similar synthetic protocol as that of Intermediate 98A and starting from Intermediate 99A (5.50 g, 20.34 mmol). $^1$H NMR (400 MHz, DMSO-$d_6$) δ ppm −0.05-0.08 (m, 9H), 0.84-0.96 (m, 2H), 1.27-1.37 (m, 2H), 3.52-3.61 (m, 2H), 4.19-4.40 (m, 3H), 5.35-5.40 (m, 2H), 8.26 (s, 1H). LCMS (Method-H): retention time: 2.62 min, [M+1] 349.2.

Intermediate 99C: (2-bromo-1-((2-(trimethylsilyl)ethoxy)methyl)-1H-imidazol-4-yl)methanol

To a stirred solution of Intermediate 99B (1.40 g, 4.01 mmol) in DCM (20 mL) at −50° C. was added Diisobutylaluminum hydride (4.01 mL, 10.02 mmol) solution in toluene (2.5 M) and the resulting mixture was stirred at ambient temperature for 16 h. The reaction mixture was quenched with MeOH (2 mL) and sodium acetate solution (75 mL) and extracted with DCM (2×100 mL). The combined organic layers were washed with brine (30 mL), dried over anhydrous sodium sulfate and evaporated under reduced pressure to obtain Intermediate 99C (1.00 g, 61.00%) as brown solid. LCMS (Method-D): retention time: 2.19 min, [M+1] 307.0. The compound was taken directly to the subsequent step without further purification or characterization.

Intermediate 99C: 2-bromo-1-((2-(trimethylsilyl)ethoxy)methyl)-1H-imidazole-4-carbaldehyde

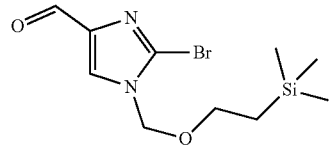 [SMILES: C[Si](C)(C)CCOCn1cc(C=O)nc1Br]

Intermediate 99C was prepared (0.48 g, 64.4%) as off white solid, by using a similar synthetic protocol as that of Intermediate 26 and starting from Intermediate 99B (1.00 g, 2.44 mmol). $^1$H NMR (400 MHz, DMSO-$d_6$) δ ppm −0.08-−0.03 (m, 9H), 0.80-0.90 (m, 2H), 3.48-3.62 (m, 2H), 5.38 (s, 2H), 8.38 (s, 1H), 9.67 (s, 1H). LCMS (Method-D): retention time 2.58 min, [M+H₂O] 305.0.

Intermediate 99D: 2-(3-methyl-2-oxo-2,3-dihydrobenzo[d]oxazol-5-yl)-1-((2-(trimethylsilyl)ethoxy)methyl)-1H-imidazole-4-carbaldehyde

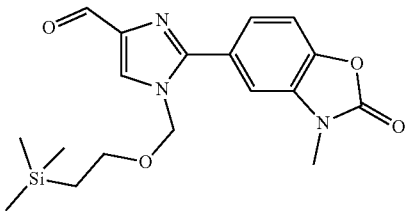 [SMILES: Cn1c(=O)oc2ccc(-c3nc(C=O)cn3COCC[Si](C)(C)C)cc21]

Intermediate 99D was prepared (0.14 g, 45.80%) as colourless viscous liquid, by using a similar synthetic protocol as that of Intermediate 10A and starting from Intermediate 3 (0.20 g, 0.66 mmol) and Intermediate 99C (0.18 g, 0.66 mmol). $^1$H NMR (400 MHz, DMSO-d$_6$) δ ppm 0.08-0.03 (m, 9H), 0.82-0.99 (m, 2H), 3.41-3.50 (m, 3H), 3.57-3.68 (m, 2H), 5.53 (s, 2H), 7.54 (d, J=8.03 Hz, 1H), 7.61-7.68 (m, 1H), 7.71 (d, J=1.51 Hz, 1H), 8.45 (s, 1H), 9.87 (s, 1H). LCMS (Method-H): retention time: 2.28 min, [M+1] 374.2.

Intermediate 99

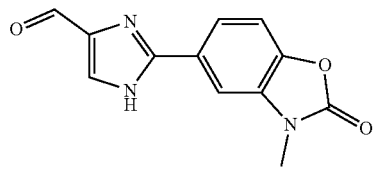 [SMILES: Cn1c(=O)oc2ccc(-c3nc(C=O)c[nH]3)cc21]

A solution of Intermediate 99D (0.14 g, 0.38 mmol) in 6 N aq. HCl (10.00 mL, 60.00 mmol) was heated at 50° C. for 16 h. The reaction mixture was cooled to ambient temperature, distilled to dryness and basified with saturated sodium bicarbonate solution (50 mL). The aqueous layers were extracted with 10% MeOH/DCM (2×50 mL). The combined organic layers were washed with brine (30 mL), dried over sodium sulfate and evaporated under reduced pressure to obtain Intermediate 99 (0.07 g, 69.10%) as a light brown solid. $^1$H NMR (300 MHz, DMSO-d$_6$) δ ppm 3.32 (s, 3H), 7.27-7.59 (m, 1H), 7.73-8.01 (m, 2H), 8.11 (br. s., 1H), 9.76 (s, 1H), 13.44 (br. s., 1H). LCMS (Method-H): retention time 0.56 min, [M+H₂O]244.2.

Intermediate 100: 5-(3-methyl-2-oxo-2,3-dihydrobenzo[d]oxazol-5-yl)nicotinaldehyde

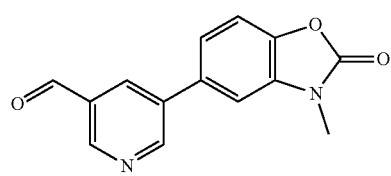 [SMILES: Cn1c(=O)oc2ccc(-c3cncc(C=O)c3)cc21]

Intermediate 100 was prepared (0.14 g, 54.50%) as an off white solid, by using a similar synthetic protocol as that of Intermediate 10A and starting from Intermediate 3 (0.25 g, 0.91 mmol) and 5-bromonicotinaldehyde (0.17 g, 0.91 mmol). $^1$H NMR (300 MHz, DMSO-d$_6$) δ ppm 3.43 (s, 3H), 7.44-7.52 (m, 1H), 7.60 (dd, J=8.50, 1.70 Hz, 1H), 7.81 (d, J=1.51 Hz, 1H), 8.55 (t, J=2.08 Hz, 1H), 9.07 (d, J=1.51 Hz, 1H), 9.23 (d, J=2.27 Hz, 1H), 10.20 (s, 1H). LCMS (Method-D): retention time 1.48 min, [M+1] 255.2.

Intermediate 101: 1-(3-ethyl-2-oxo-2,3-dihydrobenzo[d]oxazol-5-yl)-1H-pyrazole-4-carbaldehyde

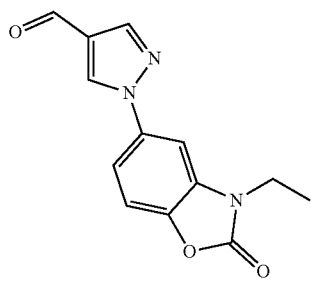 [SMILES: CCn1c(=O)oc2ccc(-n3cc(C=O)cn3)cc21]

Intermediate 101A: 5-bromo-3-ethylbenzo[d]oxazol-2(3H)-one

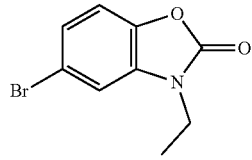

To a solution of 5-bromobenzo[d]oxazol-2(3H)-one (1.50 g, 7.01 mmol) in DMF (10 mL) was added K₂CO₃ (2.42 g, 17.52 mmol) and iodoethane (0.57 mL, 7.01 mmol). The resulting mixture was stirred at 70° C. for 2 h. The reaction mixture was cooled to ambient temperature and quenched with ice cold water. The mixture was stirred for 15 minutes. The solid precipitate was collected by suction filtration and dried under vacuum to obtain Intermediate 101A (1.50 g, 88.00%) as brown solid. $^1$H NMR (400 MHz, DMSO-d$_6$) δ ppm 1.24 (t, J=7.28 Hz, 3H), 3.85 (q, J=7.53 Hz, 2H), 7.18-7.42 (m, 2H), 7.63 (s, 1H). LCMS (Method-H): retention time 1.48 min, [M+H₂O] 261.0.

Intermediate 101

Intermediate 101 was prepared (0.04 g, 5.23%) as brown solid, by using a similar synthetic protocol as that of Intermediate 19 and starting from Intermediate 101A (0.63 g, 2.60 mmol) and 1H-pyrazole-4-carbaldehyde (0.25 g, 2.60 mmol). LCMS (Method-I): retention time 0.94 min, [M+1] 258.1. The compound was taken directly to the subsequent step without further purification or characterization.

Intermediate 102: 6-(4-methyl-1H-imidazol-1-yl)nicotinaldehyde

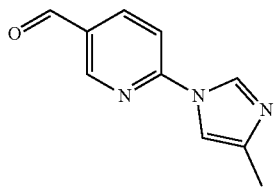

Intermediate 102 was prepared (1.45 g, 38.90%) as a brown solid, by using a similar synthetic protocol as that of Intermediate 19 and starting from 6-bromonicotinaldehyde (3.00 g, 16.13 mmol) and 4-methyl-1H-imidazole (2.65 g, 32.3 mmol). $^1$H NMR (400 MHz, DMSO-$d_6$) δ ppm 2.19 (s, 3H), 7.77 (s, 1H), 7.95 (d, J=8.56 Hz, 1H), 8.40 (dd, J=8.56, 2.20 Hz, 1H), 8.56 (d, J=1.22 Hz, 1H), 8.99 (d, J=1.96 Hz, 1H), 10.08 (s, 1H). LCMS (Method-D): retention time 0.91 min, [M+1] 188.2.

Intermediate 103: 1-(5-formylpyridin-2-yl)-1H-1, 2, 4-triazole-3-carbonitrile

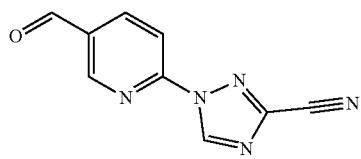 [SMILES: N#Cc1ncn(-c2ccc(C=O)cn2)n1]

Intermediate 103 was prepared (0.25 g. 46.70%) as a brown solid, by using a similar synthetic protocol as that of Intermediate 19 and starting from 6-bromonicotinaldehyde (0.50 g, 2.69 mmol) in DMF (10 mL) and 1H-1,2,4-triazole-3-carbonitrile (0.38 g, 4.03 mmol). $^1$H NMR (400 MHz, DMSO-$d_6$) δ ppm 8.14-81.6 (d, J=8.8 Hz, 1H), 8.56-8.58 (m, 1H), 9.13 (s, 1H), 9.87 (s, 1H), 10.18 (s, 1H). LCMS (Method-H): retention time 1.27 min, [M+H] 200.2.

Intermediate 104: 2-(4-methyl-1H-imidazol-1-yl)pyrimidine-5-carbaldehyde

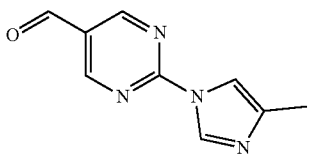

To a solution of 2-chloropyrimidine-5-carbaldehyde (3.00 g, 21.05 mmol) in DMSO (20 mL) was added $K_2CO_3$ (7.27 g, 52.60 mmol) and 4-methyl-1H-imidazole (2.59 g, 31.6 mmol). The resulting mixture was stirred at ambient temperature for 30 minutes. The reaction mixture was poured into ice cold water (50 mL) and extracted with ethyl acetate (3×100 mL). The combined organic layers were washed with brine (50 mL), dried over sodium sulfate and concentrated under reduced pressure. The residue was purified by column chromatography (Redisep-24 g, 80% EtOAc/n-hexane) to obtain Intermediate 104 (1.40 g, 34.30%) as a white solid. $^1$H NMR (400 MHz, DMSO-$d_6$) δ ppm 2.20 (s, 3H), 7.72 (t, J=1.2 Hz 1H), 8.56 (d, J 1.2 Hz, 1H), 9.26 (s, 2H) 10.09 (s, 1H). LCMS (Method-D): retention time 1.07 min, [M+H] 189.1.

Intermediate 105: 2-(3-methyl-1H-1,2,4-triazol-1-yl)pyrimidine-5-carbaldehyde

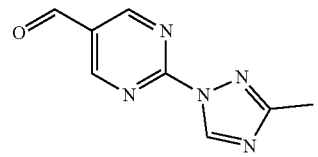

To a solution of 2-chloropyrimidine-5-carbaldehyde (0.25 g, 1.75 mmol) in THF (7 mL) was added $K_2CO_3$ (0.36 g, 2.63 mmol) and 3-methyl-1H-1,2,4-triazole (0.22 g, 2.63 mmol). The resulting mixture was stirred at 70° C. for 2 h. The reaction mixture was cooled to ambient temperature and poured into ice cold water (30 mL) and extracted with ethyl acetate (2×50 mL). The combined organic layers were washed with brine (20 mL), dried over sodium sulfate and distilled under reduced pressure. The residue was recrystallised from DCM/n-hexane to obtain Intermediate 105 (0.300 g, 70.50%) as yellow sticky material. $^1$H NMR (400 MHz, DMSO-$d_6$) δ ppm 2.34-2.43 (m, 3H), 9.29-9.40 (m, 2H), 10.10-10.25 (m, 1H), 13.69 (br. s., 1H). LCMS (Method-D): retention time 0.42 min, [M+1] 190.2.

Intermediate 106: 6-(4-formyl-1H-pyrazol-1-yl)-4-(pyrrolidin-1-yl)nicotinonitrile

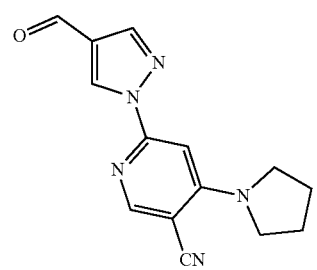 [SMILES: N#Cc1cnc(-n2cc(C=O)cn2)cc1N1CCCC1]

Intermediate 106A: 4-chloro-6-(4-formyl-1H-pyrazol-1-yl)nicotinonitrile and Intermediate 106B: 6-chloro-4-(4-formyl-1H-pyrazol-1-yl)nicotinonitrile

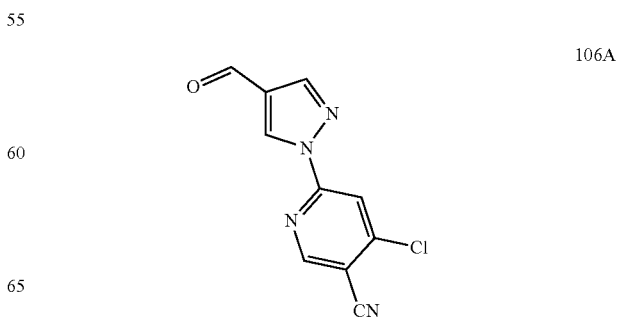

106A

-continued

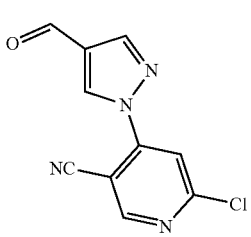

106B

To a solution of 4,6-dichloronicotinonitrile (2.50 g, 14.45 mmol) and 1H-pyrazole-4-carbaldehyde (1.26 g, 13.14 mmol) in dioxane (50 mL) was added Cs$_2$CO$_3$ (6.42 g, 19.71 mmol) and 4,5-bis(diphenylphosphino)-9,9-dimethylxanthene (0.76 g, 1.31 mmol). The reaction mixture was degassed with nitrogen for 10 minutes and Pd$_2$(dba)$_3$ (0.60 g, 0.66 mmol) was added. The resulting mixture was heated at 90° C. for 16 h. The reaction mixture was filtered through Celite® and concentrated under reduced pressure. The residue was purified by column chromatography (Redisep-80 g, 15% EtOAc/n-hexane) to obtain Intermediate 106A (0.60 g, 19.63%) as a white solid, fast eluting. $^1$H NMR (400 MHz, DMSO-d$_6$) δ ppm 8.33 (s, 1H), 8.50 (s, 1H), 9.05 (s, 1H), 9.43 (s, 1H), 9.99 (s, 1H). LCMS: The compound did not ionize well and Intermediate 106B (0.40 g, 13.09%) as white solid, slow eluting. $^1$H NMR (400 MHz, DMSO-d$_6$) δ ppm 8.33 (s, 1H), 8.50 (s, 1H), 9.05 (s, 1H), 9.43 (s, 1H), 9.99 (s, 1H). LCMS: The compound did not ionize well.

Intermediate 106

To a stirred solution of Intermediate 106A (0.150 g, 0.65 mmol) in THF (10 mL) was added K$_2$CO$_3$ (0.22 g, 1.61 mmol) and pyrrolidine (0.12 g, 1.61 mmol). The resulting mixture was stirred at ambient temperature for 2 h. Reaction mixture was filtered and distilled under reduced pressure. The residue was purified by column chromatography (Redisep-12 g, 40% EtOAc/n-hexane) to obtain Intermediate 106 (0.080 g, 46.40%) as an off white solid. $^1$H NMR (400 MHz, DMSO-d$_6$) δ ppm 1.99 (dt, J=6.27, 3.39 Hz, 4H), 3.69 (br. s., 4H), 7.11 (s, 1H), 8.30 (s, 1H), 8.49 (s, 1H), 9.26 (s, 1H), 9.95 (s, 1H). LCMS (Method-I): retention time 1.09 min, [M+1] 268.4.

Intermediate 107:
6-chloro-2-methylpyridazin-3(2H)-one

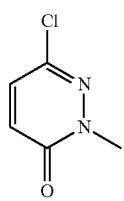

To a solution of 6-chloropyridazin-3(2H)-one (0.35 g 2.68 mmol) in DMF (10 mL) was added K$_2$CO$_3$ (0.93 g, 6.70 mmol) and methyl iodide (0.20 mL, 3.22 mmol). The resulting mixture was stirred at 25° C. for 1 h. To the reaction mixture was added ice cold water (30 mL) and the mixture was extracted with ethyl acetate (2×50 ml). The combined organic layers were washed with brine (30 mL), dried over sodium sulfate and distilled under reduced pressure to obtain Intermediate 107 (0.25 g, 56.10%) as an off white solid. $^1$H NMR (400 MHz, CDCl$_3$) δ ppm 3.75 (s, 3H), 6.92 (d, J=9.76 Hz, 1H), 7.19 (d, J=9.76 Hz, 1H). LCMS (Method-D): retention time 0.66 min, [M+1] 145.2.

Intermediate 108: 1-methyl-4-(4,4,5,5-tetramethyl-1,3,2-dioxaborolan-2-yl)-1H-pyrazole

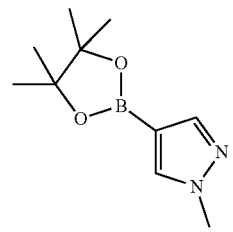

To the solution of 4-(4,4,5,5-tetramethyl-1,3,2-dioxaborolan-2-yl)-1H-pyrazole (0.40 g, 2.06 mmol) in THF (10 mL) was added NaH (0.1.00 g, 4.12 mmol) followed by methyl iodide (0.25 mL, 4.12 mmol) at 0° C. and the reaction mixture was stirred at ambient temperature for 4 hr. The reaction was quenched with saturated NH$_4$Cl solution (20 mL) and extracted with ethyl acetate (2×50 mL). The combined organic layers were washed with brine (20 mL), dried over sodium sulfate, and distilled under reduced pressure to obtain Intermediate 108 (0.40 g, 93.00%) as yellow viscous liquid. $^1$H NMR (400 MHz, CDCl$_3$) δ ppm 1.31 (s, 12H), 3.91 (s, 3H), 7.65 (s, 1H), 7.77 (s, 1H). LCMS (Method-D): retention time 1.58 min, [M+1] 209.1.

Intermediate 109: 6-(5-(aminomethyl)isoxazol-3-yl)-4-methoxynicotinonitrile

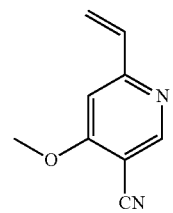

Intermediate 109A:
4-methoxy-6-vinylnicotinonitrile

To a solution of 6-bromo-4-methoxynicotinonitrile (2.00 g, 9.39 mmol) and potassium vinyltrifluoroborate (1.51 g, 11.27 mmol) in ethanol (10 mL) was added triethylamine (3.93 mL, 28.20 mmol) at ambient temperature. The reaction mixture was degassed with nitrogen for 10 minutes. 1,1'-bis(diphenylphosphino)ferrocene-palladium(II)dichloride dichloromethane complex (0.08 g, 0.09 mmol) was added and the resulting mixture was heated to 80° C. for 3 h in a sealed tube. Reaction mixture was cooled to ambient temperature, filtered through Celite®. Filtrate was concentrated to dryness, diluted with water (200 mL) and extracted with ethyl acetate (3×100 mL). The combined organic layers were washed with brine (40 mL), dried over anhydrous sodium sulfate and evaporated under reduced pressure. The residue was purified by column chromatography (Redisep-40 g, 20-35% EtOAc/n-Hexane) to obtain Intermediate 109A (1.25 g, 83.00%) as a white solid. $^1$H NMR (400 MHz, DMSO-$d_6$) δ ppm 4.03 (s, 3H), 5.69 (dd, J=10.54, 1.51 Hz, 1H), 6.45 (dd, J=17.07, 1.51 Hz, 1H), 6.86 (dd, J=17.32, 10.79 Hz, 1H), 7.40 (s, 1H), 8.74 (s, 1H). LCMS (Method-D): retention time 1.51 min, [M+H] 161.2.

Intermediate 109B:
6-formyl-4-methoxynicotinonitrile

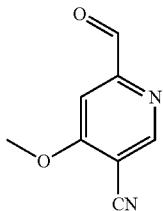

To a stirred solution of Intermediate 109A (1.20 g, 7.49 mmol) in acetone (12 mL) and H$_2$O (2 mL) was added osmium tetroxide (1.88 mL, 5.99 mmol) and sodium periodate (4.81 g, 22.48 mmol) at ambient temperature under a nitrogen atmosphere. The resulting mixture was heated at 60° C. for 1 h. The reaction mixture was cooled to ambient temperature, concentrated to dryness, diluted with water (30 mL) and extracted with ethyl acetate (2×100 mL). The combined organic layers were washed with saturated sodium carbonate solution (30 mL), brine (30 mL), dried over anhydrous sodium sulfate and evaporated under reduced pressure. The residue was purified by column chromatography (Redisep-24 g, 10-15% EtOAc/n-Hexane) to obtain Intermediate 109B (0.50 g, 41.2%) as a white solid. $^1$H NMR (400 MHz, DMSO-$d_6$) δ ppm 4.12 (s, 3H), 7.69 (s, 1H), 9.06 (s, 1H), 9.99 (s, 1H). LCMS: The compound did not ionize well.

Intermediate 109C: (E)-6-((hydroxyimino)methyl)-4-methoxynicotinonitrile

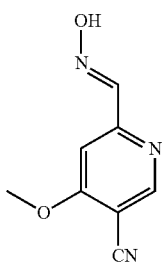

To a solution of Intermediate 109B (0.50 g, 3.08 mmol) in EtOH (10 mL) was added hydroxylamine hydrochloride (0.26 g. 3.70 mmol) and sodium acetate (0.30 g, 3.70 mmol) at ambient temperature under a nitrogen atmosphere. The resulting suspension was heated to 75° C. and for 25 minutes. The reaction mixture was cooled to ambient temperature, diluted with water (60 mL) and extracted with ethyl acetate (2×100 mL). The combined organic layers were washed with brine (30 mL), dried over anhydrous sodium sulfate and evaporated under reduced pressure. The residue was slurried with DCM (5 mL) and the suspension was collected by suction filtration and dried under vacuum to obtain Intermediate 109C (0.33 g, 60.40%) as a white solid. $^1$H NMR (400 MHz, DMSO-$d_6$) δ ppm 4.04 (s, 3H), 7.5 (s, 1H), 8.11 (s, 1H), 8.81 (s, 1H), 12.13 (s, 1H). LCMS (Method-D): retention time 0.91 min, [M+H] 178.2.

Intermediate 109D: tert-butyl ((3-(5-cyano-4-methoxypyridin-2-yl)isoxazol-5-yl)methyl)carbamate

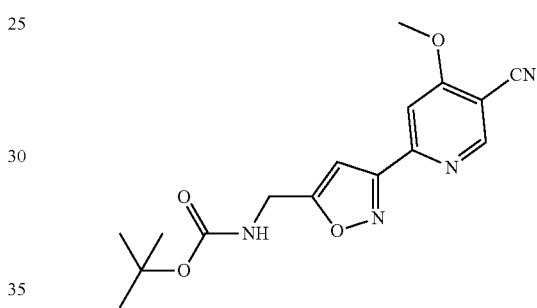

To a solution of Intermediate 109C (0.30 g 1.69 mmol) in DMF (2 mL) at 0° C. under a nitrogen atmosphere was added NCS (0.23 g, 1.69 mmol) in 3 lots over a period of 15 min and the resulting solution was heated at 50° C. for 1 h. The reaction was cooled to 0° C. and a solution of tert-butyl prop-2-yn-1-ylcarbamate (0.26 g, 1.69 mmol) in DCM (5 mL) and TEA (0.24 mL, 1.69 mmol) was added dropwise. The reaction mixture was stirred at ambient temperature for 3 h, quenched with saturated sodium bicarbonate (50 mL) and extracted with DCM (2×50 mL). The combined organic layers were washed with brine (50 mL), dried over anhydrous sodium sulfate and evaporated under reduced pressure. The residue was triturated with methanol (5 mL) and dried under vacuum obtain Intermediate 109D: 0.15 g, 26.80%) as white solid. $^1$H NMR (400 MHz, DMSO-$d_6$) δ ppm 1.42 (s, 9H), 4.11 (s, 3H), 4.36 (d, J=6.02 Hz, 2H), 6.85 (s, 1H), 7.62 (br. s., 1H), 7.78 (s, 1H), 8.94 (s, 1H). LCMS (Method-D): retention time 2.44 min, [M+H] 331.

Intermediate 109

Intermediate 109 was prepared (0.80 g, 86.000/%) as a white solid, by using a similar synthetic protocol as that of Intermediate 76 and starting from Intermediate 109D (0.12 g, 0.36 mmol). $^1$H NMR (300 MHz, DMSO-$d_6$) δ ppm 3.89 (s, 2H), 4.11 (s, 3H), 6.93 (s, 1H), 7.76-7.80 (m, 1H), 8.94 (s, 1H), (2 Exchangeable protons not observed). LCMS (Method-D): retention time 0.65 min, [M+H] 231.0.

Intermediate 110: 6-(5-(aminomethyl)isoxazol-3-yl)-4-methylnicotinonitrile

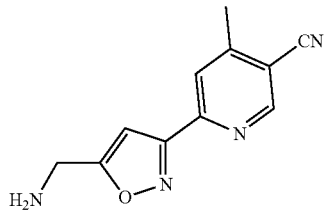 [SMILES: Cc1cc(-c2cc(CN)on2)ncc1C#N]

Intermediate 110A; 6-formyl-4-methylnicotinonitrile

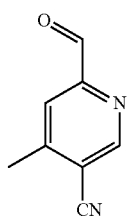

To a stirred solution of 6-bromo-4-methylnicotinonitrile (2.00 g, 10.15 mmol) in DMF (15 mL) was added sodium carbonate (1.08 g, 10.15 mmol) at ambient temperature under nitrogen atmosphere. The resulting reaction mixture was degassed with nitrogen gas for 10 minutes and added tert-butyl isocyanide (1.01 g, 12.18 mmol), 1,4-bis(diphenylphosphino)butane (0.13 g, 0.30 mmol), palladium(II) acetate (0.07 g, 0.30 mmol) and triethylsilane (1.18 g, 10.15 mmol). The reaction mixture was heated to 65° C. for 5 h and cooled to ambient temperature. The reaction mixture was filtered through Celite® and the filtrate was diluted with water (100 mL) and extracted with ethylacetate (2×100 mL). The combined organic layers were washed with brine (30 mL), dried over anhydrous sodium sulfate and evaporated under reduced pressure. To obtain Intermediate 110A (0.30 g, 20.00%). $^1$H NMR (400 MHz, DMSO-$d_6$) δ ppm 2.61 (s, 3H), 8.01 (s, 1H), 9.15 (s, 1H), 10.01 (s, 1H). LCMS (Method-D): retention time 2.45 min, [M+H] 147.0. The compound was taken directly to the subsequent step without further purification or characterization.

Intermediate 110B: (E)-6-((hydroxyimino)methyl)-4-methylnicotinonitrile

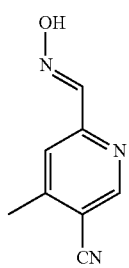

Intermediate 110B was prepared (0.08 g, 29.00%) as a white solid, by using a similar synthetic protocol as that of Intermediate 109C and starting from Intermediate 110A (0.25 g, 1.71 mmol). $^1$H NMR (400 MHz, DMSO-$d_6$) δ ppm 2.52 (s, 3H), 7.86 (s, 1H), 8.12 (s, 1H), 8.92 (s, 1H), 12.13 (s, 1H). LCMS (Method H): retention time 0.77 min, [M+H] 162.2.

Intermediate 110C: tert-butyl ((3-(5-cyano-4-methylpyridin-2-yl)isoxazol-5-yl)methyl)carbamate

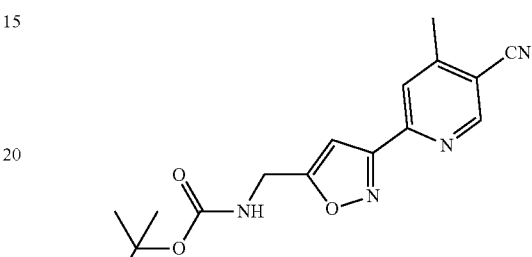

Intermediate 110C was prepared (0.05 g, 42.70%) as a white solid, by using a similar synthetic protocol as that of Intermediate 109D and starting from Intermediate 110B (0.06 g, 0.37 mmol) and tert-butyl prop-2-yn-1-ylcarbamate (0.06 g, 0.37 mmol). $^1$H NMR (400 MHz, DMSO-$d_6$) δ ppm 1.42 (s, 9H), 2.59 (s, 3H), 4.35 (d, J=5.52 Hz, 2H), 6.83 (s, 1H), 7.61 (br. s., 1H), 8.15 (s, 1H), 9.05 (s, 1H). LCMS (Method-H): retention time 2.00 min, [M+H] 315.

Intermediate 110

Intermediate 110 was prepared (0.03 g, 99.00%) as a white solid, by using a similar synthetic protocol as that of Intermediate 76 and starting from Intermediate 110C (0.05 g, 0.16 mmol). $^1$H NMR (300 MHz, DMSO-$d_6$) δ ppm 2.59 (s, 3H), 3.88 (s, 2H), 6.91 (s, 1H), 8.14 (s, 1H), 9.05 (s, 1H), (2 Exchangeable protons not observed). LCMS (Method-H): retention time 1.10 min, [M+H] 215.0.

Intermediate 111: 1-(4-(2-oxooxazolidin-3-yl)pyridin-2-yl)-1H-pyrazole-4-carbaldehyde

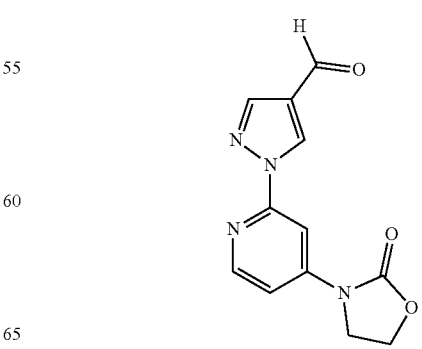

Intermediate 111A: 1-(4-aminopyridin-2-yl)-1H-pyrazole-4-carbaldehyde

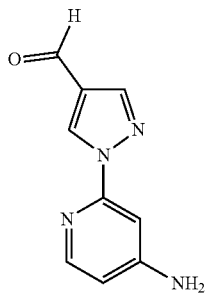 [SMILES: Nc1ccnc(-n2cc(C=O)cn2)c1]

Intermediate 111A was prepared (0.40 g, 25.50%) as a white solid, by using a similar synthetic protocol as that of Intermediate 9 and starting from 2-bromopyridin-4-amine (1.44 g, 8.33 mmol) and 1H-pyrazole-4-carbaldehyde (0.80 g, 8.33 mmol). $^1$H NMR (400 MHz, DMSO-$d_6$) δ ppm 6.49-6.53 (m, 3H), 7.12 (d, J=2.01 Hz, 1H), 7.93 (d, J=5.52 Hz, 1H), 8.21 (d, J=1.00 Hz, 1H), 9.16 (s, 1H), 9.93 (s, 1H). LCMS (Method-D): retention time 0.73 min, [M+H] 189.1.

Intermediate 111B: 2-chloroethyl (2-(4-formyl-1H-pyrazol-1-yl)pyridin-4-yl)carbamate

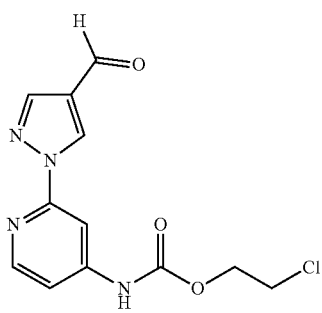 [SMILES: O=Cc1cnn(-c2cc(NC(=O)OCCCl)ccn2)c1]

To a stirred solution of Intermediate 111A (0.30 g, 1.59 mmol) in THF (10 mL) was added potassium carbonate (0.44 g, 3.19 mmol) and 2-chloroethyl chloroformate (0.27 g, 1.91 mmol) at ambient temperature under nitrogen atmosphere. The resulting reaction mixture was refluxed for 4 h. The reaction mixture was cooled to ambient temperature, quenched with aqueous solution of sodium bicarbonate (100 mL) and extracted with ethyl acetate (2×100 mL). The combined organic layers were washed with brine (50 mL), dried over anhydrous sodium sulfate and evaporated under reduced pressure. The residue was purified by silica gel column chromatography (Redisep –12 g, 20-30% EtOAc/n-hexane) to obtain Intermediate 111B (0.20 g, 42.60%) as a white solid. $^1$H NMR (400 MHz, DMSO-$d_6$) δ ppm 3.89-3.94 (m, 2H), 4.41-4.45 (m, 2H), 7.47 (dd, J=5.52, 2.01 Hz, 1H), 8.22 (d, J=2.01 Hz, 1H), 8.26-8.29 (m, 1H), 8.36 (d, J=6.02 Hz, 1H), 9.27 (s, 1H), 9.96 (s, 1H), 10.66 (s, 1H). LCMS (Method-D): retention time 1.92 min, [M+H] 295.0.

Intermediate 111

To a solution of Intermediate 111B (0.15 g, 0.51 mmol) in THF (10 mL) was added NaH (0.03 g, 1.02 mmol) under a nitrogen atmosphere and the reaction mixture stirred at ambient temperature for 4 h. The reaction was diluted with water (30 mL) and extracted with ethyl acetate (2×50 mL). The combined organic layers were washed with brine (30 mL), dried over anhydrous sodium sulfate and evaporated under reduced pressure. The residue was purified by column chromatography (Redisep-12 g, 20-30% EtOAc/n-hexane) to obtain Intermediate 111 (0.10 g, 55.50%) as a white solid. $^1$H NMR (400 MHz, DMSO-$d_6$) δ ppm 4.16 (dd, J=8.93, 6.97 Hz, 2H), 4.50-4.55 (m, 2H), 7.52 (dd, J=5.75, 2.08 Hz, 1H), 8.31 (s, 2H), 8.47 (d, J=5.87 Hz, 1H), 9.31 (s, 1H), 9.97 (s, 1H). LCMS (Method-D): retention time 1.19 min, [M+H] 259.1.

Intermediate 112: 5-(4-methyl-1H-imidazol-1-yl)pyrazine-2-carbaldehyde

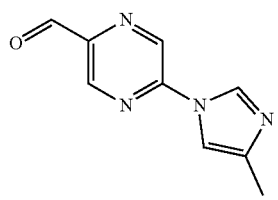

Intermediate 112A: (5-chloropyrazin-2-yl)methanol

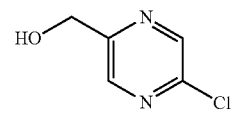

To a solution of methyl 5-chloropyrazine-2-carboxylate (8.00 g, 46.40 mmol) in THF (100 mL) was added NaBH$_4$ (3.51 g, 93.00 mmol) under nitrogen atmosphere and the reaction mixture was stirred at 0° C. for 5 h. The reaction was quenched with water (200 mL) and extracted with ethyl acetate (3×200 mL). The combined organic layers were dried over anhydrous sodium sulfate and evaporated under reduced pressure. The residue was purified by silica gel column chromatography (Redisep-40 g, 30-40% EtOAc/n-hexane) to obtain Intermediate 112A (2.00 g, 29.80%) as a yellow solid. $^1$H NMR (300 MHz, DMSO-$d_6$) δ ppm 4.64 (d, J=5.67 Hz, 2H), 5.68 (t, J=5.85 Hz, 1H), 8.53 (s, 1H), 8.72 (d, J=1.13 Hz, 1H). LCMS (Method-H): retention time 0.476 min, [M+H] 145.2.

Intermediate 112B: 5-chloropyrazine-2-carbaldehyde

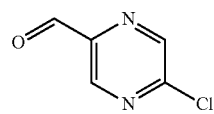

To a solution of Intermediate 112A (2.00 g, 13.84 mmol) in CHCl$_3$ (20 mL) was added active manganese dioxide (4.81 g, 55.3 mmol) and the resulting suspension was refluxed for 2 h. The reaction mixture was cooled to ambient temperature, filtered through Celite® and washed with CHCl$_3$ (200 mL). The combined filtrates were washed with brine (200 mL), dried over anhydrous sodium sulfate and evaporated under reduced pressure. The residue was purified by silica gel column chromatography (Redisep-24 g, 20-30% EtOAc/n-hexane) to obtain Intermediate 112B (1.00 g, 50.70%) as a white solid. $^1$H NMR (400 MHz, DMSO-d$_6$) δ ppm 8.98 (d, J=1.51 Hz, 1H), 9.04 (d, J=1.51 Hz, 1H), 10.07 (s, 1H). LCMS: The compound did not ionize well.

Intermediate 112

Intermediate 112 was prepared (0.40 g. crude), by using a similar synthetic protocol as that of Intermediate 9 and starting from Intermediate 112B (0.25 g, 1.75 mmol) and 4-methyl-1H-imidazole (0.21 g, 2.63 mmol). LCMS (Method-L): retention time 0.4 min, [M+H] 189.0. The compound was taken directly to the subsequent step without further purification or characterization.

Intermediate 113: 5-(1-(2-bromoethyl)-1H-pyrazol-4-yl)-4-methylisobenzofuran-1(3H)-one

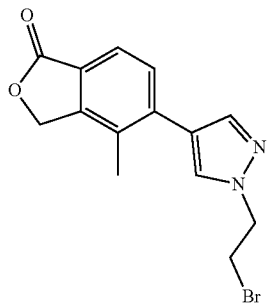 [SMILES: Cc1c(-c2cnn(CCBr)c2)ccc2c1COC2=O]

Intermediate 113A: 4-methyl-5-(1H-pyrazol-4-yl)isobenzofuran-1(3H)-one

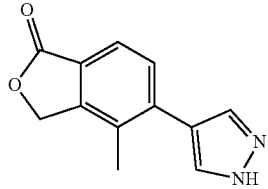 [SMILES: Cc1c(-c2cn[nH]c2)ccc2c1COC2=O]

Intermediate 113A was prepared (0.23 g, 48.80%) as a white solid, by using a similar synthetic protocol as that of Intermediate 10A and starting from 5-bromo-4-methyl-isobenzofuran-1(3H)-one (0.50 g, 2.20 mmol) and tert-butyl 4-(4,4,5,5-tetramethyl-1,3,2-dioxaborolan-2-yl)-1H-pyrazole-1-carboxylate (0.78 g. 2.64 mmol). $^1$H NMR (300 MHz, DMSO-d$_6$) δ ppm 2.27 (s, 3H), 5.43 (s, 2H), 7.63-7.69 (m, 2H), 7.87 (s, 1H), 8.16 (s, 1H), 13.18 (s, 1H). LCMS (Method-H): retention time 0.96 min, [M+H] 215.0.

Intermediate 113

To a solution of 4-methyl-5-(1H-pyrazol-4-yl)isobenzofuran-1(3H)-one (0.20 g, 0.93 mmol) in acetone (20 mL) was added Cs$_2$CO$_3$ (0.76 g, 2.33 mmol) and 1,2-dibromoethane (0.81 mL, 9.34 mmol) and the reaction mixture was refluxed for 6 h. The reaction was cooled to ambient temperature, concentrated to dryness, diluted with water (30 mL) and extracted with ethyl acetate (2×30 mL). The combined organic layers were washed with brine (20 mL), dried over anhydrous sodium sulfate and evaporated under reduced pressure. The residue was purified by column chromatography (Redisep-12 g, 20-30% EtOAc/n-Hexane) to obtain Intermediate 113

(0.15 g, 50.00%) as a white solid. $^1$H NMR (400 MHz, DMSO-d$_6$) δ ppm 2.35 (s, 3H), 3.92 (t, J=6.02 Hz, 2H), 4.59 (t, J=6.02 Hz, 2H), 5.43 (s, 2H), 7.62-7.70 (m, 2H), 7.90 (s, 1H), 8.24 (s, 1H). LCMS (Method-H): retention time 1.63 min, [M+H] 321.0.

Intermediate 114-I: (R)—N-(2-amino-1-(4-methyl-1-oxo-1,3-dihydroisobenzofuran-5-yl)ethyl)cyclopropanecarboxamide

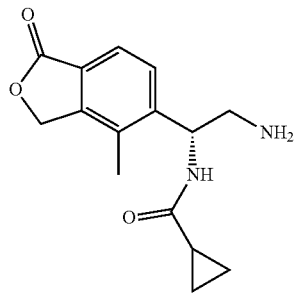 [SMILES: Cc1c([C@H](CN)NC(=O)C2CC2)ccc2c1COC2=O]

Intermediate 114A-I: (R)-tert-butyl (2-(cyclopropanecarboxamido)-2-(4-methyl-1-oxo-1,3-dihydroisobenzofuran-5-yl)ethyl)carbamate

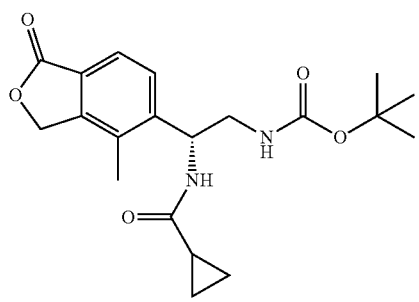 [SMILES: Cc1c([C@H](CNC(=O)OC(C)(C)C)NC(=O)C2CC2)ccc2c1COC2=O]

Intermediate 114A-I was prepared (0.12 g, 49.10%) as pale yellow oil, by using a similar synthetic protocol as that of Intermediate 50A-I and starting from Intermediate 49-I (0.50 g, 2.20 mmol). $^1$H NMR (400 MHz, DMSO-d$_6$) δ ppm 0.54-0.71 (m, 4H), 1.33 (s, 9H), 1.55-1.62 (m, 1H), 2.31 (s, 3H), 3.19 (dt, J=16.56, 6.53 Hz, 2H), 5.24-5.31 (m, 1H), 5.38 (s, 2H), 6.96 (t, J=5.77 Hz, 1H), 7.57 (d, J=8.03 Hz, 1H), 7.67 (d, J=8.03 Hz, 1H), 8.58 (d, J=8.03 Hz, 1H). LCMS (Method-D): retention time 1.85 min, [M+H] 375.0.

Intermediate 114-I

Intermediate 114-I was prepared (0.09 g, crude), by using a similar synthetic protocol as that of Intermediate 50-I and starting from Intermediate 114A-I (0.10 g, 0.26 mmol). LCMS (Method-L): retention time 0.56 min, [M+H] 276.0. The compound was taken directly to the subsequent step without further purification or characterization.

Intermediate 115:1-(3, 4-dimethyl-2-oxo-2, 3-dihydrobenzo[d]oxazol-5-yl)-1H-imidazole-4-carbaldehyde

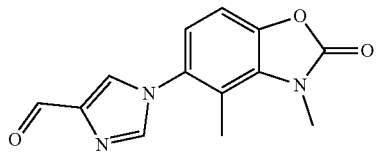 [SMILES: Cc1c(-n2cnc(C=O)c2)ccc2oc(=O)n(C)c12]

Intermediate 115A: 2-amino-6-bromopyridin-3-ol

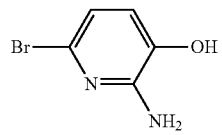

To a stirred solution of 6-bromo-2-nitropyridin-3-ol (6 g, 27.40 mmol) in EtOH (100 mL) was added iron (11.00 g, 197.00 mmol), calcium chloride (3.04 g, 27.4 mmol) and the reaction mixture for was heated at 85° C. for 16 h. The reaction mixture was cooled to ambient temperature, filtered through celite and the filtrate was evaporated under reduced pressure. The residue was purified by column chromatography (Redisep-80 g, 10-20% MeOH/DCM) to obtain Intermediate 115A (3.00 g, 57.90%) as a yellow solid. $^1$H NMR (400 MHz, DMSO-d$_6$) δ ppm 6.50 (d, J=7.78 Hz, 1H), 6.75 (d, J=7.78 Hz, 1H), 9.70 (br. s, 1H). (2 Exchangeable proton not observed). LCMS (Method-O): retention time 0.64 min, [M+2H] 191.3.

Intermediate 115B: 5-bromooxazolo [4,5-b]pyridin-2(3H)-one

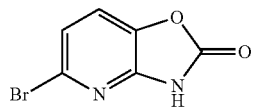

To a stirred solution of Intermediate 115A (1.00 g, 5.29 mmol) in DCM (20 mL) was added dipyridin-2-yl carbonate (1.14 g, 5.29 mmol), TEA (1.48 mL, 10.58 mmol) and the reaction mixture was stirred at ambient temperature for 16 h. The reaction mixture was concentrated to dryness and the residue was purified by column chromatography (Redisep-24 g, 0-10% MeOH/DCM) to obtain Intermediate 115B (0.50 g, 39.10%) as a yellow solid. $^1$H NMR (400 MHz, DMSO-d$_6$) δ ppm 7.32 (d, J=8.22 Hz, 1H), 7.61 (d, J=8.16 Hz, 1H), 12.67 (br.s, 1H). LCMS (Method-H): retention time 0.45 min, [M+2H] 217.0.

Intermediate 115C: 5-bromo-3,4-dimethylbenzo[d]oxazol-2(3H)-one

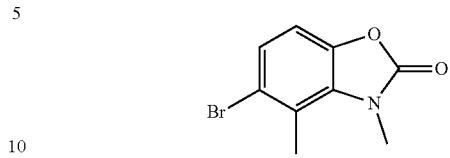

To a stirred solution of Intermediate 115B (3.50 g, 15.35 mmol) in DMSO (40 mL) was added K$_2$CO$_3$ (4.24 g, 30.70 mmol), MeI (1.92 mL, 30.7 mmol) and the reaction mixture was stirred at ambient temperature for 3 h. The reaction mixture was diluted with ice cold water (50 mL) and the solid precipitate was isolated by suction filtration to obtain Intermediate 115C (3.20 g, 63.70%) as a brown solid. $^1$H NMR (300 MHz, DMSO-d$_6$) δ ppm 2.59 (s, 3H), 3.56 (s, 3H), 7.15 (d, J=8.50 Hz, 1H), 7.38 (d, J=8.55 Hz, 1H). LCMS (Method-D): retention time 2.33 min, [M+H] 242.0.

Intermediate 115

To a stirred solution of 1H-imidazole-4-carbaldehyde (0.25 g, 2.60 mmol) in DMSO (1 mL) was added Intermediate 115 (0.69 g, 2.86 mmol), N,N-dimethylglycine (0.14 g, 1.30 mmol) and K$_2$CO$_3$ (0.90 g, 6.50 mmol) followed by copper (1) iodide (0.05, 0.26 mmol). Then the reaction mixture was heated at 110° C. for 16 h in a sealed tube. The reaction mixture was cooled to ambient temperature, concentrated to dryness, diluted with water (40 mL) and extracted with DCM (2×100 mL). The combined organic layers were washed with brine (50 mL), dried over anhydrous sodium sulfate and evaporated under reduced pressure to obtain Intermediate 115 (0.100 g, 14.94%) as a brown solid. LCMS (Method-O): retention time 0.71 min, [M+H] 258.4. The compound was taken directly to the subsequent step without further purification or characterization.

Intermediate 115: (R)-5-(2-amino-1-hydroxyethyl)-4-methoxyisobenzofuran-1(3H)-one

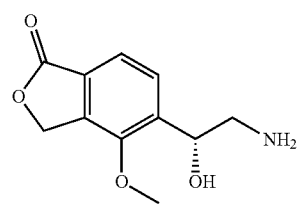 [SMILES: COc1c([C@@H](O)CN)ccc2c1COC2=O]

Intermediate 115A: 5-bromo-4-methoxyisobenzofuran-1(3H)-one

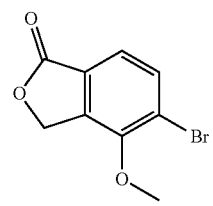

To a stirred solution of 5-amino-4-methoxyisobenzofuran-1(3H)-one (4.00 g, 22.32 mmol) in acetonitrile (100 mL) was added p-TsOH (5.10 g, 26.80 mmol), isoamyl nitrite (3.61 mL, 26.8 mmol), copper (II) bromide (0.05 g, 0.22 mmol) and tetra-n-butylammonium bromide (14.39 g, 44.6 mmol) and the reaction mixture was stirred at ambient temperature for 1 h. The reaction mixture was concentrated to dryness, diluted with water (200 mL) and extracted with ethyl acetate (3×100 mL). The combined organic layers were washed with brine (100 mL), dried over anhydrous sodium sulfate and evaporated under reduced pressure. The residue was purified by column chromatography (Redisep-40 g, 40-50% EtOAc/n-Hexane) to obtain Intermediate 115A (3.50 g. 63.90%) as yellow solid. $^1$H NMR (400 MHz, DMSO-$d_6$) δ ppm 4.01-4.04 (s, 3H) 5.74 (s, 2H) 7.42 (d, J=8.03 Hz, 1H) 7.81 (dt, J=7.97, 0.56 Hz, 1H). LCMS (Method-D): retention time 1.32 min, [M+H] 262.0.

Intermediate 115B:
4-methoxy-5-vinylisobenzofuran-1(3H)-one

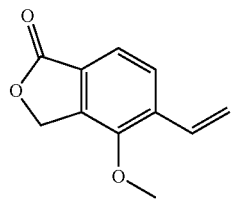

Intermediate 115B was prepared (3.00 g, 88.00%) as a yellow solid, by using a similar synthetic protocol as that of Intermediate 109A and starting from Intermediate 115A (4.00 g, 16.46 mmol). 1H NMR (400 MHz, DMSO-$d_6$) δ ppm 3.95 (s, 3H), 5.48 (dd, J=11.23, 1.13 Hz, 1H), 5.68 (s, 2H), 5.99 (dd, J=17.76, 1.13 Hz, 1H), 7.03 (dd, J=17.76, 11.23 Hz, 1H), 7.48 (d, J=7.84 Hz, 1H), 7.77 (d, J=7.84 Hz, 1H). LCMS (Method-O): retention time 1.08 min, [M+H] 191.2.

Intermediate 115C and 115D: 4-methoxy-5-(oxiran-2-yl)isobenzofuran-1(3H)-one)

Enantiomer-I (115C)

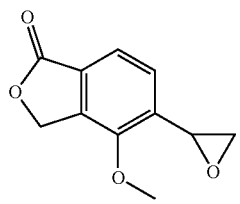

Enantiomer-II (115D)

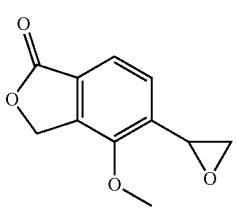

To a stirred solution of Intermediate 115B (2.00 g, 10.52 mmol) in DCM (15 mL) was added m-CPBA (3.63 g, 21.03 mmol) at 0° C. and the reaction mixture was stirred for 16 h. The reaction mixture was diluted with water (30 mL), basified with 10% NaHCO$_3$(20 mL) and extracted with DCM (2×100 mL). The combined organic layers were washed with brine (50 mL), dried over anhydrous sodium sulfate and evaporated under reduced pressure. The residue was purified by chiral SFC [Column: Lux Cellulose 4 (250×4.6 mm) 5.0 micron; 0.2% DEA in IPA, Flow: 1.0 mL/min, Temperature: 25° C., UV: 220 nm] to obtain Intermediate 115C (0.61 g, 20.48%) as yellow solid, fast eluting (retention time 5.23 min). $^1$H NMR (300 MHz, DMSO-$d_6$) δ ppm 2.75 (dd, J=5.59, 2.57 Hz, 1H), 3.20 (dd, J=5.50, 4.32 Hz, 1H), 3.31 (s, 1H), 4.02 (s, 3H), 5.73 (s, 2H), 7.25 (d, J=7.74 Hz, 1H), 7.48 (d, J=7.79 Hz, 1H). LCMS (Method-D): retention time 1.50 min, [M+H] 207.2 and Intermediate 115D (0.60 g, 19.37%) as a yellow solid, slow eluting (retention time 6.08 min). $^1$H NMR (300 MHz, DMSO-$d_6$) δ ppm 2.75 (dd, J=5.59, 2.57 Hz, 1H), 3.20 (dd, J=5.50, 4.32 Hz, 1H), 3.31 (s, 1H), 4.02 (s, 3H), 5.73 (s, 2H), 7.25 (d, J=7.74 Hz, 1H), 7.49 (d, J=7.79 Hz, 1H). LCMS (Method-D): retention time 1.44 min, [M+H] 207.2

Intermediate 115

Intermediate 115 was prepared (0.20 g, 68.40%) as a brown solid, by using a similar synthetic protocol as that of Intermediate 7-I and starting from Intermediate 115C (0.20 g, 0.97 mmol).
$^1$H NMR (300 MHz, DMSO-$d_6$) δ ppm 3.17 (m, 2H), 3.95 (s, 3H), 5.42 (m, 1H), 5.69 (s, 2H), 7.47-7.52 (m, 1H), 7.63 (d, J=7.89 Hz, 1H), (3 Exchangeable proton not observed). LCMS (Method-O): retention time 0.45 min, [M+H] 224.3.

Intermediate 116:
1-(5-formylpyridin-2-yl)-1H-pyrazole-4-carboxamide

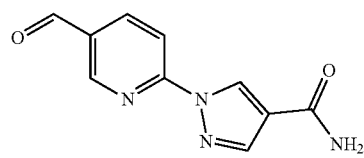 [SMILES: NC(=O)c1cnn(-c2ccc(C=O)cn2)c1]

Intermediate 116A:2-chloro-5-(1,3-dioxolan-2-yl)
pyridine (Intermediate-I)

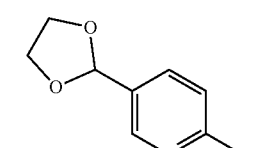

To a stirred solution of 6-chloronicotinaldehyde (5.00 g, 35.30 mmol) in toluene (100 mL) was added ethane-1,2-diol (2.63 g, 42.4 mmol), p-TsOH (0.67 g, 3.53 mmol) and the reaction mixture was refluxed under Dean-Stark conditions for 6 h. The reaction mixture was cooled to ambient temperature and washed with saturated NaHCO$_3$(50 mL) and brine (50 mL). The separated organic layer was dried over anhydrous sodium sulfate and evaporated under reduced pressure to obtain Intermediate 116A (5.50 g, 77.00%) as a yellow liquid. $^1$H NMR (400 MHz, DMSO-d$_6$) δ ppm 3.95-4.00 (m, 4H), 5.85 (s, 1H), 7.56 (m, J=8.25, 0.43 Hz, 1H), 7.91 (dd, J=8.25, 2.45 Hz, 1H), 8.48 (dd, J=1.83, 0.49 Hz, 1H). LCMS (Method-O): retention time 0.85 min, [M+H] 188.3.

Intermediate 116B: ethyl 1-(5-(1,3-dioxolan-2-yl)pyridin-2-yl)-1H-pyrazole-4-carboxylate

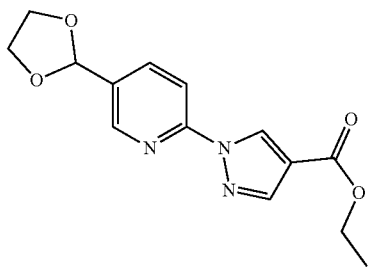 [SMILES: CCOC(=O)c1cnn(-c2ccc(C3OCCO3)cn2)c1]

Intermediate 116B was prepared (0.80 g, 27.40%) as an off-white solid, by using a similar synthetic protocol as that of Intermediate 18 and starting from Intermediate 116A (1.50 g, 8.08 mmol) and 1H-pyrazole-4-carboxylate (1.25 g, 8.89 mmol). $^1$H NMR (400 MHz, DMSO-d$_6$) δ ppm 1.31 (t, J=7.09 Hz, 3H), 3.98-4.02 (m, 2H), 4.08-4.13 (m, 2H), 4.28 (q, J=7.09 Hz, 2H), 5.90 (s, 1H), 8.01 (dd, J=8.44, 0.60 Hz, 1H), 8.08-8.11 (m, 1H), 8.23 (d, J=0.69 Hz, 1H), 8.58 (d, J=2.13 Hz, 1H), 9.00 (d, J=0.69 Hz, 1H). LCMS (Method-J): retention time 2.39 min, [M+H] 290.1.

Intermediate 116C: 1-(5-(1,3-dioxolan-2-yl)pyridin-2-yl)-1H-pyrazole-4-carboxamide

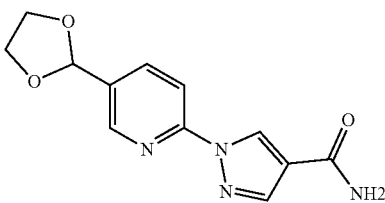 [SMILES: NC(=O)c1cnn(-c2ccc(C3OCCO3)cn2)c1]

To a stirred solution of Intermediate 116B (0.35 g, 1.21 mmol) in EtOH (10 mL) was added ammonium hydroxide (10 mL, 257 mmol) and the reaction mixture was heated at 60° C. for 40 h. The reaction mixture was cooled to ambient temperature, concentrated to dryness, diluted with water (20 mL) and extracted with 10% MeOH in DCM (3×30 mL). The combined organic layers were washed with brine (20 mL), dried over anhydrous sodium sulfate and evaporated under reduced pressure to obtain Intermediate 116C (0.20 g, 55.30%) as a yellow solid. $^1$H NMR (400 MHz, DMSO-d$_6$) δ ppm 3.98-4.03 (m, 2H), 4.09-4.13 (m, 2H), 5.90 (s, 1H), 7.24 (br. s, 1H), 7.84 (br. s, 1H), 7.98-8.01 (m, 1H), 8.09 (d, J=2.14 Hz, 1H), 8.15 (d, J=0.55 Hz, 1H), 8.57 (d, J=2.02 Hz, 1H), 9.15 (d, J=0.61 Hz, 1H). LCMS (Method-J): retention time 0.60 min, [M+H] 261.1.

Intermediate 116

To a stirred solution of Intermediate 116C (0.20 g, 0.77 mmol) in toluene (3 mL) and water (0.5 mL) was added p-TsOH (0.22 g, 1.15 mmol) and the reaction mixture was heated at 70° C. for 1 h. The reaction mixture was concentrated to dryness, diluted with water (30 mL) and the solid precipitate was isolated by suction filtration and dried under vacuum to obtain Intermediate 116 (0.120 g, 62.80%) as an off-white solid. $^1$H NMR (400 MHz, DMSO-d$_6$) δ ppm 7.30 (br. s., 1H), 7.88 (br. s., 1H), 8.13 (d, J=8.53 Hz, 1H), 8.22 (d, J=0.69 Hz, 1H), 8.46 (dd, J=8.53, 2.20 Hz, 1H), 9.05 (dd, J=2.13, 0.69 Hz, 1H), 9.24 (d, J=0.69 Hz, 1H) 10.12 (s, 1H). LCMS (Method-J): retention time 0.60 min, [M+H] 216.1.

Intermediate 117: 6-(4-formyl-1H-pyrazol-1-yl)-4-isopropoxy nicotinonitrile

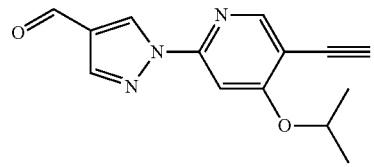

Intermediate 117 was prepared (0.45 g, 54.00%) as a pale yellow solid, by using a similar synthetic protocol as that of Intermediate 18 and starting from 6-chloro-4-isopropoxynicotinonitrile (0.61 g, 3.12 mmol) and 1H-pyrazole-4-carbaldehyde (0.30 g, 3.12 mmol). $^1$H NMR (400 MHz, DMSO-d$_6$) δ ppm 1.36 (d, J=6.05 Hz, 6H), 5.09-5.16 (m, 1H), 7.69 (s, 1H), 8.39 (s, 1H), 8.84 (s, 1H), 9.37 (d, J=0.55 Hz, 1H), 9.99 (s, 1H). LCMS (Method-J): retention time 2.36 min, [M+H] 257.2.

Intermediate 118: 2-(2-cyclopropyl-4-methyl-1H-imidazol-1-yl)pyrimidine-5-carbaldehyde

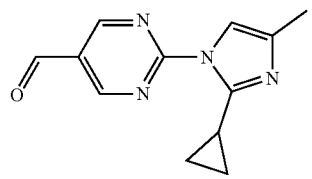 [SMILES: Cc1cn(-c2ncc(C=O)cn2)c(C2CC2)n1]

Intermediate 118 was prepared (0.25 g, 26.00%) as an off-white solid, by using a similar synthetic protocol as that of Intermediate 18 and starting from 2-chloropyrimidine-5-carbaldehyde (0.30 g, 2.11 mmol) and 2-cyclopropyl-4-methyl-1H-imidazole (0.28 g, 2.32 mmol). $^1$H NMR (400 MHz, DMSO-d$_6$) δ ppm 0.83-0.86 (m, 2H), 0.96-0.99 (m, 2H), 2.05 (m, 1H), 2.17-2.21 (s, 3H), 7.60 (d, J=1.19 Hz, 1H), 9.28 (s, 2H), 10.11 (s, 1H). LCMS (Method-O): retention time 0.99 min, [M+H] 229.1.

Intermediate 119: 1-(3-(2-oxooxazolidin-3-yl)phenyl)-1H-pyrazole-4-carbaldehyde

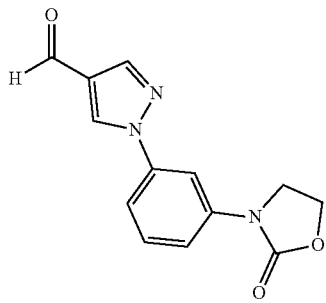 [SMILES: O=Cc1cnn(-c2cccc(N3CCOC3=O)c2)c1]

Intermediate 119 was prepared (0.50 g, 31.45) as a pale yellow solid, by using a similar synthetic protocol as that of Intermediate 9 and starting from Intermediate 119B (1.50 g, 6.20 mmol) and 1H-pyrazole-4-carbaldehyde (0.83 g, 8.68 mmol). LCMS (Method-D): retention time 0.80 min, [M+H] 258.4. The compound was taken directly to the subsequent step without further purification or characterization.

Intermediate 119A: 2-chloroethyl (3-bromophenyl)carbamate

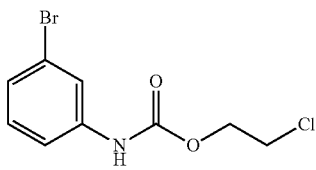 [SMILES: O=C(Nc1cccc(Br)c1)OCCCl]

Intermediate 119A was prepared (3.30 g, 97.00%) as a white solid, by using a similar synthetic protocol as that of Intermediate 111B and starting from 3-bromoaniline (1.26 mL, 11.63) and 2-chloroethyl carbonochloridate (1.45 mL, 13.95 mmol). $^1$H NMR (400 MHz, DMSO-d$_6$) δ ppm 3.86-3.89 (m, 2H), 4.33-4.38 (m, 2H), 7.17-7.21 (m, 1H), 7.22-7.28 (m, 1H), 7.41-7.46 (m, 1H), 7.75 (t, 0.1=1.76 Hz, 1H), 10.03 (s, 1H). LCMS (Method-O): retention time 1.29 min, [M+H] 280.0.

Intermediate 119B: 3-(3-bromophenyl)oxazolidin-2-one

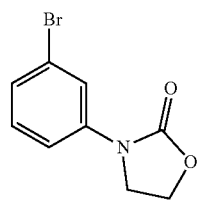 [SMILES: O=C1OCCN1c1cccc(Br)c1]

Intermediate 119B was prepared (1.80 g, 97.00%) as a white solid, by using a similar synthetic protocol as that of Intermediate 111 and starting from Intermediate 119A (2.00 g, 6.82 mmol). $^1$H NMR (400 MHz, DMSO-d$_6$) δ ppm 4.06 (dd, J=8.78, 7.28 Hz, 2H), 4.42-4.47 (m, 2H), 7.30-7.38 (m, 2H), 7.49-7.53 (m, 1H), 7.86 (t, J=1.76 Hz, 1H). LCMS (Method-O): retention time 1.06 min, [M+2H] 244.3.

Intermediate 120: 6-(4-formyl-3-methyl-2-oxo-2,3-dihydro-1H-imidazol-1-yl)-4-methylnicotinonitrile

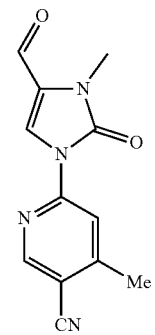 [SMILES: Cc1cc(-n2cc(C=O)n(C)c2=O)ncc1C#N]

Intermediate 120A: methyl 1-(5-cyano-4-methylpyridin-2-yl)-2-oxo-2,3-dihydro-1H-imidazole-4-carboxylate

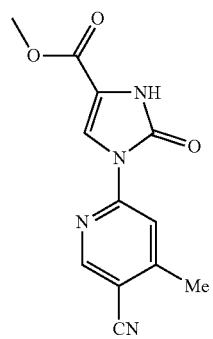 [SMILES: COC(=O)c1cn(-c2cc(C)c(C#N)cn2)c(=O)[nH]1]

Intermediate 120A was prepared (4.30 g, 79.00%) as a white solid, by using a similar synthetic protocol as that of Intermediate 47C and starting from 6-bromo-4-methylnicotinonitrile (4.16 g, 21.11 mmol) and methyl 2-oxo-2,3-dihydro-1H-imidazole-4-carboxylate (3.00 g, 21.11 mmol). $^1$H NMR (400 MHz, DMSO-d$_6$) δ ppm 2.54 (s, 3H), 3.79 (s, 3H), 7.89 (s, 1H), 8.39 (s, 1H), 8.82 (s, 1H), 11.52 (s, 1H). LCMS (Method-O): retention time 0.88 min, [M+1] 259.1.

Intermediate 120B: methyl 1-(5-cyano-4-methyl-pyridin-2-yl)-3-methyl-2-oxo-2,3-dihydro-1H-imidazole-4-carboxylate

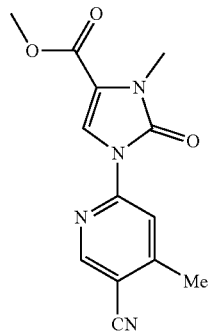 [SMILES: COC(=O)c1cn(-c2cc(C)c(C#N)cn2)c(=O)n1C]

To a stirred solution of Intermediate 120A (1.10 g, 4.26 mmol) in DMF (15 mL) was added $Cs_2CO_3$ (3.47 g, 10.65 mmol) and iodomethane (2.65 mL, 42.6 mmol) and the reaction mixture was stirred at ambient temperature for 12 h. DMF was evaporated to under reduced pressure and mixture was diluted with water (50 mL). The solid precipitate was isolated by suction filtration, washed with water (50 mL) then diethyl ether (50 mL) and dried under vacuum to obtain Intermediate 120B (1.15 g, 99.00%) as a burgundy solid. $^1$H NMR (400 MHz, DMSO-$d_6$) δ ppm 2.58 (s, 3H), 3.43 (s, 3H), 3.81 (s, 3H), 8.01 (s, 1H), 8.42 (s, 1H), 8.86 (s, 1H). LCMS (Method-O): retention time 1.07 min, [M+1] 273.5.

Intermediate 120C: 6-(4-(hydroxymethyl)-3-methyl-2-oxo-2,3-dihydro-1H-imidazol-1-yl)-4-methylnicotinonitrile

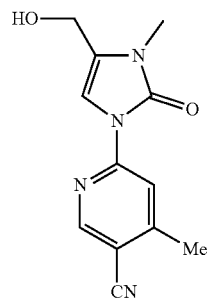 [SMILES: Cc1cc(-n2cc(CO)n(C)c2=O)ncc1C#N]

To a stirred solution of Intermediate 120B (1.30 g, 4.77 mmol) in THF (15 mL) was added $NaBH_4$ (0.90 g, 23.87 mmol) followed by MeOH (5 mL) dropwise and the reaction mixture was stirred at ambient temperature for 8 h. The reaction mixture was concentrated to dryness, diluted with water (50 mL) and extracted with ethyl acetate (2×300 mL). The combined organic layers were washed with brine (50 mL), dried over anhydrous sodium sulfate and evaporated under reduced pressure. The residue was triturated with diethyl ether (50 mL) and dried under vacuum to obtain Intermediate 120C (0.80 g, 69.000/%) as a burgundy solid. $^1$H NMR (400 MHz, DMSO-$d_6$) δ ppm 2.25 (s, 3H), 3.24 (s, 3H), 4.36 (br.s, 2H), 5.25 (br.s, 1H), 7.28 (s, 1H), 8.45 (s, 1H), 8.79 (s, 1H). LCMS (Method-O): retention time 0.69 min, [M+1]245.4.

Intermediate 120

Intermediate 120 was prepared (0.070 g, crude) as a white solid, by using a similar synthetic protocol as that of Intermediate 26 and starting from Intermediate 120C (1.50 g, 6.20 mmol). LCMS (Method-O): retention time 0.92 min, [M+1] 243.5. The compound was taken directly to the subsequent step without further purification or characterization.

Intermediate 121: 6-(4-methyl-1H-1,2,3-triazol-1-yl)nicotinaldehyde

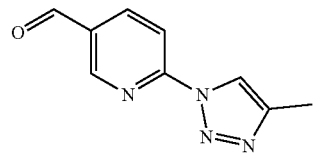

Intermediate 121A: 6-(4-methyl-1H-1,2,3-triazol-1-yl)pyridin-3-yl)methanol

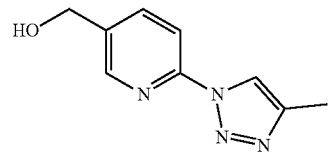

To a solution of methyl 6-(4methyl-1H-1,2,3-triazol-1-yl)nicotinate (0.70 g, 3.21 mmol) in THF (20 mL) at 0° C. was added LAH (2.67 mL, 6.42 mmol) in THF and the reaction mixture was stirred at ambient temperature for 1 h. The reaction was cooled to 0° C. and 10% NaOH solution (2 mL) was added. The mixture was stirred for 10 minutes. The reaction mixture was filtered through Celite® and washed with ethyl acetate (200 mL). The combined organic layers were dried over sodium sulfate and concentrated under reduced pressure to obtain Intermediate 121A (0.35 g, 56.50%) as an off white solid. $^1$H NMR (400 MHz, DMSO-$d_6$) δ ppm 2.32-2.39 (m, 3H), 4.62 (s, 2H), 5.47 (br. s., 1H), 7.95-8.11 (m, 2H), 8.51 (dd, J=2.08, 0.86 Hz, 1H), 8.58 (d, J=0.73 Hz, 1H). LCMS (Method-D): retention time: 0.66 min, [M+1] 191.2.

Intermediate 121

Intermediate 121: Intermediate 121 was prepared (0.27 g, 51.80%) as a brown solid, by using a similar synthetic protocol as that of Intermediate 88B and starting from Intermediate 121A (0.35 g, 1.84 mmol). $^1$H NMR (400 MHz, DMSO-$d_6$) δ ppm 2.31-2.40 (m, 3H), 8.30 (d, J=8.53 Hz, 1H), 8.44-8.54 (m, 1H), 8.70 (s, 1H), 9.10 (d, J=1.51 Hz, 1H), 10.15 (s, 1H). LCMS (Method-D): retention time 1.12 min, [M+1] 189.2.

Intermediate 122: (R)-2-((tert-butoxycarbonyl)((1-(3-methyl-2-oxo-2,3-dihydrobenzo[d]oxazol-5-yl)-1H-pyrazol-4-yl)methyl)amino)-1-(4-methyl-1-oxo-1,3-dihydroisobenzofuran-5-yl)ethyl (tert-butoxycarbonyl)-D-valinate

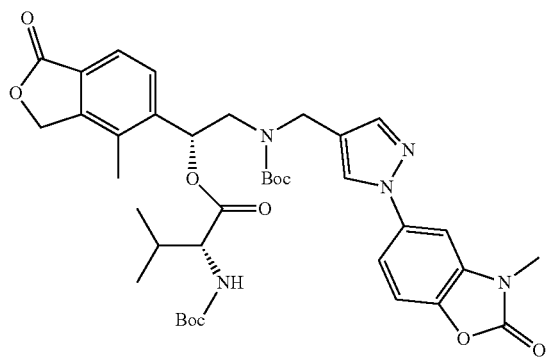 [SMILES: Cc1c([C@H](CN(Cc2cnn(-c3ccc4oc(=O)n(C)c4c3)c2)C(=O)OC(C)(C)C)OC(=O)[C@H](NC(=O)OC(C)(C)C)C(C)C)ccc2c1COC2=O]

Intermediate 122A: (R)-tert-butyl (2-hydroxy-2-(4-methyl-1-oxo-1,3-dihydroisobenzofuran-5-yl)ethyl)((1-(3-methyl-2-oxo-2,3-dihydrobenzo[d]oxazol-5-yl)-1H-pyrazol-4-yl)methyl)carbamate

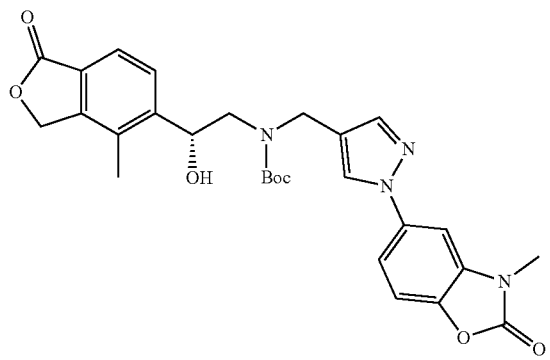 [SMILES: Cc1c([C@@H](O)CN(Cc2cnn(-c3ccc4oc(=O)n(C)c4c3)c2)C(=O)OC(C)(C)C)ccc2c1COC2=O]

Intermediate 122A was prepared (0.40 g, 48.70%) as a yellow solid, by using a similar synthetic protocol as that of Intermediate 9 and starting from Intermediate 72-I (0.50 g, 1.29 mmol) and Intermediate 3 (0.29 g, 1.29 mmol). $^1$H NMR (300 MHz, DMSO-$d_6$) δ ppm 1.41 (br. s., 9H) 2.27 (br. s., 3H) 3.28-3.38 (m, 2H) 3.38 (s, 3H) 4.28-4.48 (m, 2H) 5.13-5.23 (m, 1H) 5.35 (d, J=4.15 Hz, 2H) 5.73 (br. s., 1H) 7.38-7.43 (m, 1H) 7.50-7.56 (m, 1H) 7.61 (s, 1H) 7.69 (t, J=8.69 Hz, 3H) 8.32 (br. s., 1H). LCMS (Method-O): retention time 1.13 min, [M+H] 535.5.

Intermediate 122

To a solution of Intermediate 122A (0.10 g, 0.19 mmol) in DCM (10 mL) was added (R)-2-((tert-butoxycarbonyl) amino)-3-methylbutanoic acid (0.06 g, 0.28 mmol) and DCC (0.08 g, 0.37 mmol) followed by DMAP (0.002 g, 0.18 μmol) under a nitrogen atmosphere and the reaction mixture was stirred at ambient temperature for 16 h. The reaction mixture was filtered and the organic layer was diluted with water (20 mL), basified by 10% NaHCO$_3$ (20 mL), and extracted with DCM (3×30 mL). The combined organic layers were washed with brine (20 mL), dried over anhydrous sodium sulfate and evaporated under reduced pressure. The residue was triturated with diethyl ether (30 mL) and dried under vacuum to obtain Intermediate 122 (0.15 g, crude) as white solid. $^1$H NMR (400 MHz, DMSO-$d_6$) δ ppm 0.78-0.90 (m, 6H), 1.37-1.44 (m, 18H), 2.39 (s, 3H), 3.39 (s, 3H), 3.49-3.58 (m, 3H), 3.93-3.99 (m, 1H), 4.25 (d, J=15.06 Hz, 1H), 4.40-4.47 (m, 1H), 5.56 (d, J=8.03 Hz, 2H), 6.14-6.25 (m, 1H), 7.32 (d, J=8.53 Hz, 1H), 7.42 (d, J=8.53 Hz, 1H), 7.50-7.54 (m, 1H), 7.66 (t, J=8.28 Hz, 4H), 8.32 (br. s., 1H). LCMS (Method-O): retention time 1.53 min, [M+H] 734.6.

Intermediate 123: 3-ethyl-1-(5-formylpyridin-2-yl)-1H-pyrazole-4-carbonitrile

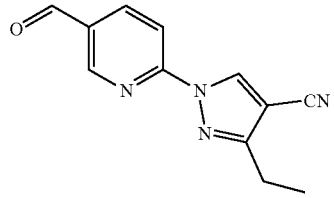 [SMILES: CCc1nn(-c2ccc(C=O)cn2)cc1C#N]

Intermediate 123A: ((E)-2-(ethoxymethylene)-3-oxopentanenitrile

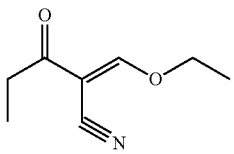

Synthesized according to literature procedures (*Australian Journal of Chemistry*, 44, (1991) 1263-1273).

Intermediate 123B: 3-ethyl-1H-pyrazole-4-carbonitrile

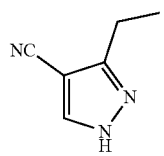

To a solution of Intermediate 123A (5.00 g, 32.60 mmol) in EtOH (50 mL) was added hydrazine hydrate (5.12 mL, 163 mmol) and the reaction mixture was stirred at ambient temperature for 1 h. The reaction mixture was diluted with ice cold water (30 mL) and extracted with 10% MeOH: DCM (2×50 mL). The combined organic layers were washed with brine (10 mL) and dried over anhydrous sodium sulfate and evaporated under reduced pressure. The residue was purified by column chromatography (Redisep-40 g, 0-2% MeOH/DCM) to obtain Intermediate 123B (3.10 g, 78.00%) as a yellow solid. $^1$H NMR (400 MHz, DMSO-d$_6$) δ ppm 1.20-1.32 (m, 3H), 2.66-2.80 (m, 2H), 4.09-4.19 (m, 1H), 8.17 (s, 1H). LCMS (Method-L): retention time 0.75 min, [M+H] 122.1.

Intermediate 123

Intermediate 123 was prepared (0.22 g, 68.70%) as a brown solid, by using a similar synthetic protocol as that of Intermediate 19 and starting from Intermediate 123B (0.19 g, 1.61 mmol) and 6-bromonicotinaldehyde (0.25 g, 1.34 mmol). $^1$H NMR (400 MHz, DMSO-d$_6$) δ ppm 1.31 (t, J=7.58 Hz, 3H), 2.82 (q, J=7.50 Hz, 2H), 8.10 (d, J=8.56 Hz, 1H), 8.47 (dd, J=8.44, 1.59 Hz, 1H), 9.03 (s, 1H), 9.43 (s, 1H), 10.12 (s, 1H). LCMS (Method-L): retention time 1.18 min, [M+H] 227.1.

Intermediate 124: 3-ethyl-1-(5-formylpyrimidin-2-yl)-1H-pyrazole-4-carbonitrile

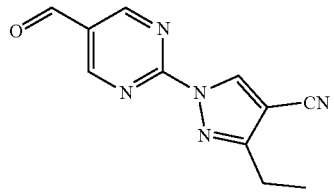 [SMILES: CCc1nn(-c2ncc(C=O)cn2)cc1C#N]

Intermediate 124 was prepared (0.23 g, 57.70%) by using similar synthetic protocol as that of Intermediate 19 and starting from Intermediate 123B (0.25 g, 1.75 mmol) and 3-ethyl-1H-pyrazole-4-carbonitrile (0.32 g, 2.63 mmol). $^1$H NMR (400 MHz, DMSO-d$_6$) δ ppm 1.31 (t, J=7.46 Hz, 3H), 2.83 (q, J=7.58 Hz, 2H), 9.34 (s, 2H), 9.49 (s, 1H), 10.15 (s, 1H), LCMS (Method-D): retention time 1.55 min, [M+H$_2$O] 246.1.

Intermediate 125: 1-(5-formylpyridin-2-yl)-3-methoxy-1H-pyrazole-4-carbonitrile

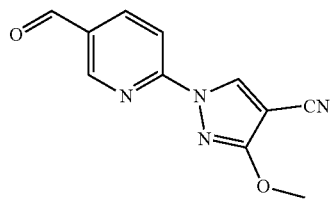 [SMILES: COc1nn(-c2ccc(C=O)cn2)cc1C#N]

Intermediate 125A:
3-methoxy-1H-pyrazole-4-carboxamide

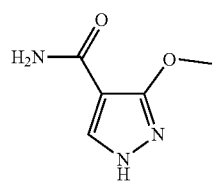

To a stirred solution of methyl 3-methoxy-1H-pyrazole-4-carboxylate (1.50 g, 9.61 mmol) in MeOH (10 mL) was added 25% ammonia solution (50 ml, 2311 mmol) and the reaction mixture was heated at 60° C. for 48 h. The reaction mixture was cooled to ambient temperature, diluted with water (50 mL) and extracted with ethyl acetate (3×50 mL). The combined organic layers were washed with brine (30 mL), dried over anhydrous sodium sulfate and evaporated under reduced pressure to obtain Intermediate 125A (1.00 g, 73.80%). $^1$H NMR (400 MHz, DMSO-d$_6$) δ ppm 3.89 (s, 3H), 6.55-6.66 (m, 1H), 6.99-7.09 (m, 1H), 7.94 (s, 1H), (1 Exchangable proton not observed). LCMS (Method-K): retention time 0.31 min, [M+H] 142.1.

Intermediate 125B:
3-methoxy-1H-pyrazole-4-carbonitrile

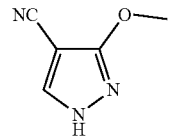

To a stirred solution of Intermediate 125A (1.00 g, 7.09 mmol) in acetonitrile (20 mL) was added POCl$_3$ (3.30 mL, 35.4 mmol) at 0° C. and the reaction mixture was heated to 100° C. for 1.5 h. The reaction mixture was cooled to ambient temperature, concentrated to dryness, diluted with water (30 mL), basified with ammonia solution (20 mL) and extracted with 10% MeOH/DCM (2×100 mL). The combined organic layers were washed with brine (50 mL), dried over anhydrous sodium sulfate and evaporated under reduced pressure to obtain Intermediate 125B (0.50 g, 48.10%) as white solid. $^1$H NMR (400 MHz, DMSO-d$_6$) δ ppm 3.90 (s, 3H), 8.34 (s, 1H), 12.75-12.94 (m, 1H), LCMS (Method-O): retention time 0.60 min, [M+H] 124.3.

Intermediate 125

Intermediate 125 was prepared (0.60 g, 72.200/%) by using similar synthetic protocol as that of Intermediate 19 and starting from Intermediate 125B (0.50 g, 4.06 mmol) and 6-bromonicotinaldehyde (0.63 g, 3.38 mmol). $^1$H NMR (400 MHz, DMSO-d$_6$) δ ppm 4.08 (s, 3H), 7.95-8.04 (m, 1H), 8.43-8.53 (m, 1H), 8.94-9.05 (m, 1H), 9.38 (s, 1H), 10.11 (s, 1H), LCMS (Method-D): retention time 2.21 min, [M+H] 229.0.

Intermediate 126: 1-(5-formylpyrimidin-2-yl)-3-methoxy-1H-pyrazole-4-carbonitrile

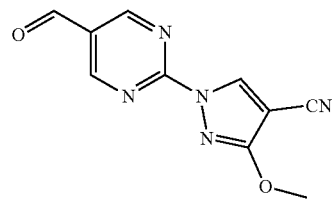 [SMILES: COc1nn(-c2ncc(C=O)cn2)cc1C#N]

Intermediate 126 was prepared (0.24 g, 60.00%) by using similar synthetic protocol as that of Intermediate 105 and starting from Intermediate 125B (0.32 g, 2.63 mmol) and 2-chloropyrimidine-5-carbaldehyde (0.25 g, 1.75 mmol). ¹H NMR (400 MHz, DMSO-d₆) δ ppm 4.07 (s, 3H), 9.26-9.34 (m, 2H), 9.45 (s, 1H), 10.07-10.15 (m, 1H), LCMS: The compound did not ionize well.

Intermediate 127-I: 5-(2-amino-1-hydroxyethyl)-4-methoxyisobenzofuran-1(3H)-one

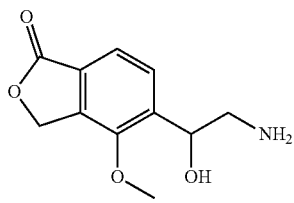 [SMILES: COc1c(C(O)CN)ccc2c1COC2=O]

Intermediate 127A: 5-bromo-4-methoxyisobenzofuran-1(3H)-one

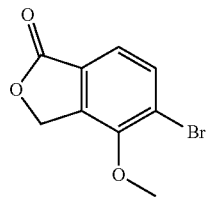

To a stirred solution of 5-amino-4-methoxyisobenzofuran-1(3H)-one (4.00 g, 22.32 mmol) in acetonitrile (100 mL) was added p-TsOH (5.10 g, 26.80 mmol), isoamyl nitrite (3.61 mL, 26.8 mmol), copper (II) bromide (0.05 g, 0.22 mmol) and tetra-n-butylammonium bromide (14.39 g, 44.6 mmol) and the reaction mixture was stirred at ambient temperature for 1 h. The reaction mixture was concentrated to dryness, diluted with water (200 mL) and extracted with ethyl acetate (3×100 mL). The combined organic layers were washed with brine (100 mL), dried over anhydrous sodium sulfate and evaporated under reduced pressure. The residue was purified by column chromatography (Redisep-40 g, 40-50% EtOAc/n-Hexane) to obtain Intermediate 127A (3.50 g, 63.90%) as yellow solid. ¹H NMR (400 MHz, DMSO-d₆) δ ppm 4.01-4.04 (s, 3H) 5.74 (s, 2H) 7.42 (d, J=8.03 Hz, 1H) 7.81 (dt, J=7.97, 0.56 Hz, 1H). LCMS (Method-D): retention time 1.32 min, [M+H] 262.0.

Intermediate 127B: 4-methoxy-5-vinylisobenzofuran-1(3H)-one

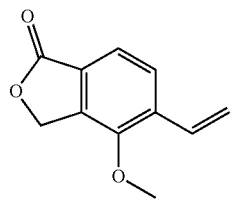

Intermediate 127B was prepared (3.00 g, 88.00%) as a yellow solid, by using a similar synthetic protocol as that of Intermediate 109A and starting from Intermediate 127A (4.00 g, 16.46 mmol). ¹H NMR (400 MHz, DMSO-d₆) δ ppm 3.95 (s, 3H), 5.48 (dd, J=11.23, 1.13 Hz, 1H), 5.68 (s, 2H), 5.99 (dd, J=17.76, 1.13 Hz, 1H), 7.03 (dd, J=17.76, 11.23 Hz, 1H), 7.48 (d, J=7.84 Hz, 1H), 7.77 (d, J=7.84 Hz, 1H). LCMS (Method-O): retention time 1.08 min, [M+H] 191.2.

Intermediate 127C and 127D: 4-methoxy-5-(oxiran-2-yl)isobenzofuran-1(3H)-one)

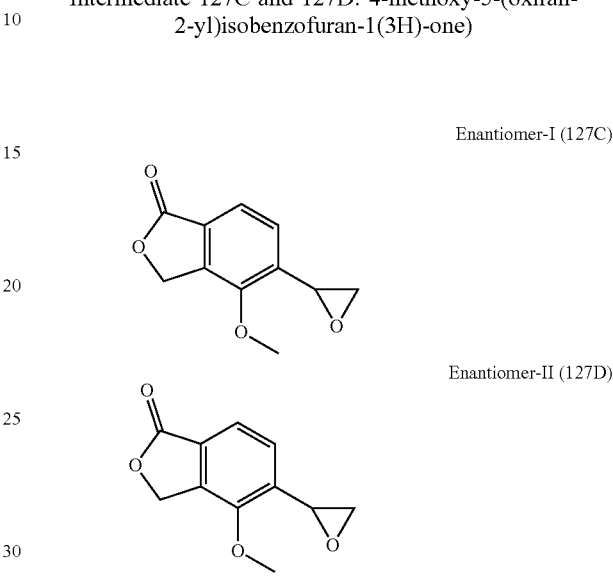

To a stirred solution of Intermediate 127B (2.00 g, 10.52 mmol) in DCM (15 mL) was added m-CPBA (3.63 g, 21.03 mmol) at 0° C. and the reaction mixture was stirred at ambient temperature for 16 h. The reaction mixture was diluted with water (30 mL), basified with 10% NaHCO₃ (20 mL) and extracted with DCM (2×100 mL). The combined organic layers were washed with brine (50 mL), dried over anhydrous sodium sulfate and evaporated under reduced pressure. The residue was purified by chiral SFC [Column: Lux Cellulose 4 (250×4.6 mm) 5.0 micron; 0.2% DEA in IPA, Flow: 1.0 mL/min, Temperature: 25° C., UV: 220 nm] to obtain Intermediate 127C (0.61 g, 20.48%) as yellow solid, fast eluting (retention time 5.23 min). ¹H NMR (300 MHz, DMSO-d₆) δ ppm 2.75 (dd, J=5.59, 2.57 Hz, 1H), 3.20 (dd, J=5.50, 4.32 Hz, 1H), 3.31 (s, 1H), 4.02 (s, 3H), 5.73 (s, 2H), 7.25 (d, J=7.74 Hz, 1H), 7.48 (d, J=7.79 Hz, 1H). LCMS (Method-D): retention time 1.50 min, [M+H] 207.2 and Intermediate 127D (0.60 g, 19.37%) as yellow solid, slow eluting (retention time 6.08 min). ¹H NMR (300 MHz, DMSO-d₆) δ ppm 2.75 (dd, J=5.59, 2.57 Hz, 1H), 3.20 (dd, J=5.50, 4.32 Hz, 1H), 3.31 (s, 1H), 4.02 (s, 3H), 5.73 (s, 2H), 7.25 (d, J=7.74 Hz, 1H), 7.49 (d, J=7.79 Hz, 1H). LCMS (Method-D): retention time 1.44 min, [M+H] 207.2

Intermediate 127-I

Intermediate 127-I was prepared (0.20 g, 68.40%) as a brown solid, by using a similar synthetic protocol as that of Intermediate 7-I and starting from Intermediate 127C (0.20 g, 0.97 mmol).
¹H NMR (300 MHz, DMSO-d₆) δ ppm 3.17 (m, 2H), 3.95 (s, 3H), 5.42 (m, 1H), 5.69 (s, 2H), 7.47-7.52 (m, 1H), 7.63 (d, J=7.89 Hz, 1H), (3 Exchangeable protons not observed). LCMS (Method-O): retention time 0.45 min, [M+H] 224.3.

Intermediate 128:
3-methyl-1H-pyrazole-4-carbonitrile

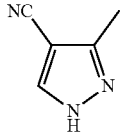

Intermediate 128A:
(E)-2-(ethoxymethylene)-3-oxobutanenitrile

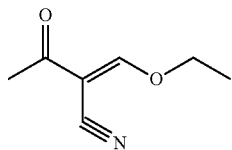

Synthesized according to literature procedures (PCT Int. Appl., 2010002774).

Intermediate 128

Intermediate 128 (14.0 g, 70.00%) was prepared by using similar synthetic protocol as that of Intermediate 123B and starting from Intermediate 128A (26.00 g, 187.00 mmol). $^1$H NMR (400 MHz, DMSO-$d_6$) δ ppm 2.67 (dt, J=3.64, 1.95 Hz, 3H), 8.31 (s, 1H), 13.28-13.32 (m, 1H), LCMS (Method-O): retention time 0.63 min, [M+H] 108.4.

Intermediate 129: 3-cyclopropyl-1-(5-formylpyridin-2-yl)-1H-pyrazole-4-carbonitrile

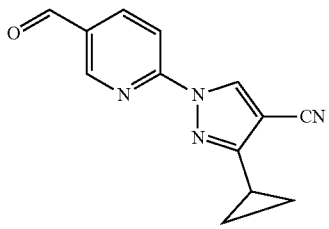 [SMILES: N#Cc1cn(-c2ccc(C=O)cn2)nc1C1CC1]

Intermediate 129B:
3-cyclopropyl-1H-pyrazole-4-carbonitrile

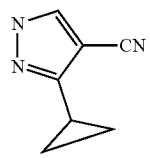

Synthesized according to literature procedures (PCT Int. Appl., 20150522641991).

Intermediate 129

Intermediate 129 was prepared (0.13 g, 56.700/%) as a brown solid, by using similar synthetic protocol as that of Intermediate 19 and starting from Intermediate 129B (0.25 g, 1.22 mmol) and 6-bromonicotinaldehyde (0.19 g, 1.02 mmol). $^1$H NMR (400 MHz, DMSO-$d_6$) S ppm 0.69-0.92 (m, 4H), 2.02-2.16 (m, 1H), 8.06 (d, J=8.53 Hz, 1H), 8.37-8.51 (m, 1H), 9.03 (d, J=1.51 Hz, 1H), 9.40 (s, 1H), 10.12 (s, 1H), LCMS (Method-O): retention time 1.20 min, [M+H] 239.1.

Intermediate 130: 3-cyclopropyl-1-(5-formylpyrimidin-2-yl)-1H-pyrazole-4-carbonitrile

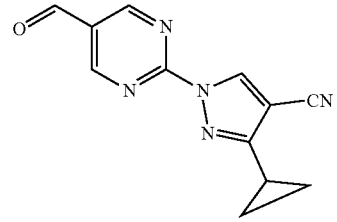 [SMILES: N#Cc1cn(-c2ncc(C=O)cn2)nc1C1CC1]

Intermediate 130 was prepared (0.22 g, 51.90%) as an off white solid, by using similar synthetic protocol as that of Intermediate 105 and starting from Intermediate 129B (0.35 g, 2.63 mmol) and 2-chloropyrimidine-5-carbaldehyde (0.25 g, 1.75 mmol). $^1$H NMR (400 MHz, DMSO-$d_6$) δ ppm 0.93-1.07 (m, 2H), 1.10-1.18 (m, 2H), 2.02-2.16 (m, 1H), 9.27-9.36 (m, 2H), 9.45 (s, 1H), 10.13 (s, 1H). LCMS (Method-D), retention time 1.70 min, [M+H] 240.2.

Intermediate 131:
3-(difluoromethyl)-1H-pyrazole-4-carbonitrile

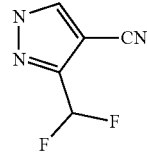

Synthesized according to literature procedures (Jpn. Kokai Tokkyo Koho, 2009215194vol).

Intermediate 132:
6-(5-formylthiazol-2-yl)-4-methylnicotinonitrile

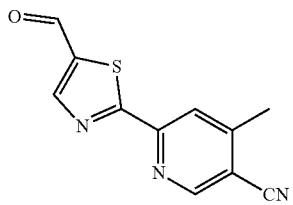 [SMILES: Cc1cc(-c2ncc(C=O)s2)ncc1C#N]

Intermediate 132A: 6-(5-(hydroxymethyl)thiazol-2-yl)-4-methylnicotinonitrile

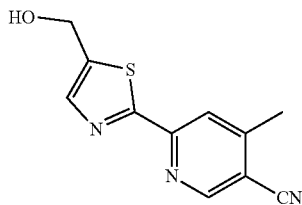 [SMILES: Cc1cc(-c2ncc(CO)s2)ncc1C#N]

A solution of (2-bromothiazol-5-yl)methanol (0.55 g, 2.83 mmol) and Intermediate 78B (1.69 g, 2.83 mmol) in dioxane (20 mL) was degassed with nitrogen for 20 minutes. Palladium tetrakistriphenylphosphine (0.33 g, 0.28 mmol), copper(I) iodide (0.05 g, 0.28 mmol) was added and reaction mixture was degassed again for 10 minutes and heated at 100° C. for 16 h. The reaction mixture was cooled to ambient temperature, diluted with ethyl acetate (20 mL), filtered through Celite® and the filtrate was concentrated under reduced pressure. The residue was purified by column chromatography (Redisep-24 g, 0-50% EtOAc/n-hexane) to obtain Intermediate 132A (0.38 g. 31.90%) as a yellow solid. $^1$H NMR (400 MHz, DMSO-d6) δ ppm 2.58 (s, 3H), 4.74 (d, J=5.02 Hz, 2H), 5.72 (s, 1H), 7.90 (s, 1H), 8.18 (s, 1H), 8.92-9.01 (m, 1H), LCMS (Method-D): retention time 1.42 min, [M+H] 232.0.

Intermediate 132

Intermediate 130 was prepared (0.15 g, 71.50%) as a white solid, by using similar synthetic protocol as that of Intermediate 26 and starting from Intermediate 132A (0.20 g, 0.48 mmol). $^1$H NMR (400 MHz, DMSO-d6) δ ppm 2.61-2.67 (m, 3H), 8.34 (s, 1H), 8.90 (s, 1H), 9.04-9.10 (m, 1H), 10.11-10.18 (m, 1H), LCMS (Method-O): retention time 1.05 min, [M+H] 230.1.

Intermediate 133: (R)-5-(2-amino-1-fluoroethyl)-4-methylisobenzofuran-1(3H)-one

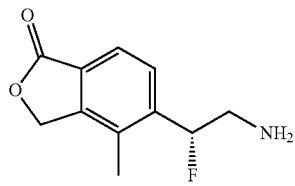

Intermediate 133A: tert-butyl (R)-(2-fluoro-2-(4-methyl-1-oxo-1,3-dihydroisobenzofuran-5-yl)ethyl)carbamate

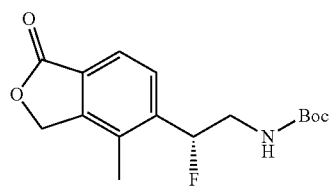 [SMILES: Cc1c([C@@H](F)CNC(=O)OC(C)(C)C)ccc2c1COC2=O]

To a stirred solution of Intermediate 49B (0.40 g, 1.30 mmol) in DCM (20 mL) at −78° C. was added DAST (0.20 ml, 1.56 mmol) and the resulting reaction mixture was stirred at ambient temperature for 1 hr. The reaction mixture was diluted with water (30 mL), basified with saturated NaHCO₃ (30 mL) and extracted with DCM (2×25 mL). The combined organic layers were washed with brine (30 mL), dried over anhydrous sodium sulfate and evaporated under reduced pressure. The residue was purified by column chromatography (Redisep-24 g, 20-40% EtOAc/n-Hexane) to obtain Intermediate 133A (0.15 g, 30.00%) as a pale yellow solid. $^1$H NMR (400 MHz, DMSO-d₆) δ ppm 1.10-1.46 (m, 9H), 2.3 (s, 3H), 3.09-3.22 (m, 2H), 5.29-5.50 (m, 2H), 5.95 (dd, J=7.03, 3.51 Hz, 1H), 7.30 (d, J=5.52 Hz, 1H), 7.48-7.62 (m, 1H), 7.70-7.89 (m, 1H). $^{19}$F NMR (400 MHz, DMSO-d₆) δ ppm −184.76. LCMS (Method-I): retention time 1.15 min, [M+H] 310.4.

Intermediate 133

To a stirred solution of Intermediate 133A (0.15 g, 0.39 mmol) in EtOAc (10 mL) at 0° C. was added 4N HCl in dioxane (2.00 mL, 8.00 mmol) and the resulting reaction mixture was stirred at ambient temperature for 16 h. The reaction mixture was concentrated to dryness and diluted with water (10 mL). The aqueous layer was washed with ethyl acetate (2×20 mL), basified with saturated NaHCO₃ and extracted with DCM (3×20 mL). The combined organic layers were washed with brine (10 mL), dried over anhydrous sodium sulfate and concentrated under reduced pressure to obtain Intermediate 133 (0.08 g, 63.00%/). $^1$H NMR (400 MHz, DMSO-dt) δ ppm 2.21-2.32 (s, 3H), 2.82-3.02 (m, 1H) 3.15-3.20 (m, 1H), 5.41-5.50 (m, 2H), 5.71-5.92 (m, 1H), 7.40-7.61 (m, 1H) 7.73 (d, J=8.03 Hz, 1H), (2 Exchangeable proton not observed). $^{19}$F NMR (400 MHz, DMSO-d₆) δ ppm −184.70. LCMS (Method-L): retention time 0.5 min, [M+H] 209.9.

Intermediate 134: 4-methyl-6-(3-(2-oxoethyl)-1H-pyrrolo[3,2-b]pyridin-1-yl)nicotinonitrile

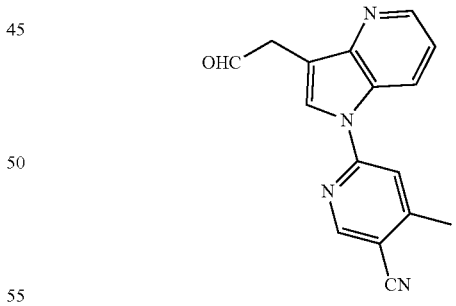

To a stirred solution of 6-bromo-4-methylnicotinonitrile (0.24 g, 1.23 mmol) in DMSO (10 mL) was added 1H-pyrrolo[3,2-b]pyridine-3-carbaldehyde (0.15 g, 1.03 mmol), copper(I) iodide (0.05 g, 0.26 mmol), cesium carbonate (0.67 g, 2.05 mmol) and L-proline (59.1 g, 0.51 mmol) and the resulting suspension was heated at 90° C. for 16 h. The reaction mixture was cooled to ambient temperature, concentrated to dryness, diluted with water (30 mL) and extracted with ethyl acetate (2×25 mL). The combined organic layers were washed with brine (20 mL), dried over anhydrous sodium sulfate and evaporated under reduced pressure. The residue was triturated with n-hexane (30 mL) to obtain Intermediate 134 (0.12 g, 9.000/%) as a pale yellow solid. LCMS (Method-I): retention time 0.91 min, [M+H] 263.3. The compound was taken directly to the subsequent step without further purification or characterization.

Intermediate 135: 4-methyl-6-(3-(2-oxoethyl)-1H-pyrrolo[2,3-b]pyridin-1-yl)nicotinonitrile

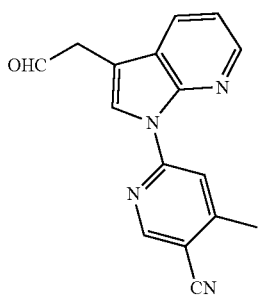 [SMILES: Cc1cc(-n2cc(CC=O)c3cccnc32)ncc1C#N]

To a stirred solution of 6-bromo-4-methylnicotinonitrile (0.113 g, 0.58 mmol) in DMSO (4 mL) was added 1H-pyrrolo[2,3-b]pyridine-3-carbaldehyde (0.70 g, 0.48 mmol), copper (I) iodide (0.04 g, 0.19 mmol) followed by $K_2CO_3$ (0.13 g, 0.96 mmol) and 2-(dimethylamino)acetic acid (0.03 g, 0.29 mmol) and the resulting suspension was heated at 110° C. for 16 h. The reaction mixture was cooled to ambient temperature, concentrated to dryness, diluted with water (40 mL) and extracted with ethyl acetate (2×25 mL). The combined organic layers were washed with brine (20 mL), dried over anhydrous sodium sulfate and evaporated under reduced pressure. The residue was triturated with n-hexane (20 mL) to obtain Intermediate 135 (0.10 g, 8.00%) as a pale yellow solid. LCMS (method-I): retention time 1.25 min, [M+H] 263.3. The compound was taken directly to the subsequent step without further purification or characterization.

Intermediate 136-I: 5-(1-amino-2-hydroxypropan-2-yl)-4-methylisobenzofuran-1(3H)-one

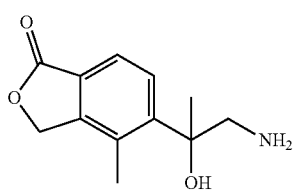 [SMILES: Cc1c(C(C)(O)CN)ccc2c1COC2=O]

Intermediate 136A: 4-methyl-5-(prop-1-en-2-yl)isobenzofuran-1(3H)-one

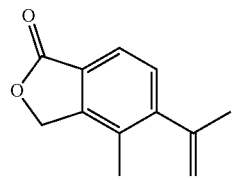

To a stirred solution of 5-bromo-4-methylisobenzofuran-1(3H)-one (1.00 g, 4.40 mmol) in dioxane (20 mL) and water (4 mL) was added $Pd(Ph_3P)_4$ (0.25 g, 0.22 mmol) and sodium carbonate (1.40 g, 13.21 mmol) followed by 4,4,5,5-tetramethyl-2-(prop-1-en-2-yl)-1,3,2-dioxaborolane (0.89 g, 5.29 mmol) and the resulting mixture was degassed with nitrogen atmosphere for 10 minutes. The reaction was stirred at 100° C. for 16 h. The reaction mixture was cooled to ambient temperature, concentrated to dryness and the residue was purified by column chromatography (Redisep-24 g, 20-40% EtOAc/n-hexane) to obtain Intermediate 136 (0.80 g, 80%) as a pale yellow solid. $^1$H NMR (400 MHz, $CDCl_3$) δ ppm 2.08 (s, 3H), 2.28 (s, 3H), 4.91-4.92 (d, J=4 Hz, 1H), 5.24 (s, 2H), 5.31-5.32 (d, J=4 Hz, 1H), 7.30 (d, J=8.03 Hz, 1H), 7.72 (s, 1H), LCMS (Method-I): retention time 1.19 min, [M+H] 189.5.

Intermediate 136B-I and 136B-II: 4-methyl-5-(2-methyloxiran-2-yl)isobenzofuran-1(3H)-one

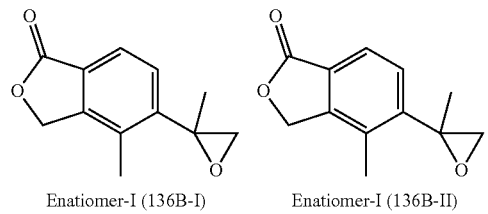

Enatiomer-I (136B-I)   Enatiomer-I (136B-II)

To a stirred solution of Intermediate 136A (0.50 g, 2.66 mmol) in DCM (25 mL) was added m-CPBA (1.52 g, 5.31 mmol) and reaction was stirred at ambient temperature for 16 h. The reaction mixture was diluted with water (30 mL), basified with 10% $NaHCO_3$ and extracted with DCM (2×50 mL). The combined organic layers were washed with brine (30 mL), dried over anhydrous sodium sulfate and evaporated under reduced pressure. The residue was purified by chiral SFC [column: Lux Amylose 2 (250×4.6 mm) 5 micron; 0.2% DEA in n-hexane: EtOH: 5:95, Flow: 2.0 mL/min, UV: 270 nm] to obtain Intermediate 136B-I (0.20 g, 36.90%) as off white solid, fast eluting (retention time 4.28 min). 1H NMR (400 MHz, $CDCl_3$) δ ppm 1.64 (s, 3H), 2.40 (s, 3H), 2.84 (d, J=5.00 Hz, 1H), 3.04 (d, J=5.25 Hz, 1H), 5.25 (s, 2H), 7.55 (s, 1H), 7.74 (d, J=8.00 Hz, 1H). LCMS (method-L): retention time 0.94 min, [M+H] 205.4. and Intermediate 136B-II (180 mg, 33.2%) as off white solid, slow eluting (retention time 6.07 min). $^1$H NMR (400 MHz, $CDCl_3$) δ ppm 1.64 (s, 3H), 2.40 (s, 3H), 2.84 (d, J=5.00 Hz, 1H), 3.04 (d, J=5.25 Hz, 1H), 5.25 (s, 2H), 7.55 (s, 1H), 7.74 (d, J=8.00 Hz, 1H). LCMS (Method-L): retention time 0.94 min, [M+H] 205.4.

Intermediate 136-I

Intermediate 136-I was prepared (0.20 g, 32.30%) as a pale yellow solid, by using similar synthetic protocol as that of Intermediate 7-1 and starting from Intermediate 136B-II (0.20 g, 0.98 mmol). $^1$H NMR (400 MHz, DMSO-$d_6$) δ ppm 1.41-1.62 (m, 3H), 2.29-2.41 (s, 3H), 2.82 (d, J=5.38 Hz, 1H), 3.08 (d, J=5.38 Hz, 1H), 5.39-5.41 (m, 3H), 7.54 (d, J=7.83 Hz, 1H), 7.61-7.75 (m, 3H), LCMS (method-I): retention time 0.51 min, [M+H] 222.4.

Intermediate 137: 1-(5-(4-methyl-5-oxo-4,5-di-hydro-1,2,4-oxadiazol-3-yl)pyridin-2-yl)-1H-pyrazole-4-carbaldehyde

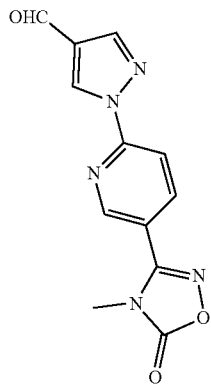 [SMILES: Cn1c(-c2ccc(-n3cc(C=O)cn3)nc2)noc1=O]

Intermediate 137 was prepared (0.10 g, 7.00%), by using a similar synthetic protocol as that of Intermediate 9 and starting from 1H-pyrazole-4-carbaldehyde (0.10 g, 1.04 mmol) and 3-(6-bromopyridin-3-yl)-4-methyl-1,2,4-oxadiazol-5(4H)-one (0.26 g, 1.04 mmol). LCMS (Method-L): retention time 0.85 min, [M+H] 272.1. The compound was taken directly to the subsequent step without further purification or characterization.

Intermediate 138-I: 5-(2-amino-1-hydroxyethyl)-3,4-dimethyl-3λ³-isobenzofuran-1(3H)-one

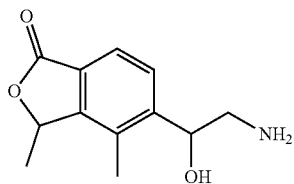 [SMILES: Cc1c(C(O)CN)ccc2c1C(C)OC2=O]

Intermediate 138A-I and 138A-II: 5-bromo-3,4-dimethylisobenzofuran-1(3H)-one

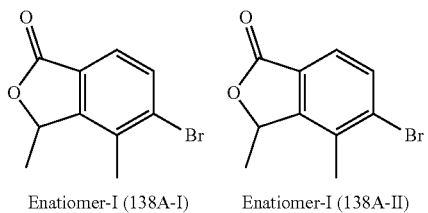

Enatiomer-I (138A-I)    Enatiomer-I (138A-II)

To a stirred solution of 5-bromo-4-methylisobenzofuran-1(3H)-one (2.0 g, 8.81 mmol) in THF (50 mL) was added LDA (11.01 mL, 22.02 mmol) at −78° C. followed by iodomethane (5.51 mL, 88 mmol) and the reaction was stirred at ambient temperature for 16 h. The reaction was poured into ice cold water (40 mL) and extracted with ethyl acetate (2×25 mL). The combined organic layers were washed with brine (30 mL), dried over anhydrous sodium sulfate and evaporated under reduced pressure. The residue was purified by Chiral SFC [Column: Chiralpak ADH (250×4.6 mm) 5 micron; 0.2% DEA in MeOH+IPA (1:1), Flow: 1.2 mL/min, Temperature: 25° C., UV: 233 nm] to obtain Intermediate 138A-I (0.20 g, 9.46%) as yellow solid, fast eluting (retention time 1.61 min) $^1$H NMR (400 MHz, CDCl$_3$) δ ppm 1.67 (d, J=6.36 Hz, 3H), 2.45 (s, 3H), 5.60 (q, J=6.60 Hz, 1H), 7.60 (d, J=8.07 Hz, 1H), 7.76 (d, J=8.07 Hz, 1H). LCMS (Method-I): retention time 1.21 min, [M+H] 243.0. and Intermediate 138A-H (0.15 g, 7.09%) as a pale yellow solid, slow eluting (retention time 1.88 min)$^1$H NMR (400 MHz, DMSO-d$_6$) δ ppm 1.56 (d, J=6.36 Hz, 3H), 2.40 (s, 3H), 5.84 (q, J=6.60 Hz, 1H), 7.60 (d, J=8.07 Hz, 1H), 7.84 (d, J=8.07 Hz, 1H), LCMS (Method-I): retention time 1.21 min, [M+H] 243.0.

Intermediate 138B-I: 3,4-dimethyl-5-(oxiran-2-yl)isobenzofuran-1(3H)-one

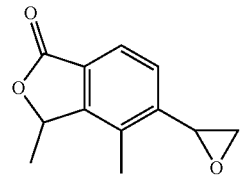

Intermediate 138B-I was prepared (0.12 g, 36.00%) as a brown colored solid, by using a similar synthetic protocol as that of Intermediate 127C and starting from Intermediate 138A-I (0.2 g, 1.06 mmol). $^1$H NMR (400 MHz, CDCl$_3$) δ ppm 1.66 (d, J=6.36 Hz, 3H), 2.45 (s, 3H), 2.7-2.75 (m, 1H), 3.20-3.24 (dd, J=5.52, 4.02 Hz, 1H), 3.49 (s, 1H), 5.58 (q, J=6.53 Hz, 1H), 7.42 (d, J=7.74 Hz, 1H), 7.75 (d, J=7.79 Hz, 1H). LCMS (Method-L): retention time 1.0 min, [M+H] 205.0.

Intermediate 138-I

Intermediate 138-I was prepared (0.10 g, 46.00%) as a brown solid, by using a similar synthetic protocol as that of Intermediate 7-1 and starting from Intermediate 138B-I (0.10 g, 0.49 mmol) 1H NMR (400 MHz, DMSO-d$_6$) δ ppm 1.58 (d, J=6.36 Hz, 3H), 2.45 (s, 3H), 3.2-3.25 (m, 2H), 4.76-4.86 (m, 1H), 5.81-5.91 (m, 1H), 7.62-7.77 (m, 3H), (2 Exchangeable proton not observed). LCMS (Method-L): retention time 0.51 min, [M+H] 222.1.

Example 35: (R)-6-(4-(((2-hydroxy-2-(4-methyl-1-oxo-1,3-dihydroisobenzofuran-5-yl)ethyl)amino)methyl)-5-methoxy-1H-pyrazol-1-yl)-4-methylnicotinonitrile

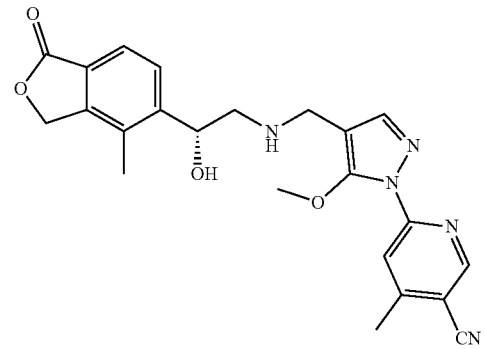 [SMILES: COc1c(CNC[C@H](O)c2ccc3c(c2C)COC3=O)cnn1-c1cc(C)c(C#N)cn1]

Example 35 was prepared (0.12 g, 35.40%), by using a similar synthetic protocol as that of Example 6-I and starting from Intermediate 7-I (0.18 g, 0.87 mmol) and Intermediate 26 (0.15 g, 0.62 mmol). $^1$H NMR (400 MHz, DMSO-$d_6$) δ ppm 2.27 (s, 3H), 2.58 (s, 3H), 2.97-3.07 (m, 1H), 3.12-3.20 (m, 1H), 4.01 (s, 3H), 4.06-4.12 (m, 2H), 5.21-5.27 (m, 1H), 5.36-5.46 (m, 2H), 6.29-6.33 (m, 1H), 7.70-7.77 (m, 2H), 7.80-7.82 (m, 1H), 8.74 (s, 1H), 8.83 (s, 1H), (1 Exchangeable proton not observed). LCMS/HPLC (Method-B): retention time 1.61 min, [M+H] 434.1, purity: 100%. (Method-A): retention time 1.31 min, [M+H] 434.1, purity: 100%, Chiral purity (Method-XVI): retention time 6.38 min, 100% ee.

Example 36: (R)-6-(4-(((2-hydroxy-2-(4-methyl-1-oxo-1,3-dihydroisobenzofuran-5-yl)ethyl)amino) methyl)-5-oxo-2,5-dihydro-1H-pyrazol-1-yl)-4-methylnicotinonitrile

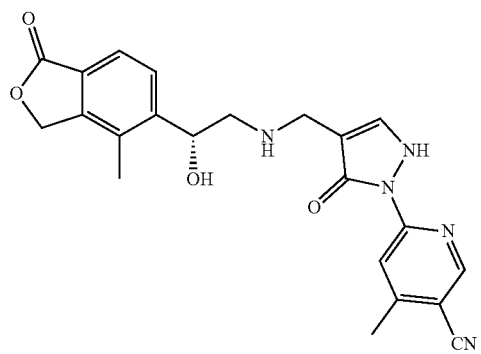 [SMILES: Cc1cc(-n2[nH]cc(CNC[C@H](O)c3ccc4c(c3C)COC4=O)c2=O)ncc1C#N]

To a stirred solution of Example 35 (0.05 g, 0.09 mmol) in acetonitrile (4 mL) was added sodium iodide (0.07 g, 0.46 mmol). The reaction mixture was stirred at ambient temperature for 10 minutes and TMS-Cl (0.058 mL, 0.457 mmol) was added. The reaction mixture was heated at 60° C. for 16 h. The reaction mixture was cooled to ambient temperature, concentrated to dryness, diluted with water (20 mL) and extracted with DCM (2×20 mL). The combined organic layers were washed with brine (50 mL), dried over anhydrous sodium sulfate and evaporated under reduced pressure. The residue was purified by HPLC [Waters XBridge C18 (19×150 mm) 5 micron; Solvent A: 0.1% TFA, Solvent B: Acetonitrile, Gradient: 5-25% B over 25 min, Flow: 15 mL/min] to obtain Example 36 (0.09 g, 17.86%). $^1$H NMR (400 MHz, DMSO-$d_6$) δ ppm 2.26 (s, 3H), 2.56 (s, 3H), 2.94-3.03 (m, 1H), 3.10-3.16 (m, 1H), 4.08 (d, J=4.02 Hz, 2H), 5.19-5.27 (m, 1H), 5.41 (d, J=5.52 Hz, 2H), 6.28-6.35 (m, 1H), 7.64 (d, J=1.00 Hz, 1H), 7.73 (d, J=5.02 Hz, 2H), 8.65 (s, 1H), 8.81 (s, 1H), 11.34-11.58 (m, 1H), (1 Exchangeable proton not observed). LCMS/HPLC (Method-B): retention time 1.00 min, [M+H] 420.0, purity: 97.20%. (Method-A): retention time 1.09 min, [M+H] 420.0, purity: 100%. Chiral purity (Method-XVIII): retention time 7.32 min, 100% ee.

Example 37: (R)-5-(4-(2-((2-hydroxy-2-(4-methyl-1-oxo-1,3-dihydroisobenzofuran-5-yl)ethyl)amino) propan-2-yl)-1H-pyrazol-1-yl)-3-methylbenzo[d]oxazol-2(3H)-one

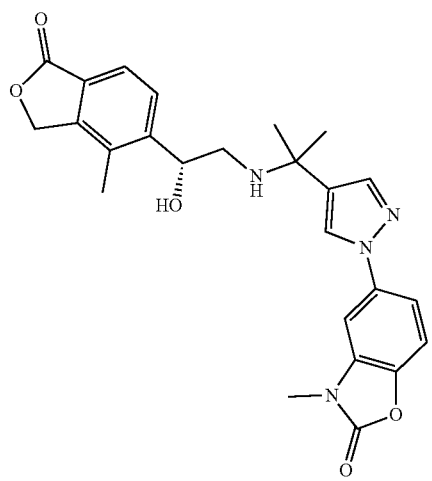 [SMILES: Cc1c([C@@H](O)CNC(C)(C)c2cnn(-c3ccc4oc(=O)n(C)c4c3)c2)ccc2c1COC2=O]

Example 37 was prepared (4.70 g, 5.34%), by using a similar synthetic protocol as that of Intermediate 9 and starting from Intermediate 45 (0.60 g, 0.19 mmol) and Intermediate 3 (0.44 g, 0.19 mmol). $^1$H NMR (400 MHz, DMSO-$d_6$) δ ppm 1.39 (br. s., 6H), 2.13 (s, 3H), 2.36-2.46 (m, 2H), 3.37 (s, 3H), 4.84-4.92 (m, 1H), 5.30 (d, J=4.52 Hz, 3H), 7.39 (d, J=8.53 Hz, 1H), 7.51 (dd, J=8.78, 2.26 Hz, 1H), 7.60 (s, 3H), 7.68 (d, J=2.51 Hz, 1H), 8.19-8.28 (m, 1H), (1 Exchangeable proton not observed). LCMS/HPLC (Method-B): retention time 1.38 min, [M+H] 463.2, purity: 98.4%. (Method-A): retention time 1.19 min, [M+H] 463.2, purity: 100%. Chiral purity (Method-V): retention time 5.43 min, 100% ee.

Example 38: N-(2-(1-(5-cyano-4-methylpyridin-2-yl)-1H-pyrazol-4-yl)ethyl)-2-(4-methyl-1-oxo-1,3-dihydroisobenzofuran-5-yl)acetamide

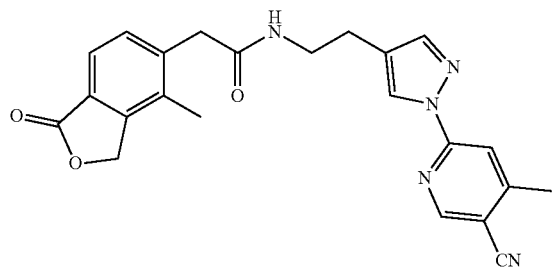 [SMILES: Cc1cc(-n2cc(CCNC(=O)Cc3ccc4c(c3C)COC4=O)cn2)ncc1C#N]

To a stirred solution of Intermediate 47 (0.05 g, 0.22 mmol) and Intermediate 48 (0.05 g, 0.22 mmol) in DCM (10 mL) was added HATU (0.17 g, 0.44 mmol) and DIPEA (0.12 mL, 0.66 mmol) and the reaction mixture was stirred at ambient temperature for 14 h. The reaction was diluted with water (20 mL) and extracted with ethyl acetate (3×25 mL). The combined organic layers were washed with brine (20 mL), dried over anhydrous sodium sulfate and evaporated under reduced pressure. The residue was dissolved in DMF (1 mL) and DMSO (1 mL). The undissolved precipitate was isolated by suction filtration and washed with MeOH (10 mL) to obtain Example 38 (0.03 g, 38.30%) as an off-white solid. $^1$H NMR (400 MHz, DMSO-d$_6$) δ ppm 2.19 (s, 3H), 2.54-2.61 (m, 3H), 2.62-2.72 (m, 2H), 3.34-3.39 (m, 2H), 3.59 (s, 2H), 5.33 (s, 2H), 7.36 (d, J=8.03 Hz, 1H), 7.51 (d, J=7.53 Hz, 1H), 7.77 (s, 1H), 7.95 (d, J 1.00 Hz, 1H), 8.17 (t, J=5.52 Hz, 1H), 8.42 (s, 1H), 8.82 (s, 1H). HPLC (Method-E): retention time 8.10 min, purity: 96.24%. (Method-G): retention time 7.25 min, purity: 96.49%. LCMS (Method-D) retention time 1.91 min, [M+H] 416.0.

Example 39: (R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl) acetamide

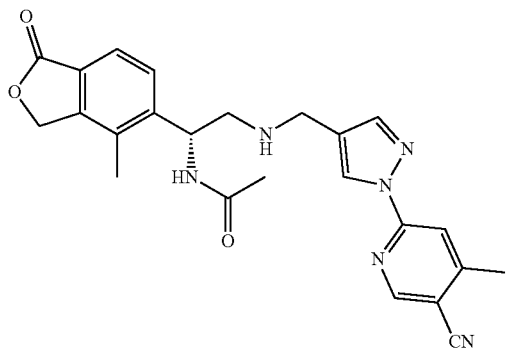 [SMILES: CC(=O)N[C@@H](CNCc1cnn(-c2cc(C)c(C#N)cn2)c1)c1ccc2c(c1C)COC2=O]

Example 39 was prepared (0.21 g, 65.90%), by using a similar synthetic protocol as that of Example 6-I and starting from Intermediate 50-I (0.02 g, 0.07 mmol) and Intermediate 9 (0.02 mg, 0.07 mmol). $^1$H NMR (400 MHz, DMSO-d$_6$) δ ppm 1.84 (s, 3H), 2.24-2.33 (m, 3H), 2.57 (s, 3H), 2.64-2.83 (m, 2H), 3.67 (br. s., 2H), 5.22 (d, J=5.87 Hz, 1H), 5.31-5.44 (m, 2H), 7.49 (d, J=8.31 Hz, 1H), 7.65 (d, J=8.07 Hz, 1H), 7.81 (s, 1H), 7.97 (s, 1H), 8.42 (d, J=8.07 Hz, 1H), 8.47 (s, 1H), 8.83 (s, 1H), (1 Exchangeable proton not observed). LCMS/HPLC (Method-A): retention time 1.14 min, [M+H] 445.1, purity: 97.82%. (Method-B): retention time 1.41 min, [M+H] 445.1, purity: 97.37%. Chiral purity (Method-XIV): retention time 6.28 min, 97.22% ee.

Example 40: (R)-6-(2-(((2-hydroxy-2-(4-methyl-1-oxo-1,3-dihydroisobenzofuran-5-yl)ethyl)amino)methyl)pyrimidin-5-yl)-4-methylnicotinonitrile

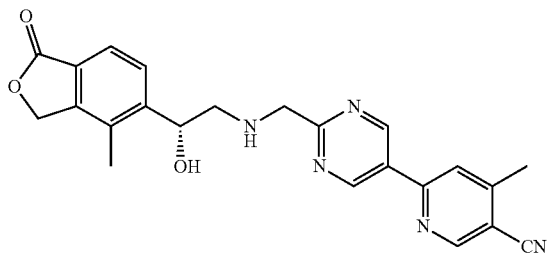

Example 40A: tert-butyl (R)-((5-(5-cyano-4-methylpyridin-2-yl)pyrimidin-2-yl)methyl)(2-hydroxy-2-(4-methyl-1-oxo-1,3-dihydroisobenzofuran-5-yl)ethyl) carbamate

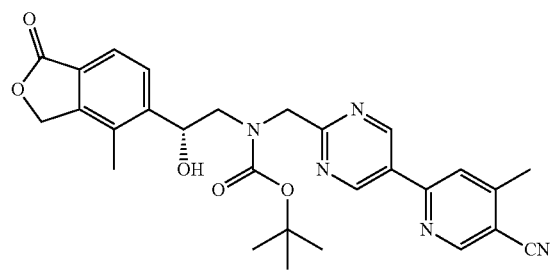

Example 40A was prepared (0.05 g, 42.20%) as an off-white solid, by using a similar synthetic protocol as that of Example 4-1 and starting from Intermediate 60-1(0.11 g, 0.23 mmol) and Intermediate 78B (0.07 g, 0.23 mmol). $^1$H NMR (400 MHz, DMSO-d$_6$) δ ppm 1.17 (d, J=7.6 Hz, 4H), 1.30 (d, J=8.4 Hz, 5H), 2.34 (s, 3H), 2.41-2.53 (m, 4H), 2.66 (s, 3H), 5.23 (br. s., 1H), 5.39 (s, 2H), 6.75 (s, 1H), 7.54-7.63 (m, 3H), 8.45 (s, 1H), 9.12 (d, J=7.6 Hz, 1H), 9.43 (d, J=7.6 Hz, 1H). LCMS: (Method-D) retention time: 1.17 min, [M+1] 516.6.

Example 40

Example 40 was prepared (0.007 g, 15.00%), by using a similar synthetic protocol as that of Intermediate 50-I and starting from Example 19A-I (0.05 g, 0.01 mmol). $^1$H NMR (400 MHz, DMSO-d$_6$) δ 2.18-2.31 (m, 3H), 2.60 (s, 3H), 2.69-2.83 (m, 2H), 3.96-4.16 (m, 2H), 5.06 (br. s., 1H), 5.38 (d, J=2.0 Hz, 2H), 5.56 (br. s., 1H), 7.67 (q, J=7.8 Hz, 2H), 8.32 (s, 1H), 9.06 (s, 1H), 9.45 (s, 2H), (1 Exchangeable proton not observed). LCMS/HPLC (Method-A): retention time 0.89 min, [M+H] 416.2, purity: 94.02%. (Method-B): retention time 1.10 min, [M+H] 416.2, purity: 93.59%. Chiral purity (Method-V): retention time 9.07 min, 85.28% ee.

Example 41: (R)-5(4-(((2-hydroxy-2-(4-methyl-1-oxo-1,3-dihydroisobenzofuran-5-yl)ethyl)amino) methyl)-1H-pyrazol-1-yl)pyrazine-2-carbonitrile

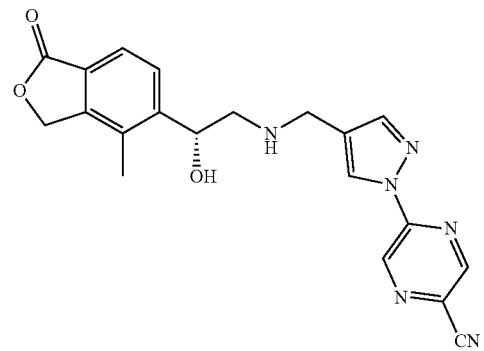 [SMILES: Cc1c([C@@H](O)CNCc2cnn(-c3cnc(C#N)cn3)c2)ccc2c1COC2=O]

Intermediate 41A: tert-butyl (R)-(1-(5-cyanopyrazin-2-yl)-1H-pyrazol-4-yl)methyl)(2-hydroxy-2-(4-methyl-1-oxo-1,3-dihydroisobenzofuran-5-yl)ethyl)carbamate

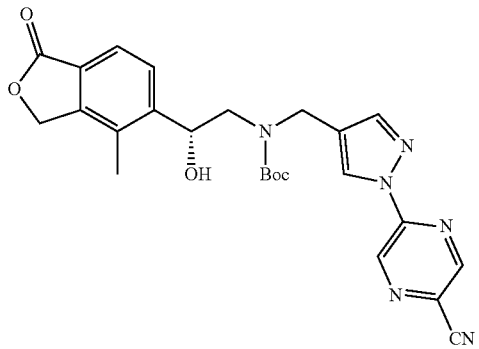 [SMILES: Cc1c([C@@H](O)CN(Cc2cnn(-c3cnc(C#N)cn3)c2)C(=O)OC(C)(C)C)ccc2c1COC2=O]

Example 41A was prepared (0.03 g, 19.75%), by using a similar synthetic protocol as that of Intermediate 9 and starting from Intermediate 72-I (0.10 g, 0.26 mmol) and 5-bromopyrazine-2-carbonitrile (0.05 g, 0.26 mmol). $^1$H NMR (300 MHz, DMSO-$d_6$) δ ppm 1.29-1.46 (m, 9H), 2.20-2.30 (m, 3H), 2.70-2.80 (m, 2H), 4.28-4.47 (m, 2H), 5.11-5.22 (m, 1H), 5.25-5.40 (m, 2H), 5.63-5.78 (m, 1H), 7.60-7.75 (m, 2H), 7.83-7.93 (m, 1H), 8.38-8.48 (m, 1H), 9.08-9.14 (m, 1H), 9.23-9.31 (m, 1H), LCMS (Method-D): retention time 2.66 min, [M+H$_2$O] 508.2.

Example 41

Example 41 was prepared (0.008 g, 41.00%), by using a similar synthetic protocol as that of Intermediate 76 and starting from Example 41A (0.03 g, 0.05 mmol). $^1$H NMR (400 MHz, DMSO-$d_6$) δ ppm 1.88 (s, 3H), 2.58-2.74 (m, 2H), 3.73 (d, J=4.40 Hz, 2H), 5.01 (dd, J=7.95, 4.28 Hz, 1H), 5.37 (d, J=3.42 Hz, 3H), 7.66 (d, J=3.91 Hz, 2H), 7.97 (s, 1H), 8.52 (s, 1H), 9.09 (d, J=1.22 Hz, 1H), 9.29 (d, J=1.47 Hz, 1H), (1 Exchangable proton not observed). LCMS/HPLC (Method-B): retention time 1.27 min, [M+H] 391.0, purity: 96.08%. (Method-A): retention time 1.03 min, [M+H] 391.1, 96.96%. Chiral purity (Method-XIV): retention time 6.78 min, 80.46% ee.

Example 42: (R)-6-(5-(((2-hydroxy-2-(4-methyl-1-oxo-1,3-dihydroisobenzofuran-5-yl)ethyl)amino)methyl)-1-methyl-1H-1,2,4-triazol-3-yl)-4-methylnicotinonitrile

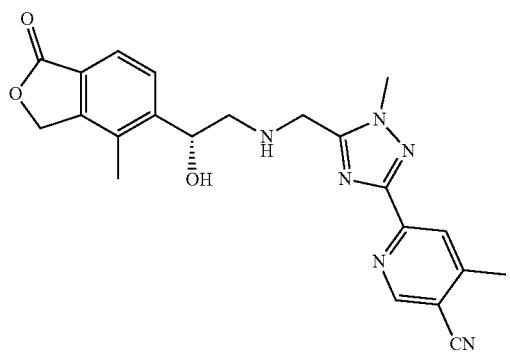 [SMILES: Cc1cc(-c2nc(CNC[C@H](O)c3ccc4c(c3C)COC4=O)n(C)n2)ncc1C#N]

Example 42A: tert-butyl (R)-((3-(5-cyano-4-methylpyridin-2-yl)-1-methyl-1H-1,2,4-triazol-5-yl)methyl)(2-hydroxy-2-(4-methyl-1-oxo-1,3-dihydroisobenzofuran-5-yl)ethyl)carbamate

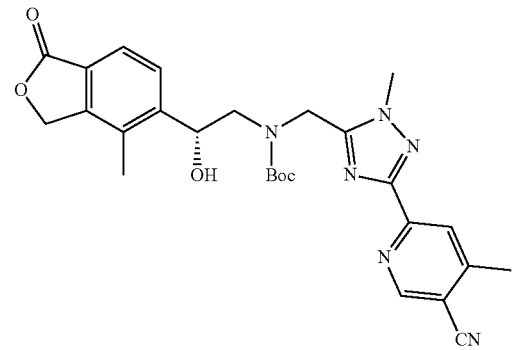 [SMILES: Cc1cc(-c2nc(CN(C[C@H](O)c3ccc4c(c3C)COC4=O)C(=O)OC(C)(C)C)n(C)n2)ncc1C#N]

Example 42A was prepared (0.11 g, 86.00%) as a pale yellow solid, by using a similar synthetic protocol as that of Example 4-I and starting from Intermediate 82 (0.14 g, 0.25 mmol) and 6-bromo-4-methylnicotinonitrile (0.08 g, 0.37 mmol). $^1$H NMR (300 MHz, DMSO-$d_6$) δ ppm 1.16-1.38 (m, 9H), 2.19-2.30 (m, 3H), 2.54-2.61 (m, 3H), 3.5-3.6 (s, 3H), 3.88-4.03 (m, 2H), 4.66-4.82 (m, 2H), 5.11-5.22 (m, 1H), 5.32-5.43 (m, 3H), 7.37-7.49 (m, 1H), 7.55-7.68 (m, 1H), 7.74-7.85 (m, 1H), 8.85-8.93 (m, 1H). LCMS/HPLC (Method-H): retention time 1.87 min, [M+H] 519.0.

Example 42

Example 42 was prepared (0.04 g, 45.60%), by using a similar synthetic protocol as that of Intermediate 76 and starting from Example 42A (0.10 g, 0.19 mmol). $^1$H NMR (400 MHz, DMSO-$d_6$) δ ppm 2.31 (s, 3H), 2.59 (s, 3H), 2.90-2.96 (m, 1H), 3.08-3.19 (m, 1H), 3.98 (s, 3H), 4.47-4.63 (m, 2H), 5.34-5.49 (m, 3H), 6.31-6.37 (m, 1H), 7.76 (s, 2H), 8.07-8.14 (m, 1H), 8.95-9.06 (m, 1H), (1 Exchangable proton not observed). LCMS/HPLC (Method-A): retention time 1.04 min, [M+H] 419.1, purity: 97.62%. (Method-B): retention time 1.23 min, [M+H] 419.0, 96.89%. Chiral purity (Method-XVIII): retention time 12.95 min, 100% ee.

Example 43: (R)-5-(1-hydroxy-2-((2-(4-(4-methyl-1-oxo-1,3-dihydroisobenzofuran-5-yl)-1H-pyrazol-1-yl)ethyl)amino)ethyl)-4-methylisobenzofuran-1(3H)-one

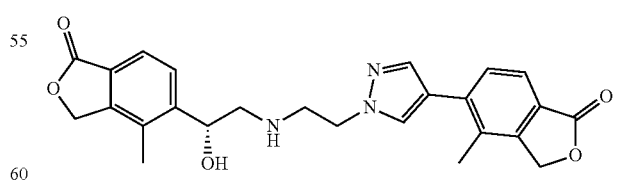

To a stirred solution of Intermediate 113 (0.08 g, 0.25 mmol) in DMF (2 mL) was added K$_2$CO$_3$ (0.07 g, 0.50 mmol) and Intermediate 7-I (0.10 g, 0.50 mmol) at ambient temperature and the reaction mixture was heated at 60° C. for 2 h. The reaction mixture was cooled to ambient temperature, diluted with water (20 mL) and extracted with ethyl acetate (2×30 mL). The combined organic layers were washed with brine (10 mL), dried over anhydrous sodium sulfate and evaporated under reduced pressure. The residue was purified by preparative HPLC [Waters XBridge C18 (19×150 mm) 5 micron; Solvent A: 0.1% TFA, Solvent B: Acetonitrile, Gradient: 5-25% B over 25 min, Flow: 15 mL/min] to obtain Example 43 (0.03 g, 26.40%). $^1$H NMR (400 MHz, DMSO-$d_6$) δ ppm 2.29 (s, 3H), 2.35 (s, 3H), 3.02 (br. s., 1H), 3.18 (d, J=12.23 Hz, 1H), 3.57 (br. s., 2H), 4.58 (t, J=6.36 Hz, 2H), 5.25 (d, J=9.29 Hz, 1H), 5.36-5.48 (m, 4H), 6.37 (d, J=3.42 Hz, 1H), 7.61-7.79 (m, 4H), 7.97 (s, 1H), 8.24 (s, 1H), 8.93 (br. s., 1H). LCMS/HPLC (Method-B): retention time 1.28 min, [M+H] 448, purity: 95.20%. (Method-A): retention time 1.12 min, [M+H] 448, purity: 94.80%. Chiral purity (Method-XVIII): retention time 14.33 min, 58.00% ee.

Example 44: (R)-1-(4-methyl-1-oxo-1,3-dihydroisobenzofuran-5-yl)-2-(((1-(3-methyl-2-oxo-2,3-dihydrobenzo[d]oxazol-5-yl)-1H-pyrazol-4-yl)methyl)amino)ethyl D-valinate

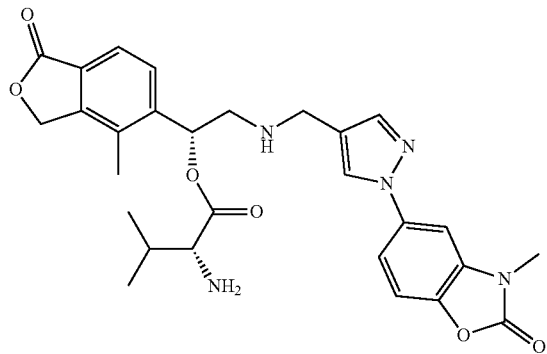 [SMILES: Cc1c([C@H](CNCc2cnn(-c3ccc4oc(=O)n(C)c4c3)c2)OC(=O)[C@H](N)C(C)C)ccc2c1COC2=O]

To a stirred solution of Intermediate 122 (0.12 g, 0.16 mmol) in DCM (5 mL) was added TFA (0.13 mL, 1.63 mmol) and the reaction mixture was stirred at ambient temperature 16 h. The reaction was concentrated to under reduced pressure. The residue was triturated with diethyl ether (30 mL) and purified by preparative HPLC [Intersil ODS (20×250 mm) 5 micron; Solvent A: 0.1% TFA, Solvent B: Acetonitrile, Gradient: 10-100% B over 15 min, Flow: 18 mL/min] to obtain Example 44 (0.11 g, 81.00%). $^1$H NMR (400 MHz, CD$_3$OD) δ ppm 1.02 (dd, J=8.53, 7.03 Hz, 6H), 2.41-2.48 (m, 1H), 2.49 (s, 3H), 3.45 (s, 3H), 3.53 (dd, J=13.80, 3.26 Hz, 1H), 3.75 (dd, J=13.80, 9.79 Hz, 1H), 4.04 (d, J=4.52 Hz, 1H), 4.32-4.44 (m, 2H), 5.40 (d, J=2.01 Hz, 2H), 6.46 (dd, J=9.79, 3.26 Hz, 1H), 7.36 (d, J=8.53 Hz, 1H), 7.51 (dd, J=8.78, 2.26 Hz, 1H), 7.59 (d, J=2.01 Hz, 1H), 7.67 (d, J=7.53 Hz, 1H), 7.78 (d, J=8.03 Hz, 1H), 7.86 (s, 1H), 8.42 (s, 1H), (3 Exchangeable protons not observed). LCMS/HPLC (Method-E): retention time 8.40 min, purity: 98.90%, (Method-G): retention time 9.82 min, purity: 95.80%, LCMS (Method-D): retention time 1.68 min, [M+H] 534.2, Chiral purity (Method-XVII): retention time 16.61 min, 100% ee.

Example 45: (R)-1-(5-(((2-hydroxy-2-(4-methyl-1-oxo-1,3-dihydroisobenzofuran-5-yl)ethyl)amino)methyl)pyrimidin-2-yl)-1H-imidazole-4-carbonitrile

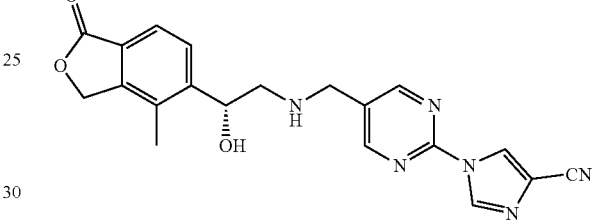

Example 45 was prepared (5.50 g, 4.70%), by using a similar synthetic protocol as that of Example 2-I and starting from Intermediate 98 (0.10 g, 0.30 mmol) and Intermediate 128 (0.08 g, 0.90 mmol). 1H NMR (400 MHz, DMSO-$d_6$) δ ppm 2.24 (s, 3H), 2.67 (d, J=7.58 Hz, 2H), 3.89 (br. s, 2H), 5.03 (br. s, 1H), 5.30-5.42 (m, 2H), 5.56 (br. s, 1H), 7.63-7.69 (m, 2H), 8.77 (d, J=0.98 Hz, 1H), 8.85 (s, 2H), 8.90 (d, J=1.22 Hz, 1H), (1 Exchangeable proton not observed). LCMS/HPLC (Method-A): retention time 0.92 min, [M+H] 391.1, purity: 100%. (Method-B): retention time 1.22 min, [M+H] 391.0, purity: 100%. Chiral purity (Method-XI): retention time 9.98 min, 100% ee.

The examples in Table 2 were synthesized using procedures in Example 1 to 13 and 35 t0 45.

| Ex. | Structure | Name | LCMS (M + H)+ | HPLC/LCMS Method: RT (min.), Purity | NMR |
|---|---|---|---|---|---|
| 46-I | 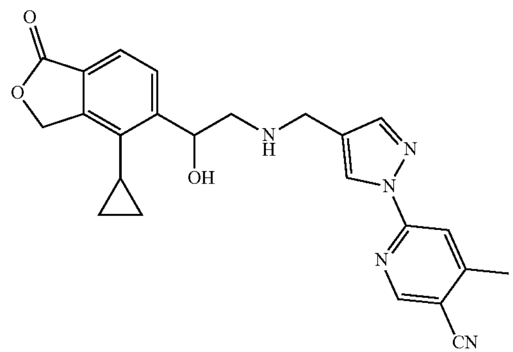 [SMILES: Cc1cc(-n2cc(CNCC(O)c3ccc4c(c3C3CC3)COC4=O)cn2)ncc1C#N] | 6-(4-((2-(4-cyclopropyl-1-oxo-1,3-dihydroisobenzofuran-5-yl)2-hydroxyethyl)amino)methyl)-1H-pyrazol-1-yl)-4-methylnicotinonitrile (Enantiomer-I) | 430.2 | L: 1.28, 98.8% B: 1.07, 100% XII: 6.66, 100% ee | 1H NMR (400 MHz, DMSO-d6) δ 0.56-0.68 (m, 1 H), 0.68-0.79 (m, 1 H), 0.82-0.94 (m, 1 H), 0.97-1.09 (m, 1 H), 1.76-1.89 (m, 1 H), 2.55-2.61 (m, 3 H), 2.69-2.86 (m, 2 H), 3.83 (br. s., 2 H), 5.34-5.58 (m, 3 H), 5.63 (br. s., 1H), 7.63-7.75 (m, 2 H), 7.88 (s, 1 H), 7.98 (s, 1 H), 8.57 (s, 1 H), 8.84 (s, 1 H), (1 Exchangeable proton not observed). |
| 47 | 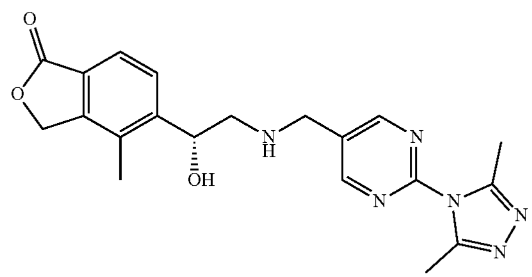 [SMILES: Cc1c([C@@H](O)CNCc2cnc(-n3c(C)nnc3C)nc2)ccc2c1COC2=O] | (R)-5-(2-(((2-(3,5-dimethyl-4H-1,2,4-triazol-5-yl)pyrimidin-4-yl)methyl)amino)-1-hydroxyethyl)-4-methylisobenzofuran-1(3H)-one | 395.2 | L: 0.82, 97.50% M: 0.61, 96.10% | 1H NMR (400 MHz, DMSO-d6) δ 1.90 (s, 1 H), 2.24 (s, 3 H), 2.30 (s, 3 H), 2.63-2.72 (m, 5 H), 3.86 (s, 2 H), 4.95-5.10 (m, 1 H), 5.25-5.44 (m, 2 H), 5.54 (br. s., 1 H), 7.51-7.78 (m, 2 H), 8.84 (s, 2 H). |

-continued

| Ex. | Structure | Name | LCMS (M + H)+ | HPLC/LCMS Method: RT (min.), Purity | NMR |
|---|---|---|---|---|---|
| 48 | 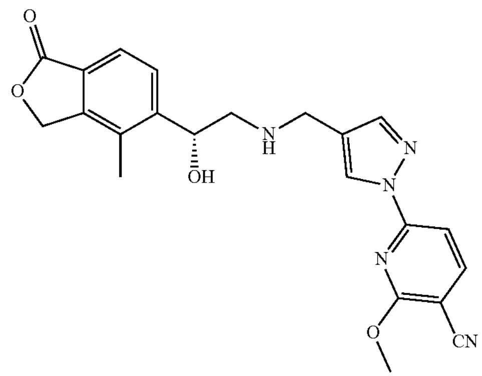 [SMILES: COc1nc(-n2cc(CNC[C@H](O)c3ccc4c(c3C)COC4=O)cn2)ccc1C#N] | (R)-6-(4-(((2-hydroxy-2-(4-methyl-1-oxo-1,3-dihydroisobenzofuran-5-yl)ethyl)amino)methyl)-1H-pyrazol-1-yl)-2-methoxynicotinonitrile | 420.1 | L: 1.32, 99.73% M: 1.06, 99.53% | 1H NMR (400 MHz, DMSO-d6) δ 2.25 (s, 3 H), 2.62-2.71 (m, 2 H), 2.74 (s, 1 H), 2.90 (s, 1 H), 3.71-3.78 (m, 2 H), 4.10 (s, 3 H), 5.04 (dd, J = 7.9, 3.8 Hz, 1 H), 5.28-5.46 (m, 2 H), 7.55 (d, J = 8.1 Hz, 1 H), 7.61-7.74 (m, 2 H), 7.86 (s, 1 H), 8.35 (d, J = 8.3 Hz, 1 H), 8.58 (s, 1 H). |
| 49 | 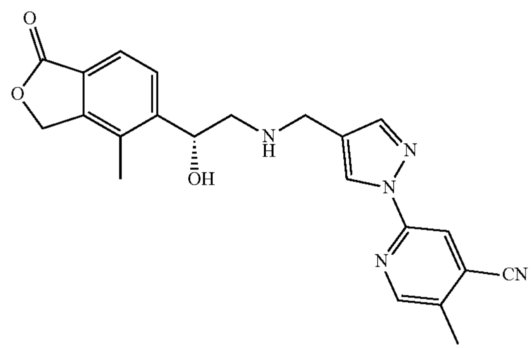 [SMILES: Cc1cnc(-n2cc(CNC[C@H](O)c3ccc4c(c3C)COC4=O)cn2)cc1C#N] | (R)-2-(4-(((2-hydroxy-2-(4-methyl-1-oxo-1,3-dihydroisobenzofuran-5-yl)ethyl)amino)methyl)-1H-pyrazol-1-yl)-5-methylisonicotinonitrile | 404.2 | L: 1.25, 93.4% M: 1.07, 95.08% XIII: 7.18, 100% ee | 1H NMR (400 MHz, DMSO-d6) δ 2.18-2.29 (m, 3 H), 2.97 (br. s., 2 H), 3.11 (br. s., 3 H), 4.23 (br. s, 2 H), 5.23 (d, J = 9.3 Hz, 1 H), 5.31-5.51 (m, 2 H), 6.35 (br. s., 1 H), 7.63-7.82 (m, 2 H), 7.97 (s, 1 H), 8.64 (s, 1 H), 8.78 (s, 1 H). (1 Exchangeable proton not observed). |

-continued

| Ex. | Structure | Name | LCMS (M + H)+ | HPLC/LCMS Method: RT (min.), Purity | NMR |
|---|---|---|---|---|---|
| 50 | 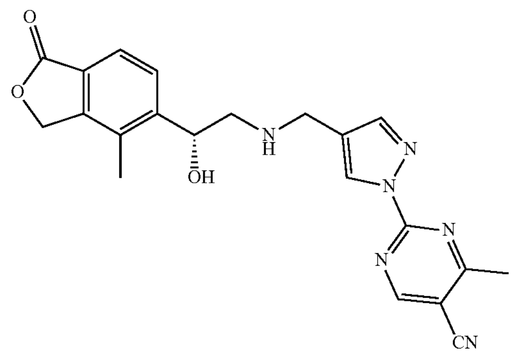 [SMILES: Cc1nc(-n2cc(CNC[C@H](O)c3ccc4c(c3C)COC4=O)cn2)ncc1C#N] | (R)-2-(4-(((2-hydroxy-2-(4-methyl-1-oxo-1,3-dihydroisobenzofuran-5-yl)ethyl)amino)methyl)-1H-pyrazol-1-yl)-4-methylpyrimidine-5-carbonitrile (Enantiomer-I) | 405.2 | P: 8.00, 97.90% Q: 8.75, 98.92% | 1H NMR (400 MHz, CD3OD) δ ppm 2.34 (s, 3 H), 2.80 (s, 3 H), 2.82-2.86 (m, 2 H), 3.90 (d, J = 2.89 Hz, 2 H), 5.19-5.24 (m, 1 H), 5.36 (s, 2 H), 7.72 (s, 1 H), 7.75-7.79 (m, 1 H), 7.95 (s, 1 H), 8.68 (s, 1 H), 9.02 (s, 1 H), (2 Exchangeable proton not observed). |
| 51 | 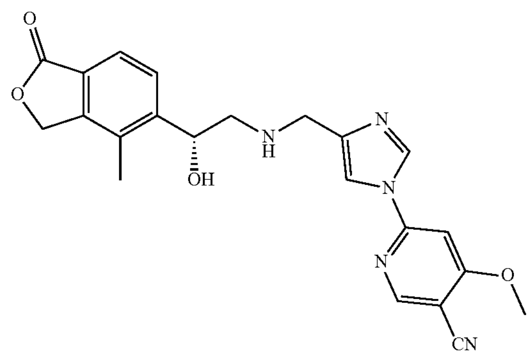 [SMILES: COc1cc(-n2cnc(CNC[C@H](O)c3ccc4c(c3C)COC4=O)c2)ncc1C#N] | (R)-6-(4-(((2-hydroxy-2-(4-methyl-1-oxo-1,3-dihydroisobenzofuran-5-yl)ethyl)amino)methyl)-1H-imidazol-1-yl)-4-methoxynicotinonitrile | 420.2 | G: 5.38, 97.23% F: 4.66, 97.98% V: 6.08, 100% ee | 1H NMR (400 MHz, DMSO-d6) δ ppm 2.24 (s, 3 H), 2.60-2.77 (m, 3 H), 3.62-3.77 (m, 2 H), 4.10 (s, 3 H) 5.02-5.04 (m, 1 H) 5.37 (d, J = 3.01 Hz, 2 H), 5.49 (d, J = 4.02 Hz, 1 H), 7.58 (s, 1 H), 7.66 (d, J = 5.52 Hz, 2 H), 7.85-7.90 (m, 1 H), 8.58-8.62 (m, 1 H), 8.73 (s, 1 H). |

| Ex. | Structure | Name | LCMS (M + H)+ | HPLC/LCMS Method: RT (min.), Purity | NMR |
|---|---|---|---|---|---|
| 52 | 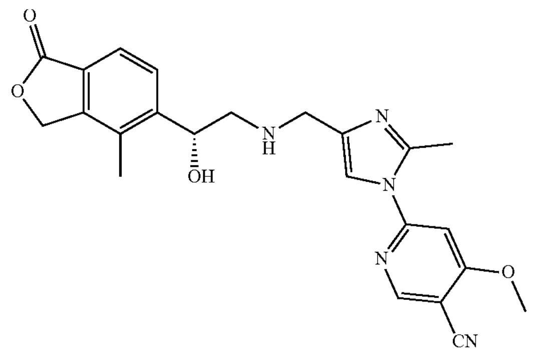 [SMILES: COc1cc(-n2cc(CNC[C@H](O)c3ccc4c(c3C)COC4=O)nc2C)ncc1C#N] | (R)-6-(4-(((2-hydroxy-2-(4-methyl-1-oxo-1,3-dihydroisobenzofuran-5-yl)ethyl)amino)methyl)-2-methyl-1H-imidazol-1-yl)-4-methoxynicotinonitrile | 434.1 | A: 1.01, 96.52%. B: 1.21, 95.84%. XI: 8.65 66% ee | 1H NMR (300 MHz, DMSO-d6) δ ppm 2.25 (s, 3 H), 2.26-2.29 (m, 3 H), 2.55 (m, 2 H), 3.64 (d, J = 6.47 Hz, 2 H), 4.09 (s, 3 H), 5.01-5.04 (m, 1H), 5.36-5.39 (m, 2 H), 7.37 (s, 1 H), 7.55 (s, 1 H), 7.67 (d, J = 3.35 Hz, 2 H), 8.79 (s, 1 H), (2 Exchangeable proton not observed). |
| 53 | 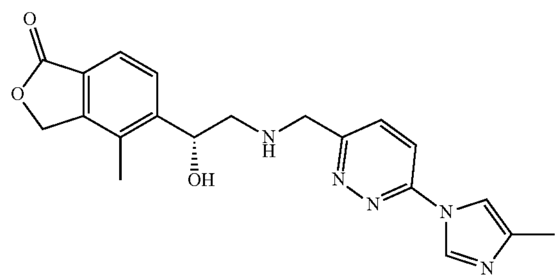 [SMILES: Cc1cn(-c2ccc(CNC[C@H](O)c3ccc4c(c3C)COC4=O)nn2)cn1] | (R)-5-(1-hydroxy-2-(((6-(4-methyl-1H-imidazol-1-yl)pyridazin-3-yl)methyl)amino)ethyl)-4-methylisobenzofuran-1(3H)-one | 380.1 | R: 0.44, 96.68% S: 1.07, 94.81% | 1H NMR (400 MHz, DMSO-d6) δ ppm 2.20 (s, 3 H), 2.23 (s, 3 H), 2.63-2.69 (m, 2 H), 4.06 (s, 3 H), 5.03 (m, J = 4.28 Hz, 1 H), 5.37 (d, J = 3.00 Hz, 2 H), 7.66 (d, J = 3.91 Hz, 2 H), 7.75 (s, 1 H), 7.88 (d, J = 9.05 Hz, 1 H), 8.08 (d, J = 9.11 Hz, 1 H), 8.50 (d, J = 1.16 Hz, 1 H), (1 Exchangeable proton not observed). |
| 54 | 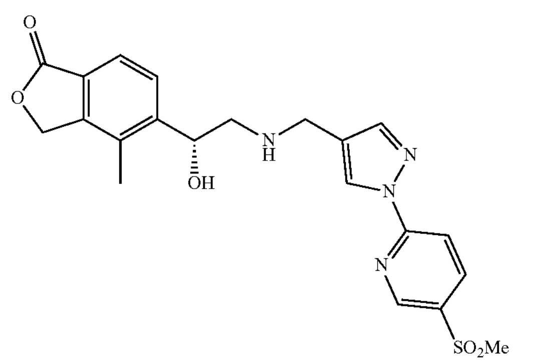 [SMILES: Cc1c([C@@H](O)CNCc2cnn(-c3ccc(S(C)(=O)=O)cn3)c2)ccc2c1COC2=O] | (R)-5-(1-hydroxy-2-(((1-(6-(methylsulfonyl)pyridin-3-yl)-1H-pyrazol-4-yl)methyl)amino)ethyl)-4-methylisobenzofuran-1(3H)-one | 442.4 | R: 1.07, 100% S: 1.28, 100% | 1H NMR (400 MHz, DMSO-d6) δ ppm 1.90 (s, 3 H), 2.23 (s, 3 H), 2.58-2.71 (m, 2 H), 3.70 (d, J = 4.22 Hz, 2 H), 4.98-5.03 (m, 1 H), 5.36 (d, J = 2.57 Hz, 2 H), 7.66 (d, J = 5.01 Hz, 2 H), 7.76 (s, 1 H), 7.84 (d, J = 8.80 Hz, 1 H), 8.19 (dd, J = 8.80, 2.45 Hz, 1 H), 8.42 (s, 1 H), 8.57 (d, J = 2.45 Hz, 1 H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 55 | 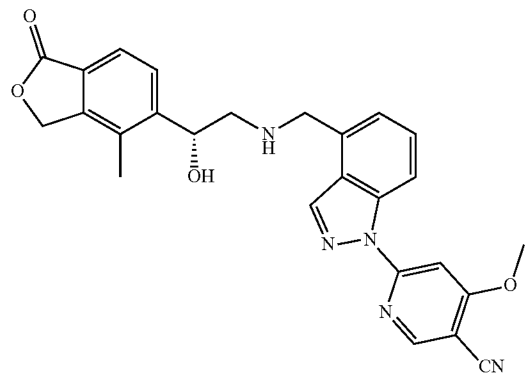 [SMILES: COc1cc(-n2ncc3c(CNC[C@H](O)c4ccc5c(c4C)COC5=O)cccc32)ncc1C#N] | ((R)-6-(4-(((2-hydroxy-2-(4-methyl-1-oxo-1,3-dihydroisobenzofuran-5-yl)ethyl)amino)methyl)-1H-indazol-1-yl)-4-methoxynicotinonitrile, | 470.2 | E: 5.96, 99.78% G: 6.16, 99.24% XX: 3.59, 100% ee | 1H NMR (400 MHz, DMSO-d6) δ ppm 2.24 (s, 3 H), 2.99-3.25 (m, 2 H), 4.20 (s, 3 H), 4.59 (br. s., 2 H), 5.29 (d, J = 10.54 Hz, 1 H), 5.40 (d, J = 5.02 Hz, 2 H), 6.33 (d, J = 3.51 Hz, 1 H), 7.35 (d, J = 7.03 Hz, 1 H), 7.46 (dd, J = 8.78, 6.78 Hz, 1 H), 7.68-7.75 (m, 2 H), 7.82 (d, J = 9.04 Hz, 1 H), 7.98 (s, 1 H), 8.94 (s, 1 H), 9.73 (s, 1 H), (1 Exchangeable proton not observed). |
| 56 | 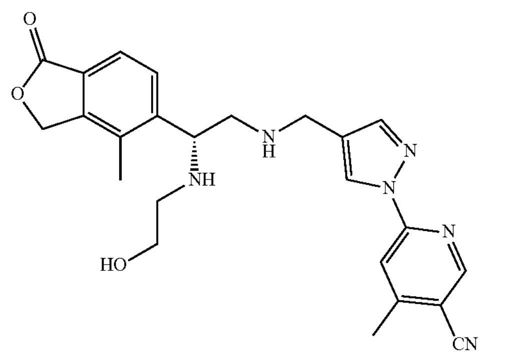 [SMILES: Cc1cc(-n2cc(CNC[C@H](NCCO)c3ccc4c(c3C)COC4=O)cn2)ncc1C#N] | (R)-6-(4-(((2-((2-hydroxyethyl)amino)-2-(4-methyl-1-oxo-1,3-dihydroisobenzofuran-5-yl)ethyl)amino)methyl)-1H-pyrazol-1-yl)-4-methylnicotinonitrile | 447.1 | S: 1.39, 98.90% R: 1.07, 99.30% XVIII: 10.65, 100% ee | 1H NMR (400 MHz, DMSO-d6) δ ppm 2.25 (s, 3 H), 2.31-2.45 (m, 2 H), 2.57 (s, 4 H), 2.65 (dd, J = 12.23, 3.42 Hz, 1 H), 3.40-3.48 (m, 2 H), 3.71 (br. s., 2 H), 4.12 (dd, J = 8.56, 3.91 Hz, 1 H), 5.36 (s, 2 H), 7.64 (d, J = 8.07 Hz, 1 H), 7.73 (d, J = 8.07 Hz, 1 H), 7.85 (s, 1 H), 7.97 (s, 1 H), 8.52 (s, 1 H), 8.83 (s, 1 H), (3 Exchangeable protons not observed). |

| Ex. | Structure | Name | LCMS (M + H)+ | HPLC/LCMS Method: RT (min.), Purity | NMR |
|---|---|---|---|---|---|
| 57 | 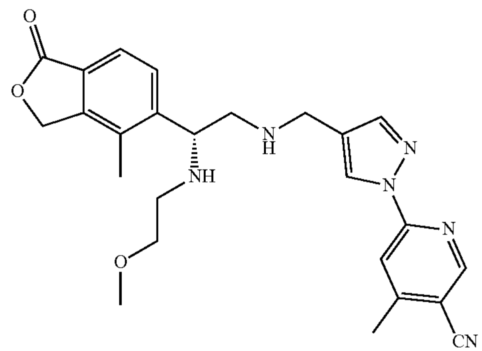 [SMILES: COCCN[C@@H](CNCc1cnn(-c2cc(C)c(C#N)cn2)c1)c1ccc2c(c1C)COC2=O] | (R)-6-(4-(((2-((2-methoxyethyl)amino)-2-(4-methyl-1-oxo-1,3-dihydroisobenzofuran-5-yl)ethyl)amino)methyl)-1H-pyrazol-1-yl)-4-methylnicotinonitrile | 461.1 | S: 1.65, 94.60% R: 1.20, 94.70% XVIII: 3.72, 99.05% ee | $^1$H NMR (400 MHz, CDCl$_3$) δ ppm 2.30 (s, 3 H), 2.59-2.63 (m, 5 H), 2.75 (dd, J = 12.05, 9.04 Hz, 1 H), 2.83-2.88 (m, 1 H), 3.35 (s, 3 H), 3.40-3.51 (m, 2 H), 3.80 (d, J = 5.02 Hz, 2 H), 4.20 (dd, J = 8.78, 4.27 Hz, 1 H), 5.25 (s, 2 H), 7.67 (d, J = 8.03 Hz, 1 H), 7.73 (s, 1 H), 7.77 (d, J = 8.03 Hz, 1 H), 7.94 (s, 1 H), 8.45 (s, 1 H), 8.58 (s, 1 H), (2 Exchangeable protons not observed). |
| 58 | 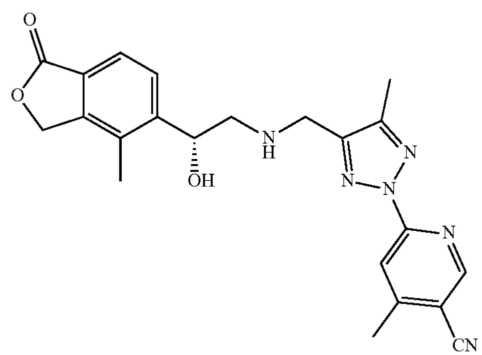 [SMILES: Cc1cc(-n2nc(C)c(CNC[C@H](O)c3ccc4c(c3C)COC4=O)n2)ncc1C#N] | (R)-6-(4-(((2-hydroxy-2-(4-methyl-1-oxo-1,3-dihydroisobenzofuran-5-yl)ethyl)amino)methyl)-5-methyl-2H-1,2,3-triazol-2-yl)-4-methylnicotinonitrile | 419.2 | S: 1.20, 94.70% R: 0.92, 94.50% XVIII: 13.67, 100% ee | $^1$H NMR (400 MHz, DMSO-d6) δ 2.22 (s, 3H), 2.33-2.37 (m, 3H), 2.58-2.63 (m, 3H), 2.69 (d, J = 15.7 Hz, 2H), 3.96 (br. s., 2H), 5.04 (br. s., 1H), 5.22-5.47 (m, 2H), 5.57 (br. s., 1H), 7.54-7.80 (m, 2H), 8.02 (s, 1H), 8.89 (s, 1H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 59 | 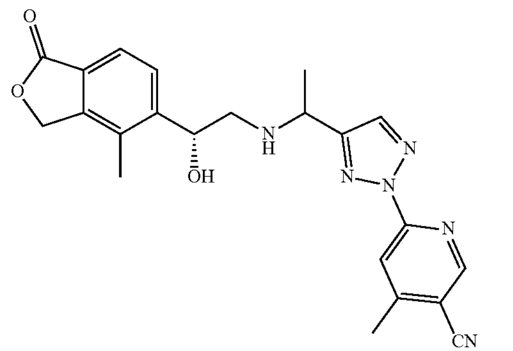 [SMILES: Cc1cc(-n2ncc(C(C)NC[C@H](O)c3ccc4c(c3C)COC4=O)n2)ncc1C#N] | 6-(4-(1-(((R)-2-hydroxy-2-(4-methyl-1-oxo-1,3-dihydroisobenzofuran-5-yl)ethyl)amino)ethyl)-2H-1,2,3-triazol-2-yl)-4-methylnicotinonitrile (Enantiomer-I: Diastereomer-I) | 419.2 | T: 7.42, 99.3% U: 6.294, 99.65% XXI: 4.20, 98.4% ee | $^1$H NMR (400 MHz, CDCl$_3$) δ 1.58 (d, J = 6.8 Hz, 3 H), 2.21 (s, 3 H), 2.66-2.69 (m, 4 H), 2.71 (d, J = 9.0 Hz, 1 H), 2.91 (dd, J = 12.3, 3.3 Hz, 1 H), 4.24 (d, J = 6.8 Hz, 1 H), 4.95-4.99 (m, 1 H), 5.21 (d, J = 2.2 Hz, 2 H), 7.72-7.79 (m, 2 H), 7.90 (s, 1 H), 8.04-8.06 (m, 1 H), 8.77 (s, 1 H), (1 Exchangeable proton not observed). |
| 60 | 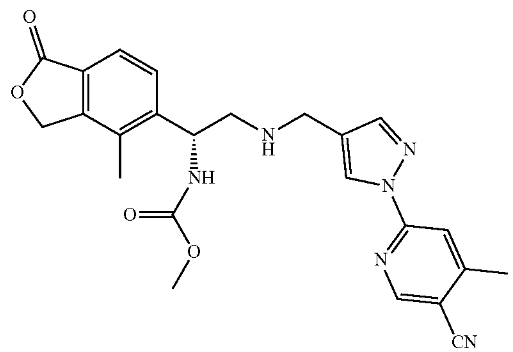 [SMILES: COC(=O)N[C@@H](CNCc1cnn(-c2cc(C)c(C#N)cn2)c1)c1ccc2c(c1C)COC2=O] | methyl (R)-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)carbamate | 461.1 (M − H) | A: 1.19, 98.49% B: 1.58, 98.49% XIV: 7.07, 97.68% ee | $^1$H NMR (400 MHz, DMSO-d$_6$) δ ppm 2.29 (s, 3 H), 2.57 (s, 3 H), 2.62-2.70 (m, 1 H), 2.72-2.83 (m, 1 H), 3.49 (s, 3 H), 3.60-3.74 (m, 2 H), 4.99 (d, J = 5.62 Hz, 1 H), 5.30-5.45 (m, 2 H), 7.51 (d, J = 8.31 Hz, 1 H), 7.65 (d, J = 8.07 Hz, 1 H), 7.80 (s, 1 H), 7.84 (d, J = 7.83 Hz, 1 H), 7.97 (s, 1 H), 8.45 (s, 1 H), 8.83 (s, 1 H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 61 | 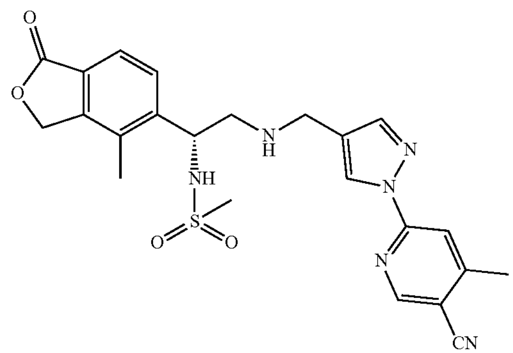 [SMILES: Cc1cc(-n2cc(CNC[C@H](NS(C)(=O)=O)c3ccc4c(c3C)COC4=O)cn2)ncc1C#N] | (R)-N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)methanesulfonamide | 481.1 | A: 1.17, 98.17% B: 1.54, 96.36% XIV: 7.07, 96.6% ee | $^1$H NMR 400 MHz, DMSO-d$_6$) δ ppm 2.28 (s, 3 H), 2.57 (s, 3 H), 2.67 (br. s., 1 H), 2.72-2.84 (m, 4 H), 3.69 (br. s., 2 H), 4.82 (br. s., 1 H), 5.30-5.44 (m, 2 H), 7.57-7.65 (m, 1 H), 7.67-7.75 (m, 1 H), 7.81 (s, 1 H), 7.97 (s, 1 H), 8.47 (s, 1 H), 8.83 (s, 1 H). (2 Exchangeable protons not observed). |
| 62 | 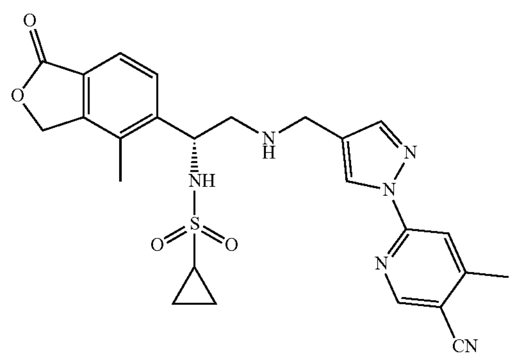 [SMILES: Cc1cc(-n2cc(CNC[C@H](NS(=O)(=O)C3CC3)c3ccc4c(c3C)COC4=O)cn2)ncc1C#N] | (R)-N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)cyclopropanesulfonamide | 507.1 | A: 1.28, 99.34% B: 1.65, 99.21% VIII: 15.82, 97.12% ee | $^1$H NMR (400 MHz, DMSO-d$_6$) δ ppm 0.59 (d, J = 11.74 Hz, 1 H), 0.65-0.88 (m, 3 H), 2.12-2.22 (m, 1 H), 2.28 (s, 3 H), 2.57 (s, 3 H), 2.64-2.76 (m, 1 H), 2.84 (dd, J = 12.96, 8.31 Hz, 1 H), 3.59-3.75 (m, 2 H), 4.78-4.89 (m, 1 H), 5.30-5.45 (m, 2 H), 7.67 (s, 2 H), 7.80 (s, 1 H), 7.97 (s, 1 H), 8.45 (s, 1 H), 8.83 (s, 1 H). (2 Exchangeable protons not observed). |

-continued

| Ex. | Structure | Name | LCMS (M + H)+ | HPLC/LCMS Method: RT (min.), Purity | NMR |
|---|---|---|---|---|---|
| 63 | 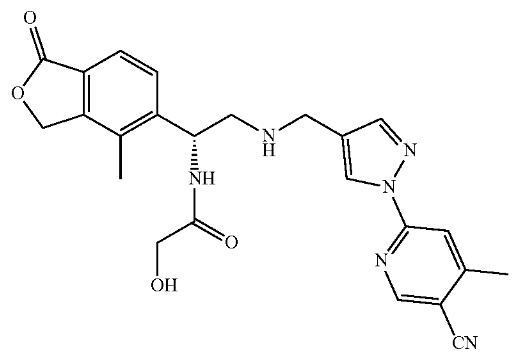 [SMILES: Cc1cc(-n2cc(CNC[C@H](NC(=O)CO)c3ccc4c(c3C)COC4=O)cn2)ncc1C#N] | (R)-N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)-2-hydroxyacetamide | 461.1 | A: 1.10, 95.96% B: 1.36, 95.32% VIII: 8.76, 100% ee | ¹H NMR (400 MHz, DMSO-d₆) δ ppm 2.27-2.35 (m, 3 H), 2.57 (s, 3 H), 2.77 (dd, J = 12.10, 5.50 Hz, 1H), 2.83-2.95 (m, 1 H), 3.66 (s, 2 H), 3.75-3.87 (m, 2 H), 5.18-5.30 (m, 1 H), 5.31-5.44 (m, 2 H), 5.52 (t, J = 5.99 Hz, 1 H) 7.52-7.59 (m, 1 H), 7.61-7.69 (m, 1 H), 7.82 (s, 1 H), 7.97 (s, 1 H), 8.31 (d, J = 7.34 Hz, 1 H), 8.48 (s, 1 H), 8.83 (s, 1 H), (1 Exchangeable proton not observed). |
| 64 | 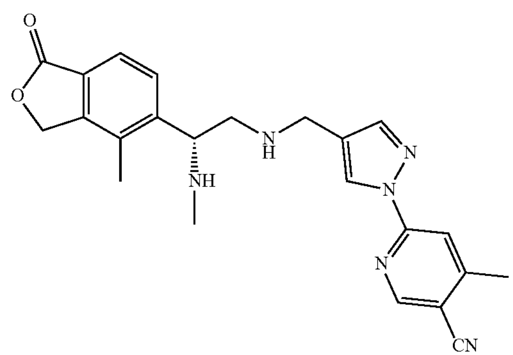 [SMILES: CN[C@@H](CNCc1cnn(-c2cc(C)c(C#N)cn2)c1)c1ccc2c(c1C)COC2=O] | (R)-4-methyl-6-(4-(((2-(4-methyl-1-oxo-1,3-dihydroisobenzofuran-5-yl)-2-(methylamino)ethyl)amino)methyl)-1H-pyrazol-1-yl)nicotinonitrile | 417.2 | A: 0.76, 96.84% B: 1.18, 98.13% XIV: 9.53, 96.34% ee | ¹H NMR (400 MHz, DMSO-d₆) δ ppm 2.13 (s, 3 H), 2.25 (s, 3 H), 2.53-2.62 (m, 5 H), 3.68-3.70 (m, 2 H), 3.93-4.09 (m, 1 H), 5.36 (s, 2 H), 7.64 (d, J = 8.0 Hz, 1 H), 7.71 (d, J = 8.0 Hz, 1 H), 7.85 (s, 1 H), 7.97 (s, 1 H), 8.51 (s, 1 H), 8.83 (s, 1 H), (2 Exchangeable protons not observed). |

| Ex. | Structure | Name | LCMS (M + H)+ | HPLC/LCMS Method: RT (min.), Purity | NMR |
|---|---|---|---|---|---|
| 65 | 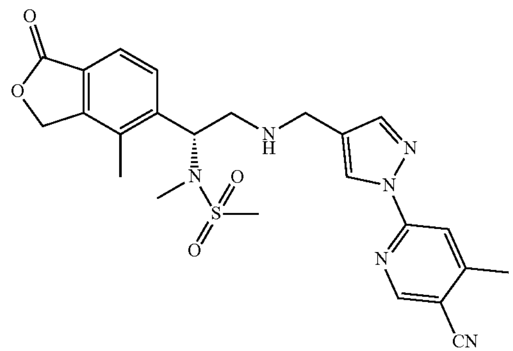 [SMILES: Cc1cc(-n2cc(CNC[C@@H](c3ccc4c(c3C)COC4=O)N(C)S(C)(=O)=O)cn2)ncc1C#N] | (R)-N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)-N-methylmethanesulfonamide | 495.0 | A: 1.13, 98.46% B: 1.71, 98.28% III: 17.00, 93.00% ee | 1H NMR (400 MHz, DMSO-d6) δ ppm 2.32 (s, 3 H), 2.57 (s, 3 H), 2.78 (s, 3 H), 2.88 (d, J = 8.07 Hz, 1 H), 2.99 (s, 3 H), 3.06-3.21 (m, 1 H), 3.73 (br. s., 2 H), 5.29 (d, J = 10.03 Hz, 1 H), 5.32-5.48 (m, 2 H), 7.57 (d, J = 8.31 Hz, 1 H), 7.67 (d, J = 8.07 Hz, 1 H), 7.86 (s, 1 H), 7.97 (s, 1 H), 8.53 (s, 1 H), 8.83 (s, 1H), (1 Exchangeable proton not observed). |
| 66 | 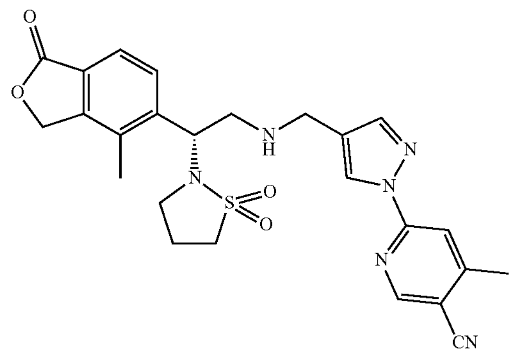 [SMILES: Cc1cc(-n2cc(CNC[C@@H](c3ccc4c(c3C)COC4=O)N3CCCS3(=O)=O)cn2)ncc1C#N] | (R)-6-(4-(((2-(1,1-dioxidoisothiazolidin-2-yl)-2-(4-methyl-1-oxo-1,3-dihydroisobenzofuran-5-yl)ethyl)amino)methyl)-1H-pyrazol-1-yl)-4-methylnicotinonitrile | 507.1 | A: 1.35, 96.38% B: 1.68, 96.27% V: 12.49, 92.79% ee | 1H NMR (400 MHz, DMSO-d6) δ ppm 2.07-2.20 (m, 1 H), 2.25-2.35 (m, 1 H), 2.39 (s, 3 H), 2.57-2.64 (m, 3 H), 2.73-2.83 (m, 1 H), 3.13-3.28 (m, 2 H), 3.47-3.60 (m, 2 H), 3.88 (br. s., 1 H), 4.26 (br. s., 2 H), 5.31-5.51 (m, 3 H), 7.66 (d, J = 8.07 Hz, 1 H), 7.72-7.80 (m, 1 H), 8.02 (d, J = 7.34 Hz, 2 H), 8.83 (s, 1 H), 8.89 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 67 | 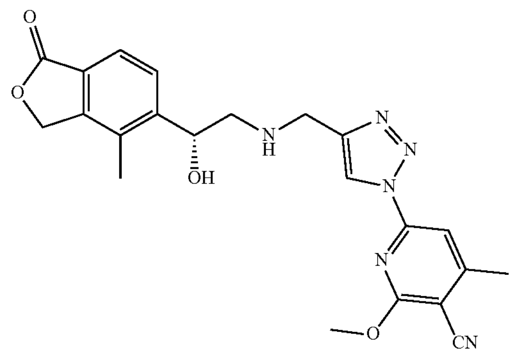 [SMILES: COc1nc(-n2cc(CNC[C@H](O)c3ccc4c(c3C)COC4=O)nn2)cc(C)c1C#N] | (R)-6-(4-(((2-hydroxy-2-(4-methyl-1-oxo-1,3-dihydroisobenzofuran-5-yl)ethyl)amino)methyl)-1H-1,2,3-triazol-1-yl)-2-methoxy-4-methylnicotinonitrile | 435.2 | A: 1.06, 100%, B: 1.29, 100%, III: 11.41, 100% ee | 1H NMR (400 MHz, DMSO-d6) δ 2.25 (s, 3 H), 2.59 (s, 3 H), 2.63-2.77 (m, 2 H), 3.84-4.01(m, 2 H), 4.04-4.16 (m, 3 H), 5.03 (br. s., 1 H), 5.25-5.42 (m, 2 H), 5.51 (br. s., 1 H), 7.56-7.72 (m, 2 H), 7.82 (s, 1 H), 8.74 (s, 1 H), (1 Exchangeable proton not observed). |
| 68 | 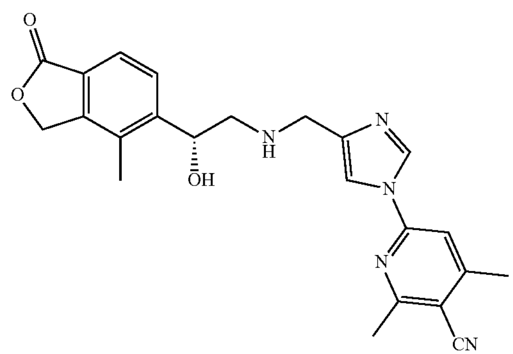 | (R)-6-(4-(((2-hydroxy-2-(4-methyl-1-oxo-1,3-dihydroisobenzofuran-5-yl)ethyl)amino)methyl)-1H-imidazol-1-yl)-2,4-dimethylnicotinonitrile | 418.1 | A: 1.18, 94.87%, B: 1.34, 96.56%, III: 8.42, 100% ee | 1H NMR (400 MHz, DMSO-d$_6$) δ ppm 2.25 (s, 3 H), 2.53 (s, 3 H), 2.61-2.79 (m, 5 H), 3.66-3.82 (m, 2 H), 5.04 (d, J = 4.89 Hz, 1 H), 5.31-5.43 (m, 2 H), 5.53 (br. s., 1 H), 7.61-7.73 (m, 2 H), 7.79 (d, J = 3.42 Hz, 1 H), 8.53 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 69 | 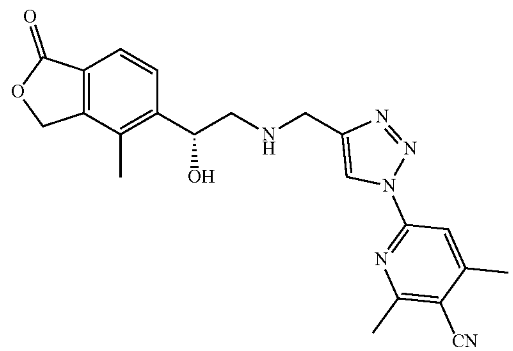 [SMILES: Cc1cc(-n2cc(CNC[C@H](O)c3ccc4c(c3C)COC4=O)nn2)nc(C)c1C#N] | (R)-6-(4-(((2-hydroxy-2-(4-methyl-1-oxo-1,3-dihydroisobenzofuran-5-yl)ethyl)amino)methyl)-1H-1,2,3-triazol-1-yl)-2,4-dimethylnicotinonitrile | 419.1 | C: 9.97, 96.44% G: 11.15, 95.97% III: 13.74, 100% ee | 1H NMR (400 MHz, DMSO-d6) δ 2.25 (s, 3 H), 2.62 (s, 3 H), 2.64-2.71 (m, 3 H), 2.73 (s, 3 H), 3.82-3.99 (m, 2 H), 4.96-5.07 (m, 1 H), 5.26-5.42 (m, 2 H), 5.48 (d, J = 3.7 Hz, 1 H), 7.56-7.71 (m, 2 H), 8.09 (s, 1 H), 8.65 (s, 1 H). |
| 70 | 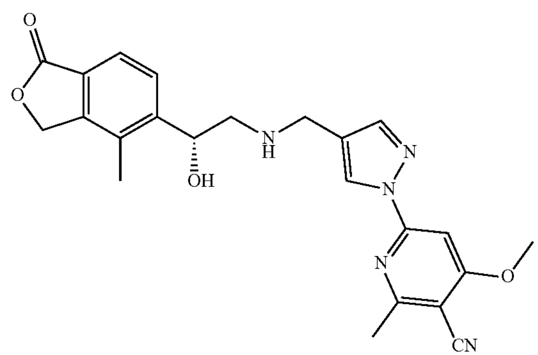 [SMILES: COc1cc(-n2cc(CNC[C@H](O)c3ccc4c(c3C)COC4=O)cn2)nc(C)c1C#N] | (R)-6-(4-(((2-hydroxy-2-(4-methyl-1-oxo-1,3-dihydroisobenzofuran-5-yl)ethyl)amino)methyl)-1H-pyrazol-1-yl)-4-methoxy-2-methylnicotinonitrile | 434.2 | A: 1.06, 100% B: 1.26, 100% V: 6.22, 100% ee | 1H NMR (400 MHz, DMSO-d6) δ 2.24 (s, 3 H), 2.62 (s, 3 H), 2.73 (br. s., 2 H), 3.80 (br. s., 2 H), 4.08 (s, 3 H), 5.06 (br. s., 1 H), 5.29-5.45 (m, 2 H), 5.62 (s, 1 H), 7.46 (s, 1 H), 7.62-7.73 (m, 2 H), 7.86 (s, 1 H), 8.55 (s, 1 H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 71 | 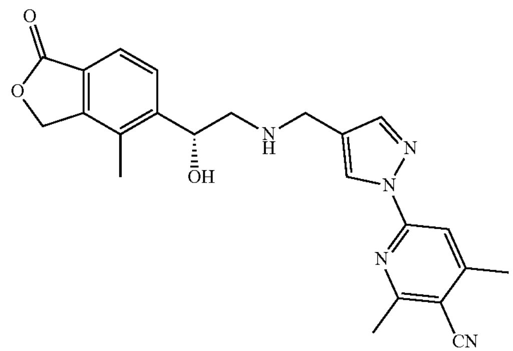 | (R)-6-(4-(((2-hydroxy-2-(4-methyl-1-oxo-1,3-dihydroisobenzofuran-5-yl)ethyl)amino)methyl)-1H-pyrazol-1-yl)-2,4-dimethylnicotinonitrile | 418.1 | A: 1.35, 99.71% B: 1.59, 98.92% XIV: 7.32, 99.68% ee | $^1$H NMR (400 MHz, DMSO-d$_6$) δ ppm 2.23 (s, 3 H), 2.55 (s, 3 H), 2.62-2.73 (m, 5 H), 3.74 (d, J = 2.93 Hz, 2 H), 5.02 (dd, J = 7.58, 3.91 Hz, 1 H), 5.27-5.44 (m, 2 H), 7.59-7.73 (m, 2 H), 7.81 (d, J = 9.54 Hz, 2 H), 8.51 (s, 1 H), (2 Exchangeable protons not observed). |
| 72 | 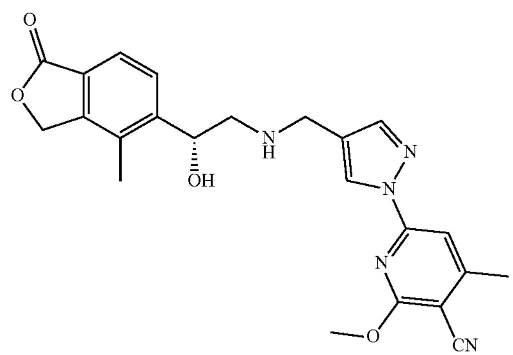 | (R)-6-(4-(((2-hydroxy-2-(4-methyl-1-oxo-1,3-dihydroisobenzofuran-5-yl)ethyl)amino)methyl)-1H-pyrazol-1-yl)-2-methoxy-4-methylnicotinonitrile | 434.2 | A: 1.11, 99.30% B: 1.34, 99.20% V: 6.06, 100% ee | $^1$H NMR (400 MHz, DMSO-d6) δ 2.27 (s, 3 H), 2.55 (s, 3 H), 3.00 (br. s., 1 H), 3.12 (br. s., 1 H), 4.09 (s, 3 H), 4.24 (br. s., 2 H), 5.25 (d, J = 10.0 Hz, 1 H), 5.33-5.52 (m, 2 H), 6.34 (br. s., 1 H), 7.58 (s, 1 H), 7.68-7.81 (m, 2 H), 8.01 (s, 1 H), 8.84 (s, 1 H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 73 | 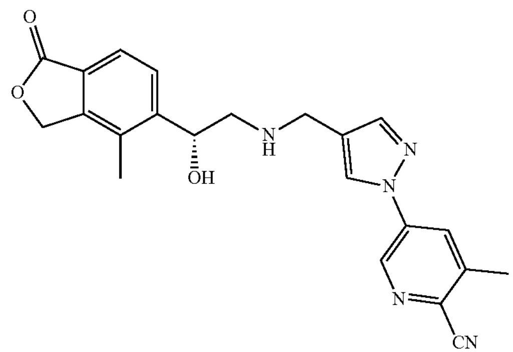 [SMILES: Cc1cc(-n2cc(CNC[C@H](O)c3ccc4c(c3C)COC4=O)cn2)cnc1C#N] | (R)-5-(4-(((2-hydroxy-2-(4-methyl-1-oxo-1,3-dihydroisobenzofuran-5-yl)ethyl)amino)methyl)-1H-pyrazol-1-yl)-3-methylpicolinonitrile | 404.1 | A: 1.11, 97.29% B: 1.31, 97.36% | 1H NMR (400 MHz, DMSO-d6) δ ppm 2.23 (s, 3 H), 2.56 (s, 3 H), 2.62-2.71 (m, 2 H), 3.72 (br. s., 2 H), 4.99-5.09 (m, 1 H), 5.37 (d, J = 3.18 Hz, 3 H), 7.67 (d, J = 5.62 Hz, 2 H), 7.84 (s, 1 H), 8.35 (d, J = 2.45 Hz, 1 H), 8.57 (s, 1 H), 9.07 (d, J = 2.20 Hz, 1 H), (1 Exchangable proton not observed). |
| 74 | 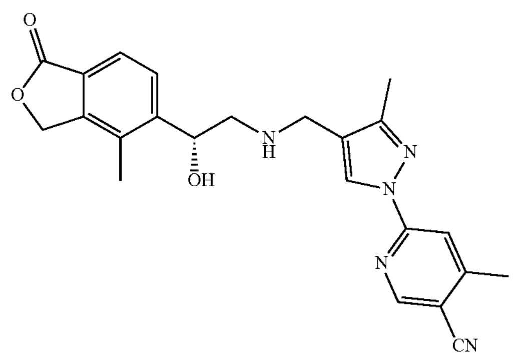 [SMILES: Cc1cc(-n2cc(CNC[C@H](O)c3ccc4c(c3C)COC4=O)c(C)n2)ncc1C#N] | (R)-6-(4-(((2-hydroxy-2-(4-methyl-1-oxo-1,3-dihydroisobenzofuran-5-yl)ethyl)amino)methyl)-3-methyl-1H-pyrazol-1-yl)-4-methylnicotinonitrile | 418.2 | A: 1.158, 98.163% B: 1.454, 100% I: 17.89 100% ee | 1H NMR (400 MHz, DMSO-d6) δ ppm 2.28 (s, 6 H), 2.61 (s, 3 H), 2.71-2.82 (m, 2 H), 3.66 (m, 2 H), 5.09 (m, 1 H), 5.37-5.47 (d, J = 3.18 Hz, 3 H), 7.63-7.69 (d, J = 8.07 Hz, 1 H), 7.89 (s, 1 H), 8.02 (s, 1 H), 8.39 (s, 1 H), 8.78 (s, 1 H), (1 Exchangable proton not observed). |

| Ex. | Structure | Name | LCMS (M + H)+ | HPLC/LCMS Method: RT (min.), Purity | NMR |
|---|---|---|---|---|---|
| 75 | 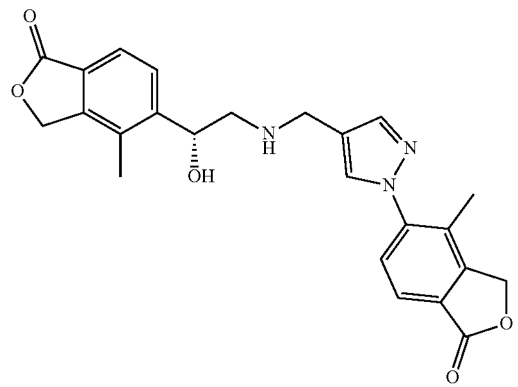 [SMILES: Cc1c([C@@H](O)CNCc2cnn(-c3ccc4c(c3C)COC4=O)c2)ccc2c1COC2=O] | (R)-5-(1-hydroxy-2-(((1-(4-methyl-1-oxo-1,3-dihydroisobenzofuran-5-yl)-1H-pyrazol-4-yl)methyl)amino)ethyl)-4-methylisobenzofuran-1(3H)-one | 434.1 | A: 1.01, 97.97% B: 1.14, 96.84% XIV: 6.13 100% ee | 1H NMR (400 MHz, DMSO-d6) δ ppm 2.25 (s, 3 H), 2.27 (s, 3 H), 3.17 (s, 2 H), 4.24 (br. s., 2 H), 5.29 (dd, J = 10.03, 1.96 Hz, 1 H), 5.41 (d, J = 5.14 Hz, 2 H), 5.50 (s, 2 H), 7.60 (d, J = 8.07 Hz, 1 H), 7.74 (s, 2 H), 7.84 (d, J = 8.07 Hz, 1 H), 7.95 (s, 1 H), 8.29 (s, 1 H), 9.04-9.41 (m, 1 H). (1 Exchangable proton not observed). |
| 76 | 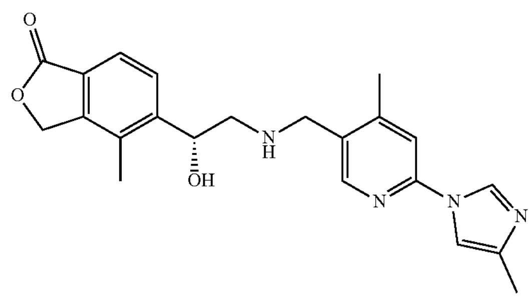 [SMILES: Cc1cn(-c2cc(C)c(CNC[C@H](O)c3ccc4c(c3C)COC4=O)cn2)cn1] | (R)-5-(1-hydroxy-2-(((4-methyl-6-(4-methyl-1H-imidazol-1-yl)pyridin-3-yl)methyl)amino)ethyl)-4-methylisobenzofuran-1(3H)-one | 393.1 | R: 0.85, 99.20% S: 1.37, 99.24% XIV: 10.36 99.10% ee | 1H NMR (400 MHz, DMSO-d6) δ ppm 2.16 (s, 3 H), 2.23 (s, 3 H), 2.36 (s, 3 H), 2.65-2.73 (m, 2 H), 3.78 (s, 2 H), 5.03 (dd, J = 7.34, 4.40 Hz, 1 H), 5.36 (d, J = 3.18 Hz, 2 H), 5.42-5.56 (m, 1 H), 7.53-7.69 (m, 4 H), 8.25 (s, 1 H), 8.34 (s, 1 H). (1 Exchangable proton not observed). |
| 77 | 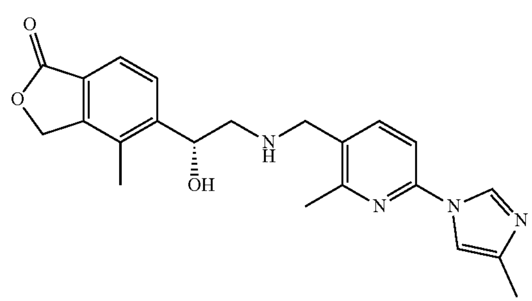 [SMILES: Cc1cn(-c2ccc(CNC[C@H](O)c3ccc4c(c3C)COC4=O)c(C)n2)cn1] | (R)-5-(1-hydroxy-2-(((2-methyl-6-(4-methyl-1H-imidazol-1-yl)pyridin-3-yl)methyl)amino)ethyl)-4-methylisobenzofuran-1(3H)-one | 393.1 | A: 0.89, 99.40% B: 1.42, 98.77% XIV: 5.58 100% ee | 1H NMR (400 MHz, DMSO-d6) δ ppm 2.16 (s, 3 H), 2.23 (s, 3 H), 2.47 (s, 3 H), 2.62-2.71 (m, 2 H), 3.77 (s, 2 H), 4.98-5.08 (m, 1 H), 5.37 (d, J = 3.18 Hz, 2 H), 5.46-5.55 (m, 1 H), 7.48 (d, J = 8.07 Hz, 2 H), 7.55-7.73 (m, 2 H), 7.80 (d, J = 8.31 Hz, 1 H), 8.34 (s, 1 H). (1 Exchangable proton not observed). |

| Ex. | Structure | Name | LCMS (M + H)+ | HPLC/LCMS Method: RT (min.), Purity | NMR |
|---|---|---|---|---|---|
| 78 | 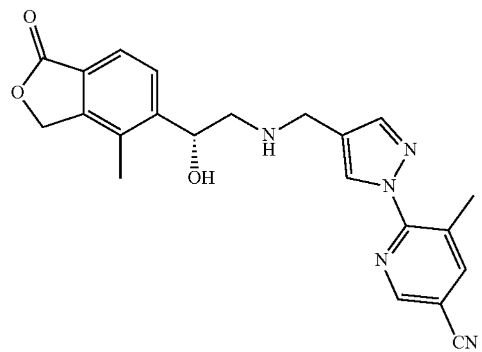 [SMILES: Cc1cc(C#N)cnc1-n1cc(CNC[C@H](O)c2ccc3c(c2C)COC3=O)cn1] | (R)-6-(4-(((2-hydroxy-2-(4-methyl-1-oxo-1,3-dihydroisobenzofuran-5-yl)ethyl)amino)methyl)-1H-pyrazol-1-yl)-5-methylnicotinonitrile | 404.1 | A: 1.02, 99.36% B: 1.34, 98.4% XIV: 6.09, 100.0% ee | $^1$H NMR (400 MHz, DMSO-$d_6$) δ ppm 2.26 (s, 3 H), 2.60 (s, 3 H), 2.97 (br. s., 1 H), 3.12 (d, J = 12.96 Hz, 1 H), 4.25 (s, 2H), 5.27 (d, J = 9.78 Hz, 1 H), 5.35-5.47 (m, 2 H), 6.38 (br. s., 1 H), 7.68-7.78 (m, 1 H), 8.00 (s, 1 H), 8.45 (d, J = 1.47 Hz, 1 H), 8.70 (s, 1 H), 8.85 (d, J = 1.96 Hz, 1 H), 9.06-9.40 (m, 1 H), (1 Exchangable proton not observed). |
| 79 | 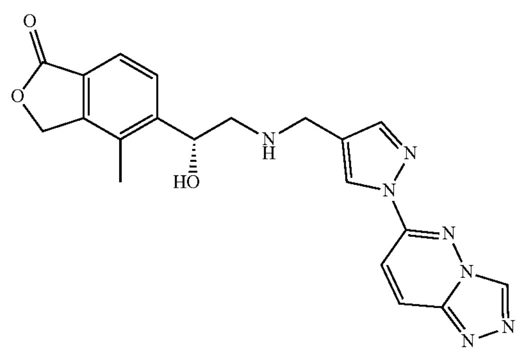 [SMILES: Cc1c([C@@H](O)CNCc2cnn(-c3ccc4nncn4n3)c2)ccc2c1COC2=O] | (R)-5-(2-(((1-([1,2,4]triazolo[4,3-b]pyridazin-6-yl)-1H-pyrazol-4-yl)methyl)amino)-1-hydroxyethyl)-4-methylisobenzofuran-1(3H)-one | 406.1 | A: 0.53, 100% B: 0.95, 94.69% | $^1$H NMR (400 MHz, DMSO-$d_6$) δ ppm 2.25 (s, 3 H), 2.61-2.72 (m, 2 H), 3.68-3.78 (m, 1 H), 4.01-4.23 (m, 1 H), 4.98-5.04 (m, 1 H), 5.35-5.44 (m, 3 H), 7.60-7.72 (m, 2 H), 7.87-7.94 (m, 1 H), 7.98-8.05 (m, 1 H), 8.40-8.57 (m, 2 H), 9.59 (s, 1 H), (1 Exchangable proton not observed). |

| Ex. | Structure | Name | LCMS (M + H)+ | HPLC/LCMS Method: RT (min.), Purity | NMR |
|---|---|---|---|---|---|
| 80 | 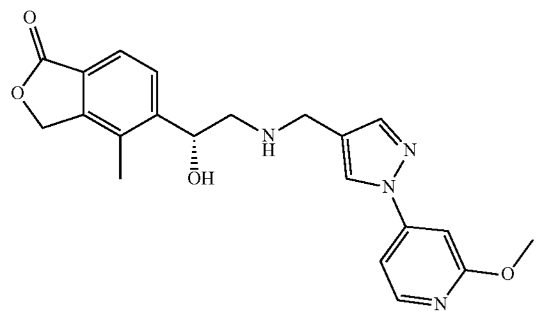 [SMILES: COc1cc(-n2cc(CNC[C@H](O)c3ccc4c(c3C)COC4=O)cn2)ccn1] | (R)-5-(1-hydroxy-2-(((1-(2-methoxypyridin-4-yl)methyl)amino)ethyl)-4-methylisobenzofuran-1(3H)-one | 395.1 | A: 0.972, 99.394% B: 1.210, 98.12% | 1H NMR (400 MHz, DMSO-d6) δ ppm 2.26 (s, 3 H), 2.92-3.05 (m, 1 H), 3.17 (s, 1 H), 3.91 (s, 3 H), 4.20 (br. s., 2 H), 5.20-5.27 (m, 1 H), 5.41 (d, J = 6.36 Hz, 3 H), 7.22 (d, J = 1.71 Hz, 1 H), 7.41-7.51 (m, 1 H), 7.74 (d, J = 2.45 Hz, 2 H), 7.97 (s, 1 H), 8.27 (d, J = 5.62 Hz, 1 H), 8.75 (s, 1 H), (1 Exchangable proton not observed). |
| 81 | 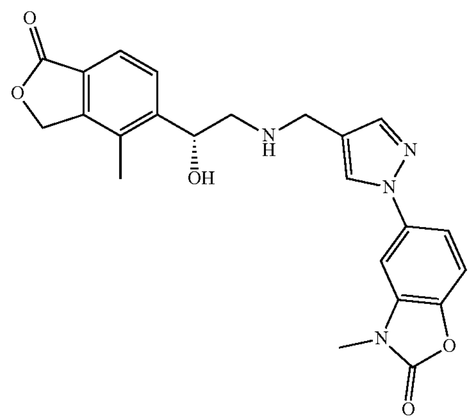 [SMILES: Cc1c([C@@H](O)CNCc2cnn(-c3ccc4oc(=O)n(C)c4c3)c2)ccc2c1COC2=O] | (R)-5-(4-(((2-hydroxy-2-(4-methyl-1-oxo-1,3-dihydroisobenzofuran-5-yl)ethyl)amino)methyl)-1H-pyrazol-1-yl)-3-methylbenzo[d]oxazol-2(3H)-one | 468.1 | E: 9.44, 98.88% G: 10.20, 98.60% XVIII: 14.38, 100% ee | 1H NMR (400 MHz, DMSO-d6) δ ppm 2.20-2.26 (m, 3 H), 2.61-2.73 (m, 2 H), 3.38-3.40 (s, 3 H), 3.66-3.73 (m, 2 H), 4.98-5.09 (m, 1 H), 5.32-5.39 (m, 2 H), 5.45-5.51 (m, 1 H), 7.39-7.43 (m, 1 H), 7.51-7.55 (m, 1 H), 7.63-7.69 (m, 3 H), 7.71-7.73 (m, 1 H), 8.32-8.36 (m, 1 H), (1 Exchangable proton not observed). |
| 82 | 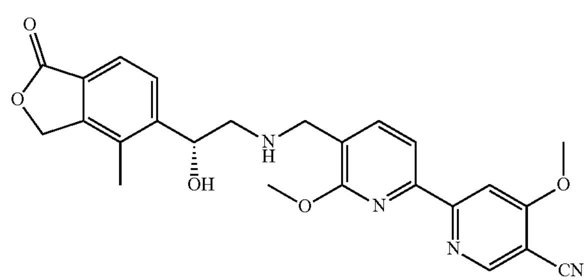 [SMILES: COc1cc(-c2ccc(CNC[C@H](O)c3ccc4c(c3C)COC4=O)c(OC)n2)ncc1C#N] | (R)-5'-(((2-hydroxy-2-(4-methyl-1-oxo-1,3-dihydroisobenzofuran-5-yl)ethyl)amino)methyl)-4,6-dimethoxy-[2,2'-bipyridine]-5-carbonitrile | 461.2 | S: 1.79, 98.54% R: 1.44, 99.37%. XIV: 6.24 100% ee. | 1H NMR (400 MHz, DMSO-d6) δ ppm 2.52 (m, 2 H), 2.89 (s, 3 H), 4.11 (s, 3 H), 4.15 (s, 3 H), 4.32 (br. s., 2 H), 5.27-5.34 (m, 1 H), 5.41 (d, J = 5.38 Hz, 2 H), 6.34-6.39 (m, 1 H), 7.75 (s, 2 H), 7.95 (s, 1 H), 8.03-8.07 (m, 1 H), 8.10 (s, 1 H), 8.93 (s, 1 H), (1 Exchangable proton not observed). |

-continued

| Ex. | Structure | Name | LCMS (M + H)+ | HPLC/LCMS Method: RT (min.), Purity | NMR |
|---|---|---|---|---|---|
| 83 | 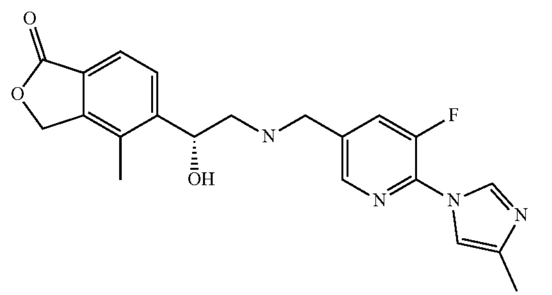 [SMILES: Cc1cn(-c2ncc(CNC[C@H](O)c3ccc4c(c3C)COC4=O)cc2F)cn1] | (R)-5-(2-(((5-fluoro-6-(4-methyl-1H-imidazol-1-yl)pyridin-3-yl)methyl)amino)-1-hydroxyethyl)-4-methylisobenzofuran-1(3H)-one (Enantiomer-I) | 397.2 | R: 0.54, 99.40% S: 1.05, 99.30% XVIII: 9.25, 100% ee | 1H NMR (400 MHz, DMSO-d6) δ ppm 2.18 (s, 3 H), 2.23 (s, 3 H), 2.59-2.69 (m, 2 H), 3.86 (s, 2 H), 5.02 (br. s., 1 H), 5.37 (d, J = 3.91 Hz, 2 H), 5.49-5.58 (m, 1 H), 7.50 (s, 1 H), 7.66 (d, J = 2.20 Hz, 2 H), 7.90 (d, J = 12.47 Hz, 1 H), 8.18 (s, 1 H), 8.29 (s, 1 H), (1 Exchangable proton not observed). F NMR (400 MHz, DMSO-d6) δ ppm-130.4. |
| 84 | 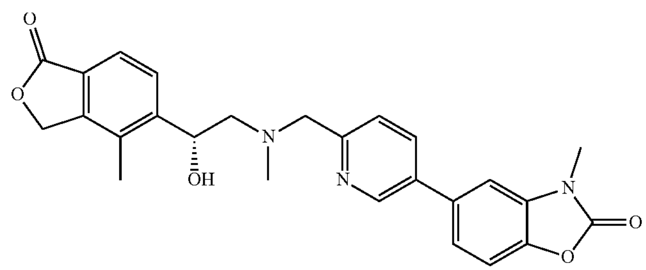 [SMILES: Cc1c([C@@H](O)CN(C)Cc2ccc(-c3ccc4oc(=O)n(C)c4c3)cn2)ccc2c1COC2=O] | (R)-5-(6-(((2-hydroxy-2-(4-methyl-1-oxo-1,3-dihydroisobenzofuran-5-yl)ethyl)(methyl)amino)methyl)pyridin-3-yl)-3-methylbenzo[d]oxazol-2(3H)-one (Enantiomer-I) | 460.0 | A: 1.18, 99.67% B: 1.62, 98.73% XVIII: 2.65, 95.25% ee | 1H NMR (400 MHz, DMSO-d6) δ ppm 2.24 (s, 3H), 2.39 (s, 3H), 2.72-2.56 (m, 2H), 3.43 (s, 2H), 3.77 (s, 3H), 5.18-5.09 (m, 1H), 5.38 (s, 3H), 7.52-7.40 (m, 3H), 7.71-7.61 (m, 3H), 8.04-7.98 (m, 1H), 8.92-8.78 (m, 1H). |
| 85 | 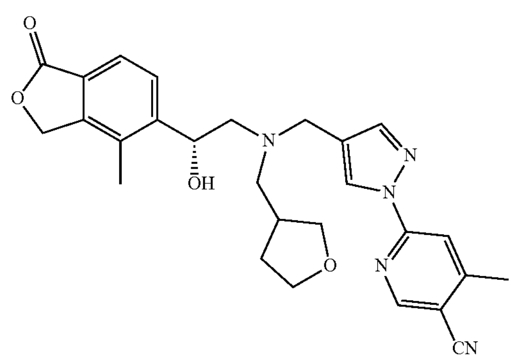 [SMILES: Cc1cc(-n2cc(CN(CC3CCOC3)C[C@H](O)c3ccc4c(c3C)COC4=O)cn2)ncc1C#N] | 6-(4-((((R)-2-hydroxy-2-(4-methyl-1-oxo-1,3-dihydroisobenzofuran-5-yl)ethyl)(tetrahydrofuran-3-yl)methyl)amino)methyl)-1H-pyrazol-1-yl)-4-methylnicotinonitrile | 488.2 | A: 1.21, 96.37% B: 1.89, 98.70% XIX: 3.29, 95.20% ee | 1H NMR (400 MHz, DMSO-d6) δ ppm 2.31-2.36 (m, 1 H), 2.41-2.46 (m, 2 H), 2.59 (s, 3 H), 2.61-2.65 (m, 2 H), 2.66-2.69 (m, 1 H), 3.14-3.22 (m, 2 H), 3.24-3.29 (m, 1 H), 3.45-3.59 (m, 3 H), 3.64-3.71 (m, 3 H), 4.04-4.13 (m, 1 H), 4.98-5.10 (m, 1 H), 5.22-5.37 (m, 3 H), 7.60-7.67 (m, 2 H), 7.74-7.83 (m, 1 H), 7.92-8.00 (m, 1 H), 8.38-8.46 (m, 1 H), 8.78-8.87 (m, 1 H). |

-continued

| Ex. | Structure | Name | LCMS (M + H)+ | HPLC/LCMS Method: RT (min.), Purity | NMR |
|---|---|---|---|---|---|
| 86 | 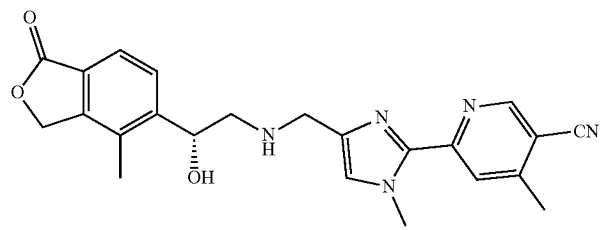 [SMILES: Cc1cc(-c2nc(CNC[C@H](O)c3ccc4c(c3C)COC4=O)cn2C)ncc1C#N] | (R)-6-(4-(((2-hydroxy-2-(4-methyl-1-oxo-1,3-dihydroisobenzofuran-5-yl)ethyl)amino)methyl)-1-methyl-1H-imidazol-2-yl)-4-methylnicotinonitrile | 418.2 | A: 1.12, 96.37% B: 1.29, 98.47% XIX: 3.29, 95.20% ee | 1H NMR (400 MHz, DMSO-d6) δ ppm 2.26 (s, 3 H), 2.55 (s, 3 H), 2.71 (d, J = 8.31 Hz, 2 H), 3.74 (d, J = 5.87 Hz, 2 H), 4.04 (s, 3 H), 5.05 (br. s., 1 H), 5.38 (d, J = 2.93 Hz, 3 H), 7.26 (s, 1 H), 7.68 (d, J = 3.42 Hz, 2 H), 8.12 (s, 1 H), 8.94 (s, 1 H). (1 Exchangable proton not observed). |
| 87 | 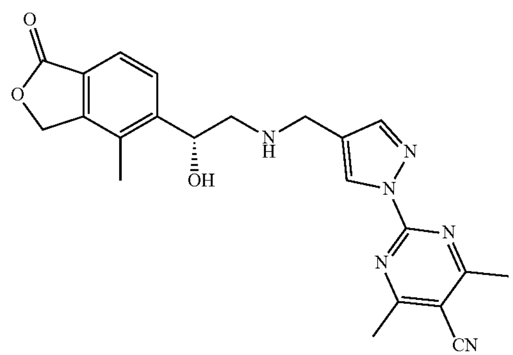 [SMILES: Cc1nc(-n2cc(CNC[C@H](O)c3ccc4c(c3C)COC4=O)cn2)nc(C)c1C#N] | (R)-2-(4-(((2-hydroxy-2-(4-methyl-1-oxo-1,3-dihydroisobenzofuran-5-yl)ethyl)amino)methyl)-1H-pyrazol-1-yl)-4,6-dimethylpyrimidine-5-carbonitrile | 419.2 | U: 7.30, 92.30% T: 6.13, 93.12% XI: 3.97, 100% ee | 1H NMR (400 MHz, DMSO-d6) δ ppm 2.24 (s, 3 H), 2.69 (s, 8 H), 3.65-3.75 (m, 2 H), 4.95-5.07 (m, 1 H), 5.31-5.42 (m, 3 H), 7.63-7.71 (m, 2 H), 7.80-7.89 (m, 1 H), 8.47-8.55 (m, 1 H). (1 Exchangable proton not observed). |
| 88 | 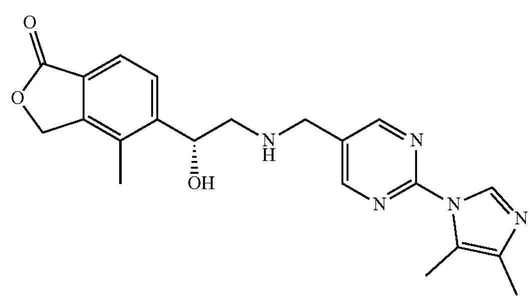 [SMILES: Cc1ncn(-c2ncc(CNC[C@H](O)c3ccc4c(c3C)COC4=O)cn2)c1C] | (R)-5-(2-(((2-(4,5-dimethyl-1H-imidazol-1-yl)pyrimidin-5-yl)methyl)amino)-1-hydroxyethyl)-4-methylisobenzofuran-1(3H)-one | 394.2 | S: 1.09, 100% R: 0.58, 94.46% XVIII: 9.83, 87.50% ee | 1H NMR (400 MHz, DMSO-d6) d 2.11 (s, 3 H), 2.25 (s, 3 H), 2.45 (s, 3 H), 2.73 (s, H), 3.92 (br. s., 2 H), 5.07 (br. s., 1 H), 5.47-5.31 (m, 2 H), 5.66 (br. s., 1 H), 7.68 (d, J = 1.0 Hz, 2 H), 8.30 (s, 1 H), 8.79 (s, 2 H). (1 Exchangable proton not observed). |

| Ex. | Structure | Name | LCMS (M + H)+ | HPLC/LCMS Method: RT (min.), Purity | NMR |
|---|---|---|---|---|---|
| 89 | 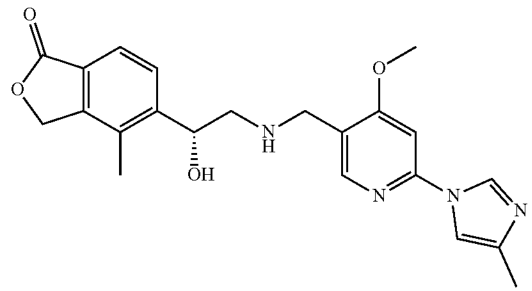 [SMILES: COc1cc(-n2cnc(C)c2)ncc1CNC[C@H](O)c1ccc2c(c1C)COC2=O] | (R)-5-(1-hydroxy-2-(((4-methoxy-6-(4-methyl-1H-imidazol-1-yl)pyridin-3-yl)methyl)amino)ethyl)-4-methylisobenzofuran-1(3H)-one | 409.2 | R: 0.59, 100%, S: 0.94, 100%, XX: 1.56, 100% ee | 1H NMR (400 MHz, DMSO-d6) δ 2.17 (s, 3 H), 2.23 (s, 3 H), 2.66-2.56 (m, 2 H), 3.81-3.62 (m, 2 H), 3.94 (s, 3 H), 5.01-4.99 (m, 1 H), 5.37 (br. s., 3 H), 7.28 (s, 1 H), 7.65 (s, 2 H), 7.69 (s, 1 H), 8.17 (s, 1 H), 8.41 (s, 1 H), (1 Exchangable proton not observed). |
| 90 | 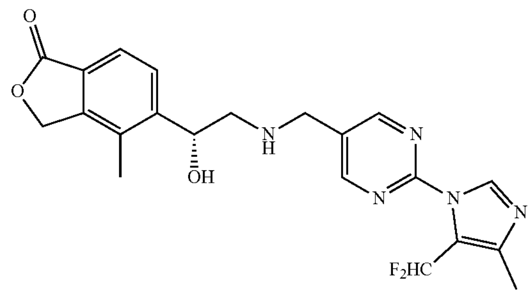 [SMILES: Cc1ncn(-c2ncc(CNC[C@H](O)c3ccc4c(c3C)COC4=O)cn2)c1C(F)F] | (R)-5-(2-(((2-(5-(difluoromethyl)-4-methyl-1H-imidazol-1-yl)pyrimidin-5-yl)methyl)amino)-1-hydroxyethyl)-4-methylisobenzofuran-1(3H)-one | 430.2 | R: 0.83, 100%, S: 1.16, 100%, XIV: 5.80, 100% ee | 1H NMR (400 MHz, DMSO-d6) δ ppm 2.25 (s, 3 H), 2.62 (s, 3 H), 2.7 (s, 1 H), 3.90 (br. s., 2 H), 4.07-4.09 (m, 1 H), 5.01-4.99 (m, 1 H), 5.45-5.29 (m, 2 H), 5.62 (s, 1 H), 6.92-7.26 (m, 1 H), 7.77-7.60 (m, 2 H), 8.45 (s, 1 H), 8.84 (s, 2 H), (1 Exchangable proton not observed). F NMR (400 MHz, DMSO-d6) δ ppm-110.9. |
| 91-I | 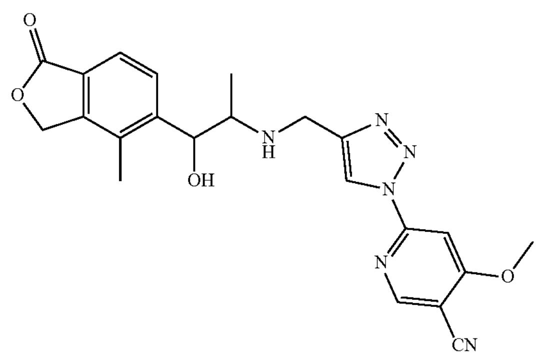 [SMILES: COc1cc(-n2cc(CNC(C)C(O)c3ccc4c(c3C)COC4=O)nn2)ncc1C#N] | 6-(4-(((1-hydroxy-1-(4-methyl-1-oxo-1,3-dihydroisobenzofuran-5-yl)propan-2-yl)amino)methyl)-1H-1,2,3-triazol-1-yl)-4-methoxynicotinonitrile (Diastereomer-I: Enantiomer-I) | 435.2 | C: 9.50, 94.41%, G: 10.75, 94.05%, XIX: 9.88, 99.63%. | 1H NMR (400 MHz, DMSO-d6) δ ppm 0.91-0.99 (m, 3 H), 2.23 (s, 3 H), 2.64-2.71 (m, 1 H), 3.87-3.95 (m, 2 H), 4.17 (s, 3 H), 4.92-4.98 (m, 1 H), 5.29-5.40 (m, 3 H), 7.51-7.68 (m, 2 H), 7.79-7.89 (m, 1 H), 8.37-8.47 (m, 1 H), 8.81-8.90 (m, 1 H), (1 Exchangable proton not observed). |

-continued

| Ex. | Structure | Name | LCMS (M+H)+ | HPLC/LCMS Method: RT (min.), Purity | NMR |
|---|---|---|---|---|---|
| 92 | 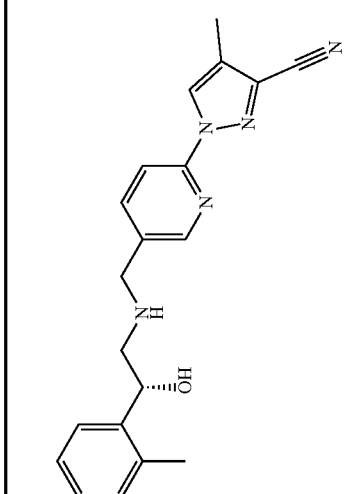 | (R)-1-(5-(((2-hydroxy-2-(4-methyl-1-oxo-1,3-dihydroisobenzofuran-5-yl)ethyl)amino)methyl)pyridin-2-yl)-4-methyl-1H-pyrazole-3-carbonitrile | 404.1 | A: 1.08, 100% B: 1.42, 100% XVII: 11.92, 100% ee | 1H NMR (400 MHz, DMSO-d6) δ ppm 2.22 (d, J = 6.5 Hz, 6 H), 2.61-2.68 (m, 2 H), 3.85 (s, 2 H), 4.97-5.08 (m, 1 H), 5.30-5.43 (m, 2 H), 5.51 (d, J = 3.5 Hz, 1 H), 7.60-7.73 (m, 2 H), 7.90(d, J = 8.5 Hz, 1 H), 7.95-8.03 (m, 1 H), 8.44 (d, J = 2.0 Hz, 1 H), 8.68 (s, 1 H), (1 Exchangeable proton not observed). |
| 93 | 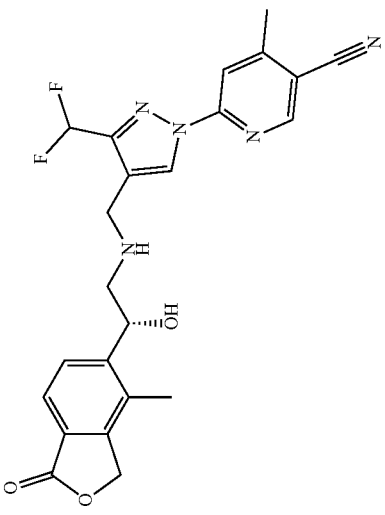 | (R)-6-(3-(difluoromethyl)-4-(((2-hydroxy-2-(4-methyl-1-oxo-1,3-dihydroisobenzofuran-5-yl)ethyl)amino)methyl)-1H-pyrazol-1-yl)-4-methylnicotinonitrile | 454.1 | A: 1.42, 99.20% B: 1.82, 98.80% VIII: 5.94, 100% ee | 1H NMR (400 MHz, DMSO-d6) δ ppm 2.23 (s, 3 H), 2.60 (s, 3 H), 2.65-2.74 (m, 2 H), 3.80 (s, 2 H) 5.01 (br. s., 1 H), 5.36 (d, J = 5.14 Hz, 2 H), 5.49 (d, J = 3.42 Hz, 1 H), 7.154 (t, J = 53.6 Hz, 1 H), 7.58-7.69 (m, 2 H), 7.99 (s, 1 H), 8.61 (s, 1 H), 8.88 (s, 1 H), (1 Exchangeable proton not observed). 19F NMR (400 MHz, DMSO-d6) δ ppm-113.9. |

| Ex. | Structure | Name | LCMS (M + H)+ | HPLC/LCMS Method: RT (min.), Purity | NMR |
|---|---|---|---|---|---|
| 94 | 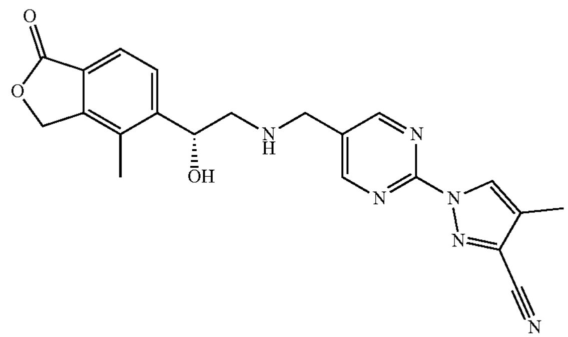 [SMILES: Cc1cn(-c2ncc(CNC[C@H](O)c3ccc4c(c3C)COC4=O)cn2)nc1C#N] | (R)-1-(5-(((2-hydroxy-2-(4-methyl-1-oxo-1,3-dihydroisobenzofuran-5-yl)ethyl)amino)methyl)pyrimidin-2-yl)-4-methyl-1H-pyrazole-3-carbonitrile | 405.2 | A: 0.87, 96.90% B: 1.16, 97.20% | 1H NMR (400 MHz, DMSO-d6) δ ppm 2.24 (s, 3 H), 2.30 (s, 3 H), 3.08 (br. s., 1 H), 3.19 (br. s., 1 H), 4.37 (br. s., 2 H), 5.24 (d, J = 9.5 Hz, 1 H), 5.49-5.33 (m, 2 H), 6.36 (br. s., 1 H), 7.82-7.67 (m, 2 H), 8.78 (s, 1 H), 9.03 (s, 2 H), 9.25 (br. s., 2 H). |
| 95 | 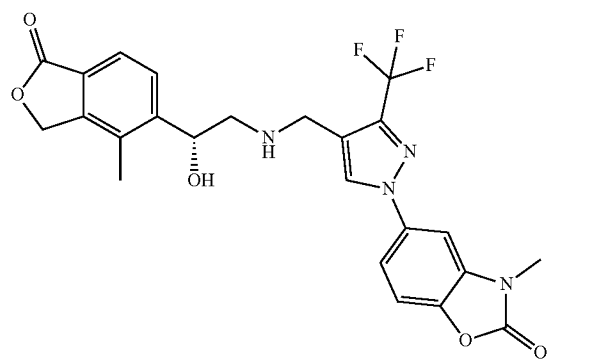 [SMILES: Cc1c([C@@H](O)CNCc2cn(-c3ccc4oc(=O)n(C)c4c3)nc2C(F)(F)F)ccc2c1COC2=O] | (R)-5-(4-(((2-hydroxy-2-(4-methyl-1-oxo-1,3-dihydroisobenzofuran-5-yl)ethyl)amino)methyl)-3-(trifluoromethyl)-1H-pyrazol-1-yl)-3-methylbenzo[d]oxazol-2(3H)-one | 503.1 | A: 1.71, 98.30% B: 2.12, 99.50% XV: 14.62 100% ee | 1H NMR (400 MHz, CD3OD) δ ppm 2.36 (s, 3 H), 3.05-3.23 (m, 2 H), 3.47 (s, 3 H), 4.26 (br. s., 2 H), 5.32 (dd, J = 9.54, 3.01 Hz, 1 H), 5.36 (d, J = 2.01 Hz, 2 H), 7.40 (d, J = 8.53 Hz, 1 H), 7.56 (dd, J = 8.53, 2.01 Hz, 1 H), 7.66 (d, J = 2.51 Hz, 1 H), 7.73-7.77 (m, 1 H), 7.80-7.84 (m, 1 H), 8.49 (s, 1 H). (2 Exchangeable proton not observed). 19F NMR (400 MHz, DMSO-d6) δ ppm-108.18. |
| 96 | 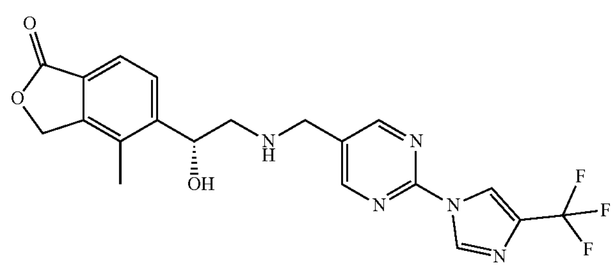 [SMILES: Cc1c([C@@H](O)CNCc2cnc(-n3cnc(C(F)(F)F)c3)nc2)ccc2c1COC2=O] | (R)-5-(1-hydroxy-2-(((2-(4-(trifluoromethyl)-1H-imidazol-1-yl)pyrimidin-5-yl)methyl)amino)ethyl)-4-methylisobenzofuran-1(3H)-one | 434.1 | A: 1.16, 99.40% B: 1.53, 98.60% XVIII: 7.88, 92.60% ee | 1H NMR (400 MHz, DMSO-d6) δ ppm 2.24 (s, 3 H), 2.62-2.70 (m, 2 H), 3.85 (s, 2 H), 5.02 (dt, J = 7.40, 4.08 Hz, 1 H), 5.37 (d, J = 5.02 Hz, 2 H), 5.51 (d, J = 4.02 Hz, 1 H), 7.66 (d, J = 3.51 Hz, 2 H), 8.51 (t, J = 1.51 Hz, 1 H), 8.75 (s, 1 H), 8.83 (s, 2 H), (1 Exchangeable proton not observed). 19F NMR (400 MHz, DMSO-d6) δ ppm-61.702. |

-continued

| Ex. | Structure | Name | LCMS (M + H)+ | HPLC/LCMS Method: RT (min.), Purity | NMR |
|---|---|---|---|---|---|
| 97 | 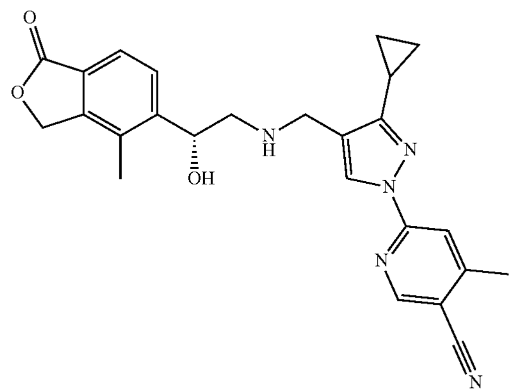 [SMILES: Cc1cc(-n2cc(CNC[C@H](O)c3ccc4c(c3C)COC4=O)c(C3CC3)n2)ncc1C#N] | (R)-6-(3-cyclopropyl-4-(((2-hydroxy-2-(4-methyl-1-oxo-1,3-dihydroisobenzofuran-5-yl)ethyl)amino)methyl)-1H-pyrazol-1-yl)-4-methylnicotinonitrile | 452.2 | A: 1.54, 99.40% B: 1.86, 100% XIV: 6.28, 99.5% ee | ¹H NMR (400 MHz, DMSO-d6) δ ppm 0.84-0.95 (m, 4 H), 1.94-2.01 (m, 1 H), 2.24 (s, 3 H), 2.55 (s, 3 H), 2.63-2.78 (m, 2 H), 3.79 (br. s., 2 H), 5.05 (br. s., 1 H), 5.31-5.42 (m, 2 H), 5.55 (br. s., 1 H), 7.58-7.71 (m, 2 H), 7.81 (s, 1 H), 8.40 (s, 1 H), 8.77 (s, 1 H), (1 Exchangeable proton not observed). |
| 98 | 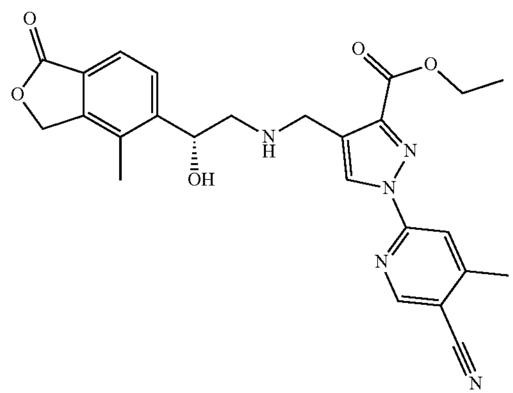 [SMILES: CCOC(=O)c1nn(-c2cc(C)c(C#N)cn2)cc1CNC[C@H](O)c1ccc2c(c1C)COC2=O] | ethyl (R)-1-(5-cyano-4-methylpyridin-2-yl)-4-(((2-hydroxy-2-(4-methyl-1-oxo-1,3-dihydroisobenzofuran-5-yl)ethyl)amino)methyl)-1H-pyrazole-3-carboxylate | 461.1 | A: 1.54, 99.80% B: 1.86, 100% III: 10.22, 100% ee | ¹H NMR (400 MHz, DMSO-d6) δ ppm 1.38 (t, J = 7.21 Hz, 3 H), 2.29 (s, 3 H), 2.66 (s, 3 H), 3.10 (d, J = 10.52 Hz, 1 H), 3.19 (br. s., 1 H), 4.37-4.50 (m, 4 H), 5.26 (br. s., 1 H), 5.42 (d, J = 6.60 Hz, 2 H), 6.34 (br. s., 1 H), 7.75 (d, J = 1.96 Hz, 2 H), 8.12 (s, 1 H), 8.97 (s, 1 H), 9.01 (s, 1 H), (2 Exchangeable protons not observed). |

| Ex. | Structure | Name | LCMS (M + H)+ | HPLC/LCMS Method: RT (min.), Purity | NMR |
|---|---|---|---|---|---|
| 99 | 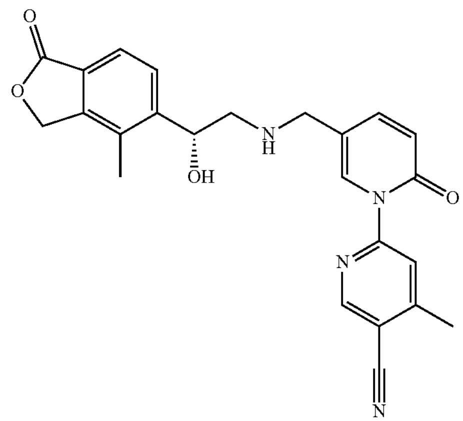 [SMILES: Cc1cc(-n2cc(CNC[C@H](O)c3ccc4c(c3C)COC4=O)ccc2=O)ncc1C#N] | (R)-5-(((2-hydroxy-2-(4-methyl-1-oxo-1,3-dihydroisobenzofuran-5-yl)ethyl)amino)methyl)-4'-methyl-2-oxo-2H-[1,2'-bipyridine]-5'-carbonitrile | 431.1 | A: 1.52, 97.86% B: 1.90, 95.97% III: 9.90, 100% ee | 1H NMR (400 MHz, DMSO-d6) δ ppm 2.22 (s, 3 H), 2.58 (s, 3 H), 2.60-2.68 (m, 2 H), 3.31 (d, 2 H), 5.00 (dd, J = 7.46, 4.03 Hz, 1 H), 5.32-5.41 (m, 3 H), 6.52 (d, J = 9.29 Hz, 1 H), 7.55 (dd, J = 9.29, 2.45 Hz, 1 H), 7.61-7.69 (m, 2 H), 7.78 (s, 1 H), 8.00 (s, 1 H), 8.98 (s, 1 H), (1 Exchangeable proton not observed). |
| 100 | 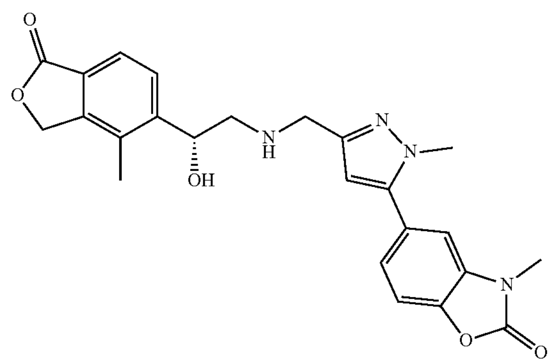 [SMILES: Cc1c([C@@H](O)CNCc2cc(-c3ccc4oc(=O)n(C)c4c3)n(C)n2)ccc2c1COC2=O] | (R)-5-(3-(((2-hydroxy-2-(4-methyl-1-oxo-1,3-dihydroisobenzofuran-5-yl)ethyl)amino)methyl)-1-methyl-1H-pyrazol-5-yl)-3-methylbenzo[d]oxazol-2(3H)-one | 431.1 | A: 1.51, 97.01% B: 1.90, 96.36% XVIII: 5.07, 91.50% ee | 1H NMR (400 MHz, DMSO-d6) δ ppm 2.27 (s, 3 H), 2.61-2.74 (m, 2 H), 3.35 (s, 3 H), 3.71 (d, J = 4.89 Hz, 2H), 3.77 (m, 3 H), 5.03 (dd, J = 8.07, 3.91 Hz, 1 H), 5.33-5.43 (m, 3 H), 6.28 (s, 1 H), 7.23 (dd, J = 8.31, 1.71 Hz, 1 H), 7.38-7.44 (m, 2 H), 7.62-7.71 (m, 2 H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 101 | 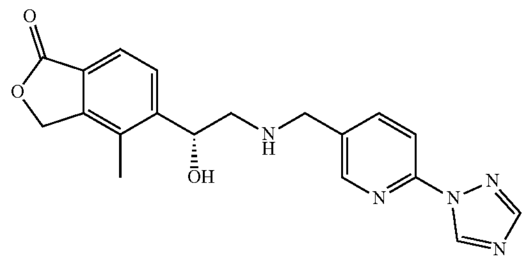 [SMILES: Cc1c([C@@H](O)CNCc2ccc(-n3cncn3)nc2)ccc2c1COC2=O] | (R)-5-(2-(((6-(1H-1,2,4-triazol-1-yl)pyridin-3-yl)methyl)amino)-1-hydroxyethyl)-4-methylisobenzofuran-1(3H)-one | 432.0 | A: 1.38, 95.70% B: 1.72, 95.10% XVIII: 13.80, 100% ee | 1H NMR (400 MHz, DMSO-d6) δ ppm 2.28 (s, 3 H), 3.03 (d, J = 11.49 Hz, 1 H), 3.11-3.19 (m, 1 H), 4.37 (s, 2 H), 5.27 (d, J = 11.25 Hz, 1 H), 5.42 (d, J = 3.91 Hz, 2 H), 6.36 (br. s., 1 H), 7.69-7.79 (m, 2 H), 7.97 (d, J = 8.31 Hz, 1 H), 8.23 (dd, J = 8.56, 2.20 Hz, 1 H), 8.35 (s, 1 H), 8.66 (d, J = 1.96 Hz, 1 H), 9.42 (s, 1 H), (1 Exchangeable proton not observed). |
| 102 | 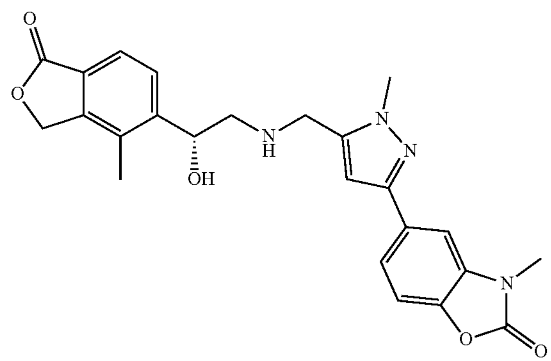 [SMILES: Cc1c([C@@H](O)CNCc2cc(-c3ccc4oc(=O)n(C)c4c3)nn2C)ccc2c1COC2=O] | (R)-5-(2-(((2-hydroxy-2-(4-methyl-1-oxo-1,3-dihydroisobenzofuran-5-yl)ethyl)amino)methyl)-1-methyl-1H-pyrazol-3-yl)-3-methylbenzo[d]oxazol-2(3H)-one | 431.0 | A: 0.87, 100% B: 1.39, 100% XVIII: 9.09, 100% ee | 1H NMR (400 MHz, DMSO-d6) δ 2.23 (s, 3 H), 2.65-2.69 (m, 2 H), 3.38 (s, 3 H), 3.80 (s, 3 H), 3.84 (br. s., 2 H), 5.02 (br. s., 1 H), 5.36 (d, J = 3.42 Hz, 2 H), 5.49-5.54 (m, 1 H), 6.61 (s, 1 H), 7.31 (d, J = 8.31 Hz, 1 H), 7.50 (d, J = 8.31, 1.71 Hz, 1 H), 7.58 (d, J = 1.71 Hz, 1 H), 7.67 (d, J = 3.67 Hz, 2 H), (1 Exchangeable proton not observed). |
| 103 | 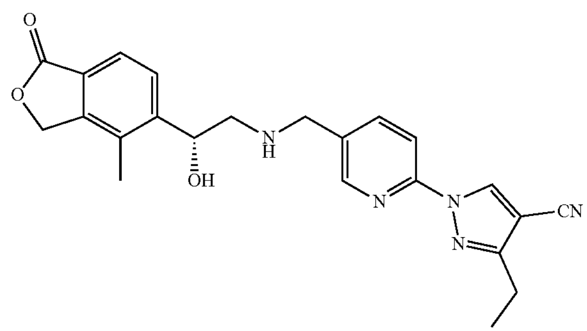 [SMILES: COc1nn(-c2ccc(CNC[C@H](O)c3ccc4c(c3C)COC4=O)cn2)cc1C#N] | (R)-3-ethyl-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile | 418.2 | A: 1.12, 100% B: 1.46, 100% III: 9.34, 100% ee | 1H NMR (400 MHz, DMSO-d6) δ 1.30 (t, J = 7.6 Hz, 3 H), 2.22 (s, 3 H), 2.66-2.57 (m, 2 H), 2.80 (q, J = 7.4 Hz, 2 H), 3.84 (s, 2 H), 5.09-4.95 (m, 1 H), 5.42-5.28 (m, 2 H), 5.51 (d, J = 3.9 Hz, 1 H), 7.72-7.60 (m, 2 H), 7.86 (d, J = 8.3 Hz, 1 H), 7.98 (dd, J = 8.3, 2.2 Hz, 1 H), 8.43 (d, J = 2.0 Hz, 1 H), 9.27 (s, 1H). (1 Exchangeable proton not observed). |

| Ex. | Structure | Name | LCMS (M + H)+ | HPLC/LCMS Method: RT (min.), Purity | NMR |
|---|---|---|---|---|---|
| 104 | 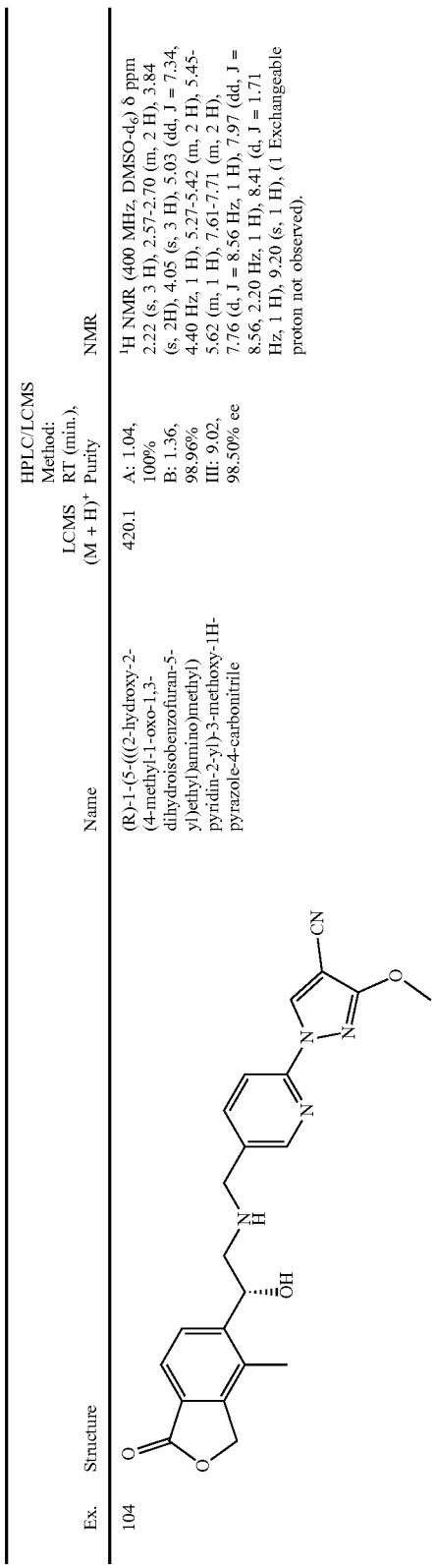 | (R)-1-(5-(((2-hydroxy-2-(4-methyl-1-oxo-1,3-dihydroisobenzofuran-5-yl)ethyl)amino)methyl)pyridin-2-yl)-3-methoxy-1H-pyrazole-4-carbonitrile | 420.1 | A: 1.04, 100% B: 1.36, 98.96% III: 9.02, 98.50% ee | $^1$H NMR (400 MHz, DMSO-$d_6$) δ ppm 2.22 (s, 3 H), 2.57-2.70 (m, 2 H), 3.84 (s, 2H), 4.05 (s, 3 H), 5.03 (dd, J = 7.34, 4.40 Hz, 1 H), 5.27-5.42 (m, 2 H), 5.45-5.62 (m, 1 H), 7.61-7.71 (m, 2 H), 7.76 (d, J = 8.56 Hz, 1 H), 7.97 (dd, J = 8.56, 2.20 Hz, 1 H), 8.41 (d, J = 1.71 Hz, 1 H), 9.20 (s, 1 H), (1 Exchangeable proton not observed). |
| 105 | 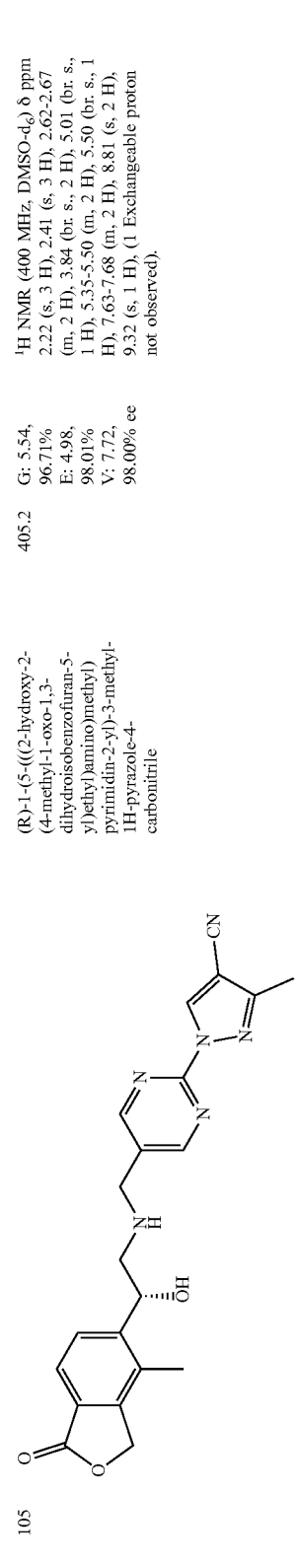 | (R)-1-(5-(((2-hydroxy-2-(4-methyl-1-oxo-1,3-dihydroisobenzofuran-5-yl)ethyl)amino)methyl)pyrimidin-2-yl)-3-methyl-1H-pyrazole-4-carbonitrile | 405.2 | G: 5.54, 96.71% E: 4.98, 98.01% V: 7.72, 98.00% ee | $^1$H NMR (400 MHz, DMSO-$d_6$) δ ppm 2.22 (s, 3 H), 2.41 (s, 3 H), 2.62-2.67 (m, 2 H), 3.84 (br. s., 2 H), 5.01 (br. s., 1 H), 5.35-5.50 (m, 2 H), 5.50 (br. s., 1 H), 7.63-7.68 (m, 2 H), 8.81 (s, 2 H), 9.32 (s, 1 H), (1 Exchangeable proton not observed). |
| 106 | 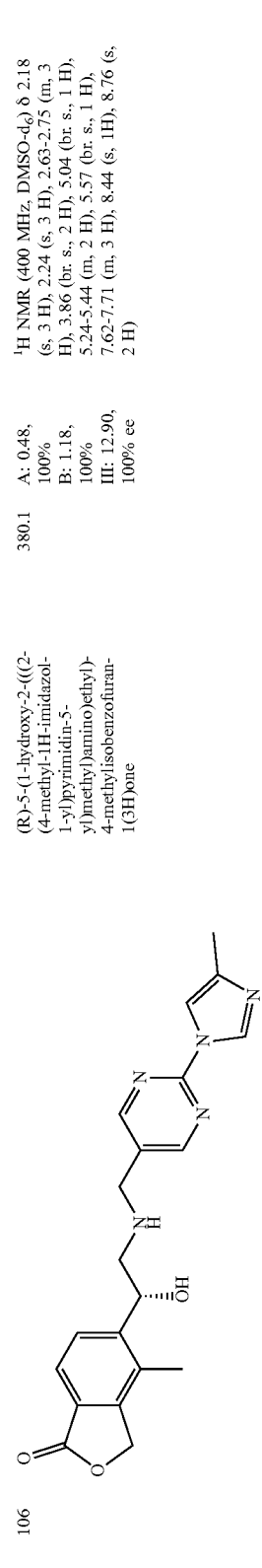 | (R)-5-(1-hydroxy-2-(((2-(4-methyl-1H-imidazol-1-yl)pyrimidin-5-yl)methyl)amino)ethyl)-4-methylisobenzofuran-1(3H)one | 380.1 | A: 0.48, 100% B: 1.18, 100% III: 12.90, 100% ee | $^1$H NMR (400 MHz, DMSO-$d_6$) δ 2.18 (s, 3 H), 2.24 (s, 3 H), 2.63-2.75 (m, 3 H), 3.86 (br. s., 2 H), 5.04 (br. s., 1 H), 5.24-5.44 (m, 2 H), 5.57 (br. s., 1 H), 7.62-7.71 (m, 3 H), 8.44 (s, 1H), 8.76 (s, 2 H) |

| Ex. | Structure | Name | LCMS (M + H)+ | HPLC/LCMS Method: RT (min.), Purity | NMR |
|---|---|---|---|---|---|
| 107 | 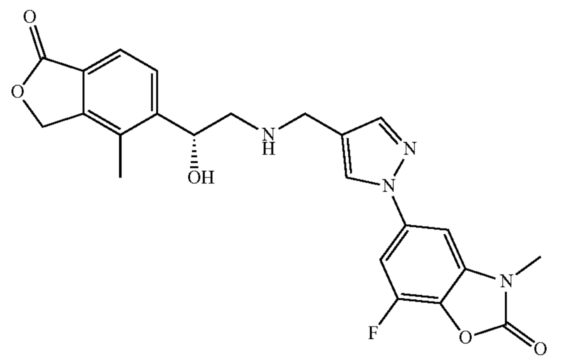 [SMILES: Cc1c([C@@H](O)CNCc2cnn(-c3cc(F)c4oc(=O)n(C)c4c3)c2)ccc2c1COC2=O] | (R)-7-fluoro-5-(4-(((2-hydroxy-2-(4-methyl-1-oxo-1,3-dihydroisobenzofuran-5-yl)ethyl)amino)methyl)-1H-pyrazol-1-yl)-3-methylbenzo[d]oxazol-2(3H)-one carbonitrile (Enantiomer-II) | 453.1 | A: 1.21, 98.25% B: 1.40, 97.46% X: 8.40, 100% ee | 1H NMR (400 MHz, DMSO-d6) δ ppm 2.24 (s, 3 H), 2.59-2.76 (m, 2 H), 3.39 (s, 3 H), 3.64-3.78 (m, 2 H), 5.03 (dd, J = 7.78, 3.76 Hz, 1 H), 5.41 (s, 2 H), 5.50 (br. s., 1 H), 7.56 (dd, J = 12.00 Hz, 2.00 Hz, 1 H), 7.63-7.73 (m, 3 H), 7.77 (d, J = 2.01 Hz, 1 H), 8.4 (s, 1 H) (1 Exchangeable proton not observed). 19F NMR (400 MHz, DMSO-d6) δ ppm-135. |
| 108 | 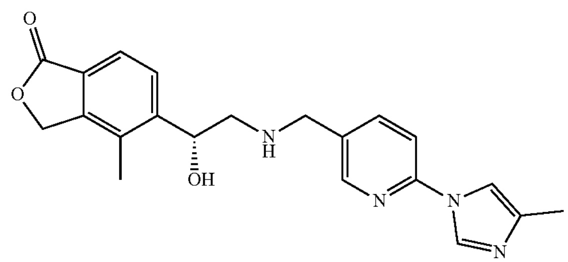 [SMILES: Cc1cn(-c2ccc(CNC[C@H](O)c3ccc4c(c3C)COC4=O)cn2)cn1] | (R)-5-(1-hydroxy-2-(((6-(4-methyl-1H-imidazol-1-yl)pyridin-3-yl)methyl)amino)ethyl)-4-methylisobenzofuran-1(3H)-one | 379.2 | C: 5.34, 96.70% G: 6.29, 97.0% X: 3.55, 96.16% ee | 1H NMR (400 MHz, DMSO-d6) δ ppm 2.17 (s, 3 H), 2.18-2.27 (s, 3 H), 2.59-2.72 (m, 2 H), 3.82 (s, 2 H), 5.03 (br. s., 1 H), 5.32-5.42 (m, 2 H), 5.50 (br. s., 1 H), 7.52-7.76 (m, 4 H), 7.90 (dd, J = 8.44, 2.32 Hz, 2 H), 8.29-8.45 (m, 1 H). (2 Exchangeable protons not observed). |
| 109 | 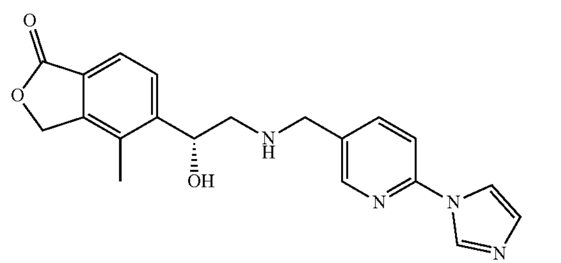 [SMILES: Cc1c([C@@H](O)CNCc2ccc(-n3ccnc3)nc2)ccc2c1COC2=O] | (R)-5-(2-(((6-(1H-imidazol-1-yl)pyridin-3-yl)methyl)amino)-1-hydroxyethyl)-4-methylisobenzofuran-1(3H)-one | 365.2 | A: 0.50, 98.28% B: 0.93, 97.22% VIII: 6.65, 95.1% ee | 1H NMR (400 MHz, DMSO-d6) δ ppm 2.23 (s, 3 H), 2.62-2.74 (m, 2 H), 3.83-3.93 (m, 2 H), 5.00-5.11 (m, 1 H), 5.37 (d, J = 2.93 Hz, 2 H), 5.57-5.66 (m, 1 H), 7.12 (s, 1 H), 7.68 (s, 2 H), 7.77 (d, J = 8.10 Hz, 1 H), 7.93-7.97 (m, 2 H), 8.41-8.46 (m, 1 H), 8.51 (s, 1 H). (1 Exchangeable proton not observed). |

-continued

| Ex. | Structure | Name | LCMS (M + H)+ | HPLC/LCMS Method: RT (min.), Purity | NMR |
|---|---|---|---|---|---|
| 110 | 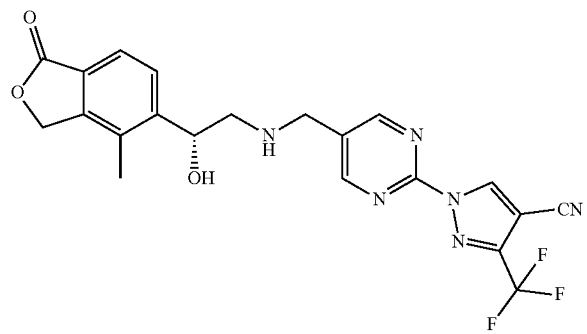 [SMILES: Cc1c([C@@H](O)CNCc2cnc(-n3cc(C#N)c(C(F)(F)F)n3)nc2)ccc2c1COC2=O] | (R)-1-(5-(((2-hydroxy-2-(4-methyl-1-oxo-1,3-dihydroisobenzofuran-5-yl)ethyl)amino)methyl)pyrimidin-2-yl)-3-(trifluoromethyl)-1H-pyrazole-4-carbonitrile | 459.2 | A: 1.08, 100% B: 1.39, 100% | 1H NMR (400 MHz, DMSO-d6) δ ppm 2.24 (s, 3 H), 2.67 (br. s, 2 H), 3.91 (br. s, 2 H), 5.04 (br. s, 1 H), 5.24-5.46 (m, 3 H), 5.56 (br. s, 1 H), 7.57-7.78 (m, 2 H), 8.86-9.02 (m, 2 H), 9.74 (s, 1 H). 19F NMR (400 MHz, DMSO-d6) δ ppm -61.58 |
| 111 | 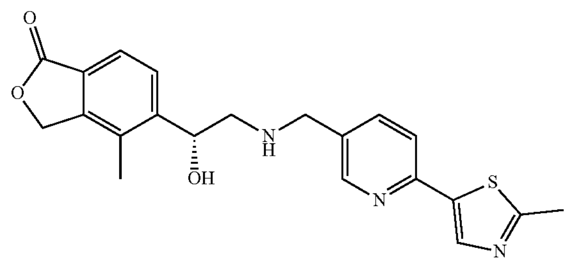 [SMILES: Cc1ncc(-c2ccc(CNC[C@H](O)c3ccc4c(c3C)COC4=O)cn2)s1] | (R)-5-(1-hydroxy-2-(((6-(2-methylthiazol-5-yl)pyridin-3-yl)methyl)amino)ethyl)-4-methylisobenzofuran-1(3H)-one | 396.2 | A: 0.76, 96.37% B: 1.05, 96.82% XVIII: 13.06, 99% ee | 1H NMR (400 MHz, DMSO-d6) δ ppm 2.22 (s, 3 H), 2.57-2.65 (m, 2 H), 2.67 (s, 3 H), 3.80 (s, 2 H), 4.94-5.12 (m, 1 H), 5.26-5.43 (m, 2 H), 5.51 (br. s, 1 H), 7.59-7.71 (m, 2 H), 7.74-7.81 (m, 1 H), 7.88 (d, J = 8.0 Hz, 1 H), 8.26 (s, 1 H), 8.46 (d, J = 1.5 Hz, 1 H), (1 Exchangeable proton not observed). |
| 112 | 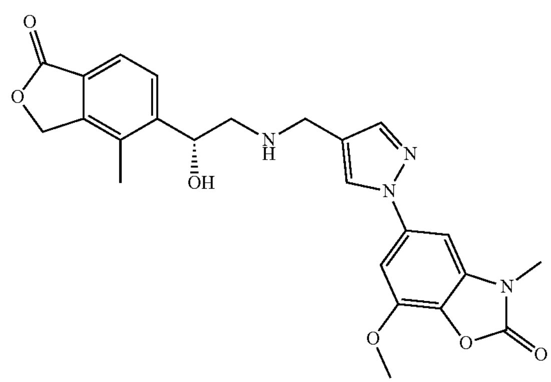 [SMILES: COc1cc(-n2cc(CNC[C@H](O)c3ccc4c(c3C)COC4=O)cn2)cc2c1oc(=O)n2C] | (R)-5-(4-(((2-hydroxy-2-(4-methyl-1-oxo-1,3-di-Hydroisobenzofuran-5-yl)ethyl)amino)methyl)-1H-pyrazol-1-yl)-7-methoxy-3-mthylbenzo[d]oxazol-2(3H)-one | 465.1 | A: 1.15, 100% B: 1.29, 99.64% III: 14.23, 100% ee | 1H NMR (400 MHz, DMSO-d6) δ ppm 2.24 (s, 3 H), 2.65-2.73 (m, 1 H), 2.74-2.80 (m, 1 H), 3.36 (s, 3 H), 3.79 (br. s., 2 H), 3.98 (s, 3 H), 5.04-5.08 (m, 1 H), 5.33-5.41 (m, 2 H), 5.61 (br. s, 1H), 7.28 (d, J = 1.96 Hz, 1 H), 7.36 (d, J = 1.96 Hz, 1 H), 7.66-7.72 (m, 3 H), 8.45 (s, 1 H). (1 Exchangeable proton not observed). |

| Ex. | Structure | Name | LCMS (M + H)+ | HPLC/LCMS Method: RT (min.), Purity | NMR |
|---|---|---|---|---|---|
| 113 | 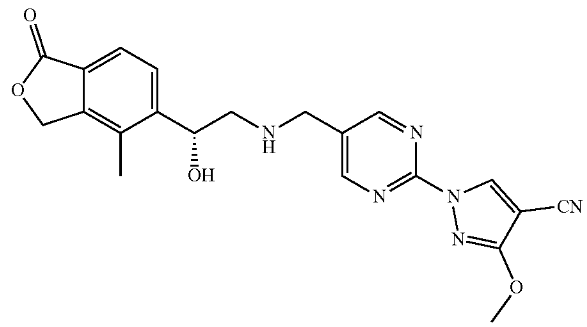 [SMILES: COc1nn(-c2ncc(CNC[C@H](O)c3ccc4c(c3C)COC4=O)cn2)cc1C#N] | (R)-1-(5-(((2-hydroxy-2-(4-methyl-1-oxo-1,3-dihydroisobenzofuran-5-yl)ethyl)amino)methyl)pyrimidin-2-yl)-3-methoxy-1H-pyrazole-4-carbonitrile | 421.2 | A: 0.89, 97.92% B: 1.11, 97.63% XVIII: 11.44, 99% ee | ¹H NMR (400 MHz, DMSO-d₆) δ ppm 2.23 (s, 3 H), 2.62-2.74 (m, 2 H), 3.85 (s, 2 H), 3.99-4.11 (s, 3 H), 4.96-5.09 (m, 1 H), 5.29-5.44 (m, 2 H), 5.52 (br. s, 1 H), 7.58-7.74 (m, 2 H), 8.79 (s, 2 H), 9.29 (s, 1 H), (1 Exchangeable proton not observed). |
| 114 | 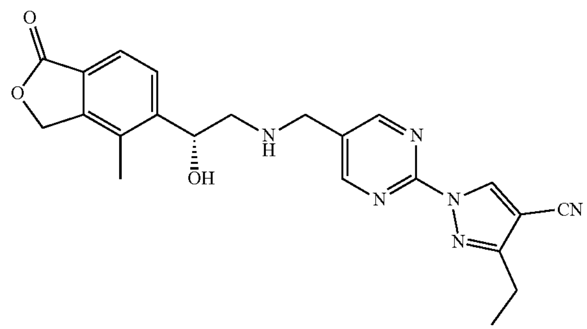 [SMILES: CCc1nn(-c2ncc(CNC[C@H](O)c3ccc4c(c3C)COC4=O)cn2)cc1C#N] | (R)-3-ethyl-1-(5-(((2-hydroxy-2-(4-methyl-1-oxo-1,3-dihydroisobenzofuran-5-yl)ethyl)amino)methyl)pyrimidin-2-yl)-1H-pyrazole-4-carbonitrile | 419.2 | A: 0.92, 98.32% B: 1.20, 100% XVIII: 11.70, 99% ee | ¹H NMR (400 MHz, DMSO-d₆) δ ppm 1.30 (t, J = 7.6 Hz, 3 H), 2.23 (s, 3 H), 2.61-2.72 (m, 2 H), 2.80 (q, J = 7.6 Hz, 2 H), 3.85 (s, 2 H), 4.91-5.11 (m, 1 H), 5.26-5.44 (m, 2 H), 5.51 (d, J = 3.9 Hz, 1 H), 7.57-7.76 (m, 2 H), 8.82 (s, 2 H), 9.34 (s, 1H), (1 Exchangeable proton not observed). |
| 115 | 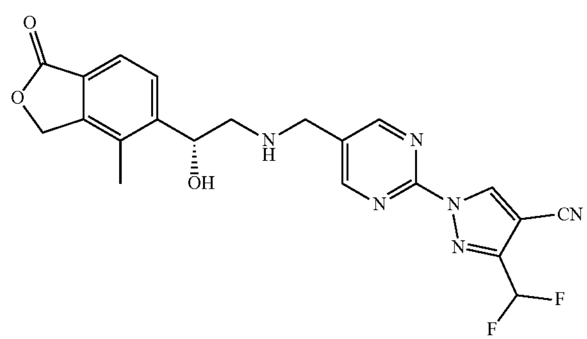 [SMILES: Cc1c([C@@H](O)CNCc2cnc(-n3cc(C#N)c(C(F)F)n3)nc2)ccc2c1COC2=O] | (R)-3-(difluoromethyl)-1-(5-((2-hydroxy-2-(4-methyl-1-oxo-1,3-dihydroisobenzofuran-5-yl)ethyl)amino)methyl)pyrimidin-2-yl)-1H-pyrazole-4-carbonitrile | 441.2 | A: 0.89, 100% B: 1.17, 100% IV: 8.25, 100% ee | ¹H NMR (400 MHz, DMSO-d₆) δ ppm 2.24 (s, 3 H), 2.61-2.73 (m, 2 H), 3.88 (s, 2 H), 4.93-5.09 (m, 1 H), 5.24-5.45 (m, 2 H), 5.51 (d, J = 3.9 Hz, 1 H), 7.36 (t, J = 52.0 Hz, 1 H), 7.58-7.76 (m, 2 H), 8.88 (s, 2 H), 9.62 (s, 1 H), (1 Exchangeable proton not observed). ¹⁹F NMR (400 MHz, DMSO-d₆) δ ppm-114.55 |

-continued

| Ex. | Structure | Name | LCMS (M + H)+ | HPLC/LCMS Method: RT (min.), Purity | NMR |
|---|---|---|---|---|---|
| 116 | 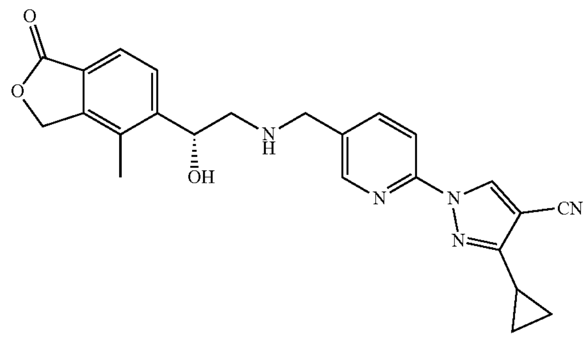 [SMILES: Cc1c([C@@H](O)CNCc2ccc(-n3cc(C#N)c(C4CC4)n3)nc2)ccc2c1COC2=O] | (R)-3-cyclopropyl-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile | 431.1 | A: 1.18, 100% B: 1.53, 100% XVIII: 10.16, 100% ee | 1H NMR (400 MHz, DMSO-d6) δ ppm 0.96-1.03 (m, 2 H), 1.04-1.13 (m, 2 H), 2.08 (ddd, J = 13.39, 8.38, 4.89 Hz, 1 H), 2.21 (s, 3 H), 2.59-2.71 (m, 3 H), 3.85 (s, 2 H), 5.03 (br. s, 1 H), 5.29-5.43 (m, 2 H), 5.53 (br. s, 1 H), 7.58-7.69 (m, 2 H), 7.81 (d, J = 8.56 Hz, 1 H), 7.96 (d, J = 6.85 Hz, 1 H), 8.42 (s, 1 H), 9.23 (s, 1 H) |
| 117 | 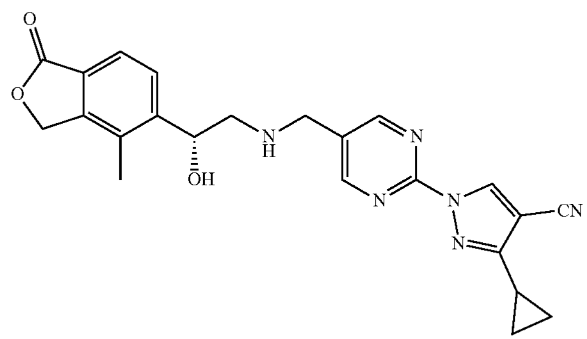 [SMILES: Cc1c([C@@H](O)CNCc2cnc(-n3cc(C#N)c(C4CC4)n3)nc2)ccc2c1COC2=O] | (R)-3-cyclopropyl-1-(5-(((2-hydroxy-2-(4-methyl-1-oxo-1,3-dihydroisobenzofuran-5-yl)ethyl)amino)methyl)pyrimidin-2-yl)-1H-pyrazole-4-carbonitrile | 431.2 | A: 0.94, 98.54% B: 1.24, 98.40% XVIII: 12.27, 93.6% ee | 1H NMR (400 MHz, DMSO-d6) δ ppm 0.92-1.03 (m, 2 H), 1.05-1.16 (m, 2 H), 2.01-2.12 (m, 1 H), 2.23 (s, 3 H), 2.60-2.72 (m, 2 H), 3.84 (s, 2 H), 4.91-5.07 (m, 1H), 5.27-5.43 (m, 2 H) 5.50 (d, J = 3.7 Hz, 1 H), 7.53-7.74 (m, 2 H), 8.80 (s, 2 H), 9.31 (s, 1 H), (1 Exchangeable proton not observed). |
| 118 | 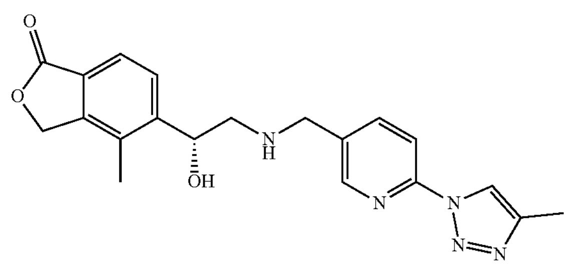 | (R)-5-(1-hydroxy-2-(((6-(4-methyl-1H-1,2,3-triazol-1-yl)pyridin-3-yl)methyl)amino)ethyl)-4-methylisobenzofuran-1(3H)-one | 380.2 | A: 0.76, 97.26% B: 1.00, 97.65% XVIII: 10.88, 100% ee | 1H NMR (400 MHz, DMSO-d6) δ ppm 2.22 (s, 3 H), 2.33-2.36 (s, 3 H), 2.59-2.70 (m, 2 H), 3.87 (s, 2 H), 5.03 (dt, J = 7.5, 3.8 Hz, 1 H), 5.27-5.43 (m, 2 H), 5.52 (d, J = 3.5 Hz, 1 H), 7.55-7.77 (m, 2 H), 8.03 (d, J = 1.5 Hz, 2 H), 8.49 (s, 1 H), 8.56 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 119 | 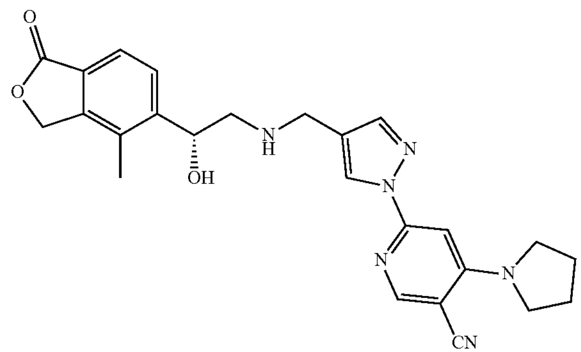 [SMILES: Cc1c([C@@H](O)CNCc2cnn(-c3cc(N4CCCC4)c(C#N)cn3)c2)ccc2c1COC2=O] | (R)-6-(4-(((2-hydroxy-2-(4-methyl-1-oxo-1,3-dihydroisobenzofuran-5-yl)ethyl)amino)methyl)-1H-pyrazol-1-yl)-4-(pyrrolidin-1-yl)nicotinonitrile | 459.2 | A: 1.12, 98.45% B: 1.41, 97.45% XIV: 9.71, 99.3% ee | 1H NMR (400 MHz, DMSO-d6) δ ppm 1.94-2.04 (m, 4 H), 2.20-2.30 (m, 3 H), 2.96 (br. s, 1 H), 3.10 (br. s, 1 H), 3.67 (br. s, 4 H), 4.22(br. s, 2 H), 5.23 (d, J = 8.6 Hz, 1 H), 5.33-5.47 (m, 2 H), 6.32 (br. s, 1 H), 7.05 (s, 1 H), 7.66-7.76 (m, 2 H), 7.94 (s, 1 H), 8.45 (s, 1 H), 8.75 (s, 1 H), 9.05 (br. s, 1 H). |
| 120 | 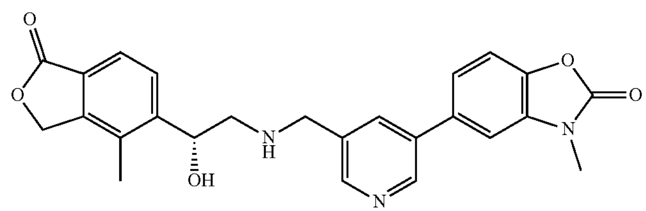 [SMILES: Cc1c([C@@H](O)CNCc2cncc(-c3ccc4oc(=O)n(C)c4c3)c2)ccc2c1COC2=O] | (R)-5-(5-(((2-hydroxy-2-(4-methyl-1-oxo-1,3-dihydroisobenzofuran-5-yl)ethyl)amino)methyl)pyridin-3-yl)-3-methylbenzo[d]oxazol-2(3H)-one | 446.0 | A: 1.02, 97.18% B: 1.32, 96.30% VI: 16.08, 96.62% ee | 1H NMR (400 MHz, DMSO-d6) δ ppm 2.21 (s, 3 H), 2.60-2.75 (m, 2 H), 3.41 (s, 3 H), 3.89 (s, 2 H), 5.04 (br. s, 1 H), 5.21-5.42 (m, 2 H), 5.53 (br. s, 1 H), 7.44 (s, 2 H), 7.59-7.73 (m, 3 H), 8.00 (s, 1 H), 8.51 (d, J = 1.71 Hz, 1 H), 8.79 (d, J = 2.20 Hz, 1 H), (1 Exchangeable proton not observed). |
| 121 | 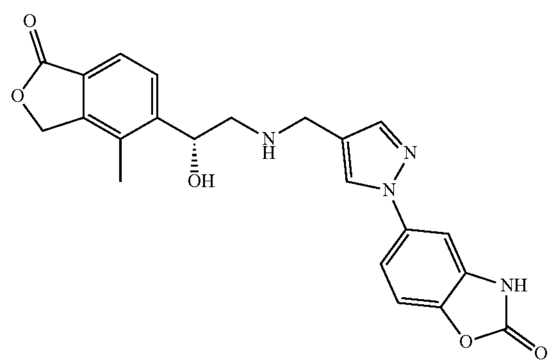 [SMILES: Cc1c([C@@H](O)CNCc2cnn(-c3ccc4oc(=O)[nH]c4c3)c2)ccc2c1COC2=O] | (R)-5-(4-(((2-hydroxy-2-(4-methyl-1-oxo-1,3-dihydroisobenzofuran-5-yl)ethyl)amino)methyl)-1H-pyrazol-1-yl)benzo[d]oxazol-2(3H)-one | 421.1 | A: 1.03, 98.05% B: 1.06, 100% XX: 3.21, 100% ee | 1H NMR (400 MHz, DMSO-d6) δ ppm 2.23 (s, 3 H), 2.57-2.79 (m, 2 H), 3.76 (br. s, 2 H), 5.04 (br. s, 1 H), 5.29-5.46 (m, 2 H), 5.56 (br. s, 1 H), 7.36 (d, J = 9.54 Hz, 1 H), 7.43-7.52 (m, 2 H), 7.63-7.77 (m, 3 H), 8.36 (s, 1 H), (2 Exchangeable protons not observed). |

| Ex. | Structure | Name | LCMS (M + H)+ | HPLC/LCMS Method: RT (min.), Purity | NMR |
|---|---|---|---|---|---|
| 122 | 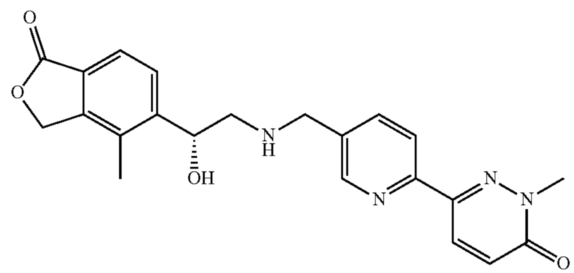 [SMILES: Cc1c([C@@H](O)CNCc2ccc(-c3ccc(=O)n(C)n3)nc2)ccc2c1COC2=O] | (R)-6-(5-(((2-hydroxy-2-(4-methyl-1-oxo-1,3-dihydroisobenzofuran-5-yl)ethyl)amino)methyl)pyridin-2-yl)-2-methylpyridazin-3(2H)-one | 407.0 | A: 0.90, 99.52% B: 1.15, 98.38% XVIII: 10.54, 100% ee | ¹H NMR (400 MHz, DMSO-d₆) δ ppm 2.21 (s, 3 H), 2.59-2.70 (m, 2 H), 3.76 (s, 3 H), 3.84 (s, 2 H), 4.98-5.08 (m, 1 H), 5.29-5.41 (m, 2 H), 5.50 (d, J = 4.40 Hz, 1 H), 7.06 (d, J = 9.78 Hz, 1 H), 7.61-7.71 (m, 2 H), 7.86 (dd, J = 8.19, 2.08 Hz, 1 H), 8.03 (d, J = 8.07 Hz, 1 H), 8.28 (d, J = 9.78 Hz, 1 H), 8.58 (s, 1 H), (1 Exchangeable proton not observed). |
| 123 | 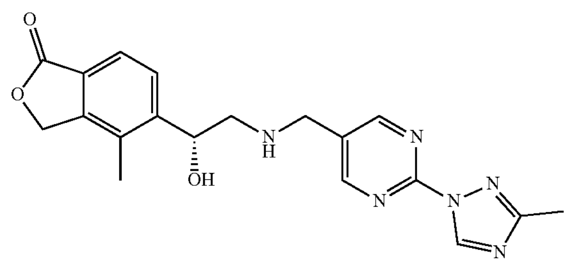 [SMILES: Cc1ncn(-c2ncc(CNC[C@H](O)c3ccc4c(c3C)COC4=O)cn2)n1] | (R)-5-(1-hydroxy-2-(((2-(3-methyl-1H-1,2,4-ttiazol-1-yl)pyrimidin-5-yl)methyl)amino)ethyl)-4-methylisobenzofuran-1(3H)-one | 381.1 | A: 0.57, 100% B: 0.76, 100% XVIII: 15.79, 96.5% ee | ¹H NMR (400 MHz, DMSO-d₆) δ ppm 2.18-2.27 (m, 3 H), 2.39 (s, 3 H), 2.60-2.72 (m, 2 H), 3.80-3.92 (m, 2 H), 5.03 (br. s, 1 H), 5.30-5.42 (m, 2 H), 5.54 (br. s, 1 H), 7.59-7.71 (m, 2 H), 8.82 (s, 2 H), 9.27 (s, 1 H), (1 Exchangeable proton not observed). |
| 124 | 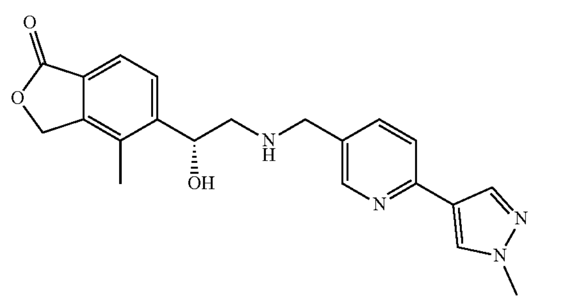 [SMILES: Cc1c([C@@H](O)CNCc2ccc(-c3cnn(C)c3)nc2)ccc2c1COC2=O] | (R)-5-(1-hydroxy-2-(((6-(1-methyl-1H-pyrazol-4-yl)pyridin-3-yl)methyl)amino)ethyl)-4-methylisobenzofuran-1(3H)-one | 379.1 | A: 0.86, 100% B: 1.15, 100% XVII: 10.14, 97.90% ee | ¹H NMR (400 MHz, DMSO-d₆) δ ppm 2.21 (s, 3 H), 2.58-2.68 (m, 2 H) 3.71 (s, 2 H), 3.87 (s, 3 H), 5.02 (dd, J = 7.21, 4.28 Hz, 1 H), 5.36 (s, 2 H), 5.36-5.41 (br. s, 1 H), 7.56 (d, J = 7.83 Hz, 1 H), 7.63-7.71 (m, 3 H), 7.95 (s, 1 H), 8.20 (s, 1 H), 8.23 (s, 1 H), 8.41 (s, 1 H). |

| Ex. | Structure | Name | LCMS (M + H)+ | HPLC/LCMS Method: RT (min.), Purity | NMR |
|---|---|---|---|---|---|
| 125 | 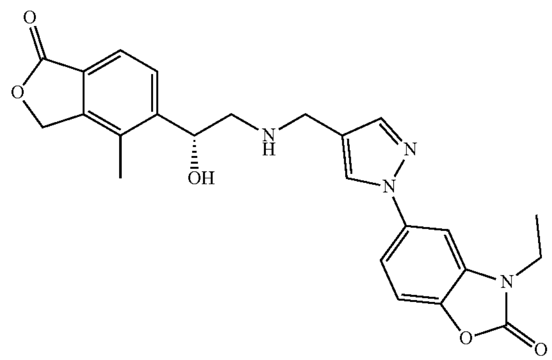 [SMILES: CCn1c(=O)oc2ccc(-n3cc(CNC[C@H](O)c4ccc5c(c4C)COC5=O)cn3)cc21] | (R)-3-ethyl-5-(4-(((2-hydroxy-2-(4-methyl-1-oxo-1,3-dihydroisobenzofuran-5-yl)ethyl)amino)methyl)-1H-pyrazol-1-yl)benzo[d]oxazol-2(3H)-one | 449.1 | A: 1.20, 98.10% B: 1.29, 97.37% XVII: 8.12, 100% ee | $^1$H NMR (400 MHz, DMSO-d$_6$) δ ppm 1.29 (t, J = 7.20 Hz, 3 H), 2.24 (s, 3 H), 2.61-2.78 (m, 2 H), 3.63-3.80 (m, 2 H), 3.91 (q, J = 7.42 Hz, 2 H), 5.04 (dd, J = 8.19, 3.79 Hz, 1 H), 5.29-5.43 (m, 2 H), 5.51 (br. s, 1 H) 7.42 (d, J = 8.80 Hz, 1 H), 7.55 (dd, J = 8.80, 2.20 Hz, 1 H), 7.60-7.74 (m, 3 H), 7.77 (d, J = 2.20 Hz, 1 H), 8.39 (s, 1 H), (1 Exchangeable proton not observed). |
| 126 | 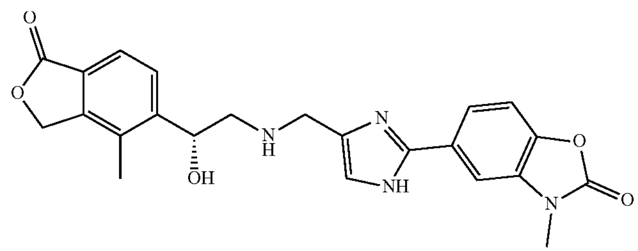 [SMILES: Cc1c([C@@H](O)CNCc2c[nH]c(-c3ccc4oc(=O)n(C)c4c3)n2)ccc2c1COC2=O] | (R)-5-(4-(((2-hydroxy-2-(4-methyl-1-oxo-1,3-dihydroisobenzofuran-5-yl)ethyl)amino)methyl)-1H-imidazol-2-yl)-3-methylbenzo[d]oxazol-2(3H)-one | 435.1 | A: 0.92, 95.23% B: 1.02, 99.32% XI: 11.30, 100% ee | $^1$H NMR (400 MHz, CD$_3$OD) δ 2.35 (s, 3 H), 2.85-2.98 (m, 1 H), 3.01-3.15 (m, 1 H), 3.38 (s, 3 H), 4.32-4.46 (m, 2 H), 5.36 (d, J = 6.02 Hz, 2 H), 5.41 (dd, J = 10.29, 2.76 Hz, 1 H), 7.41 (d, J = 8.53 Hz, 1 H), 7.49 (s, 1 H), 7.68-7.75 (m, 2 H), 7.75-7.80 (m, 1 H), 7.85 (d, J = 8.03 Hz, 1 H), (2 Exchangeable protons not observed). |
| 127 | 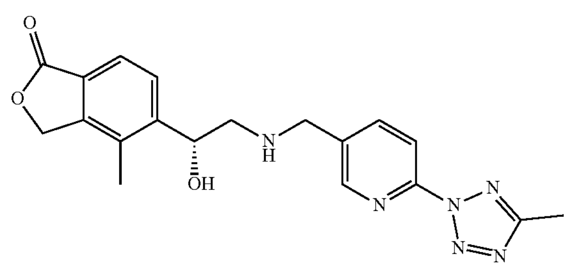 [SMILES: Cc1nnn(-c2ccc(CNC[C@H](O)c3ccc4c(c3C)COC4=O)cn2)n1] | (R)-5-(1-hydroxy-2-(((6-(5-methyl-2H-tetrazol-2-yl)pyridin-3-yl)methyl)amino)ethyl)-4-methylisobenzofuran-1(3H)-one | 381.1 | A: 0.85, 98.92% B: 1.14, 99.47% XI: 10.68, 100% ee | $^1$H NMR (400 MHz, DMSO-d$_6$) δ 2.29 (s, 3 H), 2.81 (s, 3 H), 2.95-3.09 (m, 1 H), 3.17 (br. s, 1 H), 4.42 (br. s, 2 H), 5.27 (d, J = 9.29 Hz, 1 H), 5.34-5.50 (m, 2 H), 6.37 (br. s, 1 H), 7.64-7.89 (m, 2 H), 8.10 (d, J = 8.56 Hz, 1 H), 8.32 (dd, J = 8.31, 2.20 Hz, 1 H), 8.77 (d, J = 2.20 Hz, 1 H), 9.32 (br. s, 1 H). |

| Ex. | Structure | Name | LCMS (M+H)+ | HPLC/LCMS Method: RT (min.), Purity | NMR |
|---|---|---|---|---|---|
| 128 | 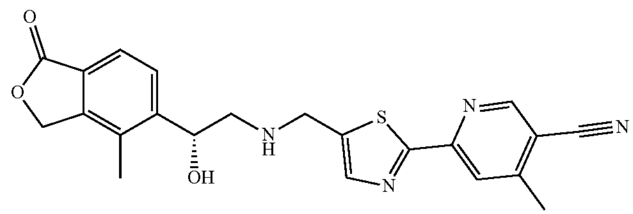 [SMILES: Cc1cc(-c2ncc(CNC[C@H](O)c3ccc4c(c3C)COC4=O)s2)ncc1C#N] | (R)-6-(5-(((2-hydroxy-2-(4-methyl-1-oxo-1,3-dihydroisobenzofuran-5-yl)ethyl)amino)methyl)thiazol-2-yl)-4-methylnicotinonitrile | 421.1 | A: 1.15, 100% B: 1.59, 100% X: 3.02 100% ee | ¹H NMR (400 MHz, DMSO-d₆) δ 2.22 (s, 3 H), 2.59 (s, 3 H), 2.64-2.73 (m, 2 H), 4.01-4.10 (m, 2 H), 5.03 (br. s, 1 H), 5.27-5.43 (m, 2 H), 5.53 (br. s, 1 H), 7.57-7.75 (m, 2 H), 7.89 (s, 1 H), 8.17 (s, 1 H), 8.94 (s, 1 H), (1 Exchangeable proton not observed). |
| 129 | 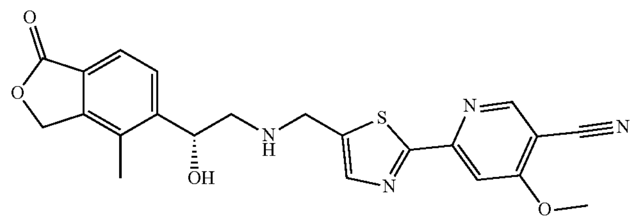 [SMILES: COc1cc(-c2ncc(CNC[C@H](O)c3ccc4c(c3C)COC4=O)s2)ncc1C#N] | (R)-6-(5-(((2-hydroxy-2-(4-methyl-1-oxo-1,3-dihydroisobenzofuran-5-yl)ethyl)amino)methyl)thiazol-2-yl)-4-methoxynicotinonitrile | 437.0 | A: 1.16, 100% B: 1.52, 99.39% X: 8.47 100% ee | ¹H NMR (400 MHz, DMSO-d₆) δ ppm 2.22 (s, 3 H), 2.61-2.77 (m, 2 H), 4.05 (s, 2 H), 4.12 (s, 3 H), 5.02 (d, J = 4.40 Hz, 1 H), 5.23-5.41 (m, 2 H), 5.52 (d, J = 4.16 Hz, 1 H), 7.57-7.71 (m, 2 H), 7.82 (s, 1 H), 7.90 (s, 1 H), 8.84 (s, 1 H), (2 Exchangeable proton not observed). |
| 130 | 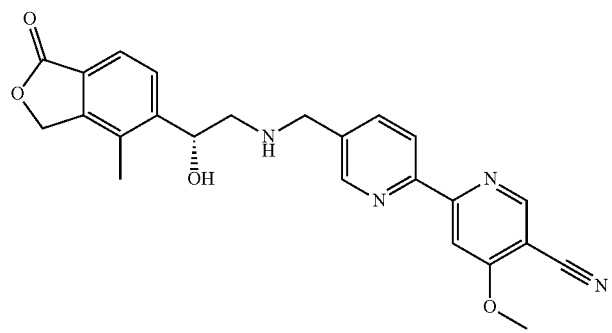 [SMILES: COc1cc(-c2ccc(CNC[C@H](O)c3ccc4c(c3C)COC4=O)cn2)ncc1C#N] | (R)-5'-(((2-hydroxy-2-(4-methyl-1-oxo-1,3-dihydroisobenzofuran-5-yl)ethyl)amino)methyl)-4-methoxy-[2,2'-bipyridine]-5-carbonitrile | 431.1 | A: 1.13, 98.42% B: 1.49, 99.38% X: 7.31 100% ee | ¹H NMR (400 MHz, DMSO-d₆) δ ppm 2.22 (s, 3 H), 2.58-2.71 (m, 2 H), 3.89 (s, 2 H), 4.12 (s, 3 H), 5.04 (br. s, 1 H), 5.30-5.42 (m, 2 H), 5.52 (br. s, 1 H), 7.59-7.71 (m, 2 H), 7.94 (dd, J = 8.19, 2.32 Hz, 1 H), 8.15 (s, 1 H), 8.38 (d, J = 8.31 Hz, 1 H), 8.67 (s, 1 H), 8.91 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 131 | 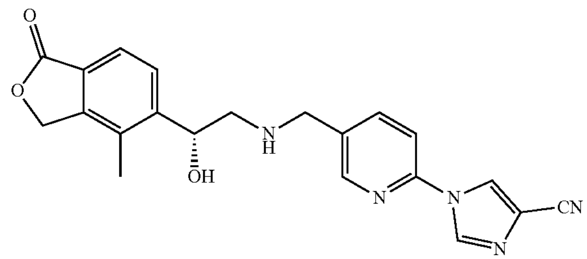 | (R)-1-(5-(((2-hydroxy-2-(4-methyl-1-oxo-1,3-dihydroisobenzofuran-5-yl)ethyl)amino)methyl)pyridin-2-yl)-1H-imidazole-4-carbonitrile | 390.1 | A: 0.92, 95.02% B: 1.19', 95.73% XIV: 5.20 89.00% ee | 1H NMR (400 MHz, DMSO-d6) δ ppm 2.21 (s, 3 H), 2.56-2.71 (m, 2 H), 3.84 (s, 2 H), 5.02 (br. s, 1 H), 5.23-5.41 (m, 2 H), 5.52 (br. s, 1 H), 7.58-7.75 (m, 2 H), 7.84 (d, J = 8.07 Hz, 1 H), 8.01 (dd, J = 8.44, 2.08 Hz, 1H), 8.47 (d, J = 1.96 Hz, 1 H), 8.73 (d, J = 1.22 Hz, 1 H), 8.90 (d, J = 1.22 Hz, 1 H), (1 Exchangeable proton not observed). |
| 132 | 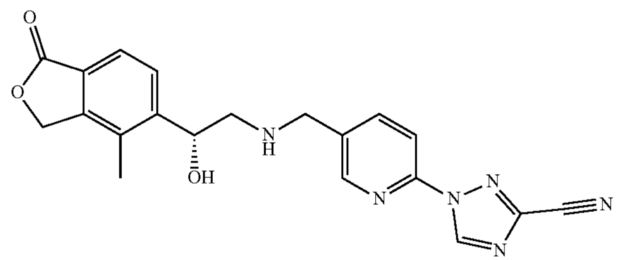 [SMILES: Cc1c([C@@H](O)CNCc2ccc(-n3cnc(C#N)n3)nc2)ccc2c1COC2=O] | (R)-1-(5-(((2-hydroxy-2-(4-methyl-1-oxo-1,3-dihydroisobenzofuran-5-yl)ethyl)amino)methyl)pyridin-2-yl)-1H-1,2,4-triazole-3-carbonitrile | 391.0 | A: 1.05, 93.87% B: 1.41, 93.07% XVIII: 10.56, 85.00% ee | 1H NMR (400 MHz, DMSO-d6) 2.28 (s, 3 H), 3.01 (br. s, 1 H), 3.16 (br. s, 1 H), 4.39 (br. s, 2 H), 5.26 (d, J = 11.25 Hz, 1 H), 5.31-5.48 (m, 2 H), 6.38 (br. s, 1 H), 7.61-7.81 (m, 2 H) 8.06 (d, J = 8.80 Hz, 1 H), 8.29 (dd, J = 8.44, 2.32 Hz, 1 H), 8.71 (d, J = 1.96 Hz, 1 H), 9.30 (br. s., 1 H), 9.79 (s, 1 H) |
| 133 | 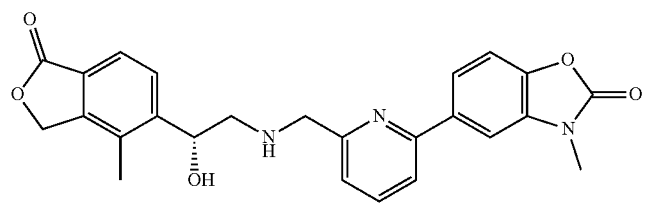 [SMILES: Cc1c([C@@H](O)CNCc2cccc(-c3ccc4oc(=O)n(C)c4c3)n2)ccc2c1COC2=O] | (R)-5-(6-(((2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one | 446.1 | A: 1.15, 96.53% B: 1.42, 94.69% | 1H NMR (400 MHz, DMSO-d6) δ ppm 2.23 (s, 3 H), 2.80-2.94 (m, 2 H), 3.43 (s, 3 H), 4.14 (br. s., 2 H), 5.18 (d, J = 6.11 Hz, 1 H), 5.31-5.44 (m, 2 H), 5.85 (br. s, 1 H), 7.39 (d, J = 7.09 Hz, 1 H), 7.45 (d, J = 8.31 Hz, 1 H), 7.64-7.74 (m, 2 H), 7.86-7.99 (m, 3 H), 8.02 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 134 | 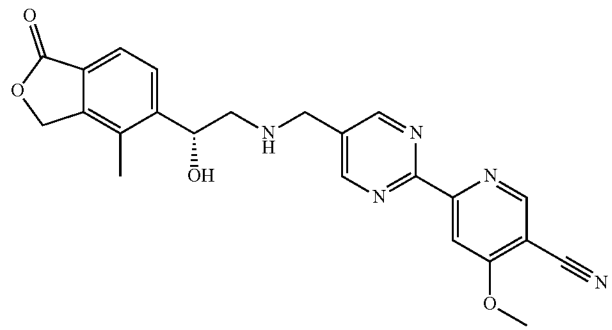 [SMILES: COc1cc(-c2ncc(CNC[C@H](O)c3ccc4c(c3C)COC4=O)cn2)ncc1C#N] | (R)-6-(5-(((2-hydroxy-2-(4-methyl-1-oxo-1,3-dihydroisobenzofuran-5-yl)ethyl)amino)methyl)pyrimidin-2-yl)-4-methoxynicotinonitrile | 432.0 | A: 1.01, 98.98% B: 1.23, 97.38% XIV: 8.24 100% ee | 1H NMR (400 MHz, DMSO-d6) δ ppm 2.23 (s, 3 H), 2.58-2.78 (m, 2 H), 3.89 (s, 2 H), 4.13 (s, 3 H), 5.02 (br. s, 1 H), 5.25-5.44 (m, 2 H), 5.51 (d, J = 4.16 Hz, 1 H), 7.56-7.73 (m, 2 H), 8.15 (s, 1 H), 8.93 (br. s, 3 H), (1 Exchangeable proton not observed) |
| 135 | 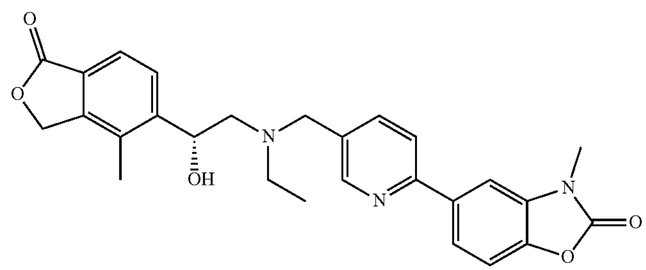 [SMILES: CCN(Cc1ccc(-c2ccc3oc(=O)n(C)c3c2)nc1)C[C@H](O)c1ccc2c(c1C)COC2=O] | (R)-5-((ethyl(2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one | 474.1 | A: 1.15, 99.85% B: 1.90, 99.55% XIII: 3.02, 99.00% ee | 1H NMR (400 MHz, DMSO-d6) δ ppm 1.00-1.03 (t, J = 7.2 Hz, 3 H), 2.17 (s, 3 H), 2.58-2.73 (m, 4 H), 3.44 (s, 3 H), 3.58-3.77 (m, 2 H), 4.94-5.08 (m, 1 H), 5.29 (d, J = 3.51 Hz, 1 H), 5.33 (s, 2 H), 7.42 (d, J = 8.03 Hz, 1 H), 7.59 (s, 2 H), 7.68 (dd, J = 8.03, 2.01 Hz, 1 H), 7.82-7.88 (m, 2 H), 7.92 (d, J = 1.51 Hz, 1 H), 8.44 (d, J = 1.51 Hz, 1 H). |
| 136 | 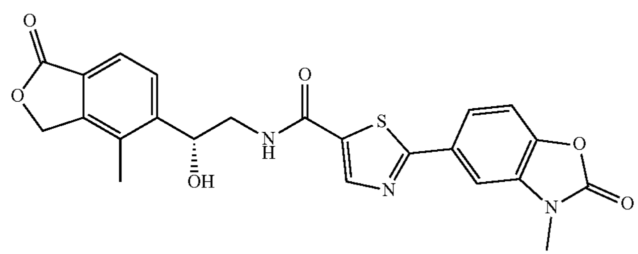 [SMILES: Cc1c([C@@H](O)CNC(=O)c2cnc(-c3ccc4oc(=O)n(C)c4c3)s2)ccc2c1COC2=O] | (R)-N-(2-hydroxy-2-(4-methyl-1-oxo-1,3-dihydroisobenzofuran-5-yl)ethyl)-2-(3-methyl-2-oxo-2,3-dihydrobenzo[d]oxazol-5-yl)thiazole-5-carboxamide | 466.0 | E: 1.73, 97.11% G: 6.79, 98.74% X: 6.94 97.22% ee | 1H NMR (400 MHz, DMSO-d6) δ ppm 2.33 (s, 3 H), 3.12-3.22 (m, 1 H), 3.43 (s, 3 H), 3.54 (d, J = 11.74 Hz, 1 H), 5.11-5.17 (m, 1 H), 5.42 (s, 2 H), 5.80 (d, J = 4.40 Hz, 1 H), 7.48 (d, J = 8.31 Hz, 1 H), 7.66-7.81 (m, 3 H), 7.87 (d, J = 1.71 Hz, 1 H), 8.51 (s, 1 H), 9.05 (t, J = 5.50 Hz, 1 H). |

| Ex. | Structure | Name | LCMS (M + H)+ | HPLC/LCMS Method: RT (min.), Purity | NMR |
|---|---|---|---|---|---|
| 137 | 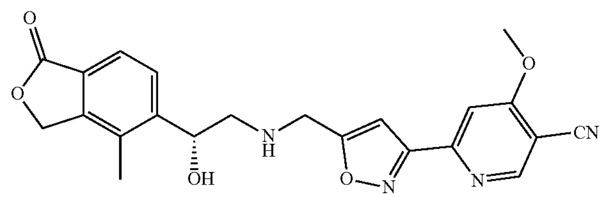 [SMILES: COc1cc(-c2cc(CNC[C@H](O)c3ccc4c(c3C)COC4=O)on2)ncc1C#N] | (R)-6-(5-(((2-hydroxy-2-(4-methyl-1-oxo-1,3-dihydroisobenzofuran-5-yl)ethyl)amino)methyl)isoxazol-3-yl)-4-methoxynicotinonitrile | 421.0 | B: 1.43, 97.10% A: 1.11, 97.60% XVIII: 8.98, 98.90% ee | $^1$H NMR (400 MHz, DMSO-$d_6$) δ 2.25 (s, 3 H), 2.63-2.73 (m, 2 H), 3.99 (s, 2 H), 4.11 (s, 3 H), 5.01 (br. s., 1 H), 5.30-5.42 (m, 2 H), 5.53 (d, J = 3.67 Hz, 1 H), 6.87 (s, 1 H), 7.62-7.70 (m, 2 H), 7.76 (s, 1 H), 8.93 (s, 1 H), (1 Exchangeable proton not observed). |
| 138 | 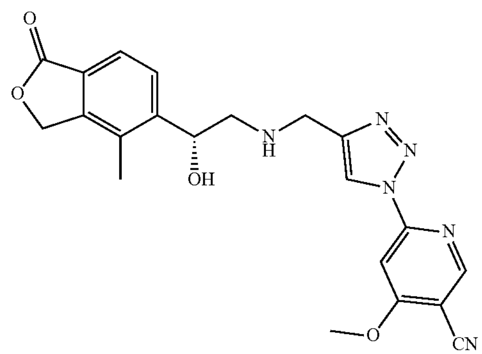 [SMILES: COc1cc(-n2cc(CNC[C@H](O)c3ccc4c(c3C)COC4=O)nn2)ncc1C#N] | (R)-6-(4-(((2-hydroxy-2-(4-methyl-1-oxo-1,3-dihydroisobenzofuran-5-yl)ethyl)amino)methyl)-1H-1,2,3-triazol-1-yl)-4-methoxynicotinonitrile | 421.2 | E: 9.52, 97.80% T: 11.10, 97.60% XIV: 7.77, 100% ee | $^1$H NMR (400 MHz, DMSO-$d_6$) δ ppm 2.25 (s, 3 H), 2.63-2.76 (m, 2 H), 3.86-3.98 (m, 2 H), 4.17 (s, 3 H), 5.03 (dd, J = 7.40, 3.89 Hz, 1 H), 5.37 (d, J = 3.76 Hz, 2 H), 5.50 (br. s., 1 H), 7.63-7.70 (m, 2 H), 7.88 (s, 1 H), 8.66 (s, 1 H), 8.88 (s, 1 H). (1 Exchangeable proton not observed). |
| 139 | 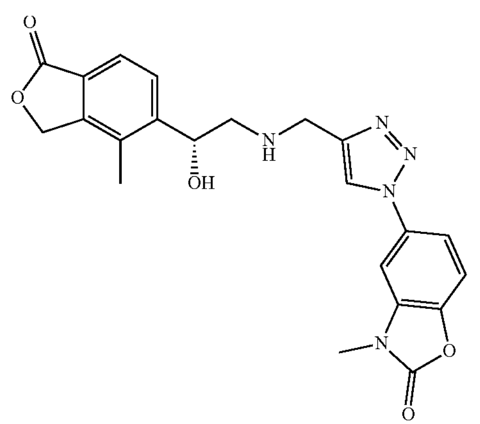 [SMILES: Cc1c([C@@H](O)CNCc2cn(-c3ccc4oc(=O)n(C)c4c3)nn2)ccc2c1COC2=O] | (R)-5-(4-(((2-hydroxy-2-(4-methyl-1-oxo-1,3-dihydroisobenzofuran-5-yl)ethyl)amino)methyl)-1H-1,2,3-triazol-1-yl)-3-methylbenzo[d]oxazol-2(3H)-one | 436.2 | E: 8.94, 98.60% T: 10.17, 98.40% XVIII: 13.44, 100% ee | $^1$H NMR (300 MHz, DMSO-$d_6$) δ ppm 2.22-2.29 (m, 3 H), 2.62-2.78 (m, 2 H), 3.40 (s, 3 H), 3.90 (d, J = 1.51 Hz, 2 H), 5.04 (br. s., 1 H), 5.37 (s, 2 H), 5.51 (br. s., 1 H), 7.49-7.55 (m, 1 H), 7.59-7.71 (m, 3 H), 7.85 (d, J = 1.89 Hz, 1 H), 8.58 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 140 | 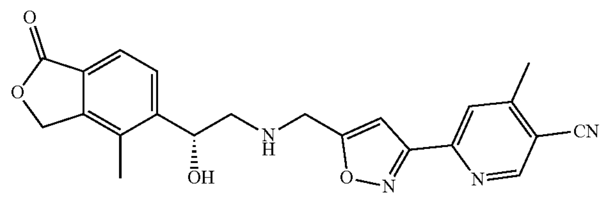 [SMILES: Cc1cc(-c2cc(CNC[C@H](O)c3ccc4c(c3C)COC4=O)on2)ncc1C#N] | (R)-6-(5-(((2-hydroxy-2-(4-methyl-1-oxo-1,3-dihydroisobenzofuran-5-yl)ethyl)amino)methyl)isoxazol-3-yl)-4-methylnicotinonitrile | 405.2 | B: 1.27, 96.40% A: 0.92, 97.00% XX: 6.59, 68.40% ee | $^1$H NMR (400 MHz, DMSO-$d_6$) δ ppm 2.25 (s, 3 H), 2.59 (s, 3 H), 2.73-2.87 (m, 2 H), 4.13 (br. s., 2 H), 5.08 (br. s., 1 H), 5.38 (d, J = 3.91 Hz, 2 H), 5.71 (br. s., 1 H), 6.95 (s, 1 H), 7.64-7.71 (m, 2 H), 8.14 (s, 1 H), 9.05 (s, 1 H), (1 Exchangeable proton not observed). |
| 141 | 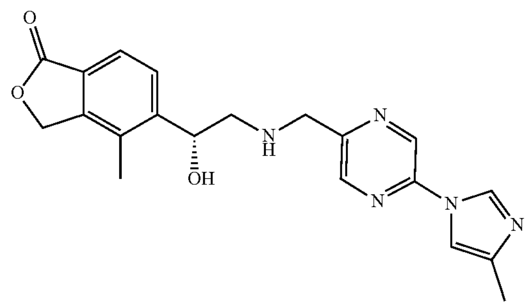 [SMILES: Cc1cn(-c2cnc(CNC[C@H](O)c3ccc4c(c3C)COC4=O)cn2)cn1] | (R)-5-(1-hydroxy-2-(((5-(4-methyl-1H-imidazol-1-yl)pyrazin-2-yl)methyl)amino)ethyl)-4-methylisobenzofuran-1(3H)-one | 380 | B: 1.13, 95.3% A: 0.43, 100% XXII: 6.65, 100% ee | $^1$H NMR (400 MHz, DMSO-$d_6$) δ ppm 2.21 (s, 3 H), 2.26-2.36 (m, 3 H), 2.89-3.15 (m, 2 H), 4.49 (br. s., 2 H), 5.28-5.49 (m, 3 H), 6.33 (br. s., 1 H), 7.68-7.82 (m, 3 H), 8.57-8.69 (m, 2 H), 9.18-9.53 (m, 2 H). |
| 142 | 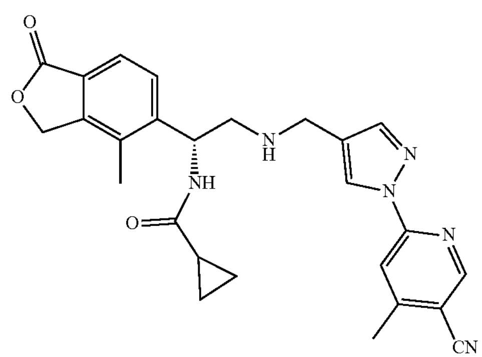 [SMILES: Cc1cc(-n2cc(CNC[C@H](NC(=O)C3CC3)c3ccc4c(c3C)COC4=O)cn2)ncc1C#N] | (R)-N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)cyclopropanecarboxamide | 417.1 | B: 1.58, 100% A: 1.28, 100% XXIII: 22.65, 93.60% ee | $^1$H NMR (400 MHz, DMSO-$d_6$) δ ppm 0.49-0.73 (m, 4 H), 1.56-1.66 (m, 1 H), 2.29 (s, 3 H), 2.58 (s, 3 H), 2.70-2.93 (m, 2H), 3.62-3.79 (m, 2H), 5.21-5.32 (m, 1 H), 5.37 (d, J = 3.91 Hz, 2 H), 7.50-7.56 (m, 1 H), 7.63-7.71 (m, 1 H), 7.78-7.86 (m, 1 H), 7.97 (s, 1 H), 8.46-8.55 (m, 1 H), 8.61-8.69 (m, 1 H), 8.83 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 143 | 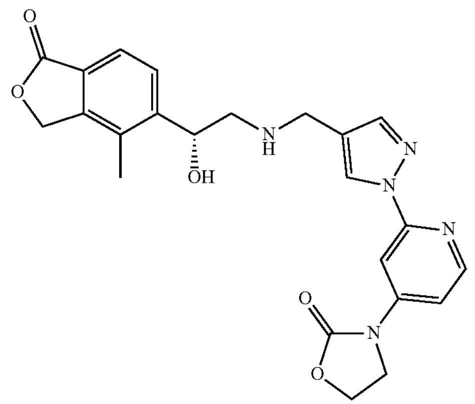 [SMILES: Cc1c([C@@H](O)CNCc2cnn(-c3cc(N4CCOC4=O)ccn3)c2)ccc2c1COC2=O] | (R)-3-(2-(4-(((2-hydroxy-2-(4-methyl-1-oxo-1,3-dihydroisobenzofuran-5-yl)ethyl)amino)methyl)-1H-pyrazol-1-yl)pyridin-4-yl)oxazolidin-2-one | 450.0 | B: 1.22, 100% A: 1.11, 100% XIV: 12.52, 98.93% ee | ¹H NMR (400 MHz, DMSO-d₆) δ ppm 2.24 (s, 3 H), 2.59-2.72 (m, 2 H), 3.66-3.77 (m, 2 H), 4.10-4.17 (m, 2 H), 4.47-4.54 (m, 2 H), 5.02 (dd, J = 7.83, 3.67 Hz, 1 H), 5.31-5.42 (m, 3 H), 7.42 (dd, J = 5.75, 2.08 Hz, 1 H), 7.63-7.70 (m, 2 H), 7.74 (s, 1 H), 8.16 (d, J = 2.20 Hz, 1H), 8.36 (d, J = 5.62 Hz, 1 H), 8.46 (s, 1 H), (1 Exchangeable proton not observed) |
| 144 | 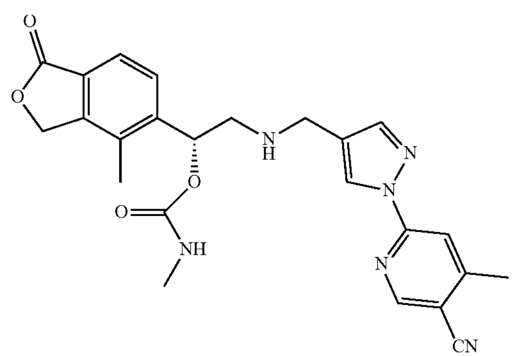 [SMILES: CNC(=O)O[C@@H](CNCc1cnn(-c2cc(C)c(C#N)cn2)c1)c1ccc2c(c1C)COC2=O] | (R)-2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl methylcarbamate | 461.1 | A: 1.19, 97.20%. B: 1.54, 98.08%. XI: 20.05 97.68% ee. | ¹H NMR (400 MHz, DMSO-d₆) δ ppm 2.30 (s, 3 H), 2.51 (s, 3 H), 2.57 (s, 3 H), 2.68-2.79 (m, 1 H), 2.90 (dd, J = 12.7, 7.6 Hz, 1 H), 3.69 (s, 2 H), 5.35-5.46 (m, 2 H), 5.90 (dd, J = 8.1, 4.4 Hz, 1 H), 7.18 (d, J = 5.1 Hz, 1 H), 7.48 (d, J = 8.1 Hz, 1 H), 7.67 (d, J = 7.8 Hz, 1 H), 7.81 (s, 1 H), 7.97 (s, 1 H), 8.46 (s, 1 H), 8.82 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 145 | (structure) | (R)-5-(4-(((2-hydroxy-2-(4-methyl-1-oxo-1,3-dihydroisobenzofuran-5-yl)ethyl]amino)methyl)-1H-pyrazol-1-yl)-3-methyloxazolo[4,5-b]pyridin-2(3H)-one | 436.1 | A: 1.09, 98.84%. B: 1.20, 100%. V: 8.10 100% ee. | 1H NMR (400 MHz, DMSO-d6) δ ppm 2.24 (s, 3 H), 2.59-2.71 (m, 2 H), 3.38 (s, 3 H), 3.67-3.76 (m, 2 H), 5.03 (dd, J = 7.95, 4.03 Hz, 1 H), 5.36 (d, J = 3.18 Hz, 2 H), 5.43-5.57 (m, 1 H), 7.59 (d, J = 8.56 Hz, 1 H), 7.64-7.74 (m, 3 H), 7.84 (d, J = 8.56 Hz, 1 H), 8.45 (s, 1 H). (1 Exchangeable proton not observed). |
| 146 | (structure) | (R)-6-(4-(((2-hydroxy-2-(4-methyl-1-oxo-1,3-dihydroisobenzofuran-5-yl)ethyl]amino)methyl)-1H-pyrazol-1-yl)-4-(methylamino)nicotinonitrile | 419.5 | A: 1.07, 100%. B: 1.23, 100%. III: 10.71 98.26% ee. | 1H NMR (300 MHz, DMSO-d6) δ ppm 2.23 (s, 3 H), 2.63-2.67 (m, 2 H), 2.88 (d, J = 4.9 Hz, 3 H), 3.75-3.66 (m, 2 H), 5.01 (br. s, 1 H), 5.39-5.32 (m, 2 H), 5.50 (br. s, 1 H), 7.03 (s, 1 H), 7.40 (d, J = 4.6 Hz, 1 H), 7.71-7.62 (m, 2 H), 7.76 (s, 1 H), 8.38 (s, 1 H), 8.42 (s, 1 H), (1 Exchangeable proton not observed). |

| Ex. | Structure | Name | LCMS (M+H)+ | HPLC/LCMS Method: RT (min.), Purity | NMR |
|---|---|---|---|---|---|
| 147 | 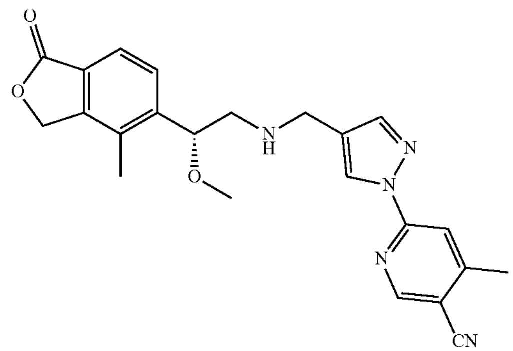 [SMILES: CO[C@@H](CNCc1cnn(-c2cc(C)c(C#N)cn2)c1)c1ccc2c(c1C)COC2=O] | (R)-6-(4-(((2-methoxy-2-(4-methyl-1-oxo-1,3-dihydroisobenzofuran-5-yl)ethyl)amino)methyl)-1H-pyrazol-1-yl)-4-methylnicotinonitrile | 418.1 | A: 1.29, 100%. B: 1.63, 100%. III: 5.00, 100% ee. | $^1$H NMR (400 MHz, DMSO-d$_6$) δ ppm 2.26 (s, 3 H), 2.31-2.35 (m, 1 H), 2.58 (s, 3 H), 2.73-2.85 (m, 2H), 3.19 (s, 3 H), 3.79 (br. s., 2 H), 4.74 (m, 1 H), 5.39 (d, J = 3.61 Hz, 2 H), 7.52 (d, J = 7.95 Hz, 1 H), 7.70 (d, J = 7.83 Hz, 1 H), 7.85 (s, 1 H), 7.98 (s, 1 H), 8.54 (s, 1 H), 8.84 (s, 1 H). |
| 148 | 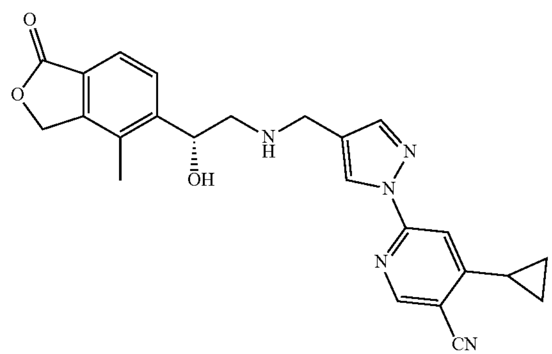 [SMILES: Cc1c([C@@H](O)CNCc2cnn(-c3cc(C4CC4)c(C#N)cn3)c2)ccc2c1COC2=O] | (R)-4-cyclopropyl-6-(4-((((2-hydroxy-2-(4-methyl-1-oxo-1,3-dihydroisobenzofuran-5-yl)ethyl)amino)methyl)-1H-pyrazol-1-yl)nicotinonitrile | 430.1 | A: 1.30, 98.47%. B: 1.55, 100%. V: 6.60 100% ee. | $^1$H NMR (400 MHz, DMSO-d$_6$) δ ppm 1.01-1.10 (m, 2 H), 1.27-1.37 (m, 2 H), 1.91 (br. s., 1 H), 2.17-2.27 (m, 2 H), 2.67 (br. s., 2 H), 3.70 (br. s., 2 H), 5.01 (br. s., 1 H), 5.36 (d, J = 3.67 Hz, 2 H), 5.48 (br. s., 1 H), 7.41 (s, 1 H), 7.62-7.72 (m, 2 H), 7.82 (s, 1 H), 8.47 (s, 1 H), 8.79 (s, 1 H). (1 Exchangeable proton not observed). |

| Ex. | Structure | Name | LCMS (M + H)⁺ | HPLC/LCMS Method: RT (min.), Purity | NMR |
|---|---|---|---|---|---|
| 149 | 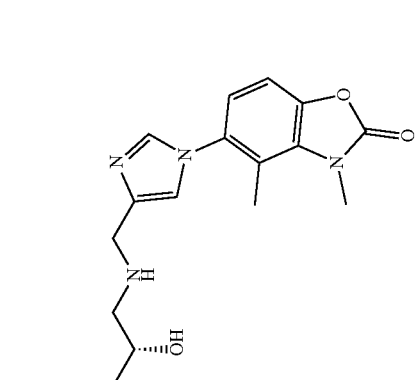 | (R)-5-(4-(((2-hydroxy-2-(4-methyl-1-oxo-1,3-dihydroisobenzofuran-5-yl)ethyl)amino)methyl)-1H-imidazol-1-yl)-3,4-dimethylbenzo[d]oxazol-2(3H)-one | 449.1 | A: 0.98, 94.38%. B: 1.12, 94.42%. | ¹H NMR (400 MHz, DMSO-d₆) δ ppm 2.25 (d, J = 2.69 Hz, 6 H), 2.64-2.83 (m, 2 H), 3.59 (s, 3 H), 3.65-3.74 (m, 2 H), 4.96-5.08 (m, 1 H), 5.30-5.42 (m, 2 H), 5.45-5.60 (m, 1 H), 7.00-7.13 (m, 2 H), 7.27-7.37 (m, 1 H), 7.67 (s, 3 H), (1 Exchangeable proton not observed) |
| 150 | 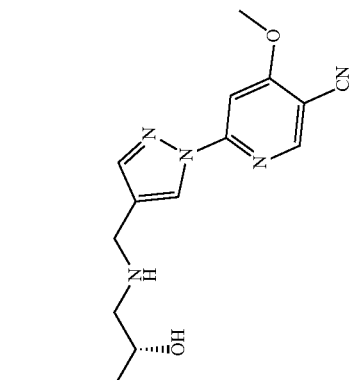 | (R)-6-(4-(((2-hydroxy-2-(4-methoxy-1-oxo-1,3-dihydroisobenzofuran-5-yl)ethyl)amino)methyl)-1H-pyrazol-1-yl)-4-methoxynicotinonitrile | 436.0 | A: 1.17, 95.91%. B: 1.30, 95.60%. V: 7.5 100% ee. | ¹H NMR (400 MHz, DMSO-d₆) δ ppm 2.54-2.62 (m, 1 H), 2.64-2.81 (m, 1 H), 3.68-3.79 (m, 2 H), 3.92 (s, 3 H), 4.10 (s, 3 H), 5.06 (br. s, 1 H), 5.45 (br. s, 1 H), 5.62-5.71 (m, 2 H), 7.49 (d, J = 7.83 Hz, 1 H), 7.59 (s, 1 H), 7.65 (d, J = 7.83 Hz, 1 H), 7.86 (s, 1 H), 8.50 (s, 1 H), 8.73 (s, 1 H), (1 Exchangeable proton not observed). |

-continued

| Ex. | Structure | Name | LCMS (M + H)+ | HPLC/LCMS Method: RT (min.), Purity | NMR |
|---|---|---|---|---|---|
| 151 | 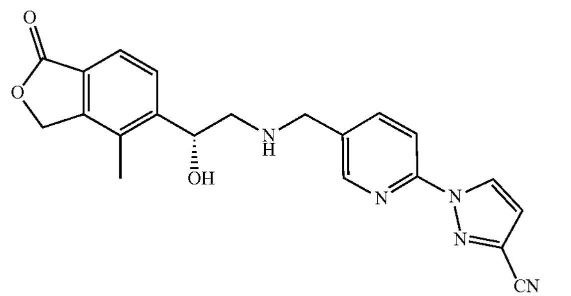 [SMILES: Cc1c([C@@H](O)CNCc2ccc(-n3ccc(C#N)n3)nc2)ccc2c1COC2=O] | (R)-1-(5-(((2-hydroxy-2-(4-methyl-1-oxo-1,3-dihydroisobenzofuran-5-yl)ethyl)amino)methyl)pyridin-2-yl)-1H-pyrazole-3-carbonitrile | 390.0 | B: 1.56, 97.95%. -:-%. -:-%. III: 8.49 100% ee. | 1H NMR (400 MHz, DMSO-d6) δ ppm 2.49 (s, 3 H), 2.64-2.71 (m, 2 H), 3.89 (s, 2 H), 5.04 (dd, J = 7.21, 3.79 Hz, 1 H), 5.37 (d, J = 3.18 Hz, 2 H), 5.50-5.60 (m, 1 H), 7.27 (d, J = 2.69 Hz, 1 H), 7.61-7.74 (m, 2 H), 7.91-7.98 (m, 1 H), 8.00-8.09 (m, 1 H), 8.47 (d, J = 1.96 Hz, 1 H), 8.85 (d, J = 2.69 Hz, 1 H), (1 Exchangeable proton not observed) |
| 152 | 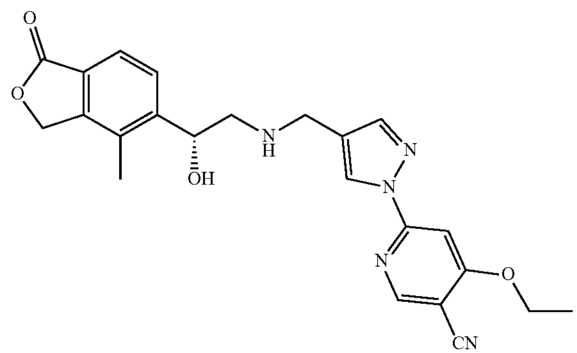 | (R)-4-ethoxy-6-(4-(((2-hydroxy-2-(4-methyl-1-oxo-1,3-dihydroisobenzofuran-5-yl)ethyl)amino)methyl)-1H-pyrazol-1-yl)nicotinonitrile | 434.1 | R: 1.08, 100%. S: 1.28, 98.31%. III: 11.38, 98.62% ee. | 1H NMR (400 MHz, DMSO-d6) δ ppm 1.42 (t, J = 6.97 Hz, 3 H), 2.24 (s, 3 H), 2.58-2.73 (m, 2 H), 3.70-3.79 (m, 2 H), 4.41 (q, J = 7.01 Hz, 2 H), 5.02 (dd, J = 7.95, 4.03 Hz, 1 H), 5.32-5.39 (m, 2 H) 5.52 (br. s., 1 H), 7.56 (s, 1 H), 7.63-7.74 (m, 2 H), 7.85 (s, 1 H), 8.50 (s, 1 H), (1 Exchangeable proton not observed). |
| 153 | 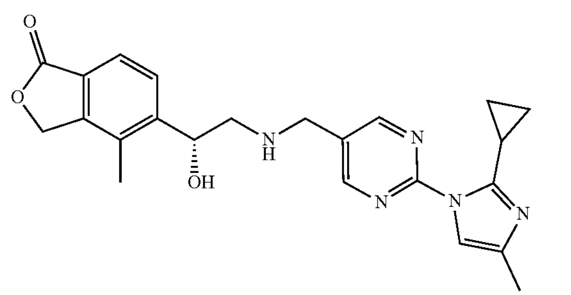 [SMILES: Cc1cn(-c2ncc(CNC[C@H](O)c3ccc4c(c3C)COC4=O)cn2)c(C2CC2)n1] | (R)-5-(2-((2-(2-cyclopropyl-4-methyl-1H-imidazol-1-yl)pyrimidin-5-yl)methyl)amino)-1-hydroxyethyl)-4-methylisobenzofuran-1(3H)-one | 420.1 | R: 0.60, 99.33%. S: 1.12, 99.36%. III: 8.19 100% ee. | 1H NMR (400 MHz, DMSO-d6) δ ppm 0.84-0.94 (m, 4 H), 2.06 (s, 3 H), 2.19-2.26 (s, 3 H), 2.67 (s, 1 H), 3.02 (dt, J = 13.14, 6.27 Hz, 1 H), 3.85 (br. s., 2 H), 5.04 (br. s., 1 H), 5.33-5.42 (m, 2 H), 5.54 (br. s., 1 H), 7.46 (s, 1 H), 7.62-7.74 (m, 2 H), 8.77 (s, 2 H), (2 Exchangeable protons not observed) |

| Ex. | Structure | Name | LCMS (M + H)+ | HPLC/LCMS Method: RT (min.), Purity | NMR |
|---|---|---|---|---|---|
| 154 | 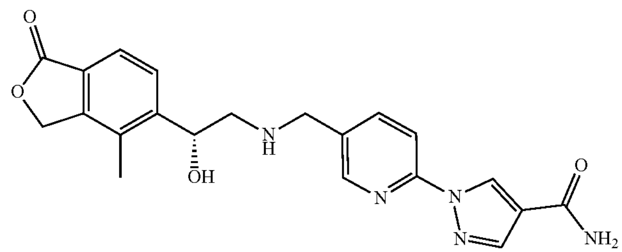 [SMILES: Cc1c([C@@H](O)CNCc2ccc(-n3cc(C(N)=O)cn3)nc2)ccc2c1COC2=O] | (R)-1-(5-(((2-hydroxy-2-(4-methyl-1-oxo-1,3-dihydroisobenzofuran-5-yl)ethyl)amino)methyl)pyridin-2-yl)-1H-pyrazole-4-carboxamide | 408.1 | R: 0.60, 100%. S: 0.79, 100%. III: 10.25, 99.44% ee. | 1H NMR (400 MHz, DMSO-d6) δ ppm 2.28 (s, 3 H), 2.96-3.07 (m, 1 H), 3.16 (d, J = 12.05 Hz, 1 H), 4.35 (s, 2 H), 5.27 (d, J = 10.54 Hz, 1 H), 5.35-5.47 (m, 2 H), 6.36 (d, J = 3.01 Hz, 1 H), 7.25 (br. s, 1 H) 7.67-7.77 (m, 2 H), 7.83 (br. s, 1 H), 8.03 (d, J = 8.53 Hz, 1 H), 8.12-8.23 (m, 2 H), 8.63 (d, J = 2.51 Hz, 1 H), 9.15 (d, J = 1.00 Hz, 1 H), (1 Exchangeable proton not observed). |
| 155 | 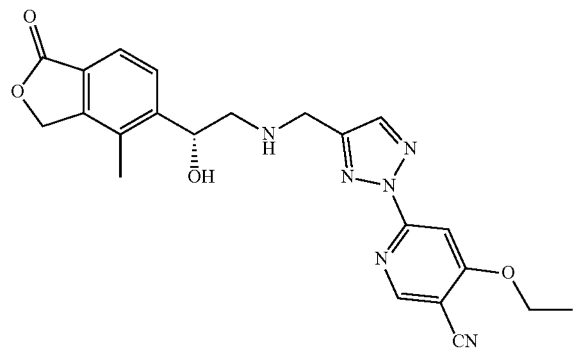 [SMILES: CCOc1cc(-n2ncc(CNC[C@H](O)c3ccc4c(c3C)COC4=O)n2)ncc1C#N] | (R)-4-ethoxy-6-(4-(((2-hydroxy-2-(4-methyl-1-oxo-1,3-dihydroisobenzofuran-5-yl)ethyl)amino)methyl)-2H-1,2,3-triazol-2-yl)nicotinonitrile | 435.2 | R: 0.97, 98.64%. S: 1.21, 99.30%. V: 9.93 96.26% ee. | 1H NMR (400 MHz, DMSO-d6) δ ppm 1.43 (t, J = 7.0 Hz, 3 H), 2.24 (s, 3 H), 2.64-2.77 (m, 2 H), 3.97 (s, 2 H), 4.44 (q, J = 6.8 Hz, 2 H), 4.96-5.11 (m, 1 H), 5.28-5.45 (m, 2 H), 5.53 (d, J = 4.2 Hz, 1 H), 7.60-7.75 (m, 3 H), 8.15 (s, 1 H), 8.82 (s, 1 H), (1 Exchangeable proton not observed). |
| 156 | 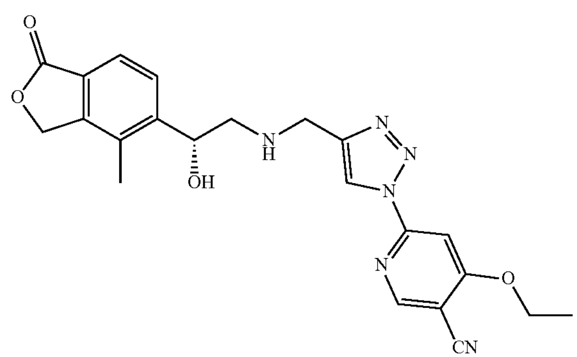 [SMILES: CCOc1cc(-n2cc(CNC[C@H](O)c3ccc4c(c3C)COC4=O)nn2)ncc1C#N] | (R)-4-ethoxy-6-(4-(((2-hydroxy-2-(4-methyl-1-oxo-1,3-dihydroisobenzofuran-5-yl)ethyl)amino)methyl)-1H-1,2,3-triazol-1-yl)nicotinonitrile | 435.2 | R: 1.03, 100%. S: 1.25, 98.19%. V: 9.57 100% ee. | 1H NMR (400 MHz, DMSO-d6) δ ppm 1.36 (t, J = 6.91 Hz, 3 H) 2.26 (s, 3 H) 2.65-2.73 (m, 2 H) 3.95 (m, 2 H) 4.40-4.50 (m, 2 H) 4.99-5.01 (m, 1 H) 5.32-5.44 (m, 2 H) 5.47-5.48 (d, J = 4.52 Hz, 1 H) 7.62-7.67 (m, 2 H) 7.84 (s, 1 H) 8.63 (s, 1 H) 8.86 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 157 | 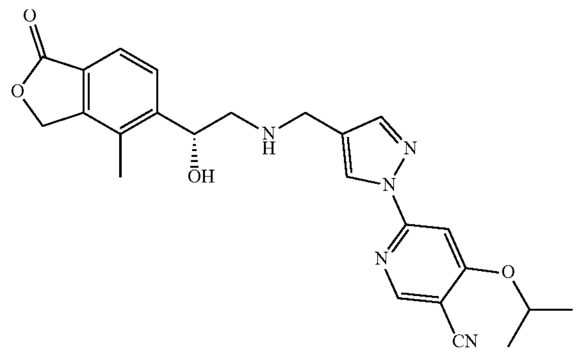 [SMILES: Cc1c([C@@H](O)CNCc2cnn(-c3cc(OC(C)C)c(C#N)cn3)c2)ccc2c1COC2=O] | (R)-6-(4-(((2-hydroxy-2-(4-methyl-1-oxo-1,3-dihydroisobenzofuran-5-yl)ethyl)amino)methyl)-1H-pyrazol-1-yl)-4-isopropoxynicotinonitrile | 448.2 | R: 1.18, 96.38% S: 1.38, 96.45% V: 6.17 98.84% ee. | 1H NMR (400 MHz, DMSO-d$_6$) δ ppm 8.71 (s, 1 H), 8.49 (s, 1 H), 7.84 (s, 1 H), 7.76-7.60 (m, 2 H), 7.57 (s, 1 H), 5.49 (br. s, 1 H), 5.26-5.43 (m, 2 H), 4.89-5.17 (m, 2 H), 3.61-3.82 (m, 2 H), 2.61-2.71 (m, 2 H), 2.23 (s, 3 H), 1.33-1.45 (m, 6 H), (1 Exchangeable proton not observed). |
| 158 | 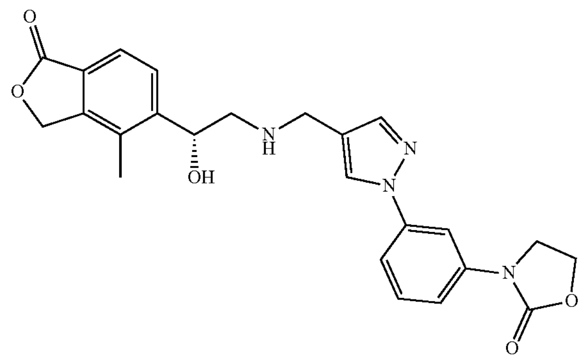 [SMILES: Cc1c([C@@H](O)CNCc2cnn(-c3cccc(N4CCOC4=O)c3)c2)ccc2c1COC2=O] | (R)-3-(3-(4-(((2-hydroxy-2-(4-methyl-1-oxo-1,3-dihydroisobenzofuran-5-yl)ethyl)amino)methyl)-1H-pyrazol-1-yl)phenyl)oxazolidin-2-one | 449 | B: 0.99, 98.10% A: 0.86, 99.50% XIV: 8.74, 98.50% ee | $^1$H NMR (400 MHz, DMSO-d$_6$) δ 2.24 (s, 3H), 2.57-2.74 (m, 2H), 3.58-3.80 (m, 2H), 4.08-4.16 (m, 2H), 4.35-4.53 (m, 2H), 5.03 (dd, J = 7.95, 4.03 Hz, 1H), 5.30-5.43 (m, 2H), 7.37-7.55 (m, 3H), 7.60-7.74 (m, 3H), 8.04 (s, 1H), 8.34 (s, 1H), (1 Exchangeable protons not observed) |

-continued

| Ex. | Structure | Name | LCMS (M + H)+ | HPLC/LCMS Method: RT (min.), Purity | NMR |
|---|---|---|---|---|---|
| 159 | 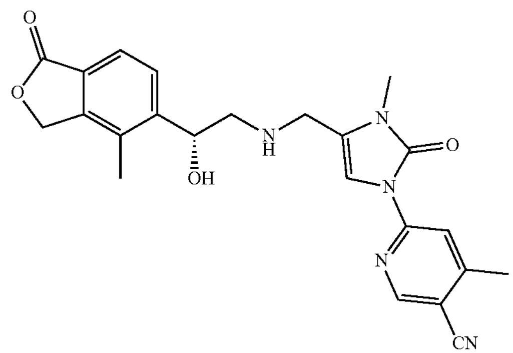 [SMILES: Cc1cc(-n2cc(CNC[C@H](O)c3ccc4c(c3C)COC4=O)n(C)c2=O)ncc1C#N] | (R)-6-(4-(((2-hydroxy-2-(4-methyl-1-oxo-1,3-dihydroisobenzofuran-5-yl)ethyl)amino)methyl)-3-methyl-2-oxo-2,3-dihydro-1H-imidazol-1-yl)-4-methylnicotinonitrile | 434.1 | S: 1.19, 99.30% R: 0.89, 100% XIX: 12.46, 99.40% ee | 1H NMR (400 MHz, DMSO-d6) δ 2.24 (s, 3 H), 2.54 (s, 3 H), 2.68-2.81 (m, 2 H), 3.17 (s, 3 H), 3.56-3.80 (m, 2 H), 5.00 (d, J = 3.4 Hz, 1 H), 5.23-5.43 (m, 2 H), 5.52 (br. s., 1 H), 7.22 (s, 1 H), 7.52-7.74 (m, 2 H), 8.44 (s, 1 H), 8.78 (s, 1H), (1 Exchangeable proton not observed). |
| 160 | 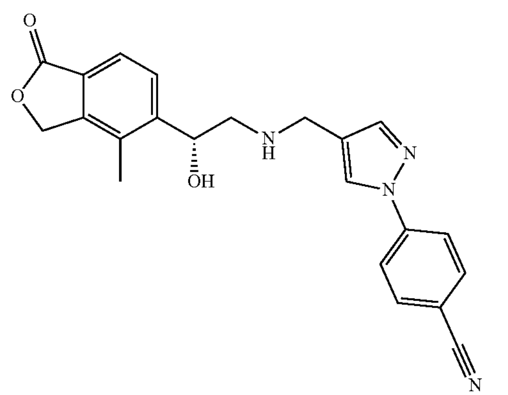 [SMILES: Cc1c([C@@H](O)CNCc2cnn(-c3ccc(C#N)cc3)c2)ccc2c1COC2=O] | (R)-4-(4-(((2-hydroxy-2-(4-methyl-1-oxo-1,3-dihydroisobenzofuran-5-yl)ethyl)amino)methyl)-1H-pyrazol-1-yl)benzonitrile | 389.2 | A: 0.90, 95.40% B: 1.01, 96.70% | 1H NMR (400 MHz, DMSO-d6) δ ppm 2.23 (s, 3 H), 2.63-2.72 (m, 2 H), 3.74 (br. s., 2 H), 5.02 (br. s., 1 H), 5.37 (d, J = 2.93 Hz, 2 H), 5.54 (br. s., 1 H), 7.62-7.71 (m, 2 H), 7.78 (s, 1 H), 7.93-8.03 (m, 4 H), 8.53 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 161 | 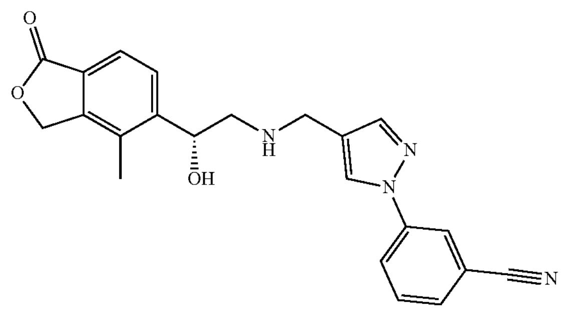 [SMILES: Cc1c([C@@H](O)CNCc2cnn(-c3cccc(C#N)c3)c2)ccc2c1COC2=O] | (R)-3-(4-(((2-hydroxy-2-(4-methyl-1-oxo-1,3-dihydroisobenzofuran-5-yl)ethyl)amino)methyl)-1H-pyrazol-1-yl)benzonitrile | 389.2 | A: 0.90, 94.6% B: 1.06, 94.10% | 1H NMR (400 MHz, DMSO-d6) δ ppm 2.23 (s, 3 H), 2.65-2.70 (m, 2 H), 3.70 (d, J = 3.42 Hz, 2 H), 5.01 (br. s., 1 H), 5.37 (d, J = 2.69 Hz, 2 H), 5.48 (s, 1 H), 7.65-7.71 (m, 3 H), 7.71-7.76 (m, 2 H), 8.16 (ddd, J = 8.01, 2.26, 1.22 Hz, 1 H), 8.27 (t, J = 1.71 Hz, 1 H), 8.50 (s, 1 H), (1 Exchangeable proton not observed). |
| 162 | 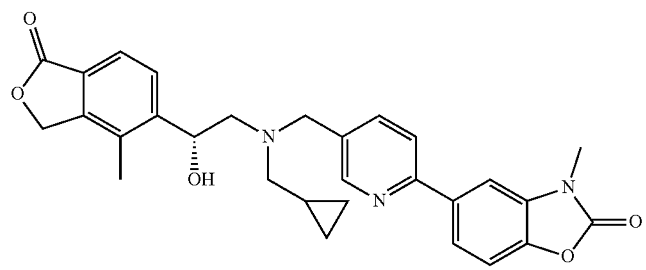 [SMILES: Cc1c([C@@H](O)CN(Cc2ccc(-c3ccc4oc(=O)n(C)c4c3)nc2)CC2CC2)ccc2c1COC2=O] | (R)-5-(5-(((cyclopropylmethyl)(2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one | 500.3 | A: 1.09, 97.80% B: 1.87, 99.20% | 1H NMR (400 MHz, DMSO-d6) δ ppm 0.08 (d, J = 5.14 Hz, 2 H), 0.44 (d, J = 7.83 Hz, 2 H), 0.85-0.95 (m, 1 H), 2.16 (s, 3 H), 2.47-2.50 (m, 1 H), 2.70-2.75 (m, 2 H), 3.43 (s, 3 H), 3.78 (d, J = 18.59 Hz, 2 H), 5.02-5.08 (m, 1 H), 5.29 (d, J = 3.91 Hz, 1 H), 5.32 (s, 2 H), 7.42 (d, J = 8.56 Hz, 1 H), 7.59 (s, 2 H), 7.65-7.71 (m, 1 H), 7.81-7.88 (m, 2 H), 7.92 (d, J = 1.71 Hz, 1 H), 8.44 (d, J = 1.71 Hz, 1 H), (1 Exchangeable proton not observed). |
| 163 | 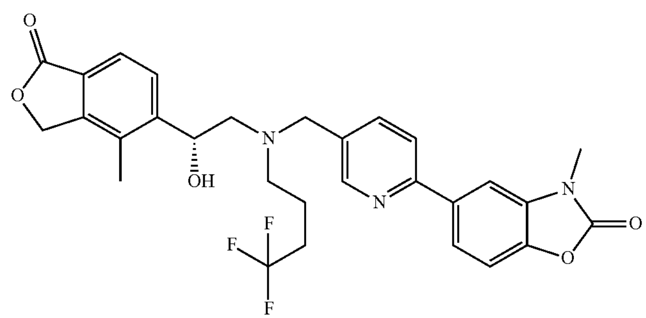 [SMILES: Cc1c([C@@H](O)CN(CCCC(F)(F)F)Cc2ccc(-c3ccc4oc(=O)n(C)c4c3)nc2)ccc2c1COC2=O] | (R)-5-(5-(((2-hydroxy-2-(4-methyl-1-oxo-1,3-dihydroisobenzofuran-5-yl)ethyl)(4,4,4-trifluorobutyl)amino)methyl)pyridin-2-yl)-3-methylbenzo[d]oxazol-2(3H)-one | 556.3 | A: 1.26, 97.70% B: 1.94, 99.20% | 1H NMR (400 MHz, DMSO-d6) δ ppm 1.56-1.67 (m, 2 H) 2.15 (s, 3 H) 2.33 (dt, J = 3.67, 1.83 Hz, 2 H) 2.58-2.69 (m, 4 H), 3.43 (s, 3 H), 3.74 (d, J = 3.67 Hz, 2 H) 5.01-5.10 (m, 1 H) 5.31 (d, J = 5.38 Hz, 2 H) 5.41 (d, J = 3.91 Hz, 1 H) 7.42 (d, J = 8.56 Hz, 1 H) 7.61-7.66 (m, 2 H) 7.74 (dd, J = 8.07, 2.20 Hz, 1 H) 7.86-7.96 (m, 3 H) 8.49 (d, J = 1.47 Hz, 1 H). 19F NMR (400 MHz, DMSO-d6) δ ppm-108.18. |

| Ex. | Structure | Name | LCMS (M + H)+ | HPLC/LCMS Method: RT (min.), Purity | NMR |
|---|---|---|---|---|---|
| 164 | 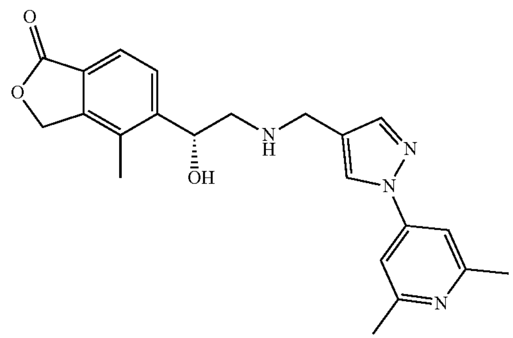 [SMILES: Cc1cc(-n2cc(CNC[C@H](O)c3ccc4c(c3C)COC4=O)cn2)cc(C)n1] | (R)-5-(2-(((1-(2,6-dimethylpyridin-4-yl)-1H-pyrazol-4-yl)methyl)amino)-1-hydroxyethyl)-4-methylisobenzofuran-1(3H)-one | 393.2 | A: 0.62, 98.80% B: 1.03, 98.30% | $^1$H NMR (400 MHz, DMSO-d6) δ ppm 2.23 (s, 3 H), 2.23 (s, 6 H), 2.59-2.71 (m, 2 H), 3.72 (br. s., 2 H), 5.03 (d, J = 4.02 Hz, 1 H), 5.38 (d, J = 3.01 Hz, 2 H), 5.54 (br. s., 1 H), 7.50 (s, 2 H), 7.64-7.72 (m, 2 H), 7.75 (s, 1 H), 8.50 (s, 1 H), (1 Exchangeable proton not observed). $^{19}$F NMR (400 MHz, DMSO-d6) δ ppm-61.702. |
| 165 | 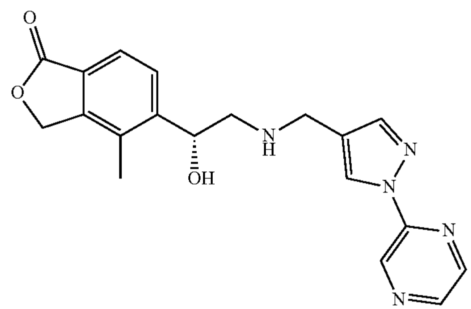 [SMILES: Cc1c([C@@H](O)CNCc2cnn(-c3cnccn3)c2)ccc2c1COC2=O] | (R)-5-(1-hydroxy-2-(((1-(pyrazin-2-yl)-1H-pyrazol-4-yl)methyl)amino)ethyl)-4-methylisobenzofuran-1(3H)-one | 366.1 | A: 0.69, 95.90% B: 1.04, 96.30% | $^1$H NMR (400 MHz, DMSO-d6) δ ppm 2.23 (s, 3 H), 2.63-2.69 (m, 2 H), 3.72 (d, J = 4.16 Hz, 2 H), 5.02 (br. s., 1 H), 5.36 (d, J = 2.93 Hz, 2 H), 5.47 (br. s., 1 H), 7.60-7.70 (m, 2 H), 7.83 (s, 1 H), 8.45 (s, 1 H), 8.52 (dd, J = 2.69, 1.47 Hz, 1 H), 8.58 (d, J = 2.20 Hz, 1 H), 9.18 (d, J = 0.98 Hz, 1 H), (1 Exchangeable proton not observed). |

-continued

| Ex. | Structure | Name | LCMS (M+H)+ | HPLC/LCMS Method: RT (min.), Purity | NMR |
|---|---|---|---|---|---|
| 166 | 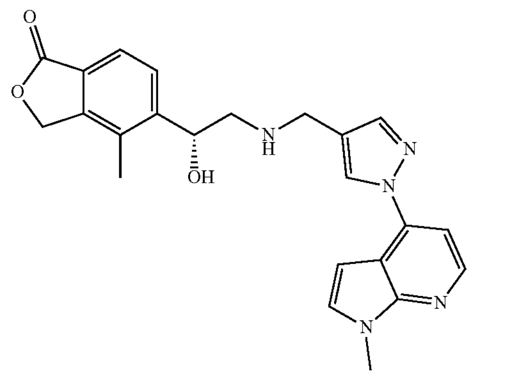 [SMILES: Cc1c([C@@H](O)CNCc2cnn(-c3ccnc4c3ccn4C)c2)ccc2c1COC2=O] | (R)-5-(1-hydroxy-2-(((1-(1-methyl-1H-pyrrolo[2,3-b]pyridin-4-yl)-1H-pyrazol-4-yl)methyl)amino)ethyl)-4-methylisobenzofuran-1(3H)-one | 418.2 | A: 1.10 98.20% B: 1.19 98.50% | 1H NMR (400 MHz, DMSO-d6) δ ppm 2.24 (s, 3 H), 2.62-2.76 (m, 2 H), 3.76 (d, J = 4.52 Hz, 2 H), 3.86 (s, 3 H), 5.04 (d, J = 3.01 Hz, 1 H), 5.36 (d, J = 3.51 Hz, 2 H), 6.99 (s, 1 H), 7.47 (d, J = 5.02 Hz, 1 H), 7.59 (d, J = 3.51 Hz, 1 H), 7.64-7.72 (m, 2 H), 7.82 (s, 1 H), 8.31 (d, J = 5.52 Hz, 1 H), 8.55 (s, 1 H), (1 Exchangeable proton not observed). |
| 167 | 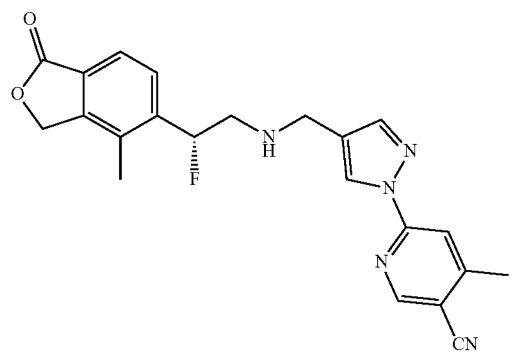 [SMILES: Cc1cc(-n2cc(CNC[C@H](F)c3ccc4c(c3C)COC4=O)cn2)ncc1C#N] | (R)-6-(4-(((2-fluoro-2-(4-methyl-1-oxo-1,3-dihydroisobenzofuran-5-yl)ethyl)amino)methyl)-1H-pyrazol-1-yl)-4-methylnicotinonitrile | 406.1 | A: 1.34, 100% B: 1.87, 100% II: 14.13, 76.37% ee | 1H NMR (400 MHz, DMSO-d6) δ ppm 2.30 (s, 3 H), 2.61 (s, 3 H), 3.38-3.64 (m, 2 H), 4.28 (s, 2 H), 5.44 (d, J = 5.14 Hz, 2 H), 6.20 (dd, J = 48 Hz, 8.4 Hz, 1 H), 7.65 (d, J = 8.07 Hz, 1 H), 7.73-7.84 (m, 1 H), 8.03 (d, J = 5.62 Hz, 2 H), 8.84 (s, 1 H), 8.90 (s, 1 H), 9.37 (br. s, 1 H), 19F NMR (400 MHz, DMSO-d6) δ ppm-73.51. |

| Ex. | Structure | Name | LCMS (M + H)+ | HPLC/LCMS Method: RT (min.), Purity | NMR |
|---|---|---|---|---|---|
| 168 | 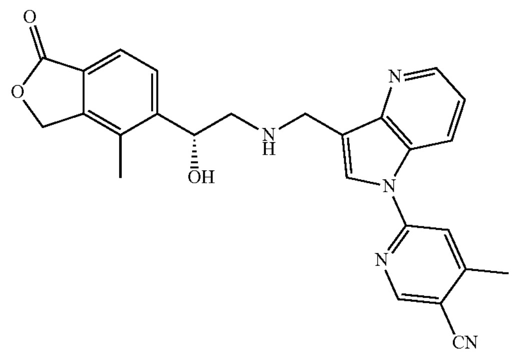 | (R)-6-(3-(((2-hydroxy-2-(4-methyl-1-oxo-1,3-dihydroisobenzofuran-5-yl)ethyl)amino)methyl)-1H-pyrrolo[3,2-b]pyridin-1-yl)-4-methylnicotinonitrile | 454.0 | A: 1.2, 100% B: 1.54, 100% XVIII: 14.28, 100% | 1H NMR (400 MHz, DMSO-d6) δ ppm 2.21 (s, 3 H), 2.61 (s, 3 H), 3.03 (m, 2 H), 4.39-4.43 (m, 2 H), 5.18-5.27 (m, 1 H), 5.38 (d, J = 6.11 Hz, 2 H), 6.12-6.10 (m, 1 H), 7.37-7.46 (m, 1 H), 7.71 (s, 2H), 7.95 (s, 1 H), 8.55 (d, J = 4.16 Hz, 1 H), 8.59 (br. s., 1 H), 8.84 (d, J = 8.31 Hz, 1 H), 8.96 (s, 1 H), (1 Exchangeable proton not observed). |
| 169 | 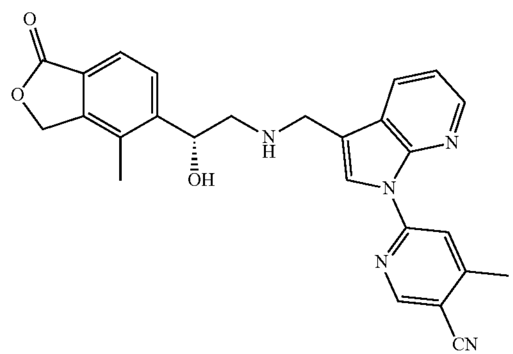 [SMILES: Cc1cc(-n2cc(CNC[C@H](O)c3ccc4c(c3C)COC4=O)c3cccnc32)ncc1C#N] | (R)-6-(3-(((2-hydroxy-2-(4-methyl-1-oxo-1,3-dihydroisobenzofuran-5-yl)ethyl)amino)methyl)-1H-pyrrolo[2,3-b]pyridin-1-yl)-4-methylnicotinonitrile | 454.0 | A: 1.38, 100% B: 1.83, 100% XVIII: 10.83, 100% | 1H NMR (400 MHz, DMSO-d6) δ ppm 2.17 (s, 3 H), 2.62 (s, 3 H), 2.65-2.78 (m, 2 H), 3.99 (s, 2 H), 5.04 (br. s., 1 H), 5.21-5.39 (m, 2 H), 5.48 (br. s, 1 H), 7.23-7.34 (m, 1 H), 7.55-7.71 (m, 2 H), 8.16 (d, J = 7.83 Hz, 1 H), 8.31 (s, 1 H), 8.44 (d, J = 4.16 Hz, 1 H), 8.86 (s, 1 H), 9.08 (s, 1 H), (1 Exchangeable proton not observed). |

| Ex. | Structure | Name | LCMS (M + H)+ | HPLC/LCMS Method: RT (min.), Purity | NMR |
|---|---|---|---|---|---|
| 170-I | 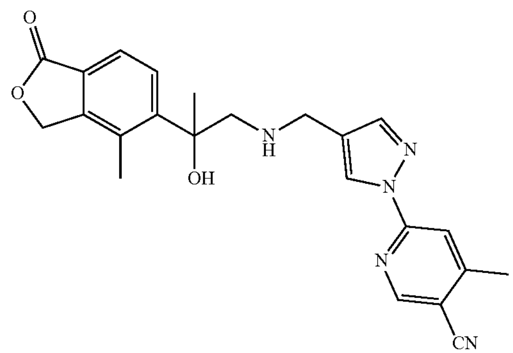 [SMILES: Cc1cc(-n2cc(CNCC(C)(O)c3ccc4c(c3C)COC4=O)cn2)ncc1C#N] | 6-(4-(((2-hydroxy-2-(4-methyl-1-oxo-1,3-dihydroisobenzofuran-5-yl)propyl)amino)methyl)-1H-pyrazol-1-yl)-4-methylnicotinonitrile (Enantiomer-1) | | S: 1.60, 100% R: 1.30, 100% XVIII: 12.57, 100% | 1H NMR (400 MHz, DMSO-d6) δ ppm 1.65 (s, 3 H), 2.28-2.43 (m, 3 H), 2.60 (s, 3 H), 3.30 (br. s, 2 H), 4.15 (br. s, 2 H), 5.28-5.45 (m, 2 H), 6.26 (s, 1 H), 7.68 (s, 1 H), 7.70 (s, 1 H), 7.95 (s, 1 H), 8.09 (s, 1 H), 8.54 (s, 1 H), 8.81 (m, 1 H), 8.88 (s, 1 H). |
| 171 | 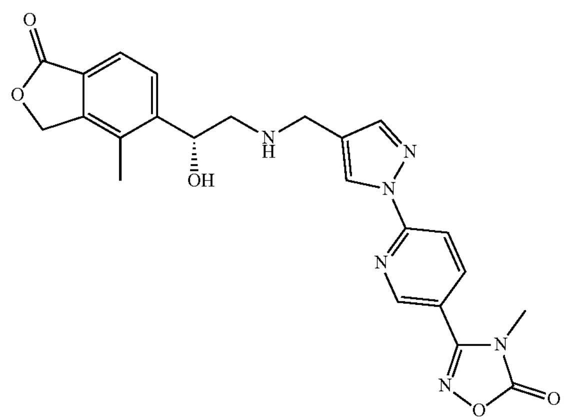 [SMILES: Cc1c([C@@H](O)CNCc2cnn(-c3ccc(-c4noc(=O)n4C)cn3)c2)ccc2c1COC2=O] | (R)-3-(6-(4-(((2-hydroxy-2-(4-methyl-1-oxo-1,3-dihydroisobenzofuran-5-yl)ethyl)amino)methyl)-1H-pyrazol-1-yl)pyridin-3-yl)-4-methyl-1,2,4-oxadiazol-5(4H)-one | 463.0 | S: 1.31, 100% R: 1.12, 100% XI: 4.67, 98.18% | 1H NMR (400 MHz, DMSO-d6) δ ppm 2.23 (s, 3 H), 2.59-2.70 (m, 2 H), 3.25 (s, 3 H), 3.72 (m, 2 H), 5.02 (dd, J = 7.83, 4.16 Hz, 1 H), 5.36 (d, J = 2.69 Hz, 2 H), 7.60-7.71 (m, 2 H), 7.83 (s, 1 H), 8.08 (d, J = 8.56 Hz, 1 H), 8.31 (d, J = 2.45 Hz, 1 H), 8.48-8.55 (m, 1 H), 8.77 (d, J = 2.45 Hz, 1 H), (2 Exchangeable protons are not seen) |

| Ex. | Structure | Name | LCMS (M + H)+ | HPLC/LCMS Method: RT (min.), Purity | NMR |
|---|---|---|---|---|---|
| 172-I | 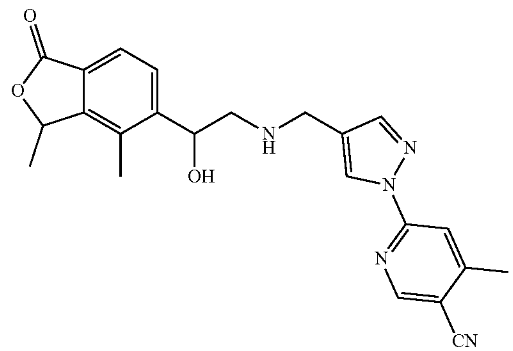 [SMILES: Cc1cc(-n2cc(CNCC(O)c3ccc4c(c3C)C(C)OC4=O)cn2)ncc1C#N] | 6-(4-(((2-(3,4-dimethyl-1-oxo-1,3-dihydroisobenzofuran-5-yl)-2-hydroxyethyl)amino)methyl)-1H-pyrazol-1-yl)-4-methylnicotinonitrile (Diastereomer-1) | 418.0 | F: 10.90, 98.00% G: 12.31, 97.21 XIX: 10.18, 98% ee | 1H NMR (400 MHz, DMSO-d6) δ ppm 1.51 (d, J = 6.60 Hz, 3 H), 2.29 (s, 3 H), 2.50 (s, 3 H), 2.65-2.70 (m, 2 H), 3.72-3.80 (m, 2H), 5.11-5.16 (m, 1 H), 5.74-5.82 (m, 1 H), 7.62-7.72 (m, 2 H), 7.82-7.85 (m, 1 H), 8.0 (s, 1 H), 8.62-8.72(m, 1 H), 8.83 (s, 1 H) (2 Exchangeable protons are not seen) |
| 172-II | 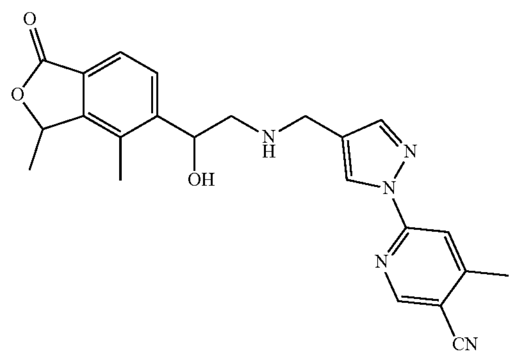 [SMILES: Cc1cc(-n2cc(CNCC(O)c3ccc4c(c3C)C(C)OC4=O)cn2)ncc1C#N] | 6-(4-(((2-(3,4-dimethyl-1-oxo-1,3-dihydroisobenzofuran-5-yl)-2-hydroxyethyl)amino)methyl)-1H-pyrazol-1-yl)-4-methylnicotinonitrile (Diastereomer-II) | 418.0 | F: 11.00, 99.36% G: 12.34, 99.75% XIX: 11.70, 100% ee | 1H NMR (400 MHz, DMSO-d6) δ ppm 1.51 (d, J = 6.60 Hz, 3 H), 2.29 (s, 3 H), 2.50 (s, 3 H), 2.65-2.70 (m, 2 H), 3.72-3.80 (m, 2H), 5.11-5.16 (m, 1 H), 5.74-5.82 (m, 1 H), 7.62-7.72 (m, 2 H), 7.82-7.85 (m, 1 H), 8.0 (s, 1 H), 8.62-8.72(m, 1 H), 8.83 (s, 1 H) (2 Exchangeable protons are not seen). |

| Ex. | Structure | Name | LCMS (M + H)+ | HPLC/LCMS Method: RT (min.), Purity | NMR |
|---|---|---|---|---|---|
| 173 | 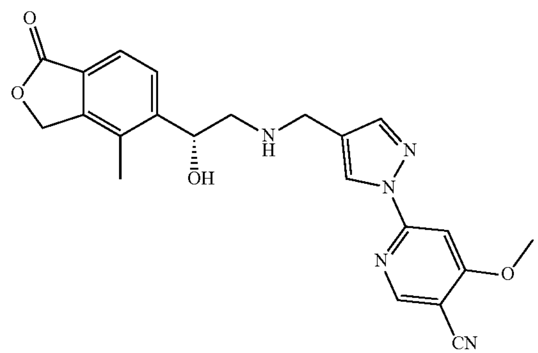 [SMILES: COc1cc(-n2cc(CNC[C@H](O)c3ccc4c(c3C)COC4=O)cn2)ncc1C#N] | (R)-6-(4-(((2-hydroxy-2-(4-methyl-1-oxo-1,3-dihydroisobenzofuran-5-yl)ethyl)amino)methyl)-1H-pyrazol-1-yl)-4-methoxynicotinonitrile | 420.0 | A: 1.14, 97.68% B: 1.36, 97.85% | $^1$H NMR (400 MHz, DMSO-d$_6$) δ 8.74 (s, 1 H), 8.50 (s, 1 H), 7.86 (s, 1 H), 7.67 (d, J = 3.9 Hz, 2 H), 7.60 (s, 1 H), 5.52-5.45 (m, 1 H), 5.37 (d, J = 3.2 Hz, 2 H), 5.06-4.97 (m, 1 H), 4.11 (s, 3 H), 3.75-3.69 (m, 2 H), 2.74-2.62 (m, 2 H), 2.24 (s, 3 H). (1 Exchangable proton not observed. |
| 174 | 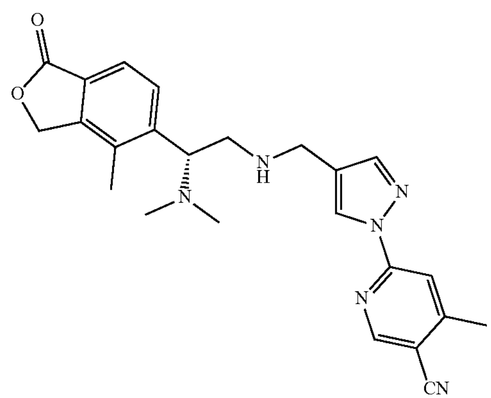 [SMILES: Cc1cc(-n2cc(CNC[C@@H](c3ccc4c(c3C)COC4=O)N(C)C)cn2)ncc1C#N] | (R)-6-(4-(((2-(dimethylamino)-2-(4-methyl-1-oxo-1,3-dihydroisobenzofuran-5-yl)ethyl)amino)methyl)-1H-pyrazol-1-yl)-4-methylnicotinonitrile | 431.1 | A: 0.99, 96.53% B: 1.57, 96.53% XII: 7.45, 100% ee | $^1$H NMR (400 MHz, DMSO-d$_6$) δ ppm 2.13 (s, 6 H), 2.29 (s, 3 H), 2.57 (s, 3 H), 2.81 (dd, J = 11.98, 7.34 Hz, 1 H), 2.98 (dd, J = 12.10, 4.77 Hz, 1 H), 3.58 (s, 2 H), 3.62-3.73 (m, 1 H), 5.37 (d, J = 3.91 Hz, 2H), 7.52-7.58 (m, 1 H), 7.60-7.66 (m, 1 H), 7.72 (s, 1 H), 7.94 (s, 1 H), 8.34 (s, 1 H), 8.80 (s, 1 H). (1 Exchangeable proton not observed). |

| Ex. | Structure | Name | LCMS (M + H)+ | HPLC/LCMS Method: RT (min.), Purity | NMR |
|---|---|---|---|---|---|
| 175 | 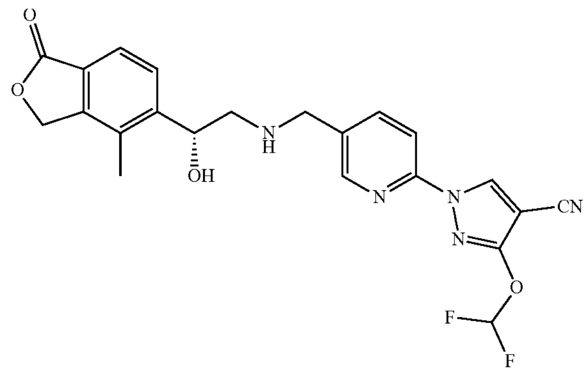 [SMILES: Cc1c([C@@H](O)CNCc2ccc(-n3cc(C#N)c(OC(F)F)n3)nc2)ccc2c1COC2=O] | (R)-3-(difluoromethoxy)-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile | 456.2 | S: 1.48, 100% R: 1.15, 100% XVIIII: 5.49, 99.36% ee | 1H NMR (400 MHz, DMSO-d6) δ ppm 2.28 (s, 3 H), 2.88-3.04 (m, 1 H), 3.14 (d, J = 12.2 Hz, 1 H), 4.34 (s, 2 H), 5.25 (d, J = 9.5 Hz, 1 H), 5.33-5.49 (m, 2 H), 6.33 (br. s., 1 H), 7.59 (t, J = 53.5 Hz, 1 H), 7.65-7.80 (m, 2 H), 7.91 (d, J = 8.3 Hz, 1 H), 8.23 (dd, J = 8.6, 2.2 Hz, 1 H), 8.63 (d, J = 2.2 Hz, 1 H), 9.23 (s, 1 H), 9.46 (s, 1H). 19F NMR (400 MHz, DMSO-d6) δ ppm-84.70. |
| 176-I | 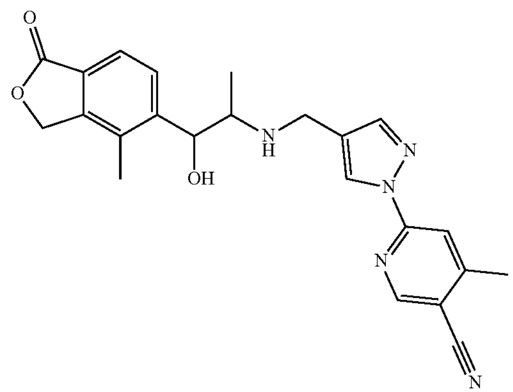 [SMILES: Cc1cc(-n2cc(CNC(C)C(O)c3ccc4c(c3C)COC4=O)cn2)ncc1C#N] | 6-(4-(((1-hydroxy-1-(4-methyl-1-oxo-1,3-dihydroisobenzofuran-5-yl)propan-2-yl)amino)methyl)-1H-pyrazol-1-yl)-4-methylnicotinonitrile (Enantiomer-I) | 418.2 | D: 1.66, 99.80% E: 11.27, 95.40% XVIII: 10.03, 97.00% ee | 1H NMR (400 MHz, DMSO-d6) δ ppm 0.90 (d, J = 6.36 Hz, 3 H), 1.99-2.11 (m, 1 H), 2.20 (s, 3 H), 2.58 (d, J = 0.49 Hz, 3 H), 2.64-2.71 (m, 1 H), 3.74 (m, 2 H), 4.90-5.09 (m, 1 H), 5.20-5.43 (m, 3 H), 7.60-7.66 (m, 2 H), 7.78 (s, 1 H), 7.96 (s, 1 H), 8.41 (s, 1 H), 8.8 (s, 1 H). |

-continued

| Ex. | Structure | Name | LCMS (M + H)+ | HPLC/LCMS Method: RT (min.), Purity | NMR |
|---|---|---|---|---|---|
| 177 | 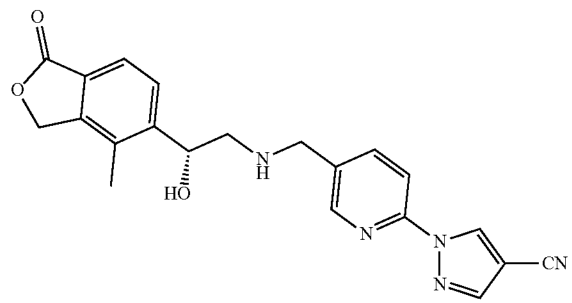 [SMILES: Cc1c([C@@H](O)CNCc2ccc(-n3cc(C#N)cn3)nc2)ccc2c1COC2=O] | ((R)-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile | 390.1 | A: 1.03, 98.99%, B: 1.37, 97.30%, VII: 19.50, 100% ee | ¹H NMR (400 MHz, DMSO-d₆) δ ppm 2.22 (s, 3 H), 2.58-2.73 (m, 2 H), 3.86 (s, 2 H), 5.02 (d, J = 3.18 Hz, 1 H), 5.26-5.41 (m, 2 H), 5.52 (br. s., 1 H), 7.57-7.73 (m, 2 H), 7.85-7.94 (m, 1 H), 8.01 (dd, J = 8.56, 2.20 Hz, 1 H), 8.40 (s, 1 H), 8.46 (s, 1 H), 9.38 (s, 1 H), (1 Exchangeable proton not observed). |
| 178 | 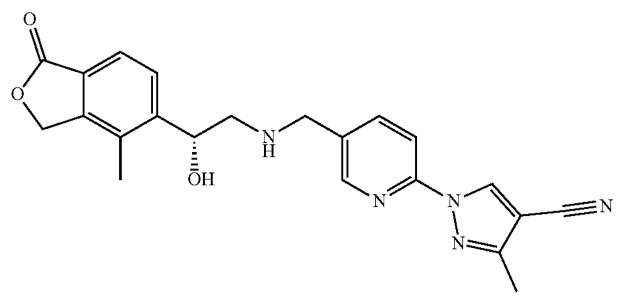 [SMILES: Cc1nn(-c2ccc(CNC[C@H](O)c3ccc4c(c3C)COC4=O)cn2)cc1C#N] | (R)-1-(5-(((2-hydroxy-2-(4-methyl-1-oxo-1,3-dihydroisobenzofuran-5-yl)ethyl)amino)methyl)pyridin-2-yl)-3-methyl-1H-pyrazole-4-carbonitrile | 404.0 | B: 1.52, 100%, A: 1.17, 100%, XXIII: 13.70, 96.00% ee | ¹H NMR (400 MHz, DMSO-d₆) δ ppm 2.22 (s, 3 H), 2.41 (s, 3 H), 2.63-2.79 (m, 2 H), 3.93 (br. s., 2 H), 5.07 (d, J = 4.40 Hz, 1 H), 5.31-5.42 (m, 2H), 5.67 (br. s., 1 H), 7.63-7.70 (m, 2 H), 7.88 (d, J = 8.31 Hz, 1 H), 8.02 (dd, J = 8.31, 1.47 Hz, 1 H), 8.46 (s, 1 H), 9.27 (s, 1 H), (1 Exchangeable proton not observed). |

BIOLOGICAL ASSAYS

The pharmacological properties of the compounds of this invention may be confirmed by a number of biological assays. The exemplified biological assays, which follow, have been carried out with compounds of the invention.

Thallium Flux Assay

Solutions and reagents: Thallium flux assay was performed using FluxOR kit (F10017, Life Technologies). Loading buffer, assay buffer and stimulus buffer were prepared using kit components. HBSS (Hank's balanced salt solution, Cat #14025-092) was purchased separately from Life Technologies.

To prepare 10 ml of loading buffer: 10 μl of FluxOR dye (reconstituted in DMSO) was first added to 100 μl of powerload concentrate and this mix along with 100 μl of Probenicid (100×) was then added to 9.79 ml of HBSS. Assay buffer (10 ml) was prepared by addition of 2 ml of FluxOR chloride free buffer (5×), 100 μl of Probenicid (100×), and 0.2 ml of Ouabain (13.77 mM) to 7.7 ml of deionized water. Stimulus buffer was composed of 15 mM $Tl_2SO_4$, 0.75 mM $K_2SO_4$ in FluxOR chloride free buffer (diluted to 1× using deionized water). The final concentration of $Tl_2SO_4$ and $K_2SO_4$ in the assay plate was 3 mM and 0.15 mM, respectively.

Plating and induction of cells: The CHO T-Rex hROMK (human $K_{ir}1.1$) stable cell line was maintained in Ham's F12 media supplemented with 10% FBS, 1% Penicillin-Streptomycin, 500 μg/ml Zeocin and 10 μg/ml Blasticidin at 37° C. in a 5% $CO_2$ incubator. One day before the experiment, the cells were dissociated by incubation with Versene solution (15040-066, Life Technologies) for 10 minutes at 37° C. followed by addition of growth media. The cell suspension was centrifuged at 1200 rpm for 5 min. After discarding the supernatant, the cells were resuspended in fresh growth media and cell concentration was determined using a hemocytometer. Next, 0.5 μg/ml of Doxycycline was added to the cell suspension to induce hROMK channel expression and 50 μl (10,000 cells/well) of cell suspension was added to each well of a poly-D lysine coated 384 well black, optically clear bottom plate (6007718, Perkin Elmer). The assay plate was kept at 37° C. in a 5% $CO_2$ incubator.

Assay protocol: On the day of experiment, media was removed and loading buffer was added (30 μl/well) to the assay plate. The cells were incubated in the loading buffer for 30 minutes at 37° C. The loading buffer was then replaced by assay buffer (30 μl/well) followed by addition of test compounds or controls. The cells were incubated with compounds for 30 minutes and the plate was then mounted on FlexStation (Molecular Devices) for fluorescence read out with excitation and emission wavelengths at 488 and 525 nm, respectively. Each well was read for 90 sec at 2 sec interval and the stimulus buffer was added after 20 seconds of baseline recording. The final DMSO concentration was either 0.5 or 1% in the assay plate. Positive and negative controls were defined by addition of DMSO or 3 μM of a standard ROMK inhibitor, respectively, to the wells instead of a test compound.

Data analysis: The slope (over a period of 15 seconds) of fluorescence increase after stimulus buffer addition was exported from SoftMax Pro into a custom made software where it was converted to % inhibition. A 10-point concentration response curve was used to estimate the $IC_{50}$ value of test compounds.

The data in Table 3 is reported with two significant figures.

TABLE 3

| Patent Example Number | Human ROMK TH Flux IC50 (nM) | Patent Example Number | Human ROMK TH Flux IC50 (nM) |
|---|---|---|---|
| 29 | 3300 | 17-I | 1500 |
| 10-I | 53 | 18-I | 230 |
| 10-II | 140 | 19-I | 150 |
| 11-I | 3700 | 1-I | 170 |
| 12-I | 78 | 1-II | 830 |
| 12-II | 520 | 21-I | 86 |
| 14-I | 4000 | 21-II | 350 |
| 15-I | 2000 | 22-I | 270 |
| 15-II | 1500 | 22-II | 820 |
| 16-I | 480 | 23-I | 160 |
| 24-I | 2400 | 39 | 58 |
| 24-II | 2400 | 40 | 340 |
| 25-I | 240 | 41 | 32 |
| 25-II | 520 | 42 | 855 |
| 27-I | 40 | 43 | 66 |
| 27-II | 240 | 44 | 140 |
| 28-I | 180 | 45 | 12 |
| 28-II | 390 | 47 | 100 |
| 2-I | 1900 | 48 | 14 |
| 30-II | 1200 | 49 | 32 |
| 31-I | 40 | 50 | 45 |
| 31-II | 370 | 51 | 73 |
| 32-I | 530 | 52 | 180 |
| 33-I | 3300 | 53 | 320 |
| 34-I | 780 | 54 | 260 |
| 3-I | 17 | 55 | 78 |
| 3-II | 59 | 56 | 80 |
| 4-I | 38 | 57 | 150 |
| 4-II | 180 | 58 | 300 |
| 5-I | 1500 | 59 | 540 |
| 7-I | 23 | 60 | 72 |
| 7-II | 200 | 61 | 27 |
| 8-I | 290 | 62 | 390 |
| 9-I | 290 | 63 | 130 |
| 35 | 1.00 | 64 | 430 |
| 36 | 390 | 65 | 38 |
| 37 | 930 | 66 | 260 |
| 38 | 340 | 67 | 20 |
| 68 | 38 | 97 | 63 |
| 69 | 14 | 98 | 100 |
| 70 | 19 | 99 | 140 |
| 71 | 22 | 100 | 170 |
| 72 | 14 | 101 | 200 |
| 73 | 36 | 102 | 220 |
| 74 | 59 | 103 | 55.2 |
| 75 | 65 | 104 | 9.4 |
| 76 | 81 | 105 | 11 |
| 77 | 190 | 106 | 26 |
| 78 | 440 | 107 | 27 |
| 79 | 530 | 108 | 35 |
| 80 | 530 | 109 | 40 |
| 81 | 30 | 110 | 42 |
| 82 | 31 | 111 | 48 |
| 83 | 46 | 112 | 66 |
| 84 | 82 | 113 | 14 |
| 85 | 230 | 114 | 17 |
| 86 | 430 | 115 | 20 |
| 87 | 40 | 116 | 20 |
| 88 | 42 | 117 | 24 |
| 89 | 92 | 118 | 70 |
| 90 | 230 | 119 | 91 |
| 92 | 6.4 | 120 | 120 |
| 93 | 15 | 121 | 160 |
| 94 | 56 | 122 | 170 |
| 95 | 56 | 123 | 210 |
| 96 | 62 | 124 | 260 |
| 125 | 390 | 153 | 520 |
| 126 | 580 | 154 | 1000 |
| 127 | 420 | 155 | 31 |
| 128 | 6.6 | 156 | 9.7 |
| 129 | 8.0 | 157 | 31 |
| 130 | 8.3 | 158 | 390 |
| 131 | 9.2 | 159 | 93 |
| 132 | 26 | 160 | 24 |
| 133 | 900 | 161 | 77 |
| 134 | 77 | 162 | 110 |

TABLE 3-continued

| Patent Example Number | Human ROMK TH Flux IC50 (nM) | Patent Example Number | Human ROMK TH Flux IC50 (nM) |
|---|---|---|---|
| 135 | 67 | 163 | 260 |
| 136 | 70 | 164 | 280 |
| 137 | 35 | 165 | 470 |
| 138 | 43 | 166 | 1300 |
| 139 | 55 | 167 | 68 |
| 140 | 56 | 168 | 120 |
| 141 | 290 | 169 | 59 |
| 142 | 480 | 171 | 1000 |
| 143 | 1,000 | 173 | 2.4 |
| 144 | 140 | 174 | 11600 |
| 145 | 130 | 175 | 3.6 |
| 146 | 25 | 177 | 0.57 |
| 147 | 37 | 178 | 3.6 |
| 148 | 200 | 170-I | 160 |
| 149 | 84 | 172-I | 850 |
| 150 | 56 | 172-II | 1800 |
| 151 | 29 | 176-I | 4.0 |
| 152 | 6.2 | 46-I | 33 |
| 91-I | 21 | | |

ROMK Manual Patch Clamp Assay

Cell culture conditions: Cells were maintained in conditions similar to those for Thallium flux assay. hROMK channel expression was induced by adding 0.6 μg/ml of Doxycycline 16-24 hrs prior to the experiments. On the day of experiment, the cells were dissociated using Versene, resuspended in growth media and plated onto coverslips 15 minutes prior to use.

Electrophysiology: The coverslip plated with cells was placed in the experiment chamber perfused with bath solution composed of (in mM): 135 NaCl, 5 KCl, 2 $CaCl_2$), 1 $MgCl_2$, 10 HEPES, 5 Glucose (pH 7.4). Patch pipettes with resistance between 2-5 Megaohms, when filled with a solution containing (in mM): 135 KCl, 1 EGTA, 1 $MgCl_2$, 10 HEPES, 2 $Na_2ATP$ (pH 7.3), were used to form gigaseals. The cells were voltage clamped at −75 mV in whole-cell configuration using an Axopatch 200b or Multiclamp 700b (Molecular Devices) amplifier controlled by pClamp Software (Molecular Devices). The current was recorded by applying a voltage step to −120 mV every 10 seconds. For each compound, 4-6 concentrations were applied for 3-8 minutes in a successive manner starting with the lowest concentration. At the end of the experiment, the cells were perfused with bath solution containing 2 mM $Ba^{2+}$ to isolate the contribution of hROMK current.

Data analysis: Raw current values (5 traces each for control, different compound concentration and $Ba^{2+}$ treatment groups) were exported from Clampfit into Microsoft Excel where the current remaining after application of $Ba^{2+}$ was subtracted from raw current to obtain hROMK specific current. These hROMK current values (average of 5 traces for each group) were then imported into a custom made template to generate a concentration response curve, which was subsequently fitted with a four parameter equation to calculate the $IC_{50}$ value of the test compound.

The data in Table 4 is reported with two significant figures.

TABLE 4

| Patent Example Number | ROMK EP IC50 (nM) | Patent Example Number | ROMK EP IC50 (nM) |
|---|---|---|---|
| 27-I | 6.8 | 87 | 71 |
| 21-I | 18 | 105 | 7.8 |
| 1-I | 19 | 106 | 9.2 |
| 22-I | 53 | 108 | 19 |
| 23-I | 15 | 115 | 20 |
| 8-I | 42 | 130 | 1.1 |
| 7-I | 4.7 | 136 | 86 |
| 6-I | 11 | 137 | 26 |
| 4-I | 12 | 138 | 18 |
| 47 | 420 | 139 | 24 |
| 50 | 49 | 140 | 16 |
| 51 | 38 | 177 | 0.15 |
| 61 | 27 | 178 | 2.1 |
| 67 | 9.3 | 46-I | 17 |
| 69 | 6.1 | 91-I | 11 |
| 81 | 12 | | | hERG Manual Patch Clamp Assay hERG electrophysiology assay: The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 $CaCl_2$), 1 $MgCl_2$, 10 Glucose, 10 HEPES (pH 7.4, NaOH) at room temperature. Borosilicate patch pipettes had tip resistances of 2-4 Mohms when filled with an internal solution containing: 130 KCl, 1 $MgCl_2$, 1 $CaCl_2$), 10 EGTA, 10 HEPES, 5 ATP-$K_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in a custom made template. The percent inhibitions at different concentrations were plotted to obtain a concentration response curve, which was subsequently fitted with a four parameter equation to calculate hERG $IC_{50}$ value.

A lower hERG % Inhibition value indicates less inhibition of the hERG current

TABLE 5

| Patent Example Number | hERG EP IC50 (% Inh @1 uM) | Patent Example Number | hERG EP IC50 (% Inh @1 uM) |
|---|---|---|---|
| 27-I | 95 | 1-I | 8.7 |
| 28-I | 94 | 22-I | 9.5 |
| 10-I | 92 | 12-I | 99 |
| 21-I | 68 | 31-I | 39 |
| 3-I | 66 | 56 | 3.7 |
| 23-I | 13 | 57 | 35 |
| 8-I | 83 | 60 | 12 |
| 19-I | 33 | 61 | 8.4 |
| 7-I | 23 | 67 | 11 |
| 6-I | 26 | 68 | 17 |

TABLE 5-continued

| Patent Example Number | hERG EP IC50 (% Inh @1 uM) | Patent Example Number | hERG EP IC50 (% Inh @1 uM) |
|---|---|---|---|
| 4-I | 22 | 69 | 15 |
| 35 | 91 | 70 | 27 |
| 39 | 2.6 | 71 | 39 |
| 41 | 50 | 72 | 35 |
| 43 | 7.1 | 73 | 31 |
| 45 | 74 | 74 | 32 |
| 47 | 9.7 | 75 | 4.3 |
| 48 | 67 | 81 | 6.0 |
| 49 | 18 | 82 | 44 |
| 50 | 8.5 | 87 | 7.5 |
| 51 | 3.4 | 88 | 3.6 |
| 52 | 13 | 92 | 24 |
| 55 | 69 | 93 | 29 |
| 94 | 13 | 128 | 22 |
| 95 | 11 | 130 | 32 |
| 96 | 19 | 131 | 79 |
| 98 | 54 | 132 | 61 |
| 104 | 42 | 133 | 59 |
| 105 | 3.4 | 134 | 3.8 |
| 106 | 2.4 | 135 | 51 |
| 107 | 20 | 136 | 15 |
| 108 | 7.3 | 137 | 7.6 |
| 109 | 12 | 138 | 10 |
| 110 | 13 | 139 | 5.9 |
| 111 | 69 | 140 | 8.6 |
| 112 | 4.2 | 146 | 61 |
| 113 | 12 | 147 | 28 |
| 114 | 25 | 148 | 72 |
| 115 | 12 | 149 | 8.6 |
| 116 | 76 | 150 | 55 |
| 117 | 32 | 151 | 45 |
| 118 | 16 | 152 | 64 |
| 155 | 20 | 169 | 79 |
| 156 | 15 | 173 | 77 |
| 159 | 6.5 | 175 | 86 |
| 160 | 89 | 177 | 98 |
| 161 | 48 | 178 | 36 |
| 162 | 44 | 176-I | 44 |
| 167 | 41 | 91-I | 19 |

What is claimed is:

1. A compound having the structure of Formula (I)

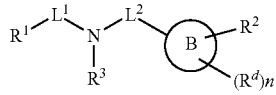

or a salt thereof, wherein:

R₁ is

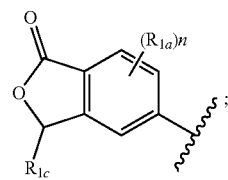

n is zero, 1 or 2;
each $R^{1a}$ is independently H, F, Cl, —OH, $C_{1-3}$ alkyl, $C_{1-3}$ fluoroalkyl, $C_{3-6}$ cycloalkyl, $C_{1-3}$ alkoxy, or $C_{1-3}$ fluoroalkoxy;
each $R^{1b}$ is independently H, $C_{1-3}$ alkyl, $C_{1-3}$ fluoroalkyl, $C_{1-6}$ cycloalkyl
$R^{1c}$ is H, $C_{1-4}$ alkyl, $C_{1-4}$ fluoroalkyl, or $C_{3-6}$ cycloalkyl;
$R^{1d}$ is H, $C_{1-3}$ alkyl, $C_{1-4}$ fluoroalkyl, or $C_{3-6}$ cycloalkyl;
$L^1$ is —CHR$^b$—, —CHR$^a$CHR$^b$—, —CH(R$^a$)C(O)—, —C(R$^b$)$_2$—, —C(R$^a$)$_2$CH(R$^b$)—, or —CH(R$^a$)C(R$^b$)$_2$—;
$L^2$ is —CH$_2$—, —C(O)—, —CH$_2$—CH$_2$—, or —C(R)$_2$—; wherein R is independently selected from hydrogen, F, $C_{1-3}$ alkyl, $C_{1-3}$ hydroxyalkyl, $C_{1-3}$ alkoxyalkyl, or $C_{1-3}$ fluoroalkyl;
$R^a$ is H, halo, —OH, $C_{1-4}$ alkyl, $C_{1-3}$ fluoroalkyl, $C_{1-3}$ hydroxyalkyl, $C_{3-6}$ cycloalkyl, alkoxy, OC(O)—$C_{1-4}$ alkyl substituted with 0-1 OH, halo or NH$_2$, NR$^{1e}$R$^{1e}$, or $C_{1-3}$ fluoroalkoxy;
each $R^{1e}$ is independently H, $C_{1-6}$ alkyl, $C_{1-6}$ fluoroalkyl, $C_{3-6}$ cycloalkyl, $C_{3-6}$ fluorocycloalkyl, C(O)-alkyl, C(O)—$C_{1-6}$ fluoroalkyl, C(O)—$C_{3-6}$ cycloalkyl, C(O) heterocyclyl, C(O)O—$C_{1-6}$ alkyl, C(O)O—$C_{3-6}$ cycloalkyl, C(O)O—$C_{1-6}$ fluoroalkyl, C(O)O—$C_{3-6}$ fluorocycloalkyl, SO$_2$—$C_{1-6}$ alkyl, SO$_2$—$C_{3-6}$ cycloalkyl, SO$_2$—$C_{3-6}$ fluoroalkyl, SO$_2$—$C_{3-6}$ fluorocycloalkyl, C(O)NR$^e$R$^e$, wherein the heterocyclyl is 5 or 6 membered ring having 1, 2, 3, or 4 heteroatoms selected from O, S, and N, and the alkyl, cycloalkyl, or heterocyclyl is substituted with 0-1 of halo, OH, CN, NH$_2$, $C_{1-3}$ alkyl, $C_{1-3}$ alkoxy, $C_{1-3}$ fluoroalkyl, $C_{1-3}$ fluoroalkoxy; or two $R^{1e}$ along with the nitrogen atom to which they are attached form a 3-7 membered heterocyclyl having 1, 2, 3, or 4 heteroatoms selected from O, S, and N, and being substituted with 0-1 halo, $C_{1-3}$ alkyl, or =O;
$R^b$ is H, $C_{1-4}$ alkyl, $C_{1-3}$ fluoroalkyl, $C_{1-3}$ hydroxyalkyl, $C_{3-6}$ cycloalkyl, $C_{1-3}$ alkoxyalkyl, or $C_{1-3}$ fluoroalkoxyalkyl;
Ring B is phenyl, pyridinyl, pyrimidinyl, pyrrazolyl, indolyl, indazolyl, thiazolyl, imidazolyl, pyridinonyl, triazolyl, tetrazolyl, oxadiazolyl, thiadiazolyl, isothiazolyl, isoxazolyl, pyrazinyl, oxazolyl, pyridazinyl, furanyl, thiophenyl, pyrrolyl, triazinyl, azaindolyl, benzimidazolyl, bezoxazolyl, bezothiazolyl, benzofuranyl, or benzothiophenyl;
$R^2$ is a $C_{6-10}$ aryl, or a 5 to 10 membered heteroaryl ring containing 1 to 4 heteroatoms selected from N, O, and S, the heteroaryl optionally containing an oxo substitution, and the heteroaryl and aryl being substituted with 0-3 $R^{2a}$;
$R^{2a}$ is OH, =O, CN, halo, C(O)N(R)$_2$, C(O)O—$C_{1-4}$ alkyl, $C_{1-4}$alkyl, $C_{1-4}$ fluoroalkyl, $C_{1-4}$ alkoxy, $C_{1-4}$ fluoroalkoxy, $C_{3-6}$ cycloalkyl, $C_{3-6}$ cycloalkoxy, SO$_2$R$^e$, or a 4 to 6 membered heterocyclyl having 1, 2, 3, or 4 heteroatoms selected from O, S, and N, and wherein the heterocyclyl is substituted with 0-3 R$^d$;
each $R^3$ is independently H, $C_{1-4}$ alkyl, $C_{1-4}$ fluoroalkyl, $C_{1-3}$ hydroxyalkyl, $C_{1-3}$ alkoxyalkyl, $C_{3-6}$cycloalkyl, —(CH$_2$)—$C_{3-6}$ cycloalkyl, —(CH$_2$)-heterocyclyl, —SO$_2$R$^e$, —C(O)R$^e$, —C(O)OR$^e$, or —C(O)NR$^e$R$^e$, wherein the heterocyclyl is a 5-6 membered ring have 1, 2, or 3 heteroatoms selected from N, O, and S;
each $R^d$ is independently H, $C_{1-3}$ alkyl, $C_{1-3}$ alkoxy, halo, OH, =O, CN OCF$_3$, OCHF$_2$, CHF$_2$ and CF$_3$, and
each $R^e$ is independently H, $C_{1-3}$ alkyl, $C_{1-3}$ fluoroalkyl, $C_{3-6}$ cycloalkyl, $C_{3-6}$ fluorocycloalkyl, $C_{1-3}$ hydroxyalkyl, $C_{1-3}$ alkoxyalkyl, $C_{6-10}$ aryl, or a 5 to 10 membered heteroaryl having 1, 2, 3, or 4 heteroatoms selected from O, S, and N; or two R$^e$ along with the nitrogen atom to which they are attached form a 3-7 membered heterocyclyl having 1, 2, 3, or 4 heteroatoms selected from O, S, and N.

2. A compound of claim 1, or salt thereof, wherein:
R² is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiazolyl, thiophenyl, 1H-1,2,3-triazolyl, 1H-benzo[d][1,2,3]triazolyl, [1,2,4]triazolo[4,3-b]pyridazinyl, 1H-benzo[d]imidazolyl, 1H-imidazolyl, 1H-pyrazolo[3,4-b]pyridinyl, 1H-pyrazolo[3,4-c]pyridinyl, 1H-pyrazolo[4,3-c]pyridinyl, 1H-pyrrolyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, pyrazolo[1,5-a]pyrimidinyl, 1H-tetrazolyl, 4H-1,2,4-triazolyl, isothiazolyl, isoxazolyl, oxazolyl, pyridazinyl, pyrimidinyl, or benzo[d]oxazol-2(3H)-only, each being substituted with with 0-3 R²ᵃ.

3. A compound of claim 2, or salt thereof, wherein:
R² is phenyl, pyridinyl, indolyl, indazolyl, benzo[d]oxazol-2(3H)-onyl, 1H-pyrazolo[4,3-b]pyridinyl, pyridin-2(1H)-onyl, 1H-pyrazolyl, [1,2,4]triazolo[1,5-a]pyridinyl, imidazo[1,2-b]pyridazinyl, pyrazinyl, pyrazolo[1,5-a]pyrimidinyl, thiophenyl, [1,2,4]triazolo[4,3-b]pyridazinyl, pyrazolo[1,5-a]pyrimidinyl, or benzo[d]oxazol-2(3H)-only, each being substituted with with 0-3 R²ᵃ.

4. A compound of claim 3, or salt thereof, wherein:
R² is phenyl, pyridinyl, indolyl, indazolyl, benzo[d]oxazol-2(3H)-onyl, 1H-pyrazolo[4,3-b]pyridinyl, or pyridin-2(1H)-onyl.

5. A compound of claim 4, or salt thereof, wherein:
Ring B is phenyl, pyridinyl, pyrimidinyl, pyrrazolyl, indolyl, indazolyl, thiazolyl, imidizolyl, pyridinonyl, 1,2-dihydro-3H pyrazol-3-onyl, 1H-1,2,3-triazolyl, pyrazinyl or pyridazinyl, or oxazolyl.

6. A compound of claim 5, or salt thereof, wherein:
Ring B is phenyl, pyridinyl, pyrimidinyl, pyrrazolyl, indolyl, or indazolyl.

7. A compound of claim 5, or salt thereof, wherein:
R¹ is:

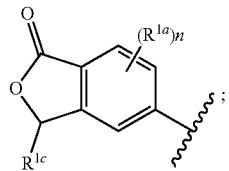

each R¹ᵃ is independently selected from F, Cl, $C_{1-3}$ alkyl, $C_{1-3}$ fluoroalkyl, and $C_{3-6}$ cycloalkyl;
R¹ᶜ is H, $C_{1-2}$ alkyl, or $C_{3-6}$ cycloalkyl;
n is zero, 1, or 2;
Rᵃ is H, F, —OH, $C_{1-2}$ alkyl, —CHF₂, —CF₃, —CH₂OH, cyclopropyl, —OCH₃, —OCHF₂, or —OCF₃;
Rᵇ is H, $C_{1-2}$ alkyl, $C_{1-2}$ hydroxyalkyl, or cyclopropyl;
Rᶜ is H or —CH₃;
each R³ is independently H, $C_{1-4}$ alkyl, —(CH₂)—$C_{3-6}$cycloalkyl, —(CH₂)-heterocyclyl wherein the heterocyclyl is a 5-6 membered ring have 1, 2, or 3 heteroatoms selected from N, O, and S, or —C(O)—$C_{1-3}$alkyl; and
each Rᵉ² is independently H, —CH₃, —CF₃, or $C_{3-6}$ cycloalkyl.

8. The compound according to claim 7, or a salt thereof, wherein:

R¹ is

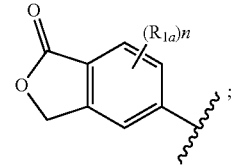

R¹ᵇ is H or —CH₃;
L¹ is —CH₂—, —CH₂CH₂—, —CH(CH₂OH)—, or —CH(OH)CH₂—;
R³ is H.

9. The compound according to claim 8, or salt thereof, wherein:
Ring B is phenyl, pyridinyl, pyrimidinyl, indolyl, or pyrrazolyl, indazolyl; and
R² is phenyl, indolyl, pyridinyl, benzo[d]oxazol-2(3H)-onyl, pyridin-2(1H)-onyl, or indazolyl.

10. A compound of claim 1, or salt thereof, wherein the compound is selected from:
5-(5-(((2-hydroxy-2-(4-methyl-1-oxo-1,3-dihydroisobenzofuran-5-yl)ethyl)(methyl)amino)methyl)pyridin-2-yl)-3-methylbenzo[d]oxazol-2(3H)-one;
1-(5-(((2-hydroxy-1-(4-methyl-1-oxo-1,3-dihydroisobenzofuran-5-yl)ethyl)(methyl)amino)methyl)pyrimidin-2-yl)-1H-indazole-4-carbonitrile;
2-fluoro-4-(5-(((2-hydroxy-2-(4-methyl-1-oxo-1,3-dihydroisobenzofuran-5-yl)ethyl)amino)methyl)pyridin-2-yl)benzonitrile;
5'-(((2-hydroxy-2-(4-methyl-1-oxo-1,3-dihydroisobenzofuran-5-yl)ethyl)amino)methyl)-4-methyl-[2,2'-bipyridine]-5-carbonitrile;
6-(4-(((2-hydroxy-2-(4-methyl-1-oxo-1,3-dihydroisobenzofuran-5-yl)ethyl)amino)methyl)-1H-pyrazol-1-yl)-4-methylnicotinonitrile;
5-(1-hydroxy-2-(((1-(1-oxo-1,3-dihydroisobenzofuran-5-yl)-1H-indol-5-yl)methyl)amino)ethyl)-4-methyl-isobenzofuran-1(3H)-one;
5-(5-(((2-hydroxy-2-(4-methyl-1-oxo-1,3-dihydroisobenzofuran-5-yl)ethyl)(methyl)amino)methyl)pyrimidin-2-yl)-3-methylbenzo[d]oxazol-2(3H)-one;
3-fluoro-4'-(((2-hydroxy-2-(4-methyl-1-oxo-1,3-dihydroisobenzofuran-5-yl)ethyl)amino)methyl)-[1,1'-biphenyl]-4-carbonitrile;
3-fluoro-4'-(((2-hydroxy-2-(4-methyl-1-oxo-1,3-dihydroisobenzofuran-5-yl)ethyl)(pyridin-3-ylmethyl)amino)methyl)-[1,1'-biphenyl]-4-carbonitrile;
1-(4-(((2-hydroxy-2-(4-methyl-1-oxo-1,3-dihydroisobenzofuran-5-yl)ethyl)(methyl)amino)methyl)phenyl)-1H-indole-3-carbonitrile;
5-(5-(((2-hydroxy-1-(4-methyl-1-oxo-1,3-dihydroisobenzofuran-5-yl)ethyl)(methyl)amino)methyl)pyrimidin-2-yl)-3-methylbenzo[d]oxazol-2(3H)-one;
3-fluoro-3'-(2-((2-hydroxy-1-(4-methyl-1-oxo-1,3-dihydroisobenzofuran-5-yl)ethyl)amino)ethyl)-[1,1'-biphenyl]-4-carbonitrile;
5-(2-(((1-(4-fluorophenyl)-1H-indazol-5-yl)methyl)amino)-1-hydroxyethyl)-4-methylisobenzofuran-1(3H)-one;
5-(2-(((2-(1H-pyrazolo[4,3-b]pyridin-1-yl)pyrimidin-5-yl)methyl)(methyl)amino)-1-hydroxyethyl)-4-methyl-isobenzofuran-1(3H)-one;

1-(5-(((2-hydroxy-2-(4-methyl-1-oxo-1,3-dihydroisobenzofuran-5-yl)ethyl)(methyl)amino)methyl)pyrimidin-2-yl)-1H-indazole-4-carbonitrile;
2-fluoro-4-(5-(((2-hydroxy-2-(4-methyl-1-oxo-1,3-dihydroisobenzofuran-5-yl)ethyl)(methyl)amino)methyl)pyrimidin-2-yl)benzonitrile;
3-fluoro-4'-(((2-hydroxy-2-(4-methyl-1-oxo-1,3-dihydroisobenzofuran-5-yl)ethyl)amino)methyl)-[1,1'-biphenyl]-4-carbonitrile;
2-fluoro-4-(5-(((2-hydroxy-2-(4-methyl-1-oxo-1,3-dihydroisobenzofuran-5-yl)ethyl)(methyl)amino)methyl)pyridin-2-yl)benzonitrile;
5'-(((2-hydroxy-2-(4-methyl-1-oxo-1,3-dihydroisobenzofuran-5-yl)ethyl)(methyl)amino)methyl)-4-methyl-[2,2'-bipyridine]-5-carbonitrile;
5-(5-(((2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one;
2-fluoro-4-(5-(((2-hydroxy-2-(3-methyl-2-oxo-2,3-dihydrobenzo[d]oxazol-5-yl)ethyl)(methyl)amino)methyl)pyridin-2-yl)benzonitrile;
1-(5-(((2-hydroxy-2-(4-methyl-1-oxo-1,3-dihydroisobenzofuran-5-yl)ethyl)(methyl)amino)methyl)pyridin-2-yl)-1H-indole-4-carbonitrile;
3-fluoro-4'-(((2-hydroxy-2-(4-methyl-1-oxo-1,3-dihydroisobenzofuran-5-yl)ethyl)(methyl)amino)methyl)-[1,1'-biphenyl]-4-carbonitrile;
1-(4-(((2-hydroxy-2-(4-methyl-1-oxo-1,3-dihydroisobenzofuran-5-yl)ethyl)(methyl)amino)methyl)phenyl)-1H-indole-4-carbonitrile;
3-fluoro-4'-((methyl((1-oxo-1,3-dihydroisobenzofuran-5-yl)methyl)amino)methyl)-[1,1'-biphenyl]-4-carbonitrile;
1-(4-(((2-hydroxy-2-(4-methyl-1-oxo-1,3-dihydroisobenzofuran-5-yl)ethyl)(methyl)amino)methyl)phenyl)-1H-indole-5-carbonitrile;
6-(4-(((2-hydroxy-2-(4-methyl-1-oxo-1,3-dihydroisobenzofuran-5-yl)ethyl)(methyl)amino)methyl)phenyl)-4-methylnicotinonitrile;
1-(4-(((2-hydroxy-2-(4-methyl-1-oxo-1,3-dihydroisobenzofuran-5-yl)ethyl)(methyl)amino)methyl)phenyl)-1H-indole-5-carbonitrile;
6-(5-(((2-hydroxy-2-(4-methyl-1-oxo-1,3-dihydroisobenzofuran-5-yl)ethyl)(methyl)amino)methyl)-1H-indol-1-yl)-4-methylnicotinonitrile;
N-((4'-cyano-3'-fluoro-[1,1'-biphenyl]-4-yl)methyl)-N-(2-hydroxy-2-(4-methyl-1-oxo-1,3-dihydroisobenzofuran-5-yl)ethyl)acetamide
(R)-6-(4-(((2-hydroxy-2-(4-methyl-1-oxo-1,3-dihydroisobenzofuran-5-yl)ethyl)amino)methyl)-5-methoxy-1H-pyrazol-1-yl)-4-methylnicotinonitrile;
(R)-6-(4-(((2-hydroxy-2-(4-methyl-1-oxo-1,3-dihydroisobenzofuran-5-yl)ethyl)amino)methyl)-5-oxo-2,5-dihydro-1H-pyrazol-1-yl)-4-methylnicotinonitrile;
(R)-5-(4-(2-((2-hydroxy-2-(4-methyl-1-oxo-1,3-dihydroisobenzofuran-5-yl)ethyl)amino)propan-2-yl)-1H-pyrazol-1-yl)-3-methylbenzo[d]oxazol-2(3H)-one;
N-(2-(1-(5-cyano-4-methylpyridin-2-yl)-1H-pyrazol-4-yl)ethyl)-2-(4-methyl-1-oxo-1,3-dihydroisobenzofuran-5-yl)acetamide,
(R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)acetamide
(R)-6-(2-(((2-hydroxy-2-(4-methyl-1-oxo-1,3-dihydroisobenzofuran-5-yl)ethyl)amino)methyl)pyrimidin-5-yl)-4-methylnicotinonitrile;
(R)-5-(4-(((2-hydroxy-2-(4-methyl-1-oxo-1,3-dihydroisobenzofuran-5-yl)ethyl)amino)methyl)-1H-pyrazol-1-yl)pyrazine-2-carbonitrile;
(R)-6-(5-(((2-hydroxy-2-(4-methyl-1-oxo-1,3-dihydroisobenzofuran-5-yl)ethyl)amino)methyl)-1-methyl-1H-1,2,4-triazol-3-yl)-4-methylnicotinonitrile;
(R)-5-(1-hydroxy-2-((2-(4-(4-methyl-1-oxo-1,3-dihydroisobenzofuran-5-yl)-1H-pyrazol-1-yl)ethyl)amino)ethyl)-4-methylisobenzofuran-1(3H)-one;
(R)-1-(4-methyl-1-oxo-1,3-dihydroisobenzofuran-5-yl)-2-4(1-(3-methyl-2-oxo-2,3-dihydrobenzo[d]oxazol-5-yl)-1H-pyrazol-4-yl)methyl)amino)ethyl D-valinate,
(R)-1-(5-(((2-hydroxy-2-(4-methyl-1-oxo-1,3-dihydroisobenzofuran-5-yl)ethyl)amino)methyl)pyrimidin-2-yl)-1H-imidazole-4-carbonitrile;
6-(4-(((2-(4-cyclopropyl-1-oxo-1,3-dihydroisobenzofuran-5-yl)2-hydroxyethyl)amino)methyl)-1H-pyrazol-1-yl)-4-methylnicotinonitrile;
(R)-5-(2-(((2-(3,5-dimethyl-4H-1,2,4-triazol-4-yl)pyrimidin-5-yl)methyl)amino)-1-hydroxyethyl)-4-methylisobenzofuran-1(3H)-one;
(R)-6-(4-(((2-hydroxy-2-(4-methyl-1-oxo-1,3-dihydroisobenzofuran-5-yl)ethyl)amino)methyl)-1H-pyrazol-1-yl)-2-methoxynicotinonitrile;
(R)-2-(4-(((2-hydroxy-2-(4-methyl-1-oxo-1,3-dihydroisobenzofuran-5-yl)ethyl)amino)methyl)-1H-pyrazol-1-yl)-5-methylisonicotinonitrile;
(R)-2-(4-(((2-hydroxy-2-(4-methyl-1-oxo-1,3-dihydroisobenzofuran-5-yl)ethyl)amino)methyl)-1H-pyrazol-1-yl)-4-methylpyrimidine-5-carbonitrile;
(R)-6-(4-(((2-hydroxy-2-(4-methyl-1-oxo-1,3-dihydroisobenzofuran-5-yl)ethyl)amino)methyl)-1H-imidazol-1-yl)-4-methoxynicotinonitrile;
(R)-6-(4-(((2-hydroxy-2-(4-methyl-1-oxo-1,3-dihydroisobenzofuran-5-yl)ethyl)amino)methyl)-2-methyl-1H-imidazol-1-yl)-4-methoxynicotinonitrile;
(R)-5-(1-hydroxy-2-(((6-(4-methyl-1H-imidazol-1-yl)pyridazin-3-yl)methyl)amino)ethyl)-4-methylisobenzofuran-1(3H)-one;
(R)-5-(1-hydroxy-2-(((1-(6-(methylsulfonyl)pyridin-3-yl)-1H-pyrazol-4-yl)methyl)amino)ethyl)-4-methylisobenzofuran-1(3H)-one;
(R)-6-(4-(((2-hydroxy-2-(4-methyl-1-oxo-1,3-dihydroisobenzofuran-5-yl)ethyl)amino)methyl)-1H-indazol-1-yl)-4-methoxynicotinonitrile;
(R)-6-(4-(((2-((2-hydroxyethyl)amino)-2-(4-methyl-1-oxo-1,3-dihydroisobenzofuran-5-yl)ethyl)amino)methyl)-1H-pyrazol-1-yl)-4-methylnicotinonitrile;
(R)-6-(4-(((2-((2-methoxyethyl)amino)-2-(4-methyl-1-oxo-1,3-dihydroisobenzofuran-5-yl)ethyl)amino)methyl)-1H-pyrazol-1-yl)-4-methylnicotinonitrile;
(R)-6-(4-(((2-hydroxy-2-(4-methyl-1-oxo-1,3-dihydroisobenzofuran-5-yl)ethyl)amino)methyl)-5-methyl-2H-1,2,3-triazol-2-yl)-4-methylnicotinonitrile;
6-(4-(1-(((R)-2-hydroxy-2-(4-methyl-1-oxo-1,3-dihydroisobenzofuran-5-yl)ethyl)amino)ethyl)-2H-1,2,3-triazol-2-yl)-4-methylnicotinonitrile;
methyl (R)-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)carbmate;
(R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)methanesulfonamide;
(R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)cyclopropanesulfonamide;

(R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)-2-hydroxyacetamide;

(R)-4-methyl-6-(4-(((2-(4-methyl-1-oxo-1,3-dihydroisobenzofuran-5-yl)-2-(methylamino)ethyl)amino)methyl)-1H-pyrazol-1-yl)nicotinonitrile;

(R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)-N-methylmethanesulfonamide;

(R)-6-(4-(((2-(1,1-dioxidoisothiazolidin-2-yl)-2-(4-methyl-1-oxo-1,3-dihydroisobenzofuran-5-yl)ethyl)amino)methyl)-1H-pyrazol-1-yl)-4-methylnicotinonitrile;

(R)-6-(4-(((2-hydroxy-2-(4-methyl-1-oxo-1,3-dihydroisobenzofuran-5-yl)ethyl)amino)methyl)-1H-1,2,3-triazol-1-yl)-2-methoxy-4-methylnicotinonitrile;

(R)-6-(4-(((2-hydroxy-2-(4-methyl-1-oxo-1,3-dihydroisobenzofuran-5-yl)ethyl)amino)methyl)-1H-imidazol-1-yl)-2,4-dimethylnicotinonitrile;

(R)-6-(4-(((2-hydroxy-2-(4-methyl-1-oxo-1,3-dihydroisobenzofuran-5-yl)ethyl)amino)methyl)-1H-1,2,3-triazol-1-yl)-2,4-dimethylnicotinonitrile;

(R)-6-(4-(((2-hydroxy-2-(4-methyl-1-oxo-1,3-dihydroisobenzofuran-5-yl)ethyl)amino)methyl)-1H-pyrazol-1-yl)-4-methoxy-2-methylnicotinonitrile;

(R)-6-(4-(((2-hydroxy-2-(4-methyl-1-oxo-1,3-dihydroisobenzofuran-5-yl)ethyl)amino)methyl)-1H-pyrazol-1-yl)-2,4-dimethylnicotinonitrile;

(R)-6-(4-(((2-hydroxy-2-(4-methyl-1-oxo-1,3-dihydroisobenzofuran-5-yl)ethyl)amino)methyl)-1H-pyrazol-1-yl)-2,4-dimethylnicotinonitrile;

(R)-5-(4-(((2-hydroxy-2-(4-methyl-1-oxo-1,3-dihydroisobenzofuran-5-yl)ethyl)amino)methyl)-1H-pyrazol-1-yl)-3-methylpicolinonitrile;

(R)-6-(4-(((2-hydroxy-2-(4-methyl-1-oxo-1,3-dihydroisobenzofuran-5-yl)ethyl)amino)methyl)-3-methyl-1H-pyrazol-1-yl)-4-methylnicotinonitrile;

(R)-5-(1-hydroxy-2-(((1-(4-methyl-1-oxo-1,3-dihydroisobenzofuran-5-yl)-1H-pyrazol-4-yl)methyl)amino)ethyl)-4-methylisobenzofuran-1(3H)-one;

(R)-5-(1-hydroxy-2-(4-methyl-6-(4-methyl-1H-imidazol-1-yl)pyridin-3-yl)methyl)amino)ethyl)-4-methylisobenzofuran-1(3H)-one;

(R)-5-(1-hydroxy-2-(((2-methyl-6-(4-methyl-1H-imidazol-1-yl)pyridin-3-yl)methyl)amino)ethyl)-4-methylisobenzofuran-1(3H)-one;

(R)-6-(4-(((2-hydroxy-2-(4-methyl-1-oxo-1,3-dihydroisobenzofuran-5-yl)ethyl)amino)methyl)-1H-pyrazol-1-yl)-5-methylnicotinonitrile;

(R)-5-(2-(((1-([1,2,4]triazolo[4,3-b]pyridazin-6-yl)-1H-pyrazol-4-yl)methyl)amino)-1-hydroxyethyl)-4-methylisobenzofuran-1(3H)-one;

(R)-5-(1-hydroxy-2-(((1-(2-methoxypyridin-4-yl)-1H-pyrazol-4-yl)methyl)amino)ethyl)-4-methylisobenzofuran-1(3H)-one;

(R)-5-(4-(((2-hydroxy-2-(4-methyl-1-oxo-1,3-dihydroisobenzofuran-5-yl)ethyl)amino)methyl)-1H-pyrazol-1-yl)-3-methylbenzo[d]oxazol-2(3H)-one;

(R)-5'-(((2-hydroxy-2-(4-methyl-1-oxo-1,3-dihydroisobenzofuran-5-yl)ethyl)amino)methyl)-4,6'-dimethoxy-[2,2'-bipyridine]-5-carbonitrile;

(R)-5-(2-(((5-fluoro-6-(4-methyl-1H-imidazol-1-yl)pyridin-3-yl)methyl)amino)-1-hydroxyethyl)-4-methylisobenzofuran-1(3H)-one;

(R)-5-(6-(((2-hydroxy-2-(4-methyl-1-oxo-1,3-dihydroisobenzofuran-5-yl)ethyl)(methyl)amino)methyl)pyridin-3-yl)-3-methylbenzo[d]oxazol-2(3H)-one;

6-(4-((((R)-2-hydroxy-2-(4-methyl-1-oxo-1,3-dihydroisobenzofuran-5-yl)ethyl)((tetrahydrofuran-3-yl)methyl)amino)methyl)-1H-pyrazol-1-yl)-4-methylnicotinonitrile;

(R)-6-(4-(((2-hydroxy-2-(4-methyl-1-oxo-1,3-dihydroisobenzofuran-5-yl)ethyl)amino)methyl)-1-methyl-1H-imidazol-2-yl)-4-methylnicotinonitrile;

(R)-2-(4-(((2-hydroxy-2-(4-methyl-1-oxo-1,3-dihydroisobenzofuran-5-yl)ethyl)amino)methyl)-1H-pyrazol-1-yl)-4,6-dimethylpyrimidine-5-carbonitrile;

(R)-5-(2-(((2-(4,5-dimethyl-1H-imidazol-1-yl)pyrimidin-5-yl)methyl)amino)-1-hydroxyethyl)-4-methylisobenzofuran-1(3H)-one;

(R)-5-(1-hydroxy-2-(((4-methoxy-6-(4-methyl-1H-imidazol-1-yl)pyridin-3-yl)methyl)amino)ethyl)-4-methylisobenzofuran-1(3H)-one;

(R)-5-(2-(((2-(5-(difluoromethyl)-4-methyl-1H-imidazol-1-yl)pyrimidin-5-yl)methyl)amino)-1-hydroxyethyl)-4-methylisobenzofuran-1(3H)-one;

6-(4-(((1-hydroxy-1-(4-methyl-1-oxo-1,3-dihydroisobenzofuran-5-yl)propan-2-yl)amino)methyl)-1H-1,2,3-triazol-1-yl)-4-methoxynicotinonitrile;

(R)-1-(5-(((2-hydroxy-2-(4-methyl-1-oxo-1,3-dihydroisobenzofuran-5-yl)ethyl)amino)methyl)pyridin-2-yl)-4-methyl-1H-pyrazole-3-carbonitrile;

(R)-6-(3-(difluoromethyl)-4-(((2-hydroxy-2-(4-methyl-1-oxo-1,3-dihydroisobenzofuran-5-yl)ethyl)amino)methyl)-1H-pyrazol-1-yl)-4-methylnicotinonitrile;

(R)-1-(5-(((2-hydroxy-2-(4-methyl-1-oxo-1,3-dihydroisobenzofuran-5-yl)ethyl)amino)methyl)pyrimidin-2-yl)-4-methyl-1H-pyrazole-3-carbonitrile;

(R)-5-(4-(((2-hydroxy-2-(4-methyl-1-oxo-1,3-dihydroisobenzofuran-5-yl)ethyl)amino)methyl)-3-(trifluoromethyl)-1H-pyrazol-1-yl)-3-methylbenzo[d]oxazol-2(3H)-one;

(R)-5-(1-hydroxy-2-(((2-(4-(trifluoromethyl)-1H-imidazol-1-yl)pyrimidin-5-yl)methyl)amino)ethyl)-4-methylisobenzofuran-1(3H)-one;

(R)-6-(3-cyclopropyl-4-(((2-hydroxy-2-(4-methyl-1-oxo-1,3-dihydroisobenzofuran-5-yl)ethyl)amino)methyl)-1H-pyrazol-1-yl)-4-methylnicotinonitrile;

ethyl (R)-1-(5-cyano-4-methylpyridin-2-yl)-4-(((2-hydroxy-2-(4-methyl-1-oxo-1,3-dihydroisobenzofuran-5-yl)ethyl)amino)methyl)-1H-pyrazole-3-carboxylate;

(R)-5-(((2-hydroxy-2-(4-methyl-1-oxo-1,3-dihydroisobenzofuran-5-yl)ethyl)amino)methyl)-4'-methyl-2-oxo-2H-[1,2'-bipyridine]-5'-carbonitrile;

(R)-5-(3-(((2-hydroxy-2-(4-methyl-1-oxo-1,3-dihydroisobenzofuran-5-yl)ethyl)amino)methyl)-1-methyl-1H-pyrazol-5-yl)-3-methylbenzo[d]oxazol-2(3H)-one;

(R)-5-(2-(((6-(1H-1,2,4-triazol-1-yl)pyridin-3-yl)methyl)amino)-1-hydroxyethyl)-4-methylisobenzofuran-1(3H)-one;

(R)-5-(5-(((2-hydroxy-2-(4-methyl-1-oxo-1,3-dihydroisobenzofuran-5-yl)ethyl)amino)methyl)-1-methyl-1H-pyrazol-3-yl)-3-methylbenzo[d]oxazol-2(3H)-one;

(R)-3-ethyl-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile;

(R)-1-(5-(((2-hydroxy-2-(4-methyl-1-oxo-1,3-dihydroisobenzofuran-5-yl)ethyl)amino)methyl)pyridin-2-yl)-3-methoxy-1H-pyrazole-4-carbonitrile;

(R)-1-(5-(((2-hydroxy-2-(4-methyl-1-oxo-1,3-dihydroisobenzofuran-5-yl)ethyl)amino)methyl)pyrimidin-2-yl)-3-methyl-1H-pyrazole-4-carbonitrile;

(R)-5-(1-hydroxy-2-(((2-(4-methyl-1H-imidazol-1-yl)pyrimidin-5-yl)methyl)amino)ethyl)-4-methylisobenzofuran-1(3H)-one;

(R)-7-fluoro-5-(4-(((2-hydroxy-2-(4-methyl-1-oxo-1,3-dihydroisobenzofuran-5-yl)ethyl)amino)methyl)-1H-pyrazol-1-yl)-3-methylbenzo[d]oxazol-2(3H)-one carbonitrile;

(R)-5-(1-hydroxy-2-(((6-(4-methyl-1H-imidazol-1-yl)pyridin-3-yl)methyl)amino)ethyl)-4-methylisobenzofuran-1(3H)-one;

(R)-5-(2-(((6-(1H-imidazol-1-yl)pyridin-3-yl)methyl)amino)-1-hydroxyethyl)-4-methylisobenzofuran-1(3H)-one;

(R)-1-(5-(((2-hydroxy-2-(4-methyl-1-oxo-1,3-dihydroisobenzofuran-5-yl)ethyl)amino)methyl)pyrimidin-2-yl)-3-(trifluoromethyl)-1H-pyrazole-4-carbonitrile;

(R)-5-(1-hydroxy-2-(((6-(2-methylthiazol-5-yl)pyridin-3-yl)methyl)amino)ethyl)-4-methylisobenzofuran-1(3H)-one;

(R)-5-(4-(((2-hydroxy-2-(4-methyl-1-oxo-1,3-di Hydroisobenzofuran-5-yl)ethyl)amino)methyl)-1H-pyrazol-1-yl)-7-methoxy-3-methylbenzo[d]oxazol-2(3H)-one;

(R)-1-(5-(((2-hydroxy-2-(4-methyl-1-oxo-1,3-dihydroisobenzofuran-5-yl)ethyl)amino)methyl)pyrimidin-2-yl)-3-methoxy-1H-pyrazole-4-carbonitrile;

(R)-3-ethyl-1-(5-(((2-hydroxy-2-(4-methyl-1-oxo-1,3-dihydroisobenzofuran-5-yl)ethyl)amino)methyl)pyrimidin-2-yl)-1H-pyrazole-4-carbonitrile;

(R)-3-(difluoromethyl)-1-(5-(((2-hydroxy-2-(4-methyl-1-oxo-1,3-dihydroisobenzofuran-5-yl)ethyl)amino)methyl)pyrimidin-2-yl)-1H-pyrazole-4-carbonitrile;

(R)-3-cyclopropyl-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile;

(R)-3-cyclopropyl-1-(5-(((2-hydroxy-2-(4-methyl-1-oxo-1,3-dihydroisobenzofuran-5-yl)ethyl)amino)methyl)pyrimidin-2-yl)-1H-pyrazole-4-carbonitrile;

(R)-5-(1-hydroxy-2-(((6-(4-methyl-1H-1,2,3-triazol-1-yl)pyridin-3-yl)methyl)amino)ethyl)-4-methylisobenzofuran-1(3H)-one;

(R)-6-(4-(((2-hydroxy-2-(4-methyl-1-oxo-1,3-dihydroisobenzofuran-5-yl)ethyl)amino)methyl)-1H-pyrazol-1-yl)-4-(pyrrolidin-1-yl)nicotinonitrile;

(R)-5-(5-(((2-hydroxy-2-(4-methyl-1-oxo-1,3-dihydroisobenzofuran-5-yl)ethyl)amino)methyl)pyridin-3-yl)-3-methylbenzo[d]oxazol-2(3H)-one;

(R)-5-(4-(((2-hydroxy-2-(4-methyl-1-oxo-1,3-dihydroisobenzofuran-5-yl)ethyl)amino)methyl)-1H-pyrazol-1-yl)benzo[d]oxazol-2(3H)-one;

(R)-6-(5-(((2-hydroxy-2-(4-methyl-1-oxo-1,3-dihydroisobenzofuran-5-yl)ethyl)amino)methyl)pyridin-2-yl)-2-methylpyridazin-3(2H)-one;

(R)-5-(1-hydroxy-2-(((2-(3-methyl-1H-1,2,4-triazol-1-yl)pyrimidin-5-yl)methyl)amino)ethyl)-4-methylisobenzofuran-1(3H)-one;

(R)-5-(1-hydroxy-2-(((6-(1-methyl-1H-pyrazol-4-yl)pyridin-3-yl)methyl)amino)ethyl)-4-methylisobenzofuran-1(3H)-one;

(R)-3-ethyl-5-(4-((2-hydroxy-2-(4-methyl-1-oxo-1,3-dihydroisobenzofuran-5-yl)ethyl)amino)methyl)-1H-pyrazol-1-yl)benzo[d]oxazol-2(3H)-one;

(R)-5-(4-(((2-hydroxy-2-(4-methyl-1-oxo-1,3-dihydroisobenzofuran-5-yl)ethyl)amino)methyl)-1H-imidazol-2-yl)-3-methylbenzo[d]oxazol-2(3H)-one;

(R)-5-(1-hydroxy-2-(((6-(5-methyl-2H-tetrazol-2-yl)pyridin-3-yl)methyl)amino)ethyl)-4-methylisobenzofuran-1(3H)-one;

(R)-6-(5-(((2-hydroxy-2-(4-methyl-1-oxo-1,3-dihydroisobenzofuran-5-yl)ethyl)amino)methyl)thiazol-2-yl)-4-methylnicotinonitrile;

(R)-6-(5-(((2-hydroxy-2-(4-methyl-1-oxo-1,3-dihydroisobenzofuran-5-yl)ethyl)amino)methyl)thiazol-2-yl)-4-methoxynicotinonitrile;

(R)-5'-(((2-hydroxy-2-(4-methyl-1-oxo-1,3-dihydroisobenzofuran-5-yl)ethyl)amino)methyl)-4-methoxy-[2,2'-bipyridine]-5-carbonitrile;

(R)-1-(5-(((2-hydroxy-2-(4-methyl-1-oxo-1,3-dihydroisobenzofuran-5-yl)ethyl)amino)methyl)pyridin-2-yl)-1H-imidazole-4-carbonitrile;

(R)-1-(5-(((2-hydroxy-2-(4-methyl-1-oxo-1,3-dihydroisobenzofuran-5-yl)ethyl)amino)methyl)pyridin-2-yl)-1H-1,2,4-triazole-3-carbonitrile;

(R)-5-(6-(((2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one;

(R)-6-(5-(((2-hydroxy-2-(4-methyl-1-oxo-1,3-dihydroisobenzofuran-5-yl)ethyl)amino)methyl)pyrimidin-2-yl)-4-methoxynicotinonitrile;

(R)-5-(5-((ethyl (2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one;

(R)—N-(2-hydroxy-2-(4-methyl-1-oxo-1,3-dihydroisobenzofuran-5-yl)ethyl)-2-(3-methyl-2-oxo-2,3-dihydrobenzo[d]oxazol-5-yl)thiazole-5-carboxamide;

(R)-6-(5-(((2-hydroxy-2-(4-methyl-1-oxo-1,3-dihydroisobenzofuran-5-yl)ethyl)amino)methyl)isoxazol-3-yl)-4-methoxynicotinonitrile;

(R)-6-(4-(((2-hydroxy-2-(4-methyl-1-oxo-1,3-dihydroisobenzofuran-5-yl)ethyl)amino)methyl)-1H-1,2,3-triazol-1-yl)-4-methoxynicotinonitrile;

(R)-5-(4-(((2-hydroxy-2-(4-methyl-1-oxo-1,3-dihydroisobenzofuran-5-yl)ethyl)amino)methyl)-1H-1,2,3-triazol-1-yl)-3-methylbenzo[d]oxazol-2(3H)-one;

(R)-6-(5-(((2-hydroxy-2-(4-methyl-1-oxo-1,3-dihydroisobenzofuran-5-yl)ethyl)amino)methyl)isoxazol-3-yl)-4-methylnicotinonitrile;

(R)-5-(1-hydroxy-2-(((5-(4-methyl-1H-imidazol-1-yl)pyrazin-2-yl)methyl)amino)ethyl)-4-methylisobenzofuran-1(3H)-one;

(R)—N-(2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl)cyclopropanecarboxamide;

(R)-3-(2-(4-(((2-hydroxy-2-(4-methyl-1-oxo-1,3-dihydroisobenzofuran-5-yl)ethyl)amino)methyl)-1H-pyrazol-1-yl)pyridin-4-yl)oxazolidin-2-one;

(R)-2-(((1-(5-cyano-4-methylpyridin-2-yl)-1H-pyrazol-4-yl)methyl)amino)-1-(4-methyl-1-oxo-1,3-dihydroisobenzofuran-5-yl)ethyl methylcarbamate;

(R)-5-(4-(((2-hydroxy-2-(4-methyl-1-oxo-1,3-dihydroisobenzofuran-5-yl)ethyl)amino)methyl)-1H-pyrazol-1-yl)-3-methyloxazolo[4,5-b]pyridin-2(3H)-one;

(R)-6-(4-(((2-hydroxy-2-(4-methyl-1-oxo-1,3-dihydroisobenzofuran-5-yl)ethyl)amino)methyl)-1H-pyrazol-1-yl)-4-(methylamino)nicotinonitrile;

(R)-6-(4-(((2-methoxy-2-(4-methyl-1-oxo-1,3-dihydroisobenzofuran-5-yl)ethyl)amino)methyl)-1H-pyrazol-1-yl)-4-methylnicotinonitrile;

(R)-4-cyclopropyl-6-(4-(((2-hydroxy-2-(4-methyl-1-oxo-1,3-dihydroisobenzofuran-5-yl)ethyl)amino)methyl)-1H-pyrazol-1-yl)nicotinonitrile;
(R)-5-(4-(((2-hydroxy-2-(4-methyl-1-oxo-1,3-dihydroisobenzofuran-5-yl)ethyl)amino)methyl)-1H-imidazol-1-yl)-3,4-dimethylbenzo[d]oxazol-2(3H)-one;
(R)-6-(4-(((2-hydroxy-2-(4-methoxy-1-oxo-1,3-dihydroisobenzofuran-5-yl)ethyl)amino)methyl)-1H-pyrazol-1-yl)-4-methoxynicotinonitrile;
(R)-1-(5-(((2-hydroxy-2-(4-methyl-1-oxo-1,3-dihydroisobenzofuran-5-yl)ethyl)amino)methyl)pyridin-2-yl)-1H-pyrazole-3-carbonitrile;
(R)-4-ethoxy-6-(4-(((2-hydroxy-2-(4-methyl-1-oxo-1,3-dihydroisobenzofuran-5-yl)ethyl)amino)methyl)-1H-pyrazol-1-yl)nicotinonitrile;
(R)-5-(2-(((2-(2-cyclopropyl-4-methyl-1H-imidazol-1-yl)pyrimidin-5-yl)methyl)amino)-1-hydroxyethyl)-4-methylisobenzofuran-1(3H)-one;
(R)-1-(5-(((2-hydroxy-2-(4-methyl-1-oxo-1,3-dihydroisobenzofuran-5-yl)ethyl)amino)methyl)pyridin-2-yl)-1H-pyrazole-4-carboxamide;
(R)-4-ethoxy-6-(4-(((2-hydroxy-2-(4-methyl-1-oxo-1,3-dihydroisobenzofuran-5-yl)ethyl)amino)methyl)-2H-1,2,3-triazol-2-yl)nicotinonitrile;
(R)-4-ethoxy-6-(4-(((2-hydroxy-2-(4-methyl-1-oxo-1,3-dihydroisobenzofuran-5-yl)ethyl)amino)methyl)-1H-1,2,3-triazol-1-yl)nicotinonitrile;
(R)-6-(4-(((2-hydroxy-2-(4-methyl-1-oxo-1,3-dihydroisobenzofuran-5-yl)ethyl)amino)methyl)-1H-pyrazol-1-yl)-4-isopropoxynicotinonitrile;
(R)-3-(3-(4-(((2-hydroxy-2-(4-methyl-1-oxo-1,3-dihydroisobenzofuran-5-yl)ethyl)amino)methyl)-1H-pyrazol-1-yl)phenyl)oxazolidin-2-one;
(R)-6-(4-(((2-hydroxy-2-(4-methyl-1-oxo-1,3-dihydroisobenzofuran-5-yl)ethyl)amino)methyl)-3-methyl-2-oxo-2,3-dihydro-1H-imidazol-1-yl)-4-methylnicotinonitrile;
(R)-4-(4-(((2-hydroxy-2-(4-methyl-1-oxo-1,3-dihydroisobenzofuran-5-yl)ethyl)amino)methyl)-1H-pyrazol-1-yl)benzonitrile;
(R)-3-(4-(((2-hydroxy-2-(4-methyl-1-oxo-1,3-dihydroisobenzofuran-5-yl)ethyl)amino)methyl)-1H-pyrazol-1-yl)benzonitrile
(R)-5-(5-(((cyclopropylmethyl)(2-hydroxy-2-(4-methyl-1-oxo-1,3-dihydroisobenzofuran-5-yl)ethyl)amino)methyl)pyridin-2-yl)-3-methylbenzo[d]oxazol-2(3H)-one;
(R)-5-(5-(((2-hydroxy-2-(4-methyl-1-oxo-1,3-dihydroisobenzofuran-5-yl)ethyl)(4,4,4-trifluorobutyl)amino)methyl)pyridin-2-yl)-3-methylbenzo[d]oxazol-2(3H)-one;
(R)-5-(2-(((1-(2, 6-dimethylpyridin-4-yl)-1H-pyrazol-4-yl)methyl)amino)-1-hydroxyethyl)-4-methylisobenzofuran-1(3H)-one;
(R)-5-(1-hydroxy-2-(((1-(pyrazin-2-yl)-1H-pyrazol-4-yl)methyl)amino)ethyl)-4-methylisobenzofuran-1(3H)-one;
(R)-5-(1-hydroxy-2-(((1-(1-methyl-1H-pyrrolo[2, 3-b]pyridin-4-yl)-1H-pyrazol-4-yl)methyl)amino)ethyl)-4-methylisobenzofuran-1(3H)-one;
(R)-6-(4-(((2-fluoro-2-(4-methyl-1-oxo-1,3-dihydroisobenzofuran-5-yl)ethyl)amino)methyl)-1H-pyrazol-1-yl)-4-methylnicotinonitrile;
(R)-6-(3-(((2-hydroxy-2-(4-methyl-1-oxo-1,3-dihydroisobenzofuran-5-yl)ethyl)amino)methyl)-1H-pyrrolo[3,2-b]pyridin-1-yl)-4-methylnicotinonitrile;
(R)-6-(3-(((2-hydroxy-2-(4-methyl-1-oxo-1,3-dihydroisobenzofuran-5-yl)ethyl)amino)methyl)-1H-pyrrolo[2,3-b]pyridin-1-yl)-4-methylnicotinonitrile;
6-(4-(((2-hydroxy-2-(4-methyl-1-oxo-1,3-dihydroisobenzofuran-5-yl)propyl)amino)methyl)-1H-pyrazol-1-yl)-4-methylnicotinonitrile;
(R)-3-(6-(4-(((2-hydroxy-2-(4-methyl-1-oxo-1,3-dihydroisobenzofuran-5-yl)ethyl)amino)methyl)-1H-pyrazol-1-yl)pyridin-3-yl)-4-methyl-1,2,4-oxadiazol-5(4H)-one;
6-(4-(((2-(3,4-dimethyl-1-oxo-1,3-dihydroisobenzofuran-5-yl)-2-hydroxyethyl)amino)methyl)-1H-pyrazol-1-yl)-4-methylnicotinonitrile;
(R)-6-(4-(((2-hydroxy-2-(4-methyl-1-oxo-1,3-dihydroisobenzofuran-5-yl)ethyl)amino)methyl)-1H-pyrazol-1-yl)-4-methoxynicotinonitrile;
(R)-6-(4-(((2-(dimethylamino)-2-(4-methyl-1-oxo-1,3-dihydroisobenzofuran-5-yl)ethyl)amino)methyl)-1H-pyrazol-1-yl)-4-methylnicotinonitrile;
(R)-3-(difluoromethoxy)-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile;
6-(4-(((1-hydroxy-1-(4-methyl-1-oxo-1,3-dihydroisobenzofuran-5-yl)propan-2-yl)amino)methyl)-1H-pyrazol-1-yl)-4-methylnicotinonitrile;
(R)-1-(5-(((2-hydroxy-2-(4-methyl-1-oxo-1,3-dihydroisobenzofuran-5-yl)ethyl)amino)methyl)pyridin-2-yl)-1H-pyrazole-4-carbonitrile; and
(R)-1-(5-(((2-hydroxy-2-(4-methyl-1-oxo-1,3-dihydroisobenzofuran-5-yl)ethyl)amino)methyl)pyridin-2-yl)-3-methyl-1H-pyrazole-4-carbonitrile.

11. A pharmaceutical composition comprising one or more compounds of claim 1, or a salt thereof; and a pharmaceutically acceptable carrier or diluent.

12. A method for the treatment of a cardiovascular disease, which comprises administering to a patient in need thereof a therapeutically effective amount of a compound of claim 1, or pharmaceutically acceptable salt thereof.

13. The method of claim 12, wherein said disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

14. A method for the prophylaxis and/or treatment of diuresis or natriuresis, which comprises administering to a patient in need thereof a therapeutically effective amount of a compound of claim 1, or pharmaceutically acceptable salt thereof.

* * * * *

UNITED STATES PATENT AND TRADEMARK OFFICE
CERTIFICATE OF CORRECTION

PATENT NO. : 10,723,723 B2  
APPLICATION NO. : 16/344823  
DATED : July 28, 2020  
INVENTOR(S) : Prashantha Gunaga et al.

Page 1 of 2

It is certified that error appears in the above-identified patent and that said Letters Patent is hereby corrected as shown below:

In the Claims

Column 319  
Line 66, Claim 1, after "cycloalkyl" insert -- ; --.

Column 320  
Line 10, Claim 1, delete "alkoxy," and insert -- $C_{1-3}$ alkoxy, --;  
Line 15, Claim 1, delete "-alkyl," and insert -- -$C_{1-6}$ alkyl, --;  
Line 34, Claim 1, delete "pyrrazolyl," and insert -- pyrazolyl, --;  
Line 39, Claim 1, delete "bezoxazolyl, bezothiazolyl" and insert -- benzoxazolyl, benzothiazolyl, --;  
Line 47, Claim 1, delete "$C_{1-4}$alkyl," and insert -- $C_{1-4}$ alkyl, --;  
Line 53, Claim 1, delete "$C_{3-6}$cycloalkyl," and insert -- $C_{3-6}$ cycloalkyl, --; and  
Line 59, Claim 1, after "CN" insert -- , --.

Column 321  
Line 16, Claim 2, delete "-only," and insert -- -onyl, --;  
Line 16, Claim 2, delete "with with" and insert -- with --;  
Line 25, Claim 3, delete "-only," and insert -- -onyl, --;  
Line 26, Claim 3, delete "with with" and insert -- with --;  
Line 32, Claim 5, delete "pyrrazolyl," and insert -- pyrazolyl, --;  
Line 37, Claim 6, delete "pyrrazolyl," and insert -- pyrazolyl, --;  
Line 60, Claim 7, delete "—$C_{3-6}$cycloalkyl," and insert -- —$C_{3-6}$ cycloalkyl, --;  
Line 63, Claim 7, delete "$C_{1-3}$alkyl;" and insert -- $C_{1-3}$ alkyl; --; and  
Line 64, Claim 7, delete "$R^{e2}$" and insert -- $R^e$ --.

Column 322  
Line 19, Claim 9, delete "pyrrazolyl," and insert -- pyrazolyl, --.

Column 323  
Line 49, Claim 10, after "acetamide" insert -- ; --;

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,723,723 B2

Line 61, Claim 10, delete "acetamide," and insert -- acetamide; --; and
Line 64, Claim 10, after "acetamide" insert -- ; --.

Column 324
Line 12, Claim 10, delete "D-valinate," and insert -- D-valinate; --;
Line 60, Claim 10, delete "carbmate;" and insert -- carbamate; --.

Column 327
Line 24-25, Claim 10, delete "-di Hydroisobenzofuran-" and insert -- -dihydroisobenzofuran- --;
Line 65, Claim 10, delete "-((2-" and insert -- -(((2- --.

Column 329
Line 1, Claim 10, delete "-((2-" and insert -- -(((2- --;
Line 43, Claim 10, after "benzonitrile" insert -- ; --.